(12) United States Patent
Brookings et al.

(10) Patent No.: US 9,550,737 B2
(45) Date of Patent: Jan. 24, 2017

(54) TNF -α MODULATING BENZIMIDAZOLES

(71) Applicant: UCB Biopharma SPRL, Brussels (BE)

(72) Inventors: Daniel Christopher Brookings, Slough (GB); Mark Daniel Calmiano, Slough (GB); Ellen Olivia Gallimore, Slough (GB); Helen Tracey Horsley, Slough (GB); Martin Clive Hutchings, Slough (GB); James Andrew Johnson, Slough (GB); Boris Kroeplien, Slough (GB); Fabien Claude Lecomte, Slough (GB); Martin Alexander Lowe, Slough (GB); Timothy John Norman, Slough (GB); John Robert Porter, Slough (GB); Joanna Rachel Quincey, Slough (GB); James Thomas Reuberson, Slough (GB); Matthew Duncan Selby, Slough (GB); Michael Alan Shaw, Slough (GB); Zhaoning Zhu, Slough (GB); Anne Marie Foley, Slough (GB)

(73) Assignee: UCB Biopharma SPRL, Brussels (BE)

( * ) Notice: Subject to any disclaimer, the term of this patent is extended or adjusted under 35 U.S.C. 154(b) by 0 days.

(21) Appl. No.: 14/406,848

(22) PCT Filed: Jun. 11, 2013

(86) PCT No.: PCT/EP2013/062062
§ 371 (c)(1),
(2) Date: Dec. 10, 2014

(87) PCT Pub. No.: WO2013/186229
PCT Pub. Date: Dec. 19, 2013

(65) Prior Publication Data
US 2015/0152065 A1 Jun. 4, 2015

(30) Foreign Application Priority Data

Jun. 11, 2012 (GB) .................................. 1210233.1
Dec. 6, 2012 (GB) .................................. 1221983.8

(51) Int. Cl.
C07D 401/04 (2006.01)
C07D 401/14 (2006.01)
C07D 403/04 (2006.01)
C07D 491/107 (2006.01)
C07D 235/12 (2006.01)
A61K 31/4184 (2006.01)
A61K 31/4192 (2006.01)
A61K 31/4439 (2006.01)
A61K 31/444 (2006.01)
A61K 31/454 (2006.01)
A61K 31/4709 (2006.01)
A61K 31/4725 (2006.01)
A61K 31/506 (2006.01)
A61K 31/5377 (2006.01)
A61K 31/541 (2006.01)
A61K 31/551 (2006.01)
C07D 405/06 (2006.01)

(52) U.S. Cl.
CPC .......... C07D 235/12 (2013.01); A61K 31/4184 (2013.01); A61K 31/4192 (2013.01); A61K 31/444 (2013.01); A61K 31/4439 (2013.01); A61K 31/454 (2013.01); A61K 31/4709 (2013.01); A61K 31/4725 (2013.01); A61K 31/506 (2013.01); A61K 31/5377 (2013.01); A61K 31/541 (2013.01); A61K 31/551 (2013.01); C07D 401/04 (2013.01); C07D 401/14 (2013.01); C07D 403/04 (2013.01); C07D 405/06 (2013.01); C07D 491/107 (2013.01)

(58) Field of Classification Search
CPC ... C07D 401/04; C07D 401/14; C07D 403/14; C07D 491/107
See application file for complete search history.

(56) References Cited

U.S. PATENT DOCUMENTS

| 4,908,372 | A | 3/1990 | Carr et al. |
| 6,124,463 | A * | 9/2000 | Beck .................... C07D 235/08 544/333 |
| 6,716,849 | B1 | 4/2004 | Freund et al. |
| 7,074,801 | B1 | 7/2006 | Yoshida et al. |
| 8,809,541 | B2 | 8/2014 | Gwak et al. |

(Continued)

FOREIGN PATENT DOCUMENTS

| EP | 0 425 921 A1 | 5/1991 |
| EP | 1 262 180 A1 | 12/2002 |

(Continued)

OTHER PUBLICATIONS

Dong et al., "Characterization of a new class of selective nonsteroidal progesterone receptor agonists", Steroids, 2004, 69(3), 201-217.

(Continued)

Primary Examiner — Sahar Javanmard
(74) Attorney, Agent, or Firm — McDonnell Boehnen Hulbert & Berghoff LLP

(57) ABSTRACT

A series of benzimidazole derivatives, being potent modulators of human TNFα activity, are accordingly of benefit in the treatment and/or prevention of various human ailments, including autoimmune and inflammatory disorders; neurological and neurodegenerative disorders; pain and nociceptive disorders; cardiovascular disorders; metabolic disorders; ocular disorders; and oncological disorders.

10 Claims, No Drawings

(56) References Cited

U.S. PATENT DOCUMENTS

| | | |
|---|---|---|
| 2003/0060461 A1 | 3/2003 | Kodama et al. |
| 2006/0089367 A1 | 4/2006 | Bleicher et al. |
| 2010/0069381 A1 | 3/2010 | Itoh |
| 2010/0222345 A1 | 9/2010 | Diaz et al. |

FOREIGN PATENT DOCUMENTS

| | | |
|---|---|---|
| EP | 2 397 471 A1 | 12/2011 |
| WO | 93/14083 | 7/1993 |
| WO | 02/098869 A2 | 12/2002 |
| WO | 03/024937 A1 | 3/2003 |
| WO | 2007/112093 A2 | 10/2007 |
| WO | 2008/153701 A1 | 12/2008 |
| WO | 2010/021693 A2 | 2/2010 |
| WO | 2010/034796 A1 | 4/2010 |
| WO | 2010/034797 A1 | 4/2010 |
| WO | 2010/120779 A2 | 10/2010 |

OTHER PUBLICATIONS

Evans et al., "Synthesis of a group of 1H-benzimidazoles and their screening for antiinflammatory activity", European Journal of Medicinal Chemistry, 1996, 31(7), 635-642.

Tansey et al., "The TNF superfamily in 2009: new pathways, new indications, and new drugs", Drug Discovery Today, 2009, 14(23-24), 1082-1088.

Carneiro et al., "Emerging Role for TNF-alpha in Erectile Dysfunction", J. Sex Med, 2010, vol. 7, 3823-3834.

Chen et al., "Synthesis and Anti-inflammatory Evaluation of Novel Benzimidazole and Imidazopyridine Derivatives", ACS Medicinal Chemistry Letters, 2013, vol. 4, 69-74.

* cited by examiner

TNF-α MODULATING BENZIMIDAZOLES

This application is a US national phase of International Application No. PCT/EP2013/062062 filed on Jun. 11, 2013, which claims priority to Great Britain Patent Application No. 1210233.1 filed on Jun. 11, 2012 and Great Britain Patent Application No. 1221983.8 filed on Dec. 6, 2012.

The present invention relates to a class of benzimidazole derivatives, and to their use in therapy. These compounds are modulators of the signalling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and oncological disorders.

TNFα is the prototypical member of the Tumour Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies; and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certulizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, *Drug Discovery Today*, 2009, 14, 1082-1088; and F. S. Carneiro et al., *J. Sexual Medicine*, 2010, 7, 3823-3834).

The compounds in accordance with the present invention, being potent modulators of human TNFα activity, are therefore beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition, the compounds in accordance with the present invention may be beneficial as pharmacological standards for use in the development of new biological tests and in the search for new pharmacological agents. Thus, in one embodiment, the compounds of this invention may be useful as radioligands in assays for detecting pharmacologically active compounds. In an alternative embodiment, certain compounds of this invention may be useful for coupling to a fluorophore to provide fluorescent conjugates that can be utilised in assays (e.g. a fluorescence polarisation assay) for detecting pharmacologically active compounds.

The compounds in accordance with the present invention potently neutralise the activity of TNFα in a commercially available HEK-293 derived reporter cell line known as HEK-Blue™ CD40L. This cell line is a stable transfectant expressing SEAP (secreted alkaline phosphatase) under the control of the IFNβ minimal promoter fused to five NF-κB binding sites. Secretion of SEAP by these cells is stimulated in a concentration-dependent manner by TNFα. When tested in the HEK-293 bioassay, the compounds of the present invention exhibit an $IC_{50}$ value of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound).

The present invention provides a compound of formula (I) or an N-oxide thereof, or a pharmaceutically acceptable salt or solvate thereof, or a glucuronide derivative thereof, or a co-crystal thereof:

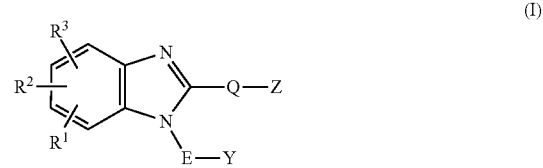

(I)

wherein

E represents a covalent bond; or E represents —S(O)$_2$— or —N(R$^4$)—; or E represents an optionally substituted straight or branched C$_{1-4}$ alkylene chain;

Q represents a covalent bond; or Q represents —O—, —S—, —S(O)—, —S(O)$_2$—, —N(R$^5$)—, —C(O)N(R$^5$)—, —N(R$^5$)C(O)—, —S(O)$_2$N(R$^5$)— or —N(R$^5$)S(O)$_2$—; or Q represents an optionally substituted straight or branched C$_{1-6}$ alkylene chain optionally comprising one, two or three heteroatom-containing linkages independently selected from —O—, —S—, —S(O)—, —S(O)$_2$—, —N(R$^5$)—, —C(O)N(R$^5$)—, —N(R$^5$)C(O)—, —S(O)$_2$N(R$^5$)— and —N(R$^5$)S(O)$_2$—;

Y represents C$_{3-7}$ cycloalkyl, aryl, C$_{3-7}$ heterocycloalkyl or heteroaryl, any of which groups may be optionally substituted by one or more substituents;

represents hydrogen, halogen or trifluoromethyl; or Z represents C$_{1-6}$ alkyl, C$_{3-7}$ cycloalkyl, aryl, C$_{3-7}$ heterocycloalkyl, C$_{3-7}$ heterocycloalkenyl or heteroaryl, any of which groups may be optionally substituted by one or more substituents; or Z represents —Z$^1$—Z$^2$ or —Z$^1$—C(O)—Z$^2$, either of which moieties may be optionally substituted by one or more substituents;

Z$^1$ represents a divalent radical derived from an aryl, C$_{3-7}$ heterocycloalkyl or heteroaryl group;

Z$^2$ represents aryl, C$_{3-7}$ heterocycloalkyl, C$_{3-7}$ heterocycloalkenyl, (C$_{4-9}$)heterobicycloalkyl, (C$_{4-9}$)spiroheterocycloalkyl or heteroaryl;

R$^1$, R$^2$ and R$^3$ independently represent hydrogen, halogen, cyano, nitro, hydroxy, trifluoromethyl, trifluoromethoxy, —OR$^a$, —SR$^a$, —SOR$^a$, —SO$_2$R$^a$, —OSO$_2$R$^a$, —SF$_5$, —NR$^b$R$^c$, —NR$^c$COR$^d$, —NR$^c$CO$_2$R$^d$, —NHCONR$^b$R$^c$, —NR$^c$SO$_2$R$^e$, —N(SO$_2$R$^e$)$_2$, —NHSO$_2$NR$^b$R$^c$, —COR$^d$, —CO$_2$R$^d$, —CONR$^b$R$^c$, —CON(OR$^a$)R$^b$ or —SO$_2$NR$^b$R$^c$; or C$_{1-6}$ alkyl, C$_{2-6}$ alkenyl, C$_{2-6}$ alkynyl, C$_{3-7}$ cycloalkyl, C$_{4-7}$ cycloalkenyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, C$_{3-7}$ heterocycloalkenyl, C$_{4-9}$ heterobicycloalkyl, heteroaryl, heteroaryl($C_{1-6}$)alkyl, ($C_{3-7}$)heterocycloalkyl-aryl-, ($C_{3-7}$)heterocycloalkyl($C_{1-6}$)alkyl-aryl-, heteroaryl-($C_{3-7}$)heterocycloalkyl-, ($C_{3-7}$)cycloalkyl-heteroaryl-, ($C_{3-7}$)cycloalkyl-($C_{1-6}$)alkyl-heteroaryl-, ($C_{4-7}$)cycloalkenyl-heteroaryl-, ($C_{4-9}$)bicycloalkyl-heteroaryl-, ($C_{3-7}$)heterocycloalkyl-heteroaryl-, ($C_{3-7}$)hetero cyclo alkyl ($C_{1-6}$)alkyl-hetero aryl-, ($C_{3-7}$)heterocycloalkenyl-heteroaryl-, ($C_{4-9}$)heterobicycloalkyl-heteroaryl-, ($C_{4-9}$)spiroheterocycloalkyl-heteroaryl- or ($C_{3-7}$)heterocycloalkyl-heteroaryl($C_{1-6}$)alkyl-, any of which groups may be optionally substituted by one or more substituents;

$R^4$ and $R^5$ independently represent hydrogen or $C_{1-6}$ alkyl;

$R^a$ represents trifluoromethyl; or $C_{1-6}$ alkyl, $C_{3-7}$ cycloalkyl, $C_{3-7}$ cycloalkyl($C_{1-6}$)-alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents;

$R^b$ and $R^c$ independently represent hydrogen or trifluoromethyl; or $C_{1-6}$ alkyl, $C_{3-7}$ cycloalkyl, $C_{3-7}$ cycloalkyl ($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents; or $R^b$ and $R^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents;

$R^d$ represents hydrogen; or $C_{1-6}$ alkyl, $C_{3-7}$ cycloalkyl, aryl, $C_{3-7}$ heterocycloalkyl or heteroaryl, any of which groups may be optionally substituted by one or more substituents; and $R^e$ represents $C_{1-6}$ alkyl, aryl or heteroaryl, any of which groups may be optionally substituted by one or more substituents; for use in the treatment and/or prevention of disorders for which the administration of a modulator of TNFα function is indicated.

In another aspect, the present invention provides a compound of formula (I) as defined above or an N-oxide thereof, or a pharmaceutically acceptable salt or solvate thereof, or a glucuronide derivative thereof, or a co-crystal thereof, for use in the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides a method for the treatment and/or prevention of disorders for which the administration of a modulator of TNFα function is indicated which comprises administering to a patient in need of such treatment an effective amount of a compound of formula (I) as defined above or an N-oxide thereof, or a pharmaceutically acceptable salt or solvate thereof, or a glucuronide derivative thereof, or a co-crystal thereof In another aspect, the present invention provides a method for the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder, which comprises administering to a patient in need of such treatment an effective amount of a compound of formula (I) as defined above or an N-oxide thereof, or a pharmaceutically acceptable salt or solvate thereof, or a glucuronide derivative thereof, or a co-crystal thereof.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of use in the invention or of their pharmaceutically acceptable salts. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of use in the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; ammonium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

The present invention also includes co-crystals within its scope. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012). Typical examples of co-crystal formers, which may be present in the co-crystal alongside the active pharmaceutical ingredient, include L-ascorbic acid, citric acid, glutaric acid, urea and nicotinamide.

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The expression "$C_{1-4}$ alkylene chain" refers to a divalent straight or branched alkylene chain containing 1 to 4 carbon atoms. Typical examples include methylene, ethylene, methylmethylene, ethylmethylene and dimethylmethylene.

Suitable $C_{2-6}$ alkenyl groups include vinyl and allyl.

Suitable $C_{2-6}$ alkynyl groups include ethynyl and propargyl.

Suitable $C_{3-7}$ cycloalkyl groups, which may comprise benzo-fused analogues thereof, include cyclopropyl, cyclobutyl, benzocyclobutenyl, cyclopentyl, indanyl, cyclohexyl and cycloheptyl.

Suitable $C_{4-7}$ cycloalkenyl groups include cyclobutenyl, cyclopentenyl, cyclohexenyl and cycloheptenyl.

Typical bicycloalkyl groups include bicyclo[3.1.0]hexanyl.

Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include oxetanyl, azetidinyl, tetrahydrofuranyl, dihydrobenzo-furanyl, dihydrobenzothienyl, pyrrolidinyl, indolinyl, isoindolinyl, oxazolidinyl, thiazolidinyl, isothiazolidinyl, imidazolidinyl, tetrahydropyranyl, chromanyl, tetrahydrothiopyranyl, piperidinyl, 1,2,3,4-tetrahydroquinolinyl, 1,2,3,4-tetrahydroisoquinolinyl, piperazinyl, 1,2,3,4-tetrahydroquinoxalinyl, homopiperazinyl, morpholinyl, benzoxazinyl, thiomorpholinyl, diazepanyl and azocanyl.

The term "$C_{3-7}$ heterocycloalkenyl" as used herein refers to monounsaturated or polyunsaturated monocyclic rings containing 3 to 7 carbon atoms and at least one heteroatom selected from oxygen, sulphur and nitrogen, and may comprise benzo-fused analogues thereof. Suitable heterocycloalkenyl groups include thiazolinyl, imidazolinyl, dihydropyranyl, dihydrothiopyranyl and 1,2,3,6-tetrahydropyridinyl.

Typical heterobicycloalkyl groups include quinuclidinyl, 3-azabicyclo[3.1.0]-hexanyl, 5-aza-2-oxabicyclo[2.2.1]heptanyl, 6-azabicyclo[3.2.0]heptanyl, 3-azabicyclo-[4.1.0]heptanyl, 5-aza-2-oxabicyclo[2.2.2]octanyl, 3-azabicyclo[3.2.1]octanyl, 8-azabicyclo[3.2.1]octanyl, 3,8-diazabicyclo[3.2.1]octanyl and 3,9-diazabicyclo[4.2.1]-nonanyl.

Suitable spiroheterocycloalkyl groups include 5-azaspiro[2.4]heptanyl, 2-oxa-6-azaspiro[3.3]heptanyl, 2-oxa-6-azaspiro[3.4]octanyl, 2-oxa-6-azaspiro[3.5]nonanyl, 2-oxa-7-azaspiro[3.5]nonanyl and 7-oxa-2-azaspiro[3.5]nonanyl.

Suitable heteroaryl groups include furyl, benzofuryl, dibenzofuryl, thienyl, thieno[2,3-c]pyrazolyl, thieno[3,4-b][1,4]dioxinyl, benzothienyl, dibenzothienyl, pyrrolyl, indolyl, pyrrolo[2,3-b]pyridinyl, pyrrolo[3,4-b]pyridinyl, pyrrolo[3,2-c]pyridinyl, pyrazolyl, pyrazolo[1,5-a]pyridinyl, pyrazolo[3,4-c]pyrimidinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]thiazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, triazolyl, [1,2,4]triazolo[1,5-a]pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of use in the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)↔ enol (CH=CHOH) tautomers or amide (NHC=O)↔ hydroxyimine (N=COH) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^{1}H$, $^{2}H$ (deuterium) or $^{3}H$ (tritium) atom, preferably $^{1}H$. Similarly, by way of example, each individual carbon atom present in formula (I), or in the formulae depicted hereinafter, may be present as a $^{12}C$, $^{13}C$ or $^{14}C$ atom, preferably $^{12}C$.

In one aspect, the present invention provides a compound of formula (I) as depicted above or an N-oxide thereof, or a pharmaceutically acceptable salt or solvate thereof, or a glucuronide derivative thereof, or a co-crystal thereof, wherein Q represents —O—, —S—, —S(O)—, —S(O)$_2$—, —N(R$^5$)—, —C(O)N(R$^5$)—, —N(R$^5$)C(O)—, —S(O)$_2$N(R$^5$)— or —N(R$^5$)S(O)$_2$—; or Q represents an optionally substituted straight or branched $C_{1-6}$ alkylene chain optionally comprising one, two or three heteroatom-containing linkages independently selected from —O—, —S—, —S(O)—, —S(O)$_2$—, —N(R$^5$)—, —C(O)N(R$^5$)—, —N(R$^5$)C(O)—, —S(O)$_2$N(R$^5$)— and —N(R$^5$)S(O)$_2$—;

Z represents $C_{3-7}$ cycloalkyl, aryl, $C_{3-7}$ heterocycloalkyl, $C_{3-7}$ heterocycloalkenyl or heteroaryl, any of which groups may be optionally substituted by one or more substituents; or Z represents —Z$^1$—Z$^2$ or —Z$^1$—C(O)—Z$^2$, either of which moieties may be optionally substituted by one or more substituents; and E, Y, R$^1$, R$^2$, R$^3$, R$^5$, Z$^1$ and Z$^2$ are as defined above.

In another aspect, the present invention provides a compound of formula (I) as depicted above or an N-oxide thereof, or a pharmaceutically acceptable salt or solvate thereof, or a glucuronide derivative thereof, or a co-crystal thereof, wherein R$^1$ represents halogen or cyano; or $C_{1-6}$ alkyl, $C_{2-6}$ alkenyl, $C_{2-6}$ alkynyl, $C_{3-7}$ cycloalkyl, $C_{4-7}$ cycloalkenyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, $C_{4-9}$ heterobicycloalkyl, heteroaryl, heteroaryl($C_{1-6}$)alkyl, ($C_{3-7}$)heterocycloalkyl-aryl-, ($C_{3-7}$)heterocycloalkyl($C_{1-6}$)alkyl-aryl-, heteroaryl($C_{3-7}$)heterocycloalkyl-, ($C_{3-7}$)cycloalkyl-heteroaryl-, ($C_{3-7}$)cycloalkyl($C_{1-6}$)alkyl-hetero aryl-, ($C_{4-7}$)cycloalkenyl-heteroaryl-, ($C_{4-9}$)bicycloalkyl-heteroaryl-, ($C_{3-7}$)heterocycloalkyl-heteroaryl-, ($C_{3-7}$)hetero cyclo alkyl($C_{1-6}$)alkyl-hetero aryl-, ($C_{3-7}$)hetero cyclo alkenyl-hetero aryl-, ($C_{4-9}$)heterobicycloalkyl-heteroaryl-, ($C_{4-9}$)spiroheterocycloalkylheteroaryl- or $(C_{3-7})$heterocycloalkyl-heteroaryl$(C_{1-6})$alkyl-, any of which groups may be optionally substituted by one or more substituents; and E, Q, Y, Z, $R^2$ and $R^3$ are as defined above.

In another aspect, the present invention provides a compound of formula (I) as depicted above or an N-oxide thereof, or a pharmaceutically acceptable salt or solvate thereof, or a co-crystal thereof, wherein $R^1$ represents halogen or cyano; or $C_{1-6}$ alkyl, $C_{2-6}$ alkenyl, $C_{2-6}$ alkynyl, $C_{3-7}$ cycloalkyl, $C_{4-7}$ cycloalkenyl, $C_{3-7}$ cycloalkyl$(C_{1-6})$alkyl, aryl, aryl$(C_{1-6})$alkyl, $C_{3-7}$ heterocycloalkyl, $C_{3-7}$ heterocycloalkyl$(C_{1-6})$alkyl, $C_{3-7}$ heterocycloalkenyl, $C_{4-9}$ heterobicycloalkyl, heteroaryl, heteroaryl $(C_{1-6})$alkyl, $(C_{3-7})$heterocycloalkyl$(C_{1-6})$alkyl-aryl-, heteroaryl$(C_{3-7})$heterocycloalkyl-, $(C_{3-7})$cycloalkyl-heteroaryl-, $(C_{3-7})$cycloalkyl-$(C_{1-6})$alkyl-hetero aryl-, $(C_{4-7})$cyclo alkenyl-hetero aryl-, $(C_{3-7})$hetero cyclo alkyl-hetero aryl-, $(C_{3-7})$hetero cyclo alkyl$(C_{1-6})$alkyl-hetero aryl-, $(C_{3-7})$hetero cyclo alkenyl-hetero aryl-, $(C_{4-9})$heterobicycloalkyl-heteroaryl- or $(C_{4-9})$spiroheterocycloalkyl-heteroaryl-, any of which groups may be optionally substituted by one or more substituents; and E, Q, Y, Z, $R^2$ and $R^3$ are as defined above.

In another aspect, the present invention provides a compound of formula (I) as depicted above or an N-oxide thereof, or a pharmaceutically acceptable salt or solvate thereof, wherein $R^1$ represents halogen or cyano; or $C_{1-6}$ alkyl, $C_{2-6}$ alkenyl, $C_{2-6}$ alkynyl, $C_{3-7}$ cycloalkyl, $C_{4-7}$ cycloalkenyl, $C_{3-7}$ cycloalkyl$(C_{1-6})$alkyl, aryl, aryl$(C_{1-6})$alkyl, $C_{3-7}$ heterocycloalkyl, $C_{3-7}$ heterocycloalkyl$(C_{1-6})$alkyl, $C_{3-7}$ heterocycloalkenyl, $C_{4-9}$ heterobicycloalkyl, heteroaryl, heteroaryl $(C_{1-6})$alkyl, $(C_{3-7})$heterocycloalkyl$(C_{1-6})$alkyl-aryl-, heteroaryl$(C_{3-7})$heterocycloalkyl-, $(C_{4-7})$cycloalkenyl-heteroaryl-, $(C_{3-7})$hetero cyclo alkyl-heteroaryl-, $(C_{3-7})$hetero cyclo alkyl$(C_{1-6})$alkyl-hetero aryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents; and E, Q, Y, Z, $R^2$ and $R^3$ are as defined above.

Where the compounds in accordance with the invention comprise an optionally substituted straight or branched alkylene chain, typical values thereof include methylene (—$CH_2$—), (methyl)methylene, ethylene (—$CH_2CH_2$—), (ethyl)methylene, (dimethyl)-methylene, (methyl)ethylene, propylene (—$CH_2CH_2CH_2$—), (propyl)methylene and (dimethyl)ethylene, any of which chains may be optionally substituted by one or more substituents. Suitably, such chains are unsubstituted, monosubstituted or disubstituted. Typically, such chains are unsubstituted or monosubstituted. In one embodiment, such chains are unsubstituted. In another embodiment, such chains are monosubstituted. In a further embodiment, such chains are disubstituted.

Examples of typical substituents on the alkylene chain which may be present in a compound in accordance with the invention include halogen, trifluoromethyl, oxo, hydroxy, $C_{1-6}$ alkoxy, trifluoromethoxy, amino, $C_{1-6}$ alkylamino, di$(C_{1-6})$alkylamino, aminocarbonyl, $C_{1-6}$ alkylaminocarbonyl and di$(C_{1-6})$alkylaminocarbonyl.

Examples of suitable substituents on the alkylene chain which may be present in a compound in accordance with the invention include halogen, trifluoromethyl, hydroxy, $C_{1-6}$ alkoxy and amino.

Specific examples of suitable substituents on the alkylene chain which may be present in a compound in accordance with the invention include fluoro, trifluoromethyl, hydroxy, methoxy and amino.

Generally, E represents a covalent bond; or E represents —N($R^4$)—; or E represents an optionally substituted straight or branched $C_{1-4}$ alkylene chain.

Typically, E represents —N($R^4$)—; or E represents an optionally substituted straight or branched $C_{1-4}$ alkylene chain.

In a selected aspect, E represents an optionally substituted straight or branched $C_{1-4}$ alkylene chain.

Suitably, E represents a covalent bond; or E represents —N($R^4$)—; or E represents methylene (—$CH_2$—), (methyl)methylene or (ethyl)methylene, any of which groups may be optionally substituted by one or more substituents.

Suitable values of E include —N($R^4$)—, —$CH_2$—, —CH($CH_3$)— and —CH($CH_2CH_3$)—; or E may represent a covalent bond.

In a first embodiment, E represents a covalent bond, whereby the integer Y is attached directly to the benzimidazole nucleus.

In a second embodiment, E represents —S(O)$_2$—.

In a third embodiment, E represents —N($R^4$)—.

In a fourth embodiment, E represents —$CH_2$—.

In a fifth embodiment, E represents —CH($CH_3$)—. In a particular aspect of that embodiment, the —CH($CH_3$)— linkage represented by E is in the (S) stereochemical configuration.

In a sixth embodiment, E represents —CH($CH_2CH_3$)—.

In a first embodiment, Q represents a covalent bond, whereby the integer Z is attached directly to the benzimidazole nucleus.

In a second embodiment, Q represents —O—, —S—, —S(O)—, —S(O)$_2$—, —N($R^5$)—, —C(O)N($R^5$)—, —N($R^5$)C(O)—, —S(O)$_2$N($R^5$)— or —N($R^5$)S(O)$_2$—. In a first aspect of that embodiment, Q represents —O—. In a second aspect of that embodiment, Q represents —S—. In a third aspect of that embodiment, Q represents —S(O)—. In a fourth aspect of that embodiment, Q represents —S(O)$_2$—. In a fifth aspect of that embodiment, Q represents —N($R^5$)—. In a sixth aspect of that embodiment, Q represents —C(O)N($R^5$)—. In a seventh aspect of that embodiment, Q represents —N($R^5$)C(O)—. In an eighth aspect of that embodiment, Q represents —S(O)$_2$N($R^5$)—. In a ninth aspect of that embodiment, Q represents —N($R^5$)S(O)$_2$—.

In a third embodiment, Q represents an optionally substituted straight or branched $C_{1-6}$ alkylene chain optionally comprising one, two or three heteroatom-containing linkages independently selected from —O—, —S—, —S(O)—, —S(O)$_2$—, —N($R^5$)—, —C(O)N($R^5$)—, —N($R^5$)C(O)—, —S(O)$_2$N($R^5$)— and —N($R^5$)S(O)$_2$—. In a first aspect of that embodiment, Q represents an optionally substituted straight or branched $C_{1-6}$ alkylene chain. In a second aspect of that embodiment, Q represents an optionally substituted straight or branched $C_{1-6}$ alkylene chain comprising one heteroatom-containing linkage independently selected from —O—, —S—, —S(O)—, —S(O)$_2$—, —N($R^5$)—, —C(O)N($R^5$)—, —N($R^5$)C(O)—, —S(O)$_2$N($R^5$)— and —N($R^5$)S(O)$_2$—. In a third aspect of that embodiment, Q represents an optionally substituted straight or branched $C_{1-6}$ alkylene chain comprising two heteroatom-containing linkages independently selected from —O—, —S—, —S(O)—, —S(O)$_2$—, —N($R^5$)—, —C(O)N($R^5$)—, —N($R^5$)C(O)—, —S(O)$_2$N($R^5$)— and —N($R^5$)S(O)$_2$—. In a fourth aspect of that embodiment, Q represents an optionally substituted straight or branched $C_{1-6}$ alkylene chain comprising three heteroatom-containing linkages independently selected from —O—, —S—, —S(O)—, —S(O)$_2$—, —N(R$^5$)—, —C(O)N(R$^5$)—, —N(R$^5$)C(O)—, —S(O)$_2$N(R$^5$)— and —N(R$^5$)S(O)$_2$—. In a fifth aspect of that embodiment, Q represents an optionally substituted straight or branched C$_{1-6}$ alkylene chain comprising one, two or three heteroatom-containing linkages independently selected from —O—, —S—, —N(R$^5$)—, —C(O)N(R$^5$)— and —N(R$^5$)C(O)—.

Typically, Q represents a covalent bond; or Q represents —S(O)— or —S(O)$_2$—; or Q represents an optionally substituted straight or branched C$_{1-6}$ alkylene chain optionally comprising one or two heteroatom-containing linkages selected from —O—, —S—, —N(R$^5$)—, —C(O)N(R$^5$)—, and —N(R$^5$)C(O)—.

Selected examples of typical substituents on the linkage represented by Q include halogen, trifluoromethyl, hydroxy, C$_{1-6}$ alkoxy and amino.

Specific examples of typical substituents on the linkage represented by Q include fluoro, trifluoromethyl, hydroxy, methoxy and amino.

Suitably, Q represents a covalent bond; or Q represents —S(O)— or —S(O)$_2$—; or Q represents —CH$_2$—, —CH(F)—, —CF$_2$—, —CH(CH$_3$)—, —CH(OH)—, —CH(OCH$_3$)—, —CH(NH$_2$)—, —CH$_2$CH$_2$—, —CH(OH)CH$_2$—, —CH(OH)CF$_2$—, —CH(OCH$_3$)CH$_2$—, —CH$_2$O—, —CH(CH$_3$)O—, —C(CH$_3$)$_2$O—, —CH(CH$_2$CH$_3$)O—, —CH(CF$_3$)O—, —CH$_2$S—, —CH$_2$N(R$^5$)—, —CH$_2$CH$_2$CH$_2$—, —CH(OH)CH$_2$CH$_2$—, —CH(OCH$_3$)CH$_2$CH$_2$—, —CH$_2$CH$_2$O—, —CH$_2$OCH$_2$—, —CH$_2$OCH(F)—, —CH$_2$OCF$_2$—, —CH$_2$OCH(CH$_3$)—, —CH(CH$_3$)OCH$_2$—, —CH$_2$OC(CH$_3$)$_2$—, —C(CH$_3$)$_2$OCH$_2$—, —CH$_2$SCH$_2$—, —CH$_2$CH$_2$N(R$^5$)—, —CH$_2$N(R$^5$)CH$_2$—, —CH$_2$CH$_2$OCH$_2$—, —CH$_2$CH$_2$N(R$^5$)C(O)—, —CH$_2$OCH$_2$CH$_2$—, —CH$_2$OCH$_2$CF$_2$—, —CH$_2$OCH$_2$CH(CH$_3$)—, —CH$_2$OCH(CH$_3$)CH$_2$—, —CH$_2$OC(CH$_3$)$_2$CH$_2$—, —CH$_2$OCH$_2$CH(CH$_3$)CH$_2$—, —CH$_2$OCH$_2$CH$_2$O—, —CH$_2$OCH$_2$C(O)N(R$^5$)— or —CH$_2$OCH$_2$CH$_2$OCH$_2$—. Additional values include —N(R$^5$)—, —CH(CH$_2$OH)—, —CH$_2$S(O)—, —CH$_2$S(O)$_2$—, —CH$_2$S(O)CH$_2$—, —CH$_2$S(O)$_2$CH$_2$—, and —CH$_2$N(R$^5$)C(O)—.

Particular values of Q include —CH$_2$—, —CH$_2$O—, —CH$_2$S—, and —CH$_2$OCH$_2$—. In a first embodiment, Q represents —CH$_2$—. In a second embodiment, Q represents —CH$_2$O—. In a third embodiment, Q represents —CH$_2$S—. In a fourth embodiment, Q represents —CH$_2$OCH$_2$—.

Generally, Y represents C$_{3-7}$ cycloalkyl, aryl or heteroaryl, any of which groups may be optionally substituted by one or more substituents. Additionally, Y may represent C$_{3-7}$ heterocycloalkyl, which group may be optionally substituted by one or more substituents.

Typically, Y represents aryl or heteroaryl, either of which groups may be optionally substituted by one or more substituents. Additionally, Y may represent C$_{3-7}$ heterocycloalkyl, which group may be optionally substituted by one or more substituents.

In a first embodiment, Y represents optionally substituted C$_{3-7}$ cycloalkyl. In one aspect of that embodiment, Y represents unsubstituted C$_{3-7}$ cycloalkyl. In another aspect of that embodiment, Y represents monosubstituted C$_{3-7}$ cycloalkyl. In a further aspect of that embodiment, Y represents disubstituted C$_{3-7}$ cycloalkyl.

In a second embodiment, Y represents optionally substituted aryl. In one aspect of that embodiment, Y represents unsubstituted aryl. In another aspect of that embodiment, Y represents monosubstituted aryl. In a further aspect of that embodiment, Y represents disubstituted aryl.

In a third embodiment, Y represents optionally substituted C$_{3-7}$ heterocycloalkyl. In one aspect of that embodiment, Y represents unsubstituted C$_{3-7}$ heterocycloalkyl. In another aspect of that embodiment, Y represents monosubstituted C$_{3-7}$ heterocycloalkyl. In a further aspect of that embodiment, Y represents disubstituted C$_{3-7}$ heterocycloalkyl.

In a fourth embodiment, Y represents optionally substituted heteroaryl. In one aspect of that embodiment, Y represents unsubstituted heteroaryl. In another aspect of that embodiment, Y represents monosubstituted heteroaryl. In a further aspect of that embodiment, Y represents disubstituted heteroaryl.

Suitably, Y represents benzocyclobutenyl, phenyl, thiazolyl or pyridinyl, any of which groups may be optionally substituted by one or more substituents. Additionally, Y may represent pyrrolidinyl, thieno[2,3-c]pyrazolyl, indazolyl, isoxazolyl and imidazo[2,1-b]thiazolyl, any of which groups may be optionally substituted by one or more substituents.

In a selected embodiment, Y represents phenyl, which group may be optionally substituted by one or more substituents.

In a selected embodiment, Y represents thiazolyl, especially thiazol-4-yl, which group may be optionally substituted by one or more substituents.

Examples of optional substituents which may be present on the moiety Y include one, two or three substituents independently selected from halogen, cyano, nitro, C$_{1-6}$ alkyl, trifluoromethyl, hydroxy, C$_{1-6}$ alkoxy, difluoromethoxy, trifluoromethoxy, C$_{1-6}$ alkylthio, C$_{1-6}$ alkylsulfinyl, C$_{1-6}$ alkylsulfonyl, amino, C$_{1-6}$ alkylamino, di(C$_{1-6}$)alkylamino, arylamino, C$_{2-6}$ alkylcarbonylamino, C$_{1-6}$ alkylsulfonylamino, formyl, C$_{2-6}$ alkylcarbonyl, C$_{3-6}$ cycloalkylcarbonyl, C$_{3-6}$ heterocycloalkylcarbonyl, carboxy, C$_{2-6}$ alkoxycarbonyl, aminocarbonyl, C$_{1-6}$ alkylaminocarbonyl, di(C$_{1-6}$)alkylaminocarbonyl, aminosulfonyl, C$_{1-6}$ alkylaminosulfonyl and di(C$_{1-6}$)alkylaminosulfonyl. Additional examples include benzyl and methylenedioxy.

Typical examples of optional substituents on the moiety Y include halogen, C$_{1-6}$ alkyl, trifluoromethyl, C$_{1-6}$ alkoxy, difluoromethoxy, trifluoromethoxy and amino. Additional examples include benzyl and methylenedioxy.

Examples of particular substituents on the moiety Y include fluoro, chloro, bromo, cyano, nitro, methyl, isopropyl, trifluoromethyl, hydroxy, methoxy, difluoromethoxy, trifluoromethoxy, methylthio, methylsulfinyl, methylsulfonyl, amino, methylamino, tert-butylamino, dimethylamino, phenylamino, acetylamino, methylsulfonylamino, formyl, acetyl, cyclopropylcarbonyl, azetidinylcarbonyl, pyrrolidinylcarbonyl, piperidinyl-carbonyl, piperazinylcarbonyl, morpholinylcarbonyl, carboxy, methoxycarbonyl, aminocarbonyl, methylaminocarbonyl, dimethylaminocarbonyl, aminosulfonyl, methylaminosulfonyl and dimethylaminosulfonyl. Additional examples include benzyl, ethoxy and methylenedioxy.

Typical examples of particular substituents on the moiety Y include fluoro, chloro, methyl, trifluoromethyl, methoxy, difluoromethoxy, trifluoromethoxy and amino. Additional examples include bromo, benzyl, ethoxy and methylenedioxy.

Suitable values of Y include benzocyclobutenyl, phenyl, fluorophenyl (including 2-fluorophenyl, 3-fluorophenyl and 4-fluorophenyl), chlorophenyl (including 2-chlorophenyl, 3-chlorophenyl and 4-chlorophenyl), difluorophenyl (including 2,6-difluorophenyl), (chloro)(fluoro)phenyl (including 5-chloro-2-fluorophenyl and 2-chloro-5-fluorophenyl), dichlorophenyl (including 2,5-dichlorophenyl and 2,6-dichlorophenyl), methylphenyl (including 4-methylphenyl), dimethylphenyl (including 2,5-dimethylphenyl and 2,6-dimethylphenyl), (trifluoromethyl)phenyl [including 2-(trifluoromethyl)phenyl], (chloro)(trifluoromethyl)phenyl [including 5-chloro-2-(trifluoromethyl)phenyl], (methyl)-(trifluoromethyl)phenyl [including 2-methyl-5-(trifluoromethyl)phenyl], bis(trifluoromethyl)phenyl [including 2,5-bis(trifluoromethyl)phenyl], methoxyphenyl (including 2-methoxyphenyl), (difluoromethoxy)phenyl [including 2-(difluoromethoxy)phenyl and 3-(difluoromethoxy)phenyl], (difluoromethoxy)(fluoro)phenyl [including 2-(difluoromethoxy)-5-fluorophenyl and 5-(difluoromethoxy)-2-fluorophenyl], (chloro)-(difluoromethoxy)phenyl [including 5-chloro-2-(difluoromethoxy)phenyl and 6-chloro-2-(difluoromethoxy)phenyl], (trifluoromethoxy)phenyl [including 2-(trifluoromethoxy)-phenyl], (amino)(chloro)phenyl (including 5-amino-2-chlorophenyl), methylthiazolyl (including 2-methyl-1,3-thiazol-4-yl), (chloro)(methyl)thiazolyl (including 5-chloro-2-methyl-1,3-thiazol-4-yl) and pyridinyl (including pyridin-3-yl and pyridin-4-yl). Additional values include (fluoro)(methoxy)phenyl, (difluoro)(difluoromethoxy)phenyl, (dichloro)(difluoromethoxy)phenyl, (bromo)(difluoromethoxy)phenyl, (difluoromethoxy)(methyl)phenyl, (difluoromethoxy)(methoxy)phenyl, bis(difluoromethoxy)-phenyl, (difluoromethoxy)(methylenedioxyoxy)phenyl, (chloro)(trifluoromethoxy)phenyl, benzylpyrrolidinyl, (methyl)(trifluoromethyl)thieno[2,3-c]pyrazolyl, methylindazolyl, methylisoxazolyl, dimethylthiazolyl, (methyl)(trifluoromethyl)thiazolyl, (ethoxy)-(methyl)thiazolyl and chloroimidazo[2,1-b]thiazolyl.

In a particular embodiment, Y represents 2-(difluoromethoxy)phenyl.

In one embodiment, Z represents hydrogen.

In another embodiment, Z is other than hydrogen.

In a selected embodiment, Z represents hydrogen; or Z represents $C_{1-6}$ alkyl, $C_{3-7}$ cycloalkyl, aryl, $C_{3-7}$ heterocycloalkyl, $C_{3-7}$ heterocycloalkenyl or heteroaryl, any of which groups may be optionally substituted by one or more substituents; or Z represents $-Z^1-Z^2$ or $-Z^1-C(O)-Z^2$, either of which moieties may be optionally substituted by one or more substituents.

In a further embodiment, Z represents $C_{1-6}$ alkyl, $C_{3-7}$ cycloalkyl, aryl, $C_{3-7}$ heterocycloalkyl, $C_{3-7}$ heterocycloalkenyl or heteroaryl, any of which groups may be optionally substituted by one or more substituents; or Z represents $-Z^1-Z^2$ or $-Z^1-C(O)-Z^2$, either of which moieties may be optionally substituted by one or more substituents.

Typically, Z represents hydrogen, fluoro or trifluoromethyl; or Z represents methyl, ethyl, n-propyl, isopropyl, n-butyl, sec-butyl, isobutyl, tert-butyl, cyclopropyl, cyclobutyl, cyclopentyl, cyclohexyl, phenyl, tetrahydrofuranyl, pyrrolidinyl, indolinyl, tetrahydropyranyl, piperidinyl, 1,2,3,4-tetrahydroquinolinyl, morpholinyl, azocanyl, thiazolinyl, furyl, thienyl, pyrazolyl, 4,5,6,7-tetrahydroindazolyl, benzoxazolyl, isoxazolyl, thiazolyl, benzothiazolyl, imidazolyl, benzimidazolyl, [1,2,4]triazolo[1,5-c]-pyrimidinyl, tetrazolyl, pyridinyl, quinolinyl, isoquinolinyl, phthalazinyl, pyrimidinyl or pyrazinyl, any of which groups may be optionally substituted by one or more substituents; or Z represents $-Z^1-Z^2$ or $-Z^1-C(O)-Z^2$, either of which moieties may be optionally substituted by one or more substituents. Additionally, Z may represent dihydrobenzothienyl, dihydroisoindolinyl, 1,2,3,4-tetrahydroisoquinolinyl, pyridazinyl or triazinyl, any of which groups may be optionally substituted by one or more substituents.

The moiety $Z^1$ represents a divalent radical derived from an aryl, $C_{3-7}$ heterocycloalkyl or heteroaryl group, any of which groups may be optionally substituted by one or more substituents. Typically, the moiety $Z^1$ represents a divalent radical derived from a phenyl, pyrrolidinyl, piperazinyl, pyrazolyl, thiazolyl, triazolyl, tetrazolyl or pyridinyl group, any of which groups may be optionally substituted by one or more substituents. Typical values of the moiety $Z^1$ include the groups of formula (Za), (Zb), (Zc), (Zd), (Ze), (Zf), (Zg), (Zh) and (Zj):

(Za)

(Zb)

(Zc)

(Zd)

(Ze)

(Zf)

(Zg)

(Zh)

(Zj)

wherein
the symbols # represent the points of attachment of the moiety $Z^1$ to the remainder of the molecule; and
the asterisks (*) represent the site of attachment of optional substituents.

Additional values of the moiety $Z^1$ include the group of formula (Zk):

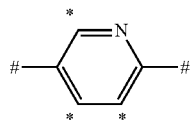

wherein and * are as defined above.

Particular values of the moiety $Z^1$ include the groups of formula (Za), (Zc), (Ze), (Zf), (Zg), (Zh) and (Zj) as depicted above.

The moiety $Z^2$ may represent aryl, $C_{3-7}$ heterocycloalkyl, $C_{3-7}$ heterocycloalkenyl or heteroaryl, any of which groups may be optionally substituted by one or more substituents. In addition, $Z^2$ may represent $(C_{4-9})$heterobicycloalkyl or $(C_{4-9})$spiroheterocycloalkyl, either of which groups may be optionally substituted by one or more substituents.

Typically, $Z^2$ represents phenyl, pyrrolidinyl, oxazolidinyl, imidazolidinyl, morpholinyl, imidazolinyl, thiazolyl, imidazolyl, tetrazolyl or pyridinyl, any of which groups may be optionally substituted by one or more substituents. Additionally, $Z^2$ may represent azetidinyl, isothiazolidinyl, piperidinyl, piperazinyl, 6-azabicyclo[3.2.0]-heptanyl, 2-oxa-6-azaspiro[3.4]octanyl, triazolyl or pyrimidinyl, any of which groups may be optionally substituted by one or more substituents.

Examples of optional substituents which may be present on the moiety Z, $Z^1$ or $Z^2$ include one, two or three substituents independently selected from halogen, cyano, nitro, $C_{1-6}$ alkyl, trifluoromethyl, oxo, hydroxy, hydroxy$(C_{1-6})$alkyl, $C_{1-6}$ alkoxy, difluoromethoxy, trifluoromethoxy, $C_{1-3}$ alkylenedioxy, $C_{1-6}$ alkylthio, $C_{1-6}$ alkylsulfinyl, $C_{1-6}$ alkylsulfonyl, amino, $C_{1-6}$ alkylamino, di$(C_{1-6})$alkylamino, di$(C_{1-6})$alkylamino$(C_{1-6})$alkyl, $C_{2-6}$ alkylcarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di$(C_{1-6})$alkylaminocarbonyl, aminosulfonyl, $C_{1-6}$ alkylaminosulfonyl, di$(C_{1-6})$alkylaminosulfonyl, aminocarbonylamino and hydrazinocarbonyl. Additional examples include thioxo, N—[$(C_{1-6})$-alkyl]-N—[$(C_{1-6})$alkylcarbonyl]amino, N—[$(C_{1-6})$alkyl]-N—[$(C_{1-6})$alkylsulfonyl]amino, cyano$(C_{1-6})$alkylaminocarbonyl and $(C_{3-7})$cycloalkylureido.

Typical examples of optional substituents on the moiety Z, $Z^1$ or $Z^2$ include halogen, cyano, nitro, $C_{1-6}$ alkyl, trifluoromethyl, oxo, hydroxy, hydroxy$(C_{1-6})$alkyl, $C_{1-6}$ alkoxy, difluoromethoxy, trifluoromethoxy, $C_{1-3}$ alkylenedioxy, $C_{1-6}$ alkylsulfonyl, amino, di$(C_{1-6})$alkylamino, di$(C_{1-6})$alkylamino$(C_{1-6})$alkyl, $C_{2-6}$ alkylcarbonylamino, $C_{1-6}$ alkylsulfonylamino, formyl, carboxy, $C_{2-6}$ alkoxycarbonyl, aminocarbonyl, $C_{1-6}$ alkylaminocarbonyl, di$(C_{1-6})$ alkylaminocarbonyl, aminocarbonylamino and hydrazinocarbonyl. Additional examples include thioxo, $C_{1-6}$ alkylthio, N—[$(C_{1-6})$alkyl]-N—[$(C_{1-6})$alkylcarbonyl]amino, N—[$(C_{1-6})$-alkyl]-N—[$(C_{1-6})$alkylsulfonyl]amino, cyano$(C_{1-6})$alkylaminocarbonyl, aminosulfonyl and $(C_{3-7})$cycloalkylureido.

Examples of particular substituents on the moiety Z, $Z^1$ or $Z^2$ include fluoro, chloro, bromo, cyano, nitro, methyl, ethyl, isopropyl, trifluoromethyl, oxo, hydroxy, hydroxymethyl, methoxy, difluoromethoxy, trifluoromethoxy, methylenedioxy, methylthio, methylsulfinyl, methylsulfonyl, amino, methylamino, tert-butylamino, dimethylamino, dimethylaminomethyl, dimethylaminoethyl, acetylamino, methylsulfonylamino, formyl, acetyl, carboxy, methoxycarbonyl, tert-butoxycarbonyl, aminocarbonyl, methylaminocarbonyl, dimethylaminocarbonyl, aminosulfonyl, methylaminosulfonyl, dimethylaminosulfonyl, aminocarbonylamino and hydrazinocarbonyl. Additional examples include thioxo, ethoxy, N-acetyl-N-methylamino, N-methyl-N-(methylsulfonyl)-amino, cyanomethylaminocarbonyl and cyclopropylureido.

Typical examples of particular substituents on the moiety Z, $Z^1$ or $Z^2$ include fluoro, chloro, bromo, cyano, nitro, methyl, ethyl, trifluoromethyl, oxo, hydroxy, hydroxymethyl, methoxy, difluoromethoxy, trifluoromethoxy, methylenedioxy, methylsulfonyl, amino, dimethylamino, dimethylaminomethyl, dimethylaminoethyl, acetylamino, methylsulfonylamino, formyl, carboxy, methoxycarbonyl, tert-butoxycarbonyl, aminocarbonyl, methylaminocarbonyl, dimethylaminocarbonyl, aminocarbonylamino and hydrazinocarbonyl. Additional examples include thioxo, methylthio, ethoxy, N-acetyl-N-methylamino, N-methyl-N-(methylsulfonyl)amino, cyanomethylaminocarbonyl, aminosulfonyl and cyclopropylureido.

Typical values of $Z^2$ include phenyl, hydroxyphenyl, oxopyrrolidinyl, dioxo-pyrrolidinyl, (hydroxy)(oxo)pyrrolidinyl, (amino)(oxo)pyrrolidinyl, (oxo)oxazolidinyl, oxoimidazolidinyl, morpholinyl, imidazolinyl, methylthiazolyl, formylthiazolyl, imidazolyl, tetrazolyl and pyridinyl. Additionally, $Z^2$ may represent oxoazetidinyl, (methyl)(oxo)pyrrolidinyl, (hydroxymethyl)(oxo)pyrrolidinyl, dioxoisothiazolidinyl, oxopiperidinyl, (methyl)(oxo)piperazinyl, oxomorpholinyl, oxo-6-azabicyclo[3.2.0]-heptanyl, oxo-2-oxa-6-azaspiro[3.4]octanyl, ethoxytriazolyl or pyrimidinyl.

Selected values of $Z^2$ include oxopyrrolidinyl and (oxo)oxazolidinyl. In one embodiment, $Z^2$ represents oxopyrrolidinyl. In another embodiment, $Z^2$ represents (oxo)oxazolidinyl.

Typical values of Z include hydrogen, fluoro, trifluoromethyl, methyl, ethyl, n-propyl, isopropyl, isobutyl, tert-butyl, cyclopropyl, cyclopentyl, cyclohexyl, oxocyclohexyl, phenyl, bromophenyl, cyanophenyl, nitrophenyl, methoxyphenyl, difluoromethoxyphenyl, trifluoromethoxyphenyl, methylenedioxyphenyl, methylsulfonylphenyl, dimethylaminophenyl, acetylaminophenyl, methylsulfonylaminophenyl, carboxyphenyl, aminocarbonylphenyl, methylaminocarbonylphenyl, dimethylaminocarbonylphenyl, aminocarbonylaminophenyl, tetrahydrofuranyl, oxopyrrolidinyl, dimethylamino-pyrrolidinyl, tert-butoxycarbonylpyrrolidinyl, indolinyl, tetrahydropyranyl, piperidinyl, ethylpiperidinyl, tert-butoxycarbonylpiperidinyl, aminocarbonylpiperidinyl, 2-oxo-3,4-dihydroquinolinyl, morpholinyl, azocanyl, oxothiazolinyl, furyl, hydroxymethylfuryl, thienyl, methylpyrazolyl, dimethylpyrazolyl, 4,5,6,7-tetrahydroindazolyl, benzoxazolyl, methylisoxazolyl, dimethylisoxazolyl, methylthiazolyl, aminothiazolyl, benzothiazolyl, methylbenzothiazolyl, aminobenzothiazolyl, imidazolyl, methylimidazolyl, methyl-benzimidazolyl, dimethyl[1,2,4]triazolo[1,5-c]pyrimidinyl, dimethylaminoethyltetrazolyl, pyridinyl, fluoropyridinyl, chloropyridinyl, cyanopyridinyl, methylpyridinyl, (cyano)-(methyl)pyridinyl, trifluoromethylpyridinyl, oxopyridinyl, methoxypyridinyl, dimethylaminomethylpyridinyl, acetylaminopyridinyl, carboxypyridinyl, methoxycarbonyl-pyridinyl, aminocarbonylpyridinyl, (aminocarbonyl)(fluoro)pyridinyl, methylaminocarbonylpyridinyl, dimethylaminocarbonylpyridinyl, hydrazinocarbonylpyridinyl, quinolinyl, isoquinolinyl, (methyl)(oxo)phthalazinyl, pyrimidinyl, pyrazinyl, oxopyrrolidinylphenyl, dioxopyrrolidinylphenyl, (hydroxy)(oxo)pyrrolidinylphenyl, (amino)(oxo)pyrrolidinylphenyl, (oxo)oxazolidinylphenyl, oxoimidazolidinylphenyl, imidazolinylphenyl, methylthiazolylphenyl, formylthiazolylphenyl, imidazolylphenyl, tetrazolylphenyl, phenylpyrrolidinyl, hydroxyphenylpiperazinyl, (methyl)(phenyl)pyrazolyl, oxoimidazolidinylthiazolyl, hydroxyphenyltriazolyl, morpholinyltetrazolyl, oxopyrrolidinylpyridinyl, (oxo)oxazolidinylpyridinyl, oxoimidazolidinylpyridinyl, pyridinylthiazolyl, pyridinyltetrazolyl and morpholinylcarbonylphenyl. Additional values include difluoromethyl, aminocarbonylaminomethyl, difluorophenyl, chlorophenyl, methylphenyl, dimethylphenyl, dimethoxyphenyl, (methylthio)phenyl, methylsulfinyl-phenyl, (bromo)(methylsulfonyl)phenyl, (methyl)(methylsulfonyl)phenyl, cyanomethyl-aminocarbonylphenyl, trioxodihydrobenzothienyl, pyrrolidinyl, methylpyrrolidinyl, oxodihydroisoindolinyl, oxopiperidinyl, 1,2,3,4-tetrahydroisoquinolinyl, aminosulfonyl-pyrazolyl, cyclopropylureidothiazolyl, [1,2,4]triazolo[1,5-c]pyrimidinyl, hydroxypyridinyl, dimethylaminopyridinyl, N-acetyl-N-methylaminopyridinyl, N-methyl-N-(methylsulfonyl)aminopyridinyl, pyridazinyl, oxopyrimidinyl, (amino)(dimethyl)-pyrimidinyl, (oxo)(thioxo)triazinyl, pyridinylpiperazinyl, pyrimidinylpiperazinyl, oxopyrrolidinylthiazolyl, oxoazetidinylpyridinyl, (methyl)(oxo)pyrrolidinylpyridinyl, (hydroxy)(oxo)pyrrolidinylpyridinyl, (hydroxymethyl)(oxo)pyrrolidinylpyridinyl, (amino)(oxo)pyrrolidinylpyridinyl, dioxoisothiazolidinylpyridinyl, oxopiperidinyl-pyridinyl, (methyl)(oxo)piperazinylpyridinyl, oxomorpholinylpyridinyl, oxo-6-azabicyclo[3.2.0]heptanylpyridinyl, oxo-2-oxa-6-azaspiro[3.4]octanylpyridinyl and ethoxytriazolylpyridinyl.

Particular values of Z include hydrogen, methyl, methylsulfonylphenyl, pyridinyl, oxopyrrolidinylphenyl, (hydroxy)(oxo)pyrrolidinylphenyl and (oxo)oxazolidinylphenyl. In a first embodiment, Z represents hydrogen. In a second embodiment, Z represents methyl. In a third embodiment, Z represents methylsulfonylphenyl. In one aspect of that embodiment, Z represents 3-(methylsulfonyl)phenyl. In a fourth embodiment, Z represents pyridinyl. In one aspect of that embodiment, Z represents pyridin-4-yl. In a fifth embodiment, Z represents oxopyrrolidinylphenyl. In one aspect of that embodiment, Z represents 3-(2-oxopyrrolidin-1-yl)phenyl. In a sixth embodiment, Z represents (hydroxy)(oxo)pyrrolidinylphenyl. In one aspect of that embodiment, Z represents 3-(3-hydroxy-2-oxopyrrolidin-1-yl)phenyl. In another aspect of that embodiment, Z represents 3-(4-hydroxy-2-oxopyrrolidin-1-yl)phenyl. In a seventh embodiment, Z represents (oxo)oxazolidinylphenyl. In one aspect of that embodiment, Z represents 3-(2-oxo-oxazolidinyl-3-yl)phenyl.

In general, $R^1$, $R^2$ and $R^3$ independently represent hydrogen, halogen, cyano, nitro, hydroxy, trifluoromethyl, trifluoromethoxy, —$OR^a$, —$SR^a$, —$SOR^a$, —$SO_2R^a$, —$NR^bR^c$, —$NR^cCOR^d$, —$NR^cCO_2R^d$, —$NHCONR^bR^c$, —$NR^cSO_2R^e$, —$N(SO_2R^e)_2$, —$NHSO_2NR^bR^c$, —$COR^d$, —$CO_2R^d$, —$CONR^bR^c$, —$CON(OR^a)R^b$ or —$SO_2NR^bR^c$; or $C_{1-6}$ alkyl, $C_{2-6}$ alkenyl, $C_{2-6}$ alkynyl, $C_{3-7}$ cycloalkyl, $C_{4-7}$ cycloalkenyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, $C_{4-9}$ heterobicycloalkyl, heteroaryl, heteroaryl($C_{1-6}$)alkyl, ($C_{3-7}$)heterocycloalkyl($C_{1-6}$)alkyl-aryl-, heteroaryl($C_{3-7}$)heterocycloalkyl-, ($C_{3-7}$)cycloalkyl-heteroaryl-, ($C_{3-7}$)cyclo alkyl($C_{1-6}$)alkyl-hetero aryl-, ($C_{4-7}$)cycloalkenyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents.

Generally, $R^1$, $R^2$ and $R^3$ independently represent hydrogen, halogen, cyano, nitro, hydroxy, trifluoromethyl, trifluoromethoxy, —$OR^a$, —$SR^a$, —$SOR^a$, —$SO_2R^a$, —$NR^bR^c$, —$NR^cOR^d$, —$NR^cCO_2R^d$, —$NHCONR^bR^c$, —$NR^cSO_2R^e$, —$N(SO_2R^e)_2$, —$NHSO_2NR^bR^c$, —$COR^d$, —$CO_2R^d$, —$CONR^bR^c$, —$CON(OR^a)R^b$ or —$SO_2NR^bR^c$; or $C_{1-6}$ alkyl, $C_{2-6}$ alkenyl, $C_{2-6}$ alkynyl, $C_{3-7}$ cycloalkyl, $C_{4-7}$ cycloalkenyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, $C_{4-9}$ heterobicycloalkyl, heteroaryl, heteroaryl($C_{1-6}$)alkyl, ($C_{3-7}$)heterocycloalkyl($C_{1-6}$)alkyl-aryl-, heteroaryl($C_{3-7}$)heterocycloalkyl-, ($C_{4-7}$)cycloalkenyl-heteroaryl-, ($C_{3-7}$)heterocycloalkyl-heteroaryl-, ($C_{3-7}$)heterocycloalkyl-($C_{1-6}$)alkyl-hetero aryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents.

Typically, $R^1$, $R^2$ and $R^3$ independently represent hydrogen, halogen, cyano or —$CO_2R^d$; or $C_{1-6}$ alkyl, aryl, $C_{3-7}$ heterocycloalkyl, $C_{3-7}$ heterocycloalkenyl, heteroaryl, ($C_{3-7}$)heterocycloalkyl($C_{1-6}$)alkyl-aryl-, heteroaryl($C_{3-7}$)heterocycloalkyl-, ($C_{4-7}$)cycloalkenyl-heteroaryl-, ($C_{3-7}$)heterocycloalkyl-heteroaryl-, ($C_{3-7}$)hetero cyclo alkyl($C_{1-6}$)alkyl-hetero aryl-, ($C_{3-7}$)hetero cyclo alkenyl-hetero aryl-, ($C_{4-9}$)heterobicycloalkyl-heteroaryl- or ($C_{4-9}$)spiroheterocycloalkyl-heteroaryl-, any of which groups may be optionally substituted by one or more substituents. Additionally, $R^1$, $R^2$ and $R^3$ may independently represent ($C_{3-7}$)cycloalkyl-heteroaryl- or ($C_{3-7}$)cycloalkyl($C_{1-6}$)alkyl-heteroaryl-, either of which groups may be optionally substituted by one or more substituents. Additionally, $R^1$, $R^2$ and $R^3$ may independently represent trifluoromethyl, —$OR^a$, —$SO_2R^a$, —$OSO_2R^a$ or —$CONR^bR^c$; or heteroaryl($C_{1-6}$)alkyl, ($C_{3-7}$)heterocycloalkyl-aryl-, ($C_{4-9}$)bicycloalkyl-heteroaryl- or ($C_{3-7}$)heterocycloalkyl-heteroaryl($C_{1-6}$)alkyl-, any of which groups may be optionally substituted by one or more substituents.

Suitably, $R^1$, $R^2$ and $R^3$ independently represent hydrogen, halogen, cyano or —$CO_2R^d$; or $C_{1-6}$ alkyl, aryl, $C_{3-7}$ heterocycloalkyl, $C_{3-7}$ heterocycloalkenyl, heteroaryl, ($C_{3-7}$)heterocycloalkyl($C_{1-6}$)alkyl-aryl-, heteroaryl($C_{3-7}$)heterocycloalkyl-, ($C_{3-7}$)heterocycloalkyl-heteroaryl-, ($C_{3-7}$)heterocycloalkyl($C_{1-6}$)alkyl-heteroaryl- or ($C_{4-9}$)spiroheterocycloalkyl-heteroaryl-, any of which groups may be optionally substituted by one or more substituents. Additionally, $R^1$, $R^2$ and $R^3$ may independently represent ($C_{3-7}$)cycloalkyl-heteroaryl- or ($C_{3-7}$)cycloalkyl($C_{1-6}$)alkyl-heteroaryl-, either of which groups may be optionally substituted by one or more substituents. Additionally, $R^1$, $R^2$ and $R^3$ may independently represent trifluoromethyl, —$OR^a$, —$SO_2R^a$, —$OSO_2R^a$ or —$CONR^bR^c$; or heteroaryl($C_{1-6}$)alkyl, ($C_{3-7}$)heterocycloalkyl-aryl-, ($C_{4-7}$)cycloalkenyl-heteroaryl-, ($C_{4-9}$)-bicycloalkyl-heteroaryl-, ($C_{4-9}$)heterobicycloalkyl-heteroaryl- or ($C_{3-7}$)heterocycloalkyl-heteroaryl($C_{1-6}$)alkyl-, any of which groups may be optionally substituted by one or more substituents.

Examples of optional substituents which may be present on $R^1$, $R^2$ or $R^3$ include one, two or three substituents independently selected from halogen, cyano, cyano($C_{1-6}$)-alkyl, nitro, $C_{1-6}$ alkyl, trifluoromethyl, trifluoroethyl, $C_{2-6}$ alkenyl, hydroxy, $C_{1-6}$ alkoxy, difluoromethoxy, trifluoromethoxy, trifluoroethoxy, $C_{1-3}$ alkylenedioxy, $C_{1-6}$ alkoxy($C_{1-6}$)-alkyl, $C_{1-6}$ alkylthio, $C_{1-6}$ alkylsulphonyl, ($C_{1-6}$)alkylsulphonyl($C_{1-6}$)alkyl, oxo, amino, $C_{1-6}$ alkylamino, di($C_{1-6}$) alkylamino, ($C_{1-6}$)alkoxy($C_{1-6}$)alkylamino, N—[($C_{1-6}$)alkyl]-N-[hydroxy-($C_{1-6}$)alkyl]amino, $C_{2-6}$ alkylcarbonylamino, $C_{2-6}$ alkoxycarbonylamino, $C_{1-6}$ alkylamino-carbonylamino, $C_{1-6}$ alkylsulphonylamino, formyl, $C_{2-6}$ alkylcarbonyl, carboxy, carboxy-($C_{1-6}$)alkyl, $C_{2-6}$ alkoxycarbonyl, $C_{2-6}$ alkoxycarbonyl($C_{1-6}$)alkyl, aminocarbonyl, $C_{1-6}$ alkylaminocarbonyl, di($C_{1-6}$)alkylaminocarbonyl, aminosulphonyl and di($C_{1-6}$)alkylaminosulphonyl. Additional examples include hydroxy($C_{1-6}$)alkyl, a carboxylic acid isostere or prodrug moiety Ω, —($C_{1-6}$)alkyl-Ω, and aminocarbonyl($C_{1-6}$)alkyl. Additional examples include difluoromethyl, difluoroethyl, $C_{1-6}$ alkylsulphinyl, hydroxy ($C_{1-6}$)alkylamino, [($C_{1-6}$)alkoxy](hydroxy)($C_{1-6}$)alkylamino, [($C_{1-6}$)alkylthio](hydroxy)($C_{1-6}$)alkylamino, di($C_{1-6}$)alkylamino($C_{1-6}$)alkylamino, N-[di($C_{1-6}$)alkylamino($C_{1-6}$)alkyl]-N-[hydroxy($C_{1-6}$)-alkyl]amino, hydroxy($C_{1-6}$)alkyl($C_{3-7}$)cycloalkylamino, (hydroxy)[($C_{3-7}$)cycloalkyl($C_{1-6}$)-alkyl]amino, ($C_{3-7}$)heterocycloalkyl($C_{1-6}$)alkylamino, oxo($C_{3-7}$)hetero cyclo alkyl($C_{1-6}$)alkylamino, ($C_{1-6}$)alkylheteroarylamino, heteroaryl($C_{1-6}$)alkylamino, ($C_{1-6}$)alkylheteroaryl($C_{1-6}$)-alkylamino, N—[($C_{1-6}$)alkyl]-N—[($C_{2-6}$)alkylcarbonyl]amino, $C_{3-6}$ alkenylcarbonylamino, bis[($C_{3-6}$)alkenylcarbonyl]amino, N—[($C_{1-6}$)alkyl]-N—[($C_{3-7}$)cycloalkylcarbonyl]amino, N-[carboxy($C_{1-6}$)alkyl]-N—[($C_{1-6}$)alkyl]amino, $C_{2-6}$ alkoxycarbonyl ($C_{1-6}$)alkylamino, N—[($C_{1-6}$)-alkyl]-N—[($C_{1-6}$) alkylsulphonyl]amino, ($C_{3-7}$)cycloalkylcarbonyl, phenylcarbonyl and hydroxy($C_{1-6}$)alkylamino carbonyl.

By the expression "carboxylic acid isostere or prodrug moiety" is meant any functional group, structurally distinct from a carboxylic acid moiety, that will be recognised by a biological system as being similar to, and thus capable of mimicking, a carboxylic acid moiety, or will be readily convertible by a biological system in vivo into a carboxylic acid moiety. A synopsis of some common carboxylic acid isosteres is presented by N. A. Meanwell in *J. Med. Chem.*, 2011, 54, 2529-2591 (cf. in particular FIGS. 25 and 26). Typical examples of suitable carboxylic acid isostere or prodrug moieties represented by Ω include the functional groups of formula (i) to (xli):

(i)
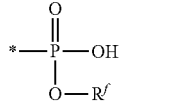

(ii)
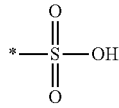

(iii)
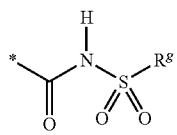

(iv)
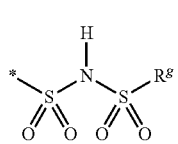

(v)
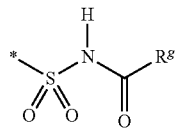

(vi)
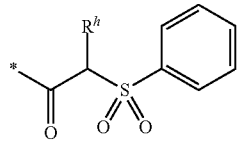

(vii)
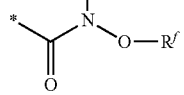

(viii)
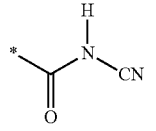

(ix)
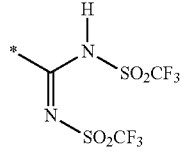

(x)
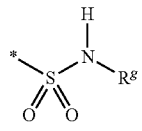

(xi)
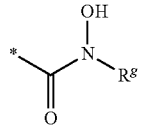

(xii)
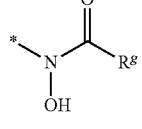

(xiii)
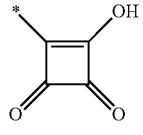

(xiv)
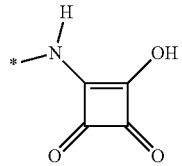

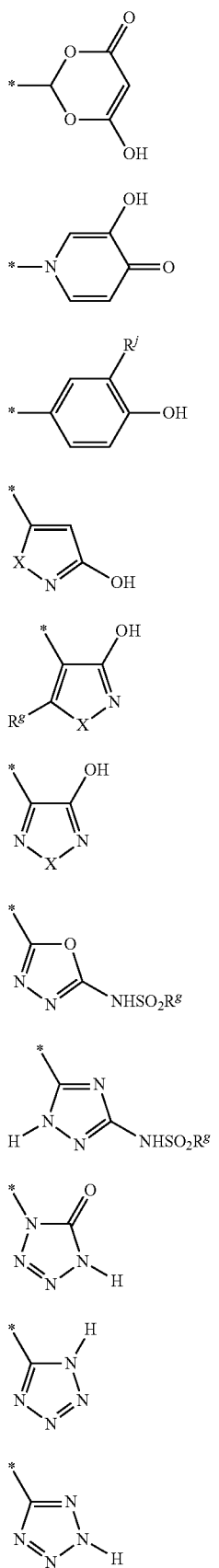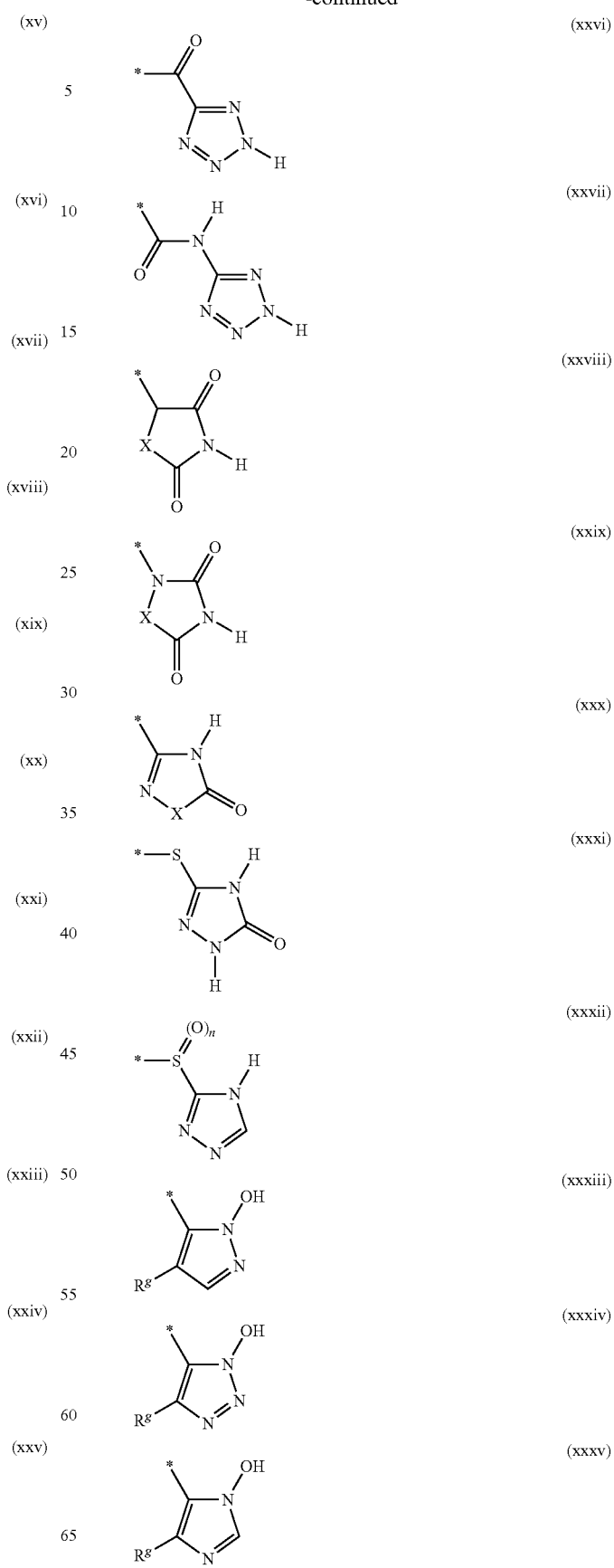

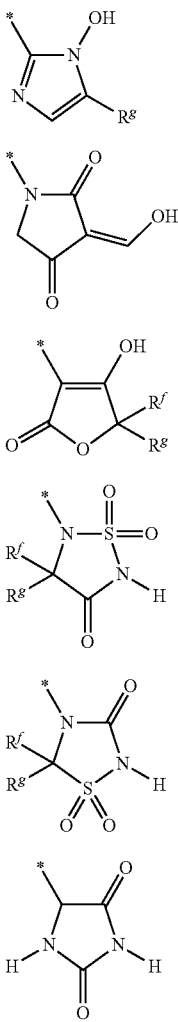

wherein
the asterisk (*) represents the site of attachment to the remainder of the molecule;

n is zero, 1 or 2;

X represents oxygen or sulphur;

$R^f$ represents hydrogen, $C_{1-6}$ alkyl or —$CH_2CH(OH)CH_2OH$;

$R^g$ represents $C_{1-6}$ alkyl, trifluoromethyl, —$CH_2CH_2F$, —$CH_2CHF_2$, —$CH_2CF_3$ or —$CF_2CF_3$;

$R^h$ represents hydrogen, cyano or —$CO_2R^d$, in which $R^d$ is as defined above; and $R^j$ represents hydrogen or halogen.

In one embodiment, n is zero. In another embodiment, n is 1. In a further embodiment, n is 2.

In one embodiment, X represents oxygen. In another embodiment, X represents sulphur.

In one embodiment, $R^f$ represents hydrogen. In another embodiment, $R^f$ represents $C_{1-6}$ alkyl, especially methyl. In a further embodiment, $R^f$ is —$CH_2CH(OH)CH_2OH$.

In one embodiment, $R^g$ represents $C_{1-6}$ alkyl, especially methyl. In another embodiment, $R^g$ represents trifluoromethyl, —$CH_2CH_2F$, —$CH_2CHF_2$, —$CH_2CF_3$ or —$CF_2CF_3$.

In a first aspect of that embodiment, $R^g$ represents trifluoromethyl. In a second aspect of that embodiment, $R^g$ represents —$CH_2CH_2F$. In a third aspect of that embodiment, $R^g$ represents —$CH_2CHF_2$. In a fourth aspect of that embodiment, $R^g$ represents —$CH_2CF_3$. In a fifth aspect of that embodiment, $R^g$ represents —$CF_2CF_3$.

In one embodiment, $R^h$ is hydrogen. In another embodiment, $R^h$ represents cyano. In a further embodiment, $R^h$ represents —$CO_2R^d$, especially methoxycarbonyl.

In one embodiment, $R^j$ represents hydrogen. In another embodiment, $R^j$ represents halogen, especially chloro.

In a selected embodiment, Ω represents tetrazolyl, especially a C-linked tetrazolyl moiety of formula (xxiv) or (xxv) as depicted above, in particular a group of formula (xxiv) as depicted above.

In another embodiment, Ω represents $C_{1-6}$ alkylsulphonylaminocarbonyl, i.e. a moiety of formula (iii) as depicted above wherein $R^g$ represents $C_{1-6}$ alkyl.

In another embodiment, Ω represents $C_{1-6}$ alkylaminosulphonyl, i.e. a moiety of formula (x) as depicted above wherein $R^g$ represents $C_{1-6}$ alkyl.

In a further embodiment, Ω represents $(C_{1-6})$alkylcarbonylaminosulphonyl, i.e. a moiety of formula (v) as depicted above wherein $R^g$ represents $C_{1-6}$ alkyl.

Suitable examples of optional substituents which may be present on $R^1$, $R^2$ or $R^3$ include one, two or three substituents independently selected from halogen, cyano, cyano-$(C_{1-6})$alkyl, $C_{1-6}$ alkyl, trifluoromethyl, trifluoroethyl, $C_{2-6}$ alkenyl, hydroxy, hydroxy$(C_{1-6})$-alkyl, $C_{1-6}$ alkoxy, trifluoroethoxy, $C_{1-6}$ alkylsulphonyl, $(C_{1-6})$alkylsulphonyl$(C_{1-6})$alkyl, oxo, amino, di$(C_{1-6})$alkylamino, $(C_{1-6})$alkoxy$(C_{1-6})$alkylamino, N—[$(C_{1-6})$alkyl]-N-[hydroxy-$(C_{1-6})$alkyl]amino, $C_{2-6}$ alkylcarbonyl, carboxy, carboxy$(C_{1-6})$alkyl, $C_{2-6}$ alkoxycarbonyl, $C_{2-6}$ alkoxycarbonyl$(C_{1-6})$alkyl, aminocarbonyl and aminocarbonyl$(C_{1-6})$alkyl. Additional examples include difluoromethyl, difluoroethyl, $C_{1-6}$ alkoxy $(C_{1-6})$alkyl, $C_{1-6}$ alkylsulphinyl, $C_{1-6}$ alkylamino, hydroxy $(C_{1-6})$alkylamino, [$(C_{1-6})$alkoxy](hydroxy)$(C_{1-6})$alkylamino, [$(C_{1-6})$alkylthio](hydroxy)$(C_{1-6})$alkylamino, di$(C_{1-6})$alkylamino$(C_{1-6})$alkylamino, N-[di$(C_{1-6})$alkylamino $(C_{1-6})$alkyl]-N-[hydroxy$(C_{1-6})$alkyl]amino, hydroxy$(C_{1-6})$alkyl$(C_{3-7})$-cycloalkylamino, (hydroxy)[$(C_{3-7})$cycloalkyl $(C_{1-6})$alkyl]amino, $(C_{3-7})$heterocycloalkyl-$(C_{1-6})$alkylamino, oxo$(C_{3-7})$heterocycloalkyl$(C_{1-6})$alkylamino, $(C_{1-6})$alkylheteroarylamino, heteroaryl$(C_{1-6})$alkylamino, $(C_{1-6})$alkylheteroaryl$(C_{1-6})$alkylamino, $C_{2-6}$ alkylcarbonylamino, N—[$(C_{1-6})$alkyl]-N—[$(C_{2-6})$alkylcarbonyl]amino, $C_{3-6}$ alkenylcarbonylamino, bis[$(C_{3-6})$alkenylcarbonyl]amino, N—[$(C_{1-6})$alkyl]-N—[$(C_{3-7})$cycloalkylcarbonyl]amino, N-[carboxy$(C_{1-6})$alkyl]-N—[$(C_{1-6})$alkyl]amino, $C_{2-6}$ alkoxycarbonylamino, $C_{2-6}$ alkoxycarbonyl$(C_{1-6})$alkylamino, N—[$(C_{1-6})$alkyl]-N—[$(C_{1-6})$alkylsulphonyl]amino, formyl, $(C_{3-7})$cycloalkylcarbonyl, phenylcarbonyl, $C_{1-6}$ alkylaminocarbonyl, hydroxy $(C_{1-6})$alkylaminocarbonyl, di$(C_{1-6})$alkylaminocarbonyl and aminosulphonyl.

Typical examples of optional substituents which may be present on $R^1$, $R^2$ or $R^3$ include one, two or three substituents independently selected from halogen, cyano, cyano-$(C_{1-6})$alkyl, $C_{1-6}$ alkyl, trifluoromethyl, trifluoroethyl, $C_{2-6}$ alkenyl, hydroxy, $C_{1-6}$ alkoxy, trifluoroethoxy, $C_{1-6}$ alkylsulphonyl, $(C_{1-6})$alkylsulphonyl$(C_{1-6})$alkyl, oxo, amino, di$(C_{1-6})$-alkylamino, $(C_{1-6})$alkoxy$(C_{1-6})$alkylamino, N—[$(C_{1-6})$alkyl]-N-[hydroxy$(C_{1-6})$alkyl]amino, $C_{2-6}$ alkylcarbonyl, carboxy, carboxy$(C_{1-6})$alkyl, $C_{2-6}$ alkoxycarbonyl, $C_{2-6}$ alkoxycarbonyl$(C_{1-6})$alkyl and aminocarbonyl.

Examples of particular substituents on $R^1$, $R^2$ or $R^3$ include fluoro, chloro, bromo, cyano, cyanoethyl, nitro, methyl, ethyl, tert-butyl, trifluoromethyl, trifluoroethyl, ethenyl, hydroxy, methoxy, isopropoxy, difluoromethoxy, trifluoromethoxy, trifluoroethoxy, methylenedioxy, ethylenedioxy, methoxymethyl, methylthio, methylsulphonyl, methylsulphonylethyl, oxo, amino, methylamino, dimethylamino, methoxyethylamino, N-(hydroxyethyl)-N-(methyl)amino, acetylamino, methoxycarbonylamino, ethoxycarbonylamino, ethylaminocarbonylamino, butylaminocarbonylamino, methylsulphonylamino, formyl, acetyl, carboxy, carboxymethyl, carboxyethyl, methoxycarbonyl, ethoxycarbonyl, tert-butoxycarbonyl, ethoxycarbonylmethyl, ethoxycarbonylethyl, aminocarbonyl, methylaminocarbonyl, dimethylaminocarbonyl, aminosulphonyl, methylaminosulphonyl and dimethylaminosulphonyl. Additional examples include hydroxyethyl, hydroxyisopropyl and aminocarbonylmethyl. Additional examples include isopropyl, isobutyl, difluoromethyl, difluoroethyl, hydroxymethyl, methoxyethyl, methylsulphinyl, ethylamino, hydroxyethylamino, hydroxypropylamino, (hydroxy)(methyl)propylamino, (hydroxy)-(methoxy)(methyl)propylamino, (hydroxy)(methylthio)butylamino, dimethylaminoethylamino, (dimethylamino)(methyl)propylamino, N-(dimethylaminoethyl)-N-(hydroxyethyl)-amino, hydroxymethylcyclopentylamino, hydroxycyclobutylmethylamino, (cyclopropyl)-(hydroxy)propylamino, morpholinylethylamino, oxopyrrolidinylmethylamino, ethyloxadiazolylamino, methylthiadiazolylamino, thiazolylmethylamino, thiazolylethylamino, pyrimidinylmethylamino, methylpyrazolylmethylamino, N-acetyl-N-methylamino, N-isopropylcarbonyl-N-methylamino, ethenylcarbonylamino, bis(ethenylcarbonyl)amino, N-cyclopropylcarbonyl-N-methylamino, N-(carboxymethyl)-N-methylamino, N-(carboxy-ethyl)-N-methylamino, tert-butoxycarbonylamino, methoxycarbonylethylamino, N-methyl-N-(methylsulphonyl)amino, isopropylcarbonyl, cyclobutylcarbonyl, phenylcarbonyl and hydroxyethylaminocarbonyl.

Suitable examples of particular substituents on $R^1$, $R^2$ or $R^3$ include fluoro, chloro, cyano, cyanoethyl, methyl, ethyl, trifluoromethyl, trifluoroethyl, ethenyl, hydroxy, hydroxyethyl, hydroxyisopropyl, methoxy, isopropoxy, trifluoroethoxy, methylsulphonyl, methylsulphonylethyl, oxo, amino, dimethylamino, methoxyethylamino, N-(hydroxy-ethyl)-N-(methyl)amino, acetyl, carboxy, carboxymethyl, carboxyethyl, ethoxycarbonyl, tert-butoxycarbonyl, ethoxycarbonylmethyl, ethoxycarbonylethyl, aminocarbonyl and aminocarbonylmethyl. Additional examples include isopropyl, isobutyl, difluoromethyl, difluoroethyl, hydroxymethyl, methoxymethyl, methoxyethyl, methylsulphinyl, ethylamino, hydroxyethylamino, hydroxypropylamino, (hydroxy)(methyl)propylamino, (hydroxy)(methoxy)(methyl)propylamino, (hydroxy)(methylthio)butylamino, dimethylaminoethylamino, (dimethylamino)(methyl)propylamino, N-(dimethylaminoethyl)-N-(hydroxyethyl)amino, hydroxymethylcyclopentylamino, hydroxycyclobutylmethylamino, (cyclopropyl)(hydroxy)propylamino, morpholinylethylamino, oxopyrrolidinylmethylamino, ethyloxadiazolylamino, methylthiadiazolylamino, thiazolylmethylamino, thiazolylethylamino, pyrimidinylmethylamino, methylpyrazolylmethylamino, acetylamino, N-acetyl-N-methylamino, N-isopropylcarbonyl-N-methylamino, ethenylcarbonylamino, bis(ethenylcarbonyl)amino, N-cyclopropylcarbonyl-N-methylamino, N-(carboxymethyl)-N-methylamino, N-(carboxyethyl)-N-methylamino, tert-butoxycarbonylamino, methoxycarbonylethylamino, N-methyl-N-(methylsulphonyl)amino, formyl, isopropylcarbonyl, cyclobutylcarbonyl, phenylcarbonyl, methoxycarbonyl, methylaminocarbonyl, hydroxyethylaminocarbonyl, dimethylaminocarbonyl and aminosulphonyl.

Typical examples of particular substituents on $R^1$, $R^2$ or $R^3$ include fluoro, chloro, cyano, cyanoethyl, methyl, trifluoromethyl, trifluoroethyl, ethenyl, hydroxy, methoxy, isopropoxy, trifluoroethoxy, methylsulphonyl, methylsulphonylethyl, oxo, amino, dimethylamino, methoxyethylamino, N-(hydroxyethyl)-N-(methyl)amino, acetyl, carboxy, carboxymethyl, carboxyethyl, ethoxycarbonyl, tert-butoxycarbonyl, ethoxycarbonylmethyl, ethoxycarbonylethyl and aminocarbonyl.

In a particular embodiment, $R^1$ is attached at the 6-position of the benzimidazole nucleus in the compounds of formula (I) above.

Typically, $R^1$ represents hydrogen, halogen, cyano or $-CO_2R^d$; or $C_{1-6}$ alkyl, aryl, $C_{3-7}$ heterocycloalkyl, $C_{3-7}$ heterocycloalkenyl, heteroaryl, $(C_{3-7})$heterocycloalkyl-$(C_{1-6})$alkyl-aryl-, heteroaryl$(C_{3-7})$heterocycloalkyl-, $(C_{4-7})$cycloalkenyl-heteroaryl-, $(C_{3-7})$heterocycloalkyl-heteroaryl-, $(C_{3-7})$hetero cyclo alkyl$(C_{1-6})$alkyl-hetero aryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents. Additionally, $R^1$ may represent $(C_{3-7})$cycloalkyl-heteroaryl- or $(C_{3-7})$cycloalkyl$(C_{1-6})$alkyl-heteroaryl-, either of which groups may be optionally substituted by one or more substituents. Additionally, $R^1$ may represent trifluoromethyl, $-OR^a$, $-SO_2R^a$, $-OSO_2R^a$ or $-CONR^bR^c$; or heteroaryl$(C_{1-6})$alkyl, $(C_{3-7})$heterocycloalkyl-aryl-, $(C_{4-9})$bicycloalkyl-heteroaryl- or $(C_{3-7})$heterocycloalkyl-heteroaryl$(C_{1-6})$alkyl-, any of which groups may be optionally substituted by one or more substituents.

Suitably, $R^1$ represents halogen, cyano or $-CO_2R^d$; or $C_{1-6}$ alkyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl$(C_{3-7})$heterocycloalkyl-, $(C_{4-7})$cycloalkenyl-heteroaryl-, $(C_{3-7})$heterocycloalkyl-heteroaryl-, $(C_{3-7})$hetero cyclo alkyl$(C_{1-6})$alkyl-hetero aryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents. Additionally, $R^1$ may represent $(C_{3-7})$cycloalkyl-heteroaryl- or $(C_{3-7})$cycloalkyl$(C_{1-6})$alkyl-heteroaryl-, either of which groups may be optionally substituted by one or more substituents. Additionally, $R^1$ may represent trifluoromethyl, $-OR^a$, $-SO_2R^a$, $-OSO_2R^a$ or $-CONR^bR^c$; or heteroaryl$(C_{1-6})$alkyl, $(C_{3-7})$heterocycloalkyl-aryl-, $(C_{4-9})$bicycloalkyl-heteroaryl- or $(C_{3-7})$heterocycloalkyl-heteroaryl$(C_{1-6})$alkyl-, any of which groups may be optionally substituted by one or more substituents.

Generally, $R^1$ represents halogen or cyano; or $C_{1-6}$ alkyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl$(C_{3-7})$heterocycloalkyl-, $(C_{4-7})$cycloalkenyl-heteroaryl-, $(C_{3-7})$heterocycloalkyl-heteroaryl-, $(C_{3-7})$hetero cyclo alkyl$(C_{1-6})$alkyl-hetero aryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents. Additionally, $R^1$ may represent $(C_{3-7})$cycloalkyl-heteroaryl- or $(C_{3-7})$cycloalkyl$(C_{1-6})$alkyl-heteroaryl-, either of which groups may be optionally substituted by one or more substituents. Additionally, $R^1$ may represent trifluoromethyl, $-OR^a$, $-SO_2R^a$, $-OSO_2R^a$ or $-CONR^bR^c$; or heteroaryl$(C_{1-6})$alkyl, $(C_{3-7})$heterocycloalkyl-aryl-, $(C_{4-9})$bicycloalkyl-heteroaryl- or $(C_{3-7})$heterocycloalkyl-heteroaryl$(C_{1-6})$alkyl-, any of which groups may be optionally substituted by one or more substituents.

More generally, $R^1$ represents halogen or cyano; or $C_{1-6}$ alkyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl($C_{3-7}$)heterocycloalkyl-, ($C_{3-7}$)heterocycloalkyl-heteroaryl-, ($C_{3-7}$)heterocycloalkyl($C_{1-6}$)alkyl-heteroaryl- or ($C_{4-9}$)spiroheterocycloalkyl-heteroaryl-, any of which groups may be optionally substituted by one or more substituents. Additionally, $R^1$ may represent ($C_{3-7}$)cycloalkyl-heteroaryl- or ($C_{3-7}$)cycloalkyl($C_{1-6}$)alkyl-heteroaryl-, either of which groups may be optionally substituted by one or more substituents. Additionally, $R^1$ may represent trifluoromethyl, —$OR^a$, —$SO_2W$, —$OSO_2R^a$ or —$CONR^bR^c$; or heteroaryl($C_{1-6}$)alkyl, ($C_{3-7}$)heterocycloalkyl-aryl-, ($C_{4-7}$)cycloalkenyl-heteroaryl-, ($C_{4-9}$)-bicycloalkyl-heteroaryl-, ($C_{4-9}$)heterobicycloalkyl-heteroaryl- or ($C_{3-7}$)heterocycloalkyl-heteroaryl($C_{1-6}$)alkyl-, any of which groups may be optionally substituted by one or more substituents.

In a first embodiment, $R^1$ represents hydrogen.

In a second embodiment, $R^1$ represents halogen. In one aspect of that embodiment, $R^1$ represents bromo. In another aspect of that embodiment, $R^1$ represents chloro.

In a third embodiment, $R^1$ represents cyano.

In a fourth embodiment, $R^1$ represents —$CO_2R^d$.

In a fifth embodiment, $R^1$ represents optionally substituted $C_{1-6}$ alkyl. In one aspect of that embodiment, $R^1$ represents optionally substituted methyl. In another aspect of that embodiment, $R^1$ represents optionally substituted ethyl.

In a sixth embodiment, $R^1$ represents optionally substituted aryl. In one aspect of that embodiment, $R^1$ represents optionally substituted phenyl.

In a seventh embodiment, $R^1$ represents optionally substituted $C_{3-7}$ heterocycloalkyl.

In an eighth embodiment, $R^1$ represents optionally substituted $C_{3-7}$ heterocycloalkenyl.

In a ninth embodiment, $R^1$ represents optionally substituted heteroaryl. In selected aspects of that embodiment, $R^1$ represents benzofuryl, thienyl, indolyl, pyrazolyl, indazolyl, isoxazolyl, imidazolyl, pyridinyl, quinolinyl, pyridazinyl, pyrimidinyl or pyrazinyl, any of which groups may be optionally substituted by one or more substituents. In a further aspect, $R^1$ represents optionally substituted thiazolyl.

In a tenth embodiment, $R^1$ represents optionally substituted ($C_{3-7}$)-heterocycloalkyl($C_{1-6}$)alkyl-aryl-. In a first aspect of that embodiment, $R^1$ represents optionally substituted pyrrolidinylmethylphenyl-. In a second aspect of that embodiment, $R^1$ represents optionally substituted piperazinylmethylphenyl-. In a third aspect of that embodiment, $R^1$ represents optionally substituted morpholinylmethylphenyl-.

In an eleventh embodiment, $R^1$ represents optionally substituted heteroaryl($C_{3-7}$)-heterocycloalkyl-. In one aspect of that embodiment, $R^1$ represents optionally substituted pyridinylpiperazinyl-.

In a twelfth embodiment, $R^1$ represents optionally substituted ($C_{3-7}$)cycloalkyl-heteroaryl-. In a first aspect of that embodiment, $R^1$ represents optionally substituted cyclopropylpyrimidinyl-. In a second aspect of that embodiment, $R^1$ represents optionally substituted cyclobutylpyrimidinyl-. In a third aspect of that embodiment, $R^1$ represents optionally substituted cyclopentylpyrimidinyl-. In a fourth aspect of that embodiment, $R^1$ represents optionally substituted cyclohexylpyrimidinyl-.

In a thirteenth embodiment, $R^1$ represents optionally substituted ($C_{3-7}$)cycloalkyl-($C_{1-6}$)alkyl-heteroaryl-. In one aspect of that embodiment, $R^1$ represents optionally substituted cyclopropylmethylpyrimidinyl-.

In a fourteenth embodiment, $R^1$ represents optionally substituted ($C_{4-7}$)-cycloalkenyl-heteroaryl-.

In a fifteenth embodiment, $R^1$ represents optionally substituted ($C_{4-9}$)bicycloalkyl-heteroaryl-. In one aspect of that embodiment, $R^1$ represents optionally substituted bicyclo[3.1.0]hexanylpyrimidinyl-.

In a sixteenth embodiment, $R^1$ represents optionally substituted ($C_{3-7}$)-heterocycloalkyl-heteroaryl-. In a first aspect of that embodiment, $R^1$ represents optionally substituted azetidinylpyridinyl-. In a second aspect of that embodiment, R' represents optionally substituted pyrrolidinylpyridinyl-. In a third aspect of that embodiment, $R^1$ represents optionally substituted isothiazolidinylpyridinyl-. In a fourth aspect of that embodiment, $R^1$ represents optionally substituted imidazolidinylpyridinyl-. In a fifth aspect of that embodiment, $R^1$ represents optionally substituted piperidinylpyridinyl-. In a sixth aspect of that embodiment, $R^1$ represents optionally substituted piperazinylpyridinyl-. In a seventh aspect of that embodiment, $R^1$ represents optionally substituted morpholinylpyridinyl-. In an eighth aspect of that embodiment, $R^1$ represents optionally substituted thiomorpholinylpyridinyl-. In a ninth aspect of that embodiment, $R^1$ represents optionally substituted diazepanylpyridinyl-. In a tenth aspect of that embodiment, $R^1$ represents optionally substituted oxetanylpyrimidinyl-. In an eleventh aspect of that embodiment, $R^1$ represents optionally substituted azetidinylpyrimidinyl-. In a twelfth aspect of that embodiment, $R^1$ represents optionally substituted tetrahydrofuranylpyrimidinyl-. In a thirteenth aspect of that embodiment, $R^1$ represents optionally substituted pyrrolidinylpyrimidinyl-. In a fourteenth aspect of that embodiment, $R^1$ represents optionally substituted isothiazolidinylpyrimidinyl-. In a fifteenth aspect of that embodiment, $R^1$ represents optionally substituted tetrahydropyranylpyrimidinyl-. In a sixteenth aspect of that embodiment, $R^1$ represents optionally substituted piperidinylpyrimidinyl-. In a seventeenth aspect of that embodiment, $R^1$ represents optionally substituted piperazinylpyrimidinyl-. In an eighteenth aspect of that embodiment, $R^1$ represents optionally substituted morpholinylpyrimidinyl-. In a nineteenth aspect of that embodiment, $R^1$ represents optionally substituted thiomorpholinylpyrimidinyl-.

In a seventeenth embodiment, $R^1$ represents optionally substituted ($C_{3-7}$)-heterocycloalkyl($C_{1-6}$)alkyl-heteroaryl-. In a first aspect of that embodiment, $R^1$ represents optionally substituted morpholinylmethylthienyl-. In a second aspect of that embodiment, $R^1$ represents optionally substituted morpholinylethylpyrazolyl-. In a third aspect of that embodiment, $R^1$ represents optionally substituted azetidinylmethylpyridinyl-. In a fourth aspect of that embodiment, $R^1$ represents optionally substituted piperazinylmethylpyridinyl-. In a fifth aspect of that embodiment, $R^1$ represents optionally substituted morpholinylmethylpyridinyl-. In a sixth aspect of that embodiment, $R^1$ represents optionally substituted thiomorpholinylmethylpyridinyl-. In a seventh aspect of that embodiment, $R^1$ represents optionally substituted morpholinylmethylpyrimidinyl-.

In an eighteenth embodiment, $R^1$ represents optionally substituted ($C_{3-7}$)-heterocycloalkenyl-heteroaryl-.

In a nineteenth embodiment, $R^1$ represents optionally substituted ($C_{4-9}$)-heterobicycloalkyl-heteroaryl-.

In a twentieth embodiment, $R^1$ represents optionally substituted ($C_{4-9}$)-spiroheterocycloalkyl-heteroaryl-.

In a twenty-first embodiment, $R^1$ represents —$OR^a$.

In a twenty-second embodiment, $R^1$ represents —$SO_2R^a$.

In a twenty-third embodiment, $R^1$ represents —$OSO_2R^a$.

In a twenty-fourth embodiment, $R^1$ represents —$CONR^bR^c$.

In a twenty-fifth embodiment, $R^1$ represents trifluoromethyl.

In a twenty-sixth embodiment, $R^1$ represents optionally substituted heteroaryl-$(C_{1-6})$alkyl. In a first aspect of that embodiment, $R^1$ represents optionally substituted imidazolylmethyl. In a second aspect of that embodiment, $R^1$ represents optionally substituted triazolylmethyl. In a third aspect of that embodiment, $R^1$ represents optionally substituted pyridinylmethyl.

In a twenty-seventh embodiment, $R^1$ represents optionally substituted $(C_{3-7})$-heterocycloalkyl-aryl-. In one aspect of that embodiment, $R^1$ represents optionally substituted piperazinylphenyl.

In a twenty-eighth embodiment, $R^1$ represents optionally substituted $(C_{3-7})$-heterocycloalkyl-heteroaryl$(C_{1-6})$alkyl-. In one aspect of that embodiment, $R^1$ represents optionally substituted morpholinylpyridinylmethyl. spiro[3.3]heptanylpyrimidinyl, 2-oxa-6-azaspiro[3.4]octanylpyrimidinyl, 2-oxa-6-azaspiro[3.5]nonanylpyrimidinyl and 2-oxa-7-azaspiro[3.5]nonanylpyrimidinyl, any of which groups may be optionally substituted by one or more substituents.

Suitable examples of optional substituents on $R^1$ include one, two or three substituents independently selected from halogen, cyano, cyano$(C_{1-6})$alkyl, $C_{1-6}$ alkyl, trifluoromethyl, trifluoroethyl, $C_{2-6}$ alkenyl, hydroxy, hydroxy$(C_{1-6})$alkyl, $C_{1-6}$ alkoxy, trifluoroethoxy, $C_{1-6}$ alkylsulphonyl, $(C_{1-6})$alkylsulphonyl$(C_{1-6})$alkyl, oxo, amino, di$(C_{1-6})$alkylamino, $(C_{1-6})$alkoxy$(C_{1-6})$alkylamino, N—[$(C_{1-6})$alkyl]-N-[hydroxy$(C_{1-6})$alkyl]-amino, $C_{2-6}$ alkylcarbonyl, carboxy, carboxy$(C_{1-6})$alkyl, $C_{2-6}$ alkoxycarbonyl, $C_{2-6}$ alkoxycarbonyl$(C_{1-6})$alkyl, aminocarbonyl and aminocarbonyl$(C_{1-6})$alkyl. Additional examples include difluoromethyl, difluoroethyl, $C_{1-6}$ alkoxy$(C_{1-6})$alkyl, $C_{1-6}$ alkylsulphinyl, $C_{1-6}$ alkylamino, hydroxy$(C_{1-6})$alkylamino, [$(C_{1-6})$alkoxy](hydroxy)$(C_{1-6})$alkylamino, [$(C_{1-6})$alkylthio](hydroxy)$(C_{1-6})$alkylamino, di$(C_{1-6})$alkylamino$(C_{1-6})$alkylamino, N-[di$(C_{1-6})$alkylamino$(C_{1-6})$alkyl]-N-[hydroxy$(C_{1-6})$alkyl]amino, hydroxy$(C_{1-6})$alkyl$(C_{3-7})$-cycloalkylamino, (hydroxy)[$(C_{3-7})$cycloalkyl$(C_{1-6})$alkyl]amino, $(C_{3-7})$heterocyclo alkyl-$(C_{1-6})$alkylamino, oxo$(C_{3-7})$heterocycloalkyl $(C_{1-6})$alkylamino, $(C_{1-6})$alkylheteroarylamino, heteroaryl$(C_{1-6})$alkylamino, $(C_{1-6})$alkylheteroaryl$(C_{1-6})$alkylamino, $C_{2-6}$ alkylcarbonylamino, N—[$(C_{1-6})$alkyl]-N—[$(C_{2-6})$alkylcarbonyl]amino, $C_{3-6}$ alkenylcarbonylamino, bis[$(C_{3-6})$alkenylcarbonyl]amino, N—[$(C_{1-6})$alkyl]-N—[$(C_{3-7})$cycloalkylcarbonyl]amino, N-[carboxy$(C_{1-6})$alkyl]-N—[$(C_{1-6})$alkyl]amino, $C_{2-6}$ alkoxycarbonylamino, $C_{2-6}$ alkoxycarbonyl$(C_{1-6})$alkylamino, N—[$(C_{1-6})$alkyl]-N—[$(C_{1-6})$alkylsulphonyl]amino, formyl, $(C_{3-7})$cycloalkylcarbonyl, phenylcarbonyl, $C_{1-6}$ alkylaminocarbonyl, hydroxy$(C_{1-6})$alkylaminocarbonyl, di$(C_{1-6})$alkylaminocarbonyl and aminosulphonyl.

Typical examples of optional substituents on $R^1$ include one, two or three substituents independently selected from halogen, cyano, cyano$(C_{1-6})$alkyl, $C_{1-6}$ alkyl, trifluoromethyl, trifluoroethyl, $C_{2-6}$ alkenyl, hydroxy, $C_{1-6}$ alkoxy, trifluoroethoxy, $C_{1-6}$ alkylsulphonyl, $(C_{1-6})$alkylsulphonyl $(C_{1-6})$alkyl, oxo, amino, di$(C_{1-6})$alkylamino, $(C_{1-6})$alkoxy $(C_{1-6})$alkylamino, N—[$(C_{1-6})$alkyl]-N-[hydroxy$(C_{1-6})$alkyl] amino, $C_{2-6}$ alkylcarbonyl, carboxy, carboxy$(C_{1-6})$alkyl, $C_{2-6}$ alkoxycarbonyl, $C_{2-6}$ alkoxycarbonyl-$(C_{1-6})$alkyl and aminocarbonyl.

Suitable examples of particular substituents on $R^1$ include one, two or three substituents independently selected from fluoro, chloro, cyano, cyanoethyl, methyl, ethyl, trifluoromethyl, trifluoroethyl, ethenyl, hydroxy, hydroxyethyl, hydroxyisopropyl, methoxy, isopropoxy, trifluoroethoxy, methylsulphonyl, methylsulphonylethyl, oxo, amino, dimethylamino, methoxyethylamino, N-(hydroxyethyl)-N-(methyl)amino, acetyl, carboxy, carboxymethyl, carboxyethyl, ethoxycarbonyl, tert-butoxycarbonyl, ethoxycarbonylmethyl, ethoxycarbonylethyl, aminocarbonyl and aminocarbonylmethyl. Additional examples include isopropyl, isobutyl, difluoromethyl, difluoroethyl, hydroxymethyl, methoxymethyl, methoxyethyl, methylsulphinyl, ethylamino, hydroxyethylamino, hydroxypropylamino, (hydroxy)(methyl)propylamino, (hydroxy)-(methoxy)(methyl)propylamino, (hydroxy)(methylthio) butylamino, dimethylaminoethylamino, (dimethylamino) (methyl)propylamino, N-(dimethylaminoethyl)-N-(hydroxyethyl)-amino, hydroxymethylcyclopentylamino, hydroxycyclobutylmethylamino, (cyclopropyl)-(hydroxy) propylamino, morpholinylethylamino, oxopyrrolidinylmethylamino, ethyloxadiazolylamino, methylthiadiazolylamino, thiazolylmethylamino, thiazolylethylamino, pyrimidinylmethylamino, methylpyrazolylmethylamino, acetylamino, N-acetyl-N-methylamino, N-isopropylcarbonyl-N-methylamino, ethenylcarbonylamino, bis(ethenylcarbonyl)-amino, N-cyclopropylcarbonyl-N-methylamino, N-(carboxymethyl)-N-methylamino, N-(carboxy ethyl)-N-methylamino, tert-butoxycarbonylamino, methoxycarbonylethylamino, N-methyl-N-(methylsulphonyl)amino, formyl, isopropylcarbonyl, cyclobutylcarbonyl, phenylcarbonyl, methoxycarbonyl, methylaminocarbonyl, hydroxyethylaminocarbonyl, dimethylaminocarbonyl and aminosulphonyl.

Typical examples of particular substituents on $R^1$ include one, two or three substituents independently selected from fluoro, chloro, cyano, cyanoethyl, methyl, trifluoromethyl, trifluoroethyl, ethenyl, hydroxy, methoxy, isopropoxy, trifluoroethoxy, methylsulphonyl, methylsulphonylethyl, oxo, amino, dimethylamino, methoxyethylamino, N-(hydroxyethyl)-N-(methyl)amino, acetyl, carboxy, carboxymethyl, carboxyethyl, ethoxycarbonyl, tert-butoxycarbonyl, ethoxycarbonylmethyl, ethoxycarbonylethyl and aminocarbonyl.

Particular values of $R^1$ include hydrogen, bromo, cyano, —$CO_2R^d$, ethoxycarbonylethyl, chlorophenyl, hydroxyphenyl, acetylphenyl, aminocarbonylphenyl, oxopiperidinyl, methylsulphonylpiperazinyl, morpholinyl, tert-butoxycarbonyl-1,2,3,6-tetrahydropyridinyl, benzofuryl, thienyl, indolyl, pyrazolyl, methylpyrazolyl, dimethylpyrazolyl, methylindazolyl, dimethylisoxazolyl, methylimidazolyl, pyridinyl, fluoropyridinyl, cyanopyridinyl, methylpyridinyl, (cyano)(methyl)pyridinyl, dimethylpyridinyl, trifluoromethylpyridinyl, ethenylpyridinyl, methoxypyridinyl, (methoxy) (methyl)pyridinyl, isopropoxypyridinyl, trifluoroethoxypyridinyl, (methyl)(trifluoroethoxy)pyridinyl, oxopyridinyl, (methyl)(oxo)pyridinyl, (dimethyl)(oxo)pyridinyl, aminopyridinyl, dimethylaminopyridinyl, methoxyethylaminopyridinyl, N-(hydroxyethyl)-N-(methyl)-aminopyridinyl, carboxypyridinyl, quinolinyl, hydroxypyridazinyl, pyrimidinyl, (ethyl)(methyl)pyrimidinyl, (hydroxyethyl)(methyl) pyrimidinyl, (hydroxyisopropyl)-(methyl)pyrimidinyl, methoxypyrimidinyl, oxopyrimidinyl, aminopyrimidinyl, dimethylaminopyrimidinyl, methoxyethylaminopyrimidinyl, (amino carbonylmethyl)-(methyl)pyrimidinyl, hydroxypyrazinyl, pyrrolidinylmethylphenyl, piperazinylmethylphenyl, pyridinylpiperazinyl, (cyclobutyl)(methyl) pyrimidinyl, (cyclopropylmethyl)-(methyl)pyrimidinyl, pyrrolidinylpyridinyl, hydroxypyrrolidinylpyridinyl, piperidinylpyridinyl, acetylpiperidinylpyridinyl, piperazinylpyridinyl, (methyl)(piperazinyl)-pyridinyl, cyanoethylpiperazinylpyridinyl, trifluoroethylpiperazinylpyridinyl, methylsulphonylpiperazinylpyridinyl, methylsulphonylethylpiperazinylpyridinyl, oxopiperazinylpyridinyl, acetylpiperazinylpyridinyl, (tert-butoxycarbonylpiperazinyl)-(methyl)pyridinyl, carboxymethylpiperazinylpyridinyl, carboxyethylpiperazinylpyridinyl, ethoxycarbonylmethylpiperazinylpyridinyl, ethoxycarbonylethylpiperazinylpyridinyl, morpholinylpyridinyl, thiomorpholinylpyridinyl, oxothiomorpholinylpyridinyl, dioxothiomorpholinylpyridinyl, oxodiazepanylpyridinyl, hydroxypyrrolidinylpyrimidinyl, (methyl)(tetrahydropyranyl)pyrimidinyl, (methyl)(piperidinyl)pyrimidinyl, (methyl)-(methylsulphonylpiperidinyl)pyrimidinyl, piperazinylpyrimidinyl, methylsulphonylpiperazinylpyrimidinyl, oxopiperazinylpyrimidinyl, tert-butoxycarbonylpiperazinylpyrimidinyl, morpholinylpyrimidinyl, thiomorpholinylpyrimidinyl, morpholinylmethylthienyl, morpholinylethylpyrazolyl, 2-oxa-6-azaspiro[3.3]heptanylpyrimidinyl, 2-oxa-6-azaspiro[3.4]octanylpyrimidinyl, 2-oxa-6-azaspiro[3.5]nonanylpyrimidinyl and 2-oxa-7-azaspiro[3.5]nonanylpyrimidinyl. Additional values include chloro, trifluoromethyl, —OR$^a$, —SO$_2$R$^a$, —OSO$_2$R$^a$, —CONR$^b$R$^c$ N-isopropylcarbonyl-N-methylaminomethyl, N-cyclopropylcarbonyl-N-methylaminomethyl, methylsulphinylphenyl, methylsulphonylphenyl, (methyl)(methylsulphonyl)phenyl, ethenylcarbonylaminophenyl, tert-butoxycarbonylaminophenyl, phenylcarbonylphenyl, aminosulphonylphenyl, isopropylcarbonylpiperidinyl, cyclobutylcarbonylpiperidinyl, methoxycarbonylpiperidinyl, methylthienyl, dihydrothieno[3,4-b][1,4]dioxinyl, oxodihydropyrrolo[3,4-b]pyridinyl, hydroxyisopropylpyridinyl, methylsulphonylpyridinyl, (difluoromethyl)(oxo)pyridinyl, (oxo)(trifluoromethyl)pyridinyl, (methoxy)(oxo)pyridinyl, acetylaminopyridinyl, bis(ethenylcarbonyl)-aminopyridinyl, N-methyl-N-(methylsulphonyl)aminopyridinyl, formylpyridinyl, aminocarbonylpyridinyl, (aminocarbonyl)(methyl)pyridinyl, methylaminocarbonylpyridinyl, hydroxyethylaminocarbonylpyridinyl, dimethylaminocarbonylpyridinyl, (isopropyl)(methyl)pyrimidinyl, (isobutyl)(methyl)pyrimidinyl, hydroxyisopropylpyrimidinyl, (methoxymethyl)(methyl)pyrimidinyl, (methoxyethyl)(methyl)pyrimidinyl, methylsulphonylpyrimidinyl, dioxopyrimidinyl, ethylaminopyrimidinyl, hydroxyethylaminopyrimidinyl, hydroxypropylaminopyrimidinyl, (hydroxy)(methyl)propylaminopyrimidinyl, (hydroxy)(methoxy)(methyl)propylaminopyrimidinyl, (hydroxy)-(methylthio)butylaminopyrimidinyl, dimethylaminoethylaminopyrimidinyl, (dimethylamino)(methyl)propylaminopyrimidinyl, N-(dimethylaminoethyl)-N-(hydroxyethyl)aminopyrimidinyl, hydroxymethylcyclopentylaminopyrimidinyl, hydroxycyclobutylmethylaminopyrimidinyl, (cyclopropyl)(hydroxy)propylaminopyrimidinyl, morpholinylethylaminopyrimidinyl, oxopyrrolidinylmethylamino-pyrimidinyl, ethyloxadiazolylaminopyrimidinyl, methylthiadiazolylaminopyrimidinyl, thiazolylmethylaminopyrimidinyl, thiazolylethylaminopyrimidinyl, pyrimidinylmethyl-aminopyrimidinyl, methylpyrazolylmethylaminopyrimidinyl, acetylaminopyrimidinyl, N-acetyl-N-methylaminopyrimidinyl, N-(carboxymethyl)-N-methylaminopyrimidinyl, N-(carboxy ethyl)-N-methylaminopyrimidinyl, methoxycarbonylethylaminopyrimidinyl, N-methyl-N-(methylsulphonyl)aminopyrimidinyl, pyrazinyl, methylimidazolylmethyl, triazolylmethyl, methylpyridinylmethyl, methoxypyridinylmethyl, piperazinylphenyl, morpholinylmethylphenyl, (cyclopropyl)(methyl)pyrimidinyl, hydroxycyclobutylpyrimidinyl, (cyclopentyl)(methyl)pyrimidinyl, carboxycyclohexylpyrimidinyl, carboxycyclohexenylpyrimidinyl, carboxybicyclo[3.1.0]hexanylpyrimidinyl, oxopyrrolidinylpyridinyl, dioxoisothiazolidinylpyridinyl, oxoimidazolidinylpyridinyl, (hydroxy)(methyl)-piperidinylpyridinyl, (chloro)(piperazinyl)pyridinyl, difluoroethylpiperazinylpyridinyl, (methyl)(oxopiperazinyl)pyridinyl, (methyl)(morpholinyl)pyridinyl, oxomorpholinylpyridinyl, (methyl)(thiomorpholinyl)pyridinyl, (methyl)(oxothiomorpholinyl)pyridinyl, hydroxyoxetanylpyrimidinyl, hydroxyazetidinylpyrimidinyl, hydroxymethylazetidinylpyrimidinyl, (tert-butoxycarbonyl)(hydroxy)azetidinylpyrimidinyl, (methyl)-(tetrahydrofuranyl)pyrimidinyl, hydroxymethylpyrrolidinylpyrimidinyl, methoxymethylpyrrolidinylpyrimidinyl, oxopyrrolidinylpyrimidinyl, (methyl)(oxo)pyrrolidinylpyrimidinyl, dimethylaminopyrrolidinylpyrimidinyl, dioxoisothiazolidinylpyrimidinyl, hydroxytetrahydropyranylpyrimidinyl, hydroxypiperidinylpyrimidinyl, hydroxymethylpiperidinylpyrimidinyl, methoxypiperidinylpyrimidinyl, oxopiperidinylpyrimidinyl, carboxypiperidinylpyrimidinyl, (carboxy)(methyl)piperidinylpyrimidinyl, (amino)(carboxy)piperidinylpyrimidinyl, (ethoxycarbonyl)(methyl)piperidinylpyrimidinyl, aminocarbonylpiperidinylpyrimidinyl, hydroxyethylpiperazinylpyrimidinyl, (methyl)(oxopiperazinyl)pyrimidinyl, methylmorpholinylpyrimidinyl, oxomorpholinylpyrimidinyl, dioxothiomorpholinylpyrimidinyl, hydroxymethylazetidinylcarbonylpyrimidinyl, piperazinylcarbonylpyrimidinyl, methylpiperazinylcarbonylpyrimidinyl, morpholinylcarbonylpyrimidinyl, thiomorpholinylcarbonylpyrimidinyl, dioxothiomorpholinylcarbonylpyrimidinyl, (methyl)(morpholinylmethyl)pyrimidinyl, carboxy-3-azabicyclo-[3.1.0]hexanylpyrimidinyl, carboxy-3-azabicyclo[4.1.0]heptanylpyrimidinyl, carboxy-3-azabicyclo[3.2.1]octanylpyrimidinyl, methoxycarbonyl-3-azabicyclo[3.2.1]octanylpyrimidinyl, oxo-2-oxa-6-azaspiro[3.4]octanylpyridinyl, difluoro-5-azaspiro[2.4]-heptanylpyrimidinyl, 7-oxa-2-azaspiro[3.5]nonanylpyrimidinyl and morpholinylpyridinylmethyl.

Selected values of R$^1$ include hydrogen, bromo, cyano, —CO$_2$R$^d$, ethoxycarbonylethyl, chlorophenyl, hydroxyphenyl, acetylphenyl, aminocarbonylphenyl, oxopiperidinyl, methylsulphonylpiperazinyl, morpholinyl, tert-butoxycarbonyl-1,2,3,6-tetrahydropyridinyl, benzofuryl, thienyl, indolyl, pyrazolyl, methylpyrazolyl, dimethylpyrazolyl, methylindazolyl, dimethylisoxazolyl, methylimidazolyl, pyridinyl, fluoropyridinyl, cyanopyridinyl, methylpyridinyl, (cyano)(methyl)pyridinyl, dimethylpyridinyl, trifluoromethylpyridinyl, ethenylpyridinyl, methoxypyridinyl, (methoxy)(methyl)pyridinyl, isopropoxypyridinyl, trifluoroethoxypyridinyl, (methyl)(trifluoroethoxy)pyridinyl, oxopyridinyl, (methyl)(oxo)pyridinyl, (dimethyl)(oxo)pyridinyl, aminopyridinyl, dimethylaminopyridinyl, methoxyethylaminopyridinyl, N-(hydroxyethyl)-N-(methyl)-aminopyridinyl, carboxypyridinyl, quinolinyl, hydroxypyridazinyl, pyrimidinyl, methoxypyrimidinyl, oxopyrimidinyl, aminopyrimidinyl, dimethylaminopyrimidinyl, methoxyethylaminopyrimidinyl, hydroxypyrazinyl, pyrrolidinylmethylphenyl, piperazinylmethylphenyl, pyridinylpiperazinyl, pyrrolidinylpyridinyl, hydroxypyrrolidinylpyridinyl, piperidinylpyridinyl, acetylpiperidinylpyridinyl, piperazinylpyridinyl, (methyl)(piperazinyl)pyridinyl, cyanoethylpiperazinylpyridinyl, trifluoroethylpiperazinylpyridinyl, methylsulphonylpiperazinylpyridinyl, methylsulphonylethylpiperazinylpyridinyl, oxopiperazinylpyridinyl, acetylpiperazinylpyridinyl, (tert-butoxycarbonylpiperazinyl)(methyl)pyridinyl, carboxymethylpiperazinylpyridinyl, carboxyethylpiperazinylpyridinyl, ethoxycarbonylmethylpiperazinylpyridinyl, ethoxycarbonylethylpiperazinylpyridinyl, morpholinylpyridinyl, thiomorpholinylpyridinyl, oxothiomorpholinylpyridinyl, dioxothiomorpholinylpyridinyl, oxodiazepanylpyridinyl, hydroxypyrrolidinylpyrimidinyl, piperazinylpyrimidinyl, methylsulphonylpiperazinylpyrimidinyl, oxopiperazinylpyrimidinyl, tert-butoxycarbonylpiperazinylpyrimidinyl, morpholinylpyrimidinyl, thiomorpholinylpyrimidinyl, morpholinylmethylthienyl, morpholinylethylpyrazolyl, 2-oxa-6-azaspiro[3.3]heptanylpyrimidinyl, 2-oxa-6-azaspiro[3.4]octanylpyrimidinyl, 2-oxa-6-azaspiro[3.5]nonanylpyrimidinyl and 2-oxa-7-azaspiro[3.5]nonanylpyrimidinyl.

Typically, $R^2$ represents hydrogen, halogen or optionally substituted $C_{1-6}$ alkyl.

Typical examples of optional substituents on $R^2$ include $C_{2-6}$ alkoxycarbonyl.

Typical examples of particular substituents on $R^2$ include ethoxycarbonyl.

In a first embodiment, $R^2$ represents hydrogen. In a second embodiment, $R^2$ represents halogen. In one aspect of that embodiment, $R^2$ represents fluoro. In another aspect of that embodiment, $R^2$ represents chloro. In a third embodiment, $R^2$ represents optionally substituted $C_{1-6}$ alkyl. In one aspect of that embodiment, $R^2$ represents monosubstituted methyl or monosubstituted ethyl.

Selected values of $R^2$ include hydrogen, fluoro and ethoxycarbonylethyl. Additionally, $R^2$ may represent chloro.

In a particular embodiment, $R^3$ represents hydrogen.

Suitably, $R^4$ represents hydrogen or methyl.

In a first embodiment, $R^4$ represents hydrogen. In a second embodiment, $R^4$ represents $C_{1-6}$ alkyl, especially methyl.

Suitably, $R^5$ represents hydrogen, methyl or ethyl.

In a first embodiment, $R^5$ represents hydrogen. In a second embodiment, $R^5$ represents $C_{1-6}$ alkyl, especially methyl or ethyl. In one aspect of that embodiment, $R^5$ represents methyl. In another aspect of that embodiment, $R^5$ represents ethyl.

Typical examples of suitable substituents on $R^a$, $R^b$, $R^c$, $R^d$ or $R^e$, or on the heterocyclic moiety —$NR^bR^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino, aminocarbonyl, $C_{1-6}$ alkylaminocarbonyl and di($C_{1-6}$)alkylaminocarbonyl.

Typical examples of specific substituents on $R^a$, $R^b$, $R^c$, $R^d$ or $R^e$, or on the heterocyclic moiety —$NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, tert-butoxycarbonylamino, acetylaminomethyl, methylsulphonylamino, aminocarbonyl, methylaminocarbonyl and dimethylaminocarbonyl.

Generally, $R^a$ represents $C_{1-6}$ alkyl, aryl, aryl($C_{1-6}$)alkyl, heteroaryl or heteroaryl($C_{1-6}$)alkyl, any of which groups may be optionally substituted by one or more substituents. Additionally, $R^a$ may represent trifluoromethyl; or $C_{3-7}$ heterocycloalkyl or $C_{3-7}$ heterocycloalkyl($C_{1-6}$)alkyl, either of which groups may be optionally substituted by one or more substituents.

Suitably, $R^a$ represents $C_{1-6}$ alkyl, aryl($C_{1-6}$)alkyl or heteroaryl($C_{1-6}$)alkyl, any of which groups may be optionally substituted by one or more substituents. Additionally, $R^a$ may represent trifluoromethyl, aryl, $C_{3-7}$ heterocycloalkyl, $C_{3-7}$ heterocycloalkyl-($C_{1-6}$)alkyl or heteroaryl, any of which groups may be optionally substituted by one or more substituents.

Selected values of $R^a$ include methyl, ethyl, benzyl and isoindolylpropyl, any of which groups may be optionally substituted by one or more substituents. Additional values include trifluoromethyl, propyl, isobutyl, phenyl, oxetanyl, azetidinyl, pyrrolidinyl and pyridinyl, any of which groups may be optionally substituted by one or more substituents Selected examples of suitable substituents on $R^a$ include $C_{1-6}$ alkoxy and oxo. Additional examples include halogen, $C_{1-6}$ alkyl, di($C_{1-6}$)alkylamino, $C_{2-6}$ alkylcarbonyl and $C_{2-6}$ alkoxycarbonyl.

Selected examples of specific substituents on $R^a$ include methoxy and oxo. Additional examples include fluoro, methyl, dimethylamino, acetyl and tert-butoxycarbonyl.

In one embodiment, $R^a$ represents optionally substituted $C_{1-6}$ alkyl. In one aspect of that embodiment, $R^a$ ideally represents unsubstituted $C_{1-6}$ alkyl, especially methyl, ethyl, propyl or isobutyl. In another aspect of that embodiment, $R^a$ ideally represents substituted $C_{1-6}$ alkyl, e.g. methoxyethyl, dimethylaminoethyl or trifluoropropyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl. In another embodiment, $R^a$ represents optionally substituted aryl($C_{1-6}$)alkyl, ideally unsubstituted aryl($C_{1-6}$)alkyl, especially benzyl. In a further embodiment, $R^a$ represents optionally substituted heteroaryl. In various aspects of that embodiment, $R^a$ represents methoxypyridinyl, oxopyridinyl and (methyl)(oxo)pyridinyl. In a further embodiment, $R^a$ represents optionally substituted heteroaryl($C_{1-6}$)alkyl, e.g. dioxoisoindolylpropyl. In a further embodiment, $R^a$ represents optionally substituted $C_{3-7}$ heterocycloalkyl, e.g. oxetanyl, azetidinyl or acetylazetidinyl. In a further embodiment, $R^a$ represents optionally substituted $C_{3-7}$ heterocycloalkyl($C_{1-6}$)alkyl, e.g. acetylpyrrolidinylmethyl or tert-butoxycarbonylpyrrolidinylmethyl. In a further embodiment, $R^a$ represents trifluoromethyl.

Specific values of $R^a$ include methyl, methoxyethyl, benzyl and dioxoisoindolylpropyl. Additional values include trifluoromethyl, ethyl, dimethylaminoethyl, propyl, trifluoropropyl, isobutyl, methylphenyl, oxetanyl, azetidinyl, acetylazetidinyl, acetylpyrrolidinylmethyl, tert-butoxycarbonylpyrrolidinylmethyl, methoxypyridinyl, oxopyridinyl and (methyl)(oxo)pyridinyl.

In a particular aspect, $R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents.

Selected values of $R^b$ include hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents. Additional values include $C_{3-7}$ cycloalkyl and heteroaryl, either of which groups may be optionally substituted by one or more substituents.

Typical values of $R^b$ include hydrogen and $C_{1-6}$ alkyl. Additional values include $C_{3-7}$ cycloalkyl and heteroaryl, either of which groups may be optionally substituted by one or more substituents.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents. Additionally, $R^b$ may represent indanyl, which group may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents. Additionally, $R^b$ may represent indanyl or pyridinyl, either of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-$(C_{1-6})$alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methylsulphonylethyl, hydroxyethyl, cyanoethyl, dimethylaminoethyl, tert-butoxycarbonylaminoethyl, dihydroxypropyl, benzyl, pyrrolidinyl, tert-butoxycarbonylpyrrolidinyl and morpholinylpropyl. Additionally, $R^b$ may represent indanyl or pyridinyl.

In one embodiment, $R^b$ represents hydrogen. In another embodiment, $R^b$ represents $C_{1-6}$ alkyl, especially methyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected examples of suitable substituents on $R^c$ include $C_{2-6}$ alkylcarbonyl and $C_{2-6}$ alkoxycarbonyl.

Selected examples of specific substituents on $R^c$ include acetyl and tert-butoxycarbonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl.

Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy$(C_{1-6})$alkyl, amino$(C_{1-6})$alkyl, cyano, oxo, $C_{2-6}$ alkylcarbonyl, carboxy, $C_{2-6}$ alkoxycarbonyl, amino, $C_{2-6}$ alkylcarbonylamino, $C_{2-6}$ alkylcarbonylamino$(C_{1-6})$alkyl, $C_{2-6}$ alkoxycarbonylamino, $C_{1-6}$ alkylsulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxycarbonylamino, methylsulphonylamino and aminocarbonyl.

Specific values of the moiety —$NR^bR^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, aminoazetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxooxazolidin-3-yl, hydroxyisoxazolidin-2-yl, thiazolidin-3-yl, oxothiazolidin-3-yl, dioxo-isothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl and oxohomopiperazin-1-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di$(C_{1-6})$alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl. In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl. In a further embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl. In a further embodiment, $R^d$ represents optionally substituted $C_{3-7}$ heterocycloalkyl, e.g. thiazolidinyl or oxothiazolidinyl.

Selected examples of specific values for $R^d$ include hydrogen, methyl, acetoxymethyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, $R^e$ represents optionally substituted $C_{1-6}$ alkyl, ideally unsubstituted $C_{1-6}$ alkyl, e.g. methyl or propyl, especially methyl. In another embodiment, $R^e$ represents optionally substituted aryl. In one aspect of that embodiment, $R^e$ represents unsubstituted aryl, especially phenyl. In another aspect of that embodiment, $R^e$ represents monosubstituted aryl, especially methylphenyl. In a further embodiment, $R^e$ represents optionally substituted heteroaryl.

Selected values of $R^e$ include methyl, propyl and methylphenyl.

One sub-class of compounds according to the invention is represented by the compounds of formula (IIA) and N-oxides thereof, and pharmaceutically acceptable salts and solvates thereof, and glucuronide derivatives thereof, and co-crystals thereof:

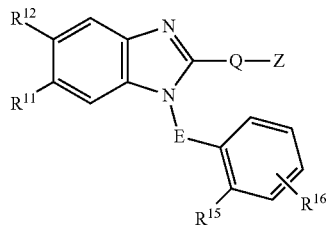

(IIA)

wherein $R^{11}$ represents halogen or cyano; or $C_{1-6}$ alkyl, aryl, $C_{3-7}$ heterocycloalkyl, $C_{3-7}$ heterocycloalkenyl, heteroaryl, heteroaryl($C_{1-6}$)alkyl, $(C_{3-7})$heterocycloalkyl-aryl-, $(C_{3-7})$heterocycloalkyl($C_{1-6}$)alkyl-aryl-, heteroaryl-$(C_{3-7})$heterocycloalkyl-, $(C_{3-7})$-cyclo alkyl-heteroaryl-, $(C_{3-7})$cycloalkyl($C_{1-6}$)alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$-heterocycloalkyl($C_{1-6}$)alkyl-heteroaryl-, $(C_{3-7})$heterocycloalkenyl-heteroaryl-, $(C_{4-9})$-heterobicycloalkyl-heteroaryl- or $(C_{4-9})$spiroheterocycloalkyl-heteroaryl-, any of which groups may be optionally substituted by one or more substituents;

$R^{12}$ represents hydrogen, halogen, trifluoromethyl or optionally substituted $C_{1-6}$ alkyl;

$R^{15}$ and $R^{16}$ independently represent hydrogen, halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, arylamino, $C_{2-6}$ alkylcarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl; and E, Q and Z are as defined above.

The present invention also provides a compound of formula (IIA) as depicted above or an N-oxide thereof, or a pharmaceutically acceptable salt or solvate thereof, or a co-crystal thereof, wherein $R^{11}$ represents halogen or cyano; or $C_{1-6}$ alkyl, aryl, $C_{3-7}$ heterocycloalkyl, $C_{3-7}$ heterocycloalkenyl, heteroaryl, $(C_{3-7})$heterocycloalkyl($C_{1-6}$)alkyl-aryl-, heteroaryl-$(C_{3-7})$ hetero cyclo alkyl-, $(C_{3-7})$cyclo alkyl-hetero aryl-, cycloalkyl($C_{1-6}$)alkyl-heteroaryl-, $(C_{4-7})$cycloalkenyl-heteroaryl-, $(C_{3-7})$heterocycloalkyl-heteroaryl-, $(C_{3-7})$hetero cyclo alkyl($C_{1-6}$)alkyl-hetero aryl-, $(C_{3-7})$heterocyclo alkenyl-hetero aryl-, $(C_{4-9})$heterobicycloalkyl-heteroaryl- or $(C_{4-9})$spiroheterocycloalkyl-heteroaryl-, any of which groups may be optionally substituted by one or more substituents;

$R^{12}$ represents hydrogen; and

E, Q, Z, $R^{15}$ and $R^{16}$ are as defined above.

The present invention also provides a compound of formula (IIA) as depicted above or an N-oxide thereof, or a pharmaceutically acceptable salt or solvate thereof, wherein $R^{11}$ represents halogen or cyano; or $C_{1-6}$ alkyl, aryl, $C_{3-7}$ heterocycloalkyl, $C_{3-7}$ heterocycloalkenyl, heteroaryl, $(C_{3-7})$heterocycloalkyl($C_{1-6}$)alkyl-aryl-, heteroaryl-$(C_{3-7})$ heterocycloalkyl-, $(C_{4-7})$cycloalkenyl-heteroaryl-, $(C_{3-7})$ heterocycloalkyl-heteroaryl-, $(C_{3-7})$hetero cyclo alkyl($C_{1-6}$) alkyl-hetero aryl-, $(C_{3-7})$hetero cyclo alkenyl-hetero aryl-, $(C_{4-9})$heterobicycloalkyl-heteroaryl- or $(C_{4-9})$spiroheterocycloalkyl-heteroaryl-, any of which groups may be optionally substituted by one or more substituents;

$R^{12}$ represents hydrogen; and

E, Q, Z, $R^{15}$ and $R^{16}$ are as defined above.

Aptly, $R^{11}$ represents halogen or cyano; or $C_{1-6}$ alkyl, aryl, $C_{3-7}$ heterocycloalkyl, $C_{3-7}$ heterocycloalkenyl, heteroaryl, $(C_{3-7})$heterocycloalkyl($C_{1-6}$)alkyl-aryl-, heteroaryl-$(C_{3-7})$ heterocycloalkyl-, $(C_{3-7})$heterocycloalkyl-heteroaryl-, $(C_{3-7})$heterocycloalkyl-$(C_{1-6})$alkyl-heteroaryl- or $(C_{4-9})$ spiroheterocycloalkyl-heteroaryl-, any of which groups may be optionally substituted by one or more substituents. Additionally, $R^{11}$ may represent $(C_{3-7})$cycloalkyl-heteroaryl- or $(C_{3-7})$cycloalkyl($C_{1-6}$)alkyl-heteroaryl-, either of which groups may be optionally substituted by one or more substituents. Additionally, $R^{11}$ may represent heteroaryl($C_{1-6}$) alkyl, $(C_{3-7})$heterocycloalkyl-aryl-, $(C_{4-7})$cycloalkenyl-heteroaryl-, $(C_{4-9})$-bicycloalkyl-heteroaryl- or $(C_{4-9})$ heterobicycloalkyl-heteroaryl-, any of which groups may be optionally substituted by one or more substituents.

Examples of optional substituents which may be present on $R^{11}$ include one, two or three substituents independently selected from halogen, cyano, cyano($C_{1-6}$)alkyl, nitro, $C_{1-6}$ alkyl, trifluoromethyl, trifluoroethyl, $C_{2-6}$ alkenyl, hydroxy, $C_{1-6}$ alkoxy, difluoromethoxy, trifluoromethoxy, trifluoroethoxy, $C_{1-3}$ alkylenedioxy, $C_{1-6}$ alkoxy($C_{1-6}$)alkyl, $C_{1-6}$ alkylthio, $C_{1-6}$ alkylsulphonyl, $(C_{1-6})$alkylsulphonyl($C_{1-6}$) alkyl, oxo, amino, $C_{1-6}$ alkylamino, di($C_{1-6}$)alkylamino, $(C_{1-6})$alkoxy($C_{1-6}$)alkylamino, N—[($C_{1-6}$)alkyl]-N-[hydroxy($C_{1-6}$)alkyl]-amino, $C_{2-6}$ alkylcarbonylamino, $C_{2-6}$ alkoxycarbonylamino, $C_{1-6}$ alkylaminocarbonyl-amino, $C_{1-6}$ alkylsulphonylamino, formyl, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)alkyl, aminocarbonyl, $C_{1-6}$ alkylaminocarbonyl, di($C_{1-6}$)alkylaminocarbonyl, aminosulphonyl and di($C_{1-6}$)alkylaminosulphonyl. Additional examples include hydroxy($C_{1-6}$)alkyl, a carboxylic acid isostere or prodrug moiety Ω as defined herein, —(C$_{1-6}$)alkyl-Ω, and aminocarbonyl(C$_{1-6}$)alkyl. Additional examples include difluoromethyl, difluoroethyl, C$_{1-6}$ alkylsulphinyl, hydroxy(C$_{1-6}$)alkylamino, [(C$_{1-6}$)alkoxy](hydroxy)(C$_{1-6}$)alkylamino, [(C$_{1-6}$)alkylthio](hydroxy)(C$_{1-6}$)alkylamino, di(C$_{1-6}$)alkylamino(C$_{1-6}$)alkylamino, N-[di(C$_{1-6}$)alkylamino(C$_{1-6}$)alkyl]-N-[hydroxy(C$_{1-6}$)alkyl]amino, hydroxy(C$_{1-6}$)alkyl(C$_{3-7}$)cycloalkylamino, (hydroxy)[(C$_{3-7}$)-cycloalkyl(C$_{1-6}$)alkyl]amino, (C$_{3-7}$)heterocycloalkyl(C$_{1-6}$)alkylamino, oxo(C$_{3-7}$)-hetero cyclo alkyl(C$_{1-6}$)alkylamino, (C$_{1-6}$)alkylheteroaryl amino, heteroaryl(C$_{1-6}$)alkylamino, (C$_{1-6}$)alkylheteroaryl (C$_{1-6}$)alkylamino, N—[(C$_{1-6}$)alkyl]-N—[(C$_{2-6}$)alkylcarbonyl]amino, C$_{3-6}$ alkenylcarbonylamino, bis[(C$_{3-6}$)alkenylcarbonyl]amino, N-[carboxy(C$_{1-6}$)alkyl]-N—[(C$_{1-6}$)-alkyl]amino, C$_{2-6}$ alkoxycarbonyl(C$_{1-6}$)alkylamino, N—[(C$_{1-6}$)alkyl]-N—[(C$_{1-6}$)alkylsulphonyl]amino, (C$_{3-7}$)cycloalkylcarbonyl, phenylcarbonyl and hydroxy(C$_{1-6}$)alkylaminocarbonyl.

Examples of particular substituents on R$^{11}$ include fluoro, chloro, bromo, cyano, cyanoethyl, nitro, methyl, ethyl, tert-butyl, trifluoromethyl, trifluoroethyl, ethenyl, hydroxy, methoxy, isopropoxy, difluoromethoxy, trifluoromethoxy, trifluoroethoxy, methylenedioxy, ethylenedioxy, methoxymethyl, methylthio, methylsulphonyl, methylsulphonylethyl, oxo, amino, methylamino, dimethylamino, methoxyethylamino, N-(hydroxyethyl)-N-(methyl)amino, acetylamino, methoxycarbonylamino, ethoxycarbonylamino, ethylaminocarbonylamino, butylaminocarbonylamino, methylsulphonylamino, formyl, acetyl, carboxy, carboxymethyl, carboxyethyl, methoxycarbonyl, ethoxycarbonyl, tert-butoxycarbonyl, ethoxycarbonylmethyl, ethoxycarbonylethyl, aminocarbonyl, methylaminocarbonyl, dimethylaminocarbonyl, aminosulphonyl, methylaminosulphonyl and dimethylaminosulphonyl. Additional examples include hydroxyethyl, hydroxyisopropyl and aminocarbonylmethyl. Additional examples include isopropyl, isobutyl, difluoromethyl, difluoroethyl, hydroxymethyl, methoxyethyl, methylsulphinyl, ethylamino, hydroxyethylamino, hydroxypropylamino, (hydroxy)(methyl)propylamino, (hydroxy)-(methoxy)(methyl)propylamino, (hydroxy)(methylthio)butylamino, dimethylaminoethylamino, (dimethylamino)(methyl)propylamino, N-(dimethylaminoethyl)-N-(hydroxyethyl)-amino, hydroxymethylcyclopentylamino, hydroxycyclobutylmethylamino, (cyclopropyl)-(hydroxy)propylamino, morpholinylethylamino, oxopyrrolidinylmethylamino, ethyloxadiazolylamino, methylthiadiazolylamino, thiazolylmethylamino, thiazolylethylamino, pyrimidinylmethylamino, methylpyrazolylmethylamino, N-acetyl-N-methylamino, N-isopropylcarbonyl-N-methylamino, ethenylcarbonylamino, bis(ethenylcarbonyl)amino, N-(carboxymethyl)-N-methylamino, N-(carboxyethyl)-N-methylamino, tert-butoxycarbonylamino, methoxycarbonylethylamino, N-methyl-N-(methylsulphonyl)amino, isopropylcarbonyl, cyclobutylcarbonyl, phenylcarbonyl and hydroxyethylaminocarbonyl.

Typically, R$^{11}$ represents C$_{1-6}$ alkyl, aryl, C$_{3-7}$ heterocycloalkyl, C$_{3-7}$ heterocycloalkenyl, heteroaryl, (C$_{3-7}$)heterocycloalkyl(C$_{1-6}$)alkyl-aryl-, heteroaryl-(C$_{3-7}$)heterocycloalkyl-, (C$_{4-7}$)cycloalkenyl-heteroaryl-, (C$_{3-7}$)heterocycloalkyl-heteroaryl-, (C$_{3-7}$)hetero cyclo alkyl(C$_{1-6}$)alkyl-hetero aryl-, (C$_{3-7}$)hetero cyclo alkenyl-hetero aryl-, (C$_{4-9}$)heterobicycloalkyl-heteroaryl- or (C$_{4-9}$)spiroheterocycloalkyl-heteroaryl-, any of which groups may be optionally substituted by one or more substituents. Additionally, R$^{11}$ may represent (C$_{3-7}$)cycloalkyl-heteroaryl- or (C$_{3-7}$)cycloalkyl(C$_{1-6}$)alkyl-heteroaryl-, either of which groups may be optionally substituted by one or more substituents. Additionally, R$^{11}$ may represent heteroaryl(C$_{1-6}$)alkyl, (C$_{3-7}$)heterocycloalkyl-aryl- or (C$_{4-9}$)bicycloalkyl-heteroaryl-, any of which groups may be optionally substituted by one or more substituents.

Generally, R$^{11}$ represents C$_{1-6}$ alkyl, aryl, C$_{3-7}$ heterocycloalkyl, C$_{3-7}$ heterocycloalkenyl, heteroaryl, (C$_{3-7}$)heterocycloalkyl(C$_{1-6}$)alkyl-aryl-, heteroaryl-(C$_{3-7}$)hetero cyclo alkyl-, (C$_{3-7}$)cyclo alkyl-hetero aryl-, (C$_{3-7}$)cycloalkyl(C$_{1-6}$)alkyl-heteroaryl-, (C$_{3-7}$)hetero cyclo alkyl-hetero aryl-, (C$_{3-7}$)heterocycloalkyl(C$_{1-6}$)alkyl-heteroaryl- or (C$_{4-9}$)spiroheterocycloalkyl-heteroaryl-, any of which groups may be optionally substituted by one or more substituents. Additionally, R$^{11}$ may represent heteroaryl(C$_{1-6}$)alkyl, (C$_{3-7}$)hetero cyclo alkyl-aryl-, (C$_{4-7}$)cyclo alkenyl-hetero aryl-, (C$_{4-9}$)bicycloalkyl-heteroaryl- or (C$_{4-9}$)heterobicycloalkyl-heteroaryl-, any of which groups may be optionally substituted by one or more substituents.

More typically, R$^{11}$ represents C$_{1-6}$ alkyl, aryl, C$_{3-7}$ heterocycloalkyl, C$_{3-7}$ heterocycloalkenyl, heteroaryl, (C$_{3-7}$)heterocycloalkyl(C$_{1-6}$)alkyl-aryl-, heteroaryl-(C$_{3-7}$)heterocycloalkyl-, (C$_{3-7}$)heterocycloalkyl-heteroaryl-, (C$_{3-7}$)heterocycloalkyl-(C$_{1-6}$)alkyl-heteroaryl- or (C$_{4-9}$)spiroheterocycloalkyl-heteroaryl-, any of which groups may be optionally substituted by one or more substituents. Additionally, R$^{11}$ may represent heteroaryl(C$_{1-6}$)alkyl, (C$_{3-7}$)heterocycloalkyl-aryl-, (C$_{3-7}$)cycloalkyl-heteroaryl-, (C$_{4-7}$)cycloalkenyl-heteroaryl-, (C$_{4-9}$)bicycloalkyl-heteroaryl- or (C$_{4-9}$)heterobicycloalkyl-heteroaryl-, any of which groups may be optionally substituted by one or more substituents.

In a first embodiment, R$^{11}$ represents halogen. In one aspect of that embodiment, R$^{11}$ represents bromo.

In a second embodiment, R$^{11}$ represents cyano.

In a third embodiment, R$^{11}$ represents optionally substituted C$_{1-6}$ alkyl. In one aspect of that embodiment, R$^{11}$ represents optionally substituted methyl. In another aspect of that embodiment, R$^{11}$ represents optionally substituted ethyl.

In a fourth embodiment, R$^{11}$ represents optionally substituted aryl. In one aspect of that embodiment, R$^{11}$ represents optionally substituted phenyl.

In a fifth embodiment, R$^{11}$ represents optionally substituted C$_{3-7}$ heterocycloalkyl.

In a sixth embodiment, R$^{11}$ represents optionally substituted C$_{3-7}$ heterocycloalkenyl.

In a seventh embodiment, R$^{11}$ represents optionally substituted heteroaryl. In selected aspects of that embodiment, R$^{11}$ represents benzofuryl, thienyl, indolyl, pyrazolyl, indazolyl, isoxazolyl, imidazolyl, pyridinyl, quinolinyl, pyridazinyl, pyrimidinyl or pyrazinyl, any of which groups may be optionally substituted by one or more substituents. In a further aspect, R$^{11}$ represents optionally substituted thiazolyl.

In an eighth embodiment, R$^{11}$ represents optionally substituted (C$_{3-7}$)-heterocycloalkyl(C$_{1-6}$)alkyl-aryl-. In a first aspect of that embodiment, R$^{11}$ represents optionally substituted pyrrolidinylmethylphenyl-. In a second aspect of that embodiment, R$^{11}$ represents optionally substituted piperazinylmethylphenyl-. In a third aspect of that embodiment, R$^{11}$ represents optionally substituted morpholinylmethylphenyl-.

In a ninth embodiment, R$^{11}$ represents optionally substituted heteroaryl-(C$_{3-7}$)-heterocycloalkyl-. In one aspect of that embodiment, R$^{11}$ represents optionally substituted pyridinylpiperazinyl-.

In a tenth embodiment, R$^{11}$ represents optionally substituted (C$_{3-7}$)cycloalkyl-heteroaryl-. In a first aspect of that embodiment, R$^{11}$ represents optionally substituted cyclopropylpyrimidinyl-. In a second aspect of that embodiment, $R^{11}$ represents optionally substituted cyclobutylpyrimidinyl-. In a third aspect of that embodiment, R' represents optionally substituted cyclopentylpyrimidinyl-. In a fourth aspect of that embodiment, $R^{11}$ represents optionally substituted cyclohexylpyrimidinyl-.

In an eleventh embodiment, $R^{11}$ represents optionally substituted $(C_{3-7})$cycloalkyl-$(C_{1-6})$alkyl-heteroaryl-. In one aspect of that embodiment, $R^{11}$ represents optionally substituted cyclopropylmethylpyrimidinyl-.

In a twelfth embodiment, $R^{11}$ represents optionally substituted $(C_{4-7})$cycloalkenyl-heteroaryl-.

In a thirteenth embodiment, $R^{11}$ represents optionally substituted $(C_{4-9})$-bicycloalkyl-heteroaryl-. In one aspect of that embodiment, $R^{11}$ represents optionally substituted bicyclo[3.1.0]hexanylpyrimidinyl-.

In a fourteenth embodiment, $R^{11}$ represents optionally substituted $(C_{3-7})$-heterocycloalkyl-heteroaryl-. In a first aspect of that embodiment, $R^{11}$ represents optionally substituted azetidinylpyridinyl-. In a second aspect of that embodiment, R' optionally substituted pyrrolidinylpyridinyl-. In a third aspect of that embodiment, $R^{11}$ represents optionally substituted isothiazolidinylpyridinyl-. In a fourth aspect of that embodiment, $R^{11}$ represents optionally substituted imidazolidinylpyridinyl-. In a fifth aspect of that embodiment, $R^{11}$ represents optionally substituted piperidinylpyridinyl-. In a sixth aspect of that embodiment, $R^{11}$ represents optionally substituted piperazinylpyridinyl-. In a seventh aspect of that embodiment, $R^{11}$ represents optionally substituted morpholinylpyridinyl-. In an eighth aspect of that embodiment, $R^{11}$ represents optionally substituted thiomorpholinylpyridinyl-. In a ninth aspect of that embodiment, $R^{11}$ represents optionally substituted diazepanylpyridinyl-. In a tenth aspect of that embodiment, $R^{11}$ represents optionally substituted oxetanylpyrimidinyl-. In an eleventh aspect of that embodiment, $R^{11}$ represents optionally substituted azetidinylpyrimidinyl-. In a twelfth aspect of that embodiment, $R^{11}$ represents optionally substituted tetrahydrofuranylpyrimidinyl-. In a thirteenth aspect of that embodiment, $R^{11}$ represents optionally substituted pyrrolidinylpyrimidinyl-. In a fourteenth aspect of that embodiment, $R^{11}$ represents optionally substituted isothiazolidinylpyrimidinyl-. In a fifteenth aspect of that embodiment, $R^{11}$ represents optionally substituted tetrahydropyranylpyrimidinyl-. In a sixteenth aspect of that embodiment, $R^{11}$ represents optionally substituted piperidinylpyrimidinyl-. In a seventeenth aspect of that embodiment, $R^{11}$ represents optionally substituted piperazinylpyrimidinyl-. In an eighteenth aspect of that embodiment, $R^{11}$ represents optionally substituted morpholinylpyrimidinyl-. In a nineteenth aspect of that embodiment, $R^{11}$ represents optionally substituted thiomorpholinylpyrimidinyl-.

In a fifteenth embodiment, $R^{11}$ represents optionally substituted $(C_{3-7})$-heterocycloalkyl$(C_{1-6})$alkyl-heteroaryl-. In a first aspect of that embodiment, $R^{11}$ represents optionally substituted morpholinylmethylthienyl-. In a second aspect of that embodiment, $R^{11}$ represents optionally substituted morpholinylethylpyrazolyl-. In a third aspect of that embodiment, $R^{11}$ represents optionally substituted azetidinylmethylpyridinyl-. In a fourth aspect of that embodiment, $R^{11}$ represents optionally substituted piperazinylmethylpyridinyl-. In a fifth aspect of that embodiment, $R^{11}$ represents optionally substituted morpholinylmethylpyridinyl-. In a sixth aspect of that embodiment, $R^{11}$ represents optionally substituted thiomorpholinylmethylpyridinyl-. In a seventh aspect of that embodiment, $R^{11}$ represents optionally substituted morpholinylmethylpyrimidinyl-.

In a sixteenth embodiment, $R^{11}$ represents optionally substituted $(C_{3-7})$-heterocycloalkenyl-heteroaryl-.

In a seventeenth embodiment, $R^{11}$ represents optionally substituted $(C_{4-9})$-heterobicycloalkyl-heteroaryl-.

In an eighteenth embodiment, $R^{11}$ represents optionally substituted $(C_{4-9})$-spiroheterocycloalkyl-heteroaryl-.

In a nineteenth embodiment, $R^{11}$ represents optionally substituted $(C_{3-7})$-heterocycloalkyl-aryl-. In one aspect of that embodiment, $R^{11}$ represents optionally substituted piperazinylphenyl.

In a twentieth embodiment, $R^{11}$ represents optionally substituted heteroaryl-$(C_{1-6})$alkyl. In a first aspect of that embodiment, $R^{11}$ represents optionally substituted triazolylmethyl. In a second aspect of that embodiment, $R^{11}$ represents optionally substituted pyridinylmethyl.

Appropriately, $R^{11}$ represents bromo or cyano; or ethyl, phenyl, piperidinyl, piperazinyl, morpholinyl, 1,2,3,6-tetrahydropyridinyl, benzofuryl, thienyl, indolyl, pyrazolyl, indazolyl, isoxazolyl, imidazolyl, pyridinyl, quinolinyl, pyridazinyl, pyrimidinyl, pyrazinyl, pyrrolidinylmethylphenyl, piperazinylmethylphenyl, pyridinylpiperazinyl, cyclobutylpyrimidinyl, cyclopropylmethylpyrimidinyl, pyrrolidinylpyridinyl, piperidinylpyridinyl, piperazinylpyridinyl, morpholinylpyridinyl, thiomorpholinylpyridinyl, diazepanylpyridinyl, pyrrolidinylpyrimidinyl, tetrahydropyranylpyrimidinyl, piperidinylpyrimidinyl, piperazinylpyrimidinyl, morpholinylpyrimidinyl, thiomorpholinylpyrimidinyl, morpholinylmethylthienyl, morpholinylethylpyrazolyl, 2-oxa-6-azaspiro[3.3]heptanylpyrimidinyl, 2-oxa-6-azaspiro[3.4]octanylpyrimidinyl, 2-oxa-6-azaspiro[3.5]nonanylpyrimidinyl and 2-oxa-7-azaspiro[3.5]nonanylpyrimidinyl, any of which groups may be optionally substituted by one or more substituents. Additionally, $R^{11}$ may represent methyl, dihydrothieno[3,4-b][1,4]dioxinyl, dihydropyrrolo[3,4-b]-pyridinyl, triazolylmethyl, pyridinylmethyl, piperazinylphenyl, morpholinylmethylphenyl, cyclopropylpyrimidinyl, cyclopentylpyrimidinyl, cyclohexylpyrimidinyl, cyclohexenyl-pyrimidinyl, bicyclo[3.1.0]hexanylpyrimidinyl, azetidinylpyridinyl, isothiazolidinylpyridinyl, imidazolidinylpyridinyl, oxetanylpyrimidinyl, azetidinylpyrimidinyl, tetrahydrofuranylpyrimidinyl, isothiazolidinylpyrimidinyl, azetidinylmethylpyridinyl, piperazinylmethylpyridinyl, morpholinylmethylpyridinyl, thiomorpholinylmethylpyridinyl, morpholinylmethylpyrimidinyl, 3-azabicyclo[3.1.0]hexanylpyrimidinyl, 3-azabicyclo[4.1.0]heptanylpyrimidinyl, 3-azabicyclo[3.2.1]octanylpyrimidinyl, 2-oxa-6-azaspiro[3.4]octanylpyridinyl, 5-azaspiro[2.4]heptanylpyrimidinyl or 7-oxa-2-azaspiro-[3.5]nonanylpyrimidinyl, any of which groups may be optionally substituted by one or more substituents.

Appositely, $R^{11}$ represents bromo or cyano; or ethyl, phenyl, piperidinyl, piperazinyl, morpholinyl, 1,2,3,6-tetrahydropyridinyl, benzofuryl, thienyl, indolyl, pyrazolyl, indazolyl, isoxazolyl, imidazolyl, pyridinyl, quinolinyl, pyridazinyl, pyrimidinyl, pyrazinyl, pyrrolidinylmethylphenyl, piperazinylmethylphenyl, pyridinylpiperazinyl, pyrrolidinylpyridinyl, piperidinylpyridinyl, piperazinylpyridinyl, morpholinylpyridinyl, thiomorpholinylpyridinyl, diazepanylpyridinyl, pyrrolidinylpyrimidinyl, piperazinylpyrimidinyl, morpholinylpyrimidinyl, thiomorpholinylpyrimidinyl, morpholinylmethylthienyl, morpholinylethylpyrazolyl, 2-oxa-6-azaspiro-[3.3]heptanylpyrimidinyl, 2-oxa-6-azaspiro[3.4]octanylpyrimidinyl, 2-oxa-6-azaspiro-[3.5]nonanylpyrimidinyl and 2-oxa-7-azaspiro[3.5]nonanylpyrimidinyl, any of which groups may be optionally substituted by one or more substituents.

Suitable examples of optional substituents on $R^{11}$ include one, two or three substituents independently selected from halogen, cyano, cyano($C_{1-6}$)alkyl, $C_{1-6}$ alkyl, trifluoromethyl, trifluoroethyl, $C_{2-6}$ alkenyl, hydroxy, hydroxy($C_{1-6}$)alkyl, $C_{1-6}$ alkoxy, trifluoroethoxy, $C_{1-6}$ alkylsulphonyl, ($C_{1-6}$)alkylsulphonyl($C_{1-6}$)alkyl, oxo, amino, di($C_{1-6}$)alkylamino, ($C_{1-6}$)alkoxy($C_{1-6}$)alkylamino, N—[($C_{1-6}$)alkyl]-N-[hydroxy($C_{1-6}$)alkyl]-amino, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)alkyl, aminocarbonyl and aminocarbonyl($C_{1-6}$)alkyl. Additional examples include difluoromethyl, difluoroethyl, $C_{1-6}$ alkoxy($C_{1-6}$)alkyl, $C_{1-6}$ alkylsulphinyl, $C_{1-6}$ alkylamino, hydroxy($C_{1-6}$)alkylamino, [($C_{1-6}$)alkoxy](hydroxy)($C_{1-6}$)alkylamino, [($C_{1-6}$)alkylthio](hydroxy)($C_{1-6}$)alkylamino, di($C_{1-6}$)alkylamino($C_{1-6}$)alkylamino, N-[di($C_{1-6}$)alkylamino($C_{1-6}$)alkyl]-N-[hydroxy($C_{1-6}$)alkyl]amino, hydroxy($C_{1-6}$)alkyl($C_{3-7}$)-cycloalkylamino, (hydroxy)[($C_{3-7}$)cyclo alkyl($C_{1-6}$)alkyl]amino, ($C_{3-7}$)hetero cyclo alkyl-($C_{1-6}$)alkylamino, oxo($C_{3-7}$)heterocycloalkyl($C_{1-6}$)alkylamino, ($C_{1-6}$)alkylheteroarylamino, heteroaryl($C_{1-6}$)alkylamino, ($C_{1-6}$)alkylheteroaryl($C_{1-6}$)alkylamino, $C_{2-6}$ alkylcarbonylamino, N—[($C_{1-6}$)alkyl]-N—[($C_{2-6}$)alkylcarbonyl]amino, $C_{3-6}$ alkenylcarbonylamino, bis[($C_{3-6}$)alkenylcarbonyl]amino, N-[carboxy($C_{1-6}$)alkyl]-N—[($C_{1-6}$)alkyl]amino, $C_{2-6}$ alkoxycarbonylamino, $C_{2-6}$ alkoxycarbonyl($C_{1-6}$)alkylamino, N—[($C_{1-6}$)alkyl]-N—[($C_{1-6}$)-alkylsulphonyl]amino, formyl, ($C_{3-7}$)cycloalkylcarbonyl, phenylcarbonyl, $C_{1-6}$ alkylaminocarbonyl, hydroxy($C_{1-6}$)alkylaminocarbonyl, di($C_{1-6}$)alkylaminocarbonyl and aminosulphonyl.

Typical examples of optional substituents on $R^{11}$ include one, two or three substituents independently selected from halogen, cyano, cyano($C_{1-6}$)alkyl, $C_{1-6}$ alkyl, trifluoromethyl, trifluoroethyl, $C_{2-6}$ alkenyl, hydroxy, $C_{1-6}$ alkoxy, trifluoroethoxy, $C_{1-6}$ alkylsulphonyl, ($C_{1-6}$)alkylsulphonyl($C_{1-6}$)alkyl, oxo, amino, di($C_{1-6}$)alkylamino, ($C_{1-6}$)alkoxy($C_{1-6}$)alkylamino, N—[($C_{1-6}$)alkyl]-N-[hydroxy($C_{1-6}$)alkyl]amino, $C_{2-6}$ alkylcarbonyl, carboxy, carboxy($C_{1-6}$)alkyl, $C_{2-6}$ alkoxycarbonyl, $C_{2-6}$ alkoxycarbonyl-($C_{1-6}$)alkyl and aminocarbonyl.

Suitable examples of particular substituents on $R^{11}$ include one, two or three substituents independently selected from fluoro, chloro, cyano, cyanoethyl, methyl, ethyl, trifluoromethyl, trifluoroethyl, ethenyl, hydroxy, hydroxyethyl, hydroxyisopropyl, methoxy, isopropoxy, trifluoroethoxy, methylsulphonyl, methylsulphonylethyl, oxo, amino, dimethylamino, methoxyethylamino, N-(hydroxyethyl)-N-(methyl)amino, acetyl, carboxy, carboxymethyl, carboxyethyl, ethoxycarbonyl, tert-butoxycarbonyl, ethoxycarbonylmethyl, ethoxycarbonylethyl, aminocarbonyl and aminocarbonylmethyl. Additional examples include isopropyl, isobutyl, difluoromethyl, difluoroethyl, hydroxymethyl, methoxymethyl, methoxyethyl, methylsulphinyl, ethylamino, hydroxyethylamino, hydroxypropylamino, (hydroxy)(methyl)propylamino, (hydroxy)-(methoxy)(methyl)propylamino, (hydroxy)(methylthio)butylamino, dimethylaminoethylamino, (dimethylamino)(methyl)propylamino, N-(dimethylaminoethyl)-N-(hydroxyethyl)-amino, hydroxymethylcyclopentylamino, hydroxycyclobutylmethylamino, (cyclopropyl)-(hydroxy) propylamino, morpholinylethylamino, oxopyrrolidinylmethylamino, ethyloxadiazolylamino, methylthiadiazolylamino, thiazolylmethylamino, thiazolylethylamino, pyrimidinylmethylamino, methylpyrazolylmethylamino, acetylamino, N-acetyl-N-methylamino, N-isopropylcarbonyl-N-methylamino, ethenylcarbonylamino, bis(ethenylcarbonyl)-amino, N-(carboxymethyl)-N-methylamino, N-(carboxyethyl)-N-methylamino, tert-butoxycarbonylamino, methoxycarbonylethylamino, N-methyl-N-(methylsulphonyl)-amino, formyl, isopropylcarbonyl, cyclobutylcarbonyl, phenylcarbonyl, methoxycarbonyl, methylaminocarbonyl, hydroxyethylaminocarbonyl, dimethylaminocarbonyl and aminosulphonyl.

Typical examples of particular substituents on $R^{11}$ include one, two or three substituents independently selected from fluoro, chloro, cyano, cyanoethyl, methyl, trifluoromethyl, trifluoroethyl, ethenyl, hydroxy, methoxy, isopropoxy, trifluoroethoxy, methylsulphonyl, methylsulphonylethyl, oxo, amino, dimethylamino, methoxyethylamino, N-(hydroxyethyl)-N-(methyl)amino, acetyl, carboxy, carboxymethyl, carboxyethyl, ethoxycarbonyl, tert-butoxycarbonyl, ethoxycarbonylmethyl, ethoxycarbonylethyl and aminocarbonyl.

Particular values of $R^{11}$ include bromo, cyano, ethoxycarbonylethyl, chlorophenyl, hydroxyphenyl, acetylphenyl, aminocarbonylphenyl, oxopiperidinyl, methylsulphonylpiperazinyl, morpholinyl, tert-butoxycarbonyl-1,2,3,6-tetrahydropyridinyl, benzofuryl, thienyl, indolyl, pyrazolyl, methylpyrazolyl, dimethylpyrazolyl, methylindazolyl, dimethylisoxazolyl, methylimidazolyl, pyridinyl, fluoropyridinyl, cyanopyridinyl, methylpyridinyl, (cyano)(methyl)pyridinyl, dimethylpyridinyl, trifluoromethylpyridinyl, ethenylpyridinyl, methoxypyridinyl, (methoxy)(methyl)pyridinyl, isopropoxypyridinyl, trifluoroethoxypyridinyl, (methyl)(trifluoroethoxy)pyridinyl, oxopyridinyl, (methyl)-(oxo)pyridinyl, (dimethyl)(oxo)pyridinyl, aminopyridinyl, dimethylaminopyridinyl, methoxyethylaminopyridinyl, N-(hydroxyethyl)-N-(methyl)aminopyridinyl, carboxypyridinyl, quinolinyl, hydroxypyridazinyl, pyrimidinyl, (ethyl)(methyl)pyrimidinyl, (hydroxyethyl)(methyl)pyrimidinyl, (hydroxyisopropyl)(methyl)pyrimidinyl, methoxypyrimidinyl, oxopyrimidinyl, aminopyrimidinyl, dimethylaminopyrimidinyl, methoxyethylaminopyrimidinyl, (aminocarbonylmethyl)(methyl)pyrimidinyl, hydroxypyrazinyl, pyrrolidinylmethylphenyl, piperazinylmethylphenyl, pyridinylpiperazinyl, (cyclobutyl)-(methyl)pyrimidinyl, (cyclopropylmethyl)(methyl)pyrimidinyl, pyrrolidinylpyridinyl, hydroxypyrrolidinylpyridinyl, piperidinylpyridinyl, acetylpiperidinylpyridinyl, piperazinylpyridinyl, (methyl)(piperazinyl)pyridinyl, cyanoethylpiperazinylpyridinyl, trifluoroethylpiperazinylpyridinyl, methylsulphonylpiperazinylpyridinyl, methylsulphonylethylpiperazinylpyridinyl, oxopiperazinylpyridinyl, acetylpiperazinylpyridinyl, (tert-butoxycarbonylpiperazinyl)(methyppyridinyl, carboxymethylpiperazinylpyridinyl, carboxyethylpiperazinylpyridinyl, ethoxycarbonylmethylpiperazinylpyridinyl, ethoxycarbonylethylpiperazinylpyridinyl, morpholinylpyridinyl, thiomorpholinylpyridinyl, oxothiomorpholinylpyridinyl, dioxothiomorpholinylpyridinyl, oxodiazepanylpyridinyl, hydroxypyrrolidinylpyrimidinyl, (methyl)(tetrahydropyranyl)pyrimidinyl, (methyl)(piperidinyl)pyrimidinyl, (methyl)(methylsulphonylpiperidinyl)pyrimidinyl, piperazinylpyrimidinyl, methylsulphonylpiperazinylpyrimidinyl, oxopiperazinylpyrimidinyl, tert-butoxycarbonylpiperazinylpyrimidinyl, morpholinylpyrimidinyl, thiomorpholinylpyrimidinyl, morpholinylmethylthienyl, morpholinylethylpyrazolyl, 2-oxa-6-azaspiro[3.3]heptanylpyrimidinyl, 2-oxa-6-azaspiro[3.4]octanylpyrimidinyl, 2-oxa-6-azaspiro[3.5]nonanylpyrimidinyl and 2-oxa-7-azaspiro[3.5]nonanylpyrimidinyl. Additional values include N-isopropylcarbonyl-N-methylaminomethyl, methylsulphinylphenyl, methylsulphonylphenyl, (methyl)(methylsulphonyl)phenyl, ethenylcarbonylaminophenyl, tert-butoxycarbonylaminophenyl, phenylcarbonylphenyl, aminosulphonylphenyl, isopropylcarbonylpiperidinyl, cyclobutylcarbonylpiperidinyl, methoxycarbonylpiperidinyl, methylthienyl, dihydrothieno[3,4-b][1,4]dioxinyl, oxodihydropyrrolo[3,4-b]-pyridinyl, hydroxyisopropylpyridinyl, methylsulphonylpyridinyl, (difluoromethyl)(oxo)-pyridinyl, (oxo)(trifluoromethyl)pyridinyl, (methoxy)(oxo)pyridinyl, acetylaminopyridinyl, bis(ethenylcarbonyl)aminopyridinyl, N-methyl-N-(methylsulphonyl)aminopyridinyl, formylpyridinyl, aminocarbonylpyridinyl, (aminocarbonyl)(methyl)pyridinyl, methylaminocarbonylpyridinyl, hydroxyethylaminocarbonylpyridinyl, dimethylaminocarbonylpyridinyl, (isopropyl)(methyl)pyrimidinyl, (isobutyl)(methyl)pyrimidinyl, hydroxyisopropylpyrimidinyl, (methoxymethyl)(methyl)pyrimidinyl, (methoxyethyl)-(methyl)pyrimidinyl, methylsulphonylpyrimidinyl, dioxopyrimidinyl, ethylaminopyrimidinyl, hydroxyethylaminopyrimidinyl, hydroxypropylaminopyrimidinyl, (hydroxy)(methyl)propylaminopyrimidinyl, (hydroxy)(methoxy)(methyl)propylaminopyrimidinyl, (hydroxy)(methylthio)butylaminopyrimidinyl, dimethylaminoethylaminopyrimidinyl, (dimethylamino)(methyl)propylaminopyrimidinyl, N-(dimethylaminoethyl)-N-(hydroxyethyl)aminopyrimidinyl, hydroxymethylcyclopentylaminopyrimidinyl, hydroxycyclobutylmethylaminopyrimidinyl, (cyclopropyl)(hydroxy)propylaminopyrimidinyl, morpholinylethylaminopyrimidinyl, oxopyrrolidinylmethylamino-pyrimidinyl, ethyloxadiazolylaminopyrimidinyl, methylthiadiazolylaminopyrimidinyl, thiazolylmethylaminopyrimidinyl, thiazolylethylaminopyrimidinyl, pyrimidinylmethyl-aminopyrimidinyl, methylpyrazolylmethylaminopyrimidinyl, acetylaminopyrimidinyl, N-acetyl-N-methylaminopyrimidinyl, N-(carboxymethyl)-N-methylaminopyrimidinyl, N-(carboxyethyl)-N-methylaminopyrimidinyl, methoxycarbonylethylaminopyrimidinyl, N-methyl-N-(methylsulphonyl)aminopyrimidinyl, pyrazinyl, triazolylmethyl, methylpyridinylmethyl, methoxypyridinylmethyl, piperazinylphenyl, morpholinylmethylphenyl, (cyclopropyl)(methyl)pyrimidinyl, hydroxycyclobutylpyrimidinyl, (cyclopentyl)(methyl)-pyrimidinyl, carboxycyclohexylpyrimidinyl, carboxycyclohexenylpyrimidinyl, carboxybicyclo[3.1.0]hexanylpyrimidinyl, oxopyrrolidinylpyridinyl, dioxoisothiazolidinylpyridinyl, oxoimidazolidinylpyridinyl, (hydroxy)(methyl)piperidinylpyridinyl, (chloro)-(piperazinyl)pyridinyl, difluoroethylpiperazinylpyridinyl, (methyl)(oxopiperazinyl)-pyridinyl, (methyl)(morpholinyl)pyridinyl, oxomorpholinylpyridinyl, (methyl)-(thiomorpholinyl)pyridinyl, (methyl)(oxothiomorpholinyl)pyridinyl, hydroxyoxetanylpyrimidinyl, hydroxyazetidinylpyrimidinyl, hydroxymethylazetidinylpyrimidinyl, (tert-butoxycarbonyl)(hydroxy)azetidinylpyrimidinyl, (methyl)(tetrahydrofuranyl)pyrimidinyl, hydroxymethylpyrrolidinylpyrimidinyl, methoxymethylpyrrolidinylpyrimidinyl, oxopyrrolidinylpyrimidinyl, (methyl)(oxo)pyrrolidinylpyrimidinyl, dimethylaminopyrrolidinylpyrimidinyl, dioxoisothiazolidinylpyrimidinyl, hydroxytetrahydropyranylpyrimidinyl, hydroxypiperidinylpyrimidinyl, hydroxymethylpiperidinylpyrimidinyl, methoxypiperidinylpyrimidinyl, oxopiperidinylpyrimidinyl, carboxypiperidinylpyrimidinyl, (carboxy)(methyl)piperidinylpyrimidinyl, (amino)(carboxy)piperidinylpyrimidinyl, (ethoxycarbonyl)(methyl)piperidinylpyrimidinyl, aminocarbonylpiperidinylpyrimidinyl, hydroxyethylpiperazinylpyrimidinyl, (methyl)(oxopiperazinyl)pyrimidinyl, methylmorpholinylpyrimidinyl, oxomorpholinylpyrimidinyl, dioxothiomorpholinylpyrimidinyl, hydroxymethylazetidinylcarbonylpyridinyl, piperazinylcarbonylpyridinyl, methylpiperazinylcarbonylpyridinyl, morpholinylcarbonylpyridinyl, thiomorpholinylcarbonylpyridinyl, dioxothiomorpholinylcarbonylpyridinyl, (methyl)(morpholinylmethyl)pyrimidinyl, carboxy-3-azabicyclo[3.1.0]hexanylpyrimidinyl, carboxy-3-azabicyclo[4.1.0]heptanylpyrimidinyl, carboxy-3-azabicyclo[3.2.1]octanylpyrimidinyl, methoxycarbonyl-3-azabicyclo[3.2.1]octanylpyrimidinyl, oxo-2-oxa-6-azaspiro[3.4]-octanylpyridinyl, difluoro-5-azaspiro[2.4]heptanylpyrimidinyl and 7-oxa-2-azaspiro-[3.5]nonanylpyrimidinyl.

Selected values of $R^{11}$ include bromo, cyano, ethoxycarbonylethyl, chlorophenyl, hydroxyphenyl, acetylphenyl, aminocarbonylphenyl, oxopiperidinyl, methylsulphonylpiperazinyl, morpholinyl, tert-butoxycarbonyl-1,2,3,6-tetrahydropyridinyl, benzofuryl, thienyl, indolyl, pyrazolyl, methylpyrazolyl, dimethylpyrazolyl, methylindazolyl, dimethylisoxazolyl, methylimidazolyl, pyridinyl, fluoropyridinyl, cyanopyridinyl, methylpyridinyl, (cyano)(methyl)pyridinyl, dimethylpyridinyl, trifluoromethylpyridinyl, ethenylpyridinyl, methoxypyridinyl, (methoxy)(methyl)pyridinyl, isopropoxypyridinyl, trifluoroethoxypyridinyl, (methyl)(trifluoroethoxy)pyridinyl, oxopyridinyl, (methyl)-(oxo)pyridinyl, (dimethyl)(oxo)pyridinyl, aminopyridinyl, dimethylaminopyridinyl, methoxyethylaminopyridinyl, N-(hydroxyethyl)-N-(methyl)aminopyridinyl, carboxypyridinyl, quinolinyl, hydroxypyridazinyl, pyrimidinyl, methoxypyrimidinyl, oxopyrimidinyl, aminopyrimidinyl, dimethylaminopyrimidinyl, methoxyethylaminopyrimidinyl, hydroxypyrazinyl, pyrrolidinylmethylphenyl, piperazinylmethylphenyl, pyridinylpiperazinyl, pyrrolidinylpyridinyl, hydroxypyrrolidinylpyridinyl, piperidinylpyridinyl, acetylpiperidinylpyridinyl, piperazinylpyridinyl, (methyl)(piperazinyl)-pyridinyl, cyanoethylpiperazinylpyridinyl, trifluoroethylpiperazinylpyridinyl, methylsulphonylpiperazinylpyridinyl, methylsulphonylethylpiperazinylpyridinyl, oxopiperazinylpyridinyl, acetylpiperazinylpyridinyl, (tert-butoxycarbonylpiperazinyl)-(methyl)pyridinyl, carboxymethylpiperazinylpyridinyl, carboxyethylpiperazinylpyridinyl, ethoxycarbonylmethylpiperazinylpyridinyl, ethoxycarbonylethylpiperazinylpyridinyl, morpholinylpyridinyl, thiomorpholinylpyridinyl, oxothiomorpholinylpyridinyl, dioxothiomorpholinylpyridinyl, oxodiazepanylpyridinyl, hydroxypyrrolidinylpyrimidinyl, piperazinylpyrimidinyl, methylsulphonylpiperazinylpyrimidinyl, oxopiperazinylpyrimidinyl, tert-butoxycarbonylpiperazinylpyrimidinyl, morpholinylpyrimidinyl, thiomorpholinylpyrimidinyl, morpholinylmethylthienyl, morpholinylethylpyrazolyl, 2-oxa-6-azaspiro[3.3]heptanylpyrimidinyl, 2-oxa-6-azaspiro[3.4]octanylpyrimidinyl, 2-oxa-6-azaspiro[3.5]nonanylpyrimidinyl and 2-oxa-7-azaspiro[3.5]nonanylpyrimidinyl.

Typical examples of optional substituents on $R^{12}$ include $C_{2-6}$ alkoxycarbonyl.

Typical examples of particular substituents on $R^{12}$ include ethoxycarbonyl.

In a first embodiment, $R^{12}$ represents hydrogen. In a second embodiment, $R^{12}$ represents halogen. In one aspect of that embodiment, $R^{12}$ represents fluoro. In another aspect of that embodiment, $R^{12}$ represents chloro. In a third embodiment, $R^{12}$ represents trifluoromethyl. In a fourth embodiment, $R^{12}$ represents optionally substituted $C_{1-6}$ alkyl. In one aspect of that embodiment, $R^{12}$ represents unsubstituted methyl. In another aspect of that embodiment, $R^{12}$ represents unsubstituted ethyl. In a further aspect of that embodiment, $R^{12}$ represents monosubstituted methyl or monosubstituted ethyl.

Typical values of $R^{12}$ include hydrogen, fluoro, chloro, trifluoromethyl, methyl and ethoxycarbonylethyl.

Suitable values of $R^{12}$ include hydrogen, fluoro, chloro, trifluoromethyl and methyl.

Typically, $R^{15}$ and $R^{16}$ may independently represent hydrogen, fluoro, chloro, bromo, cyano, nitro, methyl, isopropyl, trifluoromethyl, hydroxy, methoxy, difluoromethoxy, trifluoromethoxy, methylthio, methylsulfinyl, methylsulfonyl, amino, methylamino, tert-butylamino, dimethylamino, phenylamino, acetylamino, methylsulfonylamino, formyl, acetyl, cyclopropylcarbonyl, azetidinylcarbonyl, pyrrolidinylcarbonyl, piperidinyl-carbonyl, piperazinylcarbonyl, morpholinylcarbonyl, carboxy, methoxycarbonyl, aminocarbonyl, methylaminocarbonyl, dimethylaminocarbonyl, aminosulfonyl, methylaminosulfonyl and dimethylaminosulfonyl.

Typical values of $R^{15}$ include hydrogen, halogen, $C_{1-6}$ alkyl, trifluoromethyl, $C_{1-6}$ alkoxy, difluoromethoxy and trifluoromethoxy.

In a first embodiment, $R^{15}$ represents hydrogen. In a second embodiment, $R^{15}$ represents halogen. In a first aspect of that embodiment, $R^{15}$ represents fluoro. In a second aspect of that embodiment, $R^{15}$ represents chloro. In a third embodiment, $R^{15}$ represents $C_{1-6}$ alkyl. In one aspect of that embodiment, $R^{15}$ represents methyl. In a fourth embodiment, $R^{15}$ represents trifluoromethyl. In a fifth embodiment, $R^{15}$ represents $C_{1-6}$ alkoxy. In one aspect of that embodiment, $R^{15}$ represents methoxy. In a sixth embodiment, $R^{15}$ represents difluoromethoxy. In a seventh embodiment, $R^{15}$ represents trifluoromethoxy.

Selected values of $R^{15}$ include hydrogen, fluoro, chloro, methyl, trifluoromethyl, methoxy, difluoromethoxy and trifluoromethoxy.

Typical values of $R^{16}$ include hydrogen, halogen, $C_{1-6}$ alkyl, trifluoromethyl, difluoromethoxy and amino.

In a first embodiment, $R^{16}$ represents hydrogen. In a second embodiment, $R^{16}$ represents halogen. In a first aspect of that embodiment, $R^{16}$ represents fluoro. In a second aspect of that embodiment, $R^{16}$ represents chloro. In a third embodiment, $R^{16}$ represents $C_{1-6}$ alkyl. In one aspect of that embodiment, $R^{16}$ represents methyl. In a fourth embodiment, $R^{16}$ represents trifluoromethyl. In a fifth embodiment, $R^{16}$ represents difluoromethoxy. In a seventh embodiment, $R^{16}$ represents amino.

Selected values of $R^{16}$ include hydrogen, fluoro, chloro, methyl, trifluoromethyl, difluoromethoxy and amino.

In a particular embodiment, $R^{16}$ is attached at the para-position of the phenyl ring relative to the integer $R^{15}$.

A particular sub-group of the compounds of formula (IIA) above is represented by the compounds of formula (IIB) and N-oxides thereof, and pharmaceutically acceptable salts and solvates thereof, and glucuronide derivatives thereof, and co-crystals thereof:

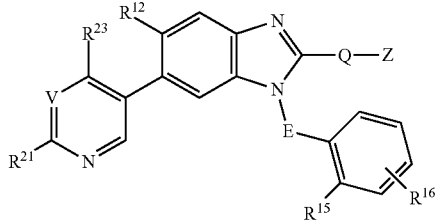

(IIB)

wherein

V represents C—$R^{22}$ or N;

$R^{21}$ represents hydrogen, halogen, cyano, $C_{1-6}$ alkyl, trifluoromethyl, $C_{2-6}$ alkenyl, $C_{2-6}$ alkynyl, hydroxy, hydroxy($C_{1-6}$)alkyl, $C_{1-6}$ alkoxy, difluoromethoxy, trifluoromethoxy, trifluoroethoxy, $C_{1-6}$ alkoxy($C_{1-6}$)alkyl, $C_{1-6}$ alkylthio, $C_{1-6}$ alkylsulphonyl, amino, $C_{1-6}$ alkylamino, di($C_{1-6}$)alkylamino, hydroxy($C_{1-6}$)alkylamino, ($C_{1-6}$)alkoxy($C_{1-6}$)-alkylamino, [($C_{1-6}$)alkoxy](hydroxy)($C_{1-6}$)alkylamino, N—[($C_{1-6}$)alkyl]-N-[hydroxy($C_{1-6}$)-alkyl]amino, [($C_{1-6}$)alkylthio](hydroxy)($C_{1-6}$)alkylamino, di($C_{1-6}$)alkylamino($C_{1-6}$)alkylamino, N-[di($C_{1-6}$)alkylamino($C_{1-6}$)alkyl]-N-[hydroxy($C_{1-6}$)alkyl]amino, hydroxy($C_{1-6}$)-alkyl($C_{3-7}$)cyclo alkylamino, (hydroxy)[($C_{3-7}$)cyclo alkyl($C_{1-6}$)alkyl]amino, ($C_{3-7}$)-hetero cyclo alkyl($C_{1-6}$)alkyl amino, oxo($C_{3-7}$)heterocycloalkyl($C_{1-6}$)alkylamino, ($C_{1-6}$)alkyl-heteroaryl amino, heteroaryl($C_{1-6}$)alkylamino, ($C_{1-6}$)alkylheteroaryl($C_{1-6}$)alkylamino, $C_{2-6}$ alkylcarbonylamino, N—[($C_{1-6}$)alkyl]-N—[($C_{2-6}$)alkylcarbonyl]amino, bis[($C_{3-6}$)alkenyl-carbonyl]amino, N-[carboxy($C_{1-6}$)alkyl]-N—[($C_{1-6}$)alkyl]amino, $C_{2-6}$ alkoxycarbonylamino, $C_{2-6}$ alkoxycarbonyl($C_{1-6}$)alkylamino, $C_{1-6}$ alkylsulphonylamino, N—[($C_{1-6}$)alkyl]-N—[($C_{1-6}$)-alkylsulphonyl]amino, formyl, $C_{2-6}$ alkylcarbonyl, carboxy, $C_{2-6}$ alkoxycarbonyl, aminocarbonyl, $C_{1-6}$ alkylaminocarbonyl, hydroxy($C_{1-6}$)alkylaminocarbonyl, di($C_{1-6}$)alkylaminocarbonyl, aminocarbonyl($C_{1-6}$)alkyl, aminosulphonyl, $C_{1-6}$ alkylaminosulphonyl or di($C_{1-6}$) alkylaminosulphonyl; or $R^{21}$ represents ($C_{3-7}$)cycloalkyl, ($C_{3-7}$)cycloalkyl($C_{1-6}$)-alkyl, ($C_{4-7}$)cycloalkenyl, ($C_{4-9}$)bicycloalkyl, ($C_{3-7}$)heterocycloalkyl, ($C_{3-7}$)-heterocycloalkyl($C_{1-6}$)alkyl, ($C_{3-7}$)heterocycloalkenyl, ($C_{4-9}$)heterobicycloalkyl or ($C_{4-9}$)spiroheterocycloalkyl, any of which groups may be optionally substituted by one or more substituents;

$R^{22}$ represents hydrogen, halogen or $C_{1-6}$ alkyl;

$R^{23}$ represents hydrogen or $C_{1-6}$ alkyl; and

E, Q, Z, $R^{12}$, $R^{15}$ and $R^{16}$ are as defined above.

The present invention also provides a compound of formula (IIB) as depicted above or an N-oxide thereof, or a pharmaceutically acceptable salt or solvate thereof, or a co-crystal thereof, wherein $R^{21}$ represents hydrogen, halogen, cyano, $C_{1-6}$ alkyl, trifluoromethyl, $C_{2-6}$ alkenyl, $C_{2-6}$ alkynyl, hydroxy, hydroxy($C_{1-6}$)alkyl, $C_{1-6}$ alkoxy, difluoromethoxy, trifluoromethoxy, trifluoroethoxy, $C_{1-6}$ alkylthio, $C_{1-6}$ alkylsulphonyl, amino, $C_{1-6}$ alkylamino, di($C_{1-6}$)alkylamino, ($C_{1-6}$)alkoxy($C_{1-6}$) alkylamino, N—[($C_{1-6}$)alkyl]-N-[hydroxy($C_{1-6}$)alkyl]-amino, $C_{2-6}$ alkylcarbonylamino, $C_{2-6}$ alkoxycarbonylamino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminocarbonyl($C_{1-6}$)alkyl, aminosulphonyl, $C_{1-6}$ alkylaminosulphonyl or di($C_{1-6}$)alkylaminosulphonyl; or $R^{21}$ represents ($C_{3-7}$)cycloalkyl, ($C_{3-7}$)cycloalkyl($C_{1-6}$)alkyl, ($C_{4-7}$)cycloalkenyl, ($C_{3-7}$)heterocycloalkyl, ($C_{3-7}$)heterocycloalkenyl, ($C_{4-9}$)heterobicycloalkyl or ($C_{4-9}$)spiroheterocycloalkyl, any of which groups may be optionally substituted by one or more substituents;

$R^{12}$ represents hydrogen; and

E, Q, Z, V, $R^{15}$, $R^{16}$ and $R^{23}$ are as defined above.

The present invention also provides a compound of formula (IIB) as depicted above or an N-oxide thereof, or a pharmaceutically acceptable salt or solvate thereof, wherein V represents CH or N;

$R^{21}$ represents hydrogen, halogen, cyano, $C_{1-6}$ alkyl, trifluoromethyl, $C_{2-6}$ alkenyl, $C_{2-6}$ alkynyl, hydroxy, $C_{1-6}$ alkoxy, difluoromethoxy, trifluoromethoxy, trifluoroethoxy, $C_{1-6}$ alkylthio, $C_{1-6}$ alkylsulphonyl, amino, $C_{1-6}$ alkylamino, di($C_{1-6}$)alkylamino, ($C_{1-6}$)alkoxy($C_{1-6}$)alkylamino, N—[($C_{1-6}$)alkyl]-N-[hydroxy($C_{1-6}$)alkyl]amino, $C_{2-6}$ alkylcarbonylamino, $C_{2-6}$ alkoxycarbonylamino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulphonyl, $C_{1-6}$ alkylaminosulphonyl or di($C_{1-6}$)alkylaminosulphonyl; or $R^{21}$ represents ($C_{4-7}$)cycloalkenyl, ($C_{3-7}$)heterocycloalkyl, ($C_{3-7}$)heterocycloalkenyl, ($C_{4-9}$)heterobicycloalkyl or ($C_{4-9}$)spiroheterocycloalkyl, any of which groups may be optionally substituted by one or more substituents;

$R^{12}$ and $R^{23}$ each represents hydrogen; and

E, Q, Z, $R^{15}$ and $R^{16}$ are as defined above.

In one embodiment, V represents C—$R^{22}$. In another embodiment, V represents N.

Suitably, $R^{21}$ represents hydrogen, halogen, cyano, $C_{1-6}$ alkyl, trifluoromethyl, $C_{2-6}$ alkenyl, hydroxy, hydroxy($C_{1-6}$) alkyl, $C_{1-6}$ alkoxy, trifluoroethoxy, amino, di($C_{1-6}$)alkylamino, ($C_{1-6}$)alkoxy($C_{1-6}$)alkylamino, N—[($C_{1-6}$)alkyl]-N-[hydroxy($C_{1-6}$)alkyl]-amino, carboxy or aminocarbonyl ($C_{1-6}$)alkyl; or $R^{21}$ represents ($C_{3-7}$)cycloalkyl, ($C_{3-7}$)cycloalkyl($C_{1-6}$)alkyl, ($C_{3-7}$)heterocycloalkyl or ($C_{4-9}$)spiroheterocycloalkyl, any of which groups may be optionally substituted by one or more substituents. Additionally, $R^{21}$ may represent $C_{1-6}$ alkoxy($C_{1-6}$)alkyl, $C_{1-6}$ alkylsulphonyl, $C_{1-6}$ alkylamino, hydroxy($C_{1-6}$)-alkylamino, [($C_{1-6}$)alkoxy](hydroxy)($C_{1-6}$)alkylamino, [($C_{1-6}$)alkylthio](hydroxy)($C_{1-6}$)-alkylamino, di($C_{1-6}$)alkylamino($C_{1-6}$)alkylamino, N-[di($C_{1-6}$)alkylamino($C_{1-6}$)alkyl]-N-[hydroxy($C_{1-6}$)alkyl]amino, hydroxy($C_{1-6}$)alkyl($C_{3-7}$)cycloalkylamino, (hydroxy)[($C_{3-7}$)-cycloalkyl($C_{1-6}$)alkyl]amino, ($C_{3-7}$)heterocycloalkyl($C_{1-6}$)alkylamino, oxo($C_{3-7}$)-hetero cyclo alkyl($C_{1-6}$)alkylamino, ($C_{1-6}$)alkylheteroarylamino, heteroaryl($C_{1-6}$)alkylamino, ($C_{1-6}$)alkylheteroaryl($C_{1-6}$)alkylamino, $C_{2-6}$ alkylcarbonylamino, N—[($C_{1-6}$)alkyl]-N-[($C_{2-6}$)-alkylcarbonyl]amino, bis[($C_{3-6}$)alkenylcarbonyl]amino, N-[carboxy($C_{1-6}$)alkyl]-N—[($C_{1-6}$)-alkyl]amino, $C_{2-6}$ alkoxycarbonyl($C_{1-6}$)alkylamino, N—[($C_{1-6}$)alkyl]-N—[($C_{1-6}$)alkylsulphonyl]amino, aminocarbonyl, $C_{1-6}$ alkylaminocarbonyl, hydroxy($C_{1-6}$)alkylaminocarbonyl or di($C_{1-6}$)alkylaminocarbonyl; or $R^{21}$ may represent ($C_{4-7}$)cycloalkenyl, ($C_{4-9}$)bicycloalkyl, ($C_{4-9}$)heterobicycloalkyl or ($C_{3-7}$)heterocycloalkyl($C_{1-6}$)alkyl, any of which groups may be optionally substituted by one or more substituents.

Typically, $R^{21}$ represents hydrogen, halogen, cyano, $C_{1-6}$ alkyl, trifluoromethyl, $C_{2-6}$ alkenyl, hydroxy, $C_{1-6}$ alkoxy, trifluoroethoxy, amino, di($C_{1-6}$)alkylamino, ($C_{1-6}$)-alkoxy($C_{1-6}$)alkylamino, N—[($C_{1-6}$)alkyl]-N-[hydroxy($C_{1-6}$)alkyl]amino or carboxy; or $R^{21}$ represents ($C_{3-7}$)heterocycloalkyl or ($C_{4-9}$)spiroheterocycloalkyl, either of which groups may be optionally substituted by one or more substituents.

Where $R^{21}$ represents an optionally substituted ($C_{3-7}$) cycloalkyl group, typical values include cyclopropyl, cyclobutyl, cyclopentyl, cyclohexyl and cycloheptyl, any of which groups may be optionally substituted by one or more substituents.

Where $R^{21}$ represents an optionally substituted ($C_{3-7}$) cycloalkyl($C_{1-6}$)alkyl group, typical values include cyclopropylmethyl, cyclobutylmethyl, cyclopentylmethyl and cyclohexylmethyl, any of which groups may be optionally substituted by one or more substituents.

Where $R^{21}$ represents an optionally substituted ($C_{4-7}$) cycloalkenyl group, typical values include cyclobutenyl, cyclopentenyl, cyclohexenyl and cycloheptenyl, any of which groups may be optionally substituted by one or more substituents.

Where $R^{21}$ represents an optionally substituted ($C_{4-9}$) bicycloalkyl group, a typical value is bicyclo[3.1.0]hexanyl, which group may be optionally substituted by one or more substituents.

Where $R^{21}$ represents an optionally substituted ($C_{3-7}$) heterocycloalkyl group, typical values include oxetanyl, azetidinyl, tetrahydrofuranyl, pyrrolidinyl, isothiazolidinyl, imidazolidinyl, tetrahydropyranyl, piperidinyl, piperazinyl, morpholinyl, thiomorpholinyl and diazepanyl, any of which groups may be optionally substituted by one or more substituents.

Where $R^{21}$ represents an optionally substituted ($C_{3-7}$) heterocycloalkyl($C_{1-6}$)alkyl group, typical values include azetidinylmethyl, piperazinylmethyl, morpholinylmethyl and thiomorpholinylmethyl, any of which groups may be optionally substituted by one or more substituents.

Where $R^{21}$ represents an optionally substituted ($C_{3-7}$) heterocycloalkenyl group, a typical value is optionally substituted 1,2,3,6-tetrahydropyridinyl.

Where $R^{21}$ represents an optionally substituted ($C_{4-9}$) heterobicycloalkyl group, typical values include quinuclidinyl, 5-aza-2-oxabicyclo[2.2.1]heptanyl, 3-azabicyclo[3.1.0]hexanyl, 3-azabicyclo[4.1.0]heptanyl, 5-aza-2-oxabicyclo[2.2.2]octanyl, 3-azabicyclo[3.2.1]octanyl, 8-azabicyclo[3.2.1]octanyl, 3,8-diazabicyclo[3.2.1]octanyl and 3,9-diazabicyclo[4.2.1]nonanyl, any of which groups may be optionally substituted by one or more substituents.

Where $R^{21}$ represents an optionally substituted ($C_{4-9}$) spiroheterocycloalkyl group, typical values include 5-azaspiro[2.4]heptanyl, 2-oxa-6-azaspiro[3.3]heptanyl, 2-oxa-6-azaspiro[3.4]octanyl, 2-oxa-6-azaspiro[3.5] nonanyl, 2-oxa-7-azaspiro[3.5]nonanyl and 7-oxa-2-azaspiro[3.5]nonanyl, any of which groups may be optionally substituted by one or more substituents.

Examples of optional substituents which may be present on $R^{21}$ include one, two or three substituents independently selected from halogen, cyano, cyano($C_{1-6}$)alkyl, $C_{1-6}$ alkyl, trifluoromethyl, trifluoroethyl, $C_{2-6}$ alkenyl, hydroxy, $C_{1-6}$ alkoxy, difluoromethoxy, trifluoromethoxy, trifluoroethoxy, $C_{1-6}$ alkylthio, $C_{1-6}$ alkylsulphonyl, ($C_{1-6}$)alkylsulphonyl ($C_{1-6}$)alkyl, oxo, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulphonylamino, formyl, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)alkyl, a carboxylic acid isostere or prodrug moiety Ω as defined herein, aminocarbonyl, $C_{1-6}$ alkylaminocarbonyl, di($C_{1-6}$)alkylaminocarbonyl, aminosulphonyl and di($C_{1-6}$)alkylaminosulphonyl. An additional example is —($C_{1-6}$)alkyl-Ω, in which Ω is as defined herein. Additional examples include difluoroethyl, hydroxy($C_{1-6}$)alkyl and $C_{1-6}$ alkoxy($C_{1-6}$)alkyl.

Suitable examples of optional substituents on $R^{21}$ include one, two or three substituents independently selected from fluoro, chloro, bromo, cyano, cyanomethyl, methyl, ethyl, trifluoromethyl, trifluoroethyl, ethenyl, hydroxy, methoxy, ethoxy, difluoromethoxy, trifluoromethoxy, trifluoroethoxy, methylthio, methylsulphonyl, methyl-sulphonylmethyl, oxo, amino, methylamino, dimethylamino, acetylamino, methoxycarbonylamino, ethoxycarbonylamino, tert-butoxycarbonylamino, methylsulphonylamino, formyl, acetyl, carboxy, carboxymethyl, carboxyethyl, methoxycarbonyl, ethoxycarbonyl, tert-butoxycarbonyl, methoxycarbonylmethyl, ethoxycarbonylmethyl, aminocarbonyl, methylaminocarbonyl, dimethylaminocarbonyl, aminosulphonyl, methylaminosulphonyl and dimethylaminosulphonyl. Additional examples include difluoroethyl, hydroxymethyl, hydroxyethyl and methoxymethyl.

Selected examples of optional substituents on $R^{21}$ include one, two or three substituents independently selected from cyano($C_{1-6}$)alkyl, trifluoroethyl, hydroxy, $C_{1-6}$ alkylsulphonyl, ($C_{1-6}$)alkylsulphonyl($C_{1-6}$)alkyl, oxo, $C_{2-6}$ alkylcarbonyl, carboxy-($C_{1-6}$)alkyl, $C_{2-6}$ alkoxycarbonyl and $C_{2-6}$ alkoxycarbonyl($C_{1-6}$)alkyl. Additional examples include halogen, $C_{1-6}$ alkyl, difluoroethyl, hydroxy($C_{1-6}$)alkyl, $C_{1-6}$ alkoxy, $C_{1-6}$ alkoxy-($C_{1-6}$)alkyl, amino, di($C_{1-6}$)alkylamino, carboxy and aminocarbonyl.

Examples of particular substituents on $R^{21}$ include cyanoethyl, trifluoroethyl, hydroxy, methylsulphonyl, methylsulphonylethyl, oxo, acetyl, carboxymethyl, carboxy-ethyl, tert-butoxycarbonyl, ethoxycarbonylmethyl and ethoxycarbonylethyl. Additional examples include fluoro, methyl, difluoroethyl, hydroxymethyl, hydroxyethyl, methoxy, methoxymethyl, amino, dimethylamino, carboxy, methoxycarbonyl and aminocarbonyl.

Suitably, $R^{21}$ represents hydrogen, fluoro, cyano, methyl, ethyl, trifluoromethyl, ethenyl, hydroxy, hydroxyethyl, hydroxyisopropyl, methoxy, isopropoxy, trifluoroethoxy, amino, dimethylamino, methoxyethylamino, N-(hydroxyethyl)-N-(methyl)amino, carboxy, aminocarbonylmethyl, cyclobutyl, cyclopropylmethyl, pyrrolidinyl, hydroxypyrrolidinyl, tetrahydropyranyl, piperidinyl, acetylpiperidinyl, methylsulphonylpiperidinyl, piperazinyl, cyanoethylpiperazinyl, trifluoroethylpiperazinyl, methylsulphonylpiperazinyl, methylsulphonylethylpiperazinyl, oxopiperazinyl, acetylpiperazinyl, tert-butoxycarbonylpiperazinyl, carboxymethylpiperazinyl, carboxyethylpiperazinyl, ethoxycarbonylmethylpiperazinyl, ethoxycarbonylethylpiperazinyl, morpholinyl, thiomorpholinyl, oxothiomorpholinyl, dioxothiomorpholinyl, oxodiazepanyl, 2-oxa-6-azaspiro[3.3]-heptanyl, 2-oxa-6-azaspiro[3.4]octanyl, 2-oxa-6-azaspiro[3.5]nonanyl or 2-oxa-7-azaspiro[3.5]nonanyl. Additionally, $R^{21}$ may represent isopropyl, isobutyl, methoxymethyl, methoxyethyl, methylsulphonyl, ethylamino, hydroxyethylamino, hydroxypropylamino, (hydroxy)(methyl)propylamino, (hydroxy)(methoxy)(methyl)propylamino, (hydroxy)(methylthio)butylamino, dimethylaminoethylamino, (dimethylamino)(methyl)-propylamino, N-(dimethylaminoethyl)-N-(hydroxyethyl)amino, hydroxymethylcyclopentylamino, hydroxycyclobutylmethylamino, (cyclopropyl)(hydroxy)propylamino, morpholinylethylamino, oxopyrrolidinylmethylamino, ethyloxadiazolylamino, methylthiadiazolylamino, thiazolylmethylamino, thiazolylethylamino, pyrimidinylmethylamino, methylpyrazolylmethylamino, acetylamino, N-acetyl-N-methylamino, bis(ethenyl-carbonyl)amino, N-(carboxymethyl)-N-methylamino, N-(carboxyethyl)-N-methylamino, methoxycarbonylethylamino, N-methyl-N-(methylsulphonyl)amino, aminocarbonyl, methylaminocarbonyl, hydroxyethylaminocarbonyl, dimethylaminocarbonyl, cyclopropyl, hydroxycyclobutyl, cyclopentyl, carboxycyclohexyl, carboxycyclohexenyl, carboxybicyclo[3.1.0]hexanyl, hydroxyoxetanyl, hydroxyazetidinyl, hydroxymethylazetidinyl, (tert-butoxycarbonyl)(hydroxy)azetidinyl, tetrahydrofuranyl, hydroxymethylpyrrolidinyl, methoxymethylpyrrolidinyl, oxopyrrolidinyl, (methyl)(oxo)pyrrolidinyl, dimethylamino-pyrrolidinyl, dioxoisothiazolidinyl, oxoimidazolidinyl, hydroxytetrahydropyranyl, hydroxypiperidinyl, hydroxymethylpiperidinyl, methoxypiperidinyl, oxopiperidinyl, carboxypiperidinyl, (carboxy)(methyl)piperidinyl, (amino)(carboxy)piperidinyl, (ethoxycarbonyl)(methyl)piperidinyl, aminocarbonylpiperidinyl, difluoroethylpiperazinyl, hydroxyethylpiperazinyl, (methyl)(oxo)piperazinyl, methylmorpholinyl, oxomorpholinyl, hydroxymethylazetidinylcarbonyl, piperazinylcarbonyl, methylpiperazinylcarbonyl, morpholinylmethyl, morpholinylcarbonyl, thiomorpholinylcarbonyl, dioxo-thiomorpholinylcarbonyl, carboxy-3-azabicyclo[3.1.0]hexanyl, methoxycarbonyl-3-azabicyclo[3.1.0]hexanyl, carboxy-3-azabicyclo[4.1.0]heptanyl, carboxy-3-azabicyclo-[3.2.1]octanyl, difluoro-5-azaspiro[2.4]heptanyl, 2-oxa-6-azaspiro[3.4]octanyl or 7-oxa-2-azaspiro[3.5]nonanyl.

Typically, $R^{21}$ represents hydrogen, fluoro, cyano, methyl, trifluoromethyl, ethenyl, hydroxy, methoxy, isopropoxy, trifluoroethoxy, amino, dimethylamino, methoxyethylamino, N-(hydroxyethyl)-N-(methyl)amino, carboxy, pyrrolidinyl, hydroxypyrrolidinyl, piperidinyl, acetylpiperidinyl, piperazinyl, cyanoethylpiperazinyl, trifluoroethylpiperazinyl, methylsulphonylpiperazinyl, methylsulphonylethylpiperazinyl, oxopiperazinyl, acetylpiperazinyl, tert-butoxycarbonylpiperazinyl, carboxymethylpiperazinyl, carboxyethylpiperazinyl, ethoxycarbonylmethylpiperazinyl, ethoxycarbonylethylpiperazinyl, morpholinyl, thiomorpholinyl, oxothiomorpholinyl, dioxothiomorpholinyl, oxodiazepanyl, 2-oxa-6-azaspiro[3.3]heptanyl, 2-oxa-6-azaspiro[3.4]octanyl, 2-oxa-6-azaspiro[3.5]nonanyl or 2-oxa-7-azaspiro[3.5]nonanyl.

In a particular embodiment, $R^{21}$ represents hydroxy($C_{1-6}$)alkyl. In one aspect of that embodiment, $R^{21}$ represents hydroxyisopropyl, especially 2-hydroxyprop-2-yl.

Generally, $R^{22}$ represents hydrogen or $C_{1-6}$ alkyl.

Suitably, $R^{22}$ represents hydrogen, chloro or methyl.

Typically, $R^{22}$ represents hydrogen or methyl.

In one embodiment, $R^{22}$ represents hydrogen. In another embodiment, $R^{22}$ represents $C_{1-6}$ alkyl, especially methyl. In a further embodiment, $R^{22}$ represents halogen, especially chloro.

Typically, $R^{23}$ represents hydrogen or methyl.

In one embodiment, $R^{23}$ represents hydrogen. In another embodiment, $R^{23}$ represents $C_{1-6}$ alkyl, especially methyl.

Particular sub-groups of the compounds of formula (IIB) above are represented by the compounds of formula (IIC), (IID) and (IIE) and N-oxides thereof, and pharmaceutically acceptable salts and solvates thereof, and glucuronide derivatives thereof, and co-crystals thereof:

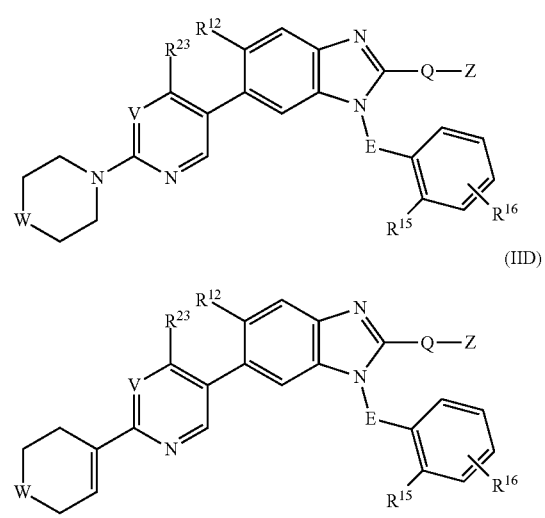

-continued (IIE)

wherein

T represents —CH$_2$— or —CH$_2$CH$_2$—;

W represents O, S, S(O), S(O)$_2$, N(R$^{31}$) or C(R$^{32}$)(R$^{33}$);

R$^{31}$ represents hydrogen, hydroxy(C$_{1-6}$)alkyl, cyano(C$_{1-6}$)alkyl, C$_{1-6}$ alkyl, trifluoromethyl, difluoroethyl, trifluoroethyl, C$_{1-6}$ alkylsulphonyl, (C$_{1-6}$)alkylsulphonyl(C$_{1-6}$)alkyl, formyl, C$_{2-6}$ alkylcarbonyl, carboxy, carboxy(C$_{1-6}$)alkyl, C$_{2-6}$ alkoxycarbonyl, C$_{2-6}$ alkoxycarbonyl(C$_{1-6}$)alkyl, a carboxylic acid isostere or prodrug moiety Ω, —(C$_{1-6}$)alkyl-Ω, aminocarbonyl, C$_{1-6}$ alkylaminocarbonyl, di(C$_{1-6}$)alkylaminocarbonyl, aminosulphonyl or di(C$_{1-6}$)alkylaminosulphonyl;

R$^{32}$ represents halogen, C$_{1-6}$ alkoxy, carboxy, carboxy(C$_{1-6}$)alkyl, C$_{2-6}$ alkoxycarbonyl, C$_{2-6}$ alkoxycarbonyl(C$_{1-6}$)alkyl, aminocarbonyl, a carboxylic acid isostere or prodrug moiety Ω, or —(C$_{1-6}$)alkyl-Ω;

R$^{33}$ represents hydrogen, halogen, C$_{1-6}$ alkyl or amino; and

V, E, Q, Z, R$^{12}$, R$^{15}$, R$^{16}$, R$^{23}$ and Ω are as defined above.

In a first embodiment, T represents —CH$_2$—. In a second embodiment, T represents —CH$_2$CH$_2$—.

Typically, W represents O, S, S(O), S(O)$_2$, N(R$^{31}$) or CF$_2$;

Suitably, W represents O, S, S(O), S(O)$_2$ or N(R$^{31}$).

In a first embodiment, W represents O. In a second embodiment, W represents S. In a third embodiment, W represents S(O). In a fourth embodiment, W represents S(O)$_2$. In a fifth embodiment, W represents N(R$^{31}$). In a sixth embodiment, W represents C(R$^{32}$)(R$^{33}$). In one aspect of the sixth embodiment, W represents CF$_2$.

Typically, R$^{31}$ represents hydrogen, cyano(C$_{1-6}$)alkyl, C$_{1-6}$ alkyl, trifluoromethyl, trifluoroethyl, C$_{1-6}$ alkylsulphonyl, (C$_{1-6}$)alkylsulphonyl(C$_{1-6}$)alkyl, formyl, C$_{2-6}$ alkylcarbonyl, carboxy, carboxy(C$_{1-6}$)alkyl, C$_{2-6}$ alkoxycarbonyl, C$_{2-6}$ alkoxycarbonyl-(C$_{1-6}$)alkyl, a carboxylic acid isostere or prodrug moiety Ω, —(C$_{1-6}$)alkyl-Ω, aminocarbonyl, C$_{1-6}$ alkylaminocarbonyl, di(C$_{1-6}$)alkylaminocarbonyl, aminosulphonyl or di(C$_{1-6}$)alkylaminosulphonyl.

Suitably, R$^{31}$ represents hydrogen, cyano(C$_{1-6}$)alkyl, trifluoroethyl, C$_{1-6}$ alkylsulphonyl, (C$_{1-6}$)alkylsulphonyl(C$_{1-6}$)alkyl, C$_{2-6}$ alkylcarbonyl, carboxy(C$_{1-6}$)alkyl, C$_{2-6}$ alkoxycarbonyl or C$_{2-6}$ alkoxycarbonyl(C$_{1-6}$)alkyl. Additionally, R$^{31}$ may represent hydroxy(C$_{1-6}$)alkyl or difluoroethyl.

Particular values of R$^{31}$ include hydrogen, cyanoethyl, methyl, ethyl, isopropyl, trifluoromethyl, trifluoroethyl, methylsulphonyl, methylsulphonylethyl, formyl, acetyl, carboxy, carboxymethyl, carboxyethyl, methoxycarbonyl, ethoxycarbonyl, tert-butoxycarbonyl, ethoxycarbonylmethyl, ethoxycarbonylethyl, aminocarbonyl, methylaminocarbonyl, dimethylaminocarbonyl, aminosulphonyl, methylaminosulphonyl and dimethylaminosulphonyl. Additional values include hydroxyethyl and difluoroethyl.

Selected values of R$^{31}$ include hydrogen, cyanoethyl, trifluoroethyl, methylsulphonyl, methylsulphonylethyl, acetyl, carboxymethyl, carboxyethyl, tert-butoxycarbonyl, ethoxycarbonylmethyl and ethoxycarbonylethyl. Additional values include hydroxyethyl and difluoroethyl.

Generally, R$^{32}$ represents halogen, carboxy, carboxy(C$_{1-6}$)alkyl, C$_{2-6}$ alkoxycarbonyl, C$_{2-6}$ alkoxycarbonyl(C$_{1-6}$)alkyl, a carboxylic acid isostere or prodrug moiety Ω, or —(C$_{1-6}$)alkyl-Ω.

Typically, R$^{32}$ represents carboxy, C$_{2-6}$ alkoxycarbonyl or tetrazolyl. Additionally, R$^{32}$ may represent C$_{1-6}$ alkoxy or aminocarbonyl.

Typical values of R$^{32}$ include fluoro, carboxy, carboxymethyl, carboxyethyl, methoxycarbonyl, ethoxycarbonyl, methoxycarbonylmethyl, methoxycarbonylethyl, ethoxycarbonylmethyl, ethoxycarbonylethyl, tetrazolyl, tetrazolylmethyl and tetrazolylethyl. Additional values include methoxy and aminocarbonyl.

Particular values of R$^{32}$ include carboxy, methoxycarbonyl, ethoxycarbonyl and tetrazolyl. Additional values include methoxy and aminocarbonyl.

In a selected embodiment, R$^{32}$ represents carboxy.

Generally, R$^{33}$ represents hydrogen, halogen or C$_{1-6}$ alkyl.

Suitably, R$^{33}$ represents hydrogen or C$_{1-6}$ alkyl.

In a first embodiment, R$^{33}$ represents hydrogen. In a second embodiment, R$^{33}$ represents halogen. In one aspect of that embodiment, R$^{33}$ represents fluoro. In a third embodiment, R$^{33}$ represents C$_{1-6}$ alkyl. In one aspect of that embodiment, R$^{33}$ represents methyl. In a fourth embodiment, R$^{33}$ represents amino.

Another sub-group of the compounds of formula (IIB) above is represented by the compounds of formula (IIF) and N-oxides thereof, and pharmaceutically acceptable salts and solvates thereof, and glucuronide derivatives thereof, and co-crystals thereof:

(IIF)

wherein

R$^{34}$ represents hydrogen, halogen, hydroxy, C$_{1-6}$ alkoxy, C$_{1-6}$ alkylthio, C$_{1-6}$ alkylsulphinyl, C$_{1-6}$ alkylsulphonyl, amino, C$_{1-6}$ alkylamino or di(C$_{1-6}$)alkylamino; and E, Q, Z, V, W, R$^{12}$, R$^{15}$, R$^{16}$ and R$^{23}$ are as defined above.

In a first embodiment, R$^{34}$ represents hydrogen. In a second embodiment, R$^{34}$ represents halogen. In one aspect of that embodiment, R$^{34}$ represents fluoro. In a third embodiment, R$^{34}$ represents hydroxy. In a fourth embodiment, R$^{34}$ represents C$_{1-6}$ alkoxy, especially methoxy. In a fifth embodiment, R$^{34}$ represents C$_{1-6}$ alkylthio, especially methylthio. In a sixth embodiment, R$^{34}$ represents C$_{1-6}$ alkylsulphinyl, especially methylsulphinyl. In a seventh embodiment, R$^{34}$ represents C$_{1-6}$ alkylsulphonyl, especially methylsulphonyl. In an eighth embodiment, R$^{34}$ represents amino. In a ninth embodiment, R$^{34}$ represents C$_{1-6}$ alkylamino, especially methylamino. In a tenth embodiment, R$^{34}$ represents di(C$_{1-6}$)alkylamino, especially dimethylamino.

Selected values of R$^{34}$ include hydrogen, fluoro, hydroxy, methoxy, methylthio, methylsulphinyl, methylsulphonyl, amino, methylamino and dimethylamino.

Suitably, R$^{34}$ represents hydrogen or hydroxy.

Further sub-groups of the compounds of formula (IIB) above are represented by the compounds of formula (IIG), (IIH), (IIJ), (IIK) and (IIL) and N-oxides thereof, and pharmaceutically acceptable salts and solvates thereof, and glucuronide derivatives thereof, and co-crystals thereof:

(IIG)
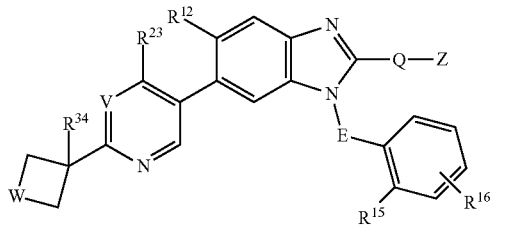

(IIH)
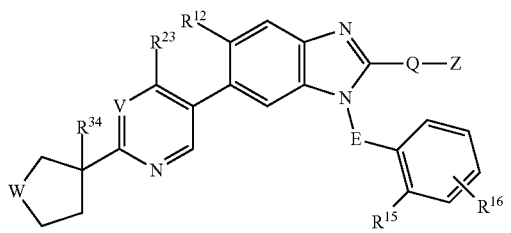

(IIJ)
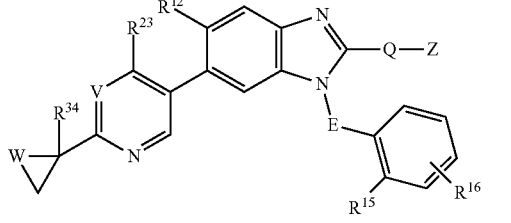

(IIK)
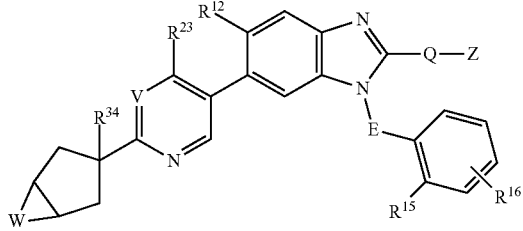

(IIL)
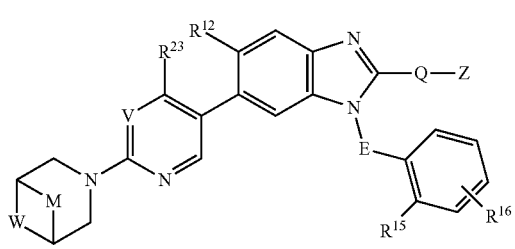

wherein
-M- represents —CH$_2$— or —CH$_2$CH$_2$—; and
E, Q, Z, V, W, R$^{12}$, R$^{15}$, R$^{16}$, R$^{23}$ and R$^{34}$ are as defined above.

In one embodiment, -M- represents —CH$_2$—. In another embodiment, -M- represents —CH$_2$CH$_2$—.

Specific novel compounds in accordance with the present invention include each of the compounds whose preparation is described in accompanying Examples 2, 3A, 3B, 5-531, 532-540, and 541-1105, and pharmaceutically acceptable salts and solvates thereof, and co-crystals thereof.

The compounds in accordance with the present invention are beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, psoriatic arthropathy, vasculitis, polymyositis, scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anaemia of chronic disease (ACD), Still's disease (juvenile and/or adult onset), Behçet's disease and Sjögren's syndrome. Autoimmune endocrine disorders include thyroiditis. Organ-specific autoimmune disorders include Addison's disease, haemolytic or pernicious anaemia, acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease (COPD), respiratory distress syndrome, sepsis, fever, muscular dystrophy (including Duchenne muscular dystrophy) and organ transplant rejection (including kidney allograft rejection).

Neurological and neurodegenerative disorders include Alzheimer's disease, Parkinson's disease, Huntington's disease, ischaemia, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction). Modulators of TNFα function may also be of use in the treatment and/or prevention of myocardial infarction (see J. J. Wu et al., *JAMA*, 2013, 309, 2043-2044).

Metabolic disorders include diabetes (including insulin-dependent diabetes mellitus and juvenile diabetes), dyslipidemia and metabolic syndrome.

Ocular disorders include retinopathy (including diabetic retinopathy, proliferative retinopathy, non-proliferative retinopathy and retinopathy of prematurity), macular oedema (including diabetic macular oedema), age-related macular degeneration (ARMD), vascularisation (including corneal vascularisation and neovascularisation), retinal vein occlusion, and various forms of uveitis and keratitis.

Oncological disorders, which may be acute or chronic, include proliferative disorders, especially cancer, and cancer-associated complications (including skeletal complications, cachexia and anaemia). Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle. Modulators of TNFα function may also be used to increase the safety of the potent anticancer effect of TNF (see F. V. Hauwermeiren et al., *J. Clin. Invest.*, 2013, 123, 2590-2603).

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule such as methotrexate or prednisolone.

The compounds of formula (I) above may be prepared by a process which comprises reacting a compound of formula Z-Q-CO$_2$H or a carboxylate salt thereof (e.g. a carboxylate salt with an alkali metal such as lithium, sodium or potassium) with a compound of formula (III):

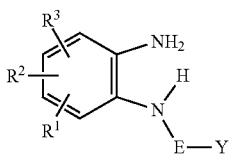

(III)

wherein E, Q, Y, Z, R$^1$, R$^2$ and R$^3$ are as defined above.

The reaction may advantageously be performed in the presence of a peptide coupling reagent such as 0-(7-azabenzotriazol-1-yl)-N,N,N',N'-tetramethyluronium hexafluorophosphate (HATU), optionally in the presence of a suitable base, e.g. an organic base such as N,N-diisopropylethylamine. The reaction is conveniently effected at ambient or elevated temperature in a suitable solvent, e.g. N,N-dimethylformamide or a chlorinated solvent such as dichloromethane. The product thereby obtained is suitably treated with an acid, ideally an organic acid such as acetic acid, or a mineral acid such as hydrochloric acid, typically at an elevated temperature.

Alternatively, the reaction may conveniently be effected in the presence of a coupling reagent such as 1-(3-dimethylaminopropyl)-3-ethylcarbodiimide hydrochloride (EDC), typically at ambient temperature in a suitable solvent, e.g. a chlorinated solvent such as dichloromethane, in the presence of a suitable base, e.g. an organic base such as triethylamine.

Alternatively, the reaction may conveniently be effected at an elevated temperature in the presence of a mineral acid, e.g. hydrochloric acid.

Alternatively, the reaction may conveniently be effected at an elevated temperature in the presence of a lower alkanol, e.g. a C$_{1-4}$ alkanol such as methanol.

In an alternative procedure, the compounds of formula (I) above wherein E represents a covalent bond or an optionally substituted straight or branched C$_{1-4}$ alkylene chain may be prepared by a process which comprises reacting a compound of formula L$^1$-E$^1$-Y with a compound of formula (IV):

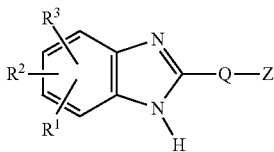

(IV)

wherein Q, Y, Z, R$^1$, R$^2$ and R$^3$ are as defined above, E$^1$ represents a covalent bond or an optionally substituted straight or branched C$_{1-4}$ alkylene chain, and L$^1$ represents a suitable leaving group.

The leaving group L$^1$ is typically a halogen atom, e.g. chloro or bromo.

The reaction is conveniently effected at ambient or elevated temperature in a suitable solvent, e.g. N,N-dimethylformamide or a chlorinated solvent such as dichloromethane. The reaction may be performed in the presence of a suitable base, e.g. an inorganic base such as potassium carbonate, cesium carbonate or sodium hydride.

The intermediates of formula (IV) above may be prepared by reacting a compound of formula Z-Q-CO$_2$H or a carboxylate salt thereof (e.g. a carboxylate salt with an alkali metal such as lithium, sodium or potassium) with a compound of formula (V):

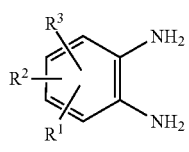

(V)

wherein Q, Z, R$^1$, R$^2$ and R$^3$ are as defined above; under conditions analogous to those described above for the reaction between compound (III) and a compound of formula Z-Q-CO$_2$H or a carboxylate salt thereof.

The intermediates of formula (III) above may be prepared by reducing a compound of formula (VI):

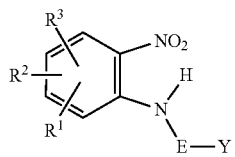

(VI)

wherein E, Y, R$^1$, R$^2$ and R$^3$ are as defined above.

The transformation is conveniently effected by catalytic hydrogenation of compound (VI), which typically comprises treating compound (VI) with gaseous hydrogen in the presence of a hydrogenation catalyst such as palladium on carbon.

Alternatively, the reduction of compound (VI) may be effected by treatment with elemental iron or zinc, typically at an elevated temperature in the presence of ammonium chloride.

Alternatively, the reduction of compound (VI) may be effected by treatment with tin(II) chloride, typically at an elevated temperature in the presence of a mineral acid such as hydrochloric acid.

The intermediates of formula (VI) wherein E represents a covalent bond or an optionally substituted straight or branched C$_{1-4}$ alkylene chain may be prepared by reacting a compound of formula L$^1$-E$^1$-Y with a compound of formula (VII):

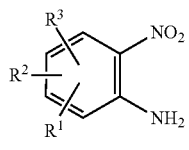

(VII)

wherein E$^1$, Y, R$^1$, R$^2$, R$^3$ and L$^1$ are as defined above; under conditions analogous to those described above for the reaction between compound (IV) and a compound of formula L$^1$-E$^1$-Y.

Alternatively, the intermediates of formula (VI) wherein E represents a covalent bond or an optionally substituted straight or branched $C_{1-4}$ alkylene chain may be prepared by reacting a compound of formula Y-$E^1$-$NH_2$ with a compound of formula (VIII):

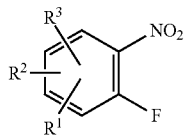

(VIII)

wherein $E^1$, Y, $R^1$, $R^2$ and $R^3$ are as defined above.

The reaction is conveniently effected at ambient or elevated temperature in a suitable solvent, e.g. 1-methyl-2-pyrrolidinone (NMP), a cyclic ether such as tetrahydrofuran, or a dipolar aprotic solvent such as N,N-dimethylformamide. The reaction may be performed in the presence of a suitable base, e.g. an inorganic base such as potassium carbonate.

In another procedure, the compounds of formula (I) above, wherein Q corresponds to a group of formula —CH(OH)-$Q^1$-, may be prepared by a process which comprises reacting an aldehyde of formula OHC-$Q^1$-Z with a compound of formula (IX):

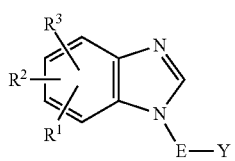

(IX)

wherein E, Y, Z, $R^1$, $R^2$ and $R^3$ are as defined above.

The reaction is conveniently effected in the presence of a strong base, e.g. n-butyllithium or lithium diisopropylamide (LDA). The reaction is carried out in a suitable solvent, e.g. a cyclic ether such as tetrahydrofuran.

The intermediates of formula (IX) above wherein E represents a covalent bond or an optionally substituted straight or branched $C_{1-4}$ alkylene chain may be prepared by reacting a compound of formula $L^1$-$E^1$-Y with a compound of formula (X):

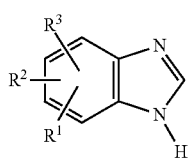

(X)

wherein $E^1$, Y, $R^1$, $R^2$, $R^3$ and $L^1$ are as defined above; under conditions analogous to those described above for the reaction between compound (IV) and a compound of formula $L^1$-$E^1$-Y.

Alternatively, the intermediates of formula (IX) above may be prepared by reacting a compound of formula (III) as defined above with formic acid, ideally at ambient temperature.

The intermediates of formula (IX) above wherein E represents —N(H)— may be prepared by reacting a compound of formula $L^2$-Y with a compound of formula (XI):

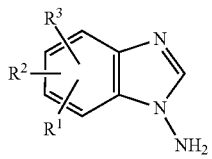

(XI)

wherein Y, $R^1$, $R^2$ and $R^3$ are as defined above, and $L^2$ represents a suitable leaving group; in the presence of a transition metal catalyst.

The leaving group $L^2$ is typically a halogen atom, e.g. bromo.

A suitable transition metal catalyst for use in the above reaction is tris(dibenzylideneacetone)dipalladium(0), in which case the reaction is conveniently performed in the presence of 2-dicyclohexylphosphino-2',4',6'-triisopropylbiphenyl. The reaction is suitably carried out at an elevated temperature in a suitable solvent, e.g. N,N-dimethylformamide, typically in the presence of a base, e.g. an inorganic base such as cesium carbonate.

In a further procedure, the compounds of formula (I) above wherein Z represents a 1H-[1,2,3]triazol-1-yl moiety, optionally substituted in the 4-position, may be prepared by a process which comprises reacting a compound of formula H—C≡C—$R^z$ with a compound of formula (XII):

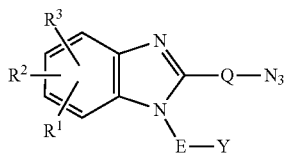

(XII)

wherein E, Q, Y, $R^1$, $R^2$ and $R^3$ are as defined above, and $R^z$ represents an optional substituent on Z.

The reaction is conveniently performed in the presence of copper sulfate pentahydrate and sodium ascorbate. Suitably, the reaction is carried out at ambient temperature in a suitable solvent, e.g. a cyclic ether solvent such as tetrahydrofuran, typically in admixture with water.

The intermediates of formula (XII) above wherein E represents a covalent bond or an optionally substituted straight or branched $C_{1-4}$ alkylene chain may be prepared by reacting a compound of formula (XIII):

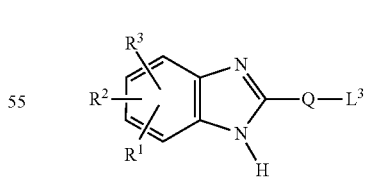

(XIII)

wherein Q, $R^1$, $R^2$ and $R^3$ are as defined above, and $L^3$ represents a suitable leaving group; with sodium azide; followed by reaction of the resulting compound with a compound of formula $L^1$-$E^1$-Y under conditions analogous to those described above for the reaction between compound (IV) and a compound of formula $L^1$-$E^1$-Y.

The leaving group $L^3$ is typically a halogen atom, e.g. chloro.

The reaction between compound (XIII) and sodium azide is conveniently effected at ambient temperature in a suitable solvent, e.g. N,N-dimethylformamide.

The compounds of formula (I) above wherein Q represents —S— may be prepared by a process which comprises reacting a compound of formula Z—S—Z with a compound of formula (IX) as defined above.

The reaction is conveniently effected at ambient temperature in a suitable solvent, e.g. N,N-dimethylformamide. The reaction may be performed in the presence of a suitable base, e.g. an inorganic base such as potassium carbonate.

In a further procedure, the compounds of formula (I) above may be prepared by a process which comprises cyclising a compound of formula (XIV):

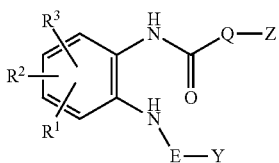

(XIV)

wherein E, Q, Y, Z, $R^1$, $R^2$ and $R^3$ are as defined above.

The cyclication reaction is conveniently effected by heating compound (XIV) in acetic acid.

The intermediates of formula (XIV) above may be prepared by a process which comprises reacting an aldehyde derivative of formula Y-$E^2$-CHO with a compound of formula (XV):

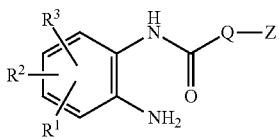

(XV)

wherein Q, Y, Z, $R^1$, $R^2$ and $R^3$ are as defined above, and -$E^2$-$CH_2$— corresponds to a group E as defined above; in the presence of a reducing agent.

The reducing agent for use in the above reaction is suitably sodium triacetoxyborohydride or sodium borohydride.

In a further procedure, the compounds of formula (I) above wherein -Q-Z represents dimethylamino may be prepared by a process which comprises reacting a compound of formula (III) as defined above with (dichloromethylene)dimethylammonium chloride.

The reaction is conveniently effected in a suitable solvent, e.g. a chlorinated solvent such as dichloromethane, typically in the presence of a base, e.g. an organic base such as N,N-diisopropylethylamine.

As will be appreciated, the compounds of formula (IX) above correspond to compounds of formula (I) wherein Q represents a covalent bond and Z is hydrogen.

Where they are not commercially available, the starting materials of formula (V), (VII), (VIII), (X), (XI), (XIII) and (XV) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (I) which contains a hydroxy group may be alkylated by treatment with the appropriate alkyl halide in the presence of a base, e.g. sodium hydride or cesium carbonate, or silver oxide. A compound of formula (I) wherein -Q-Z represents —$CH_2$OH may be arylated in a two-step procedure which comprises: (i) treatment with thionyl chloride; and (ii) treatment of the chloro derivative thereby obtained with the appropriate aryl or heteroaryl hydroxide. A compound of formula (I) wherein -Q-Z represents —$CH_2$OH may be converted into the corresponding compound of formula (I) wherein Q represents —$CH_2$S— via a two-step procedure which comprises: (i) treatment with thionyl chloride; and (ii) treatment of the chloro derivative thereby obtained with a compound of formula Z—SH, typically in the presence of a base, e.g. an inorganic base such as potassium carbonate. A compound of formula (I) which contains hydroxy may be converted into the corresponding fluoro-substituted compound by treatment with diethylaminosulfur trifluoride (DAST). A compound of formula (I) which contains hydroxy may be converted into the corresponding difluoro-substituted compound via a two-step procedure which comprises: (i) treatment with an oxidising agent, e.g. manganese dioxide; and (ii) treatment of the carbonyl-containing compound thereby obtained with DAST.

A compound of formula (I) wherein -Q-Z represents —$CH_2$OH may be converted into the corresponding compound wherein -Q-Z represents —CH(OH)Z in a two-step procedure which comprises: (i) oxidation with a suitable oxidising agent, e.g. Dess-Martin periodinane or manganese (IV) oxide; and (ii) treatment of the aldehyde derivative thereby obtained with a Grignard reagent, e.g. a compound of formula Z—MgBr or Z—MgCl.

A compound of formula (I) wherein -Q-Z represents —$CH_2$OH may be converted into the corresponding compound wherein -Q-Z represents —CH(OH)$CF_3$ in a two-step procedure which comprises: (i) oxidation with a suitable oxidising agent, e.g. Dess-Martin periodinane or manganese (IV) oxide; and (ii) treatment of the aldehyde derivative thereby obtained with (trifluoromethyl)trimethylsilane and cesium fluoride.

A compound of formula (I) which contains an N—H moiety may be alkylated by treatment with the appropriate alkyl halide, typically at an elevated temperature in an organic solvent such as acetonitrile, optionally in the presence of a base, e.g. an inorganic base such as sodium hydride. Alternatively, a compound of formula (I) which contains an N—H moiety may be alkylated by treatment with the appropriate alkyl tosylate, optionally in the presence of a base, e.g. an inorganic base such as sodium hydride, or an organic base such as 1,8-diazabicyclo[5.4.0]undec-7-ene (DBU).

A compound of formula (I) which contains an N—H moiety may be converted into the corresponding compound wherein the nitrogen atom is substituted by $C_{1-6}$ alkylsulphonyl, e.g. methylsulphonyl, by treatment with the appropriate $C_{1-6}$ alkylsulphonyl halide, e.g. a $C_{1-6}$ alkylsulphonyl chloride such as methanesulphonyl chloride, typically at ambient temperature in the presence of a base, e.g. an organic base such as triethylamine.

A compound of formula (I) which contains an —OH moiety may be converted into the corresponding compound containing an —$OSO_2R^a$ moiety by treatment with the appropriate sulphonyl halide, e.g. a sulphonyl chloride of formula $R^aSO_2Cl$, typically in the presence of a base, e.g. an organic base such as triethylamine.

A compound of formula (I) containing the moiety —S— may be converted into the corresponding compound containing the moiety —S(O)— by treatment with 3-chloroperoxybenzoic acid. Likewise, a compound of formula (I) containing the moiety —S(O)— may be converted into the corresponding compound containing the moiety —S(O)$_2$— by treatment with 3-chloroperoxybenzoic acid.

A compound of formula (I) containing an aromatic nitrogen atom may be converted into the corresponding N-oxide derivative by treatment with 3-chloroperoxybenzoic acid.

A bromophenyl derivative of formula (I) may be converted into the corresponding optionally substituted 2-oxopyrrolidin-1-ylphenyl or 2-oxooxazolidin-3-ylphenyl derivative by treatment with pyrrolidin-2-one or oxazolidin-2-one, or an appropriately substituted analogue thereof. The reaction is conveniently effected at an elevated temperature in the presence of copper(I) iodide, trans-N,N'-dimethylcyclohexane-1,2-diamine and an inorganic base such as potassium carbonate.

A compound of formula (I) wherein $R^1$ represents halogen, e.g. bromo, may be converted into the corresponding compound wherein $R^1$ represents an optionally substituted aryl or heteroaryl moiety by treatment with the appropriately substituted aryl or heteroaryl boronic acid or a cyclic ester thereof formed with an organic diol, e.g. pinacol, 1,3-propanediol or neopentyl glycol. The reaction is typically effected in the presence of a transition metal catalyst, e.g. [1,1'-bis(diphenylphosphino)ferrocene]dichloropalladium (II) or tetrakis(triphenylphosphine)palladium(0), and a base, e.g. an inorganic base such as sodium carbonate or potassium carbonate.

A compound of formula (I) wherein $R^1$ represents halogen, e.g. bromo, may be converted into the corresponding compound wherein $R^1$ represents an optionally substituted aryl or heteroaryl moiety via a two-step procedure which comprises: (i) reaction with bis(pinacolato)diboron; and (ii) reaction of the compound thereby obtained with an appropriately substituted bromoaryl or bromoheteroaryl derivative. Step (i) is conveniently effected in the presence of a transition metal catalyst such as [1,1'-bis-(diphenylphosphino)ferrocene]dichloropalladium(II). Step (ii) is conveniently effected in the presence of a transition metal catalyst such as tetrakis(triphenylphosphine)-palladium(0) and a base, e.g. an inorganic base such as sodium carbonate.

A compound of formula (I) wherein $R^1$ represents halogen, e.g. bromo, may be converted into the corresponding compound wherein $R^1$ represents an optionally substituted imidazol-1-yl moiety by treatment with the appropriately substituted imidazole derivative, typically in the presence of copper(II) acetate and an organic base such as N,N,N',N'-tetramethylethylenediamine (TMEDA).

A compound of formula (I) wherein $R^1$ represents halogen, e.g. bromo, may be converted into the corresponding compound wherein $R^1$ represents 2-(methoxycarbonyl)-ethyl via a two-step procedure which comprises: (i) reaction with methyl acrylate; and (ii) catalytic hydrogenation of the alkenyl derivative thereby obtained, typically by treatment with a hydrogenation catalyst, e.g. palladium on charcoal, under an atmosphere of hydrogen gas. Step (i) is typically effected in the presence of a transition metal catalyst, e.g. palladium(II) acetate, and a reagent such as tri(ortho-tolyl) phosphine.

A compound of formula (I) wherein $R^1$ represents 6-methoxypyridin-3-yl may be converted into the corresponding compound wherein $R^1$ represents 2-oxo-1,2-dihydropyridin-5-yl by treatment with pyridine hydrochloride.

A compound of formula (I) wherein $R^1$ represents 2-oxo-1,2-dihydropyridin-5-yl may be converted into the corresponding compound wherein $R^1$ represents 2-oxopiperidin-5-yl by catalytic hydrogenation, typically by treatment with gaseous hydrogen in the presence of a hydrogenation catalyst such as platinum(IV) oxide.

A compound of formula (I) containing an ester moiety, e.g. a $C_{2-6}$ alkoxycarbonyl group such as methoxycarbonyl or ethoxycarbonyl, may be converted into the corresponding compound containing a carboxy (—CO$_2$H) moiety by treatment with an acid, e.g. a mineral acid such as hydrochloric acid. Alternatively, the transformation may be effected by treatment with a base, typically an inorganic base such as an alkali metal hydroxide, e.g. sodium hydroxide or lithium hydroxide; or an organic base such as sodium methoxide.

A compound of formula (I) containing an N-(tert-butoxycarbonyl) moiety may be converted into the corresponding compound containing an N—H moiety by treatment with an acid, e.g. a mineral acid such as hydrochloric acid, or an organic acid such as trifluoroacetic acid.

A compound of formula (I) wherein $R^1$ represents a substituent containing at least one nitrogen atom, which substituent is linked to the remainder of the molecule via a nitrogen atom, may be prepared by reacting a compound of formula (I) wherein $R^1$ represents halogen, e.g. bromo, with the appropriate compound of formula $R^1$—H [e.g. 1-(pyridin-3-yl)piperazine]. The reaction is conveniently effected with the assistance of a transition metal catalyst, e.g. tris (dibenzylideneacetone)dipalladium(0), in the presence of an amination ligand such as 2-dicyclohexylphosphino-2',4',6'-triisopropylbiphenyl (XPhos) and a base, e.g. an inorganic base such as sodium tert-butoxide.

A compound of formula (IIA) wherein $R^{11}$ represents halogen, e.g. bromo, may be converted into the corresponding compound of formula (IIB) wherein V is N and $R^{23}$ represents methyl via a four-step procedure which comprises: (i) reaction with isopropenyl acetate; (ii) treatment with potassium fluoride; (iii) treatment of the 2-oxopropyl derivative thereby obtained with N,N-dimethylformamide dimethyl acetal, ideally at an elevated temperature; and (iv) reaction of the material thereby obtained with the appropriate amidine derivative of formula $R^{21}$—C(NH)NH$_2$. Step (i) is conveniently accomplished with the assistance of a transition metal catalyst, e.g. palladium(II) acetate, typically in the presence of tri-n-butyltin methoxide and a reagent such as tri(ortho-tolyl)phosphine. Step (iv) is typically effected at an elevated temperature in a suitable solvent, e.g. a $C_{1-4}$ alkanol such as methanol or ethanol, in the presence of a base, e.g. an alkali metal alkoxide such as sodium ethoxide or potassium tert-butoxide, or an alkali metal carbonate such as potassium carbonate.

A compound of formula (IIB) wherein $R^{21}$ represents ethenyl may be prepared by reacting a compound of formula (IIB) wherein $R^{21}$ represents halogen, e.g. chloro, with potassium vinyl trifluoroborate. The reaction is typically effected in the presence of a transition metal catalyst, e.g. [1,1'-bis(diphenylphosphino)ferrocene]dichloropalladium (II), and a base, e.g. an organic base such as triethylamine.

A compound of formula (IIB) wherein $R^{21}$ represents a substituent containing at least one nitrogen atom, which substituent is linked to the remainder of the molecule via a nitrogen atom, may be prepared by reacting a compound of formula (IIB) wherein $R^{21}$ represents halogen, e.g. chloro, with the appropriate compound of formula $R^{21}$—H [e.g. 2-methoxyethylamine, pyrrolidin-3-ol, 1-(methylsulfonyl) piperazine, piperazin-2-one, thiomorpholine, 1,4-diazepan- 5-one or an appropriately substituted azaspiroalkane] in the presence of a base, e.g. an organic base such as triethylamine.

A compound of formula (I) containing a halogen atom, e.g. chloro, may be converted into the corresponding compound containing a —N—C(O)— or —N—S(O)$_2$— moiety by treatment with the appropriate amide or sulphonamide derivative containing a —NH—C(O)— or —NH—S(O)$_2$— functionality at an elevated temperature in the presence of a transition metal salt, e.g. palladium(II) acetate, 2,2'-bis(diphenylphosphino)-1,1'-binaphthalene (BINAP), and a base, typically an inorganic base, e.g. a carbonate salt such as cesium carbonate.

A compound of formula (I) containing a carboxy (—CO$_2$H) moiety may be converted into the corresponding compound containing a —CONR$^b$R$^c$ moiety by treatment with the appropriate amine of formula H—NR$^b$R$^c$ in the presence of O-(7-azabenzotriazol-1-yl)-N,N,N',N'-tetramethyluronium hexafluorophosphate (HATU), and a base, typically an organic base such as N,N-diisopropylethylamine.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The following Examples illustrate the preparation of compounds according to the invention.

The compounds in accordance with this invention potently inhibit TNFα-induced NF-κB activation in the following assay.

Inhibition of TNFα-Induced NF-κB Activation

Stimulation of HEK-293 cells by TNFα leads to activation of the NF-κB pathway. The reporter cell line used to determine TNFα activity was purchased from InvivoGen. HEK-Blue™ CD40L is a stable transfectant expressing SEAP (secreted alkaline phosphatase) under the control of the IFNβ minimal promoter fused to five NF-κB binding sites. Secretion of SEAP by these cells is stimulated in a dose-dependent manner by TNFα (0.5 ng/mL). Compounds were diluted from 10 mM DMSO stocks (final assay concentration 0.3%) to generate a 10-point 3-fold serial dilution curve (30,000 nM to 2 nM final concentration). They were mixed with cells and stimulating ligand in a 384-well microtitre plate and incubated for 18 h. SEAP activity was determined in the supernatant using the colorimetric substrate QUANTI-Blue™ (InvivoGen). Percentage inhibitions for compound dilutions were calculated between a DMSO control and maximum inhibition (by excess control compound) and an IC$_{50}$ calculated using XLfit™ (4 parameter logistic model) in ActivityBase.

When tested in the above assay, the compounds of the accompanying Examples were all found to exhibit IC$_{50}$ values of 50 μM or better.

EXAMPLES

| Abbreviations | |
|---|---|
| DCM: dichloromethane | EtOAc: ethyl acetate |
| DMF: N,N-dimethylformamide | MeOH: methanol |
| DMSO: dimethylsulfoxide | EtOH: ethanol |
| Et$_2$O: diethyl ether | MeCN: acetonitrile |
| THF: tetrahydrofuran | DIPEA: N,N-diisopropylethylamine |
| DAST: diethylaminosulfur trifluoride | LDA: lithium diisopropylamide |
| mCPBA: 3-chloroperoxybenzoic acid | Pd(OAc)$_2$: palladium(II) acetate |
| NMP: 1-methyl-2-pyrrolidinone | DBU: 1,8-diazabicyclo[5.4.0]undec-7-ene |
| TFA: trifluoroacetic acid | DME: 1,2-dimethoxyethane |
| pTSA: p-toluenesulfonic acid | TBAF: tetra-n-butylammonium fluoride |
| SiO$_2$: silica | h: hour |
| r.t.: room temperature | RT: retention time |
| br: broad | M: mass |
| HPLC: High Performance Liquid Chromatography | |
| LCMS: Liquid Chromatography Mass Spectrometry | |
| ES+: Electrospray Positive Ionisation | |
| brine: aqueous sodium chloride solution | |
| EDC: 1-(3-dimethylaminopropyl)-3-ethylcarbodiimide hydrochloride | |
| HATU: O-(7-azabenzotriazol-1-yl)-N,N,N',N'-tetramethyluronium hexafluorophosphate | |
| TMEDA: N,N,N',N'-tetramethylethylenediamine | |
| Pd(PPh$_3$)$_4$: tetrakis(triphenylphosphine)palladium(0) | |
| Pd(PPh$_3$)$_2$Cl$_2$: bis(triphenylphosphine)dichloropalladium(II) | |
| PdCl$_2$(dppf): [1,1'-bis(diphenylphosphino)ferrocene]dichloropalladium(II) | |
| Pd$_2$(dba)$_3$: tris(dibenzylideneacetone)dipalladium(0) | |
| XPhos: 2-dicyclohexylphosphino-2',4',6'-triisopropylbiphenyl | |
| BINAP: 2,2'-bis(diphenylphosphino)-1,1'-binaphthalene | |

Nomenclature

Compounds were named with the aid of ACD/Name Batch (Network) version 11.01 and/or Accelrys Draw 4.0.

Analytical Conditions

All NMRs were obtained either at 300 MHz or at 400 MHz.

All reactions involving air- or moisture-sensitive reagents were performed under a nitrogen atmosphere using dried solvents and glassware.

Except where otherwise stated, analytical LCMS data were obtained by using Method 1 or 2 below.

Preparative HPLC for all compounds of Intermediates 1-31 and Examples 1-55 that required it was performed using Method 3 below. Preparative HPLC for all library compounds was performed using Method 4 below.

Preparative LCMS for compounds synthesized in accordance with Method J was performed using Method 5 below.

Analytical LCMS data for Examples 56-403, 410-443, 446-488, 500-507, 512, 519-523 and 525-528 were obtained using Method 6 below. Analytical LCMS data for Examples 404-409, 444, 445, 489-499, 508-511, 513-518 and 524 were obtained using Method 7 below.

All quoted LCMS RT and QC RT values are in minutes.

Method 1:

Waters X-Bridge, C18, 2.1×20 mm, 2.5 μm column.
Mobile phase A: 10 mM ammonium formate in water+0.1% formic acid
Mobile phase B: acetonitrile+5% mobile phase A+0.1% formic acid
Gradient program (flow rate 1.0 mL/min, column temperature 40° C.):

| Time | A % | B % |
|---|---|---|
| 0.00 | 95.0 | 5.0 |
| 4.00 | 5.0 | 95.0 |
| 5.00 | 5.0 | 95.0 |
| 5.10 | 95.0 | 5.0 |

Method 2:

Waters XBridge, C18, 2.1×20 mm, 2.5 μm column.
Mobile phase A: 10 mM ammonium formate in water+0.1% ammonia solution
Mobile phase B: acetonitrile+5% solvent A2+0.1% ammonia solution
Gradient program (flow rate 1.0 mL/min, column temperature 40° C.):

| Time | A % | B % |
|---|---|---|
| 0.00 | 95.0 | 5.0 |
| 4.00 | 5.0 | 95.0 |
| 5.00 | 5.0 | 95.0 |
| 5.10 | 95.0 | 5.0 |

Method 3:

Luna C18, 21.2 mm, 5 mm column, pH 2.5.
Mobile phase A: 99.92% water and 0.08% formic acid.
Mobile phase B: 99.92% acetonitrile and 0.08% formic acid.
Gradient program (flow rate 25 mL/min, column temperature ambient): variable gradient.

Method 4:

Waters XBridge Prep MS C18 ODB, 30×50 mm, 5 μm column.
Mobile phase A: water.
Mobile phase B: acetonitrile.
Mobile Phase C: NH$_4$HCO$_2$ in water (40 g/5 L).
Gradient program (flow rate 35 mL/min to 60 mL/min):

| Time | A % | B % | C % | flow rate |
|---|---|---|---|---|
| 0.00 | 85.0 | 5.0 | 10.0 | 35 |
| 1.00 | 85.0 | 5.0 | 10.0 | 35 |
| 7.00 | 80.0 | 20.0 | 0.0 | 35 |
| 7.50 | 5.0 | 95.0 | 0.0 | 35 |
| 9.00 | 5.0 | 95.0 | 0.0 | 35 |
| 9.10 | 5.0 | 95.0 | 0.0 | 60 |
| 12.00 | 5.0 | 95.0 | 0.0 | 60 |
| 12.50 | 90.0 | 10.0 | 0.0 | 35 |
| 13.00 | 85.0 | 5.0 | 10.0 | 35 |
| 16.00 | 85.0 | 5.0 | 10.0 | 35 |

Method 5:

Column: Waters X-Select C-18, 150×19 mm, 5 μm ODB in combination with Waters X-Select guard C-18, 10×19 mm, 5 μm Eluent A: 99% acetonitrile+1% 10 mM ammonium bicarbonate (pH 9.5) in MilliQ water Eluent B: 10 mM ammonium bicarbonate (pH 9.5) in MilliQ water Flow: 25 mL/min Collection: Mass and UV Gradient: 0 min 70% B, 3.0 min 70% B, 10.0 min 30% B, 10.01 min 0% B, 17.5 min 0% B, 17.51 min 70% B, 19.5 min 70% B Method 6

Waters Acquity SQD (QC LCMS)

The Waters Acquity SQD system comprises an Acquity PDA, Acquity Column Manager, Acquity Sample Manager and Acquity Sample Organiser, Acquity Binary Solvent Manager and a Waters SQD mass spectromter. The system is controlled via MassLynx 4.1.

| | |
|---|---|
| PDA | C11UPD846A |
| Column Manager | C11UPM180G |
| Sample Manager | M10UPA441M |
| Sample Organiser | F11UPO132M |
| Binary Solvent Manager | E11UPB007A |
| SQD Mass Spectrometer | LBA746 |

SQD Mass Spectrometer—ESI Source

| | |
|---|---|
| Capillary Voltage | 0.56 kV |
| Cone Voltage | 55 V |
| Extractor Voltage | 6 V |
| RF Lens | 0.2 V |
| Source Temperature | 150° C. |
| Desolvation Temperature | 350° C. |
| Desolvation Gas | 700 L/hour |
| Cone Gas | 0 L/hour |
| Mass Range | 150-650 amu |
| Scan Time | 0.1 seconds |

Chromatography

| | |
|---|---|
| Column | Waters Acquity UPLC BEH C18, 2.1 × 50 mm, 1.7 μm |
| Injection Volume | 1-5 μL |
| UV data | 210 to 400 nm |
| Sample Temperature | Ambient |
| Column Temperature | 40° C. |
| Flow Rate | 1 mL/min |
| Solvent A2 | 10 mM ammonium formate + 0.1% ammonia |
| Solvent B2 | 95% MeCN + 5% H$_2$O + 0.1% ammonia |

Gradient:

| Time | A % | B % |
|------|-----|-----|
| 0.00 | 95.0 | 5.0 |
| 0.50 | 95.0 | 5.0 |
| 1.75 | 5.0 | 95.0 |
| 2.00 | 5.0 | 95.0 |
| 2.25 | 95.0 | 5.0 |

Method 7:
Column: X-Select (50×2.1 mm, 3.5 μm)
Flow: 0.8 mL/min
Column temp: 25° C.
Eluent A: 95% acetonitrile+5% 10 mM ammonium bicarbonate
Eluent B: 10 mM ammonium bicarbonate in water
Lin. Gradient: 0 min 5% A, 3.5 min 98% A, 6 min 98% A
Detection: DAD (220-320 nm)
Detection: MSD (ESI pos/neg) mass range 100-800

Intermediate 1

(1H-Benzimidazol-2-yl)methanol

To a mixture of benzene-1,2-diamine (5.0 g, 46.3 mmol) and glycolic acid (10.5 g, 138.0 mmol) was added 4N HCl (30 mL). The reaction mixture was heated under reflux at 95° C. for 2 h, then cooled to 0° C. and neutralized with saturated aqueous NaOH. The precipitated solid was isolated by filtration and dried in vacuo to afford the title compound (5 g, 73%) as an off-white solid. $\delta_H$ (d$_6$-DMSO) 12.20 (br s, 1H), 7.49-7.47 (dd, J 5.8, 3.2 Hz, 2H), 7.13-7.11 (dd, J 5.8, 3.2 Hz, 2H), 4.68 (s, 2H). LCMS (ES$^+$) 149 (M+H)$^+$.

Intermediate 2

1-(2,5-Dimethylbenzyl)-1H-benzimidazole

Cesium carbonate (22.0 g, 100.0 mmol) and n-butylammonium iodide (12.5 g, 34.0 mmol) were added to a solution of benzimidazole (4.0 g, 34.0 mmol) in DMF (60 mL) at 0° C. The reaction mixture was stirred for 10 minutes at 0° C. and then 2,5-dimethylbenzyl bromide (6.7 g, 34.0 mmol) was added. The reaction mixture was allowed to warm to r.t. and stirred for 3 h. The mixture was quenched with ice-cold water (50 mL) and extracted with ethyl acetate (3×40 mL). The organic layers were dried over anhydrous sodium sulphate and the solvent was removed in vacuo to afford the title compound (8.0 g, 75%) as an off-white solid. $\delta_H$ (d$_6$-DMSO) 8.23 (s, 1H), 7.68-7.66 (m, 1H), 7.43-7.41 (m, 1H), 7.21-7.19 (m, 2H), 7.10 (d, J 7.6 Hz, 1H), 7.01 (d, J 7.6 Hz, 1H), 6.67 (s, 1H), 5.45 (s, 2H), 2.25 (s, 3H), 2.14 (s, 3H). LCMS (ES$^+$) 237 (M+H)$^+$.

Intermediate 3

2-(Azidomethyl)-1-(2,5-dimethylbenzyl)-1H-benzimidazole

Sodium azide (0.22 g, 3.30 mmol) was added to a solution of 2-(chloromethyl)-1H-benzimidazole (0.50 g, 3.00 mmol) in DMF (3 mL) and stirred at r.t. for 3 h. 2,5-Dimethylbenzyl bromide (0.72 g, 3.60 mmol) was added to the reaction mixture, followed by potassium carbonate (1.04 g, 7.50 mmol), and the reaction mixture was stirred at r.t. for 18 h. Water (10 mL) was added and the mixture was poured into ethyl acetate/water.

The organic layer was separated, dried (MgSO$_4$) and concentrated in vacuo to afford the title compound (824 mg, 94%) as a yellow solid. $\delta_H$ (d$_6$-DMSO) 7.73 (m, 1H), 7.37 (m, 1H), 7.24 (m, 2H), 7.13 (d, J 7.6 Hz, 1H), 6.98 (m, 1H), 6.15 (s, 1H), 5.50 (s, 2H), 4.70 (s, 2H), 2.32 (s, 3H), 2.06 (s, 3H). LCMS (ES$^+$) 292 (M+H)$^+$.

Intermediate 4

2-(Pyridin-4-ylmethyl)-1H-benzimidazole

Benzene-1,2-diamine (0.67 g, 6.18 mmol) and pyridin-4-ylacetic acid hydrochloride (1.61 g, 9.25 mmol) were stirred at 110° C. in 5M HCl (5 mL) for 18 h. The reaction mixture was neutralised with saturated aqueous sodium carbonate solution and partitioned with ethyl acetate. The organic layer was separated, dried (MgSO$_4$) and concentrated in vacuo to give a brown oil. The oil was redissolved in the minimum quantity of hot ethyl acetate and the solution left to cool to provide the desired product as pale crystals. The precipitate was filtered off and dried in vacuo to afford the title compound (285 mg, 22%) as pale yellow crystals. $\delta_H$ (d$_6$-DMSO) 12.34 (s, 1H), 8.51 (m, 2H), 7.48 (m, 2H), 7.34 (d, J 5.8 Hz, 2H), 7.15 (dd, J 6.0, 2.5 Hz, 2H), 4.22 (s, 2H). LCMS (ES$^+$) 210 (M+H)$^+$.

Intermediate 5

N-(2,5-Dimethylbenzyl)-2-nitroaniline

Sodium hydride (60% dispersion in mineral oil, 7.81 g, 195.0 mmol) was added to a stirred solution of 2-nitroaniline (30.0 g, 217.0 mmol) in DMF (20 mL) at 0° C. After 10 minutes, 2,5-dimethylbenzyl bromide (43.28 g, 217.0 mmol) was added and the reaction mixture was stirred at r.t. for 18 h, quenched with water and extracted with ethyl acetate (3×50 mL). The organic layer was separated, dried (MgSO$_4$) and concentrated in vacuo and the residue was purified by column chromatography (SiO$_2$, 5% EtOAc/hexane), yielding the title compound (30.0 g, 54%) as a yellow solid. $\delta_H$ (d$_6$-DMSO) 8.40 (t, J 5.2 Hz, 1H), 8.09 (dd, J 8.4, 1.2 Hz, 1H), 7.48 (t, J 7.6 Hz, 1H), 7.09 (d, J 8.4 Hz, 1H), 7.03 (s, 1H), 6.99 (d, J 7.6 Hz, 1H), 6.89 (d, J 8.4 Hz, 1H), 6.69 (td, J 7.6, 1.2 Hz, 1H), 4.53 (d, J 5.6 Hz, 2H), 2.28 (s, 3H), 2.20 (s, 3H).

Intermediate 6

N$^1$-(2,5-Dimethylbenzyl)benzene-1,2-diamine

Pd—C (20% w/w, 0.176 g) was added to a stirred solution of Intermediate 5 (8.8 g, 34.0 mmol) in ethyl acetate (100 mL) and the mixture was stirred at r.t. for 18 h under an atmosphere of H$_2$. The reaction mixture was filtered through a celite pad and concentrated in vacuo to give a residue which was purified by column chromatography (SiO$_2$, 15% EtOAc/hexane), yielding the title compound (10.8 g, 90%) as a brown solid. $\delta_H$ (d$_6$-DMSO) 7.10 (s, 1H), 7.05 (d, J 7.6 Hz, 1H), 6.95 (d, J 7.6 Hz, 1H), 6.55 (dd, J 7.2, 1.6 Hz, 1H), 6.46-6.38 (m, 2H), 6.32 (dd, J 7.2, 1.6 Hz, 1H), 4.77 (d, J 5.2 Hz, 1H), 4.56 (s, 2H), 4.16 (d, J 5.6 Hz, 1H), 2.28 (s, 3H), 2.21 (s, 3H). LCMS (ES$^+$) 357 (M+H)$^+$.

Intermediate 7

1-[1-(2,5-Dimethylbenzyl)-1H-benzimidazol-2-yl]ethanol

To Intermediate 6 (0.25 g, 1.11 mol), dissolved in 5M HCl (5 mL), was added sodium lactate (1.24 g, 11.1 mmol) and the reaction mixture was heated at 110° C. for 4.5 h. The reaction mixture was neutralised with saturated aqueous sodium carbonate solution (10 mL) and partitioned with ethyl acetate (20 mL). The organic layer was separated, dried (MgSO$_4$) and concentrated in vacuo. The residue was purified by column chromatography (SiO$_2$, 1:1 EtOAc/hexane), yielding the title compound (0.17 g, 55%) as a brown solid. $\delta_H$ (d$_6$-DMSO) 7.66 (d, J 7.1 Hz, 1H), 7.24 (m, 1H), 7.15 (m, 3H), 6.95 (d, J 7.6 Hz, 1H), 6.15 (s, 1H), 5.60 (d, J 6.3 Hz, 1H), 5.55 (s, 2H), 4.91 (quint, J 6.5 Hz, 1H), 2.35 (s, 3H), 2.03 (s, 3H), 1.53 (d, J 6.5 Hz, 3H). LCMS (ES$^+$) 281 (M+H)$^+$.

Intermediate 8

2-Nitro-N-(1-phenylethyl)aniline

Triethylamine (20 mL, 141.0 mmol) was added to stirred solution of 1-fluoro-2-nitrobenzene (10.0 g, 70 mmol) and α-methylbenzylamine (17.1 g, 141.0 mmol) in ethanol (50 mL) at 0° C. The reaction mixture was heated to 80° C. for 6 h and concentrated in vacuo, and the residue was extracted with ethyl acetate (3×50 mL). The organic layer was washed with saturated brine (2×20 mL), extracted, dried (MgSO$_4$) and concentrated in vacuo to give the title compound (12.0 g, 70%) as a yellow solid. $\delta_H$ (CDCl$_3$) 8.42 (br s, 1H), 8.17 (dd, J 8.4, 0.8 Hz, 1H), 7.34-7.23 (m, 6H), 6.64-6.58 (m, 2H), 4.72-4.65 (m, 1H), 1.64 (d, J 6.8 Hz, 3H).

Intermediate 9

N$^1$-(1-Phenylethyl)benzene-1,2-diamine

Zinc (61.56 g, 941.0 mmol) and ammonium formate (49.2 g, 780.0 mol) were added to a stirred solution of Intermediate 8 (38.0 g, 156.0 mmol) in methanol (300 mL) at 0° C. The reaction mixture was warmed to r.t and stirred for 5 h. The reaction mixture was filtered through a celite pad and concentrated in vacuo to give a residue which was purified by column chromatography (SiO$_2$, 10% EtOAc/hexane), yielding the title compound (25 g, 75%) as a brown solid. $\delta_H$ (d$_6$-DMSO) 7.35 (d, J 8.4 Hz, 1H), 7.27 (t, J 7.6 Hz, 2H), 7.16 (t, J 7.6 Hz, 2H), 6.50 (d, J 7.2 Hz, 1H), 6.33-6.26 (m, 2H), 6.15 (d, J 8.4 Hz, 1H), 4.83 (d, J 6.4 Hz, 1H), 4.63 (s, 2H), 4.46 (t, J 6.8 Hz, 1H), 1.44 (d, J 7.2 Hz, 3H). LCMS (ES$^+$) 213 (M+H)$^+$.

Intermediate 10

Method A

[1-(1-Phenylethyl)-1H-benzimidazol-2-yl]methanol

A mixture of Intermediate 9 (20.0 g, 94.0 mmol) and glycolic acid (21.5 g, 282.0 mol) in methanol (20 mL) was heated to 80° C. for 18 h. The reaction mixture was concentrated in vacuo and the residue triturated with diethyl ether to afford the title compound (15.0 g, 63%) as an off-white solid. $\delta_H$ (d$_6$-DMSO) 7.58 (d, J 7.6 Hz, 1H), 7.36-7.28 (m, 4H), 7.11-6.97 (m, 4H), 6.14-6.08 (m, 1H), 5.76 (t, J 5.6 Hz, 1H), 4.82 (d, J 5.6 Hz, 2H), 1.93 (d, J 6.8 Hz, 3H). LCMS (ES$^+$) 253 (M+H)$^+$.

Intermediate 11

1-(1-Phenylethyl)-1H-benzimidazole

Sodium hydride (4.40 g, 110.0 mmol) was added to a solution of benzimidazole (11.8 g, 100.0 mmol) in DMF (20 mL) at 0° C. The reaction mixture was stirred for 10 minutes at 0° C., then α-methylbenzyl bromide (100.0 mmol, 18.5 g) was added and the reaction mixture was allowed to warm to r.t. and heated to 60° C. for 1 h. The reaction mixture was quenched with saturated aqueous sodium bicarbonate solution (50 mL) and extracted with ethyl acetate (3×40 mL). The organic layers were dried over anhydrous sodium sulphate and concentrated in vacuo. The residue was purified by column chromatography (SiO$_2$, 20-100% EtOAc/isohexane), yielding the title compound (0.85 g, 7%) as a white solid. $\delta_H$ (d$_6$-DMSO) 8.54 (s, 1H), 7.67-7.63 (m, 1H), 7.43-7.40 (m, 1H), 7.33-7.25 (m, 5H), 7.17-7.12 (m, 2H), 5.48 (q, J 7.1 Hz, 1H), 1.96 (d, J 7.1 Hz, 3H).

Intermediate 12

5-Bromo-2-nitro-N-(1-phenylethyl)aniline

Triethylamine (37.9 mL, 272.0 mmol) was added to a stirred solution of 4-bromo-2-fluoro-1-nitrobenzene (30.0 g, 136.0 mmol) and α-methylbenzylamine (32.9 g, 272.0 mmol) in ethanol (200 mL) at 0° C. The reaction mixture was heated to 80° C. for 6 h, then cooled and concentrated in vacuo. The residue was dissolved in EtOAc (90 mL) and washed with saturated brine (2×30 mL). The combined organics were extracted and dried over anhydrous sodium sulfate and concentrated in vacuo to give a yellow solid. The residue was triturated with isohexane, yielding the title compound (32.0 g, 74%) as a yellow solid. $\delta_H$ (CDCl$_3$) 8.43 (br s, 1H), 8.01 (d, J 8.0 Hz, 1H), 7.48-7.26 (m, 5H), 6.83 (s, 1H), 6.70 (d, J 8.8 Hz, 1H), 4.68-4.61 (m, 1H), 1.64 (d, J 6.8 Hz, 3H).

Intermediate 13

5-Bromo-N$^1$-(1-phenylethyl)benzene-1,2-diamine

Zinc (13.4 g, 205.0 mmol) and ammonium formate (10.79 g, 171.0 mmol) were added to a stirred solution of Intermediate 12 (11.0 g, 34.2 mol) in MeOH (150 mL) at 0° C. The reaction mixture was stirred at r.t. for 5 h. The reaction mixture was filtered through a celite pad and concentrated in vacuo to give a residue which was purified by column chromatography (SiO$_2$, 10% EtOAc/isohexane), yielding the title compound (9.0 g, 90%) as a yellow solid. $\delta_H$ (d$_6$-DMSO) 7.35-7.16 (m, 5H), 6.42 (s, 2H), 6.20 (s, 1H), 5.13 (d, J 6.4 Hz, 1H), 4.86 (br s, 2H), 4.46-4.43 (m, 1H), 1.43 (d, J 6.4 Hz, 3H). LCMS (ES$^+$) 291 (M+H)$^+$.

Intermediate 14

[6-Bromo-1-(1-phenylethyl)-1H-benzimidazol-2-yl]methanol

The title compound was prepared from Intermediate 13 and glycolic acid in accordance with Method A. $\delta_H$ (d$_6$-DMSO) 7.69 (m, 1H), 7.53 (dd, J 8.6, 1.7 Hz, 1H), 7.41 (m, 6H), 6.18 (q, J 7.1 Hz, 1H), 4.96 (m, 2H), 1.97 (d, J 7.1 Hz, 3H). LCMS (ES$^+$) 333 (M+H)$^+$.

Intermediate 15

5-Bromo-2-nitroaniline

2-Fluoro-4-bromo-1-nitrobenzene (0.5 g, 2.2 mmol) was added to methanolic ammonia (10 mL) and stirred at r.t. for 18 h. The reaction mixture was then concentrated in vacuo and the residue was triturated with isohexane, yielding the title compound (0.48 g, 97%) as a yellow solid. $\delta_H$ (d$_6$-DMSO) 7.88 (d, J 8.8 Hz, 1H), 7.53 (br s, 2H), 7.25 (d, J 3.0 Hz, 1H), 6.75 (dd, J 9.2, 2.0 Hz, 1H).

Intermediate 16

5-Bromo-N-(2,5-dimethylbenzyl)-2-nitroaniline

Sodium hydride (60% dispersion in oil, 0.82 g, 20.7 mmol) was added to a stirred solution of Intermediate/5 (5.0 g, 23.0 mmol) in DMF (50 mL) at 0° C. 2,5-Dimethylbenzyl bromide (4.56 g, 23.0 mmol) was added and the reaction mixture was warmed to r.t. and stirred for 5 h. The reaction mixture was quenched with saturated aqueous ammonium chloride solution, extracted with ethyl acetate (3×50 mL), washed with water (2×30 mL), dried over anhydrous sodium sulfate and concentrated in vacuo. The residue was purified by column chromatography (SiO$_2$, 5% EtOAc/isohexane), yielding the title compound (4.89 g, 63%) as a yellow solid. $\delta_H$ (d$_6$-DMSO) 8.42 (br s, 1H), 8.01 (d, J 8.8 Hz, 1H), 7.12-6.86 (m, 4H), 6.85 (d, J 7.2, 1.6 Hz, 1H), 4.54 (d, J 5.6 Hz, 2H), 2.28 (s, 3H), 2.21 (s, 3H).

Intermediate 17

5-Bromo-N$^1$-(2,5-dimethylbenzyl)benzene-1,2-diamine

SnCl$_2$ (20.2 g, 89.4 mmol) was added to a stirred solution of Intermediate 16 (10.0 g, 29.8 mmol) in EtOH (200 mL) and the reaction mixture was heated to 80° C. for 5 h. The reaction mixture was then concentrated in vacuo and the residue neutralized with saturated aqueous sodium bicarbonate solution and extracted with DCM (3×100 mL). The combined organics were washed with water (2×50 mL), extracted, dried over anhydrous sodium sulfate and concentrated in vacuo. The residue was purified by column chromatography (SiO$_2$, 5% MeOH/DCM), yielding the title compound (5.4 g, 69%) as a dark brown oil. $\delta_H$ (d$_6$-DMSO) 7.08 (s, 1H), 7.06 (d, J 7.6 Hz, 2H), 6.97 (d, J 7.6 Hz, 1H), 6.53 (dd, J 8.4, 2.0 Hz, 1H), 6.47 (d, J 8.0 Hz, 1H), 6.45 (d, J 2.0 Hz, 1H), 5.06 (t, J 5.4 Hz, 1H), 4.77 (br s, 2H), 4.15 (d, J 5.2 Hz, 1H), 2.27 (s, 3H), 2.22 (s, 3H). LCMS (ES$^+$) 305 (M+H)$^+$.

Intermediate 18

[6-Bromo-1-(2,5-dimethylbenzyl)-1H-benzimidazol-2-yl]methanol

The title compound was prepared from Intermediate 17 and glycolic acid in accordance with Method A. $\delta_H$ (d$_6$-DMSO) 7.60 (m, 2H), 7.33 (dd, J 7.2, 1.2 Hz, 1H), 7.12 (d, J 7.6 Hz, 1H), 6.97 (d, J 7.6 Hz, 1H), 6.09 (s, 1H), 5.66 (t, J 5.6 Hz, 1H), 5.52 (s, 2H), 4.60 (d, J 6.0 Hz, 2H), 2.32 (s, 3H), 2.04 (s, 3H). LCMS (ES$^+$) 347 (M+H)$^+$.

Intermediate 19

2-(Chloromethyl)-1-(2,5-dimethylbenzyl)-1H-benzimidazole

Thionyl chloride (33.3 g, 281.0 mmol) was added to a stirred solution of Example 1 (25.0 g, 93.0 mmol) in DCM (500 mL) at 0° C. The reaction mixture was warmed to r.t. and stirred for 2 h. The reaction mixture was concentrated in vacuo and the residue triturated with ether, yielding the title compound (16.0 g, 71%) as an off-white solid. $\delta_H$ (d$_6$-DMSO) 7.79 (d, J 7.6 Hz, 1H), 7.42-7.35 (m, 3H), 7.14 (d, J 8.0 Hz, 1H), 7.00 (d, J 7.2 Hz, 1H), 6.30 (s, 1H), 5.64 (s, 2H), 5.15 (s, 2H), 2.33 (s, 3H), 2.06 (s, 3H). LCMS (ES$^+$) 285 (M+H)$^+$.

Intermediate 20

Method G

N-{4-Bromo-2-[(2,5-dimethylbenzyl)amino]phenyl}-2-(pyridin-4-ylmethyl)acetamide

4-Pyridylacetic acid hydrochloride (14.8 g, 108.0 mol) was added to a stirred solution of Intermediate 17 (22.0 g, 72.0 mmol) in DCM (400 mL) at 0° C., followed by the addition of HATU (41.1 g, 108.0 mmol) and DIPEA (24.8 mL, 144.0 mmol). The reaction mixture was stirred at r.t. for 18 h. Water (100 mL) was added and the organic layer was washed with saturated aqueous sodium bicarbonate solution. The organics were extracted, dried over sodium sulphate, and concentrated in vacuo. The residue was purified by column chromatography (SiO$_2$, 7% MeOH/DCM), yielding the title compound (31.0 g, 85%) as a yellow solid. $\delta_H$ (d$_6$-DMSO) 9.56 (br s, 1H), 8.67 (d, J 6.0 Hz, 2H), 7.68 (d, J 6.0 Hz, 2H), 7.09-7.07 (m, 3H), 6.98 (d, J 7.6 Hz, 1H), 6.71 (dd, J 7.2, 2.0 Hz, 1H), 6.64 (d, J 2.0 Hz, 1H), 5.68 (br s, 1H), 4.22 (s, 2H), 3.90 (s, 2H), 2.26 (s, 3H), 2.20 (s, 3H). LCMS (ES$^+$) 424 (M+H)$^+$.

Intermediate 21

Method H

6-Bromo-1-(2,5-dimethylbenzyl)-2-(pyridin-4-ylmethyl)-1H-benzimidazole

4N HCl (45 mL) was added to Intermediate 20 (30.0 g, 70.0 mmol) and the mixture was heated to 80° C. for 5 h, then cooled to 0° C. and neutralized with saturated aqueous sodium bicarbonate solution. The mixture was extracted with ethyl acetate (2×200 mL), dried over anhydrous sodium sulfate and concentrated in vacuo. The residue was purified by column chromatography (SiO$_2$, 4% MeOH/DCM), yielding the title compound (22.0 g, 89%) as a white solid. $\delta_H$ (d$_6$-DMSO) 8.38 (dd, J 6.4, 1.2 Hz, 2H), 7.65 (d, J 1.2 Hz, 1H), 7.64 (dd, J 13.6, 3.6 Hz, 1H), 7.34-7.31 (m, 2H), 7.18 (d, J 4.8 Hz, 1H), 7.07 (d, J 7.6 Hz, 1H), 6.90 (d, J 7.6 Hz, 1H), 5.78 (s, 1H), 5.47 (s, 2H), 4.23 (s, 2H), 2.29 (s, 3H), 1.92 (s, 3H). LCMS (ES$^+$) 408 (M+H)$^+$.

Intermediate 22

N-{4-Bromo-2-[(1-phenylethyl)amino]phenyl}-2-(pyridin-4-yl)acetamide

The title compound was prepared from Intermediate 13 and 4-pyridylacetic acid hydrochloride in accordance with Method G. $\delta_H$ (d$_6$-DMSO) 9.60 (br s, 1H), 8.53 (d, J 4.8 Hz, 2H), 7.40-7.19 (m, 7H), 7.07 (d, J 8.8 Hz, 1H), 6.65 (dd, J 8.4, 1.6 Hz, 1H), 6.47 (d, J 1.6 Hz, 1H), 5.38 (d, J 6.4 Hz, 1H), 4.55-4.52 (m, 1H), 3.77 (s, 2H), 1.39 (d, J 6.8 Hz, 3H). LCMS (ES$^+$) 410 (M+H)$^+$.

Intermediate 23

6-Bromo-1-(1-phenylethyl)-2-(pyridin-4-ylmethyl)-1H-benzimidazole

The title compound was prepared from Intermediate 22 in accordance with Method H. $\delta_H$ ($d_6$-DMSO) 8.47 (d, J 5.2 Hz, 2H), 7.55 (d, J 8.4 Hz, 2H), 7.34-7.14 (m, 8H), 6.01-5.96 (m, 1H), 4.41 (s, 2H), 1.76 (d, J 6.8 Hz, 3H). LCMS (ES$^+$) 394 (M+H)$^+$.

Intermediate 24

(Benzimidazol-1-yl)(2,5-dimethylphenyl)amine

Benzimidazol-1-ylamine (0.55 g, 4.1 mmol), 2-bromo-1,4-dimethylbenzene (0.84 g, 4.5 mmol), cesium carbonate (2.67 g, 8.3 mmol), tris(dibenzylideneacetone)-dipalladium (0) (0.19 g, 0.21 mmol) and 2-dicyclohexylphosphino-2',4',6'-triisopropylbiphenyl (0.39 g, 0.83 mmol) were dissolved in anhydrous DMF (40 mL). The reaction mixture was degassed and then heated at 100° C. for 4 h. The reaction mixture was concentrated in vacuo and partitioned between water (50 mL) and ethyl acetate (50 mL). The organic layer was extracted, dried with sodium sulfate and concentrated in vacuo. The residue was purified by column chromatography (SiO$_2$, 5% MeOH/DCM), yielding the title compound (0.54 g, 55%) as a white solid. $\delta_H$ ($d_6$-DMSO) 8.95 (s, 1H), 8.34 (s, 1H), 7.77-7.70 (m, 1H), 7.29-7.22 (m, 3H), 7.03 (d, J 7.5 Hz, 1H), 6.62-6.58 (m, 1H), 5.67 (s, 1H), 2.28 (s, 3H), 1.99 (s, 3H). LCMS (ES$^+$) 238 (M+H)$^+$.

Intermediate 25

2-(Pyridin-4-yl)propionic acid ethyl ester

Iodomethane (0.39 mL, 6.4 mmol) and sodium hydride (60% dispersion in mineral oil, 0.23 g, 6.4 mmol) were added to a solution of ethyl 4-pyridylacetate (1.0 g, 6.1 mmol) in anhydrous THF (60 mL). The reaction mixture was stirred at room temperature for 48 h and then concentrated in vacuo. The remaining oil was partitioned between DCM (100 mL) and aqueous NaHCO$_3$ solution (100 mL). The organic layer was separated, dried with sodium sulphate and concentrated in vacuo. The residue was purified by column chromatography (SiO$_2$, 5% MeOH/DCM), yielding the title compound (0.34 g, 31%) as a clear oil. $\delta_H$ ($d_6$-DMSO) 8.54-8.50 (m, 2H), 7.32-7.29 (m, 2H), 4.08 (qd, J 7.1, 1.2 Hz, 2H), 3.84 (q, J 7.1 Hz, 1H), 1.40 (d, J 7.1 Hz, 3H), 1.14 (t, J 7.1 Hz, 3H). LCMS (ES$^+$) 180 (M+H)$^+$.

Intermediate 26

{1-[2-Methyl-5-(trifluoromethyl)benzyl]-1H-benzimidazol-2-yl}methanol

The title compound was prepared from Intermediate 1 and 2-methyl-5-(trifluoromethyl)benzyl chloride in DCM, in accordance with Method B. LCMS (ES$^+$) 321 (M+H)$^+$.

Intermediate 27

[1-(2-Chloro-5-nitrobenzyl)-1H-benzimidazol-2-yl]methanol

The title compound was prepared from Intermediate 1 and 2-chloro-5-nitrobenzyl chloride in DCM, in accordance with Method B. LCMS (ES$^+$) 318 (M+H)$^+$.

Intermediate 28

[1-(5-Amino-2-chlorobenzyl)-1H-benzimidazol-2-yl]methanol

To Intermediate 27 (0.10 g, 0.32 mmol) dissolved in ethanol (10 mL) under an atmosphere of hydrogen gas was added Pd/C (0.01 g) and the reaction mixture was stirred at r.t. for 18 h. The catalyst was filtered off, and the reaction mixture was concentrated in vacuo. The residue was purified by reverse phase preparative HPLC, yielding the title compound (0.04 g, 49%) as a white solid. $\delta_H$ ($d_6$-DMSO) 7.65 (m, 1H), 7.31 (m, 1H), 7.20 (m, 2H), 7.11 (d, J 8.5 Hz, 1H), 6.46 (dd, J 8.5, 2.3 Hz, 1H), 5.80 (d, J 2.0 Hz, 1H), 5.64 (t, J 4.8 Hz, 1H), 5.50 (s, 2H), 5.13 (s, 2H), 4.68 (d, J 4.6 Hz, 2H). LCMS (ES$^+$) 288 (M+H)$^+$.

Intermediate 29

6-Bromo-1-(2,5-dimethylbenzyl)-1H-benzimidazole

A mixture of Intermediate 17 (0.40 g, 1.31 mmol) and formic acid (10 mL) was stirred at r.t. for 18 h. The reaction mixture was concentrated in vacuo and the residue partitioned between ethyl acetate and saturated aqueous sodium bicarbonate solution. The organic layer was dried over anhydrous sodium sulphate and concentrated in vacuo. The crude residue was purified by column chromatography (SiO$_2$, 20-75% EtOAc/isohexane), yielding the title compound (0.20 g, 48%) as a white solid. $\delta_H$ ($d_6$-DMSO) 8.24 (s, 1H), 7.74 (d, J 1.7 Hz, 1H), 7.64 (d, J 8.6 Hz, 1H), 7.34 (dd, J 8.6, 1.9 Hz, 1H), 7.12 (d, J 7.7 Hz, 1H), 7.02 (d, J 7.8 Hz, 1H), 6.61 (s, 1H), 5.47 (s, 2H), 2.24 (s, 3H), 2.15 (s, 3H). LCMS (ES$^+$) 316 (M+H)$^+$.

Intermediate 30

[6-Bromo-1-(2,5-dimethylbenzyl)-1H-benzimidazol-2-yl](pyridin-4-yl)methanol To diisopropylamine (2.8 mL) in THF (10 mL), cooled to 0° C., was added n-BuLi (12.5 mL, 1.6M in hexanes) and the resulting mixture was stirred at 0° C. for 10 minutes. An aliquot of this freshly prepared LDA (1.8 mL, 1.62 mmol) was added to a solution of Intermediate 29 (0.25 g, 0.81 mmol) in THF (5 mL) at −78° C. The reaction mixture was stirred for 2 h at −78° C., then pyridine-4-carboxaldehyde (0.15 mL, 1.62 mmol) was added and the reaction mixture was stirred at −78° C. for 10 minutes. The mixture was quenched with saturated aqueous sodium chloride solution and allowed to warm to r.t. The mixture was extracted with ethyl acetate (3×40 mL). The organic layers were dried over anhydrous sodium sulphate and concentrated in vacuo. The residue was purified by column chromatography (SiO$_2$, 0-10% MeOH/DCM), yielding the title compound (0.18 g, 51%) as a white solid. LCMS (ES$^+$) 423 (M+H)$^+$.

Intermediate 31

1-(2,5-Dimethylbenzyl)-2-(phenylsulfanyl)-1H-benzimidazole

The title compound was prepared from Intermediate 2 and diphenyl disulfide in THF, in accordance with Method B. $\delta_H$ ($d_6$-DMSO) 7.69-7.65 (m, 1H), 7.46-7.44 (m, 2H), 7.39-7.31 (m, 4H), 7.26-7.20 (m, 2H), 7.10 (d, J 7.6 Hz, 1H), 6.94

(d, J 7.6 Hz, 1H), 6.10 (s, 1H), 5.50 (s, 2H), 2.33 (s, 3H), 1.99 (s, 3H). LCMS (ES+) 345 (M+H)+.

Intermediate 32

5-(3-Fluoro-4-nitrophenyl)-2-methoxypyridine

6-Methoxypyridin-3-ylboronic acid (40.0 g, 262 mmol), 4-bromo-2-fluoro-1-nitrobenzene (52.3 g, 238 mmol) and $Na_2CO_3$ (76 g, 713 mmol) were mixed in 1,2-dimethoxyethane (1200 mL) and water (300 mL). The reaction mixture was purged with argon. $Pd(PPh_3)_2Cl_2$ (8.34 g, 11.89 mmol) was added and the mixture was heated to 90° C. for 1.5 h. EtOAc and water were added. The organic phase was separated and the aqueous phase was extracted twice with EtOAc. The combined organic layers were dried over $Na_2SO_4$, after which the solvent was removed in vacuo. The residue was recrystallised from toluene, affording the title compound (42.00 g, 169.2 mmol, 71%). MS [ESI+] m/z: 249 [M+H]+.

Intermediate 33

N-[2-(Difluoromethoxy)benzyl]-5-(6-methoxypyridin-3-yl)-2-nitroaniline 2-(Difluoromethoxy)benzylamine (2.093 g, 12.09 mmol) was dissolved in NMP (20 mL). Intermediate 32 (2 g, 8.06 mmol) and $K_2CO_3$ (1.336 g, 9.67 mmol) were added. This mixture was heated under microwave irradiation at 150° C. for 30 minutes. EtOAc and water were added. The organic phase was separated and the aqueous phase was extracted twice with EtOAc. The combined organic layers were washed three times with water and twice with brine. After drying over $Na_2SO_4$, the solvent was removed in vacuo. The residue was recrystallised from heptane/EtOAc (100/25 mL), to afford the title compound (2.513 g, 6.26 mmol, 78%). MS [ESI+] m/z: 402 [M+H]+.

Intermediate 34

$N^1$-[2-(Difluoromethoxy)benzyl]-5-(6-methoxypyridin-3-yl)benzene-1,2-diamine

Palladium on carbon (1.10 g, 10 wt %) was added to a solution of Intermediate 33 (2.512 g, 6.26 mmol) in EtOAc (150 mL), flushed with argon. The atmosphere was replaced with a $H_2$ atmosphere and the reaction mixture was stirred under 1 bar of $H_2$ for 1 h. The mixture was filtered through a layer of Kieselguhr. The filtrate was concentrated in vacuo. Purification using flash column chromatography with 7-60% EtOAc in heptane afforded the title compound (2.07 g, 5.57 mmol, 89%). MS [ESI+] m/z: 372 [M+H]+.

Intermediate 35

5-{4-Amino-3-[2-(difluoromethoxy)benzylamino]phenyl}pyridin-2(1H)-one

Pyridine hydrochloride (10.64 g, 92 mmol) was added to Intermediate 34 (6.84 g, 18.42 mmol). The reaction mixture was heated to 165° C. in an open vessel for 3 minutes. Water was added and the mixture was sonicated. The precipitate was filtered off and then triturated in boiling acetonitrile. Filtration of the precipitate afforded the title compound (3.822 g, 9.95 mmol, 54%). MS [ESI+] m/z: 358 [M+H]+.

Intermediate 36

N-[(5-Chloro-2-methylthiazol-4-yl)methyl]-5-(6-methoxypyridin-3-yl)-2-nitroaniline To a stirred mixture of (5-chloro-2-methylthiazol-4-yl)methanamine (14.2 g, 77 mmol) and $K_2CO_3$ (15.93 g, 115 mmol) in NMP (250 mL) was added Intermediate 32 (19.07 g, 77 mmol). The resulting mixture was stirred at 60° C. for 16 h. The reaction mixture was poured into water (1.5 L) under stirring, then isopropyl ether (200 mL) and EtOAc (20 mL) were added and stirring was continued. After 2 h the resulting precipitate was collected by filtration. Trituration with isopropyl ether (200 mL) afforded the title compound (31.07 g, 71.5 mmol, 93%). $\delta_H$ (DMSO-$d_6$, 300 MHz) 2.62 (s, 3H); 3.92 (s, 3H); 4.71 (d, 2H, J 5.4 Hz); 6.97 (d, 1H, J 8.7 Hz); 7.05 (dd, 1H, J 1.8, 9.0 Hz); 7.32 (d, 1H, J 1.8 Hz); 8.18 (m, 2H); 8.58 (d, 1H, J 2.4 Hz); 8.68 (m, 1H). MS [ESI+] m/z: 392 [M+H]+.

Intermediate 37

$N^1$-[(5-Chloro-2-methylthiazol-4-yl)methyl]-5-(6-methoxypyridin-3-yl)benzene-1,2-diamine hydrochloride To a stirred solution of $NH_4Cl$ (16.97 g, 317 mmol) in water (400 mL) was added iron powder (17.72 g, 317 mmol). A solution of Intermediate 36 (31.0 g, 79 mmol) in methanol/THF (1:1, 400 mL) was added. The resulting mixture was stirred at 70° C. Water (1 L), methanol (1 L) and EtOAc (1 L) were added under stirring. The mixture was subsequently filtered over Kieselguhr. The layers were separated and the water layer was extracted with EtOAc. The combined organic layers were washed with brine, dried with $Na_2SO_4$ and concentrated in vacuo. The residue was stirred in DCM (100 mL) and then filtered to remove salts. Hydrochloric acid (80 mL, 1M in $Et_2O$) was added with stirring. The precipitate was filtered off and then triturated overnight with water (150 mL). Filtration of the precipitate afforded the title compound (9.85 g, 23.55 mmol, 30%). $\delta_H$ (DMSO-$d_6$, 300 MHz) 2.62 (s, 3H); 4.40 (s, 2H); 6.92 (d, 1H, J 8.7 Hz); 6.98 (d, 1H, J 1.8 Hz); 7.14 (d, 1H, J 1.8 Hz); 7.30 (d, 1H, J 8.1 Hz); 7.97 (dd, 1H, J 2.4, 8.7 Hz); 8.45 (d, 1H, J 2.3 Hz); 9.71 (br s, 2H). 3H OMe signal obscured by DMSO. MS [ESI+] m/z: 362 [M+H]+.

Intermediate 38

5-{4-Amino-3-[(5-chloro-2-methylthiazol-4-ylmethyl)amino]phenyl}-1H-pyridin-2-one The title compound can be synthesized from Intermediate 37 by the method of Intermediate 35.

Intermediate 39

3-[2-(Difluoromethoxy)benzylamino]-4-nitrobenzonitrile

3-Fluoro-4-nitrobenzonitrile (19.19 g, 116 mmol) was added to a mixture of [2-(difluoromethoxy)phenyl]methanamine (20 g, 116 mmol) and $K_2CO_3$ (19.16 g, 139 mmol) in THF (200 mL). After 16 h the reaction mixture was diluted with DCM to a total volume of 1 L and then filtered over Kieselguhr. The filtrate was concentrated in vacuo and stripped with isopropyl ether to yield the title compound (36.8 g, 115 mmol, 100%). MS [ESI+] m/z: 320 [M+H]+.

Intermediate 40

4-Amino-3-[2-(difluoromethoxy)benzylamino]benzonitrile

Palladium on carbon (1 g, 10 wt %) was added to a solution of Intermediate 39 (36.8 g, 115 mmol) in EtOAc (800 mL), flushed with argon. The argon atmosphere was replaced with a $H_2$ atmosphere and the reaction mixture was stirred under 1 bar of $H_2$ for 16 h. The mixture was filtered over Kieselguhr and the filtrate was concentrated in vacuo. The residue was subsequently triturated with isopropyl ether (200 mL). Filtration of the precipitate afforded the title compound (25.4 g, 88 mmol, 76%). $\delta_H$ (DMSO-$d_6$, 300 MHz) 4.33 (d, 2H, J 5.7 Hz); 5.44 (t, 1H, J 5.7 Hz); 5.64 (s, 2H); 6.49 (d, 1H, J 1.5 Hz); 6.60 (d, 1H, J 8.3 Hz); 6.86 (dd, 1H, J 1.8, 8.1 Hz); 7.23 (m, 2H); 7.26 (t, 1H, J 74.3 Hz); 7.35 (m, 2H). MS [ESI+] m/z: 290 [M+H]+.

Intermediate 41

3-(2,5-Dichlorobenzylamino)-4-nitrobenzonitrile $K_2CO_3$ (9.42 g, 68.2 mmol) was added to a mixture of (2,5-dichlorophenyl)-methanamine (10.00 g, 56.8 mmol) and 3-fluoro-4-nitrobenzonitrile (9.44 g, 56.8 mmol) in THF (200 mL). After 16 h $Et_2O$ and water were added. The organic phase was separated and the aqueous phase was extracted twice with $Et_2O$. The combined organic layers were dried over $Na_2SO_4$, after which the solvent was removed in vacuo. The aqueous layer was extracted twice with EtOAc and the combined organic extracts were dried over $Na_2SO_4$, after which the solvent was added to the residue of the first evaporation. The solvent was then removed in vacuo, yielding the title compound (17.94 g, 52.3 mmol, 92%). $\delta_H$ (DMSO-$d_6$, 300 MHz) 4.72 (d, 2H, J 6.6 Hz); 7.09 (dd, 1H, J 1.8, 8.7 Hz); 7.41 (m, 3H); 7.54 (dd, 1H, J 4.2, 5.1 Hz); 8.24 (d, 1H, J 8.7 Hz); 8.64 (t, 1H, J 6.3 Hz). MS [ESI+] m/z: 323 [M+H]+.

Intermediate 42

4-Amino-3-(2,5-dichlorobenzylamino)benzonitrile

Palladium on carbon (0.2 g, 10 wt %) was added to a solution of Intermediate 41 (10 g, 31.0 mmol) and zinc bromide (6.88 g, 31.0 mmol) in EtOAc (200 mL), flushed with argon. The argon atmosphere was replaced with a $H_2$ atmosphere and the reaction mixture was stirred under 1 bar of $H_2$ for 5 h. The $H_2$ atmosphere was then replaced with an argon atmosphere, palladium on carbon (0.4 g, 10 wt %) was added, and the reaction was continued under a $H_2$ atmosphere for 5 h. The reaction mixture was filtered over Kieselguhr and the filtrate was subsequently washed with water and brine. After drying over $Na_2SO_4$, the solvent was concentrated in vacuo. The residue was triturated with isopropyl ether (150 mL). The precipitate was collected by filtration, to afford the title compound (6.98 g, 23.9 mmol, 77%). $\delta_H$ (DMSO-$d_6$, 300 MHz) 4.38 (d, 2H, J 5.7 Hz); 5.56 (t, 1H, J 5.7 Hz); 6.49 (d, 1H, J 1.5 Hz); 6.63 (d, 1H, J 8.1 Hz); 6.89 (dd, 1H, J 1.5, 8.1 Hz); 7.39 (m, 2H); 7.53 (m, 1H). MS [ESI+] m/z: 293 [M+H]+.

Intermediate 43

(R)-4-Nitro-3-(1-phenylethylamino)benzonitrile

3-Fluoro-4-nitrobenzonitrile (15.00 g, 90 mmol) was added to a solution of (R)-1-phenylethanamine (10.94 g, 90 mmol) in THF (300 mL). $K_2CO_3$ (14.98 g, 108 mmol) was added. After 16 h, (R)-1-phenylethanamine (2.189 g, 18.06 mmol) was added. After 1 h, EtOAc and water were added. The organic phase was separated and the aqueous phase was extracted twice with EtOAc. The combined organic layers were dried over $Na_2SO_4$, after which the solvent was removed in vacuo. The residue was triturated with $Et_2O$. The precipitate was filtered off, affording the title compound (14.86 g, 55.6 mmol, 62%).

Intermediate 44

(R)-4-Amino-3-(1-phenylethylamino)benzonitrile

Palladium on carbon (8.23 g, 10 wt %) was added to a solution of Intermediate 43 (13.78 g, 51.6 mmol) in EtOAc (1000 mL), flushed with argon. The argon atmosphere was replaced with a $H_2$ atmosphere and the reaction mixture was stirred under 1 bar of $H_2$ for 3 h. The mixture was filtered over Kieselguhr and the filtrate was concentrated in vacuo, affording the title compound (11.98 g, 50.5 mmol, 98%). $\delta_H$ (CDCl$_3$, 300 MHz) 1.55 (d, 3H, J 6.9 Hz); 3.63 (s, 1H); 3.83 (s, 2H); 4.45 (m, 1H); 6.62 (d, 1H, J 1.5 Hz); 6.66 (d, 1H, J 7.8 Hz); 6.94 (dd, 1H, J 1.8, 7.8 Hz); 7.28 (m, 5H). MS [ESI+] m/z: 238 [M+H]+.

Intermediate 45

(S)-4-Nitro-3-(1-phenylethylamino)benzonitrile

3-Fluoro-4-nitrobenzonitrile (15 g, 90 mmol) was added to a solution of (S)-1-phenylethanamine (11.49 ml, 90 mmol) in THF (150 mL). $K_2CO_3$ (18.72 g, 135 mmol) was added. After 2 h, (S)-1-phenylethanamine (3 ml, 23.57 mmol) was added. After 16 h the reaction mixture was diluted with DCM to a total volume of 1 L under stirring. After 15 minutes the precipitated salts were removed by filtration over Kieselguhr. The filtrate was concentrated in vacuo to afford the title compound (24.14 g, 90 mmol, 100%).

Intermediate 46

(S)-4-Amino-3-(1-phenylethylamino)benzonitrile

Palladium on carbon (1 g, 10 wt %) was added to a solution of Intermediate 45 (24.06 g, 90 mmol) in EtOAc (500 mL), flushed with argon. The argon atmosphere was replaced with a $H_2$ atmosphere and the reaction mixture was stirred under 1 bar of $H_2$ for 5 h. The mixture was filtered over Kieselguhr and the filtrate was concentrated in vacuo. The residue was triturated with isopropyl ether (100 mL). Filtration of the precipitate afforded the title compound (19.2 g, 81 mmol, 90%). $\delta_H$ (DMSO-$d_6$, 300 MHz) 1.46 (d, 3H, J 6.6 Hz); 4.54 (q, 1H, J 6.6 Hz); 5.32 (d, 1H, J 6.3 Hz); 5.74 (s, 2H); 6.34 (d, 1H, J 1.5 Hz); 6.55 (d, 1H, J 7.8 Hz); 6.76 (dd, 1H, J 1.7, 8.0 Hz); 7.19 (m, 1H); 7.32 (m, 4H). MS [ESI+] m/z: 238 [M+H]+.

Intermediate 47

Method K

6-Bromo-1-(2-difluoromethoxybenzyl)-2-methyl-1H-benzimidazole

Step 1:
To a solution of 2-(difluoromethoxy)benzylamine (5.00 g, 28.9 mmol) in DMF (50 mL) were added 4-bromo-2-fluoronitrobenzene (6.68 g, 30.3 mmol) and potassium carbonate (4.80 g, 34.68 mmol). The mixture was stirred at 100° C. overnight. After this time the mixture was diluted with water (100 mL) and cooled to room temperature. The resultant solid precipitate was filtered off, washed with water and dried under vacuum, to give 5-bromo-N-[2-(difluoromethoxy)benzyl]-2-nitroaniline (10.00 g, 93%) as a yellow solid. $\delta_H$ (DMSO-$d_6$, 400 MHz) 8.64 (t, J 6.1 Hz, 1H), 8.02 (d, J 9.1 Hz, 1H), 7.35-7.41 (m, 2H), 7.32 (t, J 74.0 Hz, 1H), 7.21-7.28 (m, 2H), 7.09 (d, J 1.8 Hz, 1H), 6.86 (dd, J 9.1, 1.9 Hz, 1H), 4.66 (d, J 6.2 Hz, 2H).

Step 2:
To a solution of the foregoing material (3.00 g, 8.04 mmol) in ethanol (30 mL) and 10% HCl (15 mL) was added tin(II) chloride (4.57 g, 24.12 mmol). The mixture was stirred at 80° C. overnight. After this time the mixture was basified with 10% aqueous NaOH solution (25 mL) and the mixture was cooled to room temperature. The mixture was then extracted with EtOAc (4×100 mL), and the combined organic layers were dried (Na$_2$SO$_4$), filtered and concentrated in vacuo. The crude product was purified by chromatography (SiO$_2$; 5-30% EtOAc/hexane) to obtain 5-bromo-N$^1$12-(difluoromethoxy)benzyl 1 benzene-1,2-diamine (1.74 g, 63%) as a yellow oil. $\delta_H$ (DMSO-$d_6$, 400 MHz) 7.32-7.39 (m, 2H), 7.27 (t, J 74.2 Hz, 1H), 7.20-7.25 (m, 2H), 6.48-6.56 (m, 2H), 6.34 (d, J 2.0 Hz, 1H), 5.33 (t, J 5.8 Hz, 1H), 4.76 (s, 2H), 4.30 (d, J 5.8 Hz, 2H). LCMS (ES+) 344 (M+H)$^+$, RT 2.44 minutes.

Step 3:
A solution of the foregoing material (545 mg, 1.59 mmol) in acetic acid (10 mL) was heated at 80° C. for 18 h. The reaction mixture was allowed to cool to ambient temperature, the volatiles were removed in vacuo, and the crude product was purified by chromatography (SiO$_2$; 20-60% EtOAc/hexane), to obtain the title compound (479 mg, 82%) as a brown solid. $\delta_H$ (DMSO-$d_6$, 400 MHz) 7.68 (d, J 1.8 Hz, 1H), 7.52 (d, J 8.7 Hz, 1H), 7.37-7.47 (m, 1H), 7.32 (t, J 74.2 Hz, 1H), 7.25-7.33 (m, 2H), 7.17 (td, J 7.68, 0.9 Hz, 1H), 6.75 (dd, J 7.6, 1.2 Hz, 1H), 5.49 (s, 2H), 2.48 (s, 3H). LCMS (ES+) 368 (M+H)$^+$, RT 2.67 minutes.

Intermediate 48

6-Bromo-1-(2,5-dichlorobenzyl)-2-methyl-1H-benzimidazole

From 2,5-dichlorobenzylamine in accordance with Method K.

Intermediate 49

6-Bromo-1-[5-chloro-2-(difluoromethoxy)benzyl]-2-methyl-1H-benzimidazole

From 5-chloro-2-(difluoromethoxy)-benzylamine in accordance with Method K.

Intermediate 50

6-Bromo-1-[2-(difluoromethoxy)benzyl]-5-fluoro-2-methyl-1H-benzimidazole

From 4-bromo-2,5-difluoronitrobenzene and 2-(difluoromethoxy)benzylamine in accordance with Method K.

Intermediate 51

6-Bromo-1-(2,5-dichlorobenzyl)-5-fluoro-2-methyl-1H-benzimidazole

From 4-bromo-2,5-difluoronitrobenzene and 2,5-dichlorobenzylamine in accordance with Method K.

Intermediate 52

2-(Chloromethyl)-1-[2-(difluoromethoxy)benzyl]-1H-benzimidazole-6-carbonitrile

Example 488 (2.5 g, 7.2 mmol) was treated with thionyl chloride (6 mL) and stirred at room temperature for 30 minutes. After this time, the reaction mixture was concentrated in vacuo and the residue was partitioned between DCM and saturated aqueous Na$_2$CO$_3$ solution. The aqueous phase was extracted with further DCM and the combined organic fractions were dried by passing through a phase separator cartridge, then evaporated in vacuo, to afford the title compound (2.7 g, 98%) as an off white solid. $\delta_H$ (300 MHz, DMSO) 8.08 (d, 1H, J 0.9 Hz), 7.88 (d, 1H, J 8.4 Hz), 7.65 (dd, 1H, J 8.4, 1.5 Hz), 7.41 (m, 1H), 7.10 (t, 1H, J 73.8 Hz), 7.25 (m, 1H), 7.17 (m, 1H,), 6.84 (m, 1H), 5.70 (s, 2H), 5.08 (s, 2H). LCMS (ES+) 348 (M+H)$^+$, RT 3.5 minutes.

Intermediate 53

2-{[(3-Bromophenyl)sulfanyl]methyl}-1-[2-(difluoromethoxy)benzyl]-1H-benzimidazole-6-carbonitrile A solution of Intermediate 52 (500 mg, 1.44 mmol) in DMF (10 mL) was treated with K$_2$CO$_3$ (397 mg, 2.88 mmol) and 3-bromobenzenethiol (550 mg, 2.88 mmol) and stirred at room temperature for 24 h. After this time, the reaction mixture was concentrated in vacuo and the residue was partitioned between EtOAc and water. The aqueous phase was extracted with further EtOAc and the combined organic fractions were washed with brine. After drying by passing through a phase separator cartridge, the organic layer was evaporated in vacuo and the residue was purified by column chromatography (SiO$_2$, 0-50% EtOAc in DCM) to give the title compound (256 mg, 36%) as a waxy solid. $\delta_H$ (300 MHz, DMSO) 8.00 (d, 1H, J 0.9 Hz), 7.75 (d, 1H, J 8.4 Hz), 7.60 (m, 2H), 7.30 (m, 6H), 7.12 (m, 1H), 6.70 (dd, 1H, J 7.6, 1.2 Hz), 5.67 (s, 2H), 4.62 (s, 2H). LCMS (ES+) 501 (M+H)$^+$, RT 2.80 minutes.

Intermediate 54

5-Bromo-N-(2,5-dichlorobenzyl)-2-nitroaniline

From 4-bromo-2-fluoronitrobenzene and 2,5-dichlorobenzylamine in accordance with the procedure described for Intermediate 47, Step 1.

Intermediate 55

N-(2,5-Dichlorobenzyl)-2-nitro-5-(pyridin-4-yl)aniline

Intermediate 54 (12.5 g, 33.6 mmol), pyridin-4-ylboronic acid (5.0 g, 40.3 mmol) and tetrakis(triphenylphosphine)palladium(0) (1.95 g, 1.3 mmol) were dissolved in a mixture of saturated aqueous $Na_2CO_3$ solution (50 mL) and 1,4-dioxane (250 mL). The solution was degassed with nitrogen and then heated at 120° C. for 5 h. The 1,4-dioxane was removed under vacuum and then the resultant oil was partitioned between EtOAc (200 mL) and water (200 mL). The organic layer was separated, dried and concentrated in vacuo to afford the title compound (9.95 g) as a crude oil which was used without chromatography.

Intermediate 56

$N^2$-(2,5-Dichlorobenzyl)-4-(pyridin-4-yl)benzene-1,2-diamine

Intermediate 55 (9.95 g, 26.6 mmol) was dissolved in ethanol (100 mL). Tin(II) chloride (15.1 g, 80 mmol) and HCl (10% solution, 49 mL) were added sequentially to the reaction mixture, which was then heated to 100° C. After 5 hours, 2M aqueous NaOH solution (50 mL) was added and the reaction mixture was allowed to cool to room temperature. This solution was extracted with EtOAc (3×200 mL), the organic layers were combined and dried, and the solvent was removed under reduced pressure. The resulting oil was triturated with MeCN to afford the title compound (5.1 g, 55%) as a pale solid. $\delta_H$ (DMSO-$d_6$, 300 MHz) 8.44 (m, 2H), 7.52 (m, 2H), 7.43 (m, 2H), 7.36 (dd, 1H, J 8.5, 2.7 Hz), 6.98 (dd, 1H, J 8.0, 2.0 Hz), 6.68 (m, 2H), 5.44 (m, 1H), 5.09 (s, 2H), 4.48 (d, 2H, J 5.9 Hz). LCMS (ES+) 346.2 $(M+H)^+$, RT 1.39 minutes (pH 10).

Intermediate 57

1-[2-(Difluoromethoxy)benzyl]-2-methyl-6-(4,4,5,5-tetramethyl-1,3,2-dioxaborolan-2-yl)-1H-benzimidazole Intermediate 47 (4.00 g, 10.9 mmol), bis(pinacolato)diboron (3.87 g, 15.3 mmol), potassium acetate (3.23 g, 32.8 mmol) and $PdCl_2$(dppf) (400 mg, 5 mol %) were dissolved in DMSO (25 mL) and heated to 100° C. for 30 minutes. The mixture was diluted with water (200 mL) and extracted with ethyl acetate (250 mL). The organic layer was washed with saturated brine (100 mL), dried ($Na_2SO_4$) and concentrated in vacuo. The residue was purified by chromatography (silica, 50% EtOAc, 50% isohexane gradient to 100% EtOAc) to afford the title compound (2.50 g, 55%) as an off-white solid. $\delta_H$ ($d_6$-DMSO) 7.69 (s, 1H), 7.57 (d, 1H, J 8.0 Hz), 7.51 (m, 1H), 7.37 (m, 1H), 7.34 (t, 1H, $J_{H-F}$ 73.9 Hz), 7.28 (d, 1H, J 7.6 Hz), 7.13 (dt, 1H, J 7.6, 1.0 Hz), 6.53 (dd, 1H, J 7.7, 1.1 Hz), 5.53 (s, 2H), 2.49 (s, 3H under $d_6$-DMSO signal), 1.28 (s, 12H). LCMS $(ES^+)$ 415 $(M+H)^+$.

Intermediate 58 tert-Butyl 4-(5-{1-[2-(difluoromethoxy)benzyl]-2-methyl-1H-benzimidazol-6-yl}pyridin-2-yl)piperazine-1-carboxylate The following experiment was performed three times in parallel and the crude reaction mixtures combined for work-up and purification.

A mixture of tert-butyl 4-[5-(4,4,5,5-tetramethyl-1,3,2-dioxaborolan-2-yl)pyridin-2-yl]piperazin-1-ylcarboxylate (20 g, 54.5 mmol), Intermediate 47 (24.5 g, 63.14 mmol), $PdCl_2$(dppf) (0.8 g, 1.1 mmol) and 2M aqueous sodium carbonate solution (25 mL) in 1,4-dioxane (200 mL) was degassed and heated under reflux in a nitrogen atmosphere overnight. The cooled reaction mixtures were combined, diluted with EtOAc and washed twice with brine. The organic layer was dried ($MgSO_4$) and the solvent was removed by rotary evaporation. The crude residue was purified by column chromatography using a VersaFlash column eluting with EtOAc-hexane (3:2, then 1:1, then 2:1), then 100% EtOAc. The resulting material was triturated from ether, filtered, washed with more ether and dried to give the title compound (50.5 g, 56%) as a cream solid. $\delta_H$ (DMSO-$d_6$) 8.44 (d, J 2.3 Hz, 1H), 7.85 (dd, $J_1$ 8.9 Hz, $J_2$ 2.6 Hz, 1H), 7.66 (d, J 1.3 Hz, 1H), 7.60 (d, J 8.4 Hz, 1H), 7.41 (m, 2H), 7.35 (t, $J_{H-F}$ 76 Hz, 1H), 7.27 (m, 1H), 7.16 (m, 1H), 6.92 (m, 1H), 6.79 (m, 1H), 5.54 (s, 2H), 3.52 (m, 4H), 3.44 (m, 4H), 2.50 (s, 3H), 1.43 (s, 9H). LCMS (ES+) 550 $(M+H)^+$, RT 1.61 minutes.

Intermediate 59

6-(6-Chloropyridin-3-yl)-1-[2-(difluoromethoxy)benzyl]-2-(methoxymethyl)-1H-benzimidazole A suspension of 6-chloropyridin-3-ylboronic acid (2.3 g, 18 mmol), Example 444 (3.5 g, 8.8 mmol) and a 2N aqueous solution of $K_3PO_4$ (25 mL) in DMF (50 mL) was treated with tetrakis(triphenylphosphine)palladium(0) (61 mg, 0.53 mmol) and heated to 65° C. under $N_2$. Further DMF (20 mL) was added, giving an orange/yellow solution. The mixture was heated for 2 h at 65° C. The reaction mixture was treated with further tetrakis(triphenylphosphine)palladium(0) (200 mg, 1.72 mmol). The reaction mixture was heated to 71° C. for 1 h, then allowed to cool to ambient temperature. The mixture was diluted with ethyl acetate (100 mL) and water (200 mL) and the layers were separated. The aqueous phase was extracted with further ethyl acetate (100 mL) and the combined organic layers were washed with water (100 mL) and brine (100 mL) and dried over $MgSO_4$. Removal of solvent in vacuo gave a crude yellow solid which was purified by column chromatography on $SiO_2$, eluting with dichloromethane:ethyl acetate (1:1 by volume), to give a yellow solid (1 g). Further purification by column chromatography on $SiO_2$, eluting with dichloromethane:ethyl acetate (1:1 by volume), gave the title compound (0.65 g, 17%) as a yellow solid. $\delta_H$ (300 MHz, DMSO-$d_6$) 8.71 (d, 1H), 8.14 (dd, 1H), 7.86 (s, 1H), 7.78 (d, 1H), 7.56-7.65 (m, 3H), 7.33-7.38 (m, 1H), 7.25 (d, 1H), 7.12 (t, 1H), 6.74 (d, 1H), 5.64 (s, 2H), 4.66 (s, 2H), 3.25 (s, 3H). LCMS (6120B, 3 minutes method, pH 10) m/z 430.2, RT 1.15 minutes.

Intermediate 60

5-Bromo-N-(2,5-dimethylbenzyl)-2-nitroaniline

From 4-bromo-2-fluoronitrobenzene and 2,5-dimethylbenzylamine in accordance with the procedure described for Intermediate 47, Step 1.

Intermediate 61

4-Bromo-$N^2$-(2,5-dimethylbenzyl)benzene-1,2-diamine

Zinc powder (5.8 g, 89.2 mmol) was added to a stirred suspension of Intermediate 60 (10 g, 29.9 mmol) and a saturated solution of ammonium chloride (60 mL) in ethanol (180 mL) and the mixture was stirred at 50° C. After 1.5 h, LCMS showed 50% conversion. Consequently, additional zinc dust (5 g) was added and stirring was continued at the same temperature until LCMS indicated completion of the reaction (a further 1 h). The reaction mixture was filtered through celite and the solid was thoroughly washed with DCM. The combined filtrate was then washed with 2M aqueous sodium hydroxide solution and dried (MgSO$_4$). The solvent was removed by rotary evaporation to give the title compound (5.2 g, 100%) as a brown syrup which was used without further purification. $\delta_H$ (CDCl$_3$) 7.15 (m, 2H), 7.13 (m, 1H), 7.07 (m, 1H), 6.84 (m, 1H), 6.81 (m, 1H), 6.62 (d, J 8.0 Hz, 1H), 4.19 (s, 2H), 3.53 (br s, 1H), 3.28 (br s, 1H), 2.36 (s, 3H), 2.34 (s, 3H). LCMS (ES+) 306 and 307 (M+H)$^+$, RT 162 minutes.

Intermediate 62

N-{4-Bromo-2-[(2,5-dimethylbenzyl)amino]phenyl}-2-(pyridin-4-yl)acetamide

A mixture of 2-(pyridin-4-yl)acetic acid hydrochloride salt (4.0 g, 23.1 mmol) and HATU (11.6 g, 30.5 mmol) in DCM (75 mL) was stirred in ice bath. DIPEA (15.5 mL, 89.9 mmol) was added and the mixture was stirred for 10 minutes, then a solution of Intermediate 61 (6.2 g, 20.3 mmol) in DCM (40 mL) was gradually added and stirred overnight. The reaction mixture was diluted with DCM and washed with a saturated solution of sodium bicarbonate, then dried (MgSO$_4$) and concentrated by rotary evaporation. The crude residue was purified by column chromatography on silica gel, eluting with EtOAc-hexane (1:1 then 2:1), followed by crystallization from diethylether to give the title compound (2.64 g, 31%) as off-white solid. $\delta_H$ (DMSO-d$_6$) 9.51 (s, 1H), 8.48 (m, 2H), 7.33 (d, J 5.9 Hz, 2H), 7.10 (m, 3H), 7.00 (m, 1H), 6.72 (dd, J$_1$ 8.3 Hz, J$_2$ 2.1 Hz, 1H), 6.69 (m, 1H), 5.56 (t, J 5.4 Hz, 1H), 4.22 (d, J 5.4 Hz, 2H), 3.72 (s, 2H), 2.27 (s, 3H), 2.23 (s, 3H). LCMS (ES+) 424 and 426 (M+H)$^+$, RT 1.51 minutes.

Intermediate 63

6-Bromo-1-(2,5-dimethylbenzyl)-2-(pyridin-4-ylmethyl)benzimidazole

A suspension of Intermediate 62 (2.64 g, 6.23 mmol) in glacial acetic acid (50 mL) was stirred at 100° C. for 1 h until LCMS analysis showed completion of reaction. The reaction mixture was concentrated and the residue was dissolved in DCM, then washed twice with a saturated solution of sodium bicarbonate. The organic phase was dried (MgSO$_4$) and concentrated. Diethyl ether was added and the resultant crystalline product was filtered, washed with more diethyl ether and dried, to give the title compound (2.3 g, 91%) as off-white solid. $\delta_H$ (DMSO-d$_6$) 8.39 (m, 2H), 7.64 (m, 2H), 7.34 (dd, J$_1$ 8.5 Hz, J$_2$ 1.9 Hz, 1H), 7.20 (m, 2H), 7.08 (d, J 7.6 Hz, 1H), 6.92 (d, J 7.6 Hz, 1H), 5.81 (s, 1H), 5.48 (s, 2H), 4.24 (s, 2H), 2.31 (s, 3H), 1.95 (s, 3H). LCMS (ES+) 407 and 408 (M+H)$^+$, RT 1.49 minutes.

Intermediate 64 tert-Butyl 4-({4-[1-(2,5-dimethylbenzyl)-2-(pyridin-4-ylmethyl)-1H-benzimidazol-6-yl]phenyl}methyl)piperazine-1-carboxylate A mixture of Intermediate 63 (230 mg, 0.57 mmol), tert-butyl 4-{[4-(4,4,5,5-tetramethyl-1,3,2-dioxaborolan-2-yl)phenyl]methyl}piperazine-1-carboxylate (320 mg, 0.79 mmol), tetrakis(triphenylphosphine)palladium(0) (33 mg, 0.028 mmol) and 2M aqueous sodium carbonate solution (1 mL) in 1,4-dioxane (4 mL) was degassed and heated at reflux temperature under nitrogen overnight. LCMS showed completion of reaction. The cooled reaction mixture was diluted with EtOAc and washed with brine. The organic extract was dried (MgSO$_4$) and concentrated. The crude residue was purified by column chromatography on silica gel, eluting with EtOAc-MeOH (30:1, then 20:1), to give the title compound (300 mg, 88%) as a pale yellow syrup. $\delta_H$ (DMSO-d$_6$) 8.39 (m, 2H), 7.72 (d, J 8.4 Hz, 1H), 7.66 (d, J 1.2 Hz, 1H), 7.60 (d, J 8.2 Hz, 2H), 7.52 (dd, J$_1$ 8.4 Hz, J$_2$ 1.6 Hz, 1H), 7.35 (d, J 8.1 Hz, 2H), 7.22 (d, J 5.9 Hz, 2H), 7.08 (m, 1H), 6.90 (dd, J$_1$ 7.4 Hz, J$_2$ 0.2 Hz, 1H), 5.92 (s, 1H), 5.53 (m, 2H), 4.26 (s, 2H), 3.50 (m, 2H), 3.32 (m, 4H), 2.33 (m, 7H), 1.94 (s, 3H), 1.39 (s, 9H). LCMS (ES+) 602 (M+H)$^+$, RT 1.61 minutes.

Intermediate 65

6-(2-Chlororimidin-5yl)-1-[2-difluoron(benzyl]-2-methyl-1H-benzimidazole

To Intermediate 47 (1.0 g, 2.72 mmol) under a nitrogen atmosphere were added 2-chloropyrimidin-5-ylboronic acid (533 mg, 3.27 mmol), Pd(PPh$_3$)$_4$ (158 mg, 0.136 mmol), 2M aqueous sodium carbonate solution (13 mL) and 1,4-dioxan (60 mL). The reaction was stirred at 105° C. under nitrogen for 18 h. After this time, PdCl$_2$(dppf) (100 mg, 5 mol %) and a further quantity of 2-chloropyrimidin-5-ylboronic acid (266 mg, 0.5 equiv.) were added. Heating was continued at 105° C. for 5 h. The reaction was worked up by the addition of water (50 mL). The aqueous phase was extracted with ethyl acetate (2×100 mL) and the combined organic layers were concentrated in vacuo to a black oil. The crude residue was purified by silica flash column chromatography (10-50% ethyl acetate/DCM) to give the title compound (460 mg, 42%) as a pink solid. $\delta_H$ (d$_6$-DMSO, 400 MHz) 9.12 (2H, s), 8.01 (1H, d, J 1.3 Hz), 7.72 (1H, d, J 8.4 Hz), 7.66-7.53 (2H, m), 7.40-7.35 (1H, m), 7.27 (1H, d, J 7.5 Hz), 7.19-7.13 (1H, m), 6.73-6.71 (1H, m), 5.58 (2H, s), 3H not observed (CH$_3$) under d$_6$-DMSO peak at 2.50 ppm. LCMS (pH 3) 401.6, MH+, RT 1.67 minutes, 100% UV. LCMS (pH 10) 401.6, MH+, RT 2.09 minutes, 94.9% UV.

Intermediate 66

[1-(Bicyclo[4.2.0]octa-1(6),2,4-trien-7-yl)-1H-benzimidazol-2-yl]methanol

From Intermediate 1 and 1-bromobenzocyclobutene in accordance with Method B to give the title compound. $\delta_H$ (300 MHz, DMSO-d$_6$) 7.60 (d, 1H, J 8.0 Hz), 7.47 (m, 1H), 7.35 (m, 2H), 7.19 (d, 1H, J 7.2 Hz), 7.12 (m, 1H), 6.98 (m, 1H), 6.58 (d, 1H, J 8.2 Hz), 6.38 (dd, 1H, J 4.8, 2.4 Hz), 5.67 (t, 1H, J 5.8 Hz), 4.82 (m, 2H), 3.89 (dd, 1H, J 14.4, 5.2 Hz), 3.59 (m, 1H). LCMS (ES+) 251 (M+H)+, RT 1.87 minutes (Method 2).

Intermediate 67

1-(Bicyclo[4.2.0]octa-1(6),2,4-trien-7-yl)-1H-benzimidazole

From benzimidazole and 1-bromobenzocyclobutene in accordance with Method B to give the title compound which was subsequently utilised without further purification.

Intermediate 68

1-(1-{[2-(Difluoromethoxy)phenyl]methyl}-2-methylbenzimidazol-6-yl)propan-2-one Intermediate 47 (1.1 g, 3.0 mmol), tri-n-butyltin methoxide (2.8 g, 8.6 mmol), isopropenyl acetate (0.86 g, 8.6 mmol), palladium(II) acetate (0.065 g, 0.29 mmol) and tri-o-tolylphosphine (0.91 g, 3.0 mmol) in toluene (7.5 mL) were heated under microwave irradiation at 100° C. for 2 h. The reaction mixture was then diluted with EtOAc (10 mL) and 4M aqueous potassium fluoride solution (5 mL) was added. The reaction mixture was stirred for 10 minutes. The reaction mixture was filtered through celite, then washed three times with EtOAc. The combined organic layers were separated and dried ($Na_2SO_4$), then filtered and concentrated in vacuo. The resulting dark oil was purified by chromatography ($SiO_2$; 50-100% EtOAc/hexane gradient elution) to give the title compound (0.60 g, 58%) as a brown oil. $\delta_H$ (DMSO-$d_6$, 300 MHz) 7.49 (d, 1H, J 8.2 Hz), 7.34-7.41 (m, 1H), 7.34 (t, 1H, J 73.8 Hz), 7.23-7.29 (m, 1H), 7.21 (d, 1H, J 0.8 Hz), 7.14 (td, 1H, J 7.6, 1.0 Hz), 6.97 (dd, 1H, J 8.2, 1.5 Hz), 6.65 (dd, 1H, J 7.6, 1.2 Hz), 5.44 (s, 2H), 3.76 (s, 2H), 2.47 (s, 3H), 2.06 (s, 3H). LCMS (ES+) 345 (M+H)$^+$, RT 1.68 minutes (pH 10); and (ES+) 345 (M+H)$^+$, RT 1.32 minutes (pH 3).

Intermediate 69

(Z)-3-(1-{[2-(Difluoromethoxy)phenyl]methyl}-2-methylbenzimidazol-6-yl)-4-(dimethylamino)but-3-en-2-one Intermediate 68 (0.56 g, 1.7 mmol) and N,N-dimethylformamide dimethyl acetal (3 mL) were heated at 60° C. for 4 h. The reaction mixture was allowed to cool to room temperature, then concentrated in vacuo. The resulting material was purified by triturating with $Et_2O$ (5 mL), then filtered and dried under vacuum, to give the title compound (0.426 g, 62%) as a pale yellow solid. $\delta_H$ (DMSO-$d_6$, 300 MHz) 7.45 (d, 1H, J 10.3 Hz), 7.45 (s, 1H), 7.33-7.40 (m, 1H), 7.31 (t, 1H, J 98.4 Hz), 7.22-7.27 (m, 1H), 7.13 (td, 1H, J 10.2, 1.4 Hz), 7.05 (d, 1H, J 1.2 Hz), 6.89 (dd, 1H, J 10.7, 2.0 Hz), 6.72 (dd, 1H, J 10.2, 1.7 Hz), 5.44 (s, 2H), 2.47-2.54 (m, 9H), 1.84 (s, 3H). LCMS (ES+) 400 (M+H)$^+$, RT 1.75 minutes (pH 10); and (ES+) 400 (M+H)$^+$, RT 1.29 minutes (pH 3).

Intermediate 70 tert-Butyl 4-carbamimidoylpiperidine-1-carboxylate

To a solution of tert-butyl 4-carbamoylpiperidine-1-carboxylate (1.0 g, 4.4 mmol) in anhydrous DCM (10 mL) cooled to 0° C. was added trimethyloxonium tetrafluoroborate (0.65 g, 4.4 mmol) and the reaction mixture was stirred for 3 h. Ammonia in methanol (7M; 11 mL) was then added, and the reaction mixture was stirred at room temperature for 18 h. The reaction mixture was then concentrated in vacuo to give the title compound (1.4 g, quantitative yield) as a yellow foam. $\delta_H$ (DMSO-$d_6$, 400 MHz) 8.25-8.56 (m, 3H), 4.02-4.14 (m, 2H), 2.63-2.79 (m, 2H), 2.58 (tt, J 12.4, 3.4 Hz, 1H), 1.73-1.80 (m, 2H), 1.52-1.64 (m, 2H), 1.41 (s, 9H). LCMS (ES+) 228 (M+H)$^+$, RT 1.06 minutes (pH 10); and (ES+) 228 (M+H)$^+$, RT 0.87 minutes (pH 3).

Intermediate 71 tert-Butyl 4-[5-(1-{[2-(difluoromethoxy)phenyl]methyl}-2-methylbenzimidazol-6-yl)-4-methylpyrimidin-2-yl]piperidine-1-carboxylate Intermediate 70 (0.22 g, 0.56 mmol), Intermediate 69 (0.27 g, 1.2 mmol) and sodium ethoxide (0.058 g, 0.84 mmol) in ethanol (4 mL) were heated under microwave irradiation at 80° C. for 6 h, then for 2 h at 100° C., then for 11 h at 130° C. The reaction mixture was concentrated in vacuo. The residue was then dissolved in DCM (20 mL) and washed with water (20 mL). The layers were separated and the aqueous layer was then back-extracted with DCM (3×20 mL). The organic layers were combined, passed through a phase separator and concentrated in vacuo. The resulting brown oil was then purified by chromatography ($SiO_2$; 50-100% EtOAc/hexane, then 0-20% MeOH/EtOAc gradient elution) to give the title compound (0.13 g, 43%) as an off-white solid. $\delta_H$ (DMSO-$d_6$, 300 MHz) 8.51 (s, 1H), 7.66 (d, 1H, J 8.2 Hz), 7.52 (d 1H, J 1.2 Hz), 7.35-7.41 (m, 1H), 7.31 (t, 1H, J 73.7 Hz), 7.21-7.27 (m, 2H), 7.14-7.19 (m, 1H), 6.82-6.89 (m, 1H), 5.51 (s, 2H), 2.64-3.06 (m, 4H), 2.53 (s, 3H), 2.37 (s, 3H), 2.18-2.30 (m, 1H), 1.89-1.98 (m, 2H), 1.60-1.73 (m, 2H), 1.42 (s, 9H). LCMS (ES+) 564 (M+H)$^+$, RT 2.68 minutes (pH 10); and (ES+) 508 (M+H-tBu)$^+$, RT 2.43 minutes (pH 3).

Intermediate 72

6-(2-Chloropyrimidin-5-yl)-1-{[2-(difluoromethoxy)phenyl]methyl}-5-fluoro-2-methylbenzimidazole A mixture of Intermediate 50 (0.5 g, 1 mmol), (2-chloropyrimidin-5-yl)boronic acid (0.3 g, 2 mmol), Pd(dppf)$Cl_2$ (0.03 g, 0.04 mmol) and 2M aqueous sodium carbonate solution (2 mL) in 1,4-dioxane (8 mL) was degassed and stirred at 110° C. After 6 h, further (2-chloropyrimidin-5-yl)boronic acid (60 mg) and Pd(dppf)$Cl_2$ (10 mg) were added, and the reaction mixture was degassed and stirred at the same temperature for 4 h. The cooled reaction mixture was partitioned between EtOAc and brine, then the organic layer was dried (MgSO$_4$) and concentrated. The crude residue was purified by column chromatography (hexanes: EtOAc, 3:2 to 1:1) to afford the title compound (200 mg, 40%) as a white crystalline solid. $\delta_H$ (400 MHz, DMSO-$d_6$) 8.98 (d, J 1.5 Hz, 2H), 7.86 (d, J 6.8 Hz, 1H), 7.61 (m, 1H), 7.39 (m, 1H), 7.34 (t, J 72, 76 Hz, 1H), 7.26 (d, J 7.7 Hz, 1H), 7.16 (m, 1H), 6.76 (dd, J 7.7, 1.3 Hz, 1H), 5.56 (s, 1H), 2.50 (s, 3H). LCMS (pH 10) MH+ 419, RT 1.53 minutes.

Intermediate 73

Ethyl 3-[5-(1-{[2-(difluoromethoxy)phenyl]methyl}-5-fluoro-2-methylbenzimidazol-6-yl)pyrimidin-2-yl]bicyclo[3.1.0]hex-2-ene-6-carboxylate A mixture of Intermediate 72 (0.2 g, 0.5 mmol), Intermediate 172 (0.2 g, 0.7 mmol), Pd(dppf)$Cl_2$ (20 mg, 24.5 μM) and 2M aqueous sodium carbonate solution (2 mL) in 1,4-dioxane (8 mL) was degassed and stirred at 110° C. for 1.5 h. The cooled reaction mixture was diluted with EtOAc and washed with brine, then the organic layer was dried (MgSO$_4$) and concentrated. The crude residue was purified using column chromatography (EtOAc:hexanes, 2:1) to give the title compound (150 mg, 60%) as a colourless gum. $\delta_H$ (400 MHz, DMSO-$d_6$) 8.96 (d, J 1.6 Hz, 2H), 7.83 (d, J 6.8

Hz, 1H), 7.63 (m, 1H), 7.38 (t, J 72, 76 Hz, 1H), 7.44 (m, 1H), 7.32 (m, 1H), 7.23 (m, 1H), 7.17 (d, J 1.8 Hz, 1H), 6.89 (dd, J 7.5, 0.9 Hz, 1H), 5.60 (s, 2H), 4.12 (m, 2H), 3.19 (m, 1H), 3.05 (m, 1H), 2.62 (m, 1H), 2.50 (s, 3H), 2.39 (m, 1H), 1.33 (m, 1H), 1.26 (m, 4H). LCMS (pH 10) MH+ 535, RT 1.61 minutes.

Intermediate 74

Ethyl 3-[5-(1-{[2-(difluoromethoxy)phenyl]methyl}-5-fluoro-2-methylbenzimidazol-6-yl)pyrimidin-2-yl]bicyclo[3.1.0]hexane-6-carboxylate 10% Palladium on charcoal (20 mg) was added to a solution/suspension of Intermediate 73 (150 mg, 0.28 mmol) and triethylamine (40 pt, 0.287 mmol) in ethanol (4 mL). The reaction mixture was flushed with hydrogen and hydrogenated at normal pressure overnight. The reaction mixture was filtered through celite, concentrated and purified by column chromatography (EtOAc:hexanes, 3:2) to give the title compound (0.14 g, 93%) as a clear gum. $\delta_H$ (400 MHz, DMSO-$d_6$) 8.94 (m, 2H), 7.83 (m, 1H), 7.58 (m, 1H), 7.38 (m, 1H), 7.33 (t, J 72, 76 Hz, 1H), 7.27 (m, 1H), 7.16 (m, 1H), 6.79 (m, 1H), 5.56 (s, 2H), 4.01 (m, 2H), 3.74 (m, 1H), 2.50 (s, 3H), 2.42 (m, 3H), 1.88 (m, 2H), 1.42 (m, 1H), 1.14 (m, 4H). LCMS (pH 10) MH+ 537, RT 1.61 minutes.

Intermediate 75

6-Bromo-1-{[5-chloro-2-(difluoromethoxy)phenyl]methyl}-5-fluoro-2-methylbenzimidazole Step 1:
To a stirred solution of 1-bromo-2,5-difluoro-4-nitrobenzene (9.8 g, 0.04 mol) and [5-chloro-2-(difluoromethoxy)phenyl]methanamine hydrochloride (10 g, 0.04 mol) in ethanol (100 mL) was added triethylamine (12.47 g, 0.123 mol) at 0° C. The reaction mass was heated at 80° C. for 16 h. The reaction mixture was concentrated under vacuum. The crude mass was purified by hexane wash (2×100 mL) to obtain 5-bromo-N-[5-chloro-2-(difluoromethoxy)benzyl]-4-fluoro-2-nitroaniline (15 g, 88%) as a yellow solid. $\delta_H$ (400 MHz, CDCl$_3$) 8.22 (br s, 1H), 7.99 (d, J 6.4 Hz, 1H), 7.33-7.31 (m, 2H), 7.15 (d, J 7.6 Hz, 1H), 6.99 (d, J 6.0 Hz, 1H), 6.60 (t, J 72.8 Hz, 1H), 4.54 (d, J 6.4 Hz, 2H).

Step 2:
To a stirred solution of the foregoing material (15 g, 0.035 mol) in MeOH (100 mL) at 0° C. were added zinc (13.76 g, 0.211 mol) and ammonium formate (13.34 g, 0.211 mol). The reaction mixture was stirred at 25-28° C. for 1 h. The reaction mixture was filtered through a celite bed and washed with methanol (200 mL). The filtrate was concentrated under vacuum. The residue was purified by column chromatography, using 100-200 mesh silica gel and 10% ethyl acetate in hexane as an eluent, to afford 5-bromo-N$^1$-[5-chloro-2-(difluoromethoxy)benzyl]-4-fluorobenzene-1,2-diamine (12.1 g) as a brown gum. $\delta_H$ (400 MHz, CDCl$_3$) 7.39 (d, J 2.4 Hz, 1H), 7.29-7.27 (m, 1H), 7.11 (d, J 8.4 Hz, 1H), 6.69 (d, J 6.4 Hz, 2H), 6.56 (t, J 73.2 Hz, 1H), 4.25 (s, 2H), 3.55 (br s, 3H). LCMS M+ 397, RT 3.24 minutes.

Step 3:
A solution of the foregoing material (12.10 g, 0.0306 mol) in acetic acid (150 mL) was heated under reflux at 100° C. for 16 h. The reaction mixture was concentrated under vacuum. The residue was basified with aqueous sodium bicarbonate solution (50 mL) and extracted with ethyl acetate (2×500 mL). The organic layer was dried over anhydrous Na$_2$SO$_4$, filtered and concentrated under vacuum. The residue thus obtained was purified by column chromatography, using 100-200 mesh silica gel and 60% ethyl acetate in hexane as an eluent, to afford the title compound (6 g, 50%) as a brown solid. $\delta_H$ (400 MHz, CDCl$_3$) 7.48 (d, J 8.4 Hz, 1H), 7.33-7.29 (m, 2H), 7.16 (d, J 8.4 Hz, 1H), 6.63 (t, J 72.8 Hz, —OCHF$_2$, 1H), 6.53 (d, J 2.8 Hz, 1H), 2.54 (s, 3H), 2.04 (s, 2H). LCMS M+ 421.0, RT 2.73 minutes.

Intermediate 76

Ethyl 4-[5-(1-{[5-chloro-2-(difluoromethoxy)phenyl]methyl}-5-fluoro-2-methylbenzimidazol-6-yl)pyrimidin-2-yl]cyclohex-3-ene-1-carboxylate A mixture of Intermediate 75 (1 g, 2.383 mmol), Intermediate 178 (1.195 g, 3.336 mmol), Pd(dppf)Cl$_2$ (0.0496 g, 0.0595 mmol) and 2M aqueous sodium carbonate solution (2.5 mL) in 1,4-dioxane (15 mL) was degassed and stirred at 110° C. for 2 h. The reaction mixture was partitioned between EtOAc/brine, then the aqueous layer was extracted using EtOAc. The combined organic extracts were washed with brine, dried (MgSO$_4$) and concentrated. The crude material was purified by column chromatography (EtOAc:hexanes, 1:1 to 3:2) giving a crystalline residue which was triturated in diethyl ether, filtered, washed with diethyl ether/hexanes and dried, to give the title compound (1.1 g, 81%) as a pale yellow solid. $\delta_H$ (400 MHz, DMSO-$d_6$) 8.95 (d, J 1.6 Hz, 2H), 7.83 (d, J 6.8 Hz, 1H), 7.58 (m, 1H), 7.49 (m, 1H), 7.33 (t, J 72, 76 Hz, 1H), 7.31 (m, 2H), 6.87 (d, J 2.6 Hz, 1H), 5.55 (s, 2H), 4.12 (m, 2H), 2.79 (m, 1H), 2.65 (m, 1H), 2.50 (s, 3H), 2.55 (m, 3H), 2.12 (m, 1H), 1.73 (m, 1H), 1.21 (m, 3H). LCMS (pH 10) MH+ 571, RT 1.68 minutes.

Intermediate 77

Ethyl 4-[5-(1-{[5-chloro-2-(difluoromethoxy)phenyl]methyl}-2-methylbenzimidazol-6-yl)pyrimidin-2-yl]cyclohex-3-ene-1-carboxylate A mixture of Intermediate 49 (1 g, 2.490 mmol), Intermediate 178 (1.249 g, 3.487 mmol), Pd(dppf)Cl$_2$ (0.0519 g, 0.0623 mmol) and 2M aqueous sodium carbonate solution in 1,4-dioxane (15 mL) was degassed and stirred at 110° C. for 5 h. The reaction mixture was partitioned between EtOAc/brine, then the aqueous layer was extracted using EtOAc. The combined organic extracts were washed with brine, dried (MgSO$_4$), concentrated and columned (EtOAc:hexanes, 2:1 to 3:1). The resulting material was crystallised from diethyl ether, stored in a refrigerator overnight, filtered, then washed with diethyl ether/hexanes and dried, to give the title compound (1.16 g, 84%) as an off-white solid. $\delta_H$ (400 MHz, DMSO-$d_6$) 9.09 (s, 2H), 7.96 (d, J 1.1 Hz, 1H), 7.70 (m, 1H), 7.63 (m, 1H), 7.48 (dd, J 8.8, 2.6 Hz, 1H), 7.36 (t, J 72, 76 Hz, 1H), 7.33 (m, 1H), 7.27 (m, 1H), 6.83 (d, J 2.5 Hz, 1H), 5.57 (s, 2H), 4.12 (m, 2H), 2.78 (m, 1H), 2.67 (m, 1H), 2.50 (s, 3H), 2.49 (m, 3H), 2.12 (m, 1H), 1.74 (m, 1H), 1.22 (t, J 7.1 Hz, 3H). LCMS (pH 10) MH+ 553, RT 1.63 minutes.

Intermediate 78

Ethyl 4-[5-(1-{[2-(difluoromethoxy)phenyl]methyl}-5-fluoro-2-methylbenzimidazol-6-yl)pyrimidin-2-yl]cyclohex-3-ene-1-carboxylate A mixture of Intermediate 50 (0.35 g, 0.91 mmol), Intermediate 178 (0.46 g, 1.3 mmol), Pd(dppf)Cl$_2$ (19 mg, 0.023 mmol) and 2M aqueous sodium carbonate solution (4 mL) in 1,4-dioxane (10 mL) was degassed and stirred at 110° C. for 1.5 h. The cooled reaction mixture was diluted with EtOAc and washed with brine, then the organic layer was dried (MgSO$_4$) and concentrated. The crude material was purified by column chromatography (EtOAc:hexanes, 1:1 to 3:2). The resulting material was crystallised from diethyl ether, filtered, washed with diethyl ether/hexanes and dried, to give the title compound (0.245 g, 50%) as a cream solid. $\delta_H$ (400 MHz, DMSO-d$_6$) 8.93 (d, J 1.5 Hz, 2H), 7.79 (d, J 6.8 Hz, 1H), 7.57 (m, 1H), 7.40 (m, 1H), 7.33 (t, J 72, 76 Hz, 1H), 7.27 (m, 2H), 7.17 (m, 1H), 6.82 (m, 1H), 5.56 (s, 2H), 4.11 (m, 2H), 2.76 (m, 1H), 2.66 (m, 1H), 2.50 (m, 3H), 2.49 (m, 3H), 2.12 (m, 1H), 1.74 (m, 1H), 1.21 (t, J 7.1 Hz, 3H). LCMS (pH 10) MH+ 537, RT 1.62 minutes.

Intermediate 79

Ethyl 4-[5-(1-{[2-(difluoromethoxy)phenyl]methyl}-5-fluoro-2-methylbenzimidazol-6-yl)pyrimidin-2-yl]cyclohexanecarboxylate Intermediate 78 (245 mg, 0.47 mmol) and 10% palladium on charcoal (50 mg) in MeOH (12 mL) was degassed and hydrogenated at normal pressure for 40 h. The reaction mixture was filtered through celite and was washed with MeOH. The combined filtrate and washings were concentrated and purified by column chromatography (EtOAc: hexanes, 1:1 to 3:2), to give the title compound (0.24 g, 98%) as a colourless gum. $^1$H NMR showed two isomers in a ratio of 2.5:1. $\delta_H$ (400 MHz, DMSO-d$_6$) 8.90 (m, 2H), 7.79 (m, 1H), 7.57 (m, 1H), 7.39 (m, 1H), 7.32 (t, J 72, 76 Hz, 1H), 7.26 (m, 1H), 7.18 (m, 1H), 6.79 (m, 1H), 5.55 (s, 2H), 4.09 (m, 2H), 2.99 (m, 1H), 2.66 (m, 1H), 2.50 (s, 3H), 1.99 (m, 4H), 1.84 (m, 2H), 1.69 (m, 2H), 1.20 (m, 3H). LCMS (pH 10) MH+ 539, RT 1.62 minutes.

Intermediate 80

Methyl 4-[5-(1-{[2-(difluoromethoxy)phenyl]methyl}-2-methylbenzimidazol-6-yl)-pyrimidin-2-yl]cyclohex-3-ene-1-carboxylate A mixture of Intermediate 65 (0.15 g, 0.37 mmol), Intermediate 177 (0.15 g, 0.56 mmol), Pd(dppf)Cl$_2$ (8 mg, 0.001 mmol) and 2M aqueous sodium carbonate solution (2 mL) in 1,4-dioxane (8 mL) was degassed and stirred at 110° C. for 1.5 h. The reaction mixture was partitioned between EtOAc/brine, then the organic extract was dried (MgSO$_4$). The material crystallised out on evaporation of the solvent and was triturated in diethyl ether, filtered, washed with diethyl ether and dried to give the title compound (0.164 g, 87%) as an off-white solid. $\delta_H$ (400 MHz, DMSO-d$_6$) 9.08 (s, 2H), 7.93 (d, J 1.2 Hz, 1H), 7.70 (m, 1H), 7.62 (m, 1H), 7.38 (m, 1H), 7.27 (d, J 7.6 Hz, 2H), 7.16 (m, 1H), 7.35 (t, J 72, 76 Hz, 1H), 6.80 (m, 1H), 5.57 (s, 2H), 3.65 (s, 3H), 2.70 (m, 2H), 2.59 (s, 3H), 2.49 (m, 3H), 2.11 (m, 1H), 1.73 (m, 1H). LCMS (pH 10) MH+ 505, RT 1.50 minutes.

Intermediate 81

Methyl 4-[5-(1-{[2-(difluoromethoxy)phenyl]methyl}-2-methylbenzimidazol-6-yl)-pyrimidin-2-yl]cyclohexanecarboxylate Intermediate 80 (0.164 g, 0.325 mmol) and 10% palladium on charcoal (20 mg) in MeOH (8 mL) was degassed and hydrogenated at normal pressure overnight. Further 10% palladium on charcoal (30 mg) was added, and the reaction mixture was degassed and hydrogenated at 50° C. for 6 h. The reaction mixture was filtered through celite, concentrated and columned, using first 4:1 EtOAc-hexane, then EtOAc, to give the title compound (130 mg, 79%) as a colourless gum. $\delta_H$ (400 MHz, DMSO-d$_6$) 9.03 (m, 2H), 7.90 (d, J 1.2 Hz, 1H), 7.69 (m, 1H), 7.58 (m, 1H), 7.39 (m, 1H), 7.35 (t, J 72, 76 Hz, 1H), 7.26 (m, 1H), 7.16 (m, 1H), 6.78 (d, J 7.6 Hz, 1H), 5.56 (s, 2H), 3.61 (s, 3H), 2.98 (m, 1H), 2.68 (m, 1H), 2.50 (s, 3H), 1.98 (m, 4H), 1.82 (m, 2H), 1.68 (m, 2H). LCMS (pH 10) MH+ 507, RT 1.48 minutes.

Intermediate 82

Ethyl 3-[5-(1-{[2-(difluoromethoxy)phenyl]methyl}-2-methylbenzimidazol-6-yl)-pyrimidin-2-yl]-3-azabicyclo[4.1.0]heptane-1-carboxylate A mixture of Intermediate 47 (0.16 g, 0.44 mmol), [2-(1-ethoxycarbonyl-3-azabicyclo[4.1.0]heptan-3-yl)pyrimidin-5-yl]boronic acid (0.19 g, 0.65 mmol), Pd(dppf)Cl$_2$ (0.0091 g, 0.011 mmol) and 2M aqueous sodium carbonate solution (2 mL) in 1,4-dioxane (8 mL) was degassed and stirred at 110° C. for 1.5 h. The reaction mixture was partitioned between EtOAc/brine. The organic layer was dried (MgSO$_4$) and concentrated. The crude residue was purified by column chromatography (EtOAc: hexanes, 2:1 to 4:1) and the material was crystallised from diethyl ether, filtered, washed with diethyl ether/hexanes and dried, to give the title compound (0.14 g, 60%) as a white crystalline solid. $\delta_H$ (400 MHz, DMSO-d$_6$) 8.68 (m, 2H), 7.69 (d, J 1.2 Hz, 1H), 7.61 (m, 1H), 7.43 (dd, J 8.3, 1.6 Hz, 1H), 7.39 (m, 1H), 7.35 (t, J 72, 76 Hz, 1H), 7.27 (m, 1H), 7.17 (m, 1H), 6.79 (m, 1H), 5.54 (m, 2H), 4.35 (m, 1H), 4.27 (m, 1H), 4.09 (m, 2H), 3.70 (m, 1H), 3.41 (m, 1H), 2.50 (s, 3H), 2.11 (m, 1H), 1.81 (m, 1H), 1.72 (m, 1H), 1.27 (m, 1H), 1.19 (t, J 7.1 Hz, 3H), 0.83 (dd, J 6.4, 4.5 Hz, 1H). LCMS (pH 10) MH+ 534, RT 1.58 and 1.55 minutes.

Intermediate 83

Methyl (1R)-3-[5-(1-{[2-(difluoromethoxy)phenyl]methyl}-2-methylbenzimidazol-6-yl)-pyrimidin-2-yl]-3-azabicyclo[3.1.0]hexane-1-carboxylate A mixture of Intermediate 65 (0.2 g, 0.5 mmol), methyl (1R)-3-azabicyclo[3.1.0]-hexane-1-carboxylate hydrochloride (0.1 g, 0.6 mmol) and triethylamine (0.1 g, 1 mmol) in ethanol (6 mL) was stirred at 80° C. for 5 h. Further triethylamine (0.1 mL) was added and the reaction mixture was stirred at the same temperature for a further 8 h. The reaction mixture was concentrated and the residue was partitioned between EtOAc/brine. The organic layer was washed once more with brine, then dried (MgSO$_4$), to give the title compound (0.23 g, 90%) as a white foam. $\delta_H$ (400 MHz, DMSO-d$_6$) 8.66 (s, 2H), 7.68 (s, 1H), 7.61 (d, J 8.3 Hz, 1H), 7.39 (m, 2H), 7.35 (t, J 78 Hz, 1H), 7.27 (d, J 8.1 Hz, 1H), 7.16 (m, 1H), 6.80 (d, J 7.6 Hz, 1H), 5.53 (s, 2H), 3.96 (m, 1H), 3.86 (m, 2H), 3.67 (s, 3H), 3.59 (m, 1H), 2.50 (s, 3H), 2.25 (m, 1H), 1.55 (dd, J 8.3, 4.5 Hz, 1H), 0.96 (t, J 5.0 Hz, 1H). LCMS (pH 10) MH+ 506, RT 1.51 minutes.

Intermediate 84

[removed]

Intermediate 85

{2-[(1R,5S,8r)-8-Methoxycarbonyl-3-azabicyclo[3.2.1]octan-3-yl]pyrimidin-5-yl}boronic acid Methyl (1R,5S,8r)-3-(tert-butoxycarbonyl)-3-azabicyclo[3.2.1]octane-8-carboxylate (9.0 g, 35.3 mmol) was suspended in HCl solution (2.25M in MeOH) and the reaction mixture was heated to reflux for 4 h. The reaction mixture was allowed to cool to r.t. and then concentrated in vacuo to give a white solid. (2-Chloropyrimidin-5-yl)boronic acid (5.58 g, 35.2 mmol) was added and the mixture was suspended in EtOH (130 mL). Triethylamine (9.90 mL, 70.5 mmol) was added and the reaction mixture was heated at 80° C. for 5 h. The reaction mixture was allowed to cool to r.t. and then water was added (30 mL). The reaction mixture was concentrated to around one third volume, then more water (100 mL) was added. An off-white solid precipitated out, which was filtered and washed with water (2×30 mL), to afford the title compound (8.9 g, 86%) as an off-white powder. $\delta_H$ (300 MHz, $d_6$-DMSO) 8.59 (2H, s), 8.02 (2H, s), 4.45 (2H, dd, J 13.1, 3.4 Hz), 3.62 (3H, s), 2.98 (2H, br d, J 12.4 Hz), 2.77 (1H, s), 2.59 (2H, br s), 1.66-1.63 (2H, m), 1.38-1.33 (2H, m). HPLC-MS (pH10): MH+ m/z 292, RT 0.97 minutes.

Intermediate 86

Methyl (1R,5S,8r)-3-[5-(1-{[2-(difluoromethoxy)phenyl]methyl}-5-fluoro-2-methylbenzimidazol-6-yl)pyrimidin-2-yl]-3-azabicyclo[3.2.1]octane-8-carboxylate Intermediate 50 (500 mg, 1.17 mmol), Intermediate 85 (510 mg, 1.75 mmol) and 2M aqueous $K_3PO_4$ solution (2.0 mL) were suspended in 1,4-dioxane (12 mL). The mixture was degassed (evacuated and re-filled with nitrogen 3 times). Bis[3-(diphenyl-phosphanyl)cyclopenta-2,4-dien-1-yl]iron dichloropalladium dichloromethane complex (48 mg, 0.06 mmol) was added and the mixture was again degassed, then heated at 90° C. for 36 h. The mixture was cooled to r.t., diluted with water (50 mL) and extracted with EtOAc (3×50 mL). The combined organic layers were washed with water (20 mL), dried over $Na_2SO_4$ and purified by silica gel chromatography, eluting with 35-100% ethyl acetate in isohexane, to afford the title compound (325 mg, 50%) as an off-white solid. $\delta_H$ (400 MHz, $d_6$-DMSO) 8.50 (2H, d, J 1.7 Hz), 7.60 (1H, d, J 7.0 Hz), 7.48 (1H, d, J 11.4 Hz), 7.40-7.34 (1H, m), 7.32 (1H, t, J 73.8 Hz), 7.25 (1H, dd, J 8.2, 0.7 Hz), 7.16 (1H, td, J 7.6, 1.1 Hz), 6.80 (1H, dd, J 8.0, 1.9 Hz), 5.51 (2H, s), 4.46-4.40 (2H, m), 3.63 (3H, s), 3.28 (3H, s), 3.03 (2H, br d, J 12.7 Hz), 2.79 (1H, br s), 2.62 (2H, br s), 1.70-1.65 (2H, m), 1.43-1.38 (2H, m). LCMS (pH 10): MH+ m/z 552, RT 2.35 minutes.

Intermediate 87 tert-Butyl 4-ethyl 4-methylpiperidine-1,4-dicarboxylate

To tert-butyl-4-ethyl piperidine-1,4-dicarboxylate (10.03 g, 39.0 mmol), dissolved in THF (50 mL) and cooled to 0° C. in an ice bath under nitrogen, was added dropwise LDA (2M solution in THF; 25.0 mL, 50 mmol). The mixture was stirred at 0° C. for 40 minutes. Iodomethane (3.2 mL, 51 mmol) was then added, and the mixture was stirred at 0° C. for 3 h before warming to r.t. The reaction mixture was left to stand at r.t. for 2 h. EtOAc (150 mL) was added and the mixture was washed with brine (2×100 mL). The organic layer was separated, dried ($Na_2SO_4$), and filtered under reduced pressure. The solvent was removed in vacuo to yield a brown oil which was purified by flash column chromatography on silica, using 100% isohexane to 100% EtOAc, followed by concentration in vacuo, to afford the title compound (7.92 g, 75%) as an orange oil. $\delta_H$ (300 MHz, DMSO-$d_6$) 4.10 (q, J 7.1 Hz, 2H), 3.60 (dt, J 13.6, 4.4 Hz, 2H), 2.94 (br t, J 11.7 Hz, 2H), 1.95-1.84 (m, 2H), 1.39 (s, 9H), 1.30 (ddd, J 14.0, 10.2, 4.1 Hz, 2H), 1.18 (t, J 7.1 Hz, 3H), 1.14 (s, 3H).

Intermediate 88

Ethyl 4-methylpiperidine-4-carboxylate

To Intermediate 87 (7.92 g, 29.2 mmol) dissolved in DCM (50 mL) was added 2M HCl in diethyl ether (31.0 mL). The mixture was stirred at r.t. overnight. The solvent was removed in vacuo to afford the title compound (6.16 g, 102%) as an orange/brown solid. $\delta_H$ (300 MHz, DMSO-$d_6$) 8.70 (br s, 2H), 4.13 (t, J 7.1 Hz, 2H), 3.24-3.11 (m, 2H), 2.93-2.75 (m, 2H), 2.13-2.02 (m, 2H), 1.61 (ddd, J 14.5, 10.6, 4.1, 2H), 1.20 (t, J 7.1 Hz, 3H), 1.19 (s, 3H).

Intermediate 89

[2-(4-Ethoxycarbonyl-4-methylpiperidin-1-yl)pyrimidin-5-yl]boronic acid

To (2-chloropyrimidin-5-yl)boronic acid (4.00 g, 25.3 mmol) were added Intermediate 88 (4.09 g, 23.9 mmol) and ethanol (40 mL). Triethylamine (9.0 mL, 64 mmol) was added and the mixture was heated at 80° C. for 3 h before concentrating in vacuo. The mixture was partitioned between water (100 mL) and EtOAc (100 mL). The aqueous layer was separated and re-extracted with EtOAc (2×100 mL). The organic layers were combined and washed with brine (100 mL) before separating, drying ($Na_2SO_4$), filtering under reduced pressure and removing the solvent in vacuo. The resulting brown foam was purified by column chromatography on silica, using 100% DCM to 30% MeOH/DCM, to afford the title compound (4.00 g, 74% purity) as a brown oil. LCMS (pH 10): MH+ m/z 294, RT 0.65 minutes (74%).

Intermediate 90

6-Bromo-1-{[2-chloro-6-(difluoromethoxy)phenyl]methyl}-2-methylbenzimidazole

The title compound was synthesized according to the procedure described for Intermediate 47 commencing with 6-chloro-2-(difluoromethoxy)benzylamine. LCMS (pH 10): (M+H)+ m/z 403 and 401, RT 3.58 minutes.

Intermediate 91

4-[(6-Bromo-2-methylbenzimidazol-1-yl)methyl]-2-methyl-5-(trifluoromethyl)thiazole The title compound was synthesized according to the procedure described for Intermediate 47 commencing with [2-methyl-5-(trifluoromethyl)thiazol-4-yl]-methanamine. LCMS (pH 10): (M+H)+ m/z 390 and 391, RT 2.65 minutes.

Intermediate 92

Methyl (1S,5R,8r)-3-[5-(1-{[5-chloro-2-(difluoromethoxy)phenyl]methyl}-5-fluoro-2-methylbenzimidazol-6-yl]pyrimidin-2-yl]-3-azabicyclo[3.2.1]octane-8-carboxylate Intermediate 75 (501 mg, 1.19 mmol), Intermediate 85 (523 mg, 1.80 mmol) and 1,1'-bis(diphenylphosphino)ferrocene palladium(II) dichloride dichloromethane complex (50 mg, 0.061 mmol) were suspended in 1,4-dioxane (10 mL) and 2M aqueous potassium phosphate tribasic solution (2 mL). The reaction mixture was degassed (vacuum/nitrogen) and then heated under nitrogen at 100° C. for 3 h. The reaction mixture was cooled to r.t. overnight. The reaction mixture was then diluted with EtOAc (50 mL) and washed with water (2×50 mL). The aqueous layer was back-extracted with EtOAc (2×50 mL). The combined organic layer was washed with brine (50 mL), dried ($Na_2SO_4$), filtered and concentrated in vacuo to a brown foam. The crude material was purified by column chromatography ($SiO_2$, 25-75% EtOAc in hexanes) and the resulting material was freeze-dried from acetonitrile/water to give the title compound (488 mg, 69%) as an off-white solid. $\delta_H$ (DMSO-$d_6$) 8.52 (d, 2H, J 1.7 Hz), 7.64 (d, 1H, J 7.0 Hz), 7.44-7.53 (m, 2H), 7.32 (t, 1H, J 73.4 Hz), 7.27-7.32 (m, 1H), 6.83 (d, 1H, J 2.5 Hz), 5.51 (s, 2H), 4.44 (dd, 2H, J 13.0, 3.5 Hz), 3.63 (s, 3H), 3.27-3.33 (m, 3H) ($CH_3$ group under water peak, confirmed by $D_2O$ shake), 3.00-3.07 (m, 2H), 2.79-2.81 (s, 1H), 2.59-2.66 (m, 2H), 1.63-1.72 (m, 2H), 1.36-1.46 (m, 2H). LCMS (ES+) 587 (M+H)$^+$, RT 2.81 minutes.

Intermediate 93

6-(6-Chloro-4-methylpyridin-3-yl)-1-{[2-(difluoromethoxy)phenyl]methyl}-2-methylbenzimidazole Intermediate 47 (2.01 g, 5.47 mmol) and (6-chloro-4-methylpyridin-3-yl)boronic acid (1.12 g, 6.53 mmol) were dissolved in 1,4-dioxane (20 mL). Tripotassium phosphate (1 mL, 2.0 mmol) was added and the mixture was degassed with three cycles of vacuum and nitrogen. After addition of tetrakis(triphenylphosphine)palladium(0) (3 mol %), the reaction mixture was heated to 80° C. for 3 h. Further (6-chloro-4-methylpyridin-3-yl)-boronic acid (935 mg, 5.45 mmol) was added and the reaction mixture was heated for 2 h. After cooling to room temperature the reaction mixture was filtered through celite, washing with ethyl acetate. Water was added and the aqueous layer was extracted with ethyl acetate. The combined organic phase was dried over sodium sulphate, filtered and concentrated in vacuo. Purification by flash column chromatography (Biotage SNAP 100 g, Isolera), eluting with 5-10% EtOH/DCM, yielded the title compound (1.57 g, 69%). $\delta_H$ (300 MHz, $d_6$-DMSO) 8.19 (s, 1H), 7.64 (d, J 8.3 Hz, 1H), 7.49 (s, 1H), 7.45 (d, J 1.1 Hz, 1H), 7.37 (m, 1H), 7.32 (t, J 73.8 Hz, 1H), 7.24 (dd, J 8.1, 0.6 Hz, 1H), 7.17 (dd, J 8.3, 1.6 Hz, 2H), 6.83 (dd, J 7.6, 1.4 Hz, 1H), 5.51 (s, 2H), 2.52 (s, 3H), 2.21 (s, 3H). LC-MS (pH 3) MH+ m/z 414.2, RT 1.40 minutes. LC-MS (pH10) MH+ m/z 414.2, RT 1.52 minutes.

Intermediate 94

1-(5-Boronopyrimidin-2-yl)-4-(tert-butoxycarbonylamino)piperidine-4-carboxylic acid The title compound can be prepared by reaction of 4-(tert-butoxycarbonylamino)-piperidine-4-carboxylic acid with (2-chloropyrimidin-5-yl)boronic acid in accordance with the procedure described for Intermediate 89.

Intermediate 95

1-[(2,5-Dimethylphenyl)methyl]benzimidazole-6-carbonitrile

The title compound can be synthesised from 4-cyano-2-fluoronitrobenzene and 2,5-dimethylbenzylamine according to the procedure described for Intermediates 41 and 42, followed by cyclisation with formic acid according to Method J.

Intermediate 96

Methyl 3-(2,5-dimethylbenzylamino)-4-nitrobenzoate

Prepared from methyl 3-fluoro-4-nitrobenzoate and 2,5-dimethylbenzylamine by the method described for Intermediate 16. The title compound (2 g, 63%) was obtained as a yellow solid. $\delta_H$ (300 MHz, DMSO-$d_6$) 8.45 (br s, 1H), 8.19 (d, J 8.8 Hz, 1H), 7.44 (d, J 1.6 Hz, 1H), 7.15 (dd, J 8.8, 1.6 Hz, 1H), 7.11 (s, 1H), 7.09 (d, J 6.0 Hz, 1H), 6.99 (d, J 7.2 Hz, 1H), 4.57 (d, J 6.0 Hz, 2H), 3.83 (s, 3H), 2.32 (s, 3H), 2.21 (s, 3H).

Intermediate 97

Methyl 4-amino-3-(2,5-dimethylbenzylamino)benzoate

Prepared from Intermediate 96 by the method described for Intermediate 17, giving the title compound (1 g, 56%) as an off white solid. $\delta_H$ (300 MHz, DMSO-$d_6$) 7.14 (d, J 8.0 Hz, 1H), 7.11 (s, 1H), 7.07 (d, J 7.6 Hz, 1H), 6.97 (d, J 7.6 Hz, 1H), 6.94 (s, 1H), 6.55 (d, J 7.6 Hz, 1H), 5.51 (br s, 2H), 5.00 (t, J 5.2 Hz, 1H), 4.19 (d, J 4.8 Hz, 2H), 3.69 (s, 3H), 2.29 (s, 3H), 2.22 (s, 3H). LCMS [M+H]$^+$ m/z 285, RT 3.45 minutes.

Intermediate 98

Methyl 1-(2,5-dimethylbenzyl)-2-(hydroxymethyl)-1H-benzo[d]imidazole-6-carboxylate Prepared by cyclisation of Intermediate 97 with glycolic acid in accordance with Method J, giving the title compound (0.7 g, 70%) as a brown solid. $\delta_H$ (300 MHz, DMSO-$d_6$) 7.95 (s, 1H), 7.84 (dd, J 8.6, 1.2 Hz, 1H), 7.75 (d, J 8.4 Hz, 1H), 7.13 (d, J 7.2 Hz, 1H), 6.97 (d, J 6.8 Hz, 1H), 6.12 (s, 1H), 5.68 (br s, 1H), 5.61 (s, 2H), 4.66 (d, J 6.0 Hz, 2H), 3.81 (s, 3H), 2.34 (s, 3H), 2.63 (s, 3H). LCMS m/z 325, RT 2.95 minutes.

Intermediate 99

1-[(2,5-Dimethylphenyl)methyl]-2-(hydroxymethyl)(benzimidazole-6-carboxlic acid

To a stirred solution of Intermediate 98 (0.72 g, 0.002 mmol) in THF (10 mL) was added LiOH (0.281 g, 0.007 mmol) in water (5 mL), followed by stirring at 25-31° C. for 18 h. The reaction mixture was concentrated in vacuo. The residue was taken up in water (15 mL) and washed with ethyl acetate (three portions of 20 mL). The aqueous layer was acidified by the addition of aqueous HCl solution. The resulting solid precipitate was collected by filtration and dried in vacuo, to afford the title compound (0.51 g, 73%) as a pink solid. $\delta_H$ (300 MHz, DMSO-d$_6$) 7.92 (s, 1H), 7.82 (d, J 8.8 Hz, 1H), 7.71 (d, J 8.0 Hz, 1H), 7.13 (d, J 7.2 Hz, 1H), 6.96 (d, J 7.6 Hz, 1H), 6.11 (s, 1H), 5.59 (s, 2H), 4.68 (s, 2H), 2.35 (s, 3H), 2.02 (s, 3H). LCMS m/z 311, RT 2.39 minutes.

Intermediate 100

1-[(2,5-Dichlorophenyl)methyl]-2-methylbenzimidazole-6-carboxlic acid

The title compound can be synthesized by analogous procedures to those described for the synthesis of Intermediate 99, starting from 2,5-dichlorobenzylamine.

Intermediate 101

1-[(2,5-Dichlorophenyl)methyl]-2-methylbenzimidazol-6-ol

To a stirred solution of Example 1013 (3 g, 0.009 mol) in DCM (20 mL) cooled to −78° C. was added BBr$_3$ (2.65 mL, 0.028 mol) and the reaction mixture was stirred at −78° C. for 10 minutes, then 25-28° C. for 3 h. The reaction mixture was quenched with saturated sodium bicarbonate solution and extracted with DCM (3×30 mL). The combined organic layer was dried over Na$_2$SO$_4$ and concentrated. The crude residue was purified by column chromatography, using 100-200 mesh silica gel and 3% methanol in DCM as an eluent, to obtain the title compound (2.5 g, 87%) as a pink solid. $\delta_H$ (DMSO-d$_6$) 10.05 (br s, 1H), 7.66-7.63 (m, 2H), 7.52 (dd, J 6.4, 2.0 Hz, 1H), 7.29 (s, 1H), 7.04 (dd, J 6.8, 2.0 Hz, 1H), 6.82 (d, J 2.0 Hz, 1H), 5.69 (s, 2H), 2.82 (s, 3H). LCMS m/z 307, RT 2.43 minutes.

Intermediate 102 tert-Butyl 3-{1-[(2,5-dichlorophenyl)methyl]-2-methylbenzimidazol-6-yl}oxyaz etidine-1-carboxylate To a solution of Intermediate 101 (0.2 g, 0.65 mmol) in DMF (4 mL) was added Cs$_2$CO$_3$ (0.635 g, 1.95 mmol) and the resulting mixture was stirred for 10 minutes followed by addition of tert-butyl 3-iodoazetidine-1-carboxylate (0.174 g, 0.781 mmol). The reaction mixture was heated at 100° C. for 16 h. The reaction mixture was diluted with water (5 mL) and extracted with ethyl acetate (3×10 mL). The combined organic layer was washed with brine (2×20 mL), dried over Na$_2$SO$_4$, filtered and concentrated. The crude residue was purified by column chromatography, using 100-200 mesh size silica gel and 5% MeOH in DCM as eluent.

Intermediate 103

1-[(2,5-Dichlorophenyl)methyl]-2-methylbenzimidazol-5-ol

The title compound was prepared from 1-fluoro-4-methoxy-2-nitrobenzene following the method described for Intermediate 101. LCMS [M+H]$^+$ m/z 307, RT 1.92 minutes.

Intermediate 104 tert-Butyl 2-(2-chloropyridin-4-yloxy)acetate

2-Chloropyridin-4-ol (12 g, 93 mmol) was dissolved in DMF (450 mL) and cooled to 0° C. NaH (4.45 g, 111 mmol) was added and the mixture was stirred for 30 minutes. tert-Butyl 2-bromoacetate (19.51 g, 100 mmol) was added dropwise and the resulting solution was stirred at 0° C. for 2 h. The reaction mixture was diluted with water and extracted with 3 portions of EtOAc. The combined organic layers were washed with brine (3 times), dried over sodium sulfate and concentrated in vacuo. The crude material was purified over silica gel (0-10% MeOH in DCM) to obtain the title compound (17.1 g, 70% yield, 92% purity) as a yellowish oil. LCMS (acid): [M+H]$^+$ 244, RT 1.97 minutes.

Intermediate 105

2-[(2-Chloropyridin-4-yl)oxy]acetic acid trifluoroacetic acid salt

Intermediate 104 (9.6 g, 39.4 mmol) was dissolved in DCM (100 mL). TFA (65.1 g, 571 mmol, 44 mL) was added and the solution was stirred for 48 h. The mixture was concentrated in vacuo and co-evaporated with toluene to obtain the title compound (19.0 g, 61%) as a yellow oil. LCMS (base): [M+H]$^+$ 188, RT 0.49 minutes. $\delta_H$ (400 MHz, DMSO-d$_6$) 15.00-12.00 (br s, 4H), 8.22 (d, J 5.8 Hz, 1H), 7.13 (d, J 2.2 Hz, 1H), 7.01 (dd, J 2.2, 5.8 Hz, 1H), 3.88 (s, 2H).

Intermediate 106

Methyl 2-[(2-chloropyridin-4-yl)oxy]acetate

Intermediate 105 (6.84 g, 22.68 mmol) was dissolved in anhydrous toluene (200 mL), anhydrous MeCN (200 mL) and DMF (0.094 mg, 1.286 µmol, 0.1 mL). Thionyl chloride (113 g, 950 mmol) was added and the solution was heated at 80° C. for 18 h. After concentration in vacuo and co-evaporation with toluene the resulting material was dissolved in dry MeCN (150 mL). This solution was added to an ice-cold solution of methanol (158 g, 4931 mmol) and triethylamine (48.0 g, 474 mmol). After stirring for 20 minutes the mixture was concentrated in vacuo. EtOAc (250 mL) was added and the solution was washed with saturated aqueous NaHCO$_3$ (100 mL) and brine (100 mL). The organic layer was separated, coated on hydromatrix and purified over silica gel (80 g, 5-35% EtOAc in heptane) to obtain the title compound (3.4 g, 74% yield, >95% purity) as an orange solid. LCMS (base): [M+H]$^+$ 202, RT 1.84 minutes.

Intermediate 107

Lithium 2-[(2-chloropyridin-4-yl)oxy]acetate

Intermediate 106 (3.40 g, 16.86 mmol) was dissolved in THF (40 mL), water (20 mL) and methanol (20 mL). Lithium hydroxide monohydrate (0.849 g, 20.24 mmol) was added and the solution was stirred at r.t. for 36 h. The mixture was concentrated in vacuo and co-evaporated with toluene to obtain the title compound (3.3 g) as a yellow solid. LCMS (base): [M+H]$^+$ 188, RT 0.3 minutes.

Intermediate 108

4-[({[(2-Chloropyridin-4-yl)oxy]methyl}carbonamino-3-2-difluoromethox-benzylamino]benzonitrile Intermediate 40 (4.60 g, 15.9 mmol) was dissolved in dry DMF (100 mL) and Intermediate 107 (3.30 g, 17.05 mmol) was added. After addition of HATU (13.30 g, 35.0 mmol) the mixture was stirred at r.t. under a nitrogen atmosphere for 18 h. The mixture was concentrated, dissolved in EtOAc (250 mL) and washed with water (100 mL). The layers were separated and the aqueous layer was extracted with EtOAc (100 mL). The organic layers were combined, washed with water (100 mL) and brine (100 mL), dried over sodium sulfate and coated onto hydromatrix. The coated material was purified over silica gel (80 g, 10-60% EtOAc in heptane) to afford the title compound (6.2 g, 85% yield, >95% purity) as a brownish foam. LCMS (base): [M+H]$^+$ 459, RT 2.27 minutes.

Intermediate 109

2-{[(2-Chloropyridin-4-yl)oxy]methyl}-1-[2-(difluoromethoxy)benzyl]-1H-benzo[d]imidazole-6-carbonitrile Intermediate 108 (0.7 g, 1.21 mmol) was dissolved in acetic acid (20 mL) and stirred under a nitrogen atmosphere at 80° C. for 2 h. The mixture was concentrated and the residue was dissolved in EtOAc (100 mL). The solution was washed with saturated aqueous NaHCO$_3$ solution (50 mL), diluted aqueous NaHCO$_3$ solution (1:1 saturated aqueous NaHCO$_3$ solution/water, 50 mL) and brine (100 mL). The organic phase was separated, dried over sodium sulfate and evaporated to dryness. The crude material was purified over silica gel (12 g, 10-70% EtOAc in heptane) to afford the title compound (100 mg, 19% yield, >95% purity) as a beige solid. LCMS (base): [M–H]$^−$ 439, RT 2.24 minutes.

Intermediate 110

6-(6-Chloropyridin-3-yl)-1-[2-difluoromethoxy)benzyl]-2-methyl-1H-benzo[d]imidazole Intermediate 47 (400 mg, 1.089 mmol) and (6-chloropyridin-3-yl)boronic acid (171 mg, 1.089 mmol) were dissolved DME (15 mL). A solution of cesium carbonate (1065 mg, 3.27 mmol) in water (5 mL) was added, and the mixture was degassed with argon before [1,1'-bis(diphenylphosphino)ferrocene]palladium(II) dichloride (89 mg, 0.109 mmol) was added. The reaction mixture was heated at 100° C. for 0.5 h under microwave irradiation. After cooling, the reaction mixture was diluted with water (20 mL) and extracted with EtOAc (2×50 mL). The combined organic layers were dried over sodium sulfate, evaporated in vacuo and purified over silica gel (100 g, 0-10% MeOH in DCM) to obtain the title compound as an off-white solid. δ$_H$ (400 MHz, DMSO-d$_6$) 8.56 (d, J 2.5 Hz, 1H), 7.82 (d, J 8.3 Hz, 1H), 7.81 (d, J 8.3 Hz, 1H), 7.43 (dd, J 1.6, 8.3 Hz), 7.36 (d, J 8.4 Hz), 7.37-7.29 (m, 2H), 7.19 (d, J 7.9 Hz, 1H), 7.09 (t, J 7.7 Hz), 6.84-6.48 (t, J 73.2 Hz, 1H), 6.67 (d, J~6.3 Hz, 1H), 5.44 (s, 2H), 2.61 (s, 3H). LCMS (acid): [M+H]$^+$ 400, RT 1.85 minutes.

Intermediate 111

5-(2,5-Difluoro-4-nitrophenyl)-2-methoxypyridine

A suspension of 1-bromo-2,5-difluoro-4-nitrobenzene (25 g, 105 mmol), (6-methoxypyridin-3-yl)boronic acid (19.28 g, 126 mmol) and sodium carbonate (33.4 g, 315 mmol) in DME (800 mL) and water (200 mL) was degassed with argon. Bis(triphenylphosphine)palladium(II) chloride (3.69 g, 5.25 mmol) was added and the mixture was heated at 80° C. for 1 h. After cooling, EtOAc and water were added, the layers were separated and the aqueous phase was extracted twice with EtOAc. The combined organic layers were washed with brine, dried over sodium sulfate and evaporated in vacuo, to obtain the title compound (29.3 g, 92% yield, 88% purity). LCMS (acid): [M+H]$^+$ 267, RT 2.19 minutes.

Intermediate 112

(S)-4-Fluoro-N-[1-(4-fluorophenyl)ethyl]-5-(6-methoxypyridin-3-yl)-2-nitroaniline Intermediate 111 (5 g, 18.78 mmol) and (S)-1-(4-fluorophenyl)ethylamine (4.44 g, 31.9 mmol, 4.3 mL) were dissolved in dry THF (80 mL). Potassium carbonate (3.12 g, 22.54 mmol) was added and the reaction mixture was heated under reflux for 8 days. The reaction mixture was diluted with water (100 mL) and extracted with EtOAc (3×100 mL). The combined organic layers were dried over sodium sulfate and evaporated in vacuo, to obtain the title compound (7.8 g, 89% yield, 82% purity) as an orange solid. LCMS (base): [M+H]$^+$ 386, RT 2.59 minutes.

Intermediate 113

(S)-4-Fluoro-N$^1$-1[(4-fluorophenyl)ethyl]-5-(6-methoxypyridin-3-yl)benzene-1,2-diamine Intermediate 112 (5 g, 12.97 mmol) was suspended in methanol (50 mL). Ammonium chloride (3.47 g, 64.9 mmol) in water (150 mL) was added, followed by the addition of iron powder (3.62 g, 64.9 mmol). The reaction mixture was vigorously stirred at 80° C. for 16 h, then filtered over kieselguhr. The filtrate was concentrated in vacuo. The residue was dissolved in water (20 mL) and washed with EtOAc (3×50 mL). The organic layers were combined, dried over sodium sulfate and evaporated in vacuo. The crude material was purified over silica gel (120 g, 0-50% EtOAc in heptane) to afford the title compound (3.15 g, 68% yield, 98% purity) as a brown oil. LCMS (base): [M+H]$^+$ 356, RT 2.38 minutes.

Intermediate 114

2-(6-Chloropyridin-3-yl)-N-{5-fluoro-2-[1-(4-fluorophenyl)ethylamino]-4-(6-methoxypyridin-3-yl)phenyl}acetamide Intermediate 113 (5 g, 14.07 mmol), 6-chloro-3-pyridineacetic acid (4.83 g, 28.1 mmol) and DIPEA (5.46 g, 42.2 mmol, 7.23 mL) were dissolved in DME (100 mL). Bis(2-oxo-3-oxazolidinyl)phosphinic chloride (3.58 g, 14.07 mmol) was added and the reaction mixture was stirred at 60° C. for 2 h. The mixture was cooled, diluted with EtOAc (50 mL) and washed with saturated aqueous NaHCO$_3$ solution (50 mL). The layers were separated and the aqueous phase was washed with EtOAc (2×100 mL). The combined organic layers were evaporated in vacuo to afford the title compound (8.7 g) as a brown oil. LCMS (base): [M+H]$^+$ 509, RT 2.40 minutes.

Intermediate 115

(S)-2-[(6-Chloropyridin-3-yl)methyl]-5-fluoro-1-[1-(4-fluorophenyl)ethyl]-6-(6-methoxypyridin-3-yl)-1H-benzo[d]imidazole Intermediate 114 (8.7 g, 17.09 mmol) was dissolved in acetic acid (200 mL) and heated at 110° C. for 3 h. The acetic acid was evaporated and the crude material was coated onto hydromatrix, then purified over silica gel (40 g, 0-100% EtOAc in heptane), to afford the title compound (4.36 g, 52% yield, 98% purity) as a white solid. $\delta_H$ (400 MHz, DMSO-$d_6$) 8.31 (d, J 2.3 Hz, 1H), 8.11 (d, J 1.7 Hz, 1H), 7.66-7.63 (dt, J 2.2, 8.6 Hz, 1H), 7.60-7.57 (dd, J 2.5, 5.8 Hz, 1H), 7.53 (d, J 10.7 Hz, 1H), 7.27 (d, J 8.0 Hz, 1H), 7.08-6.96 (m, 4H), 6.89 (d, J 6.6 Hz, 1H), 6.78 (d, J 8.6 Hz, 1H), 5.68 (d, J 7.0 Hz, 1H), 4.35-4.25 (dd, J 16.2, 5.2 Hz, 2H), 3.96 (s, 3H), 1.81 (d, J 7.1 Hz, 3H). LCMS (base): [M+H]$^+$ 491, RT 2.40 minutes.

Intermediate 116

1-{[2-(Difluoromethoxy)phenyl]methyl}-6-(6-methoxypyridin-3-yl)benzimidazole-2-carbaldehyde The title compound can be synthesized from Example 238 by treatment with Dess-Martin periodinane in dichloromethane.

Intermediate 117

{2-[4-(Methylsulfonyl)piperazin-1-yl]pyrimidin-5-yl}boronic acid

The title compound was synthesized from (2-chloropyrimidin-5-yl)boronic acid and 1-(methylsulfonyl)piperazine by the method described for Intermediate 89.

Intermediate 118

6-Bromo-1-[(2,5-dimethylphenyl)methyl]benzimidazole

The title compound can be synthesized from Intermediate 17 and formic acid in accordance with Method J.

Intermediate 119

{1-[(1R)-1-Phenylethyl]benzimidazol-2-yl}methanol

The title compound was synthesised in accordance with the procedure described for Intermediate 10 starting from (R)-1-phenylethylamine.

Intermediate 120

4-[(6-Bromo-1H-benzimidazol-2-yl)methoxy]benzamide

Prepared from 4-bromo-1,2-phenylenediamine and 2-(4-carbamoylphenoxy)acetic acid in accordance with Method J to give the title compound (2.80 g, 72%) as a pale brown solid. $\delta_H$ ($d_6$-DMSO) 7.87-7.76 (m, 4H), 7.53 (d, 1H, J 8.5 Hz), 7.34 (dd, 1H, J 8.5, 1.7 Hz), 7.22-7.13 (m, 3H), 5.39 (s, 2H).

Intermediate 121 tert-Butyl 4-(1-{[2-(difluoromethoxy)phenyl]methyl}-2-methylbenzimidazol-5-yl)-piperidine-1-carboxylate The title compound was prepared from Intermediate 47 and tert-butyl 4-(4,4,5,5-tetramethyl-1,3,2-dioxaborolan-2-yl)-3,6-dihydro-2H-pyridine-1-carboxylate by Method L, followed by catalytic hydrogenation with 5 mol % palladium on carbon in ethanol.

Intermediate 122

1-{[2-(Difluoromethoxy)phenyl]methyl}-2-methyl-6-(piperidin-4-yl)benzimidazole

Can be prepared from Intermediate 121 by dissolving the compound in a mixture of dichloromethane and trifluoroacetic acid (5:1 v:v) and stirring at ambient temperature for 16 h. The volatiles can be removed in vacuo to yield the title compound as the trifluoroacetate salt.

Intermediate 123

Methyl (2S,3S,4S,5R,6S)-3,4,5-triacetoxy-6-{[5-(1-{[2-(difluoromethoxy)phenyl]-methyl}-2-methyl-benzimidazol-6-yl)pyridin-2-yl]oxy}tetrahydropyran-2-carboxylate Example 405 (100 mg, 0.26 mmol) and silver carbonate (290 mg, 1.04 mmol) were suspended in toluene (10 mL) and stirred at room temperature for 15 minutes, after which time acetobromo-α-D-glucuronic acid methyl ester (110 mg, 0.28 mmol) in toluene (5 mL) was added portionwise. The reaction mixture was heated under reflux for 4 h. The reaction mixture was then cooled to room temperature. The suspension was vacuum filtered to remove solids, and the filter cake was washed with EtOAc (3×25 mL). The filtrate was concentrated in vacuo, then the residue was purified by preparative HPLC and freeze-dried from acetonitrile/water, to give the title compound (49 mg, 26%) as a white solid. $\delta_H$ (DMSO-$d_6$) 8.48-8.51 (m, 1H), 8.07 (dd, 1H, J 8.6, 2.5 Hz), 7.77 (d, 1H, J 1.3 Hz), 7.64 (d, 1H, J 8.4 Hz), 7.48 (dd, 1H, J 8.4, 1.6 Hz), 7.33-7.40 (m, 1H), 7.35 (t, 1H, J 73.8 Hz), 7.23-7.29 (m, 1H), 7.14 (td, 1H, J 7.6, 1.1 Hz), 6.96 (d, 1H, J 8.6 Hz), 6.75 (dd, 1H, J 7.7, 1.3 Hz), 6.47 (d, 1H, J 8.2 Hz), 5.61 (t, 1H, J 9.5 Hz), 5.54 (s, 2H), 5.14 (dd, 1H, J 9.5, 8.1 Hz), 5.06 (t, 1H, J 9.7 Hz), 4.71 (d, 1H, J 9.8 Hz), 3.61 (s, 3H), 2.48-2.52 (m, 3H), 2.01 (s, 3H), 1.99 (s, 3H), 1.96 (s, 3H). LCMS (ES+) 698 (M+H)$^+$, RT 2.33 minutes.

Intermediate 124

[(Amino)(3-oxopiperazin-1-yl)methylene]ammonium chloride

Piperazin-2-one (200 mg, 2.00 mmol) and 1H-pyrazole-1-carboxamidine hydrochloride (293 mg, 2.00 mmol) were dissolved in ethanol (5 mL) and heated at 80° C. for 4.5 h. The reaction mixture was cooled to 40° C. and filtered to give the title compound (213 mg, 60%) as a pale yellow solid. $\delta_H$ (DMSO-d$_6$) 8.31 (s, 1H), 7.56 (s, 4H), 3.94 (s, 2H), 3.53-3.59 (m, 2H), 3.25-3.32 (m, 2H).

Intermediate 125 tert-Butyl-{(R,E)-[2-(difluoromethoxy)phenyl]methyleneamino}-oxido-sulfonium (R)-2-Methylpropane-2-sulfinamide (40.6 g, 335 mmol) and 2-(difluoromethoxy)-benzaldehyde (160 g, 279 mmol) were dissolved in tetrahydrofuran (300 mL) under nitrogen. Titanium ethoxide (126 mL, 613 mmol) was added and the mixture was stirred overnight. The mixture was quenched with water and filtered over kieselguhr. The filtrate was diluted with EtOAc and water and the layers were separated. The water layer was extracted thrice with EtOAc. The organic layers were combined and washed with water and brine, dried with Na$_2$SO$_4$, concentrated in vacuo and co-evaporated with dichloromethane, to give the title compound (74.7 g) as a yellow oil. LCMS (pH 3): (M+H)$^+$ m/z 276, RT 2.09 minutes.

Intermediate 126

(R)—N—{(R or S)-1-[2-(Difluoromethoxy)phenyl]ethyl}-2-methylpropane-2-sulfinamide (Isomer A)

To a solution of methylmagnesium bromide in Et$_2$O (127 mL, 381 mmol) in anhydrous tetrahydrofuran (300 mL), under argon at −30° C., was added Intermediate 125 (35 g, 127 mmol) in anhydrous tetrahydrofuran (100 mL) dropwise (temperature maintained below −20° C.). The mixture was stirred at −30° C. for 30 minutes. The mixture was poured onto saturated aqueous NH$_4$Cl solution. The mixture was diluted with EtOAc and water, and the layers were separated. The aqueous layer was extracted 3 times with EtOAc. The organic layers were combined and washed with water and brine, dried with Na$_2$SO$_4$ and concentrated, to give a yellow oil (40.13 g). The batch was purified by sequential column chromatography (50-80% EtOAc in heptane, followed by 30-70% EtOAc in heptane) to give the major diastereomer (Isomer A) as a yellow oil (29 g).

Intermediate 127

(R or S)-1-[2-(Difluoromethoxy)phenyl]ethanamine hydrochloride (Isomer A)

4N HCl in methanol was prepared by dropwise addition of SOCl$_2$ (17.60 mL, 241 mmol) into methanol (118 mL) at 0° C. The solution was added to Intermediate 126 (17.5 g, 60.3 mmol) in methanol (100 mL) and the mixture was stirred for 1 h. The mixture was concentrated, then co-evaporated 3 times with ethanol and DCM, to give a yellow oil. The batch was crystallized using diisopropyl ether and the batch was triturated overnight. The mixture was filtered off and rinsed with diisopropyl ether. The residue was air-dried and the title compound (11.8 g) was isolated as a white solid. LCMS: m/z 188 (M+H)$^+$.

Intermediate 128 tert-Butyl-{(S,E)-[2-(difluoromethoxy)phenyl]methyleneamino}-oxido-sulfonium

The title compound was prepared from (S)-2-methylpropane-2-sulfinamide in accordance with the method described for Intermediate 125. LCMS (pH 3) m/z 276 (M+H)$^+$, RT 2.09 minutes.

Intermediate 129

(S)—N—{(R or S)-1-[2-(Difluoromethoxy)phenyl]ethyl}-2-methylpropane-2-sulfinamide (Isomer B)

Prepared from Intermediate 128 in accordance with the method described for Intermediate 126, to give the title compound as a yellow oil.

Intermediate 130

(R or S)-1-[2-(Difluoromethoxy)phenyl]ethanamine hydrochloride (Isomer B)

Prepared from Intermediate 129 in accordance with the method described for Intermediate 127, to give the title compound (11 g) as a white solid. LCMS: m/z 188 (M+H)$^+$.

Intermediate 131

5-Bromo-N$^1$-{1-[2-(difluoromethoxy)phenyl]ethyl}-benzene-1,2-diamine (Isomer B)

Intermediate 130 was reacted with 4-bromo-2-fluoro-1-nitrobenzene according to the first two steps of Method K to give the title compound. LCMS (pH 10): 357.0 (M+H)$^+$, RT 1.17 minutes.

Intermediate 132

5-Bromo-N$^1$-{1-[2-(difluoromethoxy)phenyl]ethyl}-benzene-1,2-diamine (Isomer A)

Intermediate 127 was reacted with 4-bromo-2-fluoro-1-nitrobenzene in accordance with the first two steps of Method K to give the title compound. LCMS (pH 10): 357.0 (M+H)$^+$, RT 1.17 minutes.

Intermediate 133

6-Bromo-5-chloro-1-{[2-(difluoromethoxy)phenyl]methyl}-2-methylbenzimidazole

The title compound was prepared from 4-bromo-5-chloro-2-fluoronitrobenzene and 2-(difluoromethoxy)benzylamine in accordance with the procedure described for Intermediate 47. LCMS (pH 10): RT 1.57 minutes, m/z 401.0, 402.0 and 403.0.

Intermediate 134

5-Chloro-6-(2-chloropyrimidin-5-yl)-1-{[2-(difluoromethoxy)phenyl]methyl}-2-methylbenzimidazole The title compound was prepared from Intermediate 133 and (2-chloropyrimidin-5-yl)boronic acid in accordance with Method L. LCMS (pH 10): RT 1.51 minutes, poor ionisation.

Intermediate 135

4-(5-Bromopyridin-2-yl)-1-methylpiperidin-4-ol 2,5-Dibromopyridine (2 g, 8.44 mmol) was stirred under nitrogen in toluene (40 mL) at −78° C. and 2.5M butyl-lithium in hexane (3.38 mL) was added dropwise over 10 minutes. The mixture was stirred for 45 minutes at −78° C., then 1-methylpiperidin-4-one (1.46 g, 0.013 mol) was added dropwise over 10 minutes. The reaction mixture was stirred for 45 minutes at −78° C. then allowed to warm to room temperature. Aqueous ammonium chloride solution (5%, 75 mL) was added to the reaction mixture, and the product was extracted into ethyl acetate (2×75 mL). The combined organic extracts were washed with water (75 mL) and brine (75 mL), dried over magnesium sulfate and concentrated under reduced pressure. The crude product was purified by using a Biotage isolera 4, SNAP HP 50 g column, eluting with 0-10% 7N methanolic ammonia in DCM, to yield the title compound (1.24 g, 54%) as a pale yellow solid. $\delta_H$ (250 MHz, CDCl$_3$) 8.57 (d, J 2.2 Hz, 1H), 7.83 (dd, J 8.5, 2.3 Hz, 1H), 7.30 (d, J 8.5 Hz, 1H), 4.82 (s, 1H), 2.91-2.73 (m, 2H), 2.54 (td, J 12.2, 2.5 Hz, 2H), 2.39 (s, 3H), 2.11 (td, J 13.0, 4.6 Hz, 2H), 1.64 (dd, J 13.6, 2.3 Hz, 2H).

Intermediate 136

5-Bromo-2-{1-methyl-4-[(trimethylsilyl)oxy]piperidin-4-yl}pyridine

Intermediate 135 (0.5 g, 1.84 mmol) and imidazole (251 mg, 3.69 mmol) were stirred in DCM (10 mL) and the yellow solution was cooled in an ice brine bath. Trimethylsilyl chloride (0.26 mL, 2.03 mmol) was added portionwise, the ice bath was removed and the reaction mixture was stirred at 20° C. for 35 minutes. Further trimethylsilyl chloride (0.05 mL, 0.37 mmol) was added to the reaction mixture, and stirring was continued at 20° C. for 1 h. The reaction mixture was washed with water (2×10 mL), dried over magnesium sulfate, filtered and concentrated under reduced pressure, to afford the title compound (644 mg, 101.7%) as a white solid. $\delta_H$ (250 MHz, CDCl$_3$) 8.59 (d, J 2.3 Hz, 1H), 7.79 (dd, J 8.5, 2.4 Hz, 1H), 7.40 (d, J 8.5 Hz, 1H), 2.67 (d, J 11.1 Hz, 2H), 2.48 (td, J 11.1, 2.4 Hz, 2H), 2.33 (s, 3H), 2.17 (td, J 12.5, 11.3, 4.2 Hz, 2H), 1.98 (d, J 12.5 Hz, 2H), −0.08 (s, 9H).

Intermediate 137

2-{1-Methyl-4-[(trimethylsilyl)oxy]piperidin-4-yl}-5-(4,4,5,5-tetramethyl-1,3,2-dioxaborolan-2-yl)pyridine Intermediate 136 (594 mg, 1.73 mmol), diboron pinacol ester (527 mg, 2.1 mmol) and potassium acetate (509 mg, 5.2 mmol) were stirred in 1,4-dioxane (5 mL) and degassed with a stream of nitrogen for 10 minutes. Pd(dppf)Cl$_2$ complex with DCM (71 mg, 0.09 mmol) was added and the mixture was heated in a sealed tube at 80° C. for 30 minutes. The reaction mixture was cooled and filtered through Celite, washing with ethyl acetate (10 mL). The residue was concentrated under vacuum to give a black oil, azeotroping with 2:1 heptane/tert-butyl methyl ether. The residue was then sonicated in 2:1 heptane/tert-butyl methyl ether (5 mL) for 5 minutes. The resulting dark grey precipitate was filtered and washed with heptane (5 mL) to afford the title compound (170 mg, 16.4%) as a grey solid. $\delta_H$ (250 MHz, CDCl$_3$) 8.87 (dd, J 1.7, 0.9 Hz, 1H), 8.02 (dd, J 7.9, 1.8 Hz, 1H), 7.46 (dd, J 7.9, 0.9 Hz, 1H), 2.67 (d, J 10.8 Hz, 2H), 2.58-2.39 (m, 2H), 2.29 (m, 5H), 1.99 (d, J 12.6 Hz, 2H), 1.34 (s, 12H), −0.10 (s, 9H).

Intermediate 138

({4-[5-(1-{[2-(Difluoromethoxy)phenyl]methyl}-5-fluoro-2-methylbenzimidazol-6-yl)-2-pyridyl]-1-methylpiperidin-4-yl}oxy)(trimethyl)silane Intermediate 137 (50.68 mg, 0.13 mmol), Intermediate 50 (50 mg, 0.13 mmol) and 2M sodium carbonate in water (0.2 mL) were stirred in 1,4-dioxane (1 mL) and degassed under a stream of nitrogen for 10 minutes. Pd(dppf)Cl$_2$ complex with DCM (6 mg, 6.49 μmol) was added and reaction mixture was heated at 80° C. for 1.5 h. The reaction mixture was filtered through Celite, concentrated under reduced pressure and purified by preparative HPLC (method D), to afford the title compound (48 mg, 62%) as a yellow oil. $\delta_H$ (500 MHz, CDCl$_3$) 8.64 (s, 1H), 7.85 (dt, J 8.3, 2.0 Hz, 1H), 7.57-7.48 (m, 2H), 7.35-7.29 (m, 1H), 7.18 (d, J 6.4 Hz, 2H), 7.09 (t, J 7.6 Hz, 1H), 6.81-6.47 (m, 2H), 5.40 (s, 2H), 2.68 (d, J 23.3 Hz, 2H), 2.58 (s, 3H), 2.48 (t, J 10.6 Hz, 2H), 2.32 (s, 3H), 2.27-2.16 (m, 2H), 2.04 (d, J 12.6 Hz, 2H), −0.07 (s, 9H). Method D 7 min uPLC-MS: MH+ m/z 569, RT 2.20 minutes (92%).

Intermediate 139

4-(5-Bromopyrimidin-2-yl)-1-methylpiperidin-4-ol

5-Bromo-2-iodopyrimidine (2 g, 7.02 mmol) was dissolved in dry toluene (30 mL) and cooled to −78° C. under nitrogen. 2.5M n-butyllithium in hexanes (2.95 mL) was added dropwise and the reaction mixture was stirred for 30 minutes before dropwise addition of 1-methylpiperidin-4-one (0.9 mL, 0.01 mol). The reaction mixture was stirred at −78° C. for 1 h. The reaction mixture was allowed to warm to room temperature and diluted with aqueous ammonium chloride solution (5%, 50 mL), then extracted with ethyl acetate (3×50 mL). The combined organic extracts were washed with brine (50 mL) and dried over magnesium sulphate, then the solvent was removed under reduced pressure. The crude residue (1.55 g) was sonicated in ethyl acetate (10 mL) and DCM (1 mL), then heptane was added. The resulting solid was filtered to afford the title compound (580 mg, 29.4%) as a brown solid. LCMS Method E: MH+ m/z 272/274, RT 1.20 minutes (100%).

Intermediate 140

5-Bromo-2-{1-methyl-4-[(trimethylsilyl)oxy]piperidin-4-yl}pyrimidine

Intermediate 139 (97%, 570 mg, 2.03 mmol) and imidazole (280 mg, 4.06 mmol) were stirred in 4:1 DCM/DMF (12.5 mL) and the solution was cooled in an ice/brine bath. Trimethylsilyl chloride (0.28 mL, 2.23 mmol) was added dropwise. The reaction mixture was allowed to warm to room temperature and stirred for 3.5 h. The reaction mixture was washed with water (2×10 mL) and brine (5 mL), dried over magnesium sulfate, filtered and concentrated. The resulting sticky residue was sonicated in ethyl acetate, adding heptane. The resulting solid was filtered off and dried in vacuo at 40° C. overnight to afford the title compound (316 mg, 45.2%) as a brown solid. $\delta_H$ (250 MHz, CDCl$_3$) 8.80 (s, 2H), 3.47 (d, J 13.4 Hz, 2H), 3.32-3.10 (m, 2H), 2.81 (d, J 4.9 Hz, 3H), 2.77-2.63 (m, 2H), 2.45 (d, J 13.7 Hz, 2H), −0.09 (d, J 1.7 Hz, 9H).

Intermediate 141

2-{1-Methyl-4-[(trimethylsilyl)oxy]piperidin-4-yl}-5-(4,4,5,5-tetramethyl-1,3,2-dioxaborolan-2-yl)pyrimidine Intermediate 140 (316 mg, 0.92 mmol), diboron pinacol ester (280 mg, 1.1 mmol) and potassium acetate (270 mg, 2.75 mmol) were stirred in 1,4-dioxane (3 mL) and degassed for 5 minutes with nitrogen. Pd(dppf)Cl$_2$ complex with DCM (37 mg, 0.05 mmol) was added. The tube was sealed under nitrogen and heated at 80° C. for 5.5 h. The reaction mixture was filtered through Celite, washing with ethyl acetate (10 mL), and concentrated to give a black oil. The residue was then sonicated in 2:1 heptane/tert-butyl methyl ether (5 mL) for 5 minutes. The resulting dark grey precipitate was filtered and the filtrate was concentrated to give crude product. This process was repeated twice to afford the title compound (232 mg, 26%) as a grey solid. $\delta_H$ (500 MHz, CDCl$_3$) 9.00 (s, 2H), 2.60 (s, 4H), 2.35 (m, 5H), 2.13 (d, J 12.2 Hz, 2H), 1.36 (s, 12H), −0.07 (s, 9H).

Intermediate 142

1-{[2-(Difluoromethoxy)phenyl]methyl}-5-fluoro-2-methyl-6-(4,4,5,5-tetramethyl-1,3,2-dioxaborolan-2-yl)benzimidazole To a stirring solution of Intermediate 50 (86%, 760 mg, 1.7 mmol) in 1,4-dioxane (35 mL) were added bis(pinacolato)diboron (1.21 g, 4.75 mmol) and potassium acetate (500 mg, 5.01 mmol). The stirring mixture was degassed with nitrogen for 10 minutes, then Pd(dppf)Cl$_2$ complex with DCM (70 mg, 0.086 mmol) was added and the mixture was stirred at 110° C. for 5 h. The reaction mixture was allowed to cool to room temperature, then diluted with dichloromethane (50 mL) and filtered through celite, washing through with further dichloromethane (30 mL). The filtrate was concentrated under vacuum to give a dark oily solid (2.47 g), which was suspended in a 1:2 mixture of diethyl ether/heptane (15 mL) and sonicated for 5 minutes. The resulting fine suspension was collected by filtration and dried by vacuum oven to afford the title compound (573 mg, 70%) as a dark brown solid. $\delta_H$ (500 MHz, CDCl$_3$) 7.58 (d, J 4.5 Hz, 1H), 7.39 (d, J 9.8 Hz, 1H), 7.34-7.29 (m, 1H), 7.19 (d, J 8.0 Hz, 1H), 7.07 (t, J 7.5 Hz, 1H), 6.67 (t, J 73.2 Hz, 1H), 6.55 (d, J 7.6 Hz, 1H), 5.39 (s, 2H), 2.52 (s, 3H), 1.35 (s, 12H).

Intermediate 143

3-(5-Bromopyrimidin-2-yl)oxetan-3-ol

5-Bromo-2-iodopyrimidine (2 g, 7.02 mmol) was dissolved in dry toluene (30 mL) and cooled to −78° C. under N$_2$. n-Butyllithium in hexanes (2.5M, 2.95 mL) was added dropwise and the reaction mixture was stirred for 30 minutes, prior to dropwise addition of oxetan-3-one (0.452 mL, 7.72 mmol). The reaction mixture was stirred at −78° C. for 30 minutes, then allowed to warm to room temperature for 1 h. The reaction mixture was diluted with water (100 mL) and extracted with ethyl acetate (3×100 mL). The combined organic extracts were successively washed with water and brine, then dried over magnesium sulphate, The solvent was removed under reduced pressure to afford a brown oily solid. The crude material was absorbed onto 25 g KP-Sil biotage column with minimal DCM, and the product was eluted using a Biotage Isolera 4 with 10-100% ethyl acetate in heptanes, to afford the title compound (687 mg, 42%) as a crystalline yellow solid. $\delta_H$ (500 MHz, DMSO-d$_6$) 9.07 (s, 2H), 6.43 (s, 1H), 4.94 (d, J 6.5 Hz, 2H), 4.67 (d, J 6.5 Hz, 2H).

Intermediate 144

1-(5-Bromopyrimidin-2-yl)cyclobutan-1-ol

5-Bromo-2-iodopyrimidine (1 g, 3.51 mmol) was suspended in dry toluene (15 mL) and cooled to −78° C. under nitrogen. m-Xylene (6 mL) was added until the reaction mixture was in solution. n-Butyllithium in hexanes (2.5M, 1.5 mL) was added dropwise and the reaction mixture was stirred for 20 minutes, prior to dropwise addition of cyclobutanone (300 mg, 4.28 mmol). The reaction mixture was stirred at −78° C. for 45 minutes and then allowed to warm to room temperature. The reaction mixture was diluted with water (50 mL) and extracted with ethyl acetate (3×40 mL). The combined organic extracts were dried over magnesium sulfate and the solvent was removed in vacuo. The resulting brown oil was dissolved in a minimum of DCM and loaded onto a 25 g silica cartridge. This was eluted on a Biotage Isolera 4, with a gradient of 0-100% ethyl acetate in heptanes, to afford the title compound (396 mg, 49%) as a bright yellow solid. $\delta_H$ (500 MHz, CD$_3$OD) 8.90 (s, 2H), 2.71-2.63 (m, 2H), 2.37 (ddd, J 12.7, 9.8, 8.2 Hz, 2H), 2.04-1.86 (m, 2H).

Intermediate 145

2-(5-Bromopyridin-2-yl)propan-2-ol 2,5-Dibromopyridine (5 g, 0.021 mol) was dissolved in toluene (100 mL). The mixture was cooled to −78° C. A 2.5 M solution of n-butyllithium in hexane (8.44 mL, 0.021 mol) was added dropwise. The mixture was stirred 30 minutes, followed by the addition of anhydrous acetone (10 mL). The mixture was stirred 45 minutes and then allowed to warm to room temperature for 1 h. The mixture was washed with aqueous ammonium chloride solution (5%, 100 mL) and water (100 mL), then brine (100 mL). The organic layer was dried over sodium sulfate, filtered and concentrated in vacuo. The residue was purified by column chromatography on silica gel (eluting with 0 to 10% ethyl acetate in heptanes) to afford the title compound (2.21 g, 48%) as a yellow oil. $\delta_H$ (500 MHz, CDCl$_3$) 8.57 (d, J 2.1 Hz, 1H), 7.81 (dd, J 8.4, 2.3 Hz, 1H), 7.31 (d, J 8.4 Hz, 1H), 4.41 (s, 1H), 1.53 (s, 6H).

Intermediate 146

5-Bromo-2-{2-[(trimethylsilyl)oxy]propan-2-yl}pyridine

Intermediate 145 (1 g, 4.63 mmol) and imidazole (630 mg, 9.26 mmol) were dissolved in DCM (20 mL) and the solution was cooled in an ice bath prior to addition of trimethylsilyl chloride (553 mg, 5.09 mmol). The ice bath was removed and the reaction mixture was stirred at room temperature for 0.75 h. Additional trimethylsilyl chloride (1.65 eq) was added and the reaction mixture was stirred for 45 minutes. The reaction mixture was washed with water (2×20 mL) and dried over magnesium sulfate. The solvent was removed under reduced pressure to afford the title compound (1.142 g, 82%) as a colourless oil. $\delta_H$ (500 MHz, CDCl$_3$) 8.54 (d, J 2.3 Hz, 1H), 7.76 (dd, J 8.5, 2.4 Hz, 1H), 7.56 (d, J 8.5 Hz, 1H), 1.58 (s, 6H), 0.15 (s, 9H).

Intermediate 147

5-(4,4,5,5-Tetramethyl-1,3,2-dioxaborolan-2-yl)-2-{2-[(trimethylsilyl)oxy]propan-2-yl}pyridine In a pressure tube, a stirring solution of Intermediate 146 (200 mg, 0.69 mmol) in 1,4-dioxane (8 mL) was treated with bis(pinacolato)diboron (211 mg, 0.83 mmol) and potassium acetate (205 mg, 2.09 mmol). The stirring mixture was degassed with nitrogen for 10 minutes, then Pd(dppf)Cl$_2$ complex with DCM (29 mg, 0.04 mmol) was added. The pressure tube was sealed and the contents were stirred at 80° C. for 1 h, then at 100° C. for 1 h. The reaction mixture was allowed to cool and then filtered through celite, washing with ethyl acetate (30 mL). The filtrate was concentrated under vacuum to give a dark brown oil, which was triturated in 2:1 ether:heptane (10 mL). The suspension was filtered and the filtrate concentrated in vacuo to give a brown oil which was loaded onto a 10 g HP-silica cartridge and eluted on a Biotage Isolera 4, from a 0-100% ethyl acetate in heptanes gradient, to afford the title compound (185 mg, 80%) as a light brown solid. $\delta_H$ (500 MHz, CDCl$_3$) 8.85 (s, 1H), 8.03 (d, J 7.8 Hz, 1H), 7.64 (d, J 7.9 Hz, 1H), 1.61 (s, 6H), 1.34 (s, 12H), 0.14 (s, 9H).

Intermediate 148

{1-[5-(1-{[2-(Difluoromethoxy)phenyl]methyl}-5-fluoro-2-methylbenzimidazol-6-yl)-pyridin-2-yl]-1-methylethoxy}(trimethyl)silane Intermediate 147 (185 mg, 0.55 mmol) and Intermediate 50 (175 mg, 0.45 mmol) were dissolved in anhydrous 1,4-dioxane (8 mL) and 2M aqueous potassium carbonate solution (0.7 mL) was added. The mixture was degassed under nitrogen for 5 minutes. Pd(dppf)Cl$_2$ complex with DCM (20 mg, 0.024 mmol) was added. The mixture was stirred at 100° C. under nitrogen for 7 h. The reaction mixture was allowed to cool, dried over sodium sulfate and concentrated under vacuum to give crude product as a dark oil (318 mg). This material was loaded onto a 10 g HP-silica cartridge and eluted on a Biotage Isolera 4, from a 0-70% ethyl acetate in heptane gradient, to afford the title compound (166 mg, 71%) as a colourless oil. $\delta_H$ (500 MHz, CDCl$_3$) 8.61 (s, 1H), 7.85 (d, J 8.0 Hz, 1H), 7.72 (d, J 8.2 Hz, 1H), 7.53 (d, J 10.8 Hz, 1H), 7.37-7.29 (m, 1H), 7.21-7.14 (m, 2H), 7.13-7.06 (m, 1H), 6.80-6.45 (m, 2H), 5.43-5.37 (m, 2H), 2.61 (s, 3H), 1.65 (s, 6H), 0.17 (s, 9H).

Intermediate 149 tert-Butyl 3-(5-bromopyrimidin-2-yl)-3-hydroxyazetidine-1-carboxylate

A solution of 5-bromo-2-iodopyrimidine (2 g, 7.02 mmol) in anhydrous toluene (25 mL) was cooled to −78° C. with stirring under nitrogen, forming a thick paste. A solution of n-butyllithium in hexanes (2.5M, 2.83 mL) was then added dropwise over 10 minutes. The reaction mixture was stirred at −78° C. for 30 minutes, then solid tert-butyl 3-oxoazetidine-1-carboxylate (1.33 g, 7.74 mmol) was added portionwise. The reaction mixture was allowed to warm to ambient temperature and stirred for 1 h. The reaction mixture was quenched with a saturated aqueous ammonium chloride solution (20 mL) and further diluted with water (20 mL). The crude material was extracted into ethyl acetate (2×30 mL). The combined organic phases were dried over sodium sulfate and concentrated under vacuum to give a brown oil (2.66 g), which was loaded onto a 50 g KP-silica cartridge and eluted from a 0-90% ethyl acetate in heptane gradient, using the biotage isolera 4, to afford the title compound (1.083 g, 46.7%) as a yellow solid. $\delta_H$ (500 MHz, CDCl$_3$) 8.84 (s, 2H), 4.91 (s, 1H), 4.35 (d, J 9.0 Hz, 2H), 4.22 (d, J 9.1 Hz, 2H), 1.48 (s, 9H).

Intermediate 150 tert-Butyl 3-(5-bromopyrimidin-2-yl)-3-[(trimethylsilyl)oxy]azetidine-1-carboxylate A solution of Intermediate 149 (1.07 g, 3.24 mmol) and imidazole (265 mg, 3.89 mmol) in dichloromethane (20 mL) was treated with trimethylsilyl chloride (0.44 mL, 3.41 mmol) at room temperature and stirred for 1 h under nitrogen. Further imidazole (100 mg) and trimethylsilyl chloride (0.15 mL) were added and stirring was continued at room temperature for another hour. The reaction mixture was washed with water (2×20 mL). The aqueous washes were extracted with dichloromethane (20 mL). The combined organic extracts were dried over sodium sulfate and concentrated in vacuo. The resulting crude brown oil (1.19 g) was loaded onto a 25 g KP-silica cartridge and eluted from a 0-30% ethyl acetate in heptane gradient, using the biotage isolera 4, to afford the title compound (814 mg, 62%) as a pale yellow solid. $\delta_H$ (500 MHz, CDCl$_3$) 8.82 (s, 2H), 4.48 (d, J 9.5 Hz, 2H), 4.17 (d, J 9.5 Hz, 2H), 1.45 (s, 9H), 0.05 (s, 9H).

Intermediate 151 tert-Butyl 3-[5-(4,4,5,5-tetramethyl-1,3,2-dioxaborolan-2-yl)pyrimidin-2-yl]-3-[(trimethylsilyl)oxy]azetidine-1-carboxylate To a stirring solution of Intermediate 150 (810 mg, 2.01 mmol) in 1,4-dioxane (20 mL) were added bis(pinacolato)diboron (610 mg, 2.40 mmol) and potassium acetate (600 mg, 6.11 mmol). The stirring mixture was degassed with nitrogen for 5 minutes, then Pd(dppf)Cl$_2$ complex with DCM (80 mg, 0.098 mmol) was added and the mixture was stirred at 100° C. for 3 h. The reaction mixture was allowed to cool and then filtered through celite, washing through with ethyl acetate (30 mL). The filtrate was concentrated in vacuo to give a dark oil which was loaded onto a 25 g KP-silica cartridge and eluted from a 0-80% ethyl acetate in heptane gradient, using the biotage isolera 4 system, to afford the title compound (578 mg, 64%) as a brown solid. $\delta_H$ (500 MHz, CDCl$_3$) 9.04 (s, 2H), 4.52 (d, J 9.2 Hz, 2H), 4.17 (d, J 9.2 Hz, 2H), 1.45 (s, 9H), 1.36 (s, 12H), 0.02 (s, 9H).

Intermediate 152

4-(5-Bromopyrimidin-2-yl)oxan-4-ol

5-Bromo-2-iodopyrimidine (2 g, 7.02 mmol) was dissolved in dry toluene (30 mL) and cooled to −78° C. under N$_2$. n-Butyllithium in hexanes (2.5M, 2.95 mL) was added dropwise and the reaction was stirred for 15 minutes, prior to dropwise addition of tetrahydro-4H-pyran-4-one (0.77 g, 7.72 mmol). The reaction mixture was stirred at −78° C. for 30 minutes and then allowed to warm to room temperature. The reaction mixture was diluted with water (50 mL) and extracted with ethyl acetate (2×50 mL). The combined organic extracts were dried over magnesium sulphate and filtered, then the solvent was removed under reduced pressure. The resulting orange oil (1.91 g) was absorbed onto a 50 g KP-Sil column and the products were eluted with 10-100% ethyl acetate in heptanes, on a Biotage Isolera 4, to afford the title compound (762 mg, 42%) as a yellow oil. $\delta_H$ (500 MHz, CDCl$_3$) 8.79 (s, 2H), 4.24 (s, 1H), 3.99-3.89 (m, 4H), 2.37 (td, J 12.3, 11.6, 6.3 Hz, 2H), 1.54 (dd, J 13.6, 2.0 Hz, 2H).

Intermediate 153

5-Bromo-2-{4-[(trimethylsilyl)oxy]oxan-4-yl}pyrimidine

Trimethylsilyl chloride (277 mg, 2.55 mmol) was added to a stirred solution of Intermediate 152 (85%, 740 mg, 2.43 mmol) and imidazole (198 mg, 2.91 mmol) in DCM (15 mL) and the reaction mixture was stirred for 1 h. Additional trimethylsilyl chloride (0.25 eq) and imidazole were added and stirring was continued for 1 h. The reaction mixture was washed with water (2×15 mL) and the aqueous phase was re-extracted with DCM (20 mL). The combined organic extracts were dried over magnesium sulphate, filtered and concentrated under reduced pressure. The resulting yellow oil was purified on Biotage Isolera Snap 25 g KP-Sil column, eluting with 0-15% ethyl acetate in heptanes, to afford the title compound (623 mg, 77%) as a yellow oil, which crystallised upon standing. $\delta_H$ (500 MHz, CDCl$_3$) 8.80 (s, 2H), 3.90 (td, J 11.0, 2.5 Hz, 2H), 3.74 (dt, J 11.4, 4.1 Hz, 2H), 2.26 (ddd, J 14.1, 10.4, 4.4 Hz, 2H), 1.99 (dt, J 11.6, 2.1 Hz, 2H), −0.05 (s, 9H).

Intermediate 154

5-(4,4,5,5-Tetramethyl-1,3,2-dioxaborolan-2-yl)-2-{4-[(trimethylsilyl)oxy]oxan-4-yl}-pyrimidine A solution of Intermediate 153 (623 mg, 1.88 mmol) in anhydrous 1,4-dioxane (25 mL) was treated with bis(pinacolato)diboron (573 mg, 2.26 mmol) and potassium acetate (0.35 mL, 5.64 mmol). The mixture was degassed with N$_2$ for 10 minutes prior to addition of Pd(dppf)Cl$_2$ complex with DCM (77 mg, 0.09 mmol). The reaction mixture was stirred at 80° C. for 1 h. The reaction mixture was concentrated in vacuo and redissolved in ethyl acetate (30 mL), then washed with 10% w/v citric acid solution (30 mL). The organic phase was dried (magnesium sulfate) and the solvent was removed under reduced pressure. The resulting crude brown oil was purified on Biotage Isolera (Snap 25 g KP-sil), eluting with 10-40% ethyl acetate in heptanes. However, good chromatography was not observed. Product-containing fractions were combined to afford the title compound (228 mg, 25%) as a yellow oil that crystallised upon standing. $\delta_H$ (500 MHz, CDCl$_3$) 9.01 (s, 2H), 3.91 (t, J 9.9 Hz, 2H), 3.79-3.69 (m, 2H), 2.38-2.23 (m, 2H), 1.98 (d, J 13.2 Hz, 2H), 1.36 (s, 12H), −0.06 (s, 9H).

Intermediate 155

5-Bromo-N-{[2-(difluoromethoxy)-5-fluorophenyl]methyl}-4-fluoro-2-nitroaniline

1-Bromo-2,5-difluoro-4-nitrobenzene (2.3 g, 9.66 mmol), [2-(difluoromethoxy)-5-fluorophenyl]methanamine (2 g, 0.01 mol) and triethylamine (1.48 mL, 0.01 mol) were stirred in DMF (10 mL) at room temperature overnight. Water (20 mL) was added and the mixture was extracted with ethyl acetate (2×50 mL). The organic phase was dried over sodium sulfate and concentrated under vacuum. The resulting yellow liquid was purified on a Biotage Isolera 4, eluting with 0-50% ethyl acetate in heptanes, to afford the title compound (3.96 g, 100%) as a yellow-orange solid. $\delta_H$ (500 MHz, CDCl$_3$) 8.29-8.13 (m, 1H), 7.99 (d, J 8.6 Hz, 1H), 7.18-7.07 (m, 3H), 7.04 (d, J 5.7 Hz, 1H), 6.45 (t, J 73.3 Hz, 1H), 4.56 (d, J 5.7 Hz, 2H).

Intermediate 156

6-Bromo-1-{[2-(difluoromethoxy)-5-fluorophenyl]methyl}-5-fluoro-2-methylbenzimidazole Intermediate 155 (3.96 g, 9.68 mmol) was dissolved in EtOH (50 mL) and glacial acetic acid (4 mL). Iron powder (2.69 g, 48.2 mmol) was added and the reaction mixture was heated at 70° C. for 45 minutes. The reaction mixture was allowed to cool to room temperature and filtered through Kieselguhr, washing through with ethyl acetate. The brown filtrate was concentrated under vacuum to give a black gum. Trimethyl orthoacetate (14 mL, 116.31 mmol) was added, followed by conc. HCl (0.3 mL), and the reaction mixture was stirred at room temperature for 45 minutes. The reaction mixture was diluted with DCM (100 mL), then washed with water (50 mL), saturated sodium hydrogencarbonate solution (80 mL) and brine (10 mL). Each aqueous wash was re-extracted with DCM (20 mL). The combined organic extracts were dried over sodium sulfate and concentrated under vacuum. The resulting green/brown solid was triturated with ethyl acetate/heptanes. The resulting green solid was dissolved in ethyl acetate (10 mL) and heptanes (30 mL) and sonicated to afford a fine brown suspension, which was collected by filtration, to afford the title compound (1.4 g, 36%) as a light brown solid. $\delta_H$ (500 MHz, CDCl$_3$) 7.54-7.37 (m, 2H), 7.18-7.08 (m, 2H), 6.54 (s, 1H), 6.36 (t, J 73.0 Hz, 1H), 5.33 (s, 2H), 2.64 (s, 3H).

Intermediate 157

5-Bromo-N-{(1R or 1S)-1-[2-(difluoromethoxy)phenyl]ethyl}-4-fluoro-2-nitroaniline (Isomer B)

A mixture of 1-bromo-2,5-difluoro-4-nitrobenzene (800 mg, 3.36 mmol), Intermediate 130 (800 mg, 3.58 mmol) and DIPEA (1.2 mL, 7.24 mmol) in DMF (10 mL) was stirred at 55° C. for 7 h, then allowed to stand at room temperature overnight. The reaction mixture was diluted with ethyl acetate (50 mL) and washed with water (3×50 mL). The aqueous layer was separated and further extracted with ethyl acetate (40 mL). The combined organic phases were dried over sodium sulfate and concentrated in vacuo. The resulting orange-coloured oil (2.3 g) was loaded onto a 25 g KP-silica cartridge and eluted from a 0-30% ethyl acetate in heptanes gradient, using the biotage isolera 4, to afford the title compound (1.20 g, 86%) as an orange-coloured oil. $\delta_H$ (500 MHz, CDCl$_3$) 8.26 (d, J 6.0 Hz, 1H), 7.93 (d, J 8.7 Hz, 1H), 7.36-7.28 (m, 2H), 7.22-7.15 (m, 2H), 6.88 (d, J 5.8 Hz, 1H), 6.69 (t, J 73.3 Hz, 1H), 5.03 (dq, J 6.6 Hz, 1H), 1.63 (d, J 6.7 Hz, 3H).

Intermediate 158

6-Bromo-1-{(1R or 1S)-1-[2-(difluoromethoxy)phenyl]ethyl}-5-fluoro-2-methylbenzimidazole (Isomer B)

A solution of Intermediate 157 (1.2 g, 2.90 mmol) in a mixture of ethanol (20 mL) and glacial acetic acid (2 mL) was treated with iron powder (810 mg, 14.5 mmol) and the mixture was stirred at 70° C. for 45 minutes. The reaction mixture was allowed to cool and then filtered through celite, washing through with ethyl acetate (100 mL). The filtrate was concentrated under vacuum. The resulting dark oil was dissolved in trimethyl orthoacetate (4.5 mL), treated with conc. HCl (0.1 mL) and stirred at room temperature for 45 minutes. The reaction mixture was diluted with DCM (50 mL) and washed with saturated sodium bicarbonate solution (40 mL). The organic layer/suspension was separated and filtered through celite. The filtrate was dried over sodium sulfate and concentrated under vacuum. The resulting brown oil was loaded onto a 10 g HP-silica cartridge and eluted from a 0-90% ethyl acetate in heptane gradient, using the biotage isolera 4, to afford the title compound (249 mg, 19%) as a brown solid. LCMS pH 10: MH+: m/z 399/401, RT 1.93 minutes (89%).

Intermediate 159

5-Bromo-N-{(1R or 1S)-1-[2-(difluoromethoxy)phenyl]ethyl}-4-fluoro-2-nitroaniline (Isomer A)

A mixture of 1-bromo-2,5-difluoro-4-nitrobenzene (2.0 g, 8.40 mmol), Intermediate 127 (2 g, 8.94 mmol) and DIPEA (3 mL, 18.11 mmol) in N,N-dimethylformamide (25 mL) was stirred at room temperature for 20 h, followed by stirring at 50° C. for 5 h. The reaction mixture was diluted with ethyl acetate (80 mL) and washed with water (3×50 mL). The combined aqueous layers were further extracted with ethyl acetate (40 mL). The combined organic phases were dried over sodium sulfate and concentrated under vacuum. The resulting orange-coloured oil (3.60 g) was loaded onto a 50 g KP-silica cartridge and eluted from a 0-30% ethyl acetate in heptanes gradient, using the biotage isolera 4, to afford the title compound (3.1 g, 85.6%) as an orange-coloured oil. $\delta_H$ (500 MHz, CDCl$_3$) 8.26 (d, J 6.0 Hz, 1H), 7.93 (d, J 8.7 Hz, 1H), 7.35-7.28 (m, 2H), 7.22-7.16 (m, 2H), 6.88 (d, J 5.8 Hz, 1H), 6.69 (t, J 73.4 Hz, 1H), 5.03 (dq, J 6.6 Hz, 1H), 1.62 (d, J 6.7 Hz, 3H).

Intermediate 160

6-Bromo-1-{(1R or 1S)-1-[2-(difluoromethoxy)phenyl]ethyl}-5-fluoro-2-methylbenzimidazole (Isomer A)

A solution of Intermediate 159 (3.1 g, 7.65 mmol) in a mixture of ethanol (50 mL) and glacial acetic acid (4 mL) was treated with iron powder (2 g, 35.81 mmol) and the mixture was stirred at 70° C. for 45 minutes. The reaction mixture was allowed to cool and then filtered through celite, washing through with ethyl acetate (100 mL). The filtrate was concentrated under vacuum to give a dark oil, which was dissolved in trimethyl orthoacetate (11 mL), treated with conc. HCl (0.3 mL) and stirred at room temperature for 45 minutes. The reaction mixture was diluted with dichloromethane (100 mL) and washed with water (50 mL) followed by saturated sodium bicarbonate solution (80 mL). The organic layer/suspension was separated and filtered through celite. The filtrate was dried over sodium sulfate and concentrated under vacuum to give a brown solid, which was suspended in hot ethyl acetate (10 mL). The suspension was diluted with heptanes (30 mL) and allowed to cool. The resulting precipitate was collected by filtration and dried by vacuum oven to afford the title compound (2.26 g, 77.9%) as a pale beige-coloured solid. LCMS Method B: MH+: m/z 399/401, RT 1.83 minutes (99%).

Intermediate 161

3-[5-(4,4,5,5-Tetramethyl-1,3,2-dioxaborolan-2-yl)pyrimidin-2-yl]oxetan-3-ol

The title compound was prepared from Intermediate 143 and bis(pinacolato)-diboron in accordance with the method described for Intermediate 154.

Intermediate 162

1-{[2-(Difluoromethoxy)phenyl]methyl}-6-(6-methoxypyridin-3-yl)benzimidazole-2-carbaldehyde Example 238 (2.80 g, 9.25 mmol) was suspended in 1,4-dioxane (100 mL) and dichloromethane (30 mL). The mixture was degassed and activated manganese(IV) oxide (8.05 g, 92.5 mmol) was added. The mixture was stirred and warmed at 30° C. for 6 h under nitrogen. Whilst still warm, the reaction mixture was filtered through a celite pad and washed well with 1,4-dioxane. The organic layers were concentrated in vacuo to give the title compound (2.05 g, 74%) as a pale purple solid. $\delta_H$ (400 MHz, DMSO-d$_6$) 10.02 (s, 1H), 8.54 (m, 1H), 8.03 (m, 3H), 7.67 (m, 1H), 7.25 (m, 4H), 6.92 (m, 1H), 6.72 (m, 1H), 5.97 (s, 2H), 3.89 (s, 3H). LCMS (pH10): MH$^+$ 410.6, RT 2.48 minutes, 97% purity by UV.

Intermediate 163

Methyl 1-{[2-(difluoromethoxy)phenyl]methyl}-2-methylbenzimidazole-6-carboxylate Prepared by a method analogous to that used to prepare Intermediate 47, starting from methyl 3-fluoro-4-nitrobenzoate, to give the title compound (12.7 g, 83%) as a brown solid. LCMS (pH 10) m/z 347 [M+H]$^+$, RT 2.32 minutes.

Intermediate 164

(1-{[2-(Difluoromethoxy)phenyl]methyl}-2-methylbenzimidazol-6-yl)methanol

To a stirred solution of lithium aluminium hydride (2.55 g 0.067 mol) in THF (20 mL) at 0° C. was added dropwise Intermediate 163 (11.7 g, 0.033 mol) dissolved in THF (10 mL) and the resulting mixture was stirred at room temperature for 2 h. The mixture was cooled to 0° C. and quenched by the addition of ethyl acetate and water. The residue was filtered, then the filtrate was dried over anhydrous sodium sulfate and concentrated in vacuo, to obtain the title compound (6.8 g, 63%) as a yellow solid. LCMS (pH 10) m/z 319 [M+H]$^+$, RT 1.72 minutes.

Intermediate 165

6-(Chloromethyl)-1-{[2-(difluoromethoxy)phenyl]methyl}-2-methylbenzimidazole

To a stirred solution of Intermediate 164 (7.5 g, 0.02 mol) in DCM (40 mL), cooled at 0° C., was added thionyl chloride (8.3 g, 0.07 mol) and reaction mass was stirred at room temperature for 3 h. The reaction mixture was concentrated in vacuo to obtain a crude solid, which was washed with ether, to obtain the title compound (7.8 g, 98%) as an off white solid compound. LCMS (pH 10) m/z 337 [M+H]$^+$, RT 2.45 minutes.

Intermediate 166

5-(Chloromethyl)-1-{[2-(difluoromethoxy)phenyl]methyl}-2-methylbenzimidazole The title compound was prepared by methods analogous to those used to prepare Intermediate 165, starting from methyl 4-fluoro-3-nitrobenzoate.

Intermediate 167

(tert-Butyl)(cyclopent-3-en-1-yloxy)dimethylsilane

Cyclopent-3-en-1-ol (10 g, 118.9 mmol) was dissolved in DMF (100 mL) at 0° C., then 1H-imidazole (17.29 mL, 261.5 mmol) was added, followed by (tert-butyl)(chloro)dimethylsilane (21.5 g, 142.7 mmol). The reaction mixture was allowed to warm, then stirred at room temperature for 14 h. The mixture was diluted with ethyl acetate (300 mL) and washed with 5% aqueous LiCl solution (2×100 mL) and brine (50 mL), then dried over sodium sulfate, filtered and concentrated in vacuo. The crude residue was purified by chromatography, eluting with 0-10% EtOAc in hexane, to afford the title compound (17.2 g, 73%) as a colourless clear liquid. $\delta_H$ (250 MHz, CDCl$_3$) 5.66 (s, 2H), 4.53 (tt, J 7.0, 3.6 Hz, 1H), 2.57 (dd, J 15.2, 6.8 Hz, 2H), 2.27 (dd, J 15.3, 3.6 Hz, 2H), 0.89 (s, 9H), 0.06 (s, 6H).

Intermediate 168

Ethyl 3-[(tert-butyldimethylsilyl)oxy]bicyclo[3.1.0]hexane-6-carboxylate 1-(2-Ethoxy-2-oxoethylidene)diazenium (6.07 mL, 48.4 mmol) in DCM (4 mL) was added slowly via syringe pump over 6 h to a stirred solution of Intermediate 167 (8 g, 40.3 mmol) and rhodium(II) acetate (178.24 mg, 0.4 mmol) in DCM (150 mL) under nitrogen at room temperature. The mixture was stirred for 14 h, then filtered through celite and concentrated under reduced pressure. The resulting crude light brown oil was purified by column chromatography, eluting with 5-30% ethyl acetate in heptane, to afford the title compound (7.15 g, 59%) as a mixture of isomers (exo:endo; 2.5:1) as a colourless clear oil. $\delta_H$ (500 MHz, CDCl$_3$) 4.12-4.03 (m, 2H), 2.13 (dd, J 13.0, 7.2 Hz, 1H), 2.05 (ddd, J 13.2, 5.8, 3.4 Hz, 1H), 1.88-1.69 (m, 4H), 1.51 (d, J 14.7 Hz, 1H), 1.28-1.19 (m, 4H), 0.88-0.82 (m, 9H), 0.04-0.03 (m, 6H).

Intermediate 169

Ethyl 3-hydroxybicyclo[3.1.0]hexane-6-carboxylate

TBAF (1M, 68.13 mL) was added dropwise to a stirred solution of Intermediate 168 (95% pure, 10.2 g, 34.06 mmol) in THF (100 mL) at room temperature, then the mixture was heated at 50° C. for 1 h. The mixture was cooled to room temperature and concentrated under reduced pressure. The resulting light brownish oil was diluted with ethyl acetate (300 mL) and washed with water (2×100 mL) and brine (50 mL), then dried over magnesium sulfate and concentrated under reduced pressure, to provide the title compound (9.4 g crude, assumed 100% conversion) as a light reddish oil. $\delta_H$ (500 MHz, CDCl$_3$) 4.15-4.05 (m, 2H), 2.26 (dd, J 13.1, 7.1 Hz, 1H), 2.20-2.11 (m, 1H), 1.99-1.93 (m, 1H), 1.92-1.84 (m, 4H), 1.84-1.75 (m, 1H), 1.64-1.53 (m, 1H), 1.30-1.20 (m, 3H).

Intermediate 170

Ethyl (1R,5S,6S)-3-oxobicyclo[3.1.0]hexane-6-carboxylate

Intermediate 169 (60% pure, 9.4 g, 33.14 mmol) was dissolved in DCM (100 mL), then Dess-Martin Periodinane (28.11 g, 0.07 mol) was added in one portion and the mixture was stirred at room temperature for 15 h. The mixture was diluted with DCM (200 mL) and washed with saturated aqueous sodium bicarbonate solution (2×100 mL), water (100 mL) and brine (50 mL), then dried over sodium sulfate and concentrated under reduced pressure. The resulting crude sticky off-white solid was purified by flash chromatography, eluting with 30-100% ethyl acetate in heptane, to afford the title compound (3.15 g, 56%) as a light brown oil. $\delta_H$ (500 MHz, CDCl$_3$) 4.15 (q, J 7.1 Hz, 2H), 2.66 (ddt, J 18.5, 3.9, 1.6 Hz, 2H), 2.31 (d, J 1.8 Hz, 1H), 2.27 (d, J 1.7 Hz, 2H), 2.18 (td, J 3.4, 1.6 Hz, 2H), 1.31-1.23 (m, 4H).

Intermediate 171

Ethyl (1S,5S,6R)-3-(trifluoromethanesulfonyloxy)bicyclo[3.1.0]hex-2-ene-6-carboxylate Intermediate 170 (3 g, 17.84 mmol) was dissolved in dry toluene (60 mL), DIPEA (12.5 mL, 71.35 mmol) was added and the reaction mixture was heated to 45° C. Triflic anhydride (12 mL, 71.35 mmol) was added, and the temperature rose to 70° C. The reaction mixture was cooled using an ice bath. The mixture was stirred for 1.5 h at 45° C. The reaction mixture was diluted with ethyl acetate (200 mL) and washed with saturated aqueous sodium bicarbonate solution (2×100 mL). The aqueous washes were extracted with ethyl acetate (200 mL) and washed with sat. sodium bicarbonate (2×100 mL). The aqueous washes were extracted (100 mL), then the organic extracts were combined, washed with brine (50 mL), dried over sodium sulfate and concentrated. The crude product was purified by chromatography, eluting with 0-20% ethyl acetate in heptane to afford the title compound (2.73 g, 51%). $\delta_H$ (250 MHz, CDCl$_3$) 5.87 (d, J 1.9 Hz, 1H), 4.14 (q, J 7.1 Hz, 2H), 3.00 (dd, J 17.2, 6.2 Hz, 1H), 2.75-2.60 (m, 1H), 2.46-2.31 (m, 1H), 2.23-2.11 (m, 1H), 1.39-1.32 (m, 1H), 1.32-1.16 (m, 3H).

Intermediate 172

Ethyl (1S,5S,6R)-3-(4,4,5,5-tetramethyl-1,3,2-dioxaborolan-2-yl)bicyclo[3.1.0]hex-2-ene-6-carboxylate Intermediate 171 (2.73 g, 9.09 mmol) was dissolved in 1,4-dioxane (60 mL) and degassed using nitrogen for 5 minutes. Bis(pinacolato)diborane (3.46 g, 13.64 mmol), potassium acetate (2.68 g, 27.28 mmol), 1,1'-bis(diphenylphosphanyl)ferrocene (0.15 g, 0.27 mmol) and Pd(dppf)Cl$_2$ complex with dichloromethane (0.22 g, 0.27 mmol) were added and the reaction mixture was heated under nitrogen at 90° C. for 18 h. The reaction mixture was diluted with ethyl acetate (200 mL) and washed with a saturated aqueous solution of sodium bicarbonate (2×100 mL). The aqueous washes were re-extracted with ethyl acetate (50 mL). The organic extracts were combined, washed with brine, dried over sodium sulfate and concentrated. The crude residue was purified by chromatography, eluting with 0-40% ethyl acetate in heptane, to afford the title compound (2.0 g, 59%) containing bis(pinacolato)diborane impurity. $\delta_H$ (250 MHz, CDCl$_3$) 6.66 (d, J 1.9 Hz, 1H), 4.11 (q, J 7.1 Hz, 2H), 2.88-2.73 (m, 1H), 2.66-2.44 (m, 2H), 2.33-2.22 (m, 1H), 1.34-1.18 (m, 16H).

Intermediate 173

6-Bromo-1-{[2-(difluoromethoxy)phenyl]methyl}-5-fluoro-2-(methoxymethyl)-benzimidazole The title compound was prepared by a method analogous to Method K, starting with 1-bromo-2,5-difluoro-4-nitrobenzene and 2-(difluoromethoxy)benzylamine, and effecting benzimidazole formation using methoxyacetic acid. LCMS (pH 10) m/z 417.6 [M+H]$^+$, RT 2.46 minutes.

Intermediate 174

2-Methyl-1-(1-phenylethyl)benzimidazol-6-ol

The title compound can be prepared by a method analogous to that used to prepare Intermediate 101, starting from 2-fluoro-4-methoxy-1-nitrobenzene and 1-phenylethanamine, according to the method of Intermediate 47, followed demethylation according to the method of Intermediate 101. QC LCMS m/z 253 (M+H)$^+$, RT 1.65 minutes.

Intermediate 175

{6-Bromo-1-[(2,5-dimethylphenyl)methyl]benzimidazol-2-yl}(phenyl)methanol

The title compound was synthesised from benzaldehyde by the method described for Intermediate 30.

Intermediate 176

1-[(2,5-Dimethylphenyl)methyl]-5-(trifluoromethyl)benzimidazole

The title compound can be synthesised from 1-fluoro-2-nitro-4-(trifluoromethyl)-benzene and (2,5-dimethylphenyl)methanamine in accordance with the first two steps of Method K and subsequent cyclisation with formic acid.

Intermediate 177

Ethyl 4-(4,4,5,5-tetramethyl-1,3,2-dioxaborolan-2-yl)cyclohex-3-ene-1-carboxylate Lithium hexamethyldisilazide in THF/ethylbenzene (1M, 5.55 mL) was added dropwise to a stirred solution of ethyl 4-oxocyclohexanecarboxylate (900 mg, 5.29 mmol) in anhydrous THF (5 mL) under an inert atmosphere at −78° C. and the mixture was stirred for 1 h. 1,1,1-Trifluoro-N-phenyl-N-[(trifluoromethyl)sulfonyl]methanesulfonamide (1.98 g, 5.55 mmol) in THF (5 mL) was added over 5 minutes and the mixture was stirred for 30 minutes. The reaction mixture was then warmed to room temperature and stirred for 12 h. The mixture was quenched with NaHSO$_4$ and diluted with ethyl acetate (250 mL), then washed with 0.5M aqueous NaOH solution (2×20 mL), saturated aqueous NH$_4$Cl solution (20 mL) and brine (20 mL). The organic fraction was then dried over MgSO$_4$ and concentrated under reduced pressure. The resulting material (1.9 g, 83%) was dissolved in 1,4-dioxane (30 mL), 4,4,5,5-tetramethyl-2-(4,4,5,5-tetramethyl-1,3,2-dioxaborolan-2-yl)-1,3,2-dioxaborolane (1.68 g, 6.6 mmol) and 1,1'-bis(diphenyl-phosphanyl)ferrocene (73 mg, 0.13 mmol) were added and the mixture was degassed with N$_2$ for 5 minutes. Bis[3-(diphenylphosphanyl)cyclopenta-2,4-dien-1-yl]iron dichloropalladium dichloromethane complex (108 mg, 0.13 mmol) was added and the mixture was heated at 90° C. for 18 h. The mixture was diluted with water (100 mL) and extracted with ethyl acetate (2×100 mL). The combined organic layers were washed with brine (50 mL), dried over MgSO$_4$ and concentrated under reduced pressure. The residue was purified by silica gel chromatography, eluting with 10-20% ethyl acetate in heptane, to afford the title compound in two batches (440 mg, 26%, 73% purity; and 362 mg, 12%, 42% purity) as a colourless oil. Method B HPLC-MS: MH+ m/z 281, RT 2.37 minutes (73%).

Intermediate 178

Ethyl 4-[5-(4,4,5,5-tetramethyl-1,3,2-dioxaborolan-2-yl)pyrimidin-2-yl]cyclohex-3-ene-1-carboxylate A stirred mixture of Intermediate 177 (13.6 g, 48.5 mmol), 5-bromo-2-iodopyrimidine (13.83 g, 48.5 mmol) and sodium carbonate (15.43 g, 146 mmol) in 1,2-dimethoxyethane (300 mL) and water (100 mL) was flushed with argon (three vacuum-argon cycles). 1,1'-Bis(diphenylphosphino)ferrocenepalladium(II) dichloride (1.189 g, 1.456 mmol) was added and the resulting mixture was stirred at 90° C. for 5 h. The reaction mixture was cooled to room temperature and quenched in water (500 mL). Brine (200 mL) and EtOAc (200 mL) were added under stirring. The layers were separated and the aqueous layer was extracted three times with EtOAc. The combined extracts were washed with brine, dried with Na$_2$SO$_4$ and concentrated in vacuo. The resulting brown oily solid (20.8 g) was used directly without further purification. A stirred mixture of the foregoing material (12.9 g, 20.73 mmol, 50%), bis(pinacolato)diboron (12.9 g, 22.86 mmol, 45%) and potassium acetate (6.10 g, 62.2 mmol) in anhydrous 1,4-dioxane (120 mL) was flushed with argon (three vacuum-argon cycles) for 5 minutes. 1,1'-Bis-(diphenylphosphino)ferrocenepalladium (II) dichloride (0.508 g, 0.622 mmol) was added and the resulting mixture was stirred at 90° C. for 1 h to give a dark brown-black suspension. The reaction mixture was cooled to room temperature and filtered over a pad of kieselguhr, which was rinsed with EtOAc. The filtrate was concentrated in vacuo to yield a crude solid, which was was triturated in boiling heptane/diisopropyl ether (1:1, 100 mL). The whole was filtered over kieselguhr and rinsed with hot heptane/diisopropyl ether (3×100 mL). The filtrate was concentrated in vacuo, yielding the title compound (11.0 g) as a pale beige solid. LCMS (pH 10): m/z 277 (mass ion for the boronic acid derivative), RT 1.76 minutes.

Example 1

Method B

[1-(2,5-Dimethylbenzyl)-1H-benzimidazol-2-yl]methanol

To a solution of Intermediate 1 (20.0 g, 135.0 mmol) in DMF (60 mL) were added 2,5-dimethylbenzyl chloride (20.9 g, 135.0 mmol) and potassium carbonate (37.3 g, 270.0 mmol). The mixture was stirred at r.t. for 18 h. Water (50 mL) was added and the mixture was poured into ethyl acetate/water. The organic layer was separated, dried (MgSO$_4$) and concentrated in vacuo to afford the title compound (21.6 g, 60%) as an off-white solid. $\delta_H$ (d$_6$-DMSO) 7.64 (d, J 7.2 Hz, 1H), 7.26 (d, J 7.2 Hz, 1H), 7.20-7.13 (m, 2H), 7.11 (d, J 7.2 Hz, 1H), 6.96 (d, J 7.2 Hz, 1H), 6.19 (s, 1H), 5.61 (t, J 5.6 Hz, 1H), 5.50 (s, 2H), 4.63 (d, J 6.0 Hz, 2H), 2.32 (s, 3H), 2.03 (s, 3H). LCMS (ES$^+$) 267 (M+H)$^+$.

Example 2

Method C

[1-(2,5-Dimethylbenzyl)-1H-benzimidazol-2-yl](pyridin-4-yl)methanol

To a solution of Intermediate 2 (0.25 g, 1.06 mmol) in THF (10 mL) at −78° C. was added 1.6M n-butyllithium (0.79 mL, 1.27 mmol) slowly dropwise and the reaction mixture was stirred for 20 minutes. Isonicotinaldehyde (0.17 g, 1.59 mmol) in THF (1 mL) was added slowly dropwise. After a further 10 minutes the reaction mixture was quenched with water (1 mL) and allowed to warm to r.t. The reaction mixture was poured into ethyl acetate/water. The organic layer was separated, dried (MgSO$_4$) and concentrated in vacuo. The residue was purified by column chromatography (SiO$_2$, 0-30% MeOH/DCM), yielding the title compound (0.2 g, 55%) as an off-white solid. $\delta_H$ (CDCl$_3$) 8.31 (d, J 5.9 Hz, 2H), 7.69 (d, J 8.0 Hz, 1H), 7.28-7.16 (m, 4H), 7.00-6.95 (m, 2H), 6.87-6.85 (m, 1H), 6.16 (s, 1H), 5.84 (s, 1H), 5.35-5.09 (dd, J$_{AB}$ 17.0 Hz, 2H), 2.25 (s, 3H), 1.89 (s, 3H). LCMS (ES$^+$) 344 (M+H)$^+$.

Examples 3A and 3B (R)-[1-(2,5-Dimethylbenzyl)-1H-benzimidazol-2-yl](phenyl)methanol and (S)-[1-(2,5-Dimethylbenzyl)-1H-benzimidazol-2-yl](phenyl)methanol Prepared from Intermediate 2 and benzaldehyde in accordance with Method C. $\delta_H$ (CDCl$_3$) 7.77 (d, J 8.1 Hz, 1H), 7.26-7.13 (m, 7H), 6.99-6.95 (m, 2H), 6.86-6.84 (m, 1H), 5.93 (s, 2H), 5.06 (dd, J$_{AB}$ 11.5 Hz, 2H), 2.12 (s, 3H), 1.93 (s, 3H). LCMS (ES$^+$) 342 (M+H)$^+$. The two enantiomers were separated by chiral preparative chromatography (Chiralpak AD, 100*500, 300 mL/min, heptane/isopropanol 95:5), RT 7.91 minutes and 10.75 minutes.

Reference Example 4

1-[1(2,5-Dimethylbenzyl)-1H-benzimidazol-2-yl]propan-1-ol

The title compound was acquired from Specs & Biospecs BV, Delft, Netherlands. LCMS (ES$^+$) 295 (M+H)$^+$.

Examples 5 to 10

The following compounds were synthesised from Intermediate 2 and the appropriate substituted aldehyde in accordance with Method C.

| Example No. | Compound Name | LCMS |
| --- | --- | --- |
| 5 | tert-Butyl 4-{[1-(2,5-dimethylbenzyl)-1H-benzimidazol-2-yl](hydroxy)methyl}piperidine-1-carboxylate | LCMS (ES$^+$) 450 (M + H)$^+$. |
| 6 | [4-(Dimethylamino)phenyl][1-(2,5-dimethylbenzyl)-1H-benzimidazol-2-yl]methanol | LCMS (ES$^+$) 386 (M + H)$^+$. |
| 7 | (1,3-Benzodioxol-5-yl)[1-(2,5-dimethylbenzyl)-1H-benzimidazol-2-yl]methanol | LCMS (ES$^+$) 387 (M + H)$^+$. |
| 8 | [1-(2,5-Dimethylbenzyl)-1H-benzimidazol-2-yl][6-(trifluoromethyl)pyridin-3-yl]methanol | LCMS (ES$^+$) 412 (M + H)$^+$. |
| 9 | 1-[1-(2,5-Dimethylbenzyl)-1H-benzimidazol-2-yl]-3-phenylpropan-1-ol | LCMS (ES$^+$) 371 (M + H)$^+$. |
| 10 | [1-(2,5-Dimethylbenzyl)-1H-benzimidazol-2-yl](furan-2-yl)methanol | LCMS (ES$^+$) 333 (M + H)$^+$. |

Example 11

3-(1-{[1-(2,5-Dimethylbenzyl)-1H-benzimidazol-2-yl]methyl}-1H-[1,2,3]triazol-4-yl)phenol 3-Ethynylphenol (0.07 mL, 0.7 mmol) and CuSO$_4$.5H$_2$O (0.02 g, 0.7 mmol) were added to a solution of Intermediate 3 (0.2 g, 0.7 mmol) in THF/water (1:1, 4 mL). A catalytic amount of sodium ascorbate was added and the mixture stirred at r.t. for 5 minutes. The reaction mixture was then poured into DCM/water. The organic layer was separated, dried (MgSO$_4$) and concentrated in vacuo. The residue was purified by column chromatography (SiO$_2$, 0-40% EtOAc/DCM), yielding the title compound (0.06 g, 21%) as a pale brown solid. $\delta_H$ (d$_6$-DMSO) 9.47 (s, 1H), 8.48 (s, 1H), 7.68 (d, J 3.5 Hz, 1H), 7.35 (d, J 5.5 Hz, 1H), 7.26-7.17 (m, 4H), 7.17 (d, J 7.9 Hz, 1H), 6.88 (d, J 7.3 Hz, 1H), 6.71 (d, J 7.2 Hz, 1H), 5.95 (s, 3H), 5.59 (s, 2H), 2.35 (s, 3H), 1.94 (s, 3H). LCMS (ES$^+$) 410 (M+H)$^+$.

Example 12

Method D 1-(2,5-Dimethylbenzyl)-2-[(pyridin-4-ylmethoxy)methyl]-1H-benzimidazole Sodium hydride (60% dispersion in oil, 0.022 g, 0.56 mmol) was added to a stirred solution of Example 1 (0.05 g, 0.19 mmol) and 4-(bromomethyl)pyridine hydrobromide (0.06 g, 0.23 mmol) in DMF (1.5 mL) at 0° C., and the reaction mixture was stirred at r.t. for 1 h. The reaction mixture was poured into ethyl acetate/water. The organic layer was separated, dried (MgSO$_4$) and concentrated in vacuo. The residue was purified by column chromatography (SiO$_2$, 0-40% EtOAc/DCM), yielding the title compound (0.05 g, 83%) as a white solid. $\delta_H$ (d$_6$-DMSO) 8.43 (d, J 5.6 Hz, 2H), 7.71 (m, 1H), 7.33 (m, 1H), 7.23 (m, 2H), 7.11 (m, 2H), 6.94 (d, J 7.6 Hz, 1H), 6.17 (s, 1H), 5.52 (s, 2H), 4.83 (s, 2H), 4.57 (s, 2H), 2.32 (s, 3H), 1.96 (s, 3H). LCMS (ES$^+$) 358 (M+H)$^+$.

Example 13

1-(2,5-Dimethylbenzyl)-2-[(pyridin-3-ylmethoxy)methyl]-1H-benzimidazole

Synthesised from Example 1 and 3-(bromomethyl)pyridine hydrobromide in accordance with Method D. LCMS (ES$^+$) 358 (M+H)$^+$.

Example 14

1-(2,5-Dichlorobenzyl)-2-(pyridin-4-ylmethyl)-1H-benzimidazole

The title compound was prepared from Intermediate 4 and 2,5-dichlorobenzyl bromide in accordance with Method B and was isolated as a yellow solid. $\delta_H$ (d$_6$-DMSO) 8.36 (d, J 5.9 Hz, 2H), 7.69 (m, 1H), 7.50 (d, J 8.5 Hz, 1H), 7.37 (m, 1H), 7.31 (dd, J 8.5, 2.4 Hz, 1H), 7.22 (m, 4H), 6.15 (d, J 2.4 Hz, 1H), 5.58 (s, 2H), 4.35 (s, 2H). LCMS (ES$^+$) 368 (M+H)$^+$.

Example 15

1-(2,5-Dimethylbenzyl)-2-(pyridin-4-ylmethyl)-1H-benzimidazole

The title compound was prepared from Intermediate 4 and 2,5-dimethylbenzyl bromide in accordance with Method B and was isolated as a yellow solid. $\delta_H$ (d$_6$-DMSO) 8.39 (m, 2H), 7.65 (m, 1H), 7.32 (m, 1H), 7.19 (m, 4H), 7.08 (d, J 7.6 Hz, 1H), 6.91 (d, J 7.6 Hz, 1H), 5.89 (s, 1H), 5.46 (s, 2H), 4.27 (s, 2H), 2.31 (s, 3H), 1.93 (s, 3H). LCMS (ES$^+$) 328 (M+H)$^+$.

Example 16

1(2,5-Dimethylbenzyl)-2-[1-(pyridin-4-ylmethoxy)ethyl]-1H-benzimidazole

The title compound was prepared from Intermediate 7 and 4-(bromomethyl)-pyridine hydrobromide in accordance with Method D. LCMS (ES+) 372 (M+H)$^+$.

Example 17

Method E

1(2,5-dimethylbenzyl)-2-{[(2-nitrobenzyl)oxy]methyl}-1H-benzimidazole

A mixture of Example 1 (0.20 g, 0.75 mmol), 2-nitrobenzyl bromide (0.16 g, 0.75 mmol) and silver oxide (0.52 g, 2.25 mmol) were stirred at r.t. in DCM for 18 h in the dark. The reaction mixture was filtered through a celite pad and concentrated in vacuo to give a residue which was purified by preparative HPLC to give the title compound. LCMS (ES$^+$) 402 (M+H)$^+$.

Example 18

1-(1-Phenylethyl)-2-[(pyridin-4-ylmethoxy)methyl]-1H-benzimidazole

The title compound was prepared from Intermediate 10 and 4-(bromomethyl)-pyridine hydrobromide in DMF, in accordance with Method E. LCMS (ES$^+$) 344 (M+H)$^+$.

Example 19

2-[(Difluoro)(pyridin-4-yl)methyl]-1-(2,5-dimethylbenzyl)-1H-benzimidazole

MnO$_2$ (1.3 g, 14.6 mmol) was added to a solution of Example 2 (0.25 g, 0.73 mmol) in DCM (10 mL) and the mixture was stirred at r.t. for 15 minutes. The reaction mixture was filtered through a celite pad, washing several times with DCM, and then concentrated in vacuo. The residue was dissolved in DCM (10 mL), DAST (0.2 mL, 1.46 mmol) was added, and the mixture was stirred at r.t. for 18 h. The reaction mixture was poured onto a 2M aqueous solution of NaOH (15 mL)/DCM, then the organic layer was separated, dried (MgSO$_4$) and concentrated in vacuo. The residue was purified by column chromatography (SiO$_2$, 0-30% EtOAc/DCM), yielding the title compound (0.04 g, 14%) as a pale brown solid. $\delta_H$ (CDCl$_3$) 8.64 (d, J 5.6 Hz, 2H), 7.77 (d, J 6.1 Hz, 1H), 7.44 (d, J 5.9 Hz, 2H), 7.27-7.20 (m, 2H), 7.07 (d, J 6.9 Hz, 1H), 7.02 (d, J 7.7 Hz, 1H), 6.89 (d, J 7.6 Hz, 1H), 6.01 (s, 1H), 5.48 (s, 2H), 2.29 (s, 3H), 1.97 (s, 3H). LCMS (ES$^+$) 364 (M+H)$^+$.

Example 20

[1-(1-Phenylethyl)-1H-benzimidazol-2-yl](pyridin-4-yl)methanol

The title compound was prepared from Intermediate 11 and isonicotinaldehyde in accordance with Method C. LCMS (ES$^+$) 330 (M+H)$^+$.

Example 21

(S)-[1-(2,5-Dimethylbenzyl)-1H-benzimidazol-2-yl](phenyl)methanamine

DIPEA (0.20 mL, 1.0 mmol), HATU (0.4 g, 1.0 mmol) and (S)-2-(tert-butoxycarbonylamino)-2-phenylacetic acid (0.25 g, 1.0 mmol) were added to a solution of Intermediate 6 (0.22 g, 1.0 mmol) in DCM (5 mL), and the reaction mixture was stirred at r.t. for 4 h. The reaction mixture was partitioned between DCM and 5% aqueous HCl solution and the organics washed with saturated aqueous sodium bicarbonate solution. The organic layer was extracted, dried (MgSO$_4$) and concentrated in vacuo. The residue was dissolved in acetic acid (5 mL) and heated to 60° C. for 18 h. The reaction mixture was concentrated in vacuo and the residue purified by column chromatography (SiO$_2$, 0-50% EtOAc/isohexane). The recovered material was dissolved in DCM (2 mL) and 4N HCl in 1,4-dioxane (2 mL) and stirred at r.t. for 18 h. The reaction mixture was concentrated in vacuo and the residue was purified by preparative HPLC, yielding the title compound (0.05 g, 7%) as a white solid. $\delta_H$ (d$_6$-DMSO) 7.69 (d, J 7.9 Hz, 1H), 7.32 (m, 2H), 7.19 (m, 5H), 7.07 (d, J 7.6 Hz, 1H), 6.89 (d, J 7.6 Hz, 1H), 5.83 (s, 1H), 5.42 (m, 2H), 5.29 (s, 1H), 2.30 (s, 3H), 1.91 (s, 3H). LCMS (ES$^+$) 342 (M+H)$^+$.

Example 22

6-Bromo-1-(1-phenylethyl)-2-[(pyridin-4-yl-methyl]-1H-benzimidazole

The title compound was prepared from Intermediate 14 and 4-(bromomethyl)-pyridine hydrobromide in DMF, in accordance with Method E. $\delta_H$ (d$_6$-DMSO) 8.82 (d, J 6.6 Hz, 2H), 7.86 (d, J 6.4 Hz, 2H), 7.66 (d, J 8.5 Hz, 1H), 7.34 (m, 7H), 6.14 (m, 1H), 5.07 (s, 2H), 4.93 (s, 2H), 1.95 (d, J 7.1 Hz, 3H). LCMS (ES$^+$) 424 (M+H)$^+$.

Example 23

Method F

1-{4-[1-(2,5-dimethylbenzyl)-2-(hydroxymethyl)-1H-benzimidazol-6-yl]phenyl}ethanone 4-Acetylphenylboronic acid (0.05 g, 0.31 mmol), and a 2M aqueous solution of sodium carbonate (1 mL) were added to a solution of Intermediate 18 (0.10 g, 0.29 mmol) in 1,4-dioxane:water (4:1, 5 mL) and the reaction mixture was degassed for 10 minutes. PdCl$_2$(dppf) (0.01 mg, 0.05 mmol) was added and the reaction mixture was degassed for 10 minutes, then heated to 100° C. for 60 minutes in a Biotage microwave reactor. Ethyl acetate was added and the mixture filtered through a Celite pad. The organic layer was separated, dried over anhydrous sodium sulphate, and concentrated in vacuo. The residue was purified by preparative HPLC, yielding the title compound as a white solid. LCMS (ES$^+$) 385 (M+H)$^+$.

Examples 24 to 28

The following compounds were synthesised from Intermediate 18 and the appropriate boronic acid in accordance with Method F.

Example 29

7-{[1-(2,5-Dimethylbenzyl)-1H-benzimidazol-2-yl]methoxy}isoquinoline

The title compound was prepared from Intermediate 19 and 7-hydroxy-isoquinoline in accordance with Method D. LCMS (ES+) 394 (M+H)$^+$.

Example 30

1-(2,5-Dimethylbenzyl)-2-{r(2-methylpyridin-3-yl)oxyl methyl}-1H-benzimidazole

The title compound was prepared from Intermediate 19 and 2-methylpyridin-3-ol in accordance with Method D. LCMS (ES+) 358 (M+H)$^+$.

Example 31

2-({[1-(2,5-Dimethylbenzyl)-1H-benzimidazol-2-yl]methyl}sulfanyl)benzothiazole

To a stirred solution of 2-mercaptobenzothiazole (0.12 g, 0.7 mmol) in DMF (6 mL) was added potassium carbonate (0.19 g, 1.40 mmol) followed by Intermediate 19 (0.20 g, 0.7 mmol) and the reaction mixture was stirred for 3-4 h at r.t. The reaction mixture was concentrated in vacuo and the residue was diluted with ethyl acetate (10 mL). The organic layer was washed with water (10 mL), dried over anhydrous sodium sulphate and concentrated in vacuo. The residue was purified by preparative HPLC, yielding the title compound. LCMS (ES$^+$) 416 (M+H)$^+$.

Example 32

4-{[1-(2,5-Dimethylbenzyl)-1H-benzimidazol-2-yl]methyl}-N,N-dimethylaniline

2-[4-(Dimethylamino)phenyl]acetic acid (0.18 mg, 1.0 mmol) was added to a stirred solution of Intermediate 6 (0.20 g, 0.88 mmol) in DCM (6 mL), EDC (0.19 g, 0.97 mmol) and triethylamine (0.37 mL, 2.65 mmol) at 0° C., and stirred at r.t. for 18 h. The reaction was diluted with water (60 mL) and extracted with ethyl acetate (3×10 mL). The organic layer was separated, dried over anhydrous sodium sulfate and concentrated in vacuo. The residue was purified by preparative HPLC, yielding the title compound. LCMS (ES$^+$) 370 (M+H)$^+$.

| Example No. | Compound Name | LCMS |
| --- | --- | --- |
| 24 | [1-(2,5-Dimethylbenzyl)-6-(pyridin-4-yl)-1H-benzimidazol-2-yl]methanol | LCMS (ES$^+$) 344 (M + H)$^+$. |
| 25 | [1-(2,5-Dimethylbenzyl)-6-(6-fluoropyridin-3-yl)-1H-benzimidazol-2-yl]methanol | LCMS (ES$^+$) 362 (M + H)$^+$. |
| 26 | [1-(2,5-Dimethylbenzyl)-6-(quinolin-6-yl)-1H-benzimidazol-2-yl]methanol | LCMS (ES$^+$) 394 (M + H)$^+$. |
| 27 | {6-[6-(Dimethylamino)pyridin-3-yl]-1-(2,5-dimethylbenzyl)-1H-benzimidazol-2-yl}methanol | LCMS (ES$^+$) 387 (M + H)$^+$. |
| 28 | [6-(6-Aminopyridin-3-yl)-1-(2,5-dimethylbenzyl)-1H-benzimidazol-2-yl]methanol | LCMS (ES$^+$) 359 (M + H)$^+$. |

Examples 33 to 35

The following compounds were synthesised from Intermediate 21 and the appropriate boronic acid in accordance with Method F.

| Example No. | Compound Name | LCMS |
|---|---|---|
| 33 | 1-(2,5-Dimethylbenzyl)-6-(6-fluoropyridin-3-yl)-2-(pyridin-4-ylmethyl)-1H-benzimidazole | LCMS (ES+) 423 (M + H)+. |
| 34 | 1-(2,5-Dimethylbenzyl)-6-(pyridin-4-yl)-2-(pyridin-4-ylmethyl)-1H-benzimidazole | LCMS (ES+) 405 (M + H)+. |
| 35 | 1-(2,5-Dimethylbenzyl)-6-(3,5-dimethylisoxazol-4-yl)-2-(pyridin-4-ylmethyl)-1H-benzimidazole | LCMS (ES+) 423 (M + H)+. |

Examples 36 to 39

The following compounds were synthesised from Intermediate 23 and the appropriate boronic acid in accordance with Method F.

| Example No. | Compound Name | LCMS |
|---|---|---|
| 36 | 1-(4-[1-(1-Phenylethyl)-2-(pyridin-4-ylmethyl)-1H-benzimidazol-6-yl]phenyl}ethanone | LCMS (ES+) 432 (M + H)+. |
| 37 | 5-[1-(1-Phenylethyl)-2-(pyridin-4-ylmethyl)-1H-benzimidazol-6-yl]pyridin-2-amine | LCMS (ES+) 406 (M + H)+. |
| 38 | N,N-Dimethy1-5-[1-(1-phenylethyl)-2-(pyridin-4-ylmethyl)-1H-benzimidazol-6-yl]pyridin-2-amine | LCMS (ES+) 434 (M + H)+. |
| 39 | 4-[1-(1-Phenylethyl)-2-(pyridin-4-ylmethyl)-1H-benzimidazol-6-yl]benzamide | LCMS (ES+) 433 (M + H)+. |

Example 40

[1-(2,5-Dimethylphenylamino)-1H-benzimidazol-2-yl](pyridin-4-yl)methanol

The title compound was prepared from Intermediate 24 and isonicotinaldehyde in accordance with Method C. $\delta_H$ ($d_6$-DMSO) 8.84 (s, 1H), 8.48-8.42 (m, 2H), 7.70-7.66 (m, 1H), 7.40-7.35 (m, 2H), 7.27-7.17 (m, 2H), 7.14-7.08 (m, 1H), 7.01 (d, J 7.6 Hz, 1H), 7.58-7.53 (m, 1H), 6.44 (d, J 6.0 Hz, 1H), 5.97 (d, J 6.0 Hz, 1H), 5.51 (s, 1H), 2.32 (s, 3H), 1.91 (s, 1H). LCMS (ES+) 345 (M+H)+.

Example 41

1-(2,5-Dimethylbenzyl)-2-[1-(pyridin-4-yl)ethyl]-1H-benzimidazole

Intermediate 25 (0.34 g, 1.91 mmol) was dissolved in THF (5 mL), and a solution of lithium hydroxide (0.09 g, 2.10 mmol) in water (5 mL) was added. The resulting solution was stirred at r.t. for 18 h and then concentrated in vacuo to afford the crude carboxylate salt. This material was then added to a solution of Intermediate 6 (0.47 g, 2.11 mmol) and HATU (0.88 g, 2.30 mmol) in DMF (20 mL). The reaction mixture was warmed to 50° C. and stirred for 1 h. The reaction mixture was concentrated in vacuo and the residue was dissolved in glacial acetic acid (20 mL) and heated at 90° C. for a further 3 h. The reaction mixture was concentrated in vacuo and the remaining oil was partitioned between DCM (50 mL) and aqueous NaHCO₃ solution (50 mL). The organic layer was separated and dried with sodium sulphate, and the resulting solution was concentrated in vacuo to afford a clear oil. The residue was purified by column chromatography (SiO₂, 5% MeOH/DCM), yielding the title compound (0.08 g, 12%) as a clear oil. $\delta_H$ ($d_6$-DMSO) 8.35-8.32 (m, 2H), 7.73 (dd, J 7.0, 1.1 Hz, 1H), 7.30-7.26 (m, 1H), 7.24-7.12 (m, 4H), 7.06-7.00 (m, 1H), 6.88-6.83 (m, 1H), 5.68 (s, 1H), 5.46 (d, J 17.5 Hz, 1H), 5.30 (d, J 17.5 Hz, 1H), 4.48 (q, J 6.9 Hz, 1H), 2.28 (s, 3H), 1.84 (s, 3H), 1.67 (d, J 6.9 Hz, 3H). LCMS (ES+) 342 (M+H)+.

Example 42

1-[2-Methyl-5-(trifluoromethyl)benzyl]-2-[(pyridin-4-ylmethoxy)methyl]-1H-benzimidazole The title compound was prepared from Intermediate 26 and 4-(bromomethyl)-pyridine hydrobromide in accordance with Method D. LCMS (ES+) 412 (M+H)+.

Example 43

4-Chloro-3-({2-[(pyridin-4-ylmethoxy)methyl]-1H-benzimidazol-1-yl}methyl)aniline The title compound was prepared from Intermediate 28 and 4-(bromomethyl)-pyridine hydrobromide in accordance with Method D. LCMS (ES+) 379 (M+H)+.

Example 44

[1-(2,5-Dimethylbenzyl)-6-(1-methyl-1H-pyrazol-4-yl)-1H-benzimidazol-2-yl](pyridin-4-yl)methanol The title compound was prepared from Intermediate 30 and 1-methyl-4-(4,4,5,5-tetramethyl-[1,3,2]dioxaborolan-2-yl)-1H-pyrazole in accordance with Method F. $\delta_H$ ($d_6$-DMSO) 8.39 (dd, J 4.5, 1.6 Hz, 2H), 8.03 (s, 1H), 7.76 (s, 1H), 7.64 (d, J 8.8 Hz, 1H), 7.44-7.41 (m, 2H), 7.28 (d, J 5.6

Hz, 2H), 7.06 (d, J 7.7 Hz, 1H), 6.87 (d, J 6.8 Hz, 1H), 6.70 (d, J 5.5 Hz, 1H), 6.01 (d, J 5.5 Hz, 1H), 5.83 (s, 1H), 5.63-5.43 (m, 2H), 3.82 (s, 3H), 2.33 (s, 3H), 1.92 (s, 3H). LCMS (ES$^+$) 424 (M+H)$^+$.

Example 45

[1-(2,5-Dimethylbenzyl)-6-{1-[2-(morpholin-4-yl) ethyl]-1H-pyrazol-4-yl}-1H-benzimidazol-2-yl] (pyridin-4-yl)methanol The title compound was prepared from Intermediate 30 and 4-{2-[4-(4,4,5,5-tetramethyl-[1,3,2]dioxaborolan-2-yl)-1H-pyrazol-1-yl]ethyl}morpholine in accordance with Method F. $\delta_H$ (d$_6$-DMSO) 8.40 (dd, J 4.5, 1.6 Hz, 2H), 8.08 (s, 1H), 7.77 (s, 1H), 7.64 (d, J 8.9 Hz, 1H), 7.43 (m, 2H), 7.28 (d, J 5.8 Hz, 2H), 7.06 (d, J 7.7 Hz, 1H), 6.87 (d, J 7.5 Hz, 1H), 6.70 (d, J 5.5 Hz, 1H), 6.02 (d, J 5.5 Hz, 1H), 5.84 (s, 1H), 5.63-5.43 (m, 2H), 4.20 (t, J 6.6 Hz, 2H), 3.53 (t, J 4.6 Hz, 4H), 2.70 (t, J 6.4 Hz, 2H), 2.39 (t, J 4.6 Hz, 4H), 2.34 (s, 3H), 1.92 (s, 3H). LCMS (ES$^+$) 523 (M+H)$^+$.

Example 46

Method I 1-(2,5-Dimethylbenzyl)-2-[(methylsulfanyl)methyl]-1H-benzimidazole 2-(Methylsulfanyl)acetic acid (0.11 g, 1.06 mmol) was added to a stirred solution of Intermediate 6 (0.20 g, 0.88 mmol) in DCM (6 mL), EDC (0.19 g, 0.97 mmol) and triethylamine (0.37 mL, 2.65 mmol) at 0° C. and stirred at r.t. for 18 h. The reaction mixture was diluted with water (60 mL) and extracted with ethyl acetate (3×10 mL). The organic layer was separated, dried over anhydrous sodium sulfate and concentrated in vacuo to give a crude product that was purified by preparative HPLC, yielding the title compound. LCMS (ES$^+$) 297 (M+H)$^+$.

Example 47

1-(2,5-Dimethylbenzyl)-2-[2-(1H-imidazol-4-yl) ethyl]-1H-benzimidazole

The title compound was prepared from Intermediate 6 and 3-(1H-imidazol-4-yl)propanoic acid in accordance with Method I. LCMS (ES$^+$) 331 (M+H)$^+$.

Example 48

1-(2,5-Dimethylbenzyl)-2-[(fluoro)(pyridin-4-yl) methyl]-1H-benzimidazole

To a solution of Example 2 (0.15 g, 0.44 mmol) in chloroform (10 mL) was added DAST (0.11 mL, 0.88 mmol). The mixture was heated to 50° C. for 30 minutes, and then the reaction mixture was poured into a 2M aqueous solution of NaOH (15 mL)/DCM. The organic layer was separated, dried over anhydrous sodium sulfate and concentrated in vacuo. The residue was purified by column chromatography (SiO$_2$, 0-30% EtOAc/DCM), yielding the title compound (0.05 g, 33%) as a white solid. $\delta_H$ (CDCl$_3$) 8.55 (d, J 5.8 Hz, 2H), 7.90 (d, J 7.9 Hz, 1H), 7.38-7.25 (m, 4H), 7.16 (d, J 8.0 Hz, 1H), 7.06 (d, J 8.0 Hz, 1H), 6.95 (d, J 7.6 Hz, 1H), 6.87 (d, J$_{HF}$ 46 Hz, 1H), 6.07 (s, 1H), 5.33 (dd, J$_{AB}$ 17.0 Hz, 2H), 2.30 (s, 3H), 2.03 (s, 3H). LCMS (ES$^+$) 346 (M+H)$^+$.

Example 49

1-(2,5-Dimethylbenzyl)-2-(phenylsulfinyl)-1H-benzimidazole

To a solution of Intermediate 31 (0.20 g, 0.58 mmol) in DCM (10 mL) at 0° C. was added mCPBA (0.210 g, 1.2 mmol). The reaction mixture was stirred for 1 h at 0° C. The reaction mixture was then quenched with saturated aqueous sodium thiosulfate solution (10 mL) and allowed to warm to ambient temperature. The reaction mixture was poured into DCM/saturated aqueous sodium carbonate solution. The organic layer was separated, dried over anhydrous sodium sulfate and concentrated in vacuo. The residue was purified by column chromatography (SiO$_2$, 0-20% EtOAc/DCM), yielding the title compound (0.20 g, 96%) as a white solid. $\delta_H$ (d$_6$-DMSO) 7.92 (d, J 8.2 Hz, 1H), 7.60-7.57 (m, 2H), 7.37-7.24 (m, 5H), 7.04 (t, J 8.5 Hz, 2H), 6.86 (d, J 7.7 Hz, 1H), 5.70 (d, J$_{AB}$ 16.9 Hz, 2H), 5.65 (s, 1H), 2.33 (s, 3H), 1.86 (s, 3H). LCMS (ES$^+$) 361 (M+H)$^+$.

Example 50

1-(2,5-Dimethylbenzyl)-2-(phenylsulfonyl)-1H-benzimidazole

To a solution of Example 49 (0.10 g, 0.28 mmol) in DCM (10 mL) at 0° C. was added mCPBA (0.50 g, 2.8 mmol). The reaction mixture was stirred for 1 h at 0° C. The reaction mixture was then quenched with saturated aqueous sodium thiosulfate solution (10 mL) and allowed to warm to ambient temperature. The reaction mixture was poured into DCM/saturated aqueous sodium carbonate solution. The organic layer was separated, dried over anhydrous sodium sulfate and concentrated in vacuo. The residue was purified by column chromatography (SiO$_2$, 0-20% EtOAc/DCM), yielding the title compound (0.04 g, 38%) as a white solid. $\delta_H$ (CDCl$_3$) 7.98-7.96 (m, 1H), 7.83 (d, J 8.2 Hz, 2H), 7.54-7.51 (m, 1H), 7.40-7.33 (m, 4H), 7.21-7.19 (m, 1H), 7.12 (d, J 7.7 Hz, 1H), 6.92 (d, J 7.6 Hz, 1H), 5.81 (s, 2H), 5.72 (s, 1H), 2.44 (s, 3H), 1.85 (s, 3H). LCMS (ES$^+$) 377 (M+H)$^+$.

Example 51

Methyl 3-{1-(2,5-dimethylbenzyl)-2-[(hydroxy) (pyridin-4-yl)methyl]-1H-benzimidazol-6-yl}propanoate To a solution of 5-bromobenzimidazole (10.0 g, 50.8 mmol) in DMF (60 mL) were added 2,5-dimethylbenzyl chloride (7.9 g, 50.8 mmol) and potassium carbonate (14.0 g, 102.0 mmol). The mixture was stirred at r.t. for 18 h. Water (50 mL) was added and the mixture was poured into ethyl acetate/water. The organic layer was separated, dried (MgSO$_4$) and concentrated in vacuo and the residue was purified by column chromatography (SiO$_2$, 0-20% EtOAc/DCM), yielding a pale brown solid (6.7 g, 42%). To a solution of the resulting material (2.0 g, 6.3 mmol) in THF (20 mL) at −78° C. was added freshly prepared LDA (0.9M in THF, 14.0 mL, 12.6 mmol) over 1 minute. The reaction mixture was stirred for 1 h and then a solution of isonicotinaldehyde (1.35 g, 12.6 mmol) in THF (2 mL) was added over 1 minute. After a further 10 minutes the reaction was quenched with water (1 mL) and allowed to warm to r.t. The reaction mixture was poured into ethyl acetate/water; and the organic layer was separated, dried over anhydrous sodium sulfate and concentrated in vacuo. The residue was purified by column chromatography (SiO$_2$, 0-20% MeOH/DCM), yielding a pale brown solid (1.9 g, 70%). To a solution of the resulting material (0.20 g, 0.48 mmol) in DMF (5 mL) were added methyl acrylate (0.08 mL, 0.96 mmol), Pd(OAc)$_2$ (0.006 g, 0.024 mmol), P(o-tolyl)$_3$ (0.020 g, 0.048 mmol) and triethylamine (4 mL). The mixture was degassed under nitrogen and heated under reflux for 1 h. The reaction mixture was poured into ethyl acetate/water, and the organic layer was separated, dried over anhydrous sodium sulfate and concentrated in vacuo. The residue was purified by column chromatography (SiO$_2$, 0-20% EtOAc/DCM), yielding a yellow oil. The resulting material was dissolved in EtOH/EtOAc (10 mL/5 mL) and Pd/C (Degussa, 5 wt %, 300 mg) was added. The suspension was degassed and stirred under a H$_2$ atmosphere (balloon) at r.t. for 18 h. The mixture was filtered on celite and the filtrate concentrated under vacuo. The residue was purified by preparative HPLC, yielding the title compound. $\delta_H$ (CDCl$_3$) 8.28 (d, J 4.5 Hz, 2H), 7.59 (d, J 8.3 Hz, 1H), 7.12 (d, J 6.0 Hz, 2H), 7.05 (dd, J 8.3, 1.4 Hz, 1H), 6.93 (d, J 7.7 Hz, 1H), 6.79-6.82 (m, 2H), 5.94 (s, 1H), 5.78 (s, 1H), 5.09 (dd, J$_{AB}$ 17.2 Hz, 2H), 3.51 (s, 3H), 2.91 (t, J 7.6 Hz, 2H), 2.51 (t, J 7.6 Hz, 2H), 2.16 (s, 3H), 1.86 (s, 3H). LCMS (ES$^+$) 430 (M+H)$^+$.

Example 52

Methyl 3-{1-(2,5-dimethylbenzyl)-2-[(hydroxy)(pyridin-4-yl)methyl]-1H-benzimidazol-5-yl}propanoate The title compound was obtained as a separated regioisomer from the reaction described in Example 51. $\delta_H$ (CDCl$_3$) 8.31 (d, J 4.5 Hz, 2H), 7.49 (s, 1H), 7.13 (d, J 5.9 Hz, 2H), 6.81-6.99 (m, 4H), 5.94 (s, 1H), 5.85 (s, 1H), 5.10 (dd, J$_{AB}$ 17.1 Hz, 2H), 3.60 (s, 3H), 2.99 (t, J 7.6 Hz, 2H), 2.60 (t, J 7.6 Hz, 2H), 2.15 (s, 3H), 1.87 (s, 3H). LCMS (ES$^+$) 430 (M+H)$^+$.

Example 53

[1-(2,5-Dimethylbenzyl)-6-(1H-pyrazol-4-yl)-1H-benzimidazol-2-yl](pyridin-4-yl)methanol The title compound was prepared from Intermediate 30 and 1H-pyrazol-4-ylboronic acid in accordance with Method F. $\delta_H$ (d$_6$-DMSO) 12.85 (s, NH, 1H), 8.40 (dd, J 4.5, 1.5 Hz, 2H), 8.10 (s, 1H), 7.82 (s, 1H), 7.64 (d, J 8.8 Hz, 1H), 7.47-7.49 (m, 2H), 7.28 (d, J 5.8 Hz, 1H), 7.16 (d, J 8.0 Hz, 1H), 7.07 (d, J 7.7 Hz, 1H), 6.85 (m, 1H), 6.70 (d, J 5.5 Hz, 1H), 6.01 (d, J 5.4 Hz, 1H), 5.85 (s, 1H), 5.54 (dd, J$_{AB}$ 36.0 Hz, 2H), 2.34 (s, 3H), 1.92 (s, 3H). LCMS (ES$^+$) 410 (M+H)$^+$.

Example 54

{1-(2,5-Dimethylbenzyl)-6-[6-(piperazin-1-yl)pyridin-3-yl]-1H-benzimidazol-2-yl}(pyridin-4-yl)methanol The title compound was prepared from Intermediate 30 and 1-[5-(4,4,5,5-tetramethyl-[1,3,2]dioxaborolan-2-yl)pyridin-2-yl]piperazine in accordance with Method F. $\delta_H$ (CDCl$_3$) 8.30 (dd, J 1.5, 4.6 Hz, 2H), 8.23 (d, J 2.4 Hz, 1H), 7.70 (d, J 8.4 Hz, 1H), 7.48 (dd, J 2.6, 8.8 Hz, 1H), 7.35 (dd, J 1.6, 8.4 Hz, 1H), 7.19-7.16 (m, 2H), 6.96 (s, 1H), 6.91 (d, J 7.7 Hz, 1H), 6.80-6.78 (m, 1H), 6.53 (d, J 8.9 Hz, 1H), 6.03 (s, 1H), 5.82 (s, 1H), 5.15 (d, J$_{AB}$ 17.1 Hz, 2H), 3.44-3.40 (m, 4H), 2.90-2.88 (m, 4H), 2.17 (s, 3H), 1.84 (s, 3H). LCMS (ES$^+$) 505 (M+H)$^+$.

Example 55

{1-(2,5-Dimethylbenzyl)-5-[4-(piperazin-1-yl)phenyl]-1H-benzimidazol-2-yl}(pyridin-4-yl)methanol To a solution of 5-bromobenzimidazole (10.0 g, 50.8 mmol) in DMF (60 mL) were added 2,5-dimethylbenzyl chloride (7.9 g, 50.8 mmol) and potassium carbonate (14.0 g, 102.0 mmol). The mixture was stirred at r.t. for 18 h. Water (50 mL) was added and the mixture was poured into ethyl acetate/water. The organic layer was separated, dried (MgSO$_4$) and concentrated in vacuo and the residue was purified by column chromatography (SiO$_2$, 0-20% EtOAc/DCM), yielding a pale brown solid (6.7 g, 42%). To a solution of the resulting material (2.0 g, 6.3 mmol) in THF (20 mL) at −78° C. was added freshly prepared LDA (0.9M in THF, 14 mL, 12.6 mmol) over 1 minute. The reaction mixture was stirred for 1 h and then a solution of isonicotinaldehyde (1.35 g, 12.6 mmol) in THF (2 mL) was added over 1 minute. After a further 10 minutes the reaction was quenched with water (1 mL) and allowed to warm to r.t. The reaction mixture was poured into ethyl acetate/water, and the organic layer was separated, dried over anhydrous sodium sulfate and concentrated in vacuo. The residue was purified by column chromatography (SiO$_2$, 0-20% MeOH/DCM), yielding a pale brown solid (1.87 g, 70%). To a solution of the resulting material (0.20 g, 0.47 mmol) in 1,4-dioxane (5 mL) were added 4-[4-(tert-butoxycarbonyl)piperazinyl]phenylboronic acid pinacol ester (0.36 g, 0.95 mmol) and Pd(PPh$_3$)$_4$ (0.03 g, 0.026 mmol), followed by a 2M aqueous solution of Na$_2$CO$_3$ (2 mL). The mixture was degassed under nitrogen and heated under reflux for 2 h. The reaction mixture was poured into ethyl acetate/water. The organic layer was separated, dried over anhydrous sodium sulfate and concentrated in vacuo. The residue was purified by column chromatography (SiO$_2$, 0-60% EtOAc/DCM). The resulting solid was dissolved in DCM (5 mL) and a 4N solution of HCl in 1,4-dioxane (1 mL) was added. The mixture was stirred at r.t. for 2 h, then concentrated in vacuo. The residue was purified by preparative HPLC, yielding the title compound (0.04 g, 15%) as an off-white solid. $\delta_H$ (d$_6$-DMSO) 8.41 (dd, J 4.6, 1.5 Hz, 2H), 7.85 (s, 1H), 7.56-7.53 (m, 2H), 7.43 (d, J 8.3 Hz, 1H), 7.32 (d, J 5.4 Hz, 2H), 7.20 (d, J 8.7 Hz, 1H), 7.06 (d, J 7.7 Hz, 1H), 6.96 (d, J 8.9 Hz, 1H), 6.87 (d, J 7.6 Hz, 1H), 6.75 (d, J 5.0 Hz, 1H), 6.11 (d, J 4.3 Hz, 1H), 5.90 (s, 1H), 5.51 (dd, J$_{AB}$ 11.6 Hz, 2H), 3.08-3.03 (m, 4H), 2.86-2.84 (m, 4H), 2.31 (s, 3H), 1.92 (s, 3H). LCMS (ES$^+$) 504 (M+H)$^+$.

Examples 56 to 106

Method J

The appropriate carboxylic acid (2 equivalents) is added to a solution of HATU (2 equivalents) in DMF (2 mL). The mixture is stirred for 30 minutes. Where HCl salts are utilised, DIPEA (3 equivalents) is added. A solution of the appropriate Intermediate (1 equivalent) in DMF (2 mL) is added and the mixture is stirred at room temperature for 24 h. The temperature is then raised to 50° C. and stirring is continued for 24 h. The solvent is evaporated and the residue dissolved in acetic acid (4 mL) and heated to 80° C. for 5 h. The acetic acid is removed by evaporation. The residue is partitioned between water/chloroform (1:1, 6 mL) at 50° C. The layers are separated by using a phase separator. The aqueous layer is washed with chloroform (4 mL) and the organic layer is evaporated to dryness. The residue is taken up in DMSO (1 mL) and purified by preparative LCMS to yield the desired product.

The following compounds were synthesized from Intermediate 35 and the appropriate carboxylic acid in accordance with the foregoing procedure.

| Example | Compound Name | QC RT | Mass Ion |
|---|---|---|---|
| 56 | 5-{1-[2-(Difluoromethoxy)benzyl]-2-[(difluoromethoxy)methyl]-1H-benzimidazol-6-yl}pyridin-2(1H)-one | 1.33 | 448 |
| 57 | 5-({1-[2-(Difluoromethoxy)benzyl]-6-(6-oxo-1,6-dihydropyridin-3-yl)-1H-benzimidazol-2-yl}methoxy)-3-methylpyridine-2-carbonitrile | 1.36 | 514 |
| 58 | 5-{1-[2-(Difluoromethoxy)benzyl]-2-(2-methoxypropan-2-yl)-1H-benzimidazol-6-yl}pyridin-2(1H)-one | 1.38 | 440 |
| 59 | 5-{2-[(Cyclohexyloxy)methyl]-1-[2-(difluoromethoxy)benzyl]-1H-benzimidazol-6-yl}pyridin-2(1H)-one | 1.51 | 481 |
| 60 | 5-{1-[2-(Difluoromethoxy)benzyl]-2-[(propan-2-yloxy)methyl]-1H-benzimidazol-6-yl}pyridin-2(1H)-one | 1.39 | 440 |
| 61 | 5-{1-[2-(Difluoromethoxy)benzyl]-2-[(tetrahydrofuran-3-ylmethoxy)methyl]-1H-benzimidazol-6-yl}pyridin-2(1H)-one | 1.29 | 482 |
| 62 | 5-(1-[2-(Difluoromethoxy)benzyl]-2-{[(2S)5-oxopyrrolidin-2-yl]methyl}-1H-benzimidazol-6-yl)pyridin-2(1H)-one | 1.17 | 465 |
| 63 | 5-{1-[2-(Difluoromethoxy)benzyl]-2-(2-methoxyethyl)-1H-benzimidazol-6-yl}pyridin-2(1H)-one | 1.28 | 426 |
| 64 | 5-{2-[(Cyclopentyloxy)methyl]-1-[2-(difluoromethoxy)benzyl]-1H-benzimidazol-6-yl}pyridin-2(1H)-one | 1.46 | 466 |
| 65 | 5-{1-[2-(Difluoromethoxy)benzyl]-2-[(3,5-dimethylisoxazol-4-yl)methyl]-1H-benzimidazol-6-yl}pyridin-2(1H)-one | 1.31 | 477 |
| 66 | 5-{1-[2-(Difluoromethoxy)benzyl]-2-(pyrazin-2-ylmethyl)-1H-benzimidazol-6-yl}pyridin-2(1H)-one | 1.21 | 460 |
| 67 | 5-(1-[2-(Difluoromethoxy)benzyl]-2-{[(5-methylisoxazol-3-yl)oxy]methyl}-1H-benzimidazol-6-yl)pyridin-2(1H)-one | 1.34 | 479 |
| 68 | N-[5-({1-[2-(Difluoromethoxy)benzyl]-6-(6-oxo-1,6-dihydropyridin-3-yl)-1H-benzimidazol-2-yl}methoxy)-pyridin-2-yl]acetamide | 1.24 | 533 |
| 69 | 5-{1-[2-(Difluoromethoxy)benzyl]-2-[(2-methyl-1,3-thiazol-4-yl)methyl]-1H-benzimidazol-6-yl}pyridin-2(1H)-one | 1.32 | 480 |
| 70 | 5-{1-[2-(Difluoromethoxy)benzyl]-2-(ethoxymethyl)-1H-benzimidazol-6-yl}pyridin-2(1H)-one | 1.32 | 426 |
| 71 | 5-{1-[2-(Difluoromethoxy)benzyl]-2-(morpholin-4-ylmethyl)-1H-benzimidazol-6-yl}pyridin-2(1H)-one | 1.27 | 467 |
| 72 | 5-{1-[2-(Difluoromethoxy)benzyl]-2-(piperidin-1-ylmethyl)-1H-benzimidazol-6-yl}pyridin-2(1H)-one | 1.48 | 466 |
| 73 | 5-{1-[2-(Difluoromethoxy)benzyl]-2-[(1S)-1-methoxyethyl]-1H-benzimidazol-6-yl}pyridin-2(1H)-one | 1.30 | 426 |
| 74 | 5-{1-[2-(Difluoromethoxy)benzyl]-2-(tetrahydro-2H-pyran-4-ylmethyl)-1H-benzimidazol-6-yl}pyridin-2(1H)-one | 1.29 | 466 |
| 75 | 5-{1-[2-(Difluoromethoxy)benzyl]-2-[(1R)-1-methoxyethyl]-1H-benzimidazol-6-yl}pyridin-2(1H)-one | 1.30 | 426 |
| 76 | 5-{1-[2-(Difluoromethoxy)benzyl]-2-(1-methoxypropyl)-1H-benzimidazol-6-yl}pyridin-2(1H)-one | 1.36 | 440 |
| 77 | 5-{1-[2-(Difluoromethoxy)benzyl]-2-[(2-methoxyethoxy)methyl]-1H-benzimidazol-6-yl}pyridin-2(1H)-one | 1.26 | 456 |
| 78 | 5-{2-(tert-Butoxymethyl)-1-[2-(difluoromethoxy)benzyl]-1H-benzimidazol-6-yl}pyridin-2(1H)-one | 1.43 | 454 |
| 79 | 5-{1-[2-(Difluoromethoxy)benzyl]-2-(tetrahydrofuran-2-yl)-1H-benzimidazol-6-yl}pyridin-2(1H)-one | 1.33 | 438 |
| 80 | 5-{1-[2-(Difluoromethoxy)benzyl]-2-(tetrahydrofuran-3-yl)-1H-benzimidazol-6-yl}pyridin-2(1H)-one | 1.25 | 438 |
| 81 | 5-(1-[2-(Difluoromethoxy)benzyl]-2-{[5-(pyridin-4-yl)-2H-tetrazol-2-yl]methyl}-1H-benzimidazol-6-yl)pyridin-2(1H)-one | 1.25 | 527 |
| 82 | N-(2-{1-[2-(Difluoromethoxy)benzyl]-6-(6-oxo-1,6-dihydropyridin-3-yl)-1H-benzimidazol-2-yl}ethyl)furan-3-carboxamide | 1.24 | 505 |
| 83 | 5-(1-[2-(Difluoromethoxy)benzyl]-2-{[4-(trifluoromethoxy)phenoxy]methyl}-1H-benzimidazol-6-yl)-pyridin-2(1H)-one | 1.55 | 558 |
| 84 | 5-{1-[2-(Difluoromethoxy)benzyl]-2-(1-hydroxypropyl)-1H-benzimidazol-6-yl}pyridin-2(1H)-one | 1.24 | 426 |

-continued

| Example | Compound Name | QC RT | Mass Ion |
|---|---|---|---|
| 85 | 5-(1-[2-(Difluoromethoxy)benzyl]-2-{[4-(1H-tetrazol-1-yl)phenoxy]methyl}-1H-benzimidazol-6-yl)pyridin-2(1H)-one | 1.30 | 543 |
| 86 | 5-{1-[2-(Difluoromethoxy)benzyl]-2-[(2-methylpropoxy)methyl]-1H-benzimidazol-6-yl}pyridin-2(1H)-one | 1.45 | 454 |
| 87 | 5-(1-[2-(Difluoromethoxy)benzyl]-2-{[5-(morpholin-4-yl)-2H-tetrazol-2-yl]methyl}-1H-benzimidazol-6-yl)-pyridin-2(1H)-one | 1.25 | 536 |
| 88 | 5-{2-[(Cyclopropylmethoxy)methyl]-1-[2-(difluoromethoxy)benzyl]-1H-benzimidazol-6-yl}pyridin-2(1H)-one | 1.38 | 452 |
| 89 | 5-(1-[2-(Difluoromethoxy)benzyl]-2-{[3-(2-oxopyrrolidin-1-yl)phenoxy]methyl}-1H-benzimidazol-6-yl)-pyridin-2(1H)-one | 1.34 | 558 |
| 90 | 5-(1-[2-(Difluoromethoxy)benzyl]-2-{[3-(methylsulfonyl)phenoxy]methyl}-1H-benzimidazol-6-yl)pyridin-2(1H)-one | 1.30 | 553 |
| 91 | 5-{1-[2-(Difluoromethoxy)benzyl]-2-[4-(trifluoromethoxy)benzyl]-1H-benzimidazol-6-yl}pyridin-2(1H)-one | 1.53 | 542 |
| 92 | 5-{1-[2-(Difluoromethoxy)benzyl]-2-[4-(methylsulfonyl)benzyl]-1H-benzimidazol-6-yl}pyridin-2(1H)-one | 1.26 | 537 |
| 93 | 5-{1-[2-(Difluoromethoxy)benzyl]-2-[3-(methylsulfonyl)benzyl]-1H-benzimidazol-6-yl}pyridin-2(1H)-one | 1.27 | 537 |
| 94 | 5-{1-[2-(Difluoromethoxy)benzyl]-2-[4-(difluoromethoxy)benzyl]-1H-benzimidazol-6-yl}pyridin-2(1H)-one | 1.44 | 524 |
| 95 | 5-{1-[2-(Difluoromethoxy)benzyl]-2-[4-(2-methyl-1,3-thiazol-4-yl)benzyl]-1H-benzimidazol-6-yl}pyridin-2(1H)-one | 1.46 | 556 |
| 96 | 5-(1-[2-(Difluoromethoxy)benzyl]-2-{[(4-oxocyclohexyl)oxy]methyl}-1H-benzimidazol-6-yl)pyridin-2(1H)-one | 1.26 | 495 |
| 97 | 5-{1-[2-(Difluoromethoxy)benzyl]-2-[(5,7-dimethyl-[1,2,4]triazolo[1,5-a]pyrimidin-2-yl)methyl]-1H-benzimidazol-6-yl}pyridin-2(1H)-one | 1.20 | 529 |
| 98 | 5-({1-[2-(Difluoromethoxy)benzyl]-6-(6-oxo-1,6-dihydropyridin-3-yl)-1H-benzimidazol-2-yl}methoxy)-3-fluoropyridine-2-carboxamide | 1.18 | 536 |
| 99 | 5-(1-[2-(Difluoromethoxy)benzyl]-2-{2-[(4-oxo-4,5-dihydro-1,3-thiazol-2-yl)amino]ethyl}-1H-benzimidazol-6-yl)pyridin-2(1H)-one | 1.14 | 511 |
| 100 | 5-{1-[2-(Difluoromethoxy)benzyl]-2-[(methylsulfanyl)methyl]-1H-benzimidazol-6-yl}pyridin-2(1H)-one | 1.31 | 428 |
| 101 | 5-{1-[2-(Difluoromethoxy)benzyl]-2-(trifluoromethyl)-1H-benzimidazol-6-yl}pyridin-2(1H)-one | 1.42 | 436 |
| 102 | 5-{1-[2-(Difluoromethoxy)benzyl]-2-(hydroxymethyl)-1H-benzimidazol-6-yl}pyridin-2(1H)-one | 1.14 | 398 |
| 103 | 5-{1-[2-(Difluoromethoxy)benzyl]-2-(2,2,2-trifluoro-1-hydroxyethyl)-1H-benzimidazol-6-yl}pyridin-2(1H)-one | 1.28 | 466 |
| 104 | 5-{1-[2-(Difluoromethoxy)benzyl]-2-(pyridin-4-ylmethyl)-1H-benzimidazol-6-yl}pyridin-2(1H)-one | 1.21 | 459 |
| 105 | 5-{1-[2-(Difluoromethoxy)benzyl]-2-(difluoromethyl)-1H-benzimidazol-6-yl}pyridin-2(1H)-one | 1.33 | 418 |
| 106 | 5-{1-[2-(Difluoromethoxy)benzyl]-2-propyl-1H-benzimidazol-6-yl}pyridin-2(1H)-one | 1.35 | 410 |

Examples 107 and 108

The following compounds were synthesized from Intermediate 38 and the appropriate carboxylic acid in accordance with Method J.

| Example | Compound Name | LCMS RT | Mass Ion |
|---|---|---|---|
| 107 | 5-{1-[(5-Chloro-2-methyl-1,3-thiazol-4-yl)methyl]-2-(pyridin-4-ylmethyl)-1H-benzimidazol-6-yl}-pyridin-2(1H)-one | 1.18 | 448 |
| 108 | 5-{1-[(5-Chloro-2-methyl-1,3-thiazol-4-yl)methyl]-2-(methoxymethyl)-1H-benzimidazol-6-yl}pyridin-2(1H)-one | 1.21 | 401 |

Examples 109 to 112

These compounds can be synthesized by a sequence of steps corresponding to the preparation of Intermediates 33, 34 and 35, followed by Method J, utilising the appropriate amine and carboxylic acid. The following compounds were prepared.

| Example | Compound Name | LCMS RT | Mass Ion |
|---|---|---|---|
| 109 | 5-{1-[5-Chloro-2-(difluoromethoxy)benzyl]-2-[(difluoromethoxy)methyl]-1H-benzimidazol-6-yl}pyridin-2(1H)-one | 1.42 | 482 |
| 110 | 5-{1-[5-Chloro-2-(difluoromethoxy)benzyl]-2-(methoxymethyl)-1H-benzimidazol-6-yl}pyridin-2(1H)-one | 1.31 | 446 |
| 111 | 5-{{1-(2,5-Dichlorobenzyl)-6-(6-oxo-1,6-dihydropyridin-3-yl)-1H-benzimidazol-2-yl]methoxy}-pyridine-2-carboxamide | 1.25 | 521 |
| 112 | 5-[1-(2,5-Dichlorobenzyl)-2-(methoxymethyl)-1H-benzimidazol-6-yl]pyridin-2(1H)-one | 1.28 | 415 |

Examples 113 to 221

These compounds can be synthesized from Intermediate 40, 42, 44 or 46 and the appropriate carboxylic acid in accordance with Method J. The following compounds were prepared.

| Example | Compound Name | LCMS RT | Mass Ion |
|---|---|---|---|
| 113 | N-[3-({6-Cyano-1-[2-(difluoromethoxy)benzyl]-1H-benzimidazol-2-yl}methoxy)phenyl]methane-sulfonamide | 1.40 | 500 |
| 114 | N-[3-({6-Cyano-1-[2-(difluoromethoxy)benzyl]-1H-benzimidazol-2-yl}methoxy)phenyl]acetamide | 1.45 | 463 |
| 115 | 1-(2,5-Dichlorobenzyl)-2-[(difluoromethoxy)-methyl]-1H-benzimidazole-6-carbonitrile | 1.57 | 383 |
| 116 | 1-[2-(Difluoromethoxy)benzyl]-2-[(3,5-dimethyl-1H-pyrazol-4-yl)methyl]-1H-benzimidazole-6-carbonitrile | 1.37 | 408 |
| 117 | N-[5-({6-Cyano-1-[2-(difluoromethoxy)benzyl]-1H benzimidazol-2-yl}methoxy)pyridin-2-yl]acetamide | 1.40 | 464 |
| 118 | 1-[2-(Difluoromethoxy)benzyl]-2-[(tetrahydrofuran-3-ylmethoxy)methyl]-1H-benzimidazole-6-carbonitrile | 1.46 | 414 |
| 119 | 1-(2,5-Dichlorobenzyl)-2-[(2-methyl-1H-benzimidazol-5-yl)methyl]-1H-benzimidazole-6-carbonitrile | 1.38 | 447 |
| 120 | 2-{[6-Cyano-1-(2,5-dichlorobenzyl)-1H-benzimidazol-2-yl]methoxy}acetamide | 1.34 | 390 |
| 121 | 1-[2-(Difluoromethoxy)benzyl]-2-[(difluoro-methoxy)methyl]-1H-benzimidazole-6-carbonitrile | 1.50 | 380 |
| 122 | 2-[(Cyclopentyloxy)methyl]-1-(2,5-dichlorobenzyl)-1H-benzimidazole-6-carbonitrile | 1.76 | 401 |
| 123 | 2-{[3-(3-Amino-2-oxopyrrolidin-1-yl)phenoxy]-methyl}-1-[2-(difluoromethoxy)benzyl]-1H-benzimidazole-6-carbonitrile | 1.41 | 505 |
| 124 | 1-[2-(Difluoromethoxy)benzyl]-2-({[3-(2-oxo-pyrrolidin-1-yl)phenyl]amino}methyl)-1H-benzimidazole-6-carbonitrile | 1.49 | 489 |
| 125 | Methyl 4-({6-cyano-1-[2-(difluoromethoxy)benzyl]-1H-benzimidazol-2-yl}methoxy)pyridine-2-carboxylate | 1.43 | 465 |
| 126 | 1-[2-(Difluoromethoxy)benzyl]-2-({[2-(2-oxo-pyrrolidin-1-yl)pyridin-4-yl]oxy}methyl)-1H-benzimidazole-6-carbonitrile | 1.49 | 490 |
| 127 | 2-{[(2-Chloropyridin-4-yl)oxy]methyl}-1-[2-(difluoromethoxy)benzyl]-1H-benzimidazole-6-carbonitrile | 1.53 | 442 |
| 128 | 1-[2-(Difluoromethoxy)benzyl]-2-{[3-(2-formyl-1,3-thiazol-4-yl)phenyl]methyl}-1H-benzimidazole-6-carbonitrile | 2.71 | 518 |
| 129 | 1-[2-(Difluoromethoxy)benzyl]-2-({[2-(2-oxo-imidazolidin-1-yl)pyridin-4-yl]oxy}methyl)-1H-benzimidazole-6-carbonitrile | 1.42 | 491 |

-continued

| Example | Compound Name | LCMS RT | Mass Ion |
|---|---|---|---|
| 130 | 1-[2-(Difluoromethoxy)benzyl]-2-{[3-(2,5-dioxo-pyrrolidin-1-yl)phenoxy]methyl}-1H-benzimidazole-6-carbonitrile | 1.48 | 503 |
| 131 | 1-[2-(Difluoromethoxy)benzyl]-2-({[2-(2-oxo-1,3-oxazolidin-3-yl)pyridin-4-yl]oxy}methyl)-1H-benzimidazole-6-carbonitrile | 1.47 | 492 |
| 132 | 2-[4-(2-Methyl-1,3-thiazol-4-yl)benzyl]-1-[(1S)-1-phenylethyl]-1H-benzimidazole-6-carbonitrile | 1.64 | 436 |
| 133 | N-(5-{[6-Cyano-1-(2,5-dichlorobenzyl)-1H-benzimidazol-2-yl]methoxy}pyridine-2-yl)acetamide | 1.43 | 467 |
| 134 | 2-{[(6-Cyano-5-methylpyridin-3-yl)oxy]methyl}-1-(2,5-dichlorobenzyl)-1H-benzimidazole-6-carbonitrile | 1.57 | 449 |
| 135 | 1-[(1R)-1-Phenylethyl]-2-{[2-(pyridin-3-yl)-1,3-thiazol-4-yl]methyl}-1H-benzimidazole-6-carbonitrile | 1.47 | 423 |
| 136 | 2-{[(6-Oxo-1,6-dihydropyridin-3-yl)oxy]methyl}-1-[(1S)-1-phenylethyl]-1H-benzimidazole-6-carbonitrile | 1.28 | 371 |
| 137 | 2-[(Difluoromethoxy)methyl]-1-[(1S)-1-phenyl-ethyl]-1H-benzimidazole-6-carbonitrile | 1.49 | 328 |
| 138 | 2-[(Cyclopentyloxy)methyl]-1-[(1S)-1-phenylethyl]-1H-benzimidazole-6-carbonitrile | 1.68 | 346 |
| 139 | 5-({6-Cyano-1-[(1S)-1-phenylethyl]-1H-benzimidazol-2-yl}methoxy)-3-fluoropyridine-2-carboxamide | 1.33 | 416 |
| 140 | 1-[2-(Difluoromethoxy)benzyl]-2-{[5-(morpholin-4-yl)-2H-tetrazol-2-yl]methyl}-1H-benzimidazole-6-carbonitrile | 1.43 | 467 |
| 141 | 2-{[3-(2-Oxopyrrolidin-1-yl)phenoxy]methyl}-1-[(1R)-1-phenylethyl]-1H-benzimidazole-6-carbonitrile | 1.52 | 438 |
| 142 | 2-[(2-Methylpropoxy)methyl]-1-[(1S)-1-phenyl-ethyl]-1H-benzimidazole-6-carbonitrile | 1.65 | 334 |
| 143 | 2-{[(6-Cyano-5-methylpyridin-3-yl)oxy]methyl}-1-[2-(difluoromethoxy)benzyl]-1H-benzimidazole-6-carbonitrile | 1.51 | 446 |
| 144 | 1-[(1S)-1-Phenylethyl]-2-[(propan-2-yloxy)methyl]-1H-benzimidazole-6-carbonitrile | 1.54 | 320 |
| 145 | 2-[(5,7-Dimethyl[1,2,4]triazolo[1,5-a]pyrimidin-2-yl)methyl]-1-[(1S)-1-phenylethyl]-1H-benzimidazole-6-carbonitrile | 1.36 | 408 |
| 146 | 1-[(1S)-1-Phenylethyl]-2-[4-(trifluoromethoxy)-benzyl]-1H-benzimidazole-6-carbonitrile | 1.71 | 422 |
| 147 | 2-[(2-Methoxyethoxy)methyl]-1-[(1S)-1-phenyl-ethyl]-1H-benzimidazole-6-carbonitrile | 1.41 | 336 |
| 148 | 2-{[(5-Methylisoxazol-3-yl)oxy]methyl}-1-[(1S)-1-phenylethyl]-1H-benzimidazole-6-carbonitrile | 1.49 | 359 |
| 149 | 1-[(1S)-1-Phenylethyl]-2-{[2-(pyridin-3-yl)-1,3-thiazol-4-yl]methyl}-1H-benzimidazole-6-carbonitrile | 1.47 | 423 |
| 150 | 2-[(2-Methyl-1,3-thiazol-4-yl)methyl]-1-[(1S)-1-phenylethyl]-1H-benzimidazole-6-carbonitrile | 1.48 | 359 |
| 151 | 2-[(3,5-Dimethylisoxazol-4-yl)methyl]-1-[(1S)-1-phenylethyl]-1H-benzimidazole-6-carbonitrile | 1.46 | 357 |
| 152 | 2-(Ethoxymethyl)-1-[(1S)-1-phenylethyl]-1H-benzimidazole-6-carbonitrile | 1.51 | 306 |
| 153 | 1-(2,5-Dichlorobenzyl)-2-{[(6-oxo-1,6-dihydro-pyridin-3-yl)oxy]methyl}-1H-benzimidazole-6-carbonitrile | 1.32 | 426 |
| 154 | 2-{[2-(2-Oxoimidazolidin-1-yl)-1,3-thiazol-4-yl]-methyl}-1-[(1S)-1-phenylethyl]-1H-benzimidazole-6-carbonitrile | 1.36 | 430 |
| 155 | 2-{[3-(Methylsulfonyl)phenoxy]methyl}-1-[(1S)-1-phenylethyl]-1H-benzimidazole-6-carbonitrile | 1.48 | 433 |
| 156 | 2-{[3-(2-Oxopyrrolidin-1-yl)phenoxy]methyl}-1-[(1S)-1-phenylethyl]-1H-benzimidazole-6-carbonitrile | 1.52 | 438 |
| 157 | 2-(2-Methoxyethyl)-1-[(1S)-1-phenylethyl]-1H-benzimidazole-6-carbonitrile | 1.41 | 306 |
| 158 | 2-[(3,5-Dimethyl-1H-pyrazol-4-yl)methyl]-1-[(1S)-1-phenylethyl]-1H-benzimidazole-6-carbonitrile | 1.35 | 356 |
| 159 | 2-{[5-(Morpholin-4-yl)-2H-tetrazol-2-yl]methyl}-1-[(1S)-1-phenylethyl]-1H-benzimidazole-6-carbonitrile | 1.43 | 415 |
| 160 | 2-[(1R)-1-Methoxyethyl]-1-[(1S)-1-phenylethyl]-1H-benzimidazole-6-carbonitrile | 1.48 | 306 |

-continued

| Example | Compound Name | LCMS RT | Mass Ion |
|---|---|---|---|
| 161 | 1-(2,5-Dichlorobenzyl)-2-(pyridin-4-ylmethyl)-1H-benzimidazole-6-carbonitrile | 2.02 | 394 |
| 162 | 1-(1-Phenylethyl)-2-(pyridin-4-ylmethyl)-1H-benzimidazole-6-carbonitrile | 1.89 | 339 |
| 163 | 1-(2,5-Dichlorobenzyl)-2-(4,5,6,7-tetrahydro-1H-indazol-5-ylmethyl)-1H-benzimidazole-6-carbonitrile | 1.47 | 437 |
| 164 | 5-(1-{6-Cyano-1-[2-(difluoromethoxy)benzyl]-1H-benzimidazol-2-yl}ethoxy)pyridine-2-carboxamide | 1.39 | 464 |
| 165 | 2-[(3-Bromophenoxy)methyl]-1-[2-(difluoromethoxy)benzyl]-1H-benzimidazole-6-carbonitrile | 1.70 | 485 |
| 166 | 1-{[6-Cyano-1-(2,5-dichlorobenzyl)-1H-benzimidazol-2-yl]methyl}piperidine-4-carboxamide | 2.85 | 442 |
| 167 | 1-[2-(Difluoromethoxy)benzyl]-2-[(2-methyl-1,3-thiazol-4-yl)methyl]-1H-benzimidazole-6-carbonitrile | 3.02 | 411 |
| 168 | 1-(2,5-Dichlorobenzyl)-2-[(propan-2-yloxy)methyl]-1H-benzimidazole-6-carbonitrile | 3.47 | 374 |
| 169 | 1-(2,5-Dichlorobenzyl)-2-[(2-methyl-1,3-thiazol-4-yl)methyl]-1H-benzimidazole-6-carbonitrile | 3.12 | 413 |
| 170 | 1-[2-(Difluoromethoxy)benzyl]-2-{[3-(methylsulfonyl)phenoxy]methyl}-1H-benzimidazole-6-carbonitrile | 3.05 | 484 |
| 171 | 1-[2-(Difluoromethoxy)benzyl]-2-{[3-(2-oxopyrrolidin-1-yl)phenoxy]methyl}-1H-benzimidazole-6-carbonitrile | 3.10 | 489 |
| 172 | 1-(2,5-Dichlorobenzyl)-2-[(tetrahydrofuran-3-ylmethoxy)methyl]-1H-benzimidazole-6-carbonitrile | 3.16 | 416 |
| 173 | 1-(4-{[6-Cyano-1-(2,5-dichlorobenzyl)-1H-benzimidazol-2-yl]methyl}phenyl)urea | 2.88 | 450 |
| 174 | 1-(2,5-Dichlorobenzyl)-2-[4-(2-methyl-1,3-thiazol-4-yl)benzyl]-1H-benzimidazole-6-carbonitrile | 3.54 | 489 |
| 175 | 1-(2,5-Dichlorobenzyl)-2-(ethoxymethyl)-1H-benzimidazole-6-carbonitrile | 3.33 | 361 |
| 176 | 1-(2,5-Dichlorobenzyl)-2-{[2-(pyridin-3-yl)-1,3-thiazol-4-yl]methyl}-1H-benzimidazole-6-carbonitrile | 3.14 | 477 |
| 177 | 1-[4-({6-Cyano-1-[2-(difluoromethoxy)benzyl]-1H-benzimidazol-2-yl}methyl)phenyl]urea | 2.78 | 448 |
| 178 | 1-[2-(Difluoromethoxy)benzyl]-2-{[2-(2-oxoimidazolidin-1-yl)-1,3-thiazol-4-yl]methyl}-1H-benzimidazole-6-carbonitrile | 2.80 | 481 |
| 179 | 1-(2,5-Dichlorobenzyl)-2-(pyrazin-2-ylmethyl)-1H-benzimidazole-6-carbonitrile | 2.94 | 394 |
| 180 | 1-[2-(Difluoromethoxy)benzyl]-2-{[2-(pyridin-3-yl)-1,3-thiazol-4-yl]methyl}-1H-benzimidazole-6-carbonitrile | 3.01 | 474 |
| 181 | 1-(2,5-Dichlorobenzyl)-2-[4-(difluoromethoxy)benzyl]-1H-benzimidazole-6-carbonitrile | 3.52 | 458 |
| 182 | 1-[2-(Difluoromethoxy)benzyl]-2-[(2-methyl-1H-benzimidazol-5-yl)methyl]-1H-benzimidazole-6-carbonitrile | 2.82 | 444 |
| 183 | 1-[2-(Difluoromethoxy)benzyl]-2-[4-(2-methyl-1,3-thiazol-4-yl)benzyl]-1H-benzimidazole-6-carbonitrile | 3.41 | 488 |
| 184 | 1-[2-(Difluoromethoxy)benzyl]-2-[(methylpropoxy)methyl]-1H-benzimidazole-6-carbonitrile | 3.42 | 386 |
| 185 | 1-[2-(Difluoromethoxy)benzyl]-2-[4-(1H-tetrazol-1-yl)benzyl]-1H-benzimidazole-6-carbonitrile | 3.00 | 458 |
| 186 | 1-[2-(Difluoromethoxy)benzyl]-2-[4-(trifluoromethoxy)benzyl]-1H-benzimidazole-6-carbonitrile | 3.58 | 474 |
| 187 | 1-[2-(Difluoromethoxy)benzyl]-2-[4-(methylsulfonyl)benzyl]-1H-benzimidazole-6-carbonitrile | 2.96 | 468 |
| 188 | 2-[(Cyclopropylmethoxy)methyl]-1-[2-(difluoromethoxy)benzyl]-1H-benzimidazole-6-carbonitrile | 3.24 | 384 |
| 189 | 2-[(Cyclopropylmethoxy)methyl]-1-(2,5-dichlorobenzyl)-1H-benzimidazole-6-carbonitrile | 3.49 | 386 |
| 190 | 1-[2-(Difluoromethoxy)benzyl]-2-{[(5-methylisoxazol-3-yl)oxy]methyl}-1H-benzimidazole-6-carbonitrile | 3.13 | 411 |
| 191 | 1-[2-(Difluoromethoxy)benzyl]-2-[(2-methyl-1H-imidazol-1-yl)methyl]-1H-benzimidazole-6-carbonitrile | 2.73 | 394 |
| 192 | 1-(2,5-Dichlorobenzyl)-2-{[2-(2-oxoimidazolidin-1-yl)-1,3-thiazol-4-yl]methyl}-1H-benzimidazole-6-carbonitrile | 2.89 | 483 |

-continued

| Example | Compound Name | LCMS RT | Mass Ion |
|---|---|---|---|
| 193 | 1-(2,5-Dichlorobenzyl)-2-[(2-methyl-1H-imidazol-1-yl)methyl]-1H-benzimidazole-6-carbonitrile | 2.86 | 396 |
| 194 | 2-[(Cyclohexyloxy)methyl]-1-[2-(difluoromethoxy)benzyl]-1H-benzimidazole-6-carbonitrile | 3.55 | 412 |
| 195 | 1-(2,5-Dichlorobenzyl)-2-[(2-methoxyethoxy)methyl]-1H-benzimidazole-6-carbonitrile | 3.15 | 390 |
| 196 | 2-[(2-Amino-1,3-benzothiazol-6-yl)methyl]-1-(2,5-dichlorobenzyl)-1H-benzimidazole-6-carbonitrile | 2.99 | 464 |
| 197 | 1-[2-(Difluoromethoxy)benzyl]-2-[4-(difluoromethoxy)benzyl]-1H-benzimidazole-6-carbonitrile | 3.36 | 456 |
| 198 | 1-[2-(Difluoromethoxy)benzyl]-2-(ethoxymethyl)-1H-benzimidazole-6-carbonitrile | 3.09 | 358 |
| 199 | 1-(2,5-Dichlorobenzyl)-2-[(2-methylpropoxy)methyl]-1H-benzimidazole-6-carbonitrile | 3.69 | 388 |
| 200 | 2-[(Cyclopentyloxy)methyl]-1-[2-(difluoromethoxy)benzyl]-1H-benzimidazole-6-carbonitrile | 3.45 | 398 |
| 201 | 1-(2,5-Dichlorobenzyl)-2-{[(2-oxo-1,2,3,4-tetrahydroquinolin-6-yl)oxy]methyl}-1H-benzimidazole-6-carbonitrile | 1.46 | 478 |
| 202 | 1-(2,5-Dichlorobenzyl)-2-{[(5-methylisoxazol-3-yl)oxy]methyl}-1H-benzimidazole-6-carbonitrile | 1.57 | 414 |
| 203 | 1-(2,5-Dichlorobenzyl)-2-{[4-(trifluoromethoxy)phenoxy]methyl}-1H-benzimidazole-6-carbonitrile | 1.79 | 493 |
| 204 | 1-(2,5-Dichlorobenzyl)-2-[4-(trifluoromethoxy)benzyl]-1H-benzimidazole-6-carbonitrile | 1.76 | 477 |
| 205 | 1-(2,5-Dichlorobenzyl)-2-{[3-(methylsulfonyl)phenoxy]methyl}-1H-benzimidazole-6-carbonitrile | 1.52 | 487 |
| 206 | 1-(2,5-Dichlorobenzyl)-2-{[3-(2-oxopyrrolidin-1-yl)phenoxy]methyl}-1H-benzimidazole-6-carbonitrile | 1.56 | 492 |
| 207 | 2-[(Cyclohexyloxy)methyl]-1-(2,5-dichlorobenzyl)-1H-benzimidazole-6-carbonitrile | 1.81 | 415 |
| 208 | 5-({6-Cyano-1-[2-(difluoromethoxy)benzyl]-1H-benzimidazol-2-yl}methoxy)pyridine-2-carbohydrazide | 1.84 | 465 |
| 209 | 1-(2,5-Dichlorobenzyl)-2-[1-(pyridin-3-yloxy)ethyl]-1H-benzimidazole-6-carbonitrile | 1.51 | 424 |
| 210 | 1-[2-(Difluoromethoxy)benzyl]-2-({[3-(2-oxopyrrolidin-1-yl)phenyl]sulfanyl}methyl)-1H-benzimidazole-6-carbonitrile | 1.53 | 506 |
| 211 | 1-[2-(Difluoromethoxy)benzyl]-2-({3-[(3S)3-hydroxy-2-oxopyrrolidin-1-yl]phenoxy}methyl)-1H-benzimidazole-6-carbonitrile | 1.42 | 505 |
| 212 | 5-{[6-Cyano-1-(2,5-dichlorobenzyl)-1H-benzimidazol-2-yl]methoxy}pyridine-2-carboxamide | 1.44 | 453 |
| 213 | 1-(2,5-Dichlorobenzyl)-2-(methoxymethyl)-1H-benzimidazole-6-carbonitrile | 1.49 | 347 |
| 214 | — | — | — |
| 215 | 1-[2-(Difluoromethoxy)benzyl]-2-[(pyridin-3-yloxy)methyl]-1H-benzimidazole-6-carbonitrile | 1.39 | 407 |
| 216 | 5-({6-Cyano-1-[2-(difluoromethoxy)benzyl]-1H-benzimidazol-2-yl}methoxy)pyridine-2-carboxamide | 1.33 | 450 |
| 217 | 1-(2,5-Dichlorobenzyl)-2-(2-methoxyethyl)-1H-benzimidazole-6-carbonitrile | 3.77 | 360 |
| 218 | 2-[(2-Amino-1,3-thiazol-4-yl)methyl]-1-(2,5-dichlorobenzyl)-1H-benzimidazole-6-carbonitrile | 3.53 | 414 |
| 219 | 1-[2-(Difluoromethoxy)benzyl]-2-({3-[(4S)-4-hydroxy-2-oxopyrrolidin-1-yl]phenoxy}methyl)-1H-benzimidazole-6-carbonitrile | 1.40 | 505 |
| 220 | 1-[2-(Difluoromethoxy)benzyl]-2-{[3-(2-oxo-1,3-oxazolidin-3-yl)phenoxy]methyl}-1H-benzimidazole-6-carbonitrile | 1.50 | 491 |
| 221 | 1-[2-(Difluoromethoxy)benzyl]-2-({3-[(4R)-4-hydroxy-2-oxopyrrolidin-1-yl]phenoxy}methyl)-1H-benzimidazole-6-carbonitrile | 1.39 | 505 |

Example 165

Alternative Preparation

2-[(3-Bromophenoxy)methyl]-1-[2-(difluoromethoxy)benzyl]-1H-benzimidazole-6-carbonitrile A solution of Intermediate 52 (2.5 g, 7.2 mmol) in DMF (50 mL) was treated with K$_2$CO$_3$ (2.7 g, 14.4 mmol) and 3-bromophenol (2.5 g, 14.4 mmol) and stirred at room temperature for 72 h. After this time, the reaction mixture was concentrated in vacuo and the residue was partitioned between DCM and water. The aqueous phase was extracted with further DCM and the combined organic fractions were washed with 10% sodium hydroxide solution. After drying (phase separator), the organic layer was evaporated in vacuo and the residue was purified by column chromatography (SiO$_2$, 0-50% EtOAc in DCM) to give the title compound (2.7 g, 77%) as a waxy solid. δ$_H$ (300 MHz, DMSO) 8.15 (d, 1H, J 0.9 Hz), 7.89 (d, 1H, J 8.4 Hz), 7.65 (dd, 1H, J 8.4, 1.5

Hz), 7.19 (m, 7H), 6.84 (m, 1H), 6.65 (dd, 1H, J 7.6, 1.2 Hz), 5.67 (s, 2H), 5.46 (s, 2H). LCMS (ES+) 485 (M+H)⁺, RT 3.00 minutes.

Example 210

Alternative Preparation

1-[2-(Difluoromethoxy)benzyl]-2-({[3-(2-oxopyrrolidin-1-yl)phenyl]sulfanyl}methyl)-1H-benzimidazole-6-carbonitrile Prepared in accordance with Method P to give the title compound (67 mg, 33%) as a white powder. $\delta_H$ (400 MHz, DMSO) 8.00 (d, 1H, J 0.9 Hz), 7.79 (d, 1H, J 8.4 Hz), 7.57 (m, 3H), 7.29 (m, 6H), 6.75 (m, 1H), 5.65 (s, 2H), 4.56 (s, 2H), 3.76 (t, 2H, J 7.0 Hz), 2.47 (m, 2H), 2.04 (m, 2H). LCMS (ES+) 505 (M+H)⁺, RT 2.30 minutes.

Example 211

Alternative Preparation (Method P)

1-[(2-Difluoromethoxy)benzyl]-2-({3-[(3S)-3-hydroxy-2-oxopyrrolidin-1-yl]phenoxy}-methyl)-1H-benzimidazole-6-carbonitrile A mixture of Example 165 (100 mg, 0.21 mmol), CuI (8 mg, 0.042 mmol), trans-N,N'-dimethylcyclohexane-1,2-diamine (6 mg, 0.042 mmol), K₂CO₃ (55 mg, 0.42 mmol) and (3S)-3-hydroxy-2-pyrrolidinone (35 mg, 0.35 mmol) in 1,4-dioxane (2 mL) was heated in under microwave irradiation, with stirring, for 2 h at 140° C. After this time, the reaction mixture was partitioned between EtOAc and H₂O. The organic phase was dried by passing through a phase separator cartridge, and evaporated in vacuo. The residue was purified by column chromatography (SiO₂, 20-100% EtOAc in hexane) to give the title compound (42 mg, 40%) as a white powder. $\delta_H$ (300 MHz, DMSO) 8.14 (d, 1H, J 0.9 Hz), 7.89 (m, 1H), 7.65 (dd, 1H, J 8.4, 1.5 Hz), 7.25 (m, 7H), 6.71 (m, 2H), 5.77 (d, 1H, J 5.8 Hz), 5.69 (s, 2H), 5.43 (s, 2H), 4.28 (m, 1H), 3.64 (m, 2H), 1.81 (dd, 1H, J 12.5, 9.2 Hz). LCMS (ES+) 505 (M+H)⁺, RT 2.10 minutes.

Example 219

Alternative Preparation

1-[2-(Difluoromethoxy)benzyl]-2-({3-[(4S)-4-hydroxy-2-oxopyrrolidin-1-yl]phenoxy}-methyl)-1H-benzimidazole-6-carbonitrile Prepared in accordance with Method P to give the title compound (75 mg, 48%) as a white powder. $\delta_H$ (400 MHz, DMSO) 8.13 (d, 1H, J 0.9 Hz), 7.90 (d, 1H, J 8.4 Hz), 7.65 (dd, 1H, J 8.4, 1.5 Hz), 7.38 (m, 1H), 7.25 (m, 4H), 7.10 (m, 2H), 6.74 (dd, 1H, J 7.5, 1.1 Hz), 6.68 (m, 1H), 5.69 (s, 2H), 5.43 (s, 2H), 5.33 (d, 1H, J 3.6 Hz), 4.38 (m, 1H), 3.97 (dd, 1H, J 10.6, 5.2 Hz), 3.52 (d, 1H, J 10.4 Hz), 2.82 (dd, 1H, J 17.0, 6.2 Hz), 2.30 (dd, 1H, J 17.0, 1.7 Hz). LCMS (ES+) 505 (M+H)⁺, RT 2.00 minutes.

Example 220

Alternative Preparation

1-[2-(Difluoromethoxy)benzyl]-2-{[3-(2-oxo-1,3-oxazolidin-3-yl)phenoxy]methyl}-1H-benzimidazole-6-carbonitrile Prepared in accordance with Method P to give the title compound as a white powder. $\delta_H$ (300 MHz, DMSO) 8.14 (d, 1H, J 0.9 Hz), 7.89 (d, 1H, J 8.4 Hz), 7.65 (dd, 1H, J 8.4, 1.5 Hz), 7.33 (m, 5H), 7.08 (td, 1H, J 7.6, 1.0 Hz), 6.99 (m, 1H), 6.69 (m, 2H), 5.69 (s, 2H), 5.44 (s, 2H), 4.42 (m, 2H), 3.97 (m, 2H). LCMS (ES+) 491.6 (M+H)⁺, RT 2.26 minutes (pH 10).

Example 221

Alternative Preparation

1-[2-(Difluoromethoxy)benzyl]-2-({3-[(4R)-4-hydroxy-2-oxopyrrolidin-1-yl]phenoxy}-methyl)-1H-benzimidazole-5-carbonitrile Prepared in accordance with Method P to give the title compound (60 mg, 38%) as a white powder. $\delta_H$ (300 MHz, DMSO) 8.13 (d, 1H, J 0.9 Hz), 7.89 (dd, 1H, J 8.4, 0.3 Hz), 7.64 (dd, 1H, J 8.4, 1.5 Hz), 7.41 (m, 1H), 7.24 (m, 4H), 7.10 (m, 2H), 6.70 (m, 2H), 5.69 (s, 2H), 5.43 (s, 2H), 5.33 (d, 1H, J 3.7 Hz), 4.37 (m, 1H), 3.96 (dd, 1H, J 10.6, 5.2 Hz), 3.51 (dd, 1H, J 10.5, 0.6 Hz), 2.81 (dd, 1H, J 17.0, 6.1 Hz), 2.29 (dd, 1H, J 16.8, 1.9 Hz). LCMS (ES+) 505 (M+H)⁺, RT 2.00 minutes.

Examples 222 to 241

These compounds can be synthesized by a sequence of steps corresponding to the preparation of Intermediates 33 and 34, followed by Method J, utilising the appropriate amine and carboxylic acid. The following compounds were prepared.

| Example | Compound Name | QC RT | Mass Ion |
| --- | --- | --- | --- |
| 222 | 1-[2-(Difluoromethoxy)benzyl]-2-[(difluoromethoxy)methyl]-6-(6-methoxypyridin-3-yl)-1H-benzimidazole | 1.59 | 462 |
| 223 | 1-[(5-Chloro-2-methyl-1,3-thiazol-4-yl)methyl]-6-(6-methoxypyridin-3-yl)-2-(pyridin-4-ylmethyl)-1H-benzimidazole | 1.48 | 463 |
| 224 | 1-[3-(Difluoromethoxy)benzyl]-2-(methoxymethyl)-6-(6-methoxypyridin-3-yl)-1H-benzimidazole | 1.54 | 426 |
| 225 | 1-[2-Chloro-6-(difluoromethoxy)benzyl]-2-(methoxymethyl)-6-(6-methoxypyridin-3-yl)-1H-benzimidazole | 1.59 | 461 |
| 226 | 1-(2,6-Difluorobenzyl)-2-(methoxymethyl)-6-(6-methoxypyridin-3-yl)-1H-benzimidazole | 1.52 | 396 |
| 227 | 1-[(5-Chloro-2-methyl-1,3-thiazol-4-yl)methyl]-2-(methoxymethyl)-6-(6-methoxypyridin-3-yl)-1H-benzimidazole | 1.54 | 416 |

-continued

| Example | Compound Name | QC RT | Mass Ion |
|---|---|---|---|
| 228 | 1-[5-Chloro-2-(difluoromethoxy)benzyl]-6-(6-methoxypyridin-3-yl)-2-(pyridin-4-ylmethyl)-1H-benzimidazole | 1.55 | 508 |
| 229 | 1-(2,6-Dichlorobenzyl)-2-(methoxymethyl)-6-(6-methoxypyridin-3-yl)-1H-benzimidazole | 1.62 | 429 |
| 230 | 1-[2-Fluoro-5-(trifluoromethoxy)benzyl]-2-(methoxymethyl)-6-(6-methoxypyridin-3-yl)-1H-benzimidazole | 1.63 | 462 |
| 231 | 1-(5-Chloro-2-fluorobenzyl)-2-(methoxymethyl)-6-(6-methoxypyridin-3-yl)-1H-benzimidazole | 1.59 | 413 |
| 232 | 2-(Methoxymethyl)-6-(6-methoxypyridin-3-yl)-1-[2-(trifluoromethyl)benzyl]-1H-benzimidazole | 1.64 | 428 |
| 233 | 1-[5-Chloro-2-(trifluoromethyl)benzyl]-2-(methoxymethyl)-6-(6-methoxypyridin-3-yl)-1H-benzimidazole | 1.69 | 463 |
| 234 | 1-[2,5-Bis(trifluoromethyl)benzyl]-2-(methoxymethyl)-6-(6-methoxypyridin-3-yl)-1H-benzimidazole | 1.69 | 496 |
| 235 | 1-[2-(Difluoromethoxy)benzyl]-2-(methoxymethyl)-6-(6-methoxypyridin-3-yl)-1H-benzimidazole | 1.55 | 426 |
| 236 | 1-[5-Chloro-2-(difluoromethoxy)benzyl]-2-[(difluoromethoxy)methyl]-6-(6-methoxypyridin-3-yl)-1H-benzimidazole | 1.64 | 496 |
| 237 | 1-[2-(Difluoromethoxy)benzyl]-6-(6-methoxypyridin-3-yl)-2-(trifluoromethyl)-1H-benzimidazole | 1.71 | 450 |
| 238 | {1-[2-(Difluoromethoxy)benzyl]-6-(6-methoxypyridin-3-yl)-1H-benzimidazol-2-yl}methanol | 1.45 | 412 |
| 239 | 1-[2-(Difluoromethoxy)benzyl]-6-(6-methoxypyridin-3-yl)-2-(pyridine-4-ylmethyl)-1H-benzimidazole | 1.50 | 473 |
| 240 | 1-[5-Chloro-2-(difluoromethoxy)benzyl]-2-(methoxymethyl)-6-(6-methoxypyridin-3-yl)-1H-benzimidazole | 1.61 | 460 |
| 241 | 2-(Methoxymethyl)-6-(6-methoxypyridin-3-yl)-1-[2-(trifluoromethoxy)benzyl]-1H-benzimidazole | 1.66 | 444 |

Examples 242 to 280

These compounds can be synthesized by a sequence of steps corresponding to the preparation of Intermediates 32, 33 and 34, followed by Method J, utilising pyridin-4-ylboronic acid, the appropriate amine and the appropriate carboxylic acid. The following compounds were prepared.

| Example | Compound Name | QC RT | Mass Ion |
|---|---|---|---|
| 242 | [1-(2,5-Dichlorobenzyl)-6-(pyridin-4-yl)-1H-benzimidazol-2-yl]methanol | 1.84 | 385 |
| 243 | 1-(2,5-Dichlorobenzyl)-6-(pyridin-4-yl)-2-[1-(pyridin-4-yl)ethyl]-1H-benzimidazole | 2.03 | 460 |
| 244 | 1-(2,5-Dichlorobenzyl)-6-(pyridin-4-yl)-2-(pyridin-4-ylmethyl)-1H-benzimidazole | 1.99 | 446 |
| 245 | 1-(2,6-Dimethylbenzyl)-6-(pyridin-4-yl)-2-(pyridin-4-ylmethyl)-1H-benzimidazole | 1.95 | 406 |
| 246 | 1-(2,5-Dichlorobenzyl)-2-{[(6-methoxypyridin-3-yl)oxy]methyl}-6-(pyridin-4-yl)-1H-benzimidazole | 2.44 | 492 |
| 247 | 5-{[1-(2,5-Dichlorobenzyl)-6-(pyridin-4-yl)-1H-benzimidazol-2-yl]methoxy}pyridine-2-carboxylic acid | 1.29 | 506 |
| 248 | 2-{[(5-Chloropyridin-2-yl)oxy]methyl}-1-(2,5-dichlorobenzyl)-6-(pyridin-4-yl)-1H-benzimidazole | 2.74 | 497 |
| 249 | 5-{[1-(2,5-Dichlorobenzyl)-6-(pyridin-4-yl)-1H-benzimidazol-2-yl]methoxy}pyridine-2-carbonitrile | 2.31 | 487 |
| 250 | 5-{[1-(2,5-Dichlorobenzyl)-6-(pyridin-4-yl)-1H-benzimidazol-2-yl]methoxy}pyridine-2-carboxamide | 1.38 | 505 |
| 251 | 1-(2,5-Dichlorobenzyl)-6-(pyridin-4-yl)-2-[2-(pyridin-3-yl)ethyl]-1H-benzimidazole | 2.08 | 460 |
| 252 | 1-(2,5-Dichlorobenzyl)-2-{[(6-fluoropyridin-3-yl)oxy]methyl}-6-(pyridin-4-yl)-1H-benzimidazole | 2.30 | 480 |
| 253 | 1-(2,5-Dichlorobenzyl)-2-(methoxymethyl)-6-(pyridin-4-yl)-1H-benzimidazole | 1.54 | 399 |
| 254 | 4-{[1-(2,5-Dichlorobenzyl)-6-(pyridin-4-yl)-1H-benzimidazol-2-yl]methoxy}-N,N-dimethylbenzamide | 2.21 | 532 |
| 255 | 4-{[1-(2,5-Dichlorobenzyl)-6-(pyridin-4-yl)-1H-benzimidazol-2-yl]methoxy}benzoic acid | 1.46 | 505 |
| 256 | 1-(2,5-Dichlorobenzyl)-6-(pyridin-4-yl)-2-{[4-(2H-tetrazol-5-yl)phenoxy]methyl}-1H-benzimidazole | 1.56 | 529 |
| 257 | 5-{[1-(2,5-Dichlorobenzyl)-6-(pyridin-4-yl)-1H-benzimidazol-2-yl]methoxy}-N-methylpyridine-2-carboxamide | 2.13 | 519 |

-continued

| Example | Compound Name | QC RT | Mass Ion |
|---|---|---|---|
| 258 | 1-(2,5-Dichlorobenzyl)-6-(pyridin-4-yl)-2-[(pyridin-3-yl-oxy)methyl]-1H-benzimidazole | 2.16 | 462 |
| 259 | 5-{[1-(2,5-Dichlorobenzyl)-6-(pyridin-4-yl)-1H-benzimidazol-2-yl]methoxy}-N,N-dimethylpyridine-2-carboxamide | 2.06 | 533 |
| 260 | 4-{[1-(2,5-Dichlorobenzyl)-6-(pyridin-4-yl)-1H-benzimidazol-2-yl]methoxy}-N-methylbenzamide | 2.14 | 518 |
| 261 | 4-{[1-(2,5-Dichlorobenzyl)-6-(pyridin-4-yl)-1H-benzimidazol-2-yl]methoxy}benzamide | 1.38 | 504 |
| 262 | (4-{[1-(2,5-Dichlorobenzyl)-6-(pyridin-4-yl)-1H-benzimidazol-2-yl]methoxy}phenyl)(morpholin-4-yl)-methanone | 2.16 | 574 |
| 263 | 1-(2,5-Dimethylbenzyl)-2-(methoxymethyl)-6-(pyridin-4-yl)-1H-benzimidazole | 1.41 | 358 |
| 264 | 1-[(1R)-1-Phenylethyl]-6-(pyridin-4-yl)-2-(pyridin-4-yl-methyl)-1H-benzimidazole | 1.88 | 391 |
| 265 | 1-[(1S)-1-Phenylethyl]-6-(pyridin-4-yl)-2-(pyridin-4-yl-methyl)-1H-benzimidazole | 1.87 | 391 |
| 266 | 1-(2,5-Dichlorobenzyl)-6-(pyridin-4-yl)-2-(pyrimidin-4-ylmethyl)-1H-benzimidazole | 1.91 | 447 |
| 267 | 2-Cyclopropyl-1-(2,5-dichlorobenzyl)-6-(pyridin-4-yl)-1H-benzimidazole | 2.39 | 395 |
| 268 | 1-(2,5-Dichlorobenzyl)-2-[(2-methoxypyridin-4-yl)-methyl]-6-(pyridin-4-yl)-1H-benzimidazole | 2.26 | 476 |
| 269 | 3-{[1-(2,6-Dimethylbenzyl)-6-(pyridin-4-yl)-1H-benzimidazol-2-yl]methoxy}benzonitrile | 1.59 | 446 |
| 270 | 4-{[1-(2,6-Dimethylbenzyl)-6-(pyridin-4-yl)-1H-benzimidazol-2-yl]methoxy}benzoic acid | 1.44 | 465 |
| 271 | 2-(4-{[1-(2,6-Dimethylbenzyl)-6-(pyridin-4-yl)-1H-benzimidazol-2-yl]methoxy}phenyl)acetamide | 1.39 | 478 |
| 272 | 1-(2,6-Dimethylbenzyl)-2-{[4-(1H-imidazol-1-yl)-phenoxy]methyl}-6-(pyridin-4-yl)-1H-benzimidazole | 1.48 | 487 |
| 273 | 1-(2,6-Dimethylbenzyl)-2-{[(6-methylpyridin-3-yl)oxy]-methyl}-6-(pyridin-4-yl)-1H-benzimidazole | 1.48 | 436 |
| 274 | 4-{[1-(2,6-Dimethylbenzyl)-6-(pyridin-4-yl)-1H-benzimidazol-2-yl]methoxy}benzonitrile | 1.58 | 446 |
| 275 | 5-{[1-(2,6-Dimethylbenzyl)-6-(pyridin-4-yl)-1H-benzimidazol-2-yl]methoxy}-2-methyl-1,3-benzothiazole | 1.63 | 492 |
| 276 | 7-{[1-(2,6-Dimethylbenzyl)-6-(pyridin-4-yl)-1H-benzimidazol-2-yl]methoxy}isoquinoline | 1.54 | 472 |
| 277 | 7-{[1-(2,6-Dimethylbenzyl)-6-(pyridin-4-yl)-1H-benzimidazol-2-yl]methoxy}quinoline | 1.56 | 472 |
| 278 | 1-(2,6-Dimethylbenzyl)-2-{[(2-methylpyridin-3-yl)oxy]-methyl}-6-(pyridin-4-yl)-1H-benzimidazole | 1.46 | 436 |
| 279 | 1-(2,6-Dimethylbenzyl)-2-{[(1-oxidopyridin-3-yl)oxy]-methyl}-6-(pyridin-4-yl)-1H-benzimidazole | 1.28 | 438 |
| 280 | 4-{2-[1-(2,5-Dichlorobenzyl)-6-(pyridin-4-yl)-1H-benzimidazol-2-yl]ethyl}benzamide | 2.16 | 502 |

Example 253

Alternative Preparation 1-(2,5-Dichlorobenzyl)-2-(methoxymethyl)-6-(pyridin-4-yl)-1H-benzimidazole Intermediate 56 (150 mg, 0.43 mmol) was dissolved in 2-methoxyacetic acid (1 mL) and heated at 100° C. for 5 h. The reaction was quenched by the addition of aqueous NaHCO$_3$ solution (25 mL) and the organic material was extracted into DCM (25 mL). The organic layer was separated and dried, and the solvent was removed under vacuum to afford a pale oil. Purification by preparative scale reverse phase HPLC afforded the title compound (40 mg, 34%) as a white solid. $\delta_H$ (DMSO, 300 MHz) 8.61 (d, 2H, J 5.8 Hz), 8.03 (d, 1H, J 1.2 Hz), 7.84 (m, 1H), 7.73 (m, 3H), 7.60 (d, 1H, J 8.6 Hz), 7.41 (dd, 1H, J 8.6, 2.5 Hz), 6.52 (d, 1H, J 2.5 Hz), 5.72 (s, 2H), 4.68 (s, 2H), 3.23 (s, 3H). LCMS (ES+) 398.0 (M+H)$^+$, RT 2.28 minutes (pH 10).

Examples 281 to 319

These compounds can be synthesized by a sequence of steps corresponding to the preparation of Intermediates 32, 33 and 34, followed by Method J, utilising 1-methyl-1H-pyrazole-4-boronic acid, the appropriate amine and the appropriate carboxylic acid. The following compounds were prepared.

| Example | Compound Name | QC RT | Mass Ion |
|---|---|---|---|
| 281 | 1-(2,5-Dichlorobenzyl)-6-(1-methyl-1H-pyrazol-4-yl)-2-{[(2-methylpyridin-3-yl)oxy]methyl}-1H-benzimidazole | 2.07 | 479 |
| 282 | 7-{[1-(2,5-Dimethylbenzyl)-6-(1-methyl-1H-pyrazol-4-yl)-1H-benzimidazol-2-yl]methoxy}quinoline | 2.51 | 475 |

| Example | Compound Name | QC RT | Mass Ion |
|---|---|---|---|
| 283 | 3-(4-{[1-(2,5-Dimethylbenzyl)-6-(1-methyl-1H-pyrazol-4-yl)-1H-benzimidazol-2-yl]methyl}-piperazin-1-yl)phenol | 2.42 | 508 |
| 284 | 1-(2,5-Dimethylbenzyl)-2-{[4-(1H-imidazol-1-yl)-phenoxy]methyl}-6-(1-methyl-1H-pyrazol-4-yl)-1H-benzimidazole | 2.31 | 490 |
| 285 | 2-(2,3-Dihydro-1H-indol-1-ylmethyl)-1-(2,5-dimethylbenzyl)-6-(1-methyl-1H-pyrazol-4-yl)-1H-benzimidazole | 2.91 | 449 |
| 286 | 7-{[1-(2,5-Dimethylbenzyl)-6-(1-methyl-1H-pyrazol-4-yl)-1H-benzimidazol-2-yl]methoxy}isoquinoline | 2.46 | 475 |
| 287 | 5-{[1-(2,5-Dimethylbenzyl)-6-(1-methyl-1H-pyrazol-4-yl)-1H-benzimidazol-2-yl]methoxy}-2-methyl-1,3-benzothiazole | 2.69 | 495 |
| 288 | 2-[5-({[1-(2,5-Dimethylbenzyl)-6-(1-methyl-1H-pyrazol-4-yl)-1H-benzimidazol-2-yl]methyl}-sulfanyl)-1H-tetrazol-1-yl]-N,N-dimethylethanamine | 2.19 | 503 |
| 289 | 2-({[1-(2,5-Dimethylbenzyl)-6-(1-methyl-1H-pyrazol-4-yl)-1H-benzimidazol-2-yl]methyl}-sulfanyl)-1,3-benzoxazole | 2.70 | 481 |
| 290 | 1-(2,5-Dimethylbenzyl)-2-{[(1-methyl-1H-benzimidazol-2-yl)sulfanyl]methyl}-6-(1-methyl-1H-pyrazol-4-yl)-1H-benzimidazole | 2.43 | 494 |
| 291 | 2-({[1-(2,5-Dimethylbenzyl)-6-(1-methyl-1H-pyrazol-4-yl)-1H-benzimidazol-2-yl]methyl}-sulfanyl)-1,3-benzothiazole | 2.80 | 497 |
| 292 | 6-{[1-(2,5-Dimethylbenzyl)-6-(1-methyl-1H-pyrazol-4-yl)-1H-benzimidazol-2-yl]methoxy}quinoline | 2.23 | 475 |
| 293 | (3S)-1-{[1-(2,5-Dimethylbenzyl)-6-(1-methyl-1H-pyrazol-4-yl)-1H-benzimidazol-2-yl]methyl}-N,N-dimethylpyrrolidin-3-amine | 2.11 | 444 |
| 294 | 2-{[3-(4,5-Dihydro-1H-imidazol-2-yl)phenoxy]-methyl}-1-(2,5-dimethylbenzyl)-6-(1-methyl-1H-pyrazol-4-yl)-1H-benzimidazole | 2.13 | 492 |
| 295 | 2-[(Benzylsulfanyl)methyl]-1-(2,5-dimethylbenzyl)-6-(1-methyl-1H-pyrazol-4-yl)-1H-benzimidazole | 2.70 | 454 |
| 296 | 1-(2,5-Dimethylbenzyl)-6-(1-methyl-1H-pyrazol-4-yl)-2-[(pyrimidin-2-ylsulfanyl)methyl]-1H-benzimidazole | 2.13 | 442 |
| 297 | 1-(2,5-Dimethylbenzyl)-6-(1-methyl-1H-pyrazol-4-yl)-2-[(pyridin-3-yloxy)methyl]-1H-benzimidazole | 2.03 | 425 |
| 298 | 4-{[1-(2,5-Dimethylbenzyl)-6-(1-methyl-1H-pyrazol-4-yl)-1H-benzimidazol-2-yl]methoxy}benzoic acid | 1.58 | 468 |
| 299 | 1-(2,5-Dimethylbenzyl)-6-(1-methyl-1H-pyrazol-4-yl)-2-{[(pyridin-4-ylmethyl)sulfanyl]methyl}-1H-benzimidazole | 2.15 | 455 |
| 300 | 4-{[1-(2,5-Dimethylbenzyl)-6-(1-methyl-1H-pyrazol-4-yl)-1H-benzimidazol-2-yl]methoxy}benzamide | 1.93 | 467 |
| 301 | 1-[1-(2,5-Dimethylbenzyl)-6-(1-methyl-1H-pyrazol-4-yl)-1H-benzimidazol-2-yl]-N-methyl-N-(pyridin-3-ylmethyl)methanamine | 2.13 | 452 |
| 302 | 1-(2,5-Dimethylbenzyl)-2-{[(4-methoxybenzyl)-sulfanyl]methyl}-6-(1-methyl-1H-pyrazol-4-yl)-1H-benzimidazole | 2.66 | 484 |
| 303 | 4-{[1-(2,5-Dimethylbenzyl)-6-(1-methyl-1H-pyrazol-4-yl)-1H-benzimidazol-2-yl]methoxy}benzonitrile | 2.39 | 449 |
| 304 | 1-(2,5-Dimethylbenzyl)-6-(1-methyl-1H-pyrazol-4-yl)-2-{[(6-methylpyridin-3-yl)oxy]methyl}-1H-benzimidazole | 2.12 | 439 |
| 305 | 1-(2,5-Dimethylbenzyl)-6-(1-methyl-1H-pyrazol-4-yl)-2-[(pyridin-2-ylsulfanyl)methyl]-1H-benzimidazole | 2.37 | 441 |
| 306 | 1-(2,5-Dichlorobenzyl)-6-(1-methyl-1H-pyrazol-4-yl)-2-(pyridin-4-ylmethyl)-1H-benzimidazole | 1.91 | 449 |
| 307 | 4-{[1-(2-Chlorobenzyl)-6-(1-methyl-1H-pyrazol-4-yl)-1H-benzimidazol-2-yl]methoxy}benzamide | 1.94 | 473 |
| 308 | 2-{[(6-Methoxypyridin-3-yl)oxy]methyl}-6-(1-methyl-1H-pyrazol-4-yl)-1-[(2-methyl-1,3-thiazol-4-yl)methyl]-1H-benzimidazole | 1.94 | 448 |
| 309 | 4-{[1-(2,5-Dichlorobenzyl)-6-(1-methyl-1H-pyrazol-4-yl)-1H-benzimidazol-2-yl]methoxy}benzamide | 2.02 | 507 |
| 310 | 1-(2,5-Dimethylbenzyl)-2-(methoxymethyl)-6-(1-methyl-1H-pyrazol-4-yl)-1H-benzimidazole | 1.43 | 361 |
| 311 | 1-(2-Chlorobenzyl)-2-{[(6-methoxypyridin-3-yl)-oxy]methyl}-6-(1-methyl-1H-pyrazol-4-yl)-1H-benzimidazole | 1.50 | 461 |

-continued

| Example | Compound Name | QC RT | Mass Ion |
|---|---|---|---|
| 312 | 1-(2-Chloro-5-fluorobenzyl)-6-(1-methyl-1H-pyrazol-4-yl)-2-[(pyridin-3-yloxy)methyl]-1H-benzimidazole | 1.38 | 449 |
| 313 | 1-(2-Chloro-5-fluorobenzyl)-2-{[(6-methoxypyridin-3-yl)oxy]methyl}-6-(1-methyl-1H-pyrazol-4-yl)-1H-benzimidazole | 2.30 | 479 |
| 314 | 4-{[1-(2-Chloro-5-fluorobenzyl)-6-(1-methyl-1H-pyrazol-4-yl)-1H-benzimidazol-2-yl]methoxy}-benzamide | 1.98 | 491 |
| 315 | 4-({6-(1-Methyl-1H-pyrazol-4-yl)-1-[(2-methyl-1,3-thiazol-4-yl)methyl]-1H-benzimidazol-2-yl}-methoxy)benzamide | 1.60 | 460 |
| 316 | 6-(1-Methyl-1H-pyrazol-4-yl)-1-[(2-methyl-1,3-thiazol-4-yl)methyl]-2-[(pyridin-3-yloxy)methyl]-1H-benzimidazole | 1.68 | 417 |
| 317 | 1-(2,5-Dichlorobenzyl)-2-[(difluoromethoxy)-methyl]-6-(1-methyl-1H-pyrazol-4-yl)-1H-benzimidazole | 1.50 | 438 |
| 318 | 1-(2-Chlorobenzyl)-6-(1-methyl-1H-pyrazol-4-yl)-2-[(pyridin-3-yloxy)methyl]-1H-benzimidazole | 2.04 | 431 |
| 319 | 1-(2,5-Dichlorobenzyl)-6-(1-methyl-1H-pyrazol-4-yl)-2-[(pyridin-3-yloxy)methyl]-1H-benzimidazole | 2.13 | 465 |

Examples 320 to 403

These compounds can be synthesized by a sequence of steps corresponding to the preparation of Intermediates 32, 33 and 34, followed by Method J, utilising the appropriate boronic acid, the appropriate amine and the appropriate carboxylic acid. Similarly, the 6-bromo derivatives can be synthesized by a sequence of steps corresponding to the preparation of Intermediates 33 and 34, followed by Method J, utilising the appropriate amine and the appropriate carboxylic acid. Examples 354 and 355 commence from 2-fluoronitrobenzene. The N-oxide derivatives can be prepared by oxidation with mCPBA. The following compounds were prepared.

| Example | Compound Name | LCMS RT | Mass Ion |
|---|---|---|---|
| 320 | 1-(2,5-Dimethylbenzyl)-6-(1H-indol-6-yl)-2-(pyridin-4-ylmethyl)-1H-benzimidazole | 2.78 | 444 |
| 321 | 6-[1-(1-Phenylethyl)-2-(pyridin-4-ylmethyl)-1H-benzimidazol-6-yl]quinoline | 2.45 | 442 |
| 322 | 1-(2,5-Dimethylbenzyl)-2-(pyridin-4-ylmethyl)-6-(thiophen-3-yl)-1H-benzimidazole | 2.90 | 411 |
| 323 | 6-Bromo-1-(2,5-dimethylbenzyl)-2-[(pyridin-4-ylmethoxy)methyl]-1H-benzimidazole | 2.55 | 437 |
| 324 | 5-[1-(2,5-Dimethylbenzyl)-2-(pyridin-4-ylmethyl)-1H-benzimidazol-6-yl]-N,N-dimethylpyridin-2-amine | 2.38 | 449 |
| 325 | 2-{[6-Bromo-1-(1-phenylethyl)-1H-benzimidazol-2-yl]methyl}-4-methylphthalazin-1(2H)-one | 2.42 | 474 |
| 326 | 1-(2,5-Dimethylbenzyl)-2-(pyridin-4-ylmethyl)-6-(pyrimidin-5-yl)-1H-benzimidazole | 1.77 | 406 |
| 327 | 1-(1-Phenylethyl)-6-[4-(1H-pyrazol-5-yl)phenyl]-2-(pyridin-4-ylmethyl)-1H-benzimidazole | 2.00 | 457 |
| 328 | 1-(1-Phenylethyl)-2-(pyridin-4-ylmethyl)-6-[4-(pyrrolidin-1-ylmethyl)phenyl]-1H-benzimidazole | 2.41 | 474 |
| 329 | 1-(2,5-Dimethylbenzyl)-6-(1,3-dimethyl-1H-pyrazol-4-yl)-2-(pyridin-4-ylmethyl)-1H-benzimidazole | 1.89 | 423 |
| 330 | 1-(2,5-Dimethylbenzyl)-2-(pyridin-4-ylmethyl)-6-[4-(pyrrolidin-1-ylmethyl)phenyl]-1H-benzimidazole | 1.73 | 488 |
| 331 | 1-(2,5-Dimethylbenzyl)-2-(pyridin-4-ylmethyl)-6-[3-(pyrrolidin-1-ylmethyl)phenyl]-1H-benzimidazole | 2.49 | 488 |
| 332 | 1-(2,5-Dichlorobenzyl)-2-{[(2-methylpyridin-3-yl)-oxy]methyl}-6-{1-[2-(morpholin-4-yl)ethyl]-1H-pyrazol-4-yl}-1H-benzimidazole | 2.04 | 579 |
| 333 | 6-(2-Chlorophenyl)-1-(2,5-dimethylbenzyl)-2-(pyridin-4-ylmethyl)-1H-benzimidazole | 2.92 | 439 |
| 334 | 4-[1-(2,5-Dimethylbenzyl)-2-(pyridin-4-ylmethyl)-1H-benzimidazol-6-yl]-2-methyl-2H-indazole | 2.30 | 459 |
| 335 | 6-(1-Benzofuran-5-yl)-1-(2,5-dimethylbenzyl)-2-(pyridin-4-ylmethyl)-1H-benzimidazole | 2.86 | 445 |
| 336 | 4-[1-(2,5-Dimethylbenzyl)-2-(pyridin-4-ylmethyl)-1H-benzimidazol-6-yl]-1-methyl-1H-indazole | 2.51 | 459 |
| 337 | 5-{[6-Bromo-1-(1-phenylethyl)-1H-benzimidazol-2-yl]methoxy}-2-methyl-1,3-benzothiazole | 3.12 | 479 |

-continued

| Example | Compound Name | LCMS RT | Mass Ion |
|---|---|---|---|
| 338 | 6-Bromo-2-{[3-(4,5-dihydro-1H-imidazol-2-yl)-phenoxy]methyl}-1-(1-phenylethyl)-1H-benzimidazole | 2.91 | 476 |
| 339 | 4-{[6-Bromo-1-(1-phenylethyl)-1H-benzimidazol-2-yl]methoxy}benzonitrile | 2.99 | 433 |
| 340 | 6-Bromo-2-{[(2-methylpyridin-3-yl)oxy]methyl}-1-(1-phenylethyl)-1H-benzimidazole | 2.69 | 423 |
| 341 | 1-(2,5-Dichlorobenzyl)-6-(2-methylpyridin-4-yl)-2-(pyridin-4-ylmethyl)-1H-benzimidazole | 2.01 | 460 |
| 342 | 4-[1-(2,5-Dichlorobenzyl)-2-(pyridin-4-ylmethyl)-1H-benzimidazol-6-yl]pyridin-2-amine | 1.81 | 461 |
| 343 | 1-(2,5-Dichlorobenzyl)-6-(3-methylpyridin-4-yl)-2-(pyridin-4-ylmethyl)-1H-benzimidazole | 2.04 | 460 |
| 344 | 2-[5-({[6-Bromo-1-(1-phenylethyl)-1H-benzimidazol-2-yl]methyl}sulfanyl)-1H-tetrazol-1-yl]-N,N-dimethylethanamine | 2.50 | 487 |
| 345 | 1-(2,5-Dichlorobenzyl)-6-(pyridin-3-yl)-2-(pyridin-4-ylmethyl)-1H-benzimidazole | 1.99 | 446 |
| 346 | 1-(3-{[6-Bromo-1-(1-phenylethyl)-1H-benzimidazol-2-yl]methoxy}pyridin-2-yl)-N,N-dimethyl-methanamine | 2.36 | 466 |
| 347 | 2-(Azocan-1-ylmethyl)-6-bromo-1-(1-phenylethyl)-1H-benzimidazole | 3.44 | 427 |
| 348 | N-{[6-Bromo-1-(1-phenylethyl)-1H-benzimidazol-2-yl]methyl}-N-(pyridin-4-ylmethyl)ethanamine | 2.62 | 450 |
| 349 | 6-Bromo-1-(1-phenylethyl)-2-{[(pyridin-4-ylmethyl)sulfanyl]methyl}-1H-benzimidazole | 2.52 | 439 |
| 350 | 1-(4-{[6-Bromo-1-(1-phenylethyl)-1H-benzimidazol-2-yl]methyl}phenyl)imidazolidin-2-one | 2.38 | 476 |
| 351 | 6-Bromo-2-[(2-ethylpiperidin-1-yl)methyl]-1-(1-phenylethyl)-1H-benzimidazole | 3.44 | 427 |
| 352 | 6-Bromo-1-(1-phenylethyl)-2-[(3-phenylpyrrolidin-1-yl)methyl]-1H-benzimidazole | 3.31 | 461 |
| 353 | 1-(2,5-Dichlorobenzyl)-6-(2,6-dimethylpyridin-4-yl)-2-(pyridin-4-ylmethyl)-1H-benzimidazole | 2.15 | 474 |
| 354 | tert-Butyl 3-{[1-(2,5-dichlorobenzyl)-1H-benzimidazol-2-yl]methoxy}pyrrolidine-1-carboxylate | 2.81 | 477 |
| 355 | 2-{[(2-Chloropyridin-4-yl)methoxy]methyl}-1-(2,5-dichlorobenzyl)-1H-benzimidazole | 2.56 | 434 |
| 356 | 1-(2,5-Dichlorobenzyl)-2-(pyridin-4-ylmethyl)-6-(pyrimidin-4-yl)-1H-benzimidazole | 1.90 | 447 |
| 357 | 1-(2,5-Dichlorobenzyl)-6-(pyridin-2-yl)-2-(pyridin-4-ylmethyl)-1H-benzimidazole | 2.19 | 446 |
| 358 | 4-[1-(2,5-Dichlorobenzyl)-2-(pyridin-4-ylmethyl)-1H-benzimidazol-6-yl]pyrimidin-2-amine | 1.80 | 462 |
| 359 | 6-Bromo-1-[1-(2-fluorophenyl)ethyl]-2-[(pyridin-4-ylmethoxy)methyl]-1H-benzimidazole | 2.43 | 441 |
| 360 | 1-(2,5-Dichlorobenzyl)-6-(1H-pyrazol-4-yl)-2-(pyridin-4-ylmethyl)-1H-benzimidazole | 1.79 | 435 |
| 361 | 4-[1-(2,5-Dichlorobenzyl)-2-(pyridin-4-ylmethyl)-1H-benzimidazol-6-yl]pyridine-2-carbonitrile | 2.25 | 471 |
| 362 | 6-Bromo-1-(2,5-dichlorobenzyl)-2-[(pyridin-3-yl-oxy)methyl]-1H-benzimidazole | 2.67 | 464 |
| 363 | 4-{1-(2,5-Dichlorobenzyl)-2-[(pyridin-3-yloxy)-methyl-1H-benzimidazol-6-yl}pyridin-2-amine | 2.08 | 477 |
| 364 | 5-{1-(2,5-Dichlorobenzyl)-2-[(pyridin-3-yloxy)-methyl]-1H-benzimidazol-6-yl}-N,N-dimethyl-pyridin-2-amine | 2.64 | 505 |
| 365 | 4-({1-(2-Chlorobenzyl)-6-[6-(dimethylamino)-pyridin-3-yl]-1H-benzimidazol-2-yl}methoxy)-benzamide | 2.39 | 513 |
| 366 | 4-{[1-(2-Chlorobenzyl)-6-(1-oxidopyridin-4-yl)-1H-benzimidazol-2-yl]methoxy}benzamide | 1.62 | 486 |
| 367 | 4-({1-(2,5-Dichlorobenzyl)-6-[6-(dimethylamino)-pyridin-3-yl]-1H-benzimidazol-2-yl}methoxy)-benzamide | 2.50 | 547 |
| 368 | 5-(2-{[(6-Methoxypyridin-3-yl)oxy]methyl}-1-[(2-methyl-1,3-thiazol-4-yl)methyl]-1H-benzimidazol-6-yl)-N,N-dimethylpyridin-2-amine | 2.38 | 488 |
| 369 | 6-Bromo-1-[1-(pyridin-4-yl)ethyl]-2-[(pyridin-4-yl-methoxy)methyl]-1H-benzimidazole | 1.89 | 424 |
| 370 | 4-{[1-(2,5-Dichlorobenzyl)-6-(pyrimidin-4-yl)-1H-benzimidazol-2-yl]methoxy}benzamide | 2.01 | 505 |
| 371 | 6-Bromo-1-(1-phenylpropyl)-2-[(pyridin-4-yl-methoxy)methyl]-1H-benzimidazole | 2.59 | 437 |

-continued

| Example | Compound Name | LCMS RT | Mass Ion |
|---|---|---|---|
| 372 | 6-Bromo-1-[1-(pyridin-3-yl)ethyl]-2-[(pyridin-4-yl-methoxy)methyl]-1H-benzimidazole | 1.91 | 424 |
| 373 | 6-Bromo-1-[1-(2-methoxyphenyl)ethyl]-2-[(pyridin-4-ylmethoxy)methyl]-1H-benzimidazole | 2.55 | 453 |
| 374 | 6-Bromo-1-[1-(4-fluorophenyl)ethyl]-2-[(pyridin-4-ylmethoxy)methyl]-1H-benzimidazole | 2.52 | 441 |
| 375 | 6-Bromo-1-[1-(3-fluorophenyl)ethyl]-2-[(pyridin-4-ylmethoxy)methyl]-1H-benzimidazole | 2.48 | 441 |
| 376 | 6-Bromo-1-[1-(4-methylphenyl)ethyl]-2-[(pyridin-4-ylmethoxy)methyl]-1H-benzimidazole | 2.68 | 437 |
| 377 | 6-Bromo-1-[2-(difluoromethoxy)benzyl]-2-[(methyl-sulfanyl)methyl]-1H-benzimidazole | 1.62 | 414 |
| 378 | 6-Bromo-1-[2-(difluoromethoxy)benzyl]-2-propyl-1H-benzimidazole | 1.65 | 396 |
| 379 | 6-Bromo-1-[2-(difluoromethoxy)benzyl]-2-(pyridin-4-ylmethyl)-1H-benzimidazole | 1.52 | 445 |
| 380 | 6-Bromo-1-[2-(difluoromethoxy)benzyl]-2-[(difluoromethoxy)methyl]-1H-benzimidazole | 1.61 | 434 |
| 381 | 5-{1-(2-Chloro-5-fluorobenzyl)-2-[(pyridin-3-yl-oxy)methyl]-1H-benzimidazol-6-yl}-N,N-dimethyl-pyridin-2-amine | 1.57 | 489 |
| 382 | 1-(2-Chlorobenzyl)-2-{[(6-methoxypyridin-3-yl)-oxy]methyl}-6-(1-oxidopyridin-4-yl)-1H-benzimidazole | 1.35 | 474 |
| 383 | 4-{[1-(2-Chloro-5-fluorobenzyl)-6-(pyrimidin-4-yl)-1H-benzimidazol-2-yl]methoxy}benzamide | 1.33 | 489 |
| 384 | 6-Bromo-1-[(5-chloro-2-methyl-1,3-thiazol-4-yl)-methyl]-2-{[(6-methoxypyridin-3-yl)oxy]methyl}-1H-benzimidazole | 1.80 | 481 |
| 385 | [6-Bromo-1-(2,6-dimethylbenzyl)-1H-benzimidazol-2-yl]methanol | 1.46 | 346 |
| 386 | 6-Bromo-1-[(1R)-1-phenylethyl]-2-[(pyridin-4-yl-methoxy)methyl]-1H-benzimidazole | 1.57 | 423 |
| 387 | 6-Bromo-1-[(1S)-1-phenylethyl]-2-[(pyridin-4-yl-methoxy)methyl]-1H-benzimidazole | 1.55 | 423 |
| 388 | 5-{[1-(2,5-Dichlorobenzyl)-6-(1-oxidopyridin-4-yl)-1H-benzimidazol-2-yl]methoxy}pyridine-2-carboxamide | 1.19 | 521 |
| 389 | 4-({1-(2-Chloro-5-fluorobenzyl)-6-[6-(dimethyl-amino)pyridin-3-yl]-1H-benzimidazol-2-yl}-methoxy)benzamide | 2.38 | 531 |
| 390 | 5-[1-(2-Chloro-5-fluorobenzyl)-2-{[(6-methoxy-pyridin-3-yl)oxy]methyl}-1H-benzimidazol-6-yl]-N,N-dimethylpyridin-2-amine | 2.79 | 519 |
| 391 | 1-(2-Chlorobenzyl)-2-[(pyridin-3-yloxy)methyl]-6-(pyrimidin-4-yl)-1H-benzimidazole | 2.02 | 429 |
| 392 | 5-[1-(2-Chlorobenzyl)-2-{[(6-methoxypyridin-3-yl)-oxy]methyl}-1H-benzimidazol-6-yl]-N,N-dimethyl-pyridin-2-amine | 2.81 | 501 |
| 393 | 1-(2-Chlorobenzyl)-6-(1-oxidopyridin-4-yl)-2-[(pyridin-3-yloxy)methyl]-1H-benzimidazole | 1.69 | 444 |
| 394 | N,N-Dimethyl-5-{1-(2-methyl-1,3-thiazol-4-yl)-methyl]-2-[(pyridin-3-yloxy)methyl]-1H-benzimidazol-6-yl}pyridin-2-amine | 2.10 | 458 |
| 395 | 4-({6-[6-(Dimethylamino)pyridin-3-yl]-1-[(2-methyl-1,3-thiazol-4-yl)methyl]-1H-benzimidazol-2-yl}methoxy)benzamide | 2.05 | 500 |
| 396 | — | — | — |
| 397 | 4-{[1-(2-Chloro-5-fluorobenzyl)-6-(1-oxidopyridin-4-yl)-1H-benzimidazol-2-yl]methoxy}benzamide | 1.17 | 504 |
| 398 | 1-(2-Chlorobenzyl)-2-{[(6-methoxypyridin-3-yl)-oxy]methyl}-6-(pyrimidin-4-yl)-1H-benzimidazole | 2.05 | 459 |
| 399 | 1-(2,5-Dichlorobenzyl)-6-(1-oxidopyridin-4-yl)-2-[(pyridin-3-yloxy)methyl]-1H-benzimidazole | 1.78 | 478 |
| 400 | 4-{[1-(2,5-Dichlorobenzyl)-6-(1-oxidopyridin-4-yl)-1H-benzimidazol-2-yl]methoxy}benzamide | 1.73 | 520 |
| 401 | 5-{1-(2-Chlorobenzyl)-2-[(pyridin-3-yloxy)methyl]-1H-benzimidazol-6-yl}-N,N-dimethylpyridin-2-amine | 2.52 | 471 |
| 402 | [6-Bromo-1-(2,5-dimethylbenzyl)-1H-benzimidazol-2-yl]methanol | 1.52 | 346 |
| 403 | 1-[2-(Difluoromethoxy)benzyl]-2-[(difluoro-methoxy)methyl]-6-[6-(piperazin-1-yl)pyridin-3-yl]-1H-benzimidazole | 1.47 | 517 |

Example 404

Method L

1-[2-(Difluoromethoxy)benzyl]-6-(6-methoxypyridin-3-yl)-2-methyl-1H-benzimidazole A mixture of Intermediate 47 (476 mg, 1.30 mmol), 6-methoxypyridin-3-ylboronic acid (1.56 mmol) and Pd(PPh$_3$)$_4$ (45 mg, 0.039 mmol) in 1,4-dioxane (10 mL) and 2M aqueous Na$_2$CO$_3$ solution (2 mL) was degassed and flushed with N$_2$ three times. The reaction mixture was heated with stirring at 90° C. until TLC or LCMS analysis indicated that the reaction was complete. The reaction mixture was allowed to cool to room temperature and evaporated in vacuo. The crude residue was suspended in EtOAc (30 mL) and washed with water. The aqueous phases were extracted with further EtOAc (4×30 mL) and the combined organic layers dried (MgSO$_4$), filtered and concentrated in vacuo. The crude product was purified by chromatography (SiO$_2$; 2-50% EtOAc in DCM) to give the title compound. $\delta_H$ (MeOD-d$_4$, 400 MHz) 8.32 (dd, J 2.5, 0.5 Hz, 1H), 7.91 (dd, J 8.7, 2.6 Hz, 1H), 7.67 (d, J 8.4 Hz, 1H), 7.52-7.54 (m, 1H), 7.47 (dd, J 8.4, 1.7 Hz, 1H), 7.35-7.42 (m, 1H), 7.24-7.28 (m, 1H), 7.17 (td, J 7.6, 1.1 Hz, 1H), 6.97 (t, J 73.6 Hz, 1H), 6.89-6.93 (m, 1H), 6.87 (dd, J 8.7, 0.6 Hz, 1H), 5.58 (s, 2H), 3.95 (s, 3H), 2.61 (s, 3H). LCMS (ES+) 396 (M+H)$^+$, RT 2.28 minutes.

Example 405

Method M

5-{1-[2-(Difluoromethoxy)benzyl]-2-methyl-1H-benzimidazol-6-yl}pyridin-2(1H)-one Example 404 (11.37 g, 28.8 mmol) and pyridine hydrochloride (13.29 g, 115 mmol) were placed in a small round-bottomed flask and placed into a pre-heated sand bath at 160° C. Once the solids had melted the mixture was heated for a further 10 minutes at 160° C. The mixture was cooled to ambient temperature and ice-water was added with vigorous stirring. The resultant solid product was collected by filtration. The crude material was triturated with 2-propanol and dried under vacuum to give the title compound (3.20 g, 29%) as a brown solid. $\delta_H$ (DMSO-d$_6$, 400 MHz) 11.22-12.16 (m, 1H), 7.82 (dd, J 9.6, 2.8 Hz, 1H), 7.61-7.66 (m, 2H), 7.57 (d, J 8.4 Hz, 1H), 7.32-7.40 (m, 2H), 7.35 (t, J 73.9 Hz, 1H), 7.24-7.29 (m, 1H), 7.11-7.16 (m, 1H), 6.66-6.70 (m, 1H), 6.41 (d, J 9.5 Hz, 1H), 5.52 (s, 2H), 2.46 (s, 3H). LCMS (ES+) 382 (M+H)$^+$, RT 1.55 minutes.

Example 406

Method N

1-(2,5-Dichlorobenzyl)-2-methyl-6-[4-(pyridin-3-yl)piperazin-1-yl]-1H-benzimidazole A mixture of Intermediate 48 (50 mg, 0.14 mmol), 1-(pyridin-3-yl)piperazine (44 mg, 0.27 mmol), XPhos ligand (12.9 mg, 0.027 mmol), Pd$_2$(dba)$_3$ (12.4 mg, 0.0135 mmol) and sodium tert-butoxide (26 mg, 0.27 mmol) in toluene (2.5 mL) was degassed and flushed with N$_2$ three times. The reaction mixture was stirred at 110° C. for 18 h. The reaction mixture was allowed to cool to room temperature and the volatiles were removed in vacuo. The residue was diluted with 5% MeOH/DCM (2 mL) and washed with water (1 mL). The organic phase was passed down a phase separator and concentrated in vacuo. The crude product was purified by mass-directed preparative HPLC to give the title compound (6.6 mg, 10%) as a white solid. $\delta_H$ (DMSO-d$_6$, 400 MHz) 8.36 (d, J 2.9 Hz, 1H), 8.02 (dd, J 4.6, 1.2 Hz, 1H), 7.61 (d, J 8.6 Hz, 1H), 7.42-7.48 (m, 2H), 7.36-7.41 (m, 1H), 7.24 (dd, J 8.4, 4.6 Hz, 1H), 7.04 (d, J 2.1 Hz, 1H), 6.97 (dd, J 8.7, 2.2 Hz, 1H), 6.45 (d, J 2.5 Hz, 1H), 5.51 (s, 2H), 3.32-3.37 (m, 4H), 3.22-3.27 (m, 4H), 2.41 (s, 3H). LCMS (ES+) 453 (M+H)$^+$, RT 1.25 minutes.

Examples 407 to 409

The following compounds were synthesized from Intermediate 48 and the appropriate amine in accordance with Method N.

| Example | Compound Name | LCMS RT | Mass Ion |
|---|---|---|---|
| 407 | 1-(2,5-Dichlorobenzyl)-2-methyl-6-[4-(pyridin-2-yl)piperazin-1-yl]-1H-benzimidazole | 2.62 | 453 (M + H)$^+$ |
| 408 | 1-(2,5-Dichlorobenzyl)-2-methyl-6-[4-(methylsulfonyl)piperazin-1-yl]-1H-benzimidazole | 2.16 | 454 (M + H)$^+$ |
| 409 | 1-(2,5-Dichlorobenzyl)-2-methyl-6-(morpholin-4-yl)-1H-benzimidazole | 2.08 | 377 (M + H)$^+$ |

Examples 410 to 433

These compounds can be synthesized from Intermediate 48 and the appropriate boronic acid or ester thereof (e.g. the pinacol ester) in accordance with Method L. If desired, PdCl$_2$(dppf) can be used as an alternative catalyst. Reagents containing NH groups can be protected as N-BOC derivatives and deprotection effected at a subsequent convenient stage by treatment with trifluoroacetic acid or hydrochloric acid. The following compounds were prepared.

| Example | Compound Name | LCMS RT | Mass Ion |
|---|---|---|---|
| 410 | 6-[1-(2,5-Dichlorobenzyl)-2-methyl-1H-benzimidazol-6-yl]pyridazin-3-ol | 1.26 | 386 (M + H)$^+$ |

| Example | Compound Name | LCMS RT | Mass Ion |
|---|---|---|---|
| 411 | 5-[1-(2,5-Dichlorobenzyl)-2-methyl-1H-benzimidazol-6-yl]pyrazin-2-ol | 0.97 | 386 (M + H)+ |
| 412 | 1-(2,5-Dichlorobenzyl)-6-(6-methoxypyridin-3-yl)-2-methyl-1H-benzimidazole | 2.58 | 399 (M + H)+ |
| 413 | 1-(2,5-Dichlorobenzyl)-2-methyl-6-(pyridin-4-yl)-1H-benzimidazole | 2.04 | 369 (M + H)+ |
| 414 | 5-[1-(2,5-Dichlorobenzyl)-2-methyl-1H-benzimidazol-6-yl]-4-methylpyridin-2(1H)-one | 1.31 | 399 (M + H)+ |
| 415 | 5-[1-(2,5-Dichlorobenzyl)-2-methyl-1H-benzimidazol-6-yl]-3-methylpyridine-2-carbonitrile | 1.54 | 408 (M + H)+ |
| 416 | 1-(2,5-Dichlorobenzyl)-6-(5-methoxypyridin-3-yl)-2-methyl-1H-benzimidazole | 1.49 | 399 (M + H)+ |
| 417 | 1-(2,5-Dichlorobenzyl)-2-methyl-6-[6-(piperazin-1-yl)pyridin-3-yl]-1H-benzimidazole | 2.01 | 453 (M + H)+ |
| 418 | 1-(2,5-Dichlorobenzyl)-6-(2-methoxypyrimidin-5-yl)-2-methyl-1H-benzimidazole | 1.27 | 400 (M + H)+ |
| 419 | tert-Butyl 4-[1-(2,5-dichlorobenzyl)-2-methyl-1H-benzimidazol-6-yl]-3,6-dihydropyridine-1(2H)-carboxylate | 2.96 | 473 (M + H)+ |
| 420 | 5-[1-(2,5-Dichlorobenzyl)-2-methyl-1H-benzimidazol-6-yl]pyrimidin-2(1H)-one | 1.12 | 386 (M + H)+ |
| 421 | 5-[1-(2,5-Dichlorobenzyl)-2-methyl-1H-benzimidazol-6-yl]-1-methylpyridin-2(1H)-one | 1.39 | 399 (M + H)+ |
| 422 | 1-(2,5-Dichlorobenzyl)-6-(3,5-dimethylisoxazol-4-yl)-2-methyl-1H-benzimidazole | 1.58 | 387 (M + H)+ |
| 423 | 5-[1-(2,5-Dichlorobenzyl)-2-methyl-1H-benzimidazol-6-yl]-6-methylpyridin-2(1H)-one | 1.27 | 399 (M + H)+ |
| 424 | 1-(2,5-Dichlorobenzyl)-2-methyl-6-(pyrimidin-5-yl)-1H-benzimidazole | 1.36 | 370 (M + H)+ |
| 425 | 1-(2,5-Dichlorobenzyl)-2-methyl-6-(1-methyl-1H-pyrazol-5-yl)-1H-benzimidazole | 1.41 | 372 (M + H)+ |
| 426 | 1-(2,5-Dichlorobenzyl)-6-(3,5-dimethyl-1H-pyrazol-4-yl)-2-methyl-1H-benzimidazole | 1.34 | 386 (M + H)+ |
| 427 | 5-[1-(2,5-Dichlorobenzyl)-2-methyl-1H-benzimidazol-6-yl]pyridin-3-amine | 1.31 | 384 (M + H)+ |
| 428 | 1-(2,5-Dichlorobenzyl)-2-methyl-6-[4-(pyrrolidin-1-ylmethyl)phenyl]-1H-benzimidazole | 1.60 | 451 (M + H)+ |
| 429 | 1-(2,5-Dichlorobenzyl)-6-(1,3-dimethyl-1H-pyrazol-4-yl)-2-methyl-1H-benzimidazole | 1.39 | 386 (M + H)+ |
| 430 | 4-[1-(2,5-Dichlorobenzyl)-2-methyl-1H-benzimidazol-6-yl]pyridin-2-amine | 1.35 | 384 (M + H)+ |
| 431 | 1-(2,5-Dichlorobenzyl)-6-(1,5-dimethyl-1H-pyrazol-4-yl)-2-methyl-1H-benzimidazole | 1.40 | 386 (M + H)+ |
| 432 | 5-[1-(2,5-Dichlorobenzyl)-2-methyl-1H-benzimidazol-6-yl]pyridin-2(1H)-one | 1.29 | 385 (M + H)+ |
| 433 | 5-[1-(2,5-Dichlorobenzyl)-2-methyl-1H-benzimidazol-6-yl]-4,6-dimethylpyridin-2(1H)-one | 1.36 | 413 (M + H)+ |

Example 434

1-(2,5-Dichlorobenzyl)-2-methyl-6-(1-oxidopyridin-4-yl)-1H-benzimidazole

From Example 413 by oxidation with mCPBA in DCM to give the title compound. LCMS 385 (M+H)+, RT 1.72 minutes.

Example 435

5-[1-(2,5-Dichlorobenzyl)-2-methyl-1H-benzimidazol-6-yl],piperidin-2-one

From Example 432 by reduction with hydrogen (100 psi) and catalytic PtO$_2$ to give the title compound. LCMS 389 (M+H)+, RT 1.27 minutes.

Example 436

1-(2,5-Dichlorobenzyl)-2-methyl-1H-benzimidazole

From 2-fluoronitrobenzene and 2,5-dichlorobenzylamine in accordance with Method K. LCMS 292 (M+H)+, RT 2.27 minutes.

Example 437

1-[5-Chloro-2-(difluoromethoxy)benzyl]-6-(6-methoxypyridin-3-yl)-2-methyl-1H-benzimidazole From Intermediate 49 and 6-methoxypyridin-3-ylboronic acid in accordance with Method L to give the title compound. LCMS 430 (M+H)+, RT 1.58 minutes.

Example 438

5-{1-[5-Chloro-2-(difluoromethoxy)benzyl]-2-methyl-1H-benzimidazol-6-yl}pyridin-2(1H)-one From Example 437 in accordance with Method M to give the title compound. LCMS 416 (M+H)+, RT 1.28 minutes.

Example 439

5-{1-[2-(Difluoromethoxy)benzyl]-5-fluoro-2-methyl-1H-benzimidazol-6-yl}pyridin-2(1H)-one From Intermediate 50 and 6-hydroxypyridin-3-ylboronic acid pinacol ester in accordance with Method L to give the title compound. LCMS 400 (M+H)+, RT 1.25 minutes.

Example 440

6-Bromo-1-[(5-chloro-2-methyl-1,3-thiazol-4-yl)methyl]-2-methyl-1H-benzimidazole From (5-chloro-2-methyl-1,3-thiazol-4-yl)methylamine in accordance with Method K to give the title compound. LCMS 357 (M+H)$^+$, RT 1.54 minutes.

Example 441

5-{1-[(5-Chloro-2-methyl-1,3-thiazol-4-yl)methyl]-2-methyl-1H-benzimidazol-6-yl}-pyridin-2(1H)one From Example 440 and 6-hydroxypyridin-3-ylboronic acid pinacol ester in accordance with Method L to give the title compound. LCMS 371 (M+H)$^+$, RT 1.17 minutes.

Example 442

1-(2,5-Dichlorobenzyl)-2-methyl-1H-benzimidazole-6-carbonitrile

From 3-fluoro-4-nitrobenzonitrile and 2,5-dichlorobenzylamine in accordance with Method K to give the title compound. LCMS 317 (M+H)$^+$, RT 1.45 minutes.

Example 443

5-[1-(2,5-Dichlorobenzyl)-5-fluoro-2-methyl-1H-benzimidazol-6-yl]pyridin-2(1H)-one From Intermediate 51 and 6-hydroxypyridin-3-ylboronic acid pinacol ester in accordance with Method L to give the title compound. LCMS 403 (M+H)$^+$, RT 1.28 minutes.

Example 444

6-Bromo-1-[2-(difluoromethoxy)benzyl]-2-(methoxymethyl)-1H-benzimidazole

A solution of 5-bromo-N$^1$[2-(difluoromethoxy)benzyl]benzene-1,2-diamine (Intermediate 47, Step 2) (8.3 g, 24 mmol) in DCM (50 mL) was treated with DIPEA (8.4 mL, 48 mmol) and methoxyacetic acid (2.2 mL, 29 mmol) followed by HATU (11 g, 29 mmol) and the mixture was stirred at ambient temperature under N$_2$ for 1 h. The mixture was then diluted with DCM (100 mL) and washed with water (100 mL). The aqueous layer was extracted with dichloromethane (200 mL) and the combined organic layers were washed with brine (100 mL) and dried over MgSO$_4$. Removal of solvent in vacuo gave a crude gum (23 g), which was taken up in acetic acid (30 mL) and heated to 100° C. under N$_2$ for 3 h. The mixture was concentrated in vacuo, and the residue was suspended in Na$_2$CO$_3$ (10% aqueous solution, 200 mL) and extracted with ethyl acetate (2×150 mL). The combined organic extracts were washed with brine (150 mL) and dried over MgSO$_4$. Removal of solvent in vacuo gave a crude solid which was purified by chromatography using a short pad of silica gel (loaded in dichloromethane, eluted with ethyl acetate:isohexane, 2:3 by volume) to give the title compound (6.2 g, 65%) as a white solid. $\delta_H$ 7.69 (d, 1H), 7.63 (d, 1H), 7.32-7.39 (m, 3H), 7.25 (d, 1H), 7.14 (t, 1H) 6.71 (d, 1H), 5.56 (s, 2H), 4.64 (s, 2H), 3.23 (s, 3H). LCMS (6120B, 3 minutes method, pH 10) m/z 397.2, RT 1.04 minutes.

Example 445

Method O

1-[2-(Difluoromethoxy)benzyl]-2-(methoxymethyl)-6-[2-(morpholin-4-yl)pyrimidin-5-yl]-1H-benzimidazole To Example 444 (50 mg, 0.12 mmol) were added 4-[5-(4,4,5,5-tetramethyl-1,3,2-dioxaborolan-2-yl)pyrimidin-2-yl]morpholine (44 mg, 0.144 mmol), Pd(PPh$_3$)$_4$ (7.5 mg, 0.006 mmol), 2M aqueous Na$_2$CO$_3$ solution (0.5 mL) and 1,4-dioxane (2.5 mL). The reaction mixture was flushed with nitrogen and heated to 105° C. under a nitrogen atmosphere for 18 h. The reaction mixture was allowed to cool to ambient temperature, MP-TMT resin (Biotage, 0.76 mmol/g, 300 mg, 0.25 mmol) was added and the solution was agitated at room temperature overnight. Ethyl acetate (20 mL) was added and the mixture was passed through a silica pad cartridge, eluting with further ethyl acetate (2×5 mL) and finally a solution of 20% methanol in ethyl acetate (2×10 mL). The combined organic phases were concentrated in vacuo. The crude residue was purified by reverse phase preparative HPLC to give the title compound (17 mg, 30%) as a white solid. LCMS (pH 3) M+H 483, RT 1.92 minutes, UV purity 100%; LCMS (pH 10) M+H 483, RT 2.23 minutes, UV purity 100%.

Examples 446 to 462

These compounds can be synthesized from Intermediate 444 and the appropriate boronic acid or ester thereof (e.g. the pinacol ester) in accordance with Method O. Reagents containing NH groups can be protected as N-BOC derivatives and deprotection effected at a subsequent convenient stage by treatment with trifluoroacetic acid or hydrochloric acid. The following compounds were prepared.

| Example | Compound Name | LCMS RT | Mass Ion |
| --- | --- | --- | --- |
| 446 | 4-{1-[2-(Difluoromethoxy)benzyl]-2-(methoxymethyl)-1H-benzimidazol-6-yl}phenol | 2.07 | 411 (M + H)$^+$ |
| 447 | 1-[2-(Difluoromethoxy)benzyl]-2-(methoxymethyl)-6-[2-(piperazin-1-yl)pyrimidin-5-yl]-1H-benzimidazole | 1.40 | 481 (M + H)$^+$ |
| 448 | 1-[2-(Difluoromethoxy)benzyl]-2-(methoxymethyl)-6-[4-(piperazin-1-ylmethyl)phenyl]-1H-benzimidazole | 1.49 | 493 (M + H)$^+$ |
| 449 | 1-[2-(Difluoromethoxy)benzyl]-2-(methoxymethyl)-6-[6-(piperazin-1-yl)pyridin-3-yl]-1H-benzimidazole | 1.41 | 480 (M + H)$^+$ |
| 450 | 1-[2-(Difluoromethoxy)benzyl]-2-(methoxymethyl)-6-[6-(propan-2-yloxy)pyridin-3-yl]-1H-benzimidazole | 1.69 | 454 (M + H)$^+$ |

-continued

| Example | Compound Name | LCMS RT | Mass Ion |
|---|---|---|---|
| 451 | 1-[2-(Difluoromethoxy)benzyl]-2-(methoxymethyl)-6-[4-(pyrrolidin-1-ylmethyl)phenyl]-1H-benzimidazole | 1.70 | 478 (M + H)+ |
| 452 | 1-[2-(Difluoromethoxy)benzyl]-2-(methoxymethyl)-6-[6-(piperidin-1-yl)pyridin-3-yl]-1H-benzimidazole | 1.71 | 479 (M + H)+ |
| 453 | 1-[2-(Difluoromethoxy)benzyl]-2-(methoxymethyl)-6-{1-[2-(morpholin-4-yl)ethyl]-1H-pyrazol-4-yl}-1H-benzimidazole | 1.36 | 498 (M + H)+ |
| 454 | 1-[2-(Difluoromethoxy)benzyl]-2-(methoxymethyl)-6-[5-(morpholin-4-ylmethyl)thiophen-3-yl]-1H-benzimidazole | 1.54 | 500 (M + H)+ |
| 455 | 1-[2-(Difluoromethoxy)benzyl]-2-(methoxymethyl)-6-[6-(trifluoromethyl)pyridin-3-yl]-1H-benzimidazole | 1.61 | 464 (M + H)+ |
| 456 | tert-Butyl 4-(5-{1-[2-(difluoromethoxy)benzyl]-2-(methoxymethyl)-1H-benzimidazol-6-yl}pyrimidin-2-yl)piperazine-1-carboxylate | 1.70 | 581 (M + H)+ |
| 457 | 1-[4-(5-{1-[2-(Difluoromethoxy)benzyl]-2-(methoxymethyl)-1H-benzimidazol-6-yl}pyridin-2-yl)piperazin-1-yl]ethanone | 1.40 | 522 (M + H)+ |
| 458 | 5-{1-[2-(Difluoromethoxy)benzyl]-2-(methoxymethyl)-1H-benzimidazol-6-yl}pyridine-2-carboxylic acid | 1.03 | 440 (M + H)+ |
| 459 | 1-[2-(Difluoromethoxy)benzyl]-2-(methoxymethyl)-6-[6-(morpholin-4-yl)pyridin-3-yl]-1H-benzimidazole | 1.50 | 481 (M + H)+ |
| 460 | 3-{1-[2-(Difluoromethoxy)benzyl]-2-(methoxymethyl)-1H-benzimidazol-6-yl}quinoline | 1.55 | 446 (M + H)+ |
| 461 | 1-[2-(Difluoromethoxy)benzyl]-2-(methoxymethyl)-6-(6-methylpyridin-3-yl)-1H-benzimidazole | 1.46 | 410 (M + H)+ |
| 462 | 5-{1-[2-(Difluoromethoxy)benzyl]-2-(methoxymethyl)-1H-benzimidazol-6-yl}pyridin-2(1H)-one | 1.22 | 412 (M + H)+ |

Example 463

Methyl 1-[2-(difluoromethoxy)benzyl]-2-methyl-1H-benzimidazole-6-carboxylate

From methyl 3-fluoro-4-nitrobenzoate in accordance with Method K to give the title compound. LCMS mass ion 347, RT 1.44 minutes.

Examples 464 to 487

These compounds can be synthesized by a sequence of steps corresponding to Method K followed by Method L, utilising the appropriate boronic acid or ester thereof (e.g. the pinacol ester), the appropriate amine and the appropriate carboxylic acid. Reagents containing NH groups can be protected as N-BOC derivatives and deprotection effected at a subsequent convenient stage by treatment with trifluoroacetic acid or hydrochloric acid. The N-oxide derivatives can be prepared by oxidation with mCPBA. The following compounds were prepared.

| Example | Compound Name | LCMS RT | Mass Ion |
|---|---|---|---|
| 464 | 1-[1-(4-Chlorophenyl)ethyl]-6-(6-methoxypyridin-3-yl)-2-methyl-1H-benzimidazole | 1.60 | 378 |
| 465 | 1-(2,6-Dimethylbenzyl)-6-(6-methoxypyridin-3-yl)-2-methyl-1H-benzimidazole | 1.58 | 358 |
| 466 | 1-[2-(Difluoromethoxy)benzyl]-6-(2,6-dimethylpyridin-4-yl)-2-methyl-1H-benzimidazole | 1.45 | 394 |
| 467 | 1-(2,6-Dichlorobenzyl)-6-(6-methoxypyridin-3-yl)-2-methyl-1H-benzimidazole | 1.59 | 399 |
| 468 | 6-(6-Methoxypyridin-3-yl)-2-methyl-1-(1-phenylpropyl)-1H-benzimidazole | 1.57 | 358 |
| 469 | 1-[(5-Chloro-2-methyl-1,3-thiazol-4-yl)methyl]-2-methyl-6-[6-(piperazin-1-yl)pyridin-3-yl]-1H-benzimidazole | 1.29 | 439 |
| 470 | 1-[2-(Difluoromethoxy)benzyl]-6-(2,6-dimethyl-1-oxidopyridin-4-yl)-2-methyl-1H-benzimidazole | 1.31 | 410 |
| 471 | 1-[2-(Difluoromethoxy)benzyl]-2-methyl-6-{6-[4-(2,2,2-trifluoroethyl)piperazin-1-yl]pyridin-3-yl}-1H-benzimidazole | 1.64 | 532 |
| 472 | 1-[2-(Difluoromethoxy)benzyl]-2-methyl-6-[6-(2,2,2-trifluoroethoxy)pyridin-3-yl]-1H-benzimidazole | 1.67 | 464 |
| 473 | tert-Butyl 4-{1-[2-(difluoromethoxy)benzyl]-2-methyl-1H-benzimidazol-6-yl}-3,6-dihydropyridine-1(2H)-carboxylate | 1.67 | 470 |

-continued

| Example | Compound Name | LCMS RT | Mass Ion |
|---|---|---|---|
| 474 | — | — | — |
| 475 | 5-{1-[2-(Difluoromethoxy)benzyl]-2-methyl-1H-benzimidazol-6-yl}-N,N-dimethylpyrimidin-2-amine | 1.50 | 410 |
| 476 | 1-[2-(Difluoromethoxy)benzyl]-2-methyl-6-[4-methyl-6-(2,2,2-trifluoroethoxy)pyridin-3-yl]-1H-benzimidazole | 1.69 | 478 |
| 477 | 1-[2-(Difluoromethoxy)benzyl]-6-(6-methoxy-pyridin-3-yl)-1H-benzimidazole | 1.48 | 382 |
| 478 | tert-Butyl 4-(5-{1-[2-(difluoromethoxy)benzyl]-2-methyl-1H-benzimidazol-6-yl}-4-methylpyridin-2-yl)piperazine-1-carboxylate | 1.93 | 564 |
| 479 | 1-[2-(Difluoromethoxy)benzyl]-2-methyl-6-[4-methyl-6-(piperazin-1-yl)pyridin-3-yl]-1H-benzimidazole | 0.96 | 464 |
| 480 | 1-[2-(Difluoromethoxy)benzyl]-6-(6-methoxy-4-methylpyridin-3-yl)-2-methyl-1H-benzimidazole | 1.53 | 410 |
| 481 | 1-(2,5-Dichlorobenzyl)-2-ethyl-6-(pyridin-4-yl)-1H-benzimidazole | 2.28 | 383 |
| 482 | 6-(6-Methoxypyridin-3-yl)-2-methyl-1-[(1S)-1-phenylethyl]-1H-benzimidazole | 1.53 | 344 |
| 483 | 5-{2-Methyl-1-[(1S)-1-phenylethyl]-1H-benzimidazol-6-yl}pyridin-2(1H)-one | 1.20 | 330 |
| 484 | 1-[(1S)-1-(3-Chlorophenyl)ethyl]-6-(6-methoxy-pyridin-3-yl)-2-methyl-1H-benzimidazole | 2.42 | 378 |
| 485 | 1-Benzyl-6-(6-methoxypyridin-3-yl)-2-methyl-1H-benzimidazole | 2.16 | 330 |
| 486 | 2-Methyl-1-[(1R)-1-phenylethyl]-6-(pyridin-4-yl)-1H-benzimidazole | 1.90 | 314 |
| 487 | 2-Methyl-1-[(1S)-1-phenylethyl]-6-(pyridin-4-yl)-1H-benzimidazole | 1.90 | 314 |

Example 471

Alternative Preparation

1-[2-(Difluoromethoxy)benzyl]-2-methyl-6-{6-[4-(2,2,2-trifluoroethyl)piperazin-1-yl]pyridin-3-yl}-1H-benzimidazole Example 490 (67 mg, 0.13 mmol), DBU (38 μL, 0.25 mmol) and 2,2,2-trifluoroethyl p-toluenesulfonate (71 mg, 0.28 mmol) were dissolved in acetonitrile (1 mL) and heated under microwave irradiation at 180° C. for 2 h. LCMS showed 24% desired product. Further microwave heating at 200° C. for 2 h, then 215° C. for 1 h, showed 40% conversion by LCMS. Solvent was removed in vacuo and the residue was purified by chromatography (silica, gradient 0 to 7% MeOH in dichloromethane), to give the title compound (19 mg, 26%) as a white solid. $\delta_H$ (d$_6$-DMSO) 8.41 (d, 1H, J 2.3 Hz), 7.82 (dd, 1H, J 8.8, 2.4 Hz), 7.64-7.57 (m, 2H), 7.48-7.37 (m, 2H), 7.35 (t, 1H, $J_{H-F}$ 73.8 Hz), 7.26 (d, 1H, J 8.8 Hz), 7.15 (t, 1H, J 7.5 Hz), 6.90 (d, 1H, J 8.8 Hz), 6.77 (d, 1H, J 6.7 Hz), 5.52 (s, 2H), 3.54-3.51 (m, 4H), 3.23 (q, 2H, $J_{H-F}$ 10.2 Hz), 2.73-2.69 (m, 4H), 2.49 (s, 3H hidden by DMSO signal). LCMS (ES$^+$) 532 (M+H)$^+$.

Example 472

Alternative Preparation

1-[2-(Difluoromethoxy)benzyl]-2-methyl-6-[6-(2,2,2-trifluoro ethoxy)pyridin-3-yl]-1H-benzimidazole Example 405 (250 mg, 0.65 mmol) was dissolved in dry THF (5 mL) and NaH (60% dispersion in oil, 29 mg, 0.71 mmol) was added. The mixture was stirred at room temperature for 5 minutes until gas evolution had ceased. Then 2,2,2-trifluoroethyl p-toluenesulfonate (182 mg, 0.71 mmol) was added and the mixture was heated to 80° C. for 18 h. The mixture was cooled, diluted with water (100 mL) and extracted with ethyl acetate (75 mL). The organic phase was dried (Na$_2$SO$_4$) and concentrated in vacuo. The residue was purified by chromatography (silica, gradient 0 to 7% MeOH in DCM) to give the title compound (31 mg, 10%) as a white solid. $\delta_H$ (d$_6$-DMSO) 8.41 (dd, 1H, J 2.5, 0.5 Hz), 8.02 (dd, 1H, J 8.6, 2.5 Hz), 7.70 (d, 1H, 0.5 Hz), 7.56 (d, 1H, J 8.4 Hz), 7.41 (dd, 1H, 8.4, 1.7 Hz), 7.32 (m, 1H), 7.28 (t, 1H, $J_{H-F}$ 73.8 Hz), 7.19 (d, 1H, J 7.5 Hz), 7.08 (dt, 1H, J 7.5, 1.2 Hz), 6.99 (dd, 1H, J 8.6, 0.5 Hz), 6.68 (dd, 1H, 7.5, 1.4 Hz), 5.48 (s, 2H), 4.96 (q, 2H, $J_{H-F}$ 9.1 Hz), 2.49 (s, 3H hidden by DMSO signal). LCMS (ES$^+$) 464 (M+H)$^+$.

Example 488

1-[2-(Difluoromethoxy)benzyl]-2-(hydroxymethyl)-1H-benzimidazole-5-carbonitrile

Synthesized from Intermediate 40 and glycolic acid in accordance with Method J.

Example 489

1-[2-(Difluoromethoxy)benzyl]-2-methyl-6-(4-methylimidazol-1-yl)-1H-benzimidazole To a mixture of Intermediate 57 (250 mg, 0.67 mmol), 4-methylimidazole (82 mg, 1.00 mmol) and Cu(OAc)$_2$ (122 mg, 0.67 mmol) in methanol:water (4:1, 30 mL) was added TMEDA (0.20 mL, 1.34 mmol). The reaction mixture was stirred at room temperature for 24 h. Solvent was removed in vacuo and the residue was purified by column chromatography (SiO$_2$, gradient 0 to 10% MeOH in dichloromethane). The product fractions were concentrated in vacuo. The resulting material was further purified by preparative HPLC and freeze-dried to afford the title compound (45 mg, 18%)

as a white solid. $\delta_H$ (d$_6$-DMSO) 8.01 (d, 1H, J 1.0 Hz), 7.71 (d, 1H, J 2.0 Hz), 7.64 (d, 1H, J 8.5 Hz), 7.40-7.35 (m, 3H), 7.35 (t, 1H, J$_{H\text{-}F}$ 73.8 Hz), 7.27 (d, 1H, J 8.0 Hz), 7.15 (m, 1H), 6.73 (d, 1H, J 7.2 Hz), 5.53 (s, 2H), 2.47 (s, 3H), 2.15 (s, 3H). LCMS (ES$^+$) 369 (M+H)$^+$.

Example 490

1-[2-(Difluoromethoxy)benzyl]-2-methyl-6-[6-(piperazin-1-yl)pyridin-3-yl]-1H-benzimidazole The following experiment was carried out twice in parallel.

Trifluoroacetic acid (100 mL) was added in portions to a chilled (0° C.) solution of Intermediate 58 (25.25 g, 46 mmol) in DCM (50 mL) and stirred in an ice-bath for 30 minutes. Each reaction mixture was evaporated to a thin syrup, poured into a stirred mixture of NaHCO$_3$/ice/water and stirred for 1 h. The solid was filtered, washed several times with water and dried by suction. The solid was recrystallized from a 1:1 mixture of 2-propanol and 1-butanol to give the title compound (34 g, 82%) as a cream solid. $\delta_H$ (DMSO-d$_6$) 8.41 (d, J 2.4 Hz, 1H), 7.81 (dd, J$_1$ 8.9 Hz, J$_2$ 2.6 Hz, 1H), 7.64 (d, J 1.3 Hz, 1H), 7.59 (m, 1H), 7.40 (m, 2H), 7.35 (t, J$_{HF}$ 76 Hz, 1H), (m, 1H), 7.16 (m, 1H), 6.86 (d, J 8.9 Hz, 1H), 6.78 (m, 1H), 5.53 (s, 2H), 3.43 (m, 4H), 2.79 (m, 4H), 2.50 (s, 3H). LCMS (ES+) 450 (M+H)$^+$, RT 1.30 minutes.

Example 491

Method Q

Ethyl 2-[4-(5-{1-[2-(difluoromethoxy)benzyl]-2-methyl-1H-benzimidazol-6-yl}pyridin-2-yl)piperazin-1-yl]acetate Example 490 (450 mg, 1.00 mmol) and ethyl bromoacetate (167 mg, 1.00 mmol) were dissolved in acetonitrile (15 mL) and heated to 70° C. for 5 h. Solvent was removed in vacuo and the residue was purified by chromatography (silica, gradient 0 to 6% MeOH in DCM) to give a pale yellow oil. Further purification was achieved by preparative HPLC to give, after freeze-drying, the title compound (143 mg, 26%) as a white solid. $\delta_H$ (d$_6$-DMSO) 8.44 (d, 1H, J 2.4 Hz), 7.86 (dd, 1H, J 8.7, 2.2 Hz), 7.70 (s, 1H), 7.63 (d, 1H, 8.1 Hz), 7.47 (d, 1H, J 8.1 Hz), 7.39 (m, 1H), 7.35 (t, 1H, J$_{H\text{-}F}$ 73.8 Hz), 7.27 (d, 1H, J 8.1 Hz), 7.17 (m, 1H), 6.94 (d, 1H, J 8.9 Hz), 6.86 (d, 1H, J 7.6 Hz), 5.57 (s, 2H), 4.14 (q, 2H, J 7.1 Hz), 3.59 (m, 2H), 2.80-2.60 (br m, 8H), 2.54 (s, 3H), 1.24 (t, 3H, J 7.1 Hz). LCMS (ES$^+$) 536 (M+H)$^+$.

Example 492

2-[4-(5-{1-[2-(Difluoromethoxy)benzyl]-2-methyl-1H-benzimidazol-6-yl}pyridin-2-yl)-piperazin-1-yl] acetic acid HCl salt Example 491 (120 mg, 0.22 mmol) was dissolved in THF (3 mL) and water (4 mL), and conc. HCl (2 mL) was added. The mixture was heated to 60° C. for 18 h, then concentrated in vacuo. The residue was purified by preparative HPLC (pH 3) to give, after freeze-drying, the title compound (45 mg, 37%) as a white solid. $\delta_H$ (d$_6$-DMSO) 8.42 (d, 1H, J 2.4 Hz), 7.82 (dd, 1H, J 8.8, 2.5 Hz), 7.64 (d, 1H, J 1.0 Hz), 7.59 (d, 1H, 8.4 Hz), 7.42-7.35 (m, 2H), 7.35 (t, 1H, J$_{H\text{-}F}$ 73.8 Hz), 7.26 (d, 1H, J 8.3 Hz), 7.16 (m, 1H), 6.90 (d, 1H, J 9.0 Hz), 6.78 (d, 1H, J 7.3 Hz), 5.53 (s, 2H), 3.22 (s, 2H), 2.70-2.62 (m, 8H), 2.50 (s, 3H, obscured by DMSO signal). LCMS (ES$^+$) 508 (M+H)$^+$.

Example 493

Method R 4-(5-{1-[2-(Difluoromethoxy)benzyl]-2-(methoxymethyl)-1H-benzimidazol-6-yl}pyridin-2-yl)piperazin-2-one A solution of Intermediate 59 (50 mg, 0.12 mmol), triethylamine (33 µL, 0.23 mmol) and piperazin-2-one (35 mg, 0.35 mmol) in DMSO (0.2 mL) was heated by microwave irradiation, in a sealed vessel, to 190° C. for 10 minutes and then to 220° C. for 10 minutes. The crude mixture was purified by preparative-HPLC to give the title compound (7 mg) as a white solid. LCMS (pH 10) m/z 495, RT 1.96 minutes.

Example 494

4-(5-{1-[2-(Difluoromethoxy)benzyl]-2-(methoxymethyl)-1H-benzimidazol-6-yl}pyridin-2-yl)thiomorpholine A solution of Intermediate 59 (300 mg, 0.7 mmol), triethylamine (197 µL, 1.40 mmol) and thiomorpholine (211 µL, 2.09 mmol) in DMSO (1.2 mL) was heated to 190° C. by microwave irradiation in a sealed tube for 10 minutes, followed by heating to 200° C. for 15 minutes and heating to 205° C. for 15 minutes. The crude reaction mixture was purified by preparative HPLC to give the title compound (80 mg) as a white, waxy solid. $\delta_H$ (DMSO-d$_6$, 300 MHz) 8.40 (d, 1H), 8.81 (dd, 1H), 7.59-7.71 (m, 2H), 7.47 (d, 1H), 7.33-7.38 (t, 2H), 7.26 (d, 1H), 7.13 (t, 1H), 6.91 (d, 1H), 6.76 (d, 1H), 5.60 (s, 2H), 4.65 (s, 2H), 3.93 (m, 4H), 3.25 (s, 3H), 2.59 (m, 4H). LCMS (pH 10) 498 (M+H)$^+$, RT 2.49 minutes.

Example 495

1-[2-(Difluoromethoxy)benzyl]-2-(methoxymethyl)-6-[6-(1-oxidothiomorpholin-4-yl)pyridin-3-yl]-1H-benzimidazole A solution of Example 494 (70 mg, 0.14 mmol) in dichloromethane (20 mL) was cooled to 0° C. and treated with mCPBA (75%, 32 mg, 0.14 mmol), added portionwise over 1 minute. The mixture was allowed to warm to ambient temperature over 1 h, then quenched with sodium metabisulphite (5% aqueous solution, 50 mL). The layers were separated and the organic phase concentrated in vacuo. The residue was purified by preparative HPLC to give the title compound (17 mg) as a white solid. $\delta_H$ (DMSO-d$_6$, 300 MHz) 8.45 (d, 1H), 7.86 (dd, 1H), 7.59-7.72 (m, 2H), 7.49 (dd, 1H), 7.32-7.38 (m, 2H), 7.26 (d, 1H), 7.03-7.15 (m, 2H), 6.76 (d, 1H), 5.61 (s, 2H), 4.66 (s, 2H), 4.17 (d, 2H), 3.95 (t, 2H), 3.25 (s, 3H), 2.87 (t, 2H), 2.68 (t, 2H). LCMS (pH 10) m/z 513.7, RT 1.88 minutes.

Example 496

1-[2-(Difluoromethoxy)benzyl]-6-[6-(1,1-dioxidothiomorpholin-4-yl)pyridin-3-yl]-2-(methoxymethyl)-1H-benzimidazole A solution of Example 494 (70 mg, 0.14 mmol) in dichloromethane (20 mL) was cooled to 0° C. and treated with mCPBA (75%, 32 mg, 0.14 mmol), added portionwise over 1 minute. The mixture was allowed to warm to ambient temperature over 1 h, then quenched with sodium metabisulphite (5% aqueous solution, 50 mL). The layers were separated and the organic phase concentrated in vacuo. The residue was purified by preparative HPLC to give the title compound (10 mg) as a white solid. $\delta_H$ (DMSO-$d_6$, 300 MHz) 8.45 (d, 1H), 7.90 (dd, 1H), 7.59-7.73 (m, 2H), 7.50 (dd, 1H), 7.24-7.38 (m, 3H), 7.09-7.15 (m, 2H), 6.76 (d, 1H), 5.61 (s, 2H), 4.66 (s, 2H), 4.09 (s, 4H), 3.25 (s, 3H), 3.11 (s, 4H). LCMS (pH 10) m/z 529.6, RT 2.09 minutes.

Example 497

5-{1-[2-(Difluoromethoxy)benzyl]-2-(methoxymethyl)-1H-benzimidazol-6-yl}-N-(2-methoxyethyl)pyridin-2-amine A solution of Intermediate 59 (50 mg, 0.12 mmol), triethylamine (33 μL, 0.23 mmol) and 2-methoxyethylamine (30 μL, 0.35 mmol) in DMSO (0.2 mL) was heated by microwave irradiation, in a sealed vessel, to 170° C. for 10 minutes and then to 190° C. for 10 minutes. The crude mixture was purified by preparative HPLC to give the title compound (3 mg) as a white solid. LCMS (pH 10) 469.8 (M+H)$^+$, RT 2.14 minutes.

Example 498

1-(5-{1-[2-(Difluoromethoxy)benzyl]-2-(methoxymethyl)-1H-benzimidazol-6-yl}pyridin-2-yl)-1,4-diazepan-5-one A solution of Intermediate 59 (50 mg, 0.12 mmol), triethylamine (49 μL, 0.35 mmol) and 1,4-diazepan-5-one (40 mg, 0.35 mmol) in DMSO (0.2 mL) was heated to 205° C. by microwave irradiation in a sealed tube for 25 minutes, then allowed to cool. The crude reaction mixture was purified by preparative HPLC to give the title compound (8 mg) as a white solid. $\delta_H$ (DMSO-$d_6$, 300 MHz) 8.41 (d, 1H), 7.82 (dd, 1H), 7.70 (d, 1H), 7.62 (m, 2H), 7.47 (dd, 1H), 7.33-7.38 (m, 1H), 7.34 (t, 1H), 7.26 (d, 1H), 7.12-7.15 (m, 1H), 6.90 (d, 1H), 6.77 (d, 1H), 5.60 (s, 2H), 4.66 (s, 2H), 4.76-3.83 (m, 4H), 3.29 (s, 2H), 3.26 (s, 3H), 3.15-3.20 (m, 2H). LCMS (pH 10) m/z 494.8, RT 1.96 minutes.

Example 499

1-(2,5-Dimethylbenzyl)-6-[4-(piperazin-1-ylmethyl)phenyl]-2-(pyridin-4-ylmethyl)-1H-benzimidazole Hydrogen chloride in 1,4-dioxane (4N; 4 mL) was added to a stirred solution of Intermediate 64 (300 mg, 0.5 mmol) in DCM (1 mL) and the mixture was stirred for 1 h. LCMS showed completion of reaction. Solvents were removed under reduced pressure. The residue was dissolved in DCM, washed twice with a saturated aqueous solution of sodium bicarbonate, dried (MgSO$_4$) and concentrated to dryness by rotary evaporation. The resulting solid material was triturated in diethyl ether, filtered, washed with diethyl ether and dried under suction, to give the title compound (205 mg, 82%) as a pale yellow solid. $\delta_H$ (DMSO-$d_6$) 8.39 (m, 2H), 7.72 (d, J 8.4 Hz, 1H), 7.66 (d, J 1.2 Hz, 1H), 7.60 (d, J 8.2 Hz, 2H), 7.52 (dd, J$_1$ 8.4 Hz, J$_2$ 1.6 Hz, 1H), 7.35 (d, J 8.1 Hz, 2H), 7.22 (d, J 5.9 Hz, 2H), 7.08 (m, 1H), 6.90 (dd, J$_1$ 7.4 Hz, J$_2$ 0.2 Hz, 1H), 5.92 (s, 1H), 5.53 (m, 2H), 4.26 (s, 2H), 3.43 (m, 2H), 2.67 (m, 4H), 2.30 (s, 3H), 2.23 (m, 4H), 1.92 (s, 3H). LCMS (ES+) 503 (M+H)$^+$, RT 1.31 minutes.

Examples 500 to 502

These compounds can be synthesized from Example 490 and the appropriate alkylating agent in accordance with Method Q. The following compounds were prepared (the alkylating agents for Examples 501 and 502 were methanesulfonylethene and acrylonitrile respectively).

| Example | Compound Name | LCMS RT | Mass Ion |
|---|---|---|---|
| 500 | Ethyl 3-[4-(5-{1-[2-(difluoromethoxy)benzyl]-2-methyl-1H-benzimidazol-6-yl}pyridin-2-yl)-piperazin-1-yl]propanoate | 1.54 | 550 (M + H)$^+$ |
| 501 | 1-[2-(Difluoromethoxy)benzyl]-2-methyl-6-(6-{4-[2-(methylsulfonyl)ethyl]piperazin-1-yl}pyridin-3-yl)-1H-benzimidazole | 1.38 | 556 |
| 502 | 3-[4-(5-{1-[2-(Difluoromethoxy)benzyl]-2-methyl-1H-benzimidazol-6-yl}pyridin-2-yl)piperazin-1-yl]-propanenitrile | 2.14 | 503 |

Example 503

3-[4-(5-{1-[2-(Difluoromethoxy)benzyl]-2-methyl-1H-benzimidazol-6-yl}pyridin-2-yl)-piperazin-1-yl] propionic acid Hydrolysis of Example 500 according to the procedure described in Example 495. LCMS RT 1.40 minutes

Examples 504 to 507

The following compounds were synthesised from Intermediate 59 and the appropriate amine in accordance with Method R.

| Example | Compound Name | LCMS RT | Mass Ion |
|---|---|---|---|
| 504 | (3R)-1-(5-{1-[2-(Difluoromethoxy)benzyl]-2-(methoxymethyl)-1H-benzimidazol-6-yl}pyridin-2-yl)pyrrolidin-3-ol | 1.39 | 481 |
| 505 | 1-[2-(Difluoromethoxy)benzyl]-2-(methoxymethyl)-6-{6-[4-(methylsulfonyl)piperazin-1-yl]pyridin-3-yl}-1H-benzimidazole | 1.48 | 558 |
| 506 | 2-[N-(5-{1-[2-(Difluoromethoxy)benzyl]-2-(methoxymethyl)-1H-benzimidazol-6-yl}pyridin-2-yl)-N-(methyl)amino]ethanol | 1.43 | 469 |
| 507 | 1-[2-(Difluoromethoxy)benzyl]-2-(methoxymethyl)-6-[6-(pyrrolidin-1-yl)pyridin-3-yl]-1H-benzimidazole | 1.60 | 465 |

Example 508

1-(5-{1-[2-(Difluoromethoxy)benzyl]-2-methyl-1H-benzimidazol-6-yl}-3',4',5',6'-tetrahydro-2'H-[2,4]bipyridinyl-1'-yl)ethanone To Intermediate 57 (458 mg, 1.11 mmol) were added 1-(5-bromo-3',4',5',6'-tetrahydro-2'H-[2,4]bipyridinyl-1'-yl)ethanone (376 mg, 1.33 mmol), Pd(PPh$_3$)$_4$ (64 mg, 0.055 mmol), 2M aqueous Na$_2$CO$_3$ solution (7 mL) and 1,4-dioxane (35 mL). The reaction mixture was stirred under N$_2$ at 105° C. for 4 h. The reaction mixture was cooled to ambient temperature, diluted with water (10 mL) and extracted with ethyl acetate (2×100 mL), and the combined organic layers were concentrated in vacuo. The crude residue was purified by silica flash column chromatography, eluting with 0-20% MeOH/ethyl acetate, to yield the title compound (348 mg, 64%). $\delta_H$ (d$_6$-DMSO, 300 MHz) 8.78 (1H, d, J 2.2 Hz), 7.90 (1H, dd, J 8.2, 2.5 Hz), 7.77 (1H, d, J 1.3 Hz), 7.64 (1H, d, J 8.4 Hz), 7.49 (1H, dd, J 8.3, 1.6 Hz), 7.40-7.34 (3H, m, incl. 1H, t, J 73.8 Hz), 7.25 (1H, d, J 7.6 Hz), 7.15 (1H, dt, J 7.5, 1.1 Hz), 6.76 (1H, dd, J 7.6, 1.2 Hz), 5.55 (2H, s), 4.53-4.43 (1H, m), 4.04-3.90 (1H, m), 3.27-3.11 (1H, m), 3.01-2.92 (1H, m), 2.73-2.58 (1H, m), 3H not observed (CH$_3$) under d$_6$-DMSO peak at 2.50 ppm, 2.03 (3H, s), 1.90-1.81 (2H, m), 1.80-1.46 (2H, m). LCMS (pH 3) 491.8, MH+, RT 1.47 minutes, 100% UV. LCMS (pH 10) 491.8, MH+, RT 2.05 minutes, 100% UV.

Example 509

5-{1-[2-(Difluoromethoxy)benzyl]-2-methyl-1H-benzimidazol-6-yl}-3-methylpyridin-2(1H)-one To Intermediate 57 (140 mg, 0.34 mmol) were added 5-bromo-3-methylpyridin-2-ol (76 mg, 0.41 mmol), Pd(PPh$_3$)$_4$ (20 mg, 0.016 mmol), 2M aqueous Na$_2$CO$_3$ solution (2 mL) and 1,4-dioxane (10 mL). The reaction mixture was stirred at 105° C. for 4 h. Further Pd(PPh$_3$)$_4$ (20 mg, 0.016 mmol) and Na$_2$CO$_3$ solution (1 mL) were added and the reaction mixture was stirred at 105° C. overnight. The reaction mixture was cooled to ambient temperature, diluted with water (1 mL) and extracted with ethyl acetate (2×20 mL). The combined organic layers were concentrated in vacuo and the crude residue was purified by silica flash column chromatography (0-10% MeOH/DCM) and then by preparative HPLC to yield, after freeze-drying, the title compound (3 mg, 2%) as a white solid. $\delta_H$ (d$_6$-DMSO) 11.59-11.25 (1H, br s), 7.72 (1H, d, J 1.4 Hz), 7.63-7.49 (3H, m), 7.40-7.33 (3H, m), 7.26 (1H, d, J 7.6 Hz), 7.16-7.11 (1H, m), 6.68-6.65 (1H, m), 5.52 (2H, s), 2.45 (3H, s), 2.00 (3H, s). LCMS (pH 3) 396.8, MH+, RT 1.33 minutes, 100% UV. LCMS (pH 10) 396.8, MH+, RT 1.66 minutes, 100% UV.

Example 510

Method S 4-(5-{1-[2-(Difluoromethoxy)benzyl]-2-methyl-1H-benzimidazol-6-yl}pyrimidin-2-yl)-piperazin-2-one To a solution of Intermediate 65 (76 mg, 0.19 mmol) in ethanol (2 mL) were added piperazin-2-one (19 mg, 0.19 mmol) and triethylamine (19 mg, 0.19 mmol). The reaction mixture was stirred at 85° C. for 18 h. The reaction mixture was cooled to ambient temperature and water (2 mL) was added. The resultant precipitate was collected by filtration and purified by flash column chromatography on silica (eluting with 5-10% MeOH in ethyl acetate) to give the title compound (30 mg, 34%) as a white solid. $\delta_H$ (d$_6$-DMSO, 300 MHz) 8.74 (2H, s), 8.13 (1H, s), 7.74 (1H, d, J 1.3 Hz), 7.62 (1H, d, J 8.5 Hz), 7.47-7.43 (1H, m), 7.37-7.34 (2H, m), 7.25 (1H, d, J 7.5 Hz), 7.18-7.11 (1H, m), 6.78-6.75 (1H, m), 5.53 (2H, s), 4.21 (2H, s), 3.95-3.92 (2H, m), 3.34-3.30 (2H, m), 3H not observed (CH$_3$) under d$_6$-DMSO peak at 2.50 ppm. LCMS (pH 3) 465.8, MH+, RT 1.38 minutes, 100% UV. LCMS (pH 10) 465.7, MH+, RT 1.69 minutes, 100% UV.

Example 511

1-[2-(Difluoromethoxy)benzyl]-2-methyl-6-{2-[4-(methylsulfonyl)piperazin-1-yl]-pyrimidin-5-yl}-1H-benzimidazole To a solution of Intermediate 65 (50 mg, 0.125 mmol) in ethanol (2 mL) were added 1-(methylsulfonyl)piperazine (22 mg, 0.125 mmol) and triethylamine (17 µL). The reaction mixture was stirred at 90° C. for 18 h, before being cooled to ambient temperature. Water (2 mL) was added. The resultant precipitate was collected by filtration and purified by flash column chromatography (silica), eluting with 100% ethyl acetate to 3% methanol in ethyl acetate, to give the title compound (22 mg, 33%) as an off white solid. $\delta_H$ (d$_6$-DMSO, 300 MHz) 8.72 (2H, s), 7.72 (1H, d, J 1.3 Hz), 7.65-7.51 (2H, m), 7.46-7.35 (2H, m), 7.25 (1H, d, J 7.6 Hz), 7.18-7.11 (1H, m), 6.78-6.75 (1H, m), 5.53 (2H, s), 3.90 (4H, t, J 5.0 Hz), 3.19 (4H, t, J 5.0 Hz), 2.89 (3H, s), 3H not observed (CH$_3$) under d$_6$-DMSO peak at 2.50 ppm. LCMS (pH 3) 529.8, MH+, RT 1.67 minutes, 100% UV. LCMS (pH 10) 529.7, MH+, RT 2.15 minutes, 99.4% UV.

Examples 512 to 518

The following compounds were synthesised from Intermediate 65 and the appropriate amine in accordance with Method S.

| Example | Compound Name | LCMS RT | Mass Ion |
|---|---|---|---|
| 512 | (3S)-1-(5-{1-[2-(Difluoromethoxy)benzyl]-2-methyl-1H-benzimidazol-6-yl}pyrimidin-2-yl)pyrrolidin-3-ol | 1.30 | 452 |
| 513 | 5-{1-[2-(Difluoromethoxy)benzyl]-2-methyl-1H-benzimidazol-6-yl}-N-(2-methoxyethyl)pyrimidin-2-amine | 1.82 | 440 |
| 514 | 1-[2-(Difluoromethoxy)benzyl]-2-methyl-6-[2-(2-oxa-6-azaspiro[3.3]hept-6-yl)pyrimidin-5-yl]-1H-benzimidazole | 1.85 | 464 |
| 515 | 1-[2-(Difluoromethoxy)benzyl]-2-methyl-6-[2-(2-oxa-7-azaspiro[3.5]non-7-yl)pyrimidin-5-yl]-1H-benzimidazole | 2.22 | 492 |
| 516 | 1-[2-(Difluoromethoxy)benzyl]-2-methyl-6-[2-(2-oxa-6-azaspiro[3.4]oct-6-yl)pyrimidin-5-yl]-1H-benzimidazole | 1.99 | 478 |
| 517 | 1-[2-(Difluoromethoxy)benzyl]-2-methyl-6-[2-(2-oxa-6-azaspiro[3.5]non-6-yl)pyrimidin-5-yl]-1H-benzimidazole | 2.32 | 492 |
| 518 | 1-[2-(Difluoromethoxy)benzyl]-2-methyl-6-[2-(thiomorpholin-4-yl)pyrimidin-5-yl]-1H-benzimidazole | 2.03 | 468 |

Examples 519 to 522

These compounds can be synthesised from Intermediate 2 and the appropriate substituted aldehyde in accordance with Method C. Reagents containing hydroxy groups can be protected as tert-butyldimethylsilanyloxy derivatives and deprotection effected at a subsequent convenient stage by conventional means. The following compounds were prepared.

| Example | Compound Name | LCMS RT | Mass Ion |
|---|---|---|---|
| 519 | [1-(2,5-Dimethylbenzyl)-1H-benzimidazol-2-yl][5-(hydroxymethyl)furan-2-yl]methanol | 2.22 | 363 |
| 520 | [1-(2,5-Dimethylbenzyl)-1H-benzimidazol-2-yl](1-methyl-1H-pyrazol-4-yl)methanol | 2.15 | 347 |
| 521 | [1-(2,5-Dimethylbenzyl)-1H-benzimidazol-2-yl]-(thiophen-3-yl)methanol | 2.70 | 349 |
| 522 | [1-(2,5-Dimethylbenzyl)-1H-benzimidazol-2-yl](3-methyl-1-phenyl-1H-pyrazol-4-yl)methanol | 2.80 | 423 |

Example 523

1-[2-(Difluoromethoxy)benzyl]-2-methyl-6-(2-methyl-1H-imidazol-1-yl)-1H-benzimidazole From Intermediate 57 by the method of Example 489 with 2-methylimidazole to give the title compound. LCMS 369 (M+H)+, RT 1.32 minutes.

Example 524

1-[2-(Difluoromethoxy)benzyl]-6-(6-ethenylpyridin-3-yl)-2-(methoxymethyl)-1H-benzimidazole To a solution of Intermediate 59 (118 mg, 0.27 mmol) in isopropanol (6 mL) were added potassium vinyl trifluoroborate (35 mg, 1.2 equiv.), triethylamine (40 μL, 1.1 equiv.) and PdCl$_2$(dppf) (5%). The mixture was degassed and heated at reflux under nitrogen for 3 h. The mixture was then allowed to cool to room temperature. Water (5 mL) was added and the mixture was stirred for another 10 minutes. The reaction mixture was poured into ethyl acetate/water and the layers were separated. The organic layer was then washed three times with brine, dried over magnesium sulphate and concentrated in vacuo. The residue was purified by gradient silica column chromatography, eluting with 0-60% ethyl acetate in DCM, followed by preparative chromatography, to afford the title compound (20 mg, 17%) as a white solid. $\delta_H$ (400 MHz, CDCl$_3$) 8.77 (d, J 1.9 Hz, 1H), 7.89 (d, J 8.3 Hz, 1H), 7.83 (dd, J 8.1, 2.4 Hz, 1H), 7.52 (dd, J 8.4, 1.7 Hz, 1H), 7.39-7.42 (m, 2H), 7.25-7.35 (m, 1H), 7.19-7.35 (m, 1H), 7.11 (dt, J 7.7, 1.1 Hz, 1H), 6.76-6.89 (m, 2H), 6.64 (t, J 73.3 Hz, 1H), 6.23 (d, J 17.5 Hz, 1H), 5.61 (s, 2H), 5.50 (dd, J 10.8, 1.2 Hz, 1H), 4.77 (s, 2H), 3.40 (s, 3H). LCMS (ES+) (M+H)+ 348, RT 2.06 minutes (Method 1); (M+H)+ 423, RT 2.30 minutes (Method 2).

Examples 525 to 528

These compounds can be synthesized by a sequence of steps corresponding to the preparation of Intermediates 32, 33 and 34, followed by Method J, utilising 6-[4-(tert-butyloxycarbonyl)piperazin-1-yl]pyridin-3-ylboronic acid, the appropriate amine and the appropriate carboxylic acid. Removal of the BOC protecting group can be effected at a subsequent convenient stage by treatment with trifluoroacetic acid or hydrochloric acid. The following compounds were prepared.

| Example | Compound Name | LCMS RT | Mass Ion |
|---|---|---|---|
| 525 | {1-[2-(Difluoromethoxy)benzyl]-6-[6-(piperazin-1-yl)pyridin-3-yl]-1H-benzimidazol-2-yl}methanol | 1.25 | 466 |
| 526 | 1-[(5-Chloro-2-methyl-1,3-thiazol-4-yl)methyl]-2-(methoxymethyl)-6-[6-(piperazin-1-yl)pyridin-3-yl]-1H-benzimidazole | 1.32 | 470 |
| 527 | 1-[(5-Chloro-2-methyl-1,3-thiazol-4-yl)methyl]-2-[(difluoromethoxy)methyl]-6-[6-(piperazin-1-yl)-pyridin-3-yl]-1H-benzimidazole | 1.40 | 506 |
| 528 | 1-[2-(Difluoromethoxy)benzyl]-6-[6-(piperazin-1-yl)pyridin-3-yl]-2-[(2,2,2-trifluoroethoxy)methyl]-1H-benzimidazole | 1.48 | 548 |

Example 529

1-(Bicyclo[4.2.0]octa-1(6),2,4-trien-7-yl)-2-[(pyridin-4-ylmethoxy)methyl]-1H-benzimidazole dihydrochloride From Intermediate 66 and 4-(bromomethyl)pyridine hydrobromide in accordance with Method D to give the title compound. $\delta_H$ (300 MHz, DMSO-d$_6$) 8.80 (d, 2H, J 6.1 Hz), 7.81 (d, 2H, J 5.6 Hz), 7.75 (d, 2H, J 8.2 Hz), 7.51 (m, 1H), 7.31 (m, 3H), 7.18 (m, 2H), 6.78 (d, 1H, J 8.0 Hz), 6.42 (m, 1H), 5.15 (m, 2H), 4.91 (m, 2H), 3.90 (m, 1H), 3.60 (m, 1H). LCMS (ES+) 342 (M+H)$^+$, RT 2.29 minutes (Method 2).

Example 530

[1-(Bicyclo[4.2.0]octa-1(6),2,4-trien-7-yl)-1H-benzimidazol-2-yl](pyridin-4-yl)methanol From Intermediate 67 and 4-pyridinecarboxaldehyde in accordance with Method C to give the title compound. $\delta_H$ (300 MHz, DMSO-d$_6$) 8.58 (d, 2H, J 6.0 Hz), 7.64 (d, 1H, J 2.9 Hz), 7.45 (m, 4H), 7.16 (m, 2H), 6.91 (m, 2H), 6.62 (m, 1H), 6.41 (m, 1H), 6.26 (m, 2H), 3.75 (m, 1H), 3.21 (m, 1H). LCMS (ES+) 328 (M+H)$^+$, RT 2.09 minutes (Method 2).

Example 531

1-(1-Cyclopentylethyl)-6-(6-methoxypyridin-3-yl)-2-methyl-1H-benzimidazole

Synthesized by a sequence of steps corresponding to the preparation of Intermediates 33 and 34, followed by Method J, utilizing 1-cyclopentylethylamine and acetic acid, to give the title compound. LCMS m/z 336 (M+H)$^+$, RT 2.47 minutes (Method 6).

Example 532

1-{[2-(Difluoromethoxy)phenyl]methyl}-2-methyl-6-[4-methyl-2-(piperidin-4-yl)-pyrimidin-5-yl]benzimidazole To a solution of Intermediate 71 (0.13 g, 0.24 mmol) in methanol (5 mL) was added 4M HCl in 1,4-dioxane (5 mL). The reaction mixture was stirred at room temperature for 18 h, after which time the reaction mixture was basified by the addition of 10% aqueous NaOH solution. Methanol was evaporated off under vacuum and the remaining aqueous solution was extracted with ethyl acetate (4×50 mL). The combined organic layers were dried (Na$_2$SO$_4$), filtered and concentrated in vacuo. The crude residue was purified by chromatography (SiO$_2$; 2%/18%/80%-4%/36%/60% NH$_3$/MeOH/DCM), and the resulting solid material was freeze-dried from acetonitrile/water/methanol, to give the title compound (0.062 g, 56%) as a white solid. $\delta_H$ (DMSO-d$_6$, 300 MHz) 8.49 (s, 1H), 7.65 (d, 1H, J 8.2 Hz), 7.51 (d, 1H, J 1.1 Hz), 7.34-7.41 (m, 1H), 7.31 (t, 1H, J 73.9 Hz), 7.13-7.27 (m, 3H), 6.83 (dd, 1H, J 7.5, 1.4 Hz), 5.51 (s, 2H), 2.98-3.08 (m, 2H), 2.80-2.92 (m, 1H), 2.55-2.66 (m, 2H), 2.52 (s, 3H), 2.36 (s, 3H), 1.78-1.89 (m, 2H), 1.64-1.76 (m, 2H). LCMS (ES+) 464 (M+H)$^+$, RT 1.91 minutes (pH 10); and (ES+) 464 (M+H)$^+$, RT 1.11 minutes (pH 3).

Example 533

1-{[2-(Difluoromethoxy)phenyl]methyl}-2-methyl-6-{4-methyl-2-[1-(methylsulfonyl)-piperidin-4-yl]pyrimidin-5-yl}benzimidazole To a solution of Example 532 (0.048 g, 0.10 mmol) in DCM (2 mL) were added triethylamine (22 µL, 0.16 mmol) and methanesulfonyl chloride (8.8 µL, 0.11 mmol). The reaction mixture was stirred at room temperature for 1.5 h. The reaction mixture was washed with brine (2 mL). The organic layer was separated by passing through a phase separator, then concentrated in vacuo. The resulting solid was freeze-dried from acetonitrile/water. The resulting pale yellow solid was purified by chromatography (SiO$_2$; 0-18% MeOH/DCM gradient elution), then further purified by preparative HPLC, to provide the title compound (0.022 g, 39%) as a white solid. $\delta_H$ (DMSO-d$_6$, 300 MHz) 8.53 (s, 1H), 7.66 (d, 1H, J 8.3 Hz), 7.52 (d, 1H, J 1.2 Hz), 7.34-7.41 (m, 1H), 7.32 (t, 1H, J 73.8 Hz), 7.20-7.27 (m, 2H), 7.16 (td, 1H, J 7.6, 1.1 Hz), 6.83 (dd, 1H, J 7.6, 1.3 Hz), 5.51 (s, 2H), 3.61-3.70 (m, 2H), 2.82-3.01 (m, 6H), 2.53 (s, 3H), 2.38 (s, 3H), 2.04-2.15 (m, 2H), 1.74-1.90 (m, 2H). LCMS (ES+) 542 (M+H)$^+$, RT 2.07 minutes (pH 10); and (ES+) 542 (M+H)$^+$, RT 1.71 minutes (pH 3).

Example 534

2-[5-(1-{[2-(Difluoromethoxy)phenyl]methyl}-2-methylbenzimidazol-6-yl)-4-methylpyrimidin-2-yl]acetamide To a solution of Intermediate 69 (0.1 g, 0.25 mmol) in EtOH (3 mL) was added sodium ethoxide (0.025 g, 0.38 mmol). The mixture was stirred for 10 minutes, followed by the addition of 3-amino-3-iminopropanamide hydrochloride (0.057 g, 0.53 mmol). The reaction mixture was heated at 80° C. for 16 h. The reaction mixture was concentrated in vacuo, then the residue was diluted with water (3 mL) and extracted with ethyl acetate. The resulting solution was dried over anhydrous Na$_2$SO$_4$, filtered and concentrated in vacuo to give, after purification by preparative HPLC, the title compound (20 mg). $\delta_H$ (400 MHz, CDCl$_3$) 7.70 (d, J 8.2 Hz, 1H), 7.50 (s, 1H), 7.31 (t, J 7.8 Hz, 1H), 7.17 (d, J 8.2 Hz, 1H), 7.14-7.00 (m, 3H), 6.67 (d, J 7.7 Hz, 1H), 6.63 (s, 2H), 6.46 (s, 2H), 5.78 (br s, 1H), 5.37 (s, 2H), 2.58 (s, 3H), 2.26 (s, 3H). LCMS m/z 438, RT 1.83 minutes.

Example 535

2-[5-(1-{[2-(Difluoromethoxy)phenyl]methyl}-2-methylbenzimidazol-6-yl)-4-methylpyrimidin-2-yl]propan-2-ol To a solution of Intermediate 69 (0.20 g, 0.50 mmol) in MeOH (3 mL) was added K$_2$CO$_3$ (0.20 g, 1.51 mmol). The mixture was stirred for 10 minutes, followed by the addition of 2-hydroxy-2-methylpropanamidine (0.108 g, 1.1 mmol). The reaction mixture was heated at 70° C. for 16 h. The volatiles were removed in vacuo, then the residue was diluted with water (5 mL) and extracted with ethyl acetate (3×10 mL). The combined organic layers were dried over anhydrous Na$_2$SO$_4$, filtered and concentrated in vacuo to give, after purification by preparative HPLC, the title compound (48 mg). $\delta_H$ (400 MHz, CDCl$_3$) 8.49 (s, 1H), 7.81 (d, J 8.2 Hz, 1H), 7.38-7.28 (m, 1H), 7.19 (ddd, J 8.0, 6.3, 1.5 Hz, 2H), 7.14-7.06 (m, 2H), 6.71-6.64 (m, 1H), 6.63 (s, 1H), 5.41 (s, 2H), 4.91 (br s, 1H), 2.62 (s, 3H), 2.44 (s, 3H), 1.61 (s, 6H). LCMS m/z 439, RT 2.10 minutes.

Example 536

1-{[2-(Difluoromethoxy)phenyl]methyl}-6-(2-ethyl-4-methylpyrimidin-5-yl)-2-methylbenzimidazole To a solution of Intermediate 69 (0.2 g, 0.50 mmol) in MeOH (3 mL) was added K$_2$CO$_3$ (0.21 g, 1.50 mmol). The mixture was stirred for 10 minutes, followed by the addition of propionamidine hydrochloride (0.12 g, 1.06 mmol). The reaction mixture was heated at 70° C. for 16 h. The reaction mixture was concentrated in vacuo, then the residue was diluted with water (3 mL) and extracted with ethyl acetate. The resulting solution was dried over anhydrous Na$_2$SO$_4$, filtered and concentrated in vacuo to give, after purification by preparative HPLC, the title compound (48 mg). $\delta_H$ (400 MHz, CDCl$_3$) 8.43 (s, 1H), 7.80 (d, J 8.2 Hz, 1H), 7.39-7.29 (m, 1H), 7.24-7.14 (m, 2H), 7.13-6.99 (m, 2H), 6.68 (d, J 7.7 Hz, 1H), 6.63 (s, 1H), 5.40 (s, 2H), 2.97 (q, J 7.6 Hz, 2H), 2.62 (s, 3H), 2.41 (s, 3H), 1.38 (t, J 7.6 Hz, 3H). LCMS m/z 409, RT 2.14 minutes.

Example 537

1-{[2-(Difluoromethoxy)phenyl]methyl}-2-methyl-6-[4-methyl-2-(tetrahydropyran-4-yl)-pyrimidin-5-yl]benzimidazole To a solution of Intermediate 69 (0.2 g, 0.50 mmol) in MeOH (3 mL) was added K$_2$CO$_3$ (0.21 g, 1.50 mmol). The mixture was stirred for 10 minutes, followed by the addition of tetrahydro-2H-pyran-4-carboxamidine hydrochloride (0.174 g, 1.063 mmol). The reaction mixture was heated at 70° C. for 16 h. The reaction mixture was concentrated in vacuo, then the residue was diluted with water (3 mL) and extracted with ethyl acetate. The resulting solution was dried over anhydrous Na$_2$SO$_4$, filtered and concentrated in vacuo to give, after purification by preparative HPLC, the title compound (27 mg). $\delta_H$ (400 MHz, CDCl$_3$) 8.45 (s, 1H), 7.80 (d, J 8.3 Hz, 1H), 7.40-7.28 (m, 1H), 7.24-7.15 (m, 1H), 7.14-7.06 (m, 2H), 6.71-6.65 (m, 2H), 6.63 (s, 1H), 5.41 (s, 2H), 4.10 (ddd, J 11.7, 4.3, 2.0 Hz, 2H), 3.57 (td, J 11.6, 2.4 Hz, 2H), 3.11 (tt, J 11.4, 4.1 Hz, 1H), 2.62 (s, 3H), 2.41 (s, 3H), 2.12-1.90 (m, 4H). LCMS m/z 465, RT 2.11 minutes.

Example 538

6-(2-Cyclobutyl-4-methylpyrimidin-5-yl)-1-{[2-(difluoromethoxy)phenyl]methyl}-2-methylbenzimidazole To a solution of Intermediate 69 (0.2 g, 0.50 mmol) in MeOH (3 mL) was added K$_2$CO$_3$ (0.207 g, 1.50 mmol). The mixture was stirred for 10 minutes, followed by the addition of cyclobutanecarboxamidine hydrochloride (0.14 g, 1.06 mmol). The reaction mixture was heated at 70° C. for 16 h. The reaction mixture was concentrated in vacuo, then the residue was diluted with water (3 mL) and extracted with ethyl acetate. The resulting solution was dried over anhydrous Na$_2$SO$_4$, filtered and concentrated in vacuo to give, after purification by preparative HPLC, the title compound (67 mg). $\delta_H$ (400 MHz, CD$_3$OD) 8.45 (s, 1H), 7.70 (d, J 8.3 Hz, 1H), 7.41-7.32 (m, 2H), 7.24 (td, J 5.6, 2.9 Hz, 2H), 7.17 (t, J 7.6 Hz, 1H), 7.00-6.90 (m, 2H), 5.56 (s, 2H), 3.80 (m, J 8.7 Hz, 1H), 2.63 (s, 3H), 2.58-2.30 (m, 7H), 2.21-1.88 (m, 2H). LCMS m/z 435, RT 2.48 minutes.

Example 539

6-[2-(Cyclopropylmethyl)-4-methylpyrimidin-5-yl]-1-{[2-(difluoromethoxy)phenyl]-methyl}-2-methyl-benzimidazole To a solution of Intermediate 69 (0.2 g, 0.50 mmol) in MeOH (3 mL) was added K$_2$CO$_3$ (0.21 g, 1.50 mmol). The mixture was stirred for 10 minutes, followed by the addition of 2-(cyclopropyl)acetamidine hydrochloride (0.14 g, 1.06 mmol). The reaction mixture was heated at 70° C. for 16 h. The reaction mixture was concentrated in vacuo, then the residue was diluted with water (3 mL) and extracted with ethyl acetate. The resulting solution was dried over anhydrous Na$_2$SO$_4$, filtered and concentrated in vacuo to give, after purification by preparative HPLC, the title compound (14 mg). $\delta_H$ (400 MHz, CD$_3$OD) 8.45 (s, 1H), 7.71 (d, J 8.3 Hz, 1H), 7.37 (q, J 7.4, 5.8 Hz, 2H), 7.29-7.20 (m, 2H), 7.17 (t, J 7.6 Hz, 1H), 6.96 (d, J 7.7 Hz, 1H), 6.93 (s, 1H), 5.56 (s, 2H), 2.80 (d, J 7.0 Hz, 2H), 2.63 (s, 3H), 2.40 (s, 3H), 1.23 (ddt, J 10.4, 7.6, 4.5 Hz, 1H), 0.59-0.45 (m, 2H), 0.30 (m, J 4.6 Hz, 2H). LCMS m/z 435, RT 2.33 minutes.

Example 540

1-[5-(1-{[2-(Difluoromethoxy)phenyl]methyl}-2-methylbenzimidazol-6-yl)-4-methylpyrimidin-2-yl]ethanol To a solution of Intermediate 69 (0.2 g, 0.50 mmol) in EtOH (3 mL) was added potassium tert-butoxide (0.11 g, 1.00 mmol). The mixture was stirred for 10 minutes, followed by the addition of 2-hydroxypropionamidine hydrochloride (0.13 g, 1.06 mmol). The reaction mixture was heated at 80° C. for 16 h. The reaction mixture was concentrated in vacuo, then the residue was diluted with water (3 mL) and extracted with ethyl acetate. The resulting solution was dried over anhydrous Na$_2$SO$_4$, filtered and concentrated in vacuo to give, after purification by preparative HPLC, the title compound (5 mg). $\delta_H$ (400 MHz, CD$_3$OD) 8.51 (d, J 1.8 Hz, 1H), 7.71 (dd, J 8.2, 1.7 Hz, 1H), 7.36 (d, J 8.9 Hz, 2H), 7.30-7.19 (m, 2H), 7.17 (t, J 7.6 Hz, 1H), 6.99-6.90 (m, 2H), 5.56 (s, 2H), 4.10 (m, 1H), 2.64 (d, J 1.7 Hz, 3H), 2.42 (d, J 1.6 Hz, 3H), 1.54 (dd, J 6.6, 1.7 Hz, 3H). LCMS m/z 425, RT 1.90 minutes.

Examples 541 & 542

Sodium (1R,5S)-3-[5-(1-{[2-(difluoromethoxy)phenyl]methyl}-5-fluoro-2-methylbenzimidazol-6-yl)pyrimidin-2-yl]bicyclo[3.1.0]hexane-6-carboxylate Aqueous sodium hydroxide solution (equivalent to 10.5 mg, 0.26 mmol) was added to a solution of Intermediate 74 (0.14 g, 0.26 mmol) in THF-MeOH-water (1:1:1; 6 mL) and stirred overnight. The reaction mixture was stirred at 60° C. for 4 h, then at 70° C. for 3 h. The reaction mixture was concentrated, diluted with water, and filtered through celite to remove turbidity. The resulting clear colourless aqueous solution was freeze-dried to give a white lyophilised solid (90 mg, 70%) consisting of two stereoisomers that were separated by preparative HPLC.

Isomer A (22 mg, 37%) was obtained as a white lyophilised solid. $\delta_H$ (300 MHz, DMSO-d$_6$) 8.88 (d, J 1.7 Hz, 2H), 7.76 (d, J 6.9 Hz, 1H), 7.57 (m, 1H), 7.37 (m, 1H), 7.32 (t, J 72, 76 Hz, 1H), 7.26 (m, 1H), 7.16 (m, 1H), 6.79 (m, 1H), 5.54 (s, 2H), 3.14 (m, 1H), 2.50 (s, 3H), 2.21 (m, 4H), 1.86 (s, 2H), 1.63 (t, J 2.8 Hz, 1H). LCMS (pH 10) MH+509, RT 1.44 minutes.

Isomer B (17 mg, 28%) was obtained as a white lyophilised solid $\delta_H$ (300 MHz, DMSO-d$_6$) 8.88 (d, J 1.5 Hz, 2H), 7.77 (m, 1H), 7.56 (m, 1H), 7.38 (m, 1H), 7.32 (t, J 72, 76 Hz, 1H), 7.26 (m, 1H), 7.16 (m, 1H), 6.80 (dd, J 7.7, 0.8 Hz, 1H), 5.55 (s, 2H), 3.15 (m, 1H), 2.50 (s, 3H), 2.26 (m, 2H), 2.17 (m, 2H), 1.87 (m, 2H), 1.64 (t, J 2.8 Hz, 1H). LCMS (pH 10) MH+ 509, RT 1.84 minutes.

Example 543

4-[5-(1-{[5-Chloro-2-(difluoromethoxy)phenyl]methyl}-5-fluoro-2-methylbenzimidazol-6-yl)pyrimidin-2-yl]cyclohex-3-ene-1-carboxylic acid 2M Sodium hydroxide solution (0.350 mL, 0.70 mmol) was added to a solution of Intermediate 76 (200 mg, 0.35 mmol) in THF-MeOH-water (1:1:1; 6 mL) and stirred over 3 days at r.t. The reaction mixture was concentrated, then ice-water was added and neutralised using acetic acid. The solid was filtered, washed with water and dried by suction. A fraction was purified by HPLC to give the title compound (12 mg, 6%) as a white solid. $\delta_H$ (400 MHz, DMSO-d$_6$) 8.94 (d, J 1.7 Hz, 2H), 7.82 (m, 1H), 7.58 (m, 1H), 7.47 (dd, J 8.8, 2.6 Hz, 1H), 7.32 (t, J 72, 76 Hz, 1H), 7.29 (m, 2H), 6.86 (m, 1H), 5.54 (s, 2H), 2.75 (m, 1H), 2.50 (s, 3H), 2.45 (m, 4H), 2.10 (m, 1H), 1.70 (m, 1H). LCMS (pH 10) MH+ 543, RT 2.19 minutes.

Example 544

4-[5-(1-{[5-Chloro-2-(difluoromethoxy)phenyl]methyl}-2-methylbenzimidazol-6-yl)-pyrimidin-2-yl]cyclohex-3-ene-1-carboxylic acid 2M Sodium hydroxide solution (0.375 mL, 0.75 mmol) was added to a solution of Intermediate 77 (200 mg, 0.36 mmol) in THF-MeOH-water (1:1:1; 6 mL) and stirred for 3 days at r.t. The reaction mixture was concentrated under reduced pressure, then ice-water was added and neutralised using acetic acid. The resulting solid was filtered, washed with cold water and dried by suction, to give the title compound (0.2 g, 100%) as an off-white solid. $\delta_H$ (400 MHz, DMSO-d$_6$) 12.2 (br, 1H, COOH), 9.09 (s, 2H), 7.96 (d, J 1.1 Hz, 1H), 7.70 (m, 1H), 7.63 (dd, J 8.4, 1.5 Hz, 1H), 7.48 (dd, J 8.8, 2.6 Hz, 1H), 7.35 (t, J 72, 76 Hz, 1H), 7.33 (m, 1H), 7.26 (m, 1H), 6.83 (d, J 2.5 Hz, 1H), 5.56 (s, 2H), 2.77 (m, 1H), 2.50 (s, 3H), 2.49 (m, 4H), 2.11 (m, 1H), 1.72 (m, 1H). LCMS (pH 10) MH+ 526, RT 1.32 minutes.

Example 545

Sodium 4-[5-(1-{[2-(difluoromethoxy)phenyl]methyl}-5-fluoro-2-methylbenzimidazol-6-yl)pyrimidin-2-yl]cyclohexanecarboxylate Intermediate 79 (0.1 g, 0.186 mmol) was dissolved in MeOH (5 mL) and sodium methoxide (2 equivalents) in methanol was added. The clear solution was stirred at 60° C. overnight, then left stirring at the same temperature for a further 24 h. Water (1 mL) was added and stirred at the same temperature for 1 h. The reaction mixture was concentrated and freeze-dried. The white lyophilised solid was dissolved in water, then loaded onto a C$_{18}$ column and eluted with water, 10%, 20% and finally 30% MeOH. The pure fractions were concentrated and freeze-dried to give the title compound (61 mg, 60%) as a white lyophilised solid. The ratio of the two isomers was 3:1. $\delta_H$ (400 MHz, DMSO-d$_6$) 8.88 (m, 2H), 7.78 (m, 1H), 7.57 (m, 1H), 7.38 (m, 1H), 7.26 (m, 1H), 7.32 (t, J 72, 76 Hz, 1H), 7.16 (m, 1H), 6.79 (m, 1H), 5.55 (s, 2H), 2.77 (m, 1H), 2.50 (s, 3H), 2.07 (m, 1H), 1.94 (m, 3H), 1.83 (m, 1H), 1.56 (m, 2H), 1.39 (m, 2H). LCMS (pH 10) MH+ 511, RT 1.72 minutes (major isomer) and RT 2.01 minutes (minor isomer).

Example 546

Sodium 4-[5-(1-{[2-(difluoromethoxy)phenyl]methyl}-2-methylbenzimidazol-6-yl)-pyrimidin-2-yl]cyclohexanecarboxylate Intermediate 81 (130 mg, 0.257 mmol) was dissolved in MeOH (2 mL) and sodium methoxide (2 equivalents) was added and stirred at 70° C. for 44 h. The reaction mixture was concentrated to remove MeOH, diluted with water and washed with diethyl ether. The aqueous layer was freeze-dried. The lyophilised solid was dissolved in water and applied to RP column chromatography (40% MeOH). The isolated clean material was concentrated and freeze-dried to give the title compound (98 mg, 74%) as a white lyophilised solid. $\delta_H$ (400 MHz, DMSO-d$_6$) 8.99 (m, 2H), 7.88 (d, J 0.8 Hz, 1H), 7.69 (m, 1H), 7.56 (m, 1H), 7.38 (m, 1H), 7.35 (t, J 72, 76 Hz, 1H), 7.27 (m, 1H), 7.16 (m, 1H), 6.79 (d, J 7.1 Hz, 1H), 5.56 (s, 2H), 2.78 (m, 1H), 2.50 (s, 3H), 1.98 (m, 4H), 1.82 (m, 1H), 1.57 (m, 2H), 1.40 (m, 2H). LCMS (pH 10) MH+ 493, RT 1.58 and 1.94 minutes.

Example 547

Sodium (1S,6R)-3-[5-(1-{[2-(difluoromethoxy)phenyl]methyl}-2-methylbenzimidazol-6-yl)pyrimidin-2-yl]-3-azabicyclo[4.1.0]heptane-1-carboxylate A mixture of Intermediate 82 (134 mg, 0.25 mmol) and sodium hydroxide (10 mg, 0.25 mmol) in THF-MeOH-water (1:1:1; 6 mL) was stirred at 60° C. for 2 h. The reaction mixture was concentrated, diluted with water, and washed with diethyl ether. The aqueous layer was freeze-dried to give the title compound (0.135 g, 98%) as a white lyophilised solid. $\delta_H$ (400 MHz, DMSO-$d_6$) 8.35 (s, 2H), 7.42 (s, 1H), 7.35 (m, 1H), 7.15 (m, 2H), 7.10 (t, J 72, 76 Hz, 1H), 7.01 (d, J 8.1 Hz, 1H), 6.92 (m, 1H), 6.54 (m, 1H), 5.27 (m, 2H), 3.96 (m, 2H), 3.40 (m, 1H), 3.05 (m, 1H), 2.5 (s, 3H), 1.72 (m, 1H), 1.47 (m, 1H), 1.12 (m, 1H), 0.67 (m, 1H), −0.04 (m, 1H). LCMS (pH 10) MH+ 506, RT 1.17 minutes.

Example 548

Sodium (1R,5R)-3-[5-[1-[[2-(difluoromethoxy)phenyl]methyl]-2-methylbenzimidazol-6-yl]pyrimidin-2-yl]-3-azabicyclo[3.1.0]-hexane-1-carboxylate Intermediate 83 (0.24 g, 0.47 mmol) was dissolved in THF-MeOH-water (1:1:1; 4 mL), sodium hydroxide (21 mg, 0.47 mmol) was added and the mixture was stirred at 70° C. for 2 h. The clear solution was concentrated, diluted with water and washed with EtOAc. The aqueous layer was freeze-dried to give the title compound (0.23 g, 95%) as a white solid. $\delta_H$ (400 MHz, DMSO-$d_6$) 8.61 (s, 2H), 7.66 (s, 1H), 7.60 (m, 1H), 7.38 (m, 2H), 7.35 (t, J 74 Hz, 1H), 7.27 (d, J 8.1 Hz, 1H), 7.16 (m, 1H), 6.80 (d, J 7.5 Hz, 1H), 5.52 (s, 2H), 3.87 (m, 1H), 3.74 (m, 2H), 3.52 (dd, J 11.1, 4.4 Hz, 1H), 2.50 (s, 3H), 1.68 (m, 1H), 1.31 (m, 1H), 0.33 (m, 1H). LCMS (pH 10) MH+ 492, RT 1.53 minutes.

Example 549

(1R,5S,8r)-3-[5-(1-{[2-(difluoromethoxy)phenyl]methyl}-5-fluoro-2-methylbenzimidazol-6-yl)pyrimidin-2-yl]-3-azabicyclo[3.2.1]octane-8-carboxylic acid Intermediate 86 (365 mg, 0.66 mmol) was dissolved in THF (10 mL) and water (5 mL). Lithium hydroxide monohydrate (111 mg, 2.65 mmol) was added and the mixture was stirred at r.t. for 6 h. The mixture was partitioned between water (50 mL) and EtOAc (50 mL) and the phases were separated. The aqueous layer was acidified to pH 3-4 with 2M HCl. A precipitate formed and was filtered, to afford the title compound (182 mg, 51%) as an off-white solid. $\delta_H$ (300 MHz, $d_6$-DMSO) 12.20 (1H, s), 8.50 (2H, d, J 1.7 Hz), 7.61-7.56 (1H, m), 7.48 (1H, d, J 11.3 Hz), 7.41-7.34 (1H, m), 7.32 (1H, t, J 73.9 Hz), 7.27-7.22 (1H, m), 7.18-7.13 (1H, m), 6.81-8.78 (1H, s), 5.51 (2H, s), 4.45-4.40 (2H, m), 3.28 (3H, s), 3.03-2.99 (2H, m), 2.66 (1H, s), 2.59 (2H, br s), 1.71-1.66 (2H, m), 1.42-1.36 (2H, m). LCMS (pH 10): MH+ m/z 538, RT 1.98 minutes (100%). LCMS (pH 3): MH+ m/z 538, RT 2.14 minutes (100%).

Example 550

1-[5-(1-{[2-Chloro-6-(difluoromethoxy)phenyl]methyl}-2-methylbenzimidazol-6-yl)-pyrimidin-2-yl]-4-methylpiperidine-4-carboxylic acid To Intermediate 90 (258 mg, 0.642 mmol) was added [1,1'-bis(diphenyl-phosphino)ferrocene]dichloropalladium (II) (45.5 mg, 0.062 mmol) in a microwave vial and the reaction mixture was degassed under three cycles of vacuum and nitrogen. To the dry reaction materials were added 2M aqueous potassium carbonate solution (0.63 mL, 1.26 mmol) and Intermediate 89 (269 mg, 0.68 mmol) dissolved in THF (4 mL). The reaction mixture was degassed under three cycles of vacuum and nitrogen and was heated under microwave irradiation at 100° C. for 3 h. The reaction mixture was cooled to r.t. and left to stand overnight. The reaction mixture was partitioned between water (5 mL) and DCM (5 mL) and was filtered through a phase separation cartridge. The solution was concentrated in vacuo. The resulting material was purified by flash column chromatography on silica, using 50% EtOAc/isohexane to 100% EtOAc. To the resulting brown-coloured oil (187 mg, 0.328 mmol, 51%) were added THF (4 mL), water (1 mL) and lithium hydroxide monohydrate (66.5 mg, 1.585 mmol). The mixture was stirred at r.t. for 3 days. The reaction mixture was heated at 80° C. for 3 h. THF (4 mL) was added and the mixture was heated at 70° C. overnight. MeOH (1 mL) was added and the reaction mixture was heated at 70° C. for 3 h. The reaction mixture was cooled to r.t. and then acidified to pH 3 using 2M aqueous hydrochloric acid. The mixture was partitioned between EtOAc (20 mL) and water (20 mL). The aqueous layer was removed and the organic layer was washed with water (20 mL). The organic layer was separated, dried ($Na_2SO_4$), and filtered under reduced pressure. The solvent was removed in vacuo to yield a brown oil. The reaction mixture was purified by preparative HPLC to afford the title compound (40.9 mg, 23%) as a white solid which was freeze-dried from water/acetonitrile overnight. $\delta_H$ (300 MHz, DMSO-$d_6$) 8.49 (s, 2H), 7.60-7.01 (m, 7H), 5.58 (s, 2H), 4.26 (br d, J 13.4 Hz, 2H), 3.36-3.22 (m, 2H), 2.59 (s, 3H), 2.01 (br d, J 12.5 Hz, 2H), 1.39-1.24 (m, 2H), 1.16 (s, 3H). LCMS (pH 3): MH+ m/z 543, RT 1.80 minutes (94%). LCMS (pH 10): MH+ m/z 543, RT 1.99 minutes (97.8%).

Example 551

1-[5-(1-{[2-(Difluoromethoxy)phenyl]methyl}-2-methylbenzimidazol-6-yl)pyrimidin-2-yl]-4-methylpiperidine-4-carboxylic acid Prepared from Intermediate 47 and Intermediate 89 according to the procedure described for Example 550 to afford the title compound (57 mg) as a white solid. $\delta_H$ (300 MHz, DMSO-$d_6$) 8.64 (s, 2H), 7.67 (s, 1H), 7.59 (s, 1H), 7.41 (dd, J 8.4, 1.2 Hz, 1H), 7.38-7.32 (m, 1H), 7.36 (t, J 82.3 Hz, 1H), 7.26 (d, J 8.0 Hz, 1H), 7.15 (t, J 7.6 Hz, 1H), 6.79 (d, J 7.1 Hz, 1H), 5.52 (s, 2H), 4.24 (dt, J 14.0, 4.3 Hz, 2H), 3.36-3.24 (m, 2H), 2.49 (s, under DMSO peak, 3H), 2.05-1.94 (m, 2H), 1.42-1.29 (m, 2H), 1.16 (s, 3H). LCMS (pH 3): MH+ m/z 509, RT 1.64 minutes (100%). LCMS (pH 10): MH+ m/z 509, RT 1.27 minutes (100%).

Example 552

4-Methyl-1-[5-(2-methyl-1-{[2-methyl-5-(trifluoromethyl)thiazol-4-yl]methyl}-benzimidazol-6-yl)pyrimidin-2-yl]piperidine-4-carboxylic acid Prepared from Intermediate 91 and Intermediate 89 according to the procedure described for Example 550 to afford the title compound (30 mg) as a white solid. $\delta_H$ (300 MHz, DMSO-$d_6$) 12.35 (br s, 1H), 8.58 (s, 2H), 7.56 (d, J 1.3 Hz, 1H), 7.51 (d, J 8.4 Hz, 1H), 7.34 (dd, J 8.2, 1.7 Hz, 1H), 5.58 (s, 2H), 4.25-4.14 (m, 2H), 3.30-3.19 (m, 2H under water peak), 2.51 (d, J 0.7 Hz, 3H), 2.48 (s, 3H), 1.99-1.88 (m, 2H), 1.36-1.24 (m, 2H), 1.11 (s, 3H). LCMS (pH 3): MH+ m/z 532, RT 2.02 minutes (94%). LCMS (pH 10): MH+ m/z 532, RT 2.06 minutes (94%).

Example 553

(1S,5R)-3-[5-(1-{[5-Chloro-2-(difluoromethoxy) phenyl]methyl}-5-fluoro-2-methylbenzimidazol-6-yl)pyrimidin-2-yl]-3-azabicyclo[3.2.1]octane-8-carboxylic acid To a stirred solution of Intermediate 92 (487 mg, 0.83 mmol) in THF (20 mL) was added lithium hydroxide monohydrate (144 mg, 3.4318 mmol) in water (8 mL) and the reaction mixture was stirred at r.t. for 18 h. The reaction mixture was acidified with 2M aqueous HCl solution, diluted with water (10 mL), and extracted with EtOAc (7×25 mL). The combined organic layer was washed with brine (100 mL), dried ($Na_2SO_4$), filtered and concentrated in vacuo. The crude material was purified by column chromatography ($SiO_2$, 0-100% MeOH in DCM), and the resulting material was freeze-dried from acetonitrile/water, to give the title compound (105 mg, 22%) as an off-white solid. $\delta_H$ (DMSO-$d_6$) 12.03-12.61 (m, 1H), 8.51 (d, 2H, J 1.7 Hz), 7.64 (d, 1H, J 7.0 Hz), 7.49 (d, 1H, J 11.2 Hz), 7.47 (dd, 1H, J 8.8, 2.8 Hz), 7.32 (t, 1H, J 73.4 Hz), 7.29 (d, 1H, J 8.8 Hz), 6.83 (d, 1H, J 2.6 Hz), 5.51 (s, 2H), 4.43 (dd, 2H, J 12.9, 3.2 Hz), 3.01 (d, 2H, J 12.1 Hz), 2.56-2.65 (m, 3H), 2.48-2.53 (m, 3H) ($CH_3$ group under DMSO peak), 1.65-1.74 (m, 2H), 1.33-1.43 (m, 2H). LCMS (ES+) 573 (M+H)$^+$, RT 1.80 minutes.

Example 554

4-[5-(1-{[2-(Difluoromethoxy)phenyl]methyl}-2-methylbenzimidazol-6-yl)-4-methylpyridin-2-yl] thiomorpholine Intermediate 93 (840 mg, 2.03 mmol), triethylamine (0.57 mL, 4.06 mmol) and thiomorpholine (0.62 mL, 6.09 mmol) were dissolved in NMP (2.5 mL) and heated under microwave irradiation for 3 h at 200° C. The reaction mixture was diluted with water and extracted with ethyl acetate. The combined organic phase was washed with brine, dried over sodium sulphate, concentrated and reduced in vacuo. The crude material was purified by flash column chromatography (Biotage SNAP 50 g), eluting with 0-100% DCM/MeOH/$NH_3$ (9/1/0.1 v/v/v) in DCM. Further purification by preparative HPLC yielded the title compound (205 mg, 21%). $\delta_H$ (400 MHz, DMSO-$d_6$) 7.91 (s, 1H), 7.59 (d, J 8.2 Hz, 1H), 7.38 (t, J 7.4 Hz, 1H), 7.32 (t, J 74.0 Hz, 1H), 7.31 (s, 1H), 7.26 (d, J 8.1 Hz, 1H), 7.17 (t, J 7.6 Hz, 1H), 7.11 (dd, J 8.2, 1.1 Hz, 1H), 6.84 (d, J 7.3 Hz, 1H), 6.76 (s, 1H), 5.49 (s, 2H), 3.92 (m, 4H), 2.60 (m, 4H), 2.53 (s, 3H), 2.13 (s, 3H). LCMS (pH 3) MH+ m/z 481.8, RT 1.52 minutes. LCMS (pH 10) MH+ m/z 481.8, RT 2.33 minutes.

Example 555

4-[5-(1-{[2-(Difluoromethoxy)phenyl]methyl}-2-methylbenzimidazol-6-yl)-4-meth pyridin-2-yl]-1,4-thiazinane 1-oxide Example 554 (425 mg, 0.88 mmol) was dissolved in DCM (10 mL) and cooled to 0° C. 3-Chloroperoxybenzoic acid (228 mg, 1.32 mmol) was added and the reaction mixture was stirred for 90 minutes prior to quenching with a 5% sodium metabisulphite solution. The aqueous layer was extracted with DCM. The combined organic phase was washed with aqueous sodium bicarbonate solution, dried over sodium sulphate, filtered and concentrated in vacuo. Purification by flash column chromatography (Biotage SNAP 50 g, Isolera), eluting with 0-50% DCM/MeOH/$NH_3$ (9/1/0.1 v/v/v) in DCM, and subsequent concentration in vacuo, yielded the title compound (160 mg, 36%). $\delta_H$ (400 MHz, DMSO-$d_6$) 7.95 (s, 1H), 7.59 (d, J 8.3 Hz, 1H), 7.38 (t, J 7.7 Hz, 1H), 7.32 (t, J 73.9 Hz, 1H), 7.31 (s, 1H), 7.26 (d, J 8.1 Hz, 1H), 7.17 (t, J 7.7 Hz, 1H), 7.12 (d, J 8.2 Hz, 1H), 6.91 (s, 1H), 6.85 (d, J 7.5 Hz, 1H), 5.58 (s, 2H), 4.13 (m, 2H), 3.95 (m, 2H), 2.88 (m, 2H), 2.65 (m, 2H), 2.54 (s, 3H), 2.15 (s, 3H). LCMS (pH 3) MH+ m/z 497.6, RT 1.22 minutes. LCMS (pH10) MH+ m/z 497.8, RT 1.88 minutes.

Example 556

4-[5-(1-{[2-(Difluoromethoxy)phenyl]methyl}-2-methylbenzimidazol-6-yl)-4-methylpyridin-2-yl] piperazin-2-one Intermediate 93, triethylamine (0.23 mL, 1.65 mmol) and piperazin-2-one (246 mg, 2.46 mmol) were dissolved in NMP (2.5 mL) and heated at 200° C. under microwave irradiation for 5 h. A further equivalent of piperazin-2-one (82 mg, 0.82 mmol) was added and the reaction mixture was heated at 200° C. for a further 3 h. The reaction mixture was then diluted with water and extracted with ethyl acetate. The combined organic phase was washed with brine, dried over sodium sulphate, concentrated and reduced in vacuo. The crude product was purified by flash column chromatography (Biotage SNAP 50 g), eluting with 50-90% DCM/MeOH/$NH_3$ (9/1/0.1 v/v/v) in DCM. Concentration in vacuo yielded a yellow oil, to which was added water and acetonitrile. Filtration yielded the title compound (285 mg, 73%). $\delta_H$ (300 MHz, DMSO-$d_6$) 8.07 (br s, 1H), 7.92 (s, 1H), 7.58 (d, J 8.3 Hz, 1H), 7.37 (t, J 7.8 Hz, 1H), 7.32 (t, J 73.9 Hz, 1H), 7.31 (s, 1H), 7.24 (m, 1H), 7.16 (td, J 7.5, 1.0 Hz, 1H), 7.10 (dd, J 8.2, 1.6 Hz, 1H), 6.85 (dd, J 7.6, 1.3 Hz, 1H), 6.76 (s, 1H), 5.49 (s, 2H), 4.00 (s, 2H), 3.73 (m, 2H), 3.28 (m, 2H), 2.52 (s, 3H), 2.13 (s, 3H). LCMS (pH 3) MH+ m/z 478.8, RT 1.14 minutes. LCMS (pH 10) MH+ m/z 478.8, RT 1.67 minutes.

Example 557

4-[5-(1-{[2-(Difluoromethoxy)phenyl]methyl}-2-methylbenzimidazol-5-yl)-4-methylpyridin-2-yl] morpholine Intermediate 93 (680 mg, 1.64 mmol), triethylamine (0.46 mL, 3.28 mmol) and morpholine (0.43 mL, 4.92 mmol) were dissolved in NMP (2.5 mL) and heated at 200° C. under microwave irradiation for 5 h. The reaction mixture was then diluted with water and extracted with ethyl acetate. The combined organic phase was washed with brine, dried over sodium sulphate, concentrated and reduced in vacuo. Purification by preparative HPLC yielded the title compound (490 mg, 64%). $\delta_H$ (300 MHz, DMSO-$d_6$) 7.92 (s, 1H), 7.58 (d, J 8.4 Hz, 1H), 7.37 (m, 1H), 7.31 (t, J 74.1 Hz, 1H), 7.30 (d, J 1.1 Hz, 1H), 7.24 (m, 1H), 7.16 (td, J 7.6, 1.1 Hz, 1H), 7.09 (dd, J 8.2, 1.6 Hz, 1H), 6.84 (dd, J 7.6, 1.3 Hz, 1H), 6.75 (s, 1H), 5.49 (s, 2H), 3.70 (m, 4H), 3.43 (m, 4H), 2.53 (s, 3H), 2.12 (s, 3H). LCMS (pH 3) MH+ m/z 465.8, RT 1.38 minutes. LCMS (pH 10) MH+ m/z 465.8, RT 1.90 minutes.

Examples 558 to 615

The following compounds can be synthesized from 2-(difluoromethoxy)benzylamine and 4-bromo-2-fluoronitrobenzene following the synthetic sequence described in steps 1 and 2 of Intermediate 47, followed by cyclisation with the appropriate carboxylic acid in accordance with Method J and (except where the 6-substituent is bromo) subsequent reaction with the appropriate boronic acid or ester in accordance with Method L.

| Example | Compound Name | QC LCMS RT (min) | Mass Ion (M + H)+ |
|---|---|---|---|
| 558 | 5-{1-[2-(Difluoromethoxy)benzyl]-2-[(methylsulfonyl)methyl]-1H-benzimidazol-6-yl}pyridin-2(1H)-one | 1.18 | 460 |
| 559 | 5-{1-[2-(Difluoromethoxy)benzyl]-2-[(methylsulfinyl)methyl]-1H-benzimidazol-6-yl}pyridin-2(1H)-one | 1.11 | 444 |
| 560 | 6-Bromo-1-[2-(difluoromethoxy)benzyl]-2-[(1-oxidopyridin-4-yl)methyl]-1H-benzimidazole | 1.38 | 461 |
| 561 | 5-{1-[2-(Difluoromethoxy)benzyl]-2-[(2-oxo-piperidin-1-yl)methyl]-1H-benzimidazol-6-yl}-pyridin-2(1H)-one | 1.24 | 479 |
| 562 | 5-{2-(Cyclohexylmethyl)-1-[2-(difluoromethoxy)-benzyl]-1H-benzimidazol-6-yl}pyridin-2(1H)-one | 1.55 | 465 |
| 563 | 5-{1-[2-(Difluoromethoxy)benzyl]-2-(tetrahydro-2H-pyran-3-ylmethyl)-1H-benzimidazol-6-yl}pyridin-2(1H)-one | 1.32 | 466 |
| 564 | 5-{1-[2-(Difluoromethoxy)benzyl]-2-(2,2,2-trifluoro-ethyl)-1H-benzimidazol-6-yl}pyridin-2(1H)-one | 1.34 | 450 |
| 565 | 5-(2-{[(2-Chloropyridin-4-yl)oxy]methyl}-1-[2-(difluoromethoxy)benzyl]-1H-benzimidazol-6-yl)-pyridin-2(1H)-one | 1.35 | 509 and 511 |
| 566 | — | — | — |
| 567 | 5-(1-[2-(Difluoromethoxy)benzyl]-2-{[2-(pyridin-3-yl)-1,3-thiazol-4-yl]methyl}-1H-benzimidazol-6-yl)-pyridin-2(1H)-one | 1.31 | 542 |
| 568 | 5-(1-[2-(Difluoromethoxy)benzyl]-2-{[4-(pyrimidin-2-yl)piperazin-1-yl]methyl}-1H-benzimidazol-6-yl)-pyridin-2(1H)-one | 1.38 | 544 |
| 569 | 5-(1-[2-(Difluoromethoxy)benzyl]-2-{[4-(2-oxo-pyrrolidin-1-yl)phenoxy]methyl}-1H-benzimidazol-6-yl)pyridin-2(1H)-one | 1.33 | 557 |
| 570 | 5-{1-[2-(Difluoromethoxy)benzyl]-2-[(trifluoro-methoxy)methyl]-1H-benzimidazol-6-yl}pyridin-2(1H)-one | 1.39 | 466 |
| 571 | 1-[3-({6-Bromo-1-[2-(difluoromethoxy)benzyl]-1H-benzimidazol-2-yl}methoxy)phenyl]pyrrolidin-2-one | 1.59 | 542 and 544 |
| 572 | 1-[3-({1-[2-(Difluoromethoxy)benzyl]-6-[4-(pyrrolidin-1-ylmethyl)phenyl]-1H-benzimidazol-2-yl}methoxy)phenyl]pyrrolidin-2-one | 1.7 | 623 |
| 573 | 5-{1-[2-(Difluoromethoxy)benzyl]-2-[4-(methylsulfonyl)benzyl]-1H-benzimidazol-6-yl}pyridine-2-carboxamide | 1.89 | 563 |
| 574 | 1-[3-({1-[2-(Difluoromethoxy)benzyl]-6-(6-methoxypyridin-3-yl)-1H-benzimidazol-2-yl}-methoxy)phenyl]pyrrolidin-2-one | 2.52 | 571 |
| 575 | N-(5-{1-[2-(Difluoromethoxy)benzyl]-2-[4-(methylsulfonyl)benzyl]-1H-benzimidazol-6-yl}pyrimidin-2-yl)-N-methylmethanesulfonamide | 2.16 | 628 |
| 576 | 1-[2-(Difluoromethoxy)benzyl]-6-(6-methoxy-pyridin-3-yl)-2-[4-(methylsulfonyl)benzyl]-1H-benzimidazole | 2.35 | 550 |
| 577 | 1-[3-({1-[2-(Difluoromethoxy)benzyl]-6-[4-(methylsulfonyl)phenyl]-1H-benzimidazol-2-yl}methoxy)-phenyl]pyrrolidin-2-one | 1.5 | 618 |
| 578 | 1-[3-({1-[2-(Difluoromethoxy)benzyl]-6-(1-methyl-1H-pyrazol-4-yl)-1H-benzimidazol-2-yl}methoxy)-phenyl]pyrrolidin-2-one | 1.41 | 544 |
| 579 | 1-[2-(Difluoromethoxy)benzyl]-6-(1-methyl-1H-pyrazol-4-yl)-2-(pyridin-4-ylmethyl)-1H-benzimidazole | 1.31 | 446 |
| 580 | 5-{1-[2-(Difluoromethoxy)benzyl]-2-(pyridin-4-ylmethyl)-1H-benzimidazol-6-yl}pyridine-2-carboxamide | 1.28 | 489 |
| 581 | 1-[2-(Difluoromethoxy)benzyl]-6-[4-(methylsulfonyl)phenyl]-2-(pyridin-4-ylmethyl)-1H-benzimidazole | 1.38 | 520 |
| 582 | 5-(1-[2-(Difluoromethoxy)benzyl]-2-{[3-(2-oxo-pyrrolidin-1-yl)phenoxy]methyl}-1H-benzimidazol-6-yl)pyridine-2-carboxamide | 1.4 | 584 |

-continued

| Example | Compound Name | QC LCMS RT (min) | Mass Ion (M + H)+ |
|---|---|---|---|
| 583 | 1-[2-(Difluoromethoxy)benzyl]-2-[4-(methyl-sulfonyl)benzyl]-6-[4-(methylsulfonyl)phenyl]-1H-benzimidazole | 1.43 | 597 |
| 584 | 1-[2-(Difluoromethoxy)benzyl]-6-(1-methyl-1H-pyrazol-4-yl)-2-[4-(methylsulfonyl)benzyl]-1H-benzimidazole | 1.36 | 523 |
| 585 | 5-{1-[2-(Difluoromethoxy)benzyl]-2-[4-(methyl-sulfonyl)benzyl]-1H-benzimidazol-6-yl}-1-methyl-pyridin-2(1H)-one | 1.3 | 550 |
| 586 | 5-(1-[2-(Difluoromethoxy)benzyl]-2-{[3-(2-oxo-pyrrolidin-1-yl)phenoxy]methyl}-1H-benzimidazol-6-yl)-1-(difluoromethyl)pyridin-2(1H)-one | 1.5 | 607 |
| 587 | 5-(1-[2-(Difluoromethoxy)benzyl]-2-{[3-(2-oxo-pyrrolidin-1-yl)phenoxy]methyl}-1H-benzimidazol-6-yl)-1-methoxypyridin-2(1H)-one | 1.39 | 587 |
| 588 | 5-(1-[2-(Difluoromethoxy)benzyl]-2-{[3-(2-oxo-pyrrolidin-1-yl)phenoxy]methyl}-1H-benzimidazol-6-yl)-1-methylpyridin-2(1H)-one | 1.37 | 571 |
| 589 | 5-{1-[2-(Difluoromethoxy)benzyl]-2-[4-(methyl-sulfonyl)benzyl]-1H-benzimidazol-6-yl}-N-methyl-pyridine-2-carboxamide | 1.39 | 577 |
| 590 | 5-{1-[2-(Difluoromethoxy)benzyl]-2-[4-(methyl-sulfonyl)benzyl]-1H-benzimidazol-6-yl}-1-(difluoromethyl)pyridin-2(1H)-one | 1.43 | 586 |
| 591 | 1-[3-({1-[2-(Difluoromethoxy)benzyl]-6-[6-(trifluoromethyl)pyridin-3-yl]-1H-benzimidazol-2-yl}methoxy)phenyl]pyrrolidin-2-one | 1.66 | 609 |
| 592 | 1-[2-(Difluoromethoxy)benzyl]-2-[4-(methyl-sulfonyl)benzyl]-6-[6-(trifluoromethyl)pyridin-3-yl]-1H-benzimidazole | 1.59 | 588 |
| 593 | 1-[2-(Difluoromethoxy)benzyl]-2-[4-(methyl-sulfonyl)benzyl]-6-[3-(methylsulfonyl)phenyl]-1H-benzimidazole | 1.45 | 597 |
| 594 | 4-{1-[2-(Difluoromethoxy)benzyl]-2-[4-(methyl-sulfonyl)benzyl]-1H-benzimidazol-6-yl}-benzenesulfonamide | 1.37 | 598 |
| 595 | 1-[2-(Difluoromethoxy)benzyl]-2-[4-(methyl-sulfonyl)benzyl]-6-[6-(methylsulfonyl)pyridin-3-yl]-1H-benzimidazole | 1.39 | 598 |
| 596 | 2-(5-{1-[2-(Difluoromethoxy)benzyl]-2-[4-(methyl-sulfonyl)benzyl]-1H-benzimidazol-6-yl}pyrimidin-2-yl)propan-2-ol | 1.41 | 579 |
| 597 | 1-[2-(Difluoromethoxy)benzyl]-6-[4-(methyl-sulfinyl)phenyl]-2-[4-(methylsulfonyl)benzyl]-1H-benzimidazole | 1.36 | 581 |
| 598 | 1-[2-(Difluoromethoxy)benzyl]-6-[2-methyl-4-(methylsulfonyl)phenyl]-2-[4-(methylsulfonyl)-benzyl]-1H-benzimidazole | 1.46 | 611 |
| 599 | 5-{1-[2-(Difluoromethoxy)benzyl]-2-[4-(methyl-sulfonyl)benzyl]-1H-benzimidazol-6-yl}pyrimidin-2(1H)-one | 1.17 | 537 |
| 600 | N-(5-{1-[2-(Difluoromethoxy)benzyl]-2-[4-(methyl-sulfonyl)benzyl]-1H-benzimidazol-6-yl}pyrimidin-2-yl)-N-methylacetamide | 1.4 | 592 |
| 601 | 1-[2-(Difluoromethoxy)benzyl]-2-[4-(methyl-sulfonyl)benzyl]-6-[2-(methylsulfonyl)pyrimidin-5-yl]-1H-benzimidazole | 1.36 | 599 |
| 602 | 1-[2-(Difluoromethoxy)benzyl]-2-[3-methyl-4-(methylsulfonyl)benzyl]-6-[4-(methylsulfonyl)-phenyl]-1H-benzimidazole | 1.41 | 611 |
| 603 | N-(5-{1-[2-(Difluoromethoxy)benzyl]-2-(pyridin-4-ylmethyl)-1H-benzimidazol-6-yl}pyrimidin-2-yl)-N-methylmethanesulfonamide | 1.35 | 551 |
| 604 | 2-[3-Bromo-4-(methylsulfonyl)benzyl]-1-[2-(difluoromethoxy)benzyl]-6-[4-(methylsulfonyl)-phenyl]-1H-benzimidazole | 1.44 | 675 and 677 |
| 605 | 5-({1-[2-(Difluoromethoxy)benzyl]-6-[4-(methyl-sulfonyl)phenyl]-1H-benzimidazol-2-yl}methyl)-1-benzothiophen-3(2H)-one 1,1-dioxide | 1.29 | 623 |
| 606 | 5-{1-[2-(Difluoromethoxy)benzyl]-2-[4-(methyl-sulfonyl)benzyl]-1H-benzimidazol-6-yl}-1-methoxy-pyridin-2(1H)-one | 1.29 | 566 |

| Example | Compound Name | QC LCMS RT (min) | Mass Ion (M + H)+ |
|---|---|---|---|
| 607 | 1-[2-(Difluoromethoxy)benzyl]-2-[4-(methylsulfonyl)benzyl]-6-[2-(methylsulfonyl)pyridin-4-yl]-1H-benzimidazole | 1.39 | 598 |
| 608 | 5-{1-[2-(Difluoromethoxy)benzyl]-2-[4-(methylsulfonyl)benzyl]-1H-benzimidazol-6-yl}-3-methylpyridine-2-carboxamide | 1.33 | 577 |
| 609 | 1-[2-(Difluoromethoxy)benzyl]-2-[2-methyl-4-(methylsulfonyl)benzyl]-6-[4-(methylsulfonyl)phenyl]-1H-benzimidazole | 1.4 | 611 |
| 610 | 5-{1-[2-(Difluoromethoxy)benzyl]-2-[4-(methylsulfonyl)benzyl]-1H-benzimidazol-6-yl}-N,N-dimethylpyridine-2-carboxamide | 1.32 | 591 |
| 611 | 1-[2-(Difluoromethoxy)benzyl]-6-[3-methyl-4-(methylsulfonyl)phenyl]-2-[4-(methylsulfonyl)benzyl]-1H-benzimidazole | 1.47 | 611 |
| 612 | N-[5-(1-[2-(Difluoromethoxy)benzyl]-2-{[3-(2-oxopyrrolidin-1-yl)phenoxy]methyl}-1H-benzimidazol-6-yl)pyrimidin-2-yl]-N-methylmethanesulfonamide | 1.46 | 649 |
| 613 | 1-[2-(Difluoromethoxy)benzyl]-2-[3-(methylsulfonyl)benzyl]-6-[4-(methylsulfonyl)phenyl]-1H-benzimidazole | 1.39 | 597 |
| 614 | 1-[2-(Difluoromethoxy)benzyl]-6-[2-methyl-3-(methylsulfonyl)phenyl]-2-[4-(methylsulfonyl)benzyl]-1H-benzimidazole | 1.43 | 611 |
| 615 | 3-{1-[2-(Difluoromethoxy)benzyl]-2-[4-(methylsulfonyl)benzyl]-1H-benzimidazol-6-yl}-5,6-dihydro-7H-pyrrolo[3,4-b]pyridin-7-one | 1.26 | 575 |

Examples 616 to 625

The following compounds can be synthesized from 5-chloro-2-(difluoromethoxy)-benzylamine and 4-bromo-2-fluoronitrobenzene following the synthetic sequence described in steps 1 and 2 of Intermediate 47, followed by cyclisation with the appropriate carboxylic acid in accordance with Method J and subsequent reaction with the appropriate boronic acid in accordance with Method L.

Examples 626 to 645

The following compounds can be synthesized from (S)-1-(4-fluorophenyl)ethylamine and 4-bromo-2-fluoronitrobenzene or 4-cyano-2-fluoronitrobenzene following the synthetic sequence described in steps 1 and 2 of Intermediate 47, followed by cyclisation with the appropriate carboxylic acid in accordance with Method J and (except where the 6-substituent is bromo or cyano) reaction with the appropriate boronic acid or ester in accordance with Method L.

| Example | Compound Name | QC LCMS RT (min) | Mass Ion (M + H)+ |
|---|---|---|---|
| 616 | 1-[5-Chloro-2-(difluoromethoxy)benzyl]-2-[4-(methylsulfonyl)benzyl]-6-[4-(methylsulfonyl)phenyl]-1H-benzimidazole | 1.41 | 631 and 633 |
| 617 | 1-[5-Chloro-2-(difluoromethoxy)benzyl]-6-(1-methyl-1H-pyrazol-4-yl)-2-[4-(methylsulfonyl)benzyl]-1H-benzimidazole | 1.35 | 557 and 559 |
| 618 | 1-[5-Chloro-2-(difluoromethoxy)benzyl]-6-[4-(methylsulfonyl)phenyl]-2-(pyridin-4-ylmethyl)-1H-benzimidazole | 1.37 | 554 and 556 |
| 619 | 1-[3-({1-[5-Chloro-2-(difluoromethoxy)benzyl]-6-[4-(methylsulfonyl)phenyl]-1H-benzimidazol-2-yl}methoxy)phenyl]pyrrolidin-2-one | 1.48 | 652 and 654 |
| 620 | 5-{1-[5-Chloro-2-(difluoromethoxy)benzyl]-2-(pyridin-4-ylmethyl)-1H-benzimidazol-6-yl}pyridin-2(1H)-one | 1.19 | 492 and 494 |
| 621 | 1-[5-Chloro-2-(difluoromethoxy)benzyl]-6-(1-methyl-1H-pyrazol-4-yl)-2-(pyridin-4-ylmethyl)-1H-benzimidazole | 1.31 | 480 and 482 |
| 622 | 5-(1-[5-Chloro-2-(difluoromethoxy)benzyl]-2-{[3-(2-oxopyrrolidin-1-yl)phenoxy]methyl}-1H-benzimidazol-6-yl)pyridin-2(1H)-one | 1.32 | 591 and 593 |
| 623 | 5-{1-[5-Chloro-2-(difluoromethoxy)benzyl]-2-[4-(methylsulfonyl)benzyl]-1H-benzimidazol-6-yl}-pyridin-2(1H)-one | 1.24 | 570 and 572 |
| 624 | 1-[5-Chloro-2-(difluoromethoxy)benzyl]-2-methyl-6-(1-methyl-1H-pyrazol-4-yl)-1H-benzimidazole | 1.35 | 402 and 404 |
| 625 | 1-[3-({1-[5-Chloro-2-(difluoromethoxy)benzyl]-6-(1-methyl-1H-pyrazol-4-yl)-1H-benzimidazol-2-yl}methoxy)phenyl]pyrrolidin-2-one | 1.43 | 578 and 580 |

| Example | Compound Name | QC LCMS RT (min) | Mass Ion (M + H)+ |
|---|---|---|---|
| 626 | 3-[3-({6-Bromo-1-[(1S)-1-(4-fluorophenyl)ethyl]-1H-benzimidazol-2-yl}methoxy)phenyl]-1,3-oxazolidin-2-one | 1.6 | 510 and 512 |
| 627 | 3-[3-({1-[(1S)-1-(4-Fluorophenyl)ethyl]-6-(6-methoxypyridin-3-yl)-1H-benzimidazol-2-yl}-methoxy)phenyl]-1,3-oxazolidin-2-one | 1.57 | 539 |
| 628 | 6-Bromo-1-[(1S)-1-(4-fluorophenyl)ethyl]-2-[4-(methylsulfonyl)benzyl]-1H-benzimidazole | 1.58 | 487 and 489 |
| 629 | 1-[3-({6-Bromo-1-[(1S)-1-(4-fluorophenyl)ethyl]-1H-benzimidazol-2-yl}methoxy)phenyl]pyrrolidin-2-one | 1.66 | 508 and 510 |
| 630 | N-(5-{1-[(1S)1-(4-Fluorophenyl)ethyl]-2-methyl-1H-benzimidazol-6-yl}pyrimidin-2-yl)-N-methyl-methanesulfonamide | 2.06 | 440 |
| 631 | 5-(1-[(1S)-1-(4-Fluorophenyl)ethyl]-2-{[3-(2-oxo-pyrrolidin-1-yl)phenoxy]methyl}-1H-benzimidazol-6-yl)pyridin-2(1H)-one | 1.87 | 523 |
| 632 | 5-{1-[(1S)-1-(4-Fluorophenyl)ethyl]-2-[4-(methyl-sulfonyl)benzyl]-1H-benzimidazol-6-yl}pyridin-2(1H)-one | 1.64 | 502 |
| 633 | 5-{1-[(1S)1-(4-Fluorophenyl)ethyl]-2-methyl-1H-benzimidazol-6-yl}pyridin-2(1H)-one | 1.56 | 348 |
| 634 | N-[5-(1-[(1S)1-(4-Fluorophenyl)ethyl]-2-{[3-(2-oxopyrrolidin-1-yl)phenoxy]methyl}-1H-benzimidazol-6-yl)pyrimidin-2-yl]-N-methyl-methanesulfonamide | 2.37 | 615 |
| 635 | 1-[(1S)-1-(4-Fluorophenyl)ethyl]-6-(6-methoxy-pyridin-3-yl)-2-[4-(methylsulfinyl)benzyl]-1H-benzimidazole | 2.27 | 500 |
| 636 | 3-[4-({1-[(1S)-1-(4-Fluorophenyl)ethyl]-6-(6-methoxypyridin-3-yl)-1H-benzimidazol-2-yl}-methyl)phenyl]-1,3-oxazolidin-2-one | 2.41 | 523 |
| 637 | 1-[(1S)-1-(4-Fluorophenyl)ethyl]-2-[4-(methyl-sulfonyl)benzyl]-1H-benzimidazole-6-carbonitrile | 1.42 | 434 |
| 638 | 1-[(1S)-1-(4-Fluorophenyl)ethyl]-6-(6-methoxy-pyridin-3-yl)-2-[4-(methylsulfonyl)benzyl]-1H-benzimidazole | 1.52 | 516 |
| 639 | 1-[(1S)-1-(4-Fluorophenyl)ethyl]-2-(pyridin-4-yl-methyl)-1H-benzimidazole-6-carbonitrile | 1.35 | 357 |
| 640 | 1-[(1S)-1-(4-Fluorophenyl)ethyl]-2-{[3-(2-oxo-pyrrolidin-1-yl)phenoxy]methyl}-1H-benzimidazole-6-carbonitrile | 1.51 | 455 |
| 641 | 1-[3-({1-[(1S)-1-(4-Fluorophenyl)ethyl]-6-(6-methoxypyridin-3-yl)-1H-benzimidazol-2-yl}-methoxy)phenyl]pyrrolidin-2-one | 1.62 | 537 |
| 642 | 1-[(1S)-1-(4-Fluorophenyl)ethyl]-6-(6-methoxy-pyridin-3-yl)-2-(pyridin-4-ylmethyl)-1H-benzimidazole | 1.49 | 439 |
| 643 | 1-[(1S)-1-(4-Fluorophenyl)ethyl]-6-(1-methyl-1H-pyrazol-4-yl)-2-[4-(methylsulfonyl)benzyl]-1H-benzimidazole | 1.36 | 489 |
| 644 | 1-[(1S)-1-(4-Fluorophenyl)ethyl]-2-[4-(methyl-sulfonyl)benzyl]-6-[4-(methylsulfonyl)phenyl]-1H-benzimidazole | 1.38 | 563 |
| 645 | 5-(1-[(1S)-1-(4-Fluorophenyl)ethyl]-2-{[3-(2-oxo-1,3-oxazolidin-3-yl)phenoxy]methyl}-1H-benzimidazol-6-yl)pyridin-2(1H)-one | 1.28 | 525 |

Examples 646 to 648

The following compounds can be synthesized from 6-chloro-(2-difluoromethoxy)-benzylamine and 4-bromo-2-fluoronitrobenzene following the synthetic sequence described in steps 1 and 2 of Intermediate 47, followed by cyclisation with the appropriate carboxylic acid in accordance with Method J and reaction with the appropriate boronic acid or ester in accordance with Method L.

| Example | Compound Name | QC LCMS RT (min) | Mass Ion (M + H)+ |
|---|---|---|---|
| 646 | 1-[3-({1-[2-Chloro-6-(difluoromethoxy)benzyl]-6-(1-methyl-1H-pyrazol-4-yl)-1H-benzimidazol-2-yl}-methoxy)phenyl]pyrrolidin-2-one | 1.46 | 578 and 580 |
| 647 | 5-{1-[2-Chloro-6-(difluoromethoxy)benzyl]-2-methyl-1H-benzimidazol-6-yl}pyridin-2(1H)-one | 1.25 | 415 and 417 |

-continued

| Example | Compound Name | QC LCMS RT (min) | Mass Ion (M + H)+ |
|---|---|---|---|
| 648 | 5-(1-[2-Chloro-6-(difluoromethoxy)benzyl]-2-{[3-(2-oxopyrrolidin-1-yl)phenoxy]methyl}-1H-benzimidazol-6-yl)pyridin-2(1H)-one | 1.3 | 591 and 593 |

Examples 649 to 741

The following compounds can be synthesized by a sequence of steps corresponding to the preparation of Intermediate 34 followed by Method J, utilizing the appropriate boronic acid (except where the 6-substituent is bromo), the appropriate amine and the appropriate carboxylic acid. Examples 649, 687, 689, 690, 693, 695, 698-700, 702, 707 and 712-714 commence from 2-fluoronitrobenzene.

| Example | Compound Name | QC LCMS RT (min) | Mass Ion (M + H)+ |
|---|---|---|---|
| 649 | 1-Methyl-3-({2-[(pyridin-4-ylmethoxy)methyl]-1H-benzimidazol-1-yl}methyl)-1H-indazole | 1.97 | 384 |
| 650-669 | — | — | — |
| 670 | [6-Bromo-1-(1-phenylethyl)-1H-benzimidazol-2-yl]-methanol | 2.15 | 331 and 333 |
| 671 | 1-(1-Phenylethyl)-6-(1H-pyrazol-4-yl)-2-(pyridin-4-ylmethyl)-1H-benzimidazole | 1.78 | 380 |
| 672 | 6-(2-Fluoropyridin-3-yl)-1-(1-phenylethyl)-2-(pyridin-4-ylmethyl)-1H-benzimidazole | 2.34 | 409 |
| 673 | 6-(1H-Indol-6-yl)-1-(1-phenylethyl)-2-(pyridin-4-yl-methyl)-1H-benzimidazole | 2.62 | 429 |
| 674 | 1-(1-Phenylethyl)-2-(pyridin-4-ylmethyl)-6-(thiophen-3-yl)-1H-benzimidazole | 2.73 | 396 |
| 675 | 6-(6-Fluoropyridin-3-yl)-1-(1-phenylethyl)-2-(pyridin-4-ylmethyl)-1H-benzimidazole | 2.43 | 409 |
| 676 | 8-[1-(1-Phenylethyl)-2-(pyridin-4-ylmethyl)-1H-benzimidazol-6-yl]quinoline | 2.19 | 441 |
| 677 | 2-Methyl-5-[1-(1-phenylethyl)-2-(pyridin-4-yl-methyl)-1H-benzimidazol-6-yl]-2H-indazole | 2.09 | 444 |
| 678 | 6-(4-Methylthiophen-3-yl)-1-(1-phenylethyl)-2-(pyridin-4-ylmethyl)-1H-benzimidazole | 2.56 | 410 |
| 679 | 6-Bromo-1-(1-phenylethyl)-2-[2-(pyrazin-2-yl)-ethyl]-1H-benzimidazole | 2.52 | 408 |
| 680 | 2-Methyl-6-[1-(1-phenylethyl)-2-(pyridin-4-yl-methyl)-1H-benzimidazol-6-yl]-2H-indazole | 2.15 | 444 |
| 681 | 6-[3-(Morpholin-4-ylmethyl)phenyl]-1-(1-phenyl-ethyl)-2-(pyridin-4-ylmethyl)-1H-benzimidazole | 2.45 | 489 |
| 682 | 6-Bromo-2-[2-(1H-imidazol-1-yl)ethyl]-1-(1-phenyl-ethyl)-1H-benzimidazole | 2.31 | 395 and 397 |
| 683 | 6-(2,3-Dihydrothieno[3,4-b][1,4]dioxin-5-yl)-1-(2,5-dimethylbenzyl)-2-(pyridin-4-ylmethyl)-1H-benzimidazole | 2.61 | 468 |
| 684 | 1-{[6-Bromo-1-(1-phenylethyl)-1H-benzimidazol-2-yl]methyl}pyrimidin-2(1H)-one | 2.08 | 409 and 411 |
| 685 | 6-Bromo-1-(2,5-dichlorobenzyl)-2-(pyridin-4-yl-methyl)-1H-benzimidazole | 2.39 | 447 and 449 |
| 686 | 4-{[6-Bromo-1-(1-phenylethyl)-1H-benzimidazol-2-yl]methoxy}benzoe acid | 1.9 | 451 and 453 |
| 687 | 2-[1-(2,5-Dichlorobenzyl)-1H-benzimidazol-2-yl]-2-phenylethanol | 2.58 | 397, 399 and 401 |
| 688 | 6-Bromo-1-[(1R)-1-phenylethyl]-2-(pyridin-4-yl-methyl)-1H-benzimidazole | 2.28 | 392 and 394 |
| 689 | 1-(2,5-Dichlorobenzyl)-2-{[(1-methylpyrrolidin-3-yl)oxy]methyl}-1H-benzimidazole | 2.3 | 390, 392 and 394 |
| 690 | 1-(2,5-Dichlorobenzyl)-2-[(pyrrolidin-3-yloxy)-methyl]-1H-benzimidazole | 2.1 | 376, 378 and 400 |
| 691 | 1-(2,5-Dichlorobenzyl)-6-(pyridin-4-yl)-1H-benzimidazole | 2.05 | 354, 356 and 358 |
| 692 | 1-(2,5-Dichlorobenzyl)-6-(pyridin-4-yl)-2-(trifluoro-methyl)-1H-benzimidazole | 2.68 | 422, 424 and 426 |
| 693 | 4-({[1-(2,5-Dichlorobenzyl)-1H-benzimidazol-2-yl]-methoxy}methyl)-N,N-dimethylpyridin-2-amine | 2.6 | 441, 443 and 445 |
| 694 | 1-(2,5-Dichlorobenzyl)-6-(pyridin-4-yl)-2-({[6-(trifluoromethyl)pyridin-3-yl]oxy}methyl)-1H-benzimidazole | 2.57 | 529, 531 and 533 |
| 695 | 1-[(1R)-1-Phenylethyl]-2-[(pyridin-4-ylmethoxy)-methyl]-1H-benzimidazole | 2.14 | 343 |

-continued

| Example | Compound Name | QC LCMS RT (min) | Mass Ion (M + H)+ |
|---|---|---|---|
| 696 | N-(Cyanomethyl)-4-{[1-(2,5-dichlorobenzyl)-6-(pyridin-4-yl)-1H-benzimidazol-2-yl]methoxy}-benzamide | 1.61 | 542, 544 and 546 |
| 697 | 6-Bromo-2-{[(6-methoxypyridin-3-yl)oxy]methyl}-1-[(2-methyl-1,3-thiazol-4-yl)methyl]-1H-benzimidazole | 1.53 | 445 and 447 |
| 698 | [1-(5-Fluoro-2-methoxybenzyl)-1H-benzimidazol-2-yl]methanol | 1.88 | 287 |
| 699 | 1-(2,5-Dichlorobenzyl)-2-{[(6-methoxypyridin-3-yl)-oxy]methyl}-1H-benzimidazole | 1.66 | 414, 416 and 418 |
| 700 | 4-{[1-(2,5-Dichlorobenzyl)-1H-benzimidazol-2-yl]-methoxy}benzamide | 1.48 | 426, 428 and 430 |
| 701 | 5-{[6-Bromo-1-(2,5-dichlorobenzyl)-1H-benzimidazol-2-yl]methoxy}pyridine-2-carboxamide | 1.58 | 506, 508 and 510 |
| 702 | 5-{[1-(2,5-Dichlorobenzyl)-1H-benzimidazol-2-yl]-methoxy}pyridine-2-carboxamide | 1.47 | 427, 429 and 431 |
| 703 | 1-[(2-Methyl-1,3-thiazol-4-yl)methyl]-6-(1-oxido-pyridin-4-yl)-2-[(pyridin-3-yloxy)methyl]-1H-benzimidazole | 1.11 | 430 |
| 704 | 4-({1-[(2-Methyl-1,3-thiazol-4-yl)methyl]-6-(1-oxidopyridin-4-yl)-1H-benzimidazol-2-yl}methoxy)-benzamide | 1.07 | 472 |
| 705 | 4-({1-[(2-Methyl-1,3-thiazol-4-yl)methyl]-6-(pyrimidin-4-yl)-1H-benzimidazol-2-yl}methoxy)-benzamide | 1.19 | 457 |
| 706 | 1-[(2-Methyl-1,3-thiazol-4-yl)methyl]-2-[(pyridin-3-yloxy)methyl]-6-(pyrimidin-4-yl)-1H-benzimidazole | 1.23 | 415 |
| 707 | (1-{[1-Methyl-3-(trifluoromethyl)-1H-thieno[2,3-c]-pyrazol-5-yl]methyl}-1H-benzimidazol-2-yl)-methanol | 1.4 | 367 |
| 708 | 1-(2,6-Dimethylbenzyl)-6-(pyridin-4-yl)-2-[(pyridin-3-yloxy)methyl]-1H-benzimidazole | 1.24 | 421 |
| 709 | 3-{[1-(2,6-Dimethylbenzyl)-6-(pyridin-4-yl)-1H-benzimidazol-2-yl]methoxy}pyridine-2-carboxamide | 1.3 | 464 |
| 710 | {1-[(2-Methyl-1,3-thiazol-4-yl)methyl]-6-(pyridin-4-yl)-1H-benzimidazol-2-yl}methanol | 1.15 | 337 |
| 711 | 1-[(5-Methylisoxazol-3-yl)methyl]-6-(1-methyl-1H-pyrazol-4-yl)-2-(pyridin-4-ylmethyl)-1H-benzimidazole | 1.18 | 385 |
| 712 | {1-[5-Chloro-2-(difluoromethoxy)benzyl]-1H-benzimidazol-2-yl}methanol | 1.44 | 338 and 340 |
| 713 | 4-{[1-(2,5-Dichlorobenzyl)-1H-benzimidazol-2-yl]-methoxy}pyridine-2-carboxamide | 1.48 | 427, 429 and 431 |
| 714 | 1-(2,5-Dichlorobenzyl)-2-[(pyrimidin-5-yloxy)-methyl]-1H-benzimidazole | 1.43 | 385, 387 and 389 |
| 715 | 1-[(1R)-1-(4-Chlorophenyl)ethyl]-6-(6-methoxy-pyridin-3-yl)-2-methyl-1H-benzimidazole | 1.59 | 377 and 379 |
| 716 | 2-[(Cyclopropylmethoxy)methyl]-6-(6-methoxy-pyridin-3-yl)-1-[(1R)-1-phenylethyl]-1H-benzimidazole | 1.7 | 414 |
| 717 | 6-(6-Methoxypyridin-3-yl)-2-[4-(methylsulfonyl)-benzyl]-1-[(1R)-1-phenylethyl]-1H-benzimidazole | 1.55 | 498 |
| 718 | 6-(6-Methoxypyridin-3-yl)-1-[(1R)-1-phenylethyl]-2-(pyrazin-2-ylmethyl)-1H-benzimidazole | 1.5 | 422 |
| 719 | 2-[(3,5-Dimethyl-1H-pyrazol-4-yl)methyl]-6-(6-methoxypyridin-3-yl)-1-[(1R)-1-phenylethyl]-1H-benzimidazole | 1.48 | 438 |
| 720 | 2-(Ethoxymethyl)-6-(6-methoxypyridin-3-yl)-1-[(1R)-1-phenylethyl]-1H-benzimidazole | 1.62 | 388 |
| 721 | 6-(6-Methoxypyridin-3-yl)-2-[(2-methyl-1,3-thiazol-4-yl)methyl]-1-[(1R)-1-phenylethyl]-1H-benzimidazole | 1.62 | 441 |
| 722 | 6-(6-Methoxypyridin-3-yl)-2-[(2-methyl-1H-imidazol-1-yl)methyl]-1-[(1R)-1-phenylethyl]-1H-benzimidazole | 1.45 | 424 |
| 723 | 6-(6-Methoxypyridin-3-yl)-1-[(1R)-1-phenylethyl]-2-(pyridin-4-ylmethyl)-1H-benzimidazole | 1.5 | 421 |
| 724 | 6-(6-Methoxypyridin-3-yl)-2-{[3-(methylsulfonyl)-phenoxy]methyl}-1-[(1S)-1-phenylethyl]-1H-benzimidazole | 1.61 | 514 |
| 725 | 1-[3-({6-(6-Methoxypyridin-3-yl)-1-[(1R)-1-phenyl-ethyl]-1H-benzimidazol-2-yl}methoxy)phenyl]-pyrrolidin-2-one | 1.64 | 519 |
| 726 | 6-({6-(6-Methoxypyridin-3-yl)-1-[(1S)-1-phenyl-ethyl]-1H-benzimidazol-2-yl}methoxy)-3,4-dihydro-quinolin-2(1H)-one | 1.55 | 505 |

-continued

| Example | Compound Name | QC LCMS RT (min) | Mass Ion (M + H)+ |
|---|---|---|---|
| 727 | 6-(6-Methoxypyridin-3-yl)-2-[4-(methylsulfonyl)benzyl]-1-[(1S)-1-phenylethyl]-1H-benzimidazole | 1.51 | 498 |
| 728 | 6-({6-(6-Methoxypyridin-3-yl)-1-[(1S)-1-phenylethyl]-1H-benzimidazol-2-yl}methoxy)-2,3-dihydro-1H-isoindol-1-one | 1.5 | 491 |
| 729 | 6-(6-Methoxypyridin-3-yl)-1-[(1S)-1-phenylethyl]-2-[4-(1H-tetrazol-1-yl)benzyl]-1H-benzimidazole | 1.57 | 488 |
| 730 | 6-(6-Methoxypyridin-3-yl)-1-[(1S)-1-phenylethyl]-2-(pyrazin-2-ylmethyl)-1H-benzimidazole | 1.5 | 422 |
| 731 | 1-[3-({6-(6-Methoxypyridin-3-yl)-1-[(1S)-1-phenylethyl]-1H-benzimidazol-2-yl}methoxy)phenyl]pyrrolidin-2-one | 1.64 | 519 |
| 732 | 6-(6-Methoxypyridin-3-yl)-2-[3-(methylsulfonyl)benzyl]-1-[(1S)-1-phenylethyl]-1H-benzimidazole | 1.56 | 498 |
| 733 | 2-[(Difluoromethoxy)methyl]-6-(6-methoxypyridin-3-yl)-1-[(1S)-1-phenylethyl]-1H-benzimidazole | 1.62 | 410 |
| 734 | 4-({6-(6-Methoxypyridin-3-yl)-1-[(1S)-1-phenylethyl]-1H-benzimidazol-2-yl}methyl)-1,3-thiazol-2-amine | 1.48 | 442 |
| 735 | 3-Fluoro-5-({6-(6-methoxypyridin-3-yl)-1-[(1S)-1-phenylethyl]-1H-benzimidazol-2-yl}methoxy)pyridine-2-carboxamide | 1.46 | 498 |
| 736 | 6-(6-Methoxypyridin-3-yl)-2-[(2-methyl-1H-imidazol-1-yl)methyl]-1-[(1S)-1-phenylethyl]-1H-benzimidazole | 1.46 | 424 |
| 737 | 6-(6-Methoxypyridin-3-yl)-2-[(2-methyl-1,3-thiazol-4-yl)methyl]-1-[(1S)-1-phenylethyl]-1H-benzimidazole | 1.61 | 441 |
| 738 | 6-(6-Methoxypyridin-3-yl)-2-{[(5-methylisoxazol-3-yl)oxy]methyl}-1-[(1S)-1-phenylethyl]-1H-benzimidazole | 2.51 | 441 |
| 739 | 5-({6-(6-Methoxypyridin-3-yl)-1-[(1S)-1-phenylethyl]-1H-benzimidazol-2-yl}methoxy)pyridin-2(1H)-one | 1.42 | 453 |
| 740 | 2-[(Cyclopropylmethoxy)methyl]-6-(6-methoxypyridin-3-yl)-1-[(1S)-1-phenylethyl]-1H-benzimidazole | 1.73 | 414 |
| 741 | 2-(Ethoxymethyl)-6-(6-methoxypyridin-3-yl)-1-[(1S)-1-phenylethyl]-1H-benzimidazole | 1.68 | 388 |

Examples 742 to 768

Examples 742, 748-750 and 757-768 can be synthesized from Intermediate 17 by cyclisation with the appropriate carboxylic acid according to Method J and subsequent reaction with the appropriate boronic acid or ester in accordance with Method L.

Examples 743-747 and 751-756 can be synthesized from Intermediate 6 or Intermediate 9, as appropriate, by cyclisation with the appropriate carboxylic acid according to Method J.

| Example | Compound Name | QC LCMS RT (min) | Mass Ion (M + H)+ |
|---|---|---|---|
| 742 | 1-(2,5-Dimethylbenzyl)-6-(1-methyl-1H-pyrazol-4-yl)-2-(pyridin-4-ylmethyl)-1H-benzimidazole | 2.17 | 408 |
| 743 | 1-(2,5-Dimethylbenzyl)-2-[(pyridin-2-ylsulfanyl)methyl]-1H-benzimidazole | 2.61 | 360 |
| 744 | 3-(4-{[1-(2,5-Dimethylbenzyl)-1H-benzimidazol-2-yl]methyl}piperazin-1-yl)phenol | 2.53 | 427 |
| 745 | 2-{[(2,3-Difluorobenzyl)oxy]methyl}-1-(2,5-dimethylbenzyl)-1H-benzimidazole | 2.88 | 393 |
| 746 | 2-[2-(4-Chlorophenoxy)ethyl]-1-(1-phenylethyl)-1H-benzimidazole | 2.89 | 377 |
| 747 | 2-({[1-(2,5-Dimethylbenzyl)-1H-benzimidazol-2-yl]methyl}sulfanyl)-1,3-benzoxazole | 2.88 | 400 |
| 748 | 8-[1-(2,5-Dimethylbenzyl)-2-(pyridin-4-ylmethyl)-1H-benzimidazol-6-yl]quinoline | 2.87 | 455 |
| 749 | 1-{3-[1-(2,5-Dimethylbenzyl)-2-(pyridin-4-ylmethyl)-1H-benzimidazol-6-yl]phenyl}ethanone | 2.74 | 446 |
| 750 | 1-(2,5-Dimethylbenzyl)-6-(1-methyl-1H-pyrazol-4-yl)-2-(trifluoromethyl)-1H-benzimidazole | 2.59 | 385 |

-continued

| Example | Compound Name | QC LCMS RT (min) | Mass Ion (M + H)+ |
|---|---|---|---|
| 751 | 2-[5-({[1-(2,5-Dimethylbenzyl)-1H-benzimidazol-2-yl]methyl}sulfanyl)-1H-tetrazol-1-yl]-N,N-dimethyl-ethanamine | 2.59 | 422 |
| 752 | 1-(2,5-Dimethylbenzyl)-2-[(pyridin-4-ylsulfanyl)-methyl]-1H-benzimidazole | 2.52 | 360 |
| 753 | 2-{[(2,5-Dimethylbenzyl)oxy]methyl}-1-(1-phenyl-ethyl)-1H-benzimidazole | 3.2 | 371 |
| 754 | 7-{[1-(1-Phenylethyl)-1H-benzimidazol-2-yl]-methoxy}quinoline | 2.64 | 380 |
| 755 | 2-Methyl-5-{[1-(1-phenylethyl)-1H-benzimidazol-2-yl]methoxy}-1,3-benzothiazole | 2.83 | 400 |
| 756 | 1-(2,5-Dimethylbenzyl)-2-[(pyridin-3-yloxy)methyl]-1H-benzimidazole | 2.45 | 344 |
| 757 | 1-(2,5-Dimethylbenzyl)-6-(2-fluoropyridin-3-yl)-2-(pyridin-4-ylmethyl)-1H-benzimidazole | 2.21 | 423 |
| 758 | 5-[1-(2,5-Dimethylbenzyl)-2-(pyridin-4-ylmethyl)-1H-benzimidazol-6-yl]pyridin-2-amine | 1.95 | 420 |
| 759 | 5-[1-(2,5-Dimethylbenzyl)-2-(pyridin-4-ylmethyl)-1H-benzimidazol-6-yl]pyrimidine-2,4(1H,3H)-dione | 1.54 | 438 |
| 760 | 1-(2,5-Dimethylbenzyl)-6-(1-methyl-1H-pyrazol-4-yl)-2-{[(2-methylpyridin-3-yl)oxy]methyl}-1H-benzimidazole | 2.23 | 438 |
| 761 | 1-(2,5-Dimethylbenzyl)-6-(1-methyl-1H-pyrazol-4-yl)-2-{[4-(pyridin-2-yl)piperazin-1-yl]methyl}-1H-benzimidazole | 2.67 | 492 |
| 762 | 3-{[1-(2,5-Dimethylbenzyl)-6-(1-methyl-1H-pyrazol-4-yl)-1H-benzimidazol-2-yl]methoxy}benzonitrile | 2.58 | 448 |
| 763 | N-Benzyl-1-[1-(2,5-dimethylbenzyl)-6-(1-methyl-1H-pyrazol-4-yl)-1H-benzimidazol-2-yl]-N-methyl-methanamine | 2.96 | 450 |
| 764 | 2-{[1-(2,5-Dimethylbenzyl)-6-(1-methyl-1H-pyrazol-4-yl)-1H-benzimidazol-2-yl]methyl}-1,2,3,4-tetrahydroisoquinoline | 2.99 | 462 |
| 765 | 1-[1-(2,5-Dimethylbenzyl)-6-(1-methyl-1H-pyrazol-4-yl)-1H-benzimidazol-2-yl]-N-methyl-N-(pyridin-2-ylmethyl)methanamine | 2.45 | 451 |
| 766 | 1-[1-(2,5-Dimethylbenzyl)-6-(1-methyl-1H-pyrazol-4-yl)-1H-benzimidazol-2-yl]-N-(furan-2-ylmethyl)-N-methylmethanamine | 2.71 | 440 |
| 767 | 1-(2,5-Dimethylbenzyl)-6-(1-methyl-1H-pyrazol-4-yl)-2-{[(1-oxidopyridin-3-yl)oxy]methyl}-1H-benzimidazole | 1.67 | 440 |
| 768 | 1-(2,5-Dimethylbenzyl)-6-(1-methyl-1H-pyrazol-4-yl)-2-{[(thiophen-2-ylmethyl)sulfanyl]methyl}-1H-benzimidazole | 2.66 | 459 |

Examples 769 to 773

The following compounds can be synthesized from Intermediate 18 and the appropriate boronic acid or ester in accordance with Method L.

| Example | Compound Name | QC LCMS RT (min) | Mass Ion (M + H)+ |
|---|---|---|---|
| 769 | [1-(2,5-Dimethylbenzyl)-6-(1H-indol-6-yl)-1H-benzimidazol-2-yl]methanol | 2.48 | 382 |
| 770 | [6-(2-Chlorophenyl)-1-(2,5-dimethylbenzyl)-1H-benzimidazol-2-yl]methanol | 2.8 | 376 and 378 |
| 771 | [1-(2,5-Dimethylbenzyl)-6-(thiophen-3-yl)-1H-benzimidazol-2-yl]methanol | 2.58 | 349 |
| 772 | 4-[1-(2,5-Dimethylbenzyl)-2-(hydroxymethyl)-1H-benzimidazol-6-yl]benzamide | 1.75 | 386 |
| 773 | 1-{3-[1-(2,5-Dimethylbenzyl)-2-(hydroxymethyl)-1H-benzimidazol-6-yl]phenyl}ethanone | 2.42 | 385 |

Examples 774 & 775

Example 774 can be synthesized from Intermediate 47 by treatment with the appropriate boronic acid in accordance with Method L.

Example 775 can be synthesized by a sequence of steps corresponding to the preparation of Intermediate 47 commencing from 3-bromo-2-fluoronitrobenzene and subsequent reaction with the appropriate boronic acid or ester in accordance with Method L.

| Example | Compound Name | QC LCMS RT (min) | Mass Ion (M + H)+ |
|---|---|---|---|
| 774 | 1-[2-(Difluoromethoxy)benzyl]-2-methyl-6-[3-(methylsulfonyl)phenyl]-1H-benzimidazole | 1.43 | 443 |
| 775 | 1-[2-(Difluoromethoxy)benzyl]-7-(6-methoxy-pyridin-2-yl)-2-methyl-1H-benzimidazole | 1.48 | 396 |

Example 776

The following compound can be synthesized by a sequence of steps corresponding to the preparation of Intermediate 47 commencing from 5-bromo-2-fluoronitrobenzene and subsequent reaction with the appropriate boronic acid or ester in accordance with Method L.

| Example | Compound Name | QC LCMS RT (min) | Mass Ion (M + H)+ |
|---|---|---|---|
| 776 | 4-(2-{1-[2-(Difluoromethoxy)benzyl]-2-methyl-1H-benzimidazol-5-yl}pyrimidin-5-yl)piperazin-2-one | 1.31 | 465 |

Examples 777 to 780

The following compounds can be synthesized from Intermediate 49 and the appropriate boronic acid or ester in accordance with Method L.

| Example | Compound Name | QC LCMS RT (min) | Mass Ion (M + H)+ |
|---|---|---|---|
| 777 | 1-[5-Chloro-2-(difluoromethoxy)benzyl]-2-methyl-6-[4-(methylsulfonyl)phenyl]-1H-benzimidazole | 1.44 | 476 and 478 |
| 778 | 4-{1-[5-Chloro-2-(difluoromethoxy)benzyl]-2-methyl-1H-benzimidazol-6-yl}benzenesulfonamide | 1.37 | 477 and 479 |
| 779 | 1-(5-{1-[5-Chloro-2-(difluoromethoxy)benzyl]-2-methyl-1H-benzimidazol-6-yl}pyrimidin-2-yl)-piperidine-4-carboxylic acid | 1.18 | 527 and 529 |
| 780 | 1-(5-{1-[5-Chloro-2-(difluoromethoxy)benzyl]-2-methyl-1H-benzimidazol-6-yl}pyrimidin-2-yl)-4-methylpiperidine-4-carboxylic acid | 1.19 | 541 and 543 |

Examples 781 to 784

The following compounds can be synthesized from Intermediate 75 and the appropriate boronic acid or ester in accordance with Method L.

| Example | Compound Name | QC LCMS RT (min) | Mass Ion (M + H)+ |
|---|---|---|---|
| 781 | 1-[5-Chloro-2-(difluoromethoxy)benzyl]-5-fluoro-2-methyl-6-[4-(methylsulfonyl)phenyl]-1H-benzimidazole | 1.46 | 494 and 496 |
| 782 | 4-{1-[5-Chloro-2-(difluoromethoxy)benzyl]-5-fluoro-2-methyl-1H-benzimidazol-6-yl}benzene-sulfonamide | 1.39 | 495 and 497 |
| 783 | 1-(5-{1-[5-Chloro-2-(difluoromethoxy)benzyl]-5-fluoro-2-methyl-1H-benzimidazol-6-yl}pyrimidin-2-yl)piperidine-4-carboxylic acid | 1.2 | 545 and 547 |
| 784 | 1-(5-{1-[5-Chloro-2-(difluoromethoxy)benzyl]-5-fluoro-2-methyl-1H-benzimidazol-6-yl}pyrimidin-2-yl)-4-methylpiperidine-4-carboxylic acid | 1.23 | 559 and 561 |

Examples 785 to 789

The following compounds can be synthesized from Intermediate 50 and the appropriate boronic acid or ester in accordance with Method L.

| Example | Compound Name | QC LCMS RT (min) | Mass Ion (M + H)+ |
|---|---|---|---|
| 785 | 1-[2-(Difluoromethoxy)benzyl]-5-fluoro-2-methyl-6-[2-(morpholin-4-yl)pyrimidin-5-yl]-1H-benzimidazole | 1.5 | 470 |
| 786 | 1-[2-(Difluoromethoxy)benzyl]-5-fluoro-2-methyl-6-{2-[4-(methylsulfonyl)piperazin-1-yl]pyrimidin-5-yl}-1H-benzimidazole | 1.47 | 547 |
| 787 | 1-(5-{1-[2-(Difluoromethoxy)benzyl]-5-fluoro-2-methyl-1H-benzimidazol-6-yl}pyrimidin-2-yl)-piperidine-4-carboxylic acid | 1.18 | 512 |
| 788 | 4-{1-[2-(Difluoromethoxy)benzyl]-5-fluoro-2-methyl-1H-benzimidazol-6-yl}benzenesulfonamide | 1.37 | 462 |
| 789 | 4-(5-{1-[2-(Difluoromethoxy)benzyl]-5-fluoro-2-methyl-1H-benzimidazol-6-yl}pyrimidin-2-yl)-piperazin-2-one | 1.31 | 483 |

Examples 790 to 800

Examples 790, 791 and 793-800 can be synthesized from Intermediate 47 and the appropriate boronic acid or ester in accordance with Method L.

Example 792 can be prepared by an analogous procedure.

| Example | Compound Name | QC LCMS RT (min) | Mass Ion (M + H)+ |
|---|---|---|---|
| 790 | 5-{1-[2-(Difluoromethoxy)benzyl]-2-methyl-1H-benzimidazol-6-yl}pyridine-2-carbaldehyde | 1.44 | 394 |
| 791 | N-(4-{1-[2-(Difluoromethoxy)benzyl]-2-methyl-1H-benzimidazol-6-yl}phenyl)prop-2-enamide | 1.49 | 434 |
| 792 | tert-Butyl {4-[1-(2,5-dimethylbenzyl)-2-methyl-1H-benzimidazol-6-yl]phenyl}carbamate | 1.75 | 442 |
| 793 | tert-Butyl (4-{1-[2-(difluoromethoxy)benzyl]-2-methyl-1H-benzimidazol-6-yl}phenyl)carbamate | 1.63 | 480 |
| 794 | (4-{1-[2-(Difluoromethoxy)benzyl]-2-methyl-1H-benzimidazol-6-yl}phenyl)(phenyl)methanone | 1.67 | 469 |
| 795 | 5-{1-[2-(Difluoromethoxy)benzyl]-2-methyl-1H-benzimidazol-6-yl}pyridine-2-carboxamide | 1.3 | 409 |
| 796 | 4-{1-[2-(Difluoromethoxy)benzyl]-2-methyl-1H-benzimidazol-6-yl}benzenesulfonamide | 1.35 | 444 |
| 797 | 5-{1-[2-(Difluoromethoxy)benzyl]-2-methyl-1H-benzimidazol-6-yl}-N-methylpyridine-2-carboxamide | 1.37 | 423 |
| 798 | 1-[2-(Difluoromethoxy)benzyl]-6-(3,5-dimethyl-isoxazol-4-yl)-2-methyl-1H-benzimidazole | 1.45 | 384 |
| 799 | 1-(5-{1-[2-(Difluoromethoxy)benzyl]-2-methyl-1H-benzimidazol-6-yl}pyrimidin-2-yl)piperidine-4-carboxylic acid | 1.19 | 494 |
| 800 | 1-[2-(Difluoromethoxy)benzyl]-2-methyl-6-[4-(methylsulfonyl)phenyl]-1H-benzimidazole | 1.39 | 443 |

Examples 801 to 840

The following compounds can be synthesized from Intermediate 65 and the appropriate amine in accordance with Method S.

| Example | Compound Name | QC LCMS RT (min) | Mass Ion (M + H)+ |
|---|---|---|---|
| 801 | 5-{1-[2-(Difluoromethoxy)benzyl]-2-methyl-1H-benzimidazol-6-yl}-N-(2-methoxyethyl)pyrimidin-2-amine | 1.38 | 440 |

-continued

| Example | Compound Name | QC LCMS RT (min) | Mass Ion (M + H)+ |
|---|---|---|---|
| 802 | 1-[2-(Difluoromethoxy)benzyl]-2-methyl-6-[2-(morpholin-4-yl)pyrimidin-5-yl]-1H-benzimidazole | 1.49 | 452 |
| 803 | 1-[2-(Difluoromethoxy)benzyl]-6-[2-(1,1-dioxido-thiomorpholin-4-yl)pyrimidin-5-yl]-2-methyl-1H-benzimidazole | 1.41 | 500 |
| 804 | [1-(5-{1-[2-(Difluoromethoxy)benzyl]-2-methyl-1H-benzimidazol-6-yl}pyrimidin-2-yl)piperidin-3-yl]-methanol | 1.45 | 480 |
| 805 | 3-[(5-{1-[2-(Difluoromethoxy)benzyl]-2-methyl-1H-benzimidazol-6-yl}pyrimidin-2-yl)amino]propan-1-ol | 1.28 | 440 |
| 806 | {1-[(5-{1-[2-(Difluoromethoxy)benzyl]-2-methyl-1H-benzimidazol-6-yl}pyrimidin-2-yl)amino]-cyclopentyl}methanol | 1.47 | 480 |
| 807 | 1-(5-{1-[2-(Difluoromethoxy)benzyl]-2-methyl-1H-benzimidazol-6-yl}pyrimidin-2-yl)piperidin-3-ol | 1.38 | 466 |
| 808 | 2-[(5-{1-[2-(Difluoromethoxy)benzyl]-2-methyl-1H-benzimidazol-6-yl}pyrimidin-2-yl)amino]ethanol | 1.26 | 426 |
| 809 | N'-(5-{1-[2-(Difluoromethoxy)benzyl]-2-methyl-1H-benzimidazol-6-yl}pyrimidin-2-yl)-N,N-dimethyl-ethane-1,2-diamine | 1.35 | 453 |
| 810 | 5-{1-[2-(Difluoromethoxy)benzyl]-2-methyl-1H-benzimidazol-6-yl}-N-[2-(morpholin-4-yl)ethyl]-pyrimidin-2-amine | 1.34 | 495 |
| 811 | Methyl N-(5-{1-[2-(difluoromethoxy)benzyl]-2-methyl-1H-benzimidazol-6-yl}pyrimidin-2-yl)-β-alaninate | 1.4 | 468 |
| 812 | (3S)-1-(5-{1-[2-(Difluoromethoxy)benzyl]-2-methyl-1H-benzimidazol-6-yl}pyrimidin-2-yl)-N,N-dimethylpyrrolidin-3-amine | 1.35 | 479 |
| 813 | 2-[4-(5-{1-[2-(Difluoromethoxy)benzyl]-2-methyl-1H-benzimidazol-6-yl}pyrimidin-2-yl)piperazin-1-yl]ethanol | 1.32 | 495 |
| 814 | (3R)-1-(5-{1-[2-(Difluoromethoxy)benzyl]-2-methyl-1H-benzimidazol-6-yl}pyrimidin-2-yl)-N,N-dimethylpyrrolidin-3-amine | 1.41 | 478 |
| 815 | 1-[(5-{1-[2-(Difluoromethoxy)benzyl]-2-methyl-1H-benzimidazol-6-yl}pyrimidin-2-yl)amino]-3-methoxy-2-methylpropan-2-ol | 1.38 | 484 |
| 816 | 5-{1-[2-(Difluoromethoxy)benzyl]-2-methyl-1H-benzimidazol-6-yl}-N-(pyrimidin-5-ylmethyl)-pyrimidin-2-amine | 1.33 | 474 |
| 817 | (2S)-2-[(5-{1-[2-(Difluoromethoxy)benzyl]-2-methyl-1H-benzimidazol-6-yl}pyrimidin-2-yl)-amino]propan-1-ol | 1.33 | 440 |
| 818 | 1-[(5-{1-[2-(Difluoromethoxy)benzyl]-2-methyl-1H-benzimidazol-6-yl}pyrimidin-2-yl)amino]-2-methyl-propan-2-ol | 1.34 | 454 |
| 819 | 1-[2-(Difluoromethoxy)benzyl]-6-[2-(4-methoxy-piperidin-1-yl)pyrimidin-5-yl]-2-methyl-1H-benzimidazole | 1.54 | 480 |
| 820 | 1-[2-(Difluoromethoxy)benzyl]-6-{2-[(2S)-2-(methoxymethyl)pyrrolidin-1-yl]pyrimidin-5-yl}-2-methyl-1H-benzimidazole | 1.55 | 480 |
| 821 | 2-Cyclopropyl-1-[(5-{1-[2-(difluoromethoxy)-benzyl]-2-methyl-1H-benzimidazol-6-yl}pyrimidin-2-yl)amino]propan-2-ol | 1.41 | 480 |
| 822 | 5-{1-[2-(Difluoromethoxy)benzyl]-2-methyl-1H-benzimidazol-6-yl}-N-[2-(1,3-thiazol-2-yl)ethyl]-pyrimidin-2-amine | 1.4 | 493 |
| 823 | 1-(5-{1-[2-(Difluoromethoxy)benzyl]-2-methyl-1H-benzimidazol-6-yl}pyrimidin-2-yl)piperidine-4-carboxamide | 1.32 | 493 |
| 824 | (2S)2-[(5-{1-[2-(Difluoromethoxy)benzyl]-2-methyl-1H-benzimidazol-6-yl}pyrimidin-2-yl)-amino]-4-(methylsulfanyl)butan-1-ol | 1.38 | 500 |
| 825 | 1-[2-(Difluoromethoxy)benzyl]-2-methyl-6-[2-(2-methylmorpholin-4-yl)pyrimidin-5-yl]-1H-benzimidazole | 1.52 | 466 |
| 826 | [1-(5-{1-[2-(Difluoromethoxy)benzyl]-2-methyl-1H-benzimidazol-6-yl}pyrimidin-2-yl)azetidin-3-yl]-methanol | 1.25 | 452 |
| 827 | 5-{1-[2-(Difluoromethoxy)benzyl]-2-methyl-1H-benzimidazol-6-yl}-N-ethylpyrimidin-2-amine | 1.41 | 410 |

-continued

| Example | Compound Name | QC LCMS RT (min) | Mass Ion $(M + H)^+$ |
|---|---|---|---|
| 828 | 5-{1-[2-(Difluoromethoxy)benzyl]-2-methyl-1H-benzimidazol-6-yl}-N-(5-methyl-1,3,4-thiadiazol-2-yl)pyrimidin-2-amine | 1.37 | 480 |
| 829 | 5-{1-[2-(Difluoromethoxy)benzyl]-2-methyl-1H-benzimidazol-6-yl}-N-(5-ethyl-1,3,4-oxadiazol-2-yl)-pyrimidin-2-amine | 1.3 | 478 |
| 830 | 4-{[(5-{1-[2-(Difluoromethoxy)benzyl]-2-methyl-1H-benzimidazol-6-yl}pyrimidin-2-yl)amino]-methyl}pyrrolidin-2-one | 1.24 | 479 |
| 831 | 5-{1-[2-(Difluoromethoxy)benzyl]-2-methyl-1H-benzimidazol-6-yl}-N-(1,3-thiazol-2-ylmethyl)-pyrimidin-2-amine | 1.38 | 479 |
| 832 | N-(5-{1-[2-(Difluoromethoxy)benzyl]-2-methyl-1H-benzimidazol-6-yl}pyrimidin-2-yl)-N-methylalanine | 1.13 | 467 |
| 833 | [(2S)-1-(5-{1-[2-(Difluoromethoxy)benzyl]-2-methyl-1H-benzimidazol-6-yl}pyrimidin-2-yl)-pyrrolidin-2-yl]methanol | 1.4 | 466 |
| 834 | N-(5-{1-[2-(Difluoromethoxy)benzyl]-2-methyl-1H-benzimidazol-6-yl}pyrimidin-2-yl)-N-methylglycine | 1.12 | 454 |
| 835 | 1-[2-(Difluoromethoxy)benzyl]-2-methyl-6-[2-(7-oxa-2-azaspiro[3.5]non-2-yl)pyrimidin-5-yl]-1H-benzimidazole | 1.39 | 492 |
| 836 | $N^1$-(5-{1-[2-(Difluoromethoxy)benzyl]-2-methyl-1H-benzimidazol-6-yl}pyrimidin-2-yl)-$N^2,N^2$,2-trimethylpropane-1,2-diamine | 1.43 | 481 |
| 837 | 6-[2-(1,1-Difluoro-5-azaspiro[2.4]hept-5-yl)-pyrimidin-5-yl]-1-[2-(difluoromethoxy)benzyl]-2-methyl-1H-benzimidazole | 1.58 | 498 |
| 838 | 5-{1-[2-(Difluoromethoxy)benzyl]-2-methyl-1H-benzimidazol-6-yl}-N-[(1-methyl-1H-pyrazol-4-yl)-methyl]pyrimidin-2-amine | 1.33 | 476 |
| 839 | cis-3-{[(5-{1-[2-(Difluoromethoxy)benzyl]-2-methyl-1H-benzimidazol-6-yl}pyrimidin-2-yl)-amino]methyl}cyclobutanol | 1.3 | 466 |
| 840 | 2-{(5-{1-[2-(Difluoromethoxy)benzyl]-2-methyl-1H-benzimidazol-6-yl}pyrimidin-2-yl)[2-(dimethyl-amino)ethyl]amino}ethanol | 1.29 | 497 |

Examples 841 to 859 tert-Butyl 4-[5-(4-acetamido-3-aminophenyl)pyridin-2-yl]piperazine-1-carboxylate (200 mg, 0.486 mmol) and the appropriate aldehyde were dissolved in dichloromethane, then sodium triacetoxyborohydride (155 mg, 0.729 mmol) was added portionwise. The reaction mixture was stirred at room temperature for several hours. Where necessary, sodium borohydride (45 mg, 1.189 mmol) was added and the mixture was stirred overnight. The reaction was then quenched with water. The layers were separated and the aqueous layer was extracted twice with DCM. The organic layer was dried over sodium sulphate and the solvent was removed in vacuo. The resulting material was dissolved in acetic acid (2 mL) and heated at 80° C. for 6 h, then evaporated to dryness. The crude material was purified by column chromatography over silica. The resulting material was then dissolved in dichloromethane and treated with 1M HCl in diethyl ether (2 mL). The solvents were removed in vacuo to afford the title compound as the hydrochloride salt.

| Example | Compound Name | QC LCMS RT (min) | Mass Ion $(M + H)^+$ |
|---|---|---|---|
| 841 | 2-Methyl-1-[1-(2-methyl-1,3-thiazol-4-yl)ethyl]-6-[6-(piperazin-1-yl)pyridin-3-yl]-1H-benzimidazole | 1.17 | 419 |
| 842 | 1-[(2,5-Dimethyl-1,3-thiazol-4-yl)methyl]-2-methyl-6-[6-(piperazin-1-yl)pyridin-3-yl]-1H-benzimidazole | 1.51 | 419 |
| 843 | 1-[2-(Difluoromethoxy)-6-fluorobenzyl]-2-methyl-6-[6-(piperazin-1-yl)pyridin-3-yl]-1H-benzimidazole | 1.83 | 468 |
| 844 | 1-[(5-Ethoxy-2-methyl-1,3-thiazol-4-yl)methyl]-2-methyl-6-[6-(piperazin-1-yl)pyridin-3-yl]-1H-benzimidazole | 1.56 | 449 |
| 845 | 1-[2-(Difluoromethoxy)-3-methoxybenzyl]-2-methyl-6-[6-(piperazin-1-yl)pyridin-3-yl]-1H-benzimidazole | 1.32 | 480 |
| 846 | 1-{(1R)-1-[5-Chloro-2-(difluoromethoxy)phenyl]-ethyl}-2-methyl-6-[6-(piperazin-1-yl)pyridin-3-yl]-1H-benzimidazole | 1.36 | 497 and 499 |
| 847 | 1-[2-(Difluoromethoxy)-5-methylbenzyl]-2-methyl-6-[6-(piperazin-1-yl)pyridin-3-yl]-1H-benzimidazole | 1.35 | 464 |

| Example | Compound Name | QC LCMS RT (min) | Mass Ion (M + H)+ |
|---|---|---|---|
| 848 | 1-{[6-(Difluoromethoxy)-1,3-benzodioxol-5-yl]-methyl}-2-methyl-6-[6-(piperazin-1-yl)pyridin-3-yl]-1H-benzimidazole | 1.29 | 494 |
| 849 | 1-{(1S)-1-[5-chloro-2-(difluoromethoxy)phenyl]-ethyl}-2-methyl-6-[6-(piperazin-1-yl)pyridin-3-yl]-1H-benzimidazole | 1.36 | 497 and 499 |
| 850 | 1-[2-(Difluoromethoxy)-5-methoxybenzyl]-2-methyl-6-[6-(piperazin-1-yl)pyridin-3-yl]-1H-benzimidazole | 1.34 | 480 |
| 851 | 1-[3-Bromo-2-(difluoromethoxy)benzyl]-2-methyl-6-[6-(piperazin-1-yl)pyridin-3-yl]-1H-benzimidazole | 1.38 | 528 and 530 |
| 852 | 1-[2-(Difluoromethoxy)-4-methoxybenzyl]-2-methyl-6-[6-(piperazin-1-yl)pyridin-3-yl]-1H-benzimidazole | 1.31 | 480 |
| 853 | 1-[3,5-Dichloro-2-(difluoromethoxy)benzyl]-2-methyl-6-[6-(piperazin-1-yl)pyridin-3-yl]-1H-benzimidazole | 1.43 | 518, 520 and 522 |
| 854 | 1-[2-Chloro-6-(trifluoromethoxy)benzyl]-2-methyl-6-[6-(piperazin-1-yl)pyridin-3-yl]-1H-benzimidazole | 1.44 | 501 and 503 |
| 855 | 1-[2-(Difluoromethoxy)-5-fluorobenzyl]-2-methyl-6-[6-(piperazin-1-yl)pyridin-3-yl]-1H-benzimidazole | 1.39 | 468 |
| 856 | 1-[2-(Difluoromethoxy)-3-fluorobenzyl]-2-methyl-6-[6-(piperazin-1-yl)pyridin-3-yl]-1H-benzimidazole | 1.4 | 468 |
| 857 | 1-[2-(Difluoromethoxy)-3,5-difluorobenzyl]-2-methyl-6-[6-(piperazin-1-yl)pyridin-3-yl]-1H-benzimidazole | 1.41 | 486 |
| 858 | 1-[2-Chloro-5-(difluoromethoxy)benzyl]-2-methyl-6-[6-(piperazin-1-yl)pyridin-3-yl]-1H-benzimidazole | 1.38 | 483 and 485 |
| 859 | 1-[2,5-Bis(difluoromethoxy)benzyl]-2-methyl-6-[6-(piperazin-1-yl)pyridin-3-yl]-1H-benzimidazole | 1.36 | 516 |

Examples 860 to 867

The following compounds can be synthesized from Intermediate 69 and the appropriate amidine in accordance with the experimental protocol described for Example 534.

| Example | Compound Name | QC LCMS RT (min) | Mass Ion (M + H)+ |
|---|---|---|---|
| 860 | 6-(2-Cyclopentyl-4-methylpyrimidin-5-yl)-1-[2-(difluoromethoxy)benzyl]-2-methyl-1H-benzimidazole | 1.63 | 449 |
| 861 | 1-[2-(Difluoromethoxy)benzyl]-2-methyl-6-[4-methyl-2-(tetrahydrofuran-2-yl)pyrimidin-5-yl]-1H-benzimidazole | 1.4 | 451 |
| 862 | 1-[2-(Difluoromethoxy)benzyl]-2-methyl-6-[4-methyl-2-(propan-2-yl)pyrimidin-5-yl]-1H-benzimidazole | 1.53 | 423 |
| 863 | 6-(2-Cyclopropyl-4-methylpyrimidin-5-yl)-1-[2-(difluoromethoxy)benzyl]-2-methyl-1H-benzimidazole | 1.49 | 421 |
| 864 | 1-[2-(Difluoromethoxy)benzyl]-6-[2-(methoxy-methyl)-4-methylpyrimidin-5-yl]-2-methyl-1H-benzimidazole | 1.32 | 425 |
| 865 | 1-[2-(Difluoromethoxy)benzyl]-2-methyl-6-[4-methyl-2-(2-methylpropyl)pyrimidin-5-yl]-1H-benzimidazole | 1.55 | 437 |
| 866 | 1-[2-(Difluoromethoxy)benzyl]-6-[2-(2-methoxy-ethyl)-4-methylpyrimidin-5-yl]-2-methyl-1H-benzimidazole | 1.37 | 439 |
| 867 | 1-[2-(Difluoromethoxy)benzyl]-2-methyl-6-[4-methyl-2-(morpholin-4-ylmethyl)pyrimidin-5-yl]-1H-benzimidazole | 1.31 | 480 |

Examples 868 to 882

The following compounds can be synthesized from Intermediate 40 and the appropriate carboxylic acid in accordance with Method J.

| Example | Compound Name | QC LCMS RT (min) | Mass Ion (M + H)+ |
|---|---|---|---|
| 868 | 1-({6-Cyano-1-[2-(difluoromethoxy)benzyl]-1H-benzimidazol-2-yl}methyl)piperidine-4-carboxamide | 1.32 | 440 |
| 869 | 1-[2-(Difluoromethoxy)benzyl]-2-[(2,6-dimethoxyphenoxy)methyl]-1H-benzimidazole-6-carbonitrile | 1.60 | 466 |
| 870 | 1-[2-(Difluoromethoxy)benzyl]-2-(pyrazin-2-ylmethyl)-1H-benzimidazole-6-carbonitrile | 1.36 | 392 |
| 871 | 1-[2-(Difluoromethoxy)benzyl]-2-[(propan-2-yloxy)methyl]-1H-benzimidazole-6-carbonitrile | 1.55 | 372 |
| 872 | 1-[2-(Difluoromethoxy)benzyl]-2-[(1S)-1-methoxyethyl]-1H-benzimidazole-6-carbonitrile | 1.47 | 358 |
| 873 | 1-[2-(Difluoromethoxy)benzyl]-2-({[6-(5-ethoxy-4H-1,2,4-triazol-3-yl)pyridin-3-yl]oxy}methyl)-1H-benzimidazole-6-carbonitrile | 1.4 | 518 |
| 874 | 1-[2-(Difluoromethoxy)benzyl]-2-{[(6-oxo-1,6-dihydropyridin-3-yl)oxy]methyl}-1H-benzimidazole-6-carbonitrile | 1.29 | 423 |
| 875 | 2-[(2-Amino-1,3-thiazol-4-yl)methyl]-1-[2-(trifluoromethoxy)benzyl]-1H-benzimidazole-6-carbonitrile | 1.46 | 430 |
| 876 | 1-[2-(Difluoromethoxy)benzyl]-2-{[(4-oxocyclohexyl)oxy]methyl}-1H-benzimidazole-6-carbonitrile | 1.46 | 426 |
| 877 | N-(2-{6-Cyano-1-[2-(difluoromethoxy)benzyl]-1H-benzimidazol-2-yl}ethyl)furan-3-carboxamide | 1.42 | 437 |
| 878 | 1-[2-(Difluoromethoxy)benzyl]-2-[(trifluoromethoxy)methyl]-1H-benzimidazole-6-carbonitrile | 1.57 | 398 |
| 879 | 1-[4-({6-Cyano-1-[2-(difluoromethoxy)benzyl]-1H-benzimidazol-2-yl}methyl)-1,3-thiazol-2-yl]-3-cyclopropylurea | 1.42 | 495 |
| 880 | 1-[2-(Difluoromethoxy)benzyl]-2-{[2-(2-oxopyrrolidin-1-yl)-1,3-thiazol-4-yl]methyl}-1H-benzimidazole-6-carbonitrile | 1.51 | 480 |
| 881 | 1-[2-(Difluoromethoxy)benzyl]-2-methyl-1H-benzimidazole-6-carbonitrile | 1.39 | 314 |
| 882 | 1-[2-(Difluoromethoxy)benzyl]-2-(pyridin-4-ylmethyl)-1H-benzimidazole-6-carbonitrile | 1.32 | 391 |

Examples 883 to 896

Under a nitrogen atmosphere, Intermediate 115 (0.102 mmol) was dissolved in degassed dry toluene (4 mL). BINAP (0.020 mmol), cesium carbonate (0.204 mmol), the appropriate amide, urea or sulphonamide (0.122 mmol) and palladium acetate (0.015 mmol) were added and the reaction mixture was heated at 90° C. for 18 h. The reaction mixture was evaporated in vacuo, suspended in water (2 mL) and extracted with DCM (2×4 mL). The organic layers were evaporated to dryness, dissolved in DMSO (1 mL), and purified by preparative mass-directed HPLC, to provide the title compound.

| Example | Compound Name | QC LCMS RT (min) | Mass Ion (M + H)+ |
|---|---|---|---|
| 883 | N-[5-({5-Fluoro-1-[(1S)-1-(4-fluorophenyl)ethyl]-6-(6-methoxypyridin-3-yl)-1H-benzimidazol-2-yl}methyl)pyridin-2-yl]acetamide | 1.51 | 514 |
| 884 | 1-[5-({5-Fluoro-1-[(1S)-1-(4-fluorophenyl)ethyl]-6-(6-methoxypyridin-3-yl)-1H-benzimidazol-2-yl}methyl)pyridin-2-yl]imidazolidin-2-one | 1.51 | 540 |
| 885 | 4-[5-({5-Fluoro-1-[(1S)-1-(4-fluorophenyl)ethyl]-6-(6-methoxypyridin-3-yl)-1H-benzimidazol-2-yl}methyl)pyridin-2-yl]morpholin-3-one | 1.55 | 556 |
| 886 | N-[5-({5-Fluoro-1-[(1S)-1-(4-fluorophenyl)ethyl]-6-(6-methoxypyridin-3-yl)-1H-benzimidazol-2-yl}methyl)pyridin-2-yl]-N-methylmethanesulfonamide | 1.60 | 564 |
| 887 | 3-[5-({5-Fluoro-1-[(1S)-1-(4-fluorophenyl)ethyl]-6-(6-methoxypyridin-3-yl)-1H-benzimidazol-2-yl}methyl)pyridin-2-yl]-1,3-oxazolidin-2-one | 1.58 | 542 |
| 888 | 1-[5-({5-Fluoro-1-[(1S)-1-(4-fluorophenyl)ethyl]-6-(6-methoxypyridin-3-yl)-1H-benzimidazol-2-yl}methyl)pyridin-2-yl]pyrrolidin-2-one | 1.6 | 528 |

| Example | Compound Name | QC LCMS RT (min) | Mass Ion (M + H)+ |
|---|---|---|---|
| 889 | N-[5-({5-Fluoro-1 -[(1S)-1-(4-fluorophenyl)ethyl]-6-(6-methoxypyridin-3-yl)-1H-benzimidazol-2-yl}-methyl)pyridin-2-yl]-N-methylacetamide | 1.51 | 528 |
| 890 | 2-{[6-(1,1-Dioxidoisothiazolidin-2-yl)pyridin-3-yl]-methyl}-5-fluoro-1-[(1S)-1-(4-fluorophenyl)ethyl]-6-(6-methoxypyridin-3-yl)-1H-benzimidazole | 1.57 | 576 |
| 891 | 1-[5-({5-Fluoro-1-[(1S)-1-(4-fluorophenyl)ethyl]-6-(6-methoxypyridin-3-yl)-1H-benzimidazol-2-yl}-methyl)pyridin-2-yl]azetidin-2-one | 1.56 | 526 |
| 892 | 6-[5-({5-Fluoro-1-[(1S)-1-(4-fluorophenyl)ethyl]-6-(6-methoxypyridin-3-yl)-1H-benzimidazol-2-yl}-methyl)pyridin-2-yl]-2-oxa-6-azaspiro[3.4]octan-7-one | 1.54 | 582 |
| 893 | 1-[5-({5-Fluoro-1-[(1S)-1-(4-fluorophenyl)ethyl]-6-(6-methoxypyridin-3-yl)-1H-benzimidazol-2-yl}-methyl)pyridin-2-yl]-5-(hydroxymethyl)pyrrolidin-2-one | 1.5 | 570 |
| 894 | 1-[5-({5-Fluoro-1-[(1S)-1-(4-fluorophenyl)ethyl]-6-(6-methoxypyridin-3-yl)-1H-benzimidazol-2-yl}-methyl)pyridin-2-yl]-5-methylpyrrolidin-2-one | 1.64 | 554 |
| 895 | 6-[5-({5-Fluoro-1-[(1S)-1-(4-fluorophenyl)ethyl]-6-(6-methoxypyridin-3-yl)-1H-benzimidazol-2-yl}-methyl)pyridin-2-yl]-6-azabicyclo[3.2.0]heptan-7-one | 1.66 | 566 |
| 896 | 1-[5-({5-Fluoro-1-[(1S)-1-(4-fluorophenyl)ethyl]-6-(6-methoxypyridin-3-yl)-1H-benzimidazol-2-yl}-methyl)pyridin-2-yl]-4-(hydroxymethyl)pyrrolidin-2-one | 1.49 | 570 |

Examples 897 to 904

Method T

To a stirred solution of 5-bromopyridine-2-carboxylic acid (0.2 g, 1.0 mmol) in DCM (5 mL) were added HATU (0.56 g, 1.4 mmol) and DIPEA (0.3 g, 2.9 mmol). The reaction mixture was stirred for 10 minutes at 0° C., followed by the addition of the appropriate amine (1.1 mmol). The reaction mass was stirred at 25-28° C. for 18 h, after which time the reaction mixture was diluted with DCM (50 mL) and washed with water (two portions of 30 mL). The organic layer was dried over $Na_2SO_4$ and concentrated under vacuum. The resulting material was utilised without further purification in a palladium-catalysed coupling reaction with Intermediate 57 in accordance with Method L.

| Example | Compound Name | QC LCMS RT (min) | Mass Ion (M + H)+ |
|---|---|---|---|
| 897 | (5-{1-[2-(Difluoromethoxy)benzyl]-2-methyl-1H-benzimidazol-6-yl}pyridin-2-yl)(thiomorpholin-4-yl)methanone | 1.43 | 495 |
| 898 | 5-{1-[2-(Difluoromethoxy)benzyl]-2-methyl-1H-benzimidazol-6-yl}-N,N-dimethylpyridine-2-carboxamide | 1.33 | 437 |
| 899 | (5-{1-[2-(Difluoromethoxy)benzyl]-2-methyl-1H-benzimidazol-6-yl}pyridin-2-yl)(morpholin-4-yl)methanone | 1.31 | 479 |
| 900 | (5-{1-[2-(Difluoromethoxy)benzyl]-2-methyl-1H-benzimidazol-6-yl}pyridin-2-yl)(4-methylpiperazin-1-yl)methanone | 1.29 | 492 |
| 901 | (5-{1-[2-(Difluoromethoxy)benzyl]-2-methyl-1H-benzimidazol-6-yl}pyridin-2-yl)(piperazin-1-yl)-methanone | 1.23 | 478 |
| 902 | (5-{1-[2-(Difluoromethoxy)benzyl]-2-methyl-1H-benzimidazol-6-yl}pyridin-2-yl)(1,1-dioxido-thiomorpholin-4-yl)methanone | 1.33 | 527 |
| 903 | 5-{1-[2-(Difluoromethoxy)benzyl]-2-methyl-1H-benzimidazol-6-yl}-N-(2-hydroxyethyl)pyridine-2-carboxamide | 1.3 | 453 |
| 904 | (5-{1-[2-(Difluoromethoxy)benzyl]-2-methyl-1H-benzimidazol-6-yl}pyridin-2-yl)[3-(hydroxymethyl)-azetidin-1-yl]methanone | 1.29 | 479 |

Examples 905 to 920

A suspension of the appropriate amide, urea or sulphonamide (0.150 mmol), Intermediate 65 or 110 (0.125 mmol), BINAP (0.025 mmol) and cesium carbonate (0.2 mmol) in toluene (5 mL) was degassed with argon while stirring for 15 minutes. Palladium(II) acetate (0.020 mmol) was added and the reaction mixture was heated at 90° C. for 18 h. The reaction mixture was washed with water (2×2 mL). The organic layer was evaporated in vacuo. The crude material was purified by preparative mass-directed HPLC to provide the title compound.

| Example | Compound Name | QC LCMS RT (min) | Mass Ion (M + H)+ |
|---|---|---|---|
| 905 | 1-(5-{1-[2-(Difluoromethoxy)benzyl]-2-methyl-1H-benzimidazol-6-yl}pyridin-2-yl)-4-methylpiperazin-2-one | 1.36 | 478 |
| 906 | 1-[2-(Difluoromethoxy)benzyl]-6-[6-(1,1-dioxido-isothiazolidin-2-yl)pyridin-3-yl]-2-methyl-1H-benzimidazole | 1.42 | 485 |
| 907 | 1-(5-{1-[2-(Difluoromethoxy)benzyl]-2-methyl-1H-benzimidazol-6-yl}pyridin-2-yl)pyrrolidin-2-one | 1.46 | 449 |
| 908 | N-(5-{1-[2-(Difluoromethoxy)benzyl]-2-methyl-1H-benzimidazol-6-yl}pyridin-2-yl)-N-methyl-methanesulfonamide | 1.46 | 473 |
| 909 | 1-(5-{1-[2-(Difluoromethoxy)benzyl]-2-methyl-1H-benzimidazol-6-yl}pyrimidin-2-yl)piperidin-2-one | 1.35 | 464 |
| 910 | 1-(5-{1-[2-(Difluoromethoxy)benzyl]-2-methyl-1H-benzimidazol-6-yl}pyrimidin-2-yl)imidazolidin-2-one | 1.35 | 450 |
| 911 | 1-(5-{1-[2-(Difluoromethoxy)benzyl]-2-methyl-1H-benzimidazol-6-yl}pyrimidin-2-yl)-5-methyl-pyrrolidin-2-one | 1.39 | 464 |
| 912 | N-(5-{1-[2-(Difluoromethoxy)benzyl]-2-methyl-1H-benzimidazol-6-yl}pyrimidin-2-yl)-N-methyl-acetamide | 1.39 | 438 |
| 913 | N-(5-{1-[2-(Difluoromethoxy)benzyl]-2-methyl-1H-benzimidazol-6-yl}pyridin-2-yl)acetamide | 1.35 | 423 |
| 914 | N-(5-{1-[2-(Difluoromethoxy)benzyl]-2-methyl-1H-benzimidazol-6-yl}pyrimidin-2-yl)-N-methyl-methanesulfonamide | 1.38 | 474 |
| 915 | N-(5-{1-[2-(Difluoromethoxy)benzyl]-2-methyl-1H-benzimidazol-6-yl}pyrimidin-2-yl)acetamide | 1.26 | 424 |
| 916 | 6-(5-{1-[2-(Difluoromethoxy)benzyl]-2-methyl-1H-benzimidazol-6-yl}pyridin-2-yl)-2-oxa-6-azaspiro-[3.4]octan-7-one | 1.36 | 491 |
| 917 | 4-(5-{1-[2-(Difluoromethoxy)benzyl]-2-methyl-1H-benzimidazol-6-yl}pyridin-2-yl)morpholin-3-one | 1.39 | 465 |
| 918 | 1-(5-{1-[2-(Difluoromethoxy)benzyl]-2-methyl-1H-benzimidazol-6-yl}pyrimidin-2-yl)pyrrolidin-2-one | 1.34 | 450 |
| 919 | 1-[2-(Difluoromethoxy)benzyl]-6-[2-(1,1-dioxido-isothiazolidin-2-yl)pyrimidin-5-yl]-2-methyl-1H-benzimidazole | 1.35 | 486 |
| 920 | 4-(5-{1-[2-(Difluoromethoxy)benzyl]-2-methyl-1H-benzimidazol-6-yl}pyrimidin-2-yl)morpholin-3-one | 1.3 | 466 |

Examples 921 to 934

A suspension of the appropriate amide or sulphonamide (0.250 mmol), Intermediate 109 (0.227 mmol), BINAP (0.045 mmol) and cesium carbonate (0.340 mmol) in toluene (5 mL) was degassed with argon while stirring for 15 minutes. Palladium(II) acetate (0.034 mmol) was added and the reaction mixture was heated at 90° C. for 18 h. The reaction mixture was washed with water (2×2 mL). The aqueous layers were combined and extracted with EtOAc (2×3 mL). The combined organic layers were washed with brine (2 mL) and evaporated in vacuo. The crude material was purified by preparative mass-directed HPLC to provide the title compound.

| Example | Compound Name | QC LCMS RT (min) | Mass Ion (M + H)+ |
|---|---|---|---|
| 921 | 1-[2-(Difluoromethoxy)benzyl]-2-[({2-[(3S)-3-hydroxy-2-oxopyrrolidin-1-yl]pyridin-4-yl}oxy)-methyl]-1H-benzimidazole-6-carbonitrile | 1.37 | 506 |
| 922 | 1-[2-(Difluoromethoxy)benzyl]-2-({[2-(2-methyl-5-oxopyrrolidin-1-yl)pyridin-4-yl]oxy}methyl)-1H-benzimidazole-6-carbonitrile | 1.52 | 504 |

-continued

| Example | Compound Name | QC LCMS RT (min) | Mass Ion (M + H)+ |
|---|---|---|---|
| 923 | 1-[2-(Difluoromethoxy)benzyl]-2-({[2-(4-methyl-2-oxopyrrolidin-1-yl)pyridin-4-yl]oxy}methyl)-1H-benzimidazole-6-carbonitrile | 1.54 | 504 |
| 924 | 1-[2-(Difluoromethoxy)benzyl]-2-({[2-(4-methyl-2-oxopiperazin-1-yl)pyridin-4-yl]oxy}methyl)-1H-benzimidazole-6-carbonitrile | 1.38 | 519 |
| 925 | N-[4-({6-Cyano-1-[2-(difluoromethoxy)benzyl]-1H-benzimidazol-2-yl}methoxy)pyridin-2-yl]acetamide | 1.39 | 464 |
| 926 | 1-[2-(Difluoromethoxy)benzyl]-2-({[2-(2-oxo-piperidin-1-yl)pyridin-4-yl]oxy}methyl)-1H-benzimidazole-6-carbonitrile | 1.41 | 504 |
| 927 | 1-[2-(Difluoromethoxy)benzyl]-2-[({2-[2-(hydroxy-methyl)-5-oxopyrrolidin-1-yl]pyridin-4-yl}oxy)-methyl]-1H-benzimidazole-6-carbonitrile | 1.39 | 520 |
| 928 | N-[4-({6-Cyano-1-[2-(difluoromethoxy)benzyl]-1H-benzimidazol-2-yl}methoxy)pyridin-2-yl]-N-methyl-methanesulfonamide | 1.48 | 514 |
| 929 | 1-[2-(Difluoromethoxy)benzyl]-2-({[2-(7-oxo-2-oxa-6-azaspiro[3.4]oct-6-yl)pyridin-4-yl]oxy}methyl)-1H-benzimidazole-6-carbonitrile | 1.42 | 532 |
| 930 | 1-[2-(Difluoromethoxy)benzyl]-2-({[2-(2-oxo-azetidin-1-yl)pyridin-4-yl]oxy}methyl)-1H-benzimidazole-6-carbonitrile | 1.44 | 476 |
| 931 | 1-[2-(Difluoromethoxy)benzyl]-2-({[2-(7-oxo-6-azabicyclo[3.2.0]hept-6-yl)pyridin-4-yl]oxy}-methyl)-1H-benzimidazole-6-carbonitrile | 1.55 | 516 |
| 932 | 2-({[2-(3-Amino-2-oxopyrrolidin-1-yl)pyridin-4-yl]-oxy}methyl)-1-[2-(difluoromethoxy)benzyl]-1H-benzimidazole-6-carbonitrile | 1.35 | 505 |
| 933 | 1-[2-(Difluoromethoxy)benzyl]-2-({[2-(1,1-dioxido-isothiazolidin-2-yl)pyridin-4-yl]oxy}methyl)-1H-benzimidazole-6-carbonitrile | 1.43 | 526 |
| 934 | N-[4-({6-Cyano-1-[2-(difluoromethoxy)benzyl]-1H-benzimidazol-2-yl}methoxy)pyridin-2-yl]-N-methyl-acetamide | 1.37 | 478 |

Examples 935 to 963

The following compounds can be synthesized from Intermediate 46 and the appropriate carboxylic acid in accordance with Method J.

| Example | Compound Name | QC LCMS RT (min) | Mass Ion (M + H)+ |
|---|---|---|---|
| 935 | 2-[(2,6-Dimethoxyphenoxy)methyl]-1-[(1S)-1-phenylethyl]-1H-benzimidazole-6-carbonitrile | 1.63 | 414 |
| 936 | 1-[(1S)-1-Phenylethyl]-2-{[4-(trifluoromethoxy)-phenoxy]methyl}-1H-benzimidazole-6-carbonitrile | 1.74 | 438 |
| 937 | 1-({6-Cyano-1-[(1S)-1-phenylethyl]-1H-benzimidazol-2-yl}methyl)-1H-pyrazole-4-sulfonamide | 1.3 | 407 |
| 938 | 2-{[4-(2-Oxopyrrolidin-1-yl)phenoxy]methyl}-1-[(1S)-1-phenylethyl]-1H-benzimidazole-6-carbonitrile | 1.49 | 437 |
| 939 | 2-[3-(Methylsulfonyl)benzyl]-1-[(1S)-1-phenyl-ethyl]-1H-benzimidazole-6-carbonitrile | 1.45 | 416 |
| 940 | 2-[(Cyclopropylmethoxy)methyl]-1-[(1S)-1-phenyl-ethyl]-1H-benzimidazole-6-carbonitrile | 1.59 | 332 |
| 941 | 2-[4-(Methylsulfonyl)benzyl]-1-[(1S)-1-phenyl-ethyl]-1H-benzimidazole-6-carbonitrile | 1.43 | 416 |
| 942 | 1-[(1S)-1-Phenylethyl]-2-[4-(1H-tetrazol-1-yl)-benzyl]-1H-benzimidazole-6-carbonitrile | 1.46 | 406 |
| 943 | 1-[4-({6-Cyano-1-[(1S)-1-phenylethyl]-1H-benzimidazol-2-yl}methyl)phenyl]urea | 1.35 | 396 |
| 944 | 1-[(1S)-1-Phenylethyl]-2-([1,2,4]triazolo[1,5-a]-pyrimidin-2-ylmethyl)-1H-benzimidazole-6-carbonitrile | 1.3 | 380 |
| 945 | 1-[(1S)-1-Phenylethyl]-2-(piperidin-1-ylmethyl)-1H-benzimidazole-6-carbonitrile | 1.71 | 345 |
| 946 | 2-(Cyclopentylmethyl)-1-[(1S)-1-phenylethyl]-1H-benzimidazole-6-carbonitrile | 1.67 | 330 |

| Example | Compound Name | QC LCMS RT (min) | Mass Ion (M + H)⁺ |
|---|---|---|---|
| 947 | N-[5-({6-Cyano-1-[(1S)-1-phenylethyl]-1H-benzimidazol-2-yl}methoxy)pyridin-2-yl]acetamide | 1.4 | 412 |
| 948 | 2-[(2-Methyl-1H-benzimidazol-5-yl)methyl]-1-[(1S)-1-phenylethyl]-1H-benzimidazole-6-carbonitrile | 1.36 | 392 |
| 949 | 2-{[(6-Cyano-5-methylpyridin-3-yl)oxy]methyl}-1-[(1S)-1-phenylethyl]-1H-benzimidazole-6-carbonitrile | 1.54 | 394 |
| 950 | 1-[(1S)-1-Phenylethyl]-2-(tetrahydro-2H-pyran-4-yl-methyl)-1H-benzimidazole-6-carbonitrile | 1.46 | 346 |
| 951 | 2-[(2-Amino-4,6-dimethylpyrimidin-5-yl)methyl]-1-[(1S)-1-phenylethyl]-1H-benzimidazole-6-carbonitrile | 1.35 | 383 |
| 952 | 2-[2-(5-Oxo-3-thioxo-2,3,4,5-tetrahydro-1,2,4-triazin-6-yl)ethyl]-1-[(1S)-1-phenylethyl]-1H-benzimidazole-6-carbonitrile | 1.18 | 403 |
| 953 | 2-[4-(Difluoromethoxy)benzyl]-1-[(1S)-1-phenyl-ethyl]-1H-benzimidazole-6-carbonitrile | 1.63 | 404 |
| 954 | 1-(4-{6-Cyano-1-[(1S)-1-phenylethyl]-1H-benzimidazol-2-yl}butyl)urea | 1.29 | 362 |
| 955 | N-({6-Cyano-1-[(1S)-1-phenylethyl]-1H-benzimidazol-2-yl}methyl)-5-hydroxypyridine-3-carboxamide | 1.19 | 398 |
| 956 | 1-[(1S)-1-Phenylethyl]-2-(pyrazin-2-ylmethyl)-1H-benzimidazole-6-carbonitrile | 1.37 | 340 |
| 957 | 2-{[(2-Oxo-1,2,3,4-tetrahydroquinolin-6-yl)oxy]-methyl}-1-[(1S)-1-phenylethyl]-1H-benzimidazole-6-carbonitrile | 1.43 | 423 |
| 958 | N-(2-{6-Cyano-1-[(1S)-1-phenylethyl]-1H-benzimidazol-2-yl}ethyl)pyridine-4-carboxamide | 1.34 | 396 |
| 959 | 1-[(1S)-1-Phenylethyl]-2-{[4-(pyrimidin-2-yl)-piperazin-1-yl]methyl}-1H-benzimidazole-6-carbonitrile | 1.55 | 424 |
| 960 | 2-(1-Methoxypropyl)-1-[(1S)-1-phenylethyl]-1H-benzimidazole-6-carbonitrile | 1.56 | 320 |
| 961 | 1-[(1S)-1-Phenylethyl]-2-(tetrahydro-2H-pyran-3-yl-methyl)-1H-benzimidazole-6-carbonitrile | 1.49 | 346 |
| 962 | N-(2-{6-Cyano-1-[(1S)-1-phenylethyl]-1H-benzimidazol-2-yl}ethyl)furan-3-carboxamide | 1.4 | 385 |
| 963 | 2-[(2-Amino-1,3-thiazol-4-yl)methyl]-1-[(1S)-1-phenylethyl]-1H-benzimidazole-6-carbonitrile | 1.36 | 360 |

Examples 964 to 973

The following compounds can be synthesized by a sequence of steps corresponding to the preparation of Intermediate 46, commencing from 4-cyano-2-fluoronitrobenzene and (5-chloro-2-methylthiazol-4-yl)methanamine, followed by cyclisation with the appropriate carboxylic acid in accordance with Method J.

| Example | Compound Name | QC LCMS RT (min) | Mass Ion (M + H)⁺ |
|---|---|---|---|
| 964 | 1-[(5-Chloro-2-methyl-1,3-thiazol-4-yl)methyl]-2-[(tetrahydrofuran-3-ylmethoxy)methyl]-1H-benzimidazole-6-carbonitrile | 1.43 | 402 and 404 |
| 965 | 1-[(5-Chloro-2-methyl-1,3-thiazol-4-yl)methyl]-2-[4-(methylsulfonyl)benzyl]-1H-benzimidazole-6-carbonitrile | 1.4 | 456 and 458 |
| 966 | 1-[(5-Chloro-2-methyl-1,3-thiazol-4-yl)methyl]-2-[(3,5-dimethyl-1H-pyrazol-4-yl)methyl]-1H-benzimidazole-6-carbonitrile | 1.36 | 396 and 398 |
| 967 | 1-[(5-Chloro-2-methyl-1,3-thiazol-4-yl)methyl]-2-{[2-(pyridin-3-yl)-1,3-thiazol-4-yl]methyl}-1H-benzimidazole-6-carbonitrile | 1.46 | 462 and 404 |
| 968 | 1-[(5-Chloro-2-methyl-1,3-thiazol-4-yl)methyl]-2-{[3-(methylsulfonyl)phenoxy]methyl}-1H-benzimidazole-6-carbonitrile | 1.46 | 472 and 474 |
| 969 | 1-[(5-Chloro-2-methyl-1,3-thiazol-4-yl)methyl]-2-{[3-(2-oxopyrrolidin-1-yl)phenoxy]methyl}-1H-benzimidazole-6-carbonitrile | 1.51 | 477 and 479 |

-continued

| Example | Compound Name | QC LCMS RT (min) | Mass Ion (M + H)+ |
|---|---|---|---|
| 970 | 1-[(5-Chloro-2-methyl-1,3-thiazol-4-yl)methyl]-2-{[2-(2-oxoimidazolidin-1-yl)-1,3-thiazol-4-yl]-methyl}-1H-benzimidazole-6-carbonitrile | 1.34 | 469 and 471 |
| 971 | 1-[(5-Chloro-2-methyl-1,3-thiazol-4-yl)methyl]-2-{[(3-oxo-2,3-dihydro-1H-isoindol-5-yl)oxy]methyl}-1H-benzimidazole-6-carbonitrile | 1.37 | 449 and 451 |
| 972 | 1-[(5-Chloro-2-methyl-1,3-thiazol-4-yl)methyl]-2-[(cyclopropylmethoxy)methyl]-1H-benzimidazole-6-carbonitrile | 1.57 | 372 and 374 |
| 973 | 1-[(5-Chloro-2-methyl-1,3-thiazol-4-yl)methyl]-2-(pyridin-4-ylmethyl)-1H-benzimidazole-6-carbonitrile | 1.32 | 379 and 381 |

Examples 974 to 986

The following compounds can be synthesized from Intermediate 44 and the appropriate carboxylic acid in accordance with Method J.

| Example | Compound Name | QC LCMS RT (min) | Mass Ion (M + H)+ |
|---|---|---|---|
| 974 | 2-{[3-(Methylsulfonyl)phenoxy]methyl}-1-[(1R)-1-phenylethyl]-1H-benzimidazole-6-carbonitrile | 1.48 | 432 |
| 975 | 2-[(2-Methyl-1,3-thiazol-4-yl)methyl]-1-[(1R)-1-phenylethyl]-1H-benzimidazole-6-carbonitrile | 1.46 | 359 |
| 976 | 2-(Ethoxymethyl)-1-[(1R)-1-phenylethyl]-1H-benzimidazole-6-carbonitrile | 1.51 | 306 |
| 977 | 2-[(Cyclopropylmethoxy)methyl]-1-[(1R)-1-phenylethyl]-1H-benzimidazole-6-carbonitrile | 1.56 | 332 |
| 978 | 2-{[4-(2-Oxopyrrolidin-1-yl)phenoxy]methyl}-1-[(1R)-1-phenylethyl]-1H-benzimidazole-6-carbonitrile | 1.5 | 437 |
| 979 | 2-{[(5-Methylisoxazol-3-yl)oxy]methyl}-1-[(1R)-1-phenylethyl]-1H-benzimidazole-6-carbonitrile | 1.51 | 359 |
| 980 | 2-[(2-Methyl-1H-imidazol-1-yl)methyl]-1-[(1R)-1-phenylethyl]-1H-benzimidazole-6-carbonitrile | 1.32 | 342 |
| 981 | 1-[(1R)-1-Phenylethyl]-2-(pyrazin-2-ylmethyl)-1H-benzimidazole-6-carbonitrile | 1.36 | 340 |
| 982 | 2-{[(2-Oxo-1,2,3,4-tetrahydroquinolin-6-yl)oxy]methyl}-1-[(1R)-1-phenylethyl]-1H-benzimidazole-6-carbonitrile | 1.45 | 423 |
| 983 | 2-[3-(Methylsulfonyl)benzyl]-1-[(1R)-1-phenylethyl]-1H-benzimidazole-6-carbonitrile | 1.44 | 416 |
| 984 | 2-[4-(Methylsulfonyl)benzyl]-1-[(1R)-1-phenylethyl]-1H-benzimidazole-6-carbonitrile | 1.43 | 416 |
| 985 | 2-(2-Methoxyethyl)-1-[(1R)-1-phenylethyl]-1H-benzimidazole-6-carbonitrile | 1.42 | 306 |
| 986 | 1-[(1R)-1-Phenylethyl]-2-[4-(1H-tetrazol-1-yl)-benzyl]-1H-benzimidazole-6-carbonitrile | 1.46 | 406 |

Examples 987 to 995

The following compounds can be synthesized from Intermediate 42 and the appropriate carboxylic acid in accordance with Method J.

| Example | Compound Name | QC LCMS RT (min) | Mass Ion (M + H)+ |
|---|---|---|---|
| 987 | 2-(Cyclohexylmethyl)-1-(2,5-dichlorobenzyl)-1H-benzimidazole-6-carbonitrile | 1.81 | 398, 400 and 402 |
| 988 | 1-(2,5-Dichlorobenzyl)-2-{[4-(1H-tetrazol-1-yl)-phenoxy]methyl}-1H-benzimidazole-6-carbonitrile | 1.52 | 476, 478 and 480 |
| 989 | 1-(2,5-Dichlorobenzyl)-2-{[4-(2-oxopyrrolidin-1-yl)-phenoxy}methyl}-1H-benzimidazole-6-carbonitrile | 1.54 | 491, 493 and 495 |
| 990 | — | — | — |
| 991 | 1-(2,5-Dichlorobenzyl)-2-(1-hydroxyethyl)-1H-benzimidazole-6-carbonitrile | 1.42 | 346, 348 and 350 |

-continued

| Example | Compound Name | QC LCMS RT (min) | Mass Ion $(M + H)^+$ |
|---|---|---|---|
| 992 | 1-(2,5-Dichlorobenzyl)-2-(difluoromethyl)-1H-benzimidazole-6-carbonitrile | 1.59 | 352, 354 and 356 |
| 993 | 1-(2,5-Dichlorobenzyl)-2-[(1S)-1-methoxyethyl]-1H-benzimidazole-6-carbonitrile | 1.57 | 360, 362 and 364 |
| 994 | 1-(2,5-Dichlorobenzyl)-2-[(piperidin-4-yloxy)-methyl]-1H-benzimidazole-6-carbonitrile | 1.33 | 415, 417 and 419 |
| 995 | 1-(2,5-Dichlorobenzyl)-2-[(piperidin-3-yloxy)-methyl]-1H-benzimidazole-6-carbonitrile | 1.4 | 415, 417 and 419 |

Examples 996 to 1002

The following compounds can be synthesized from Intermediate 48 and the appropriate boronic acid or ester in accordance with Method L.

| Example | Compound Name | QC LCMS RT (min) | Mass Ion $(M + H)^+$ |
|---|---|---|---|
| 996 | 1-(2,5-Dichlorobenzyl)-2-methyl-6-(pyridin-4-yl)-1H-benzimidazole | 2.04 | 368, 370 and 372 |
| 997 | 1-(2,5-Dichlorobenzyl)-2-methyl-6-(pyridin-3-yl)-1H-benzimidazole | 2.14 | 368, 370 and 372 |
| 998 | 1-(2,5-Dichlorobenzyl)-2-methyl-6-(1-methyl-1H-pyrazol-4-yl)-1H-benzimidazole | 2.04 | 371, 373 and 375 |
| 999 | 1-(2,5-Dichlorobenzyl)-2-methyl-6-(1-oxidopyridin-3-yl)-1H-benzimidazole | 1.78 | 384, 386 and 388 |
| 1000 | 4-[1-(2,5-Dichlorobenzyl)-2-methyl-1H-benzimidazol-6-yl]pyridin-2(1H)-one | 1.29 | 384, 386 and 388 |
| 1001 | 1-(2,5-Dichlorobenzyl)-2-methyl-6-(pyrazin-2-yl)-1H-benzimidazole | 1.42 | 369, 371 and 373 |
| 1002 | 1H-(2,5-Dichlorobenzyl)-2-methyl-6-(1-methyl-1H-pyrazol-3-yl)-1H-benzimidazole | 1.42 | 371,373 and 375 |

Examples 1003 to 1006

The following compounds can be synthesized from Intermediate 2 and the appropriate aldehyde in accordance with Method C.

| Example | Compound Name | QC LCMS RT (min) | Mass Ion $(M + H)^+$ |
|---|---|---|---|
| 1003 | [1-(2,5-Dimethylbenzyl)-1H-benzimidazol-2-yl]-(phenyl)methanol | 2.57 | 343 |
| 1004 | [1-(2,5-Dimethylbenzyl)-1H-benzimidazol-2-yl](4-methylphenyl)methanol | 1.67 | 357 |
| 1005 | [1-(2,5-Dimethylbenzyl)-1H-benzimidazol-2-yl]-(thiophen-2-yl)methanol | 2.5 | 349 |
| 1006 | [1-(2,5-Dimethylbenzyl)-1H-benzimidazol-2-yl]-(pyridazin-4-yl)methanol | 1.87 | 345 |

Example 1007

Methyl (1S,5R,8r)-3-[5-(1-{[5-chloro-2-(difluoromethoxy)phenyl]methyl}-2-methylbenzimidazol-6-yl)pyrimidin-2-yl]-3-azabicyclo[3.2.1.]octane-3-carboxylate Prepared from Intermediate 49 and Intermediate 85 according to Method L, giving the title compound (510 mg) as a pale powder. $\delta_H$ (300 MHz, DMSO-$d_6$) 8.66 (s, 2H), 7.72 (m, H), 7.62 (d, H), 7.46 (m, H), 7.48 (t, 1H, J 74 Hz), 7.30 (d, 1H, J 8.8 Hz), 6.79 (d, H, J 3.0 Hz), 5.51 (s, 2H), 4.43 (dd, 2H, J 12.9, 3.4 Hz), 3.63 (s, 3H), 3.33 (s, 3H), 3.02 (d, H, J 12.1 Hz), 2.78 (s, 1H), 2.61 (s, 2H), 1.66 (m, 2H), 1.40 (m, 2H). QC LCMS m/z 569, RT 1.67 minutes.

Example 1008

Sodium (1S,5R,8r)-3-[5-(1-{[5-chloro-2-(difluoromethoxy)phenyl]methyl}-2-methylbenzimidazol-6-yl)pyrimidin-2-yl]-3-azabicyclo[3.2.1]octane-8-carboxylate A solution of Example 1007 (485 mg, 0.85 mmol) in THF (5 mL) and methanol (5 mL) was treated with aqueous NaOH solution (10% w/v, 3 mL) and heated at 70° C. for 2 h. The mixture was concentrated in vacuo (to 3 mL) and acidified by addition of AcOH (to pH approximately 4.5), then the resulting grey solid precipitate was collected by filtration. The crude solid was suspended in water (50 mL) and treated with aqueous NaOH solution (10% w/v, 370 µL, 0.85 mmol) and MeCN (20 mL), then freeze-dried, to give the title compound (429 mg, 87%) as a white solid. QC LCMS m/z 554, RT 1.21 minutes.

Example 1009

4-Amino-1-[5-(1-{[5-chloro-2-(difluoromethoxy) phenyl]methyl}-2-methylbenzimidazol-6-yl)pyrimidin-2-yl]piperidine-4-carboxylic acid hydrochloride Prepared from Intermediate 49 and Intermediate 94 according to Method L, followed by treatment with 6M HCl in 1,4-dioxane, to give the title compound (315 mg) as a beige solid. $\delta_H$ (300 MHz, DMSO-$d_6$) 8.78 (m, 5H), 8.12 (s, 1H), 7.87 (s, 2H), 7.60 (t, 1H, J 74 Hz), 7.50-7.57 (m, 2H), 7.31 (d 1H), 5.75 (s, 2H), 4.11 (m, 2H), 3.92 (m, 2H), 2.84 (s, 3H), 2.10 (m, 2H), 1.92 (m, 2H). QC LCMS m/z 543, RT 1.18 minutes.

Example 1010

1-[5-(1-{(1R)-1-[2-(difluoromethoxy)phenyl]ethyl}-2-methylbenzimidazol-6-yl)-pyrimidin-2-yl]piperidine-4-carboxylic acid The title compound can be synthesised from Example 1058 and 1-(5-boronopyrimidin-2-yl)piperidine-4-carboxylic acid in accordance with Method L. QC LCMS m/z 509, RT 1.17 minutes.

Example 1011

N-(2,3-Dihydro-1H-inden-2-yl)-1-(2,5-dimethylbenzyl)-2-(hydroxymethyl)-1H-benzimidazole-6-carboxamide To a stirred solution of Intermediate 99 (100 mg, 0.32 mmol) in DCM:DMF (1:1; 6 mL) was added HATU (135 mg, 0.35 mmol) at 0° C., followed by the addition of indan-2-amine (42 mg, 0.32 mmol) and DIPEA (49 µL, 0.48 mmol). The reaction mixture was stirred for 12 h at 25-31° C. The reaction mixture was diluted with water (60 mL) and extracted with ethyl acetate (three portions of 10 mL). The organic layer was concentrated in vacuo and the residue was purified by preparative HPLC to give the title compound. QC LCMS m/z 426, RT 2.34 minutes.

Example 1012

1-(2,5-Dichlorobenzyl)-2-methyl-N-(pyridin-4-yl)-1H-benzimidazole-6-carboxamide

The title compound was prepared from Intermediate 100 and 4-aminopyridine by a method analogous to that described for Example 1011. QC LCMS m/z 412, RT 1.34 minutes.

Example 1013

1-(2,5-Dichlorobenzyl)-6-methoxy-2-methyl-1H-benzimidazole

The title compound can be synthesised from 2-fluoro-4-methoxynitrobenzene and 2,5-dichlorobenzylamine according to the procedure described for Intermediate 47. $\delta_H$ (DMSO-$d_6$) 7.60 (d, J 8.4 Hz, 1H), 7.47-7.01 (m, 3H), 7.01 (d, J 2 Hz, 1H), 6.40 (d, J 2.4 Hz, 1H), 5.50 (s, 2H), 3.72 (s, 3H), 2.40 (s, 3H). QC LCMS m/z 321 [M+H]$^+$, RT 1.53 minutes.

Example 1014

1-(2,5-Dichlorobenzyl)-2-methyl-1H-benzimidazol-6-yl 2-methylpropane-1-sulfonate To a solution of Intermediate 101 (0.1 g, 0.26 mmol) in DCM (4 mL) was added triethylamine (0.077 g, 0.76 mmol) at 0° C. The resulting mixture was stirred for 10 minutes, then 2-methylpropanesulfonyl chloride (97 mg, 0.63 mmol) was added. The reaction mixture was allowed to stir at ambient temperature for 18 h, after which time the reaction mixture was quenched with water (5 mL) and extracted with DCM (10 mL). The combined organic layer was washed with brine (2×20 mL), dried (Na$_2$SO$_4$), and concentrated. The crude material was purified using column chromatography on silica gel, eluting with methanol in DCM (8% v/v), to give the title compound. QC LCMS m/z 427, RT 1.61 minutes.

Example 1015

1-(2,5-Dichlorobenzyl)-2-methyl-1H-benzimidazol-6-yl ethanesulfonate

The title compound was prepared from Intermediate 101 and ethanesulphonyl chloride according to the procedure described for Example 1014. QC LCMS m/z 399, RT 1.49 minutes.

Example 1016

1-(2,5-Dichlorobenzyl)-2-methyl-1H-benzimidazol-6-yl 3,3,3-trifluoropropane-1-sulfonate The title compound was prepared from Intermediate 101 and 3,3,3-trifluoropropane-1-sulfonyl chloride according to the procedure described for Example 1014. QC LCMS m/z 467, RT 1.59 minutes.

Example 1017

1-(2,5-Dichlorobenzyl)-2-methyl-1H-benzimidazol-6-yl propane-1-sulfonate

The title compound was prepared from Intermediate 101 and propane-1-sulfonyl chloride according to the procedure described for Example 1014. QC LCMS m/z 413, RT 1.56 minutes.

Example 1018

6-(Azetidin-3-yloxy)-1-(2,5-dichlorobenzyl)-2-methyl-1H-benzimidazole

A solution of Intermediate 102 in dichloromethane was treated with trifluoroacetic acid (5:1 v:v), stirring at ambient temperature until the reaction was complete. The volatiles were removed in vacuo. The free base was isolated by dissolving the residue in dichloromethane and treating with a saturated aqueous solution of sodium bicarbonate. The organics were further washed with brine, dried with anhydrous sodium sulphate, filtered and concentrated in vacuo, to give the title compound. QC LCMS m/z 362, RT 1.31 minutes.

Example 1019 tert-Butyl 3-({[1-(2,5-dichlorobenzyl)-2-methyl-1H-benzimidazol-6-yl]oxy}methyl)-pyrrolidine-1-carboxylate The title compound was obtained from Intermediate 101 and tert-butyl 3-(bromo-methyl)pyrrolidine-1-carboxylate by a method analogous to that used to prepare Intermediate 102. QC LCMS m/z 490, RT 1.66 minutes.

Example 1020

1-[3-({[1-(2,5-dichlorobenzyl)-2-methyl-1H-benzimidazol-6-yl]oxy}methyl)pyrrolidin-1-yl]ethanone Prepared from Example 1019 by treatment with trifluoroacetic acid as described for Example 1018, followed by treatment with 1.5 equivalents of triethylamine and acetic anhydride in dichloromethane. The reaction mixture was stirred at ambient temperature until complete. The reaction mixture was quenched with water, the organic layers were separated, dried with anhydrous sodium sulphate, and filtered, then the solvents were removed in vacuo to afford the title compound. QC LCMS m/z 432, RT 1.39 minutes.

Example 1021

1-[3-({[1-(2,5-Dichlorobenzyl)-2-methyl-1H-benzimidazol-5-yl]oxy}methyl)pyrrolidin-1-yl]ethanone The title compound was prepared from Intermediate 103 using the method described for the preparation of Example 1020. QC LCMS m/z 432, RT 1.45 minutes.

Example 1022

1-(2,5-Dichlorobenzyl)-5-[(6-methoxypyridin-3-yl) oxy]-2-methyl-1H-benzimidazole The title compound can be prepared from Intermediate 103 and 3-bromo-6-methoxypyridine via copper-catalysed coupling in accordance with Method P. QC LCMS m/z 414, RT 1.59 minutes.

Example 1023

5-{[1-(2,5-Dichlorobenzyl)-2-methyl-1H-benzimidazol-5-yl]oxy}pyridin-2(1H)-one

The title compound can be prepared from Example 1022 in accordance with Method M. QC LCMS m/z 400, RT 1.35 minutes.

Example 1024

5-{[1-(2,5-Dichlorobenzyl)-2-methyl-1H-benzimidazol-5-yl]oxy}-1-methylpyridin-2(1H)-one Prepared by treatment of Example 1023 with sodium hydride in DMF and quenching with methyl iodide. The resulting reaction mixture was stirred at ambient temperature until the reaction was complete. The reaction mixture was poured into water, and extracted with ethyl acetate. The combined organic layers were washed with brine, dried over sodium sulphate and filtered, then the volatiles were removed in vacuo. The resulting crude residue was purified by preparative HPLC. QC LCMS m/z 414, RT 1.41 minutes.

Example 1025

{6-(6-Methoxypyridin-3-yl)-1-[(1S)-1-phenylethyl] benzimidazol-2-yl}[4-(methyl-sulfonyl)phenyl] methanol Example 717 (0.5 g, 1.01 mmol), N-bromosuccinimide (18 mg, 1.01 mmol) and 2,2'-azobis(2-methylpropionitrile) (10 mg, 0.06 mmol) were heated in refluxing carbon tetrachloride (2.5 mL) whilst open to air. After 4 h, the volatiles were removed in vacuo and the residue was purified by column chromatography, to afford the title compound (30 mg) as an off white solid. $\delta_H$ (300 MHz, DMSO-$d_6$) 8.17 (d, 1H, J 2.5 Hz), 7.97 (m, 1H), 7.89 (m, 1H), 7.76 (m, 2H), 7.73 (m, 1H), 7.69 (dd, 1H, J 8.5, 2.4 Hz), 7.35 (m, 4H), 7.20 (d, 1H, J 2.0 Hz), 7.12 (s, 1H), 7.04 (dd, 1H, J 12.3, 1.2 Hz), 6.98 (m, 1H), 6.79 (d, 1H, J 8.6 Hz), 6.41 (d, 1H, J 16.3 Hz), 6.18 (m, 1H), 3.85 (s, 3H), 3.31 (s, 3H), 3.19 (d, 3H, J 14.7 Hz). LCMS (pH 3) (M+H)$^+$ 514.7, RT 2.13 minutes. LCMS (pH 10) (M+H)' 514.70, RT 1.50 minutes.

Example 1026

(1-{[2-(Difluoromethoxy)phenyl]methyl}-6-(6-methoxypyridin-3-yl)benzimidazol-2-yl)-[4-(methylsulfanyl)phenyl]methanol Intermediate 116 (0.5 g, 1.2 mmol) was dissolved in tetrahydrofuran (10 mL) and cooled to 0° C., whereupon 4-thioanisolemagnesium bromide (2.9 mL, 1.46 mmol, 0.50 mol/L) was added. After 2 h, the reaction mixture was quenched by addition of saturated aqueous NH$_4$Cl solution and extracted with DCM. The organic layers were dried with Na$_2$SO$_4$, filtered and evaporated, to give the title compound, a sample of which was purified by column chromatography on silica gel. $\delta_H$ (300 MHz, DMSO-$d_6$) 8.40 (m, 1H), 7.93 (dd, 1H, J 8.6, 2.6 Hz), 7.74 (d, 1H, J 8.4 Hz), 7.53 (m, 2H), 7.34 (m), 7.24 (m, 4H), 7.11 (m, 2H), 6.93 (m, 1H), 6.86 (dd, 1H, J 8.6, 0.4 Hz), 6.55 (d, 1H, J 5.2 Hz), 6.30 (dd, 1H, J 7.8, 1.1 Hz), 6.05 (d, 1H, J 5.1 Hz), 5.60 (m, 2H), 3.86 (s, 3H), 2.41 (s, 3H). LCMS (pH 3) (M+H)$^+$ 517, RT 2.69 minutes. LCMS (pH 10) (M+H)$^+$ 517, RT 2.83 minutes.

Example 1027

(1-{[2-(Difluoromethoxy)phenyl]methyl}-6-(6-methoxypyridin-3-yl)benzimidazol-2-yl)-[4-(methylsulfonyl)phenyl]methanol Example 1026 (200 mg, 0.375 mmol) was dissolved in dichloromethane (10 mL) at 0° C. and 3-chloroperoxybenzoic acid (136 mg, 0.79 mmol) was added. After 2 h at 0° C. the reaction mixture was washed with aqueous sodium thiosulphate and sodium carbonate solutions, dried over sodium sulphate, and evaporated onto silica. Purification by column chromatography gave the title compound (100 mg, 47%). $\delta_H$ (300 MHz, CDCl$_3$) 8.15 (d, 1H, J 2.4 Hz), 7.76 (d, 1H, J 8.4 Hz), 7.65 (m, 2H), 7.56 (m, 3H), 7.39 (dd, 1H, J 8.4, 1.5 Hz), 7.13 (m, 1H), 7.01 (m, 2H), 6.71 (m, 2H), 6.59 (t, 1H, J 73.2 Hz), 6.29 (s, 1H), 6.04 (d, 1H, J 7.4 Hz), 5.55

(m, 1H), 5.21 (m, 1H), 3.85 (s, 3H), 2.93 (s, 3H). LCMS (pH 3) (M+H)+ 566, RT 2.21 minutes. LCMS (pH 10) (M+H)+ 566, RT 2.25 minutes.

Example 1028

1-(4-{[6-(6-methoxypyridin-3-yl)-1-(1-phenylethyl) benzimidazol-2-yl]methyl}thiazol-2-yl)imidazolidin-2-one The title compound can be synthesized from 6-methoxy-pyridin-3-ylboronic acid, (S)-1-phenylethylamine and 2-[2-(2-oxoimidazolidin-1-yl)thiazol-4-yl]acetic acid by a sequence of steps corresponding to the preparation of Intermediate 34 followed by Method J. QC LCMS m/z 511 (M+H)+, RT 1.52 minutes.

Example 1029

5-(2-{[2-(2-oxoimidazolidin-1-yl)thiazol-4-yl] methyl}-1-(1-phenylethyl)benzimidazol-6-yl)-1H-pyridin-2-one Example 1028 (20 mg, 0.04 mmol) was treated with pyridine hydrochloride (18 mg, 0.16 mmol) in accordance with Method M to give the title compound (10 mg, 51%). $\delta_H$ (300 MHz, DMSO-$d_6$) 11.72 (m, 1H), 7.57 (m, 3H), 7.45 (m, 1H), 7.30 (m, 6H), 7.07 (s, 1H), 6.83 (s, 1H), 6.38 (d, 1H, J 9.4 Hz), 6.14 (m, 1H), 4.37 (d, 2H, J 0.4 Hz), 3.89 (m, 2H), 3.43 (m, 2H), 1.86 (d, 3H, J 7.0 Hz). LCMS (pH 3) (M+H)+ 497.7, RT 1.32 minutes. LCMS (pH 10) (M+H)+ 497.6, RT 1.54 minutes.

Example 1030

1-{[2-(Difluoromethoxy)phenyl]methyl}-2-{[3-(2-oxopyrrolidin-1-yl)phenyl]sulfonyl-methyl}benzimidazole-6-carbonitrile Example 210 (50 mg, 0.10 mmol) was dissolved in DCM (5 mL) and cooled using an ice bath. mCPBA (18 mg, 0.10 mmol) was added and the reaction mixture was stirred for 1 h. The reaction mixture was diluted with DCM (10 mL) and washed with aqueous sodium carbonate solution, before drying over sodium sulphate and evaporating in vacuo. The residue was dissolved in DCM (5 mL), a further equivalent of mCPBA (18 mg, 0.10 mmol) was added and the reaction mixture was stirred for 1 h. The reaction mixture was diluted with DCM (10 mL) and washed with aqueous sodium carbonate solution before drying over sodium sulphate and evaporating in vacuo. The residue was purified by column chromatography (SiO$_2$, 1-15% MeOH in DCM) to give the title compound (10 mg, 19%) as a white powder. LCMS (ES+) 537 (M+H)+, RT 2.10 minutes.

Example 1031

Ethyl 4-methyl-1-[5-(2-methyl-1-{[2-methyl-5-(trif-luoromethyl)thiazol-4-yl]methyl}-benzimidazol-6-yl)pyrimidin-2-yl]piperidine-4-carboxylate To Intermediate 91 (250 mg, 0.64 mmol) was added [1,1'-bis(diphenyl-phosphino)ferrocene]dichloropalladium (II) (47.1 mg, 0.063 mmol) in a microwave vial and the reaction mixture was degassed under three cycles of vacuum and nitrogen. To the dry reaction materials were added potassium carbonate (0.63 mL, 2M solution, 1.26 mmol) and Intermediate 89 (269 mg, 0.68 mmol) dissolved in tetrahydrofuran (4 mL). The reaction mixture was degassed under three cycles of vacuum and nitrogen and was heated under microwave irradiation at 100° C. for 3 h. The reaction mixture was cooled to room temperature and left to stand overnight. The reaction mixture was partitioned between water (5 mL) and dichloromethane (5 mL) and was filtered through a phase separation cartridge, then the organic layer was concentrated in vacuo. The crude material was purified by flash column chromatography on silica. Gradient elution with 50% ethyl acetate/isohexane to 100% ethyl acetate afforded the title compound (154 mg, 43%). LCMS (pH 3): MH+ m/z 560, RT 2.51 minutes (100%). LCMS (pH 10): MH+ m/z 560, RT 2.84 minutes (98%).

Example 1032

Ethyl 1-[5-(1-{[2-(difluoromethoxy)phenyl] methyl}-2-methylbenzimidazol-6-yl)-pyrimidin-2-yl]-4-methylpiperidine-4-carboxylate The title compound was synthesized from Intermediate 47 and Intermediate 89 by the method described for Example 1031. LCMS (pH 3): MH+ m/z 537, RT 2.39 minutes (100%). LCMS (pH 10): MH+ m/z no mass ion observed, RT 2.77 minutes (98%).

Example 1033

Ethyl 1-[5-(1-{[2-chloro-6-(difluoromethoxy)phe-nyl]methyl}-2-methylbenzimidazol-6-yl)pyrimidin-2-yl]-4-methylpiperidine-4-carboxylate The title compound was synthesized from Intermediate 89 and Intermediate 90 by the method described for Example 1031. LCMS (pH 3): MH+ m/z 571, RT 2.34 minutes (93%). LCMS (pH 10): MH+ m/z 571, RT 2.57 minutes (93%).

Example 1034

2-Methyl-4-[(2-methyl-6-{2-[4-(methylsulfonyl) piperazin-1-yl]pyrimidin-5-yl}-benzimidazol-1-yl) methyl]-5-(trifluoromethyl)thiazole To Intermediate 117 (105 mg, 0.37 mmol) were added [1,1'-bis(diphenyl-phosphino)ferrocene]dichloropalladium (II) (11.6 mg, 0.016 mmol) and Intermediate 91 (118.0 mg, 0.30 mmol). The solids were sealed in a microwave vial and degassed under three cycles of vacuum and nitrogen. To this was added 1,2-dimethoxyethane (3 mL), and the mixture was degassed under three cycles of vacuum and nitrogen. To this was added 2M aqueous potassium carbonate solution (0.3 mL, 0.6 mmol), and the reaction mixture was degassed under three cycles of vacuum and nitrogen before heating for 3 h at 100° C. The reaction mixture was partitioned between water (5 mL) and dichloromethane (5 mL), the organic layer was filtered through a phase separation cartridge and the solvent was removed in vacuo. The crude reaction material was purified by preparative HPLC to afford the title compound (10 mg). $\delta_H$ (400 MHz, DMSO-$d_6$) 8.72 (s, 2H), 8.46 (s, 4.06H, formate), 7.67 (d, J 1.2 Hz, 1H), 7.60 (d, J 8.3 Hz, 1H), 7.44 (dd, J 8.3, 1.6 Hz, 1H), 5.67 (s, 2H), 5.59 (s, J 0.4 Hz, 0.17H), 3.89-3.95 (m, 4H), 3.19-3.24 (m, 4H), 2.91 (m, 3H), 2.91 (s, 3H), 2.59 (s, 3H), 2.56 (s, 3H). LCMS (pH 3): MH+ m/z 553, RT 2.14 minutes (100%). LCMS (pH 10): MH+ m/z 553, RT 1.90 minutes (100%).

Example 1035

1-{[2-Chloro-6-(difluoromethoxy)phenyl]methyl}-2-methyl-6-{2[4-(methylsulfonyl)-piperazin-1-yl]pyrimidin-5-yl}benzimidazole The title compound was prepared from Intermediate 117 and Intermediate 90 by the method described for Example 1034. $\delta_H$ (400 MHz, DMSO-$d_6$) 8.58 (s, 2H), 8.39 (s, formate, 0.55H), 7.57 (d, J 8.3 Hz, 1H), 7.47-7.53 (m, 2H), 7.36-7.40 (m, 2H), 7.30 (t, J 72.3 Hz, 1H), 7.27 (dd, J 6.5, 2.4 Hz, 1H), 5.60 (s, 2H), 3.88-3.94 (m, 4H), 3.19-3.24 (m, 4H), 2.91 (s, 3H), 2.59 (s, 3H). LCMS (pH 3): MH$^+$ m/z 564, RT 1.90 minutes (100%). LCMS (pH 10): MH$^+$ m/z 564, RT 2.11 minutes (100%).

Example 1036

1-{[2-Chloro-5-(difluoromethoxy)phenyl]methyl}-2-methyl-6-{2-[4-(methylsulfonyl)-piperazin-1-yl]pyrimidin-5-yl}benzimidazole The title compound was prepared from Intermediate 117 and Intermediate 49 by the method described for Example 1034. $\delta_H$ (400 MHz, DMSO-$d_6$) 8.75 (s, 2H), 8.53 (s, formate, 0.09H), 7.78 (s, 1H), 7.62-7.68 (m, 2H), 7.49 (dd, J 8.3, 1.2 Hz, 1H), 7.19 (dd, J 8.7, 2.7 Hz, 1H), 7.10 (t, J 73.5 Hz, 1H), 6.29 (d, J 2.6 Hz, 1H), 5.61 (s, 2H), 3.88-3.94 (m, 4H), 3.17-3.24 (m, 4H), 2.90 (s, 3H), 2.48 (s, 3H). LCMS (pH 3): MH$^+$ m/z 564, RT 2.01 minutes (100%). LCMS (pH 10): RT 2.24 minutes (100%).

Example 1037

4-(1-{6-[5-Chloro-6-(piperazin-1-yl)pyridin-3-yl]-2-methylbenzimidazol-1-yl}ethyl)-2-methylthiazole 4-Bromo-2-fluoronitrobenzene was reacted with [5-chloro-6-(piperazin-1-yl)-pyridin-3-yl]boronic acid in accordance with Method L. The resulting material was dissolved in DMF and treated with 1-(2-methylthiazol-4-yl)ethanamine (1.2 equivalents) and potassium carbonate (1.5 equivalents). The reaction mixture was heated at 60° C. until LCMS confirmed that the reaction was complete. The reaction mixture was poured into water and extracted with dichloromethane. The organic layers were dried with sodium sulphate and filtered, and the volatiles were removed in vacuo. The resulting material was dissolved in ethanol and treated with zinc (5 equivalents) and ammonium chloride (10 equivalents). The mixture was stirred at ambient temperature or 60° C. until LCMS confirmed that the reaction was complete. The reaction mixture was diluted with dichloromethane and filtered through celite. The organic phase was washed with brine, separated, dried over sodium sulphate and filtered. The volatiles were removed in vacuo. The residue was dissolved in glacial acetic acid and heated to 100° C. until LCMS confirmed that the reaction was complete. The volatiles were removed in vacuo and the crude residue was purified by mass-directed preparative HPLC, to give the title compound (19 mg, 61%) as a white solid. $\delta_H$ (400 MHz, DMSO-$d_6$) 8.47 (d, J 2.1 Hz, 1H), 8.01 (d, J 2.2 Hz, 1H), 7.70 (d, J 0.8 Hz, 1H), 7.65 (d, J 1.2 Hz, 1H), 7.57 (d, J 8.4 Hz, 1H), 7.43 (d, J 8.3, 1.6 Hz, 1H), 5.98 (q, J 6.8 Hz, 1H), 3.18-3.25 (m, 4H), 2.83-2.90 (m, 4H), 2.58 (s, 3H), 2.58 (s, 3H), 1.96 (d, J 7.2 Hz, 3H). LCMS (pH 10): MH$^+$ m/z 454, RT 1.80 minutes (100%). LCMS (pH 3): MH$^+$ m/z 454, RT 1.07 minutes (100%).

Example 1038

6-Chloro-5-{[2-(methoxymethyl)-6-(6-methoxypyridin-3-yl)benzimidazol-1-yl]methyl}-imidazo[2,1-b]thiazole Can be synthesised from Intermediate 32 and (6-chloroimidazo[2,1-b]thiazol-5-yl)methanamine according to the method described for Intermediate 33, followed by reaction with 2-methoxyacetic acid in accordance with Method J, to give the title compound. LCMS (pH 3): MH$^+$ m/z 440.6, RT 1.94 minutes (100%). LCMS (pH 10): MH$^+$ m/z 440.6, RT 2.00 minutes (100%).

Example 1039

1-(1-Benzylpyrrolidin-3-yl)-6-(6-methoxypyridin-3-yl)-2-methylbenzimidazole

The title compound was synthesised by the procedure described for Example 1037 utilising 6-methoxypyridin-3-ylboronic acid and 1-benzylpyrrolidin-3-amine. LCMS (pH 3): MH$^+$ m/z 400, RT 1.25 minutes (100%). LCMS (pH 10): MH$^+$ m/z 400, RT 2.58 minutes (100%).

Example 1040

{6-Bromo-1-[(2,5-dimethylphenyl)methyl]benzimidazol-2-yl}(pyridin-4-yl)methanol

Lithium diisopropylamine (10 mL, 7.77 mmol) was added dropwise to a stirred solution of Intermediate 118 (2.00 g, 6.37 mmol) in tetrahydrofuran (50 mL) at −78° C. The mixture was stirred at −78° C. for 2 h before dropwise addition of 4-pyridine carboxaldehyde (1.3 mL, 1.46 g, 13.61 mmol). The mixture was stirred for 10 minutes before quenching with brine (20 mL) and warming to ambient temperature. The mixture was partitioned between ethyl acetate (100 mL) and water (100 mL). The organic layer was separated and the aqueous layer was re-extracted with ethyl acetate (4×100 mL). The organic layers were combined, dried (Na$_2$SO$_4$) and filtered, and the solvent was removed in vacuo. The resulting dark brown oil was triturated with isohexane/ethyl acetate to yield a solid, which was filtered under reduced pressure and washed with isohexane, to afford the title compound (1.61 g, 60%) as a brown solid. LCMS (pH 3): MH$^+$ m/z 424, RT 1.82 minutes (93%). LCMS (pH 10): MH$^+$ m/z 424, RT 2.32 minutes (92%).

Examples 1041 & 1042

(R)- and (S)-{1-[(2,5-Dimethylphenyl)methyl]-6-(1-methylpyrazol-4-yl)benzimidazol-2-yl}(pyridin-4-yl)methanol To Example 1040 (1.71 g, 3.73 mmol) in 1,2-dimethoxyethane (100 mL) was added water (10 mL) and the reaction mixture was degassed under three cycles of vacuum and nitrogen. 1-Methylpyrazol-4-ylboronate ester (1.26 g, 6.06 mmol) was added and the mixture was degassed. Tetrakis(triphenylphosphine)palladium(0) (480 mg, 0.42 mmol) and 2M aqueous sodium carbonate solution (4.1 mL, 8.2 mmol) were added and the mixture was degassed. The mixture was heated to 80° for 2 h before cooling to room temperature.

The mixture was diluted with ethyl acetate (200 mL) and washed with water (100 mL). The organic phase was separated and the aqueous phase was rewashed with ethyl acetate (2×100 mL). The organic layers were combined, dried ($Na_2SO_4$) and filtered under reduced pressure to afford a brown oil, which was purified by flash column chromatography on silica (20% ethyl acetate/isohexane to 100% ethyl acetate, 100% dichloromethane to 20% ethanol/dichloromethane), to afford a racemic mixture. A portion was purified by chiral preparative HPLC to afford the separate enantiomers of the title compound as off-white solids.

Enantiomer A: LCMS (pH 3): $MH^+$ m/z 424, RT 1.40 minutes (94%). LCMS (pH 10): $MH^+$ m/z 424, RT 1.84 minutes (100%).

Enantiomer B: LCMS (pH 3): $MH^+$ m/z 424, RT 1.39 minutes (100%). LCMS (pH 10): $MH^+$ m/z 424, RT 1.84 minutes (94%).

Example 1043

1-[(2,5-Dimethylphenyl)methyl]-2-[(hydroxy)(pyridin-4-yl)methyl]benzimidazole-6-carbonitrile The title compound can be prepared from Intermediate 95 by the procedure described for Example 1040. $\delta_H$(300 MHz, DMSO-$d_6$) 8.41 (d, 2H, J 6.1 Hz), 7.85-7.91 (m, 1H), 7.61 (d, 1H, J 9.9 Hz) 7.30 (d, 2H, J 5.8 Hz), 6.98 (m, 2H), 6.11 (s, 1H), 5.72 (s, 1H), 5.62 (q, 2H), 2.31 (s, 3H), 1.91 (s, 3H). QC LCMS m/z 370, RT 1.39 minutes.

Example 1044

1-[(1R)-1-Phenylethyl]-2-(pyridin-4-ylmethoxymethyl)benzimidazole

To Intermediate 119 (100 mg, 0.40 mmol) and 4-(bromomethyl)pyridine hydrogen bromide (96 mg, 0.38 mmol) dissolved in DMF (1.5 mL) was added sodium hydride (60% dispersion in mineral oil, 46 mg, 1.14 mmol). The reaction mixture was stirred for 10 minutes and the mixture was partitioned between aqueous sodium bicarbonate solution (20 mL) and dichloromethane (20 mL). The organic layer was separated and the aqueous layer was re-extracted with dichloromethane (20 mL). The organic layers were combined, dried ($Na_2SO_4$) and filtered under reduced pressure, then the solvent was removed in vacuo. The resulting dark brown oil was purified by flash column chromatography on NH-silica (100% isohexane to 100% ethyl acetate) to afford the title compound (52 mg, 51%) as a straw coloured gum. LCMS (pH 3): $MH^+$ m/z 344, RT 1.17 minutes (100%). LCMS (pH 10): $MH^+$ m/z 344, RT 2.08 minutes (100%).

Example 1045

1-[(1S)-1-Phenylethyl]-2-(pyridin-4-ylmethoxymethyl)benzimidazole

Prepared by an analogous procedure to that described for Example 1044 commencing from (S)-1-phenylethylamine. The crude material was purified by preparative HPLC to afford the title compound (159 mg, 28%) as a colourless gum. LCMS (pH 3): $MH^+$ m/z 344, RT 1.22 minutes (100%). LCMS (pH10): $MH^+$ m/z 344, RT 2.08 minutes (100%).

Example 1046

6-Bromo-1-[1-(2-fluorophenyl)ethyl]-2-methylbenzimidazole

The title compound was prepared in accordance with the procedure described for Example 1037, omitting the Suzuki coupling step and commencing from 1-(2-fluoro-phenyl)ethylamine. The acetic acid cyclisation step required subsequent heating to 100° C. in toluene with pTSA (1.0 equivalent). Upon removal of solvent, the tosylate salt was obtained as an off-white solid. $\delta_H$ ($d_6$-DMSO) 7.94 (m, 1H), 7.78 (s, 1H), 7.73 (d, 1H, J 8.6 Hz), 7.62 (d, 1H, J 8.6 Hz), 7.53-7.47 (m, 3H), 7.43-7.37 (m, 1H), 7.23-7.18 (m, 1H), 7.11 (d, 2H, J 7.8 Hz), 6.39 (q, 1H, J 7.1 Hz), 2.83 (s, 3H), 2.30 (s, 3H), 2.02 (d, 3H, J 7.1 Hz). LCMS (pH10), $MH^+$ (333/335), RT 2.31 minutes.

Example 1047

4-({6-[6-(Dimethylamino)pyridin-3-yl]-1-[(5-methylisoxazol-3-yl)methyl]benzimidazol-2-yl}methoxy)benzamide Prepared in two steps from Intermediate 120 by Method B using 3-(chloromethyl)-5-methylisoxazole, followed by Suzuki coupling with 2-(dimethylamino)pyridin-5-ylboronic acid in accordance with Method L, and subsequent purification by mass-directed HPLC, to give the title compound as a pale pink solid. LCMS (pH 10), $MH^+$ m/z 483, RT 2.14 minutes.

Example 1048

(Cyclobutyl)(4-{1-[2-(difluoromethoxy)benzyl]-2-methyl-1H-benzimidazol-6-yl}-piperidin-1-yl)methanone The title compound was prepared from Intermediate 122 and cyclobutane-carboxylic acid in accordance with Method G. QC LCMS m/z 545, RT 1.52 minutes.

Example 1049

1-(4-{1-[2-(Difluoromethoxy)benzyl]-2-methyl-1H-benzimidazol-6-yl}piperidin-1-yl)-2-methylpropan-1-one The title compound was prepared from Intermediate 122 and 2-methylpropanoic acid in accordance with Method G. QC LCMS m/z 442, RT 1.45 minutes.

Example 1050

1-[2-(Difluoromethoxy)benzyl]-6-[1-(ethylsulfonyl)piperidin-4-yl]-2-methyl-1H-benzimidazole The title compound was prepared using a method analogous to that used to prepare Example 533, using Intermediate 122 and ethanesulphonyl chloride. QC LCMS m/z 464, RT 1.46 minutes.

Example 1051

(2S,3S,4S,5R,6S)-6-{[5-(1-{[2-(Difluoromethoxy)phenyl]methyl}-2-methylbenzimidazol-6-yl)pyridin-2-yl]oxy}-3,4,5-trihydroxytetrahydropyran-2-carboxylic acid To a stirred solution of Intermediate 123 (43 mg, 0.062 mmol) in acetone (2 mL) were added 1N aqueous sodium hydroxide solution (0.5 mL) and water (0.75 mL). The resultant mixture was stirred at room temperature for 2 h, after which time the reaction mixture was concentrated in vacuo. The crude material was purified by preparative HPLC and freeze dried from acetonitrile/water, to give the title compound (23 mg, 68%) as a white solid. $\delta_H$ (CD$_3$OD) 8.24 (d, 1H, J 2.3 Hz), 7.86 (dd, 1H, J 8.6, 2.5 Hz), 7.57 (d, 1H, J 8.4 Hz), 7.47 (d, 1H, J 1.2 Hz), 7.40 (dd, 1H, J 8.4, 1.6 Hz), 7.24-7.31 (m, 1H), 7.12-7.17 (m, 1H), 7.07 (td, 1H, J 7.5, 1.0 Hz), 6.88 (d, 1H, J 8.7 Hz), 6.86 (t, 1H, J 73.6 Hz), 6.84 (dd, 1H, J 7.9, 1.4 Hz), 5.66-5.71 (m, 1H), 5.49 (s, 2H), 3.79-3.85 (m, 1H), 3.42-3.50 (m, 3H), 2.52 (s, 3H). LCMS (ES+) 558 (M+H)$^+$, RT 0.82 minutes.

Example 1052

4-(5-{1-[2-(Difluoromethoxy)benzyl]-2-methyl-1H-benzimidazol-6-yl}-4-methylpyrimidin-2-yl)piperazin-2-one To a stirred solution of Intermediate 69 (200 mg, 0.50 mmol) and Intermediate 124 (179 mg, 1.25 mmol) in ethanol was added sodium ethoxide (68 mg, 1.25 mmol) and the reaction mixture was heated at 80° C. for 48 h. After this time, the reaction mixture was cooled to room temperature, concentrated in vacuo and partitioned between DCM (25 mL) and water (25 mL). The layers were separated and the aqueous phase was back-extracted with 10% MeOH/DCM (3×25 mL). The combined organic layers were passed down a phase separator and concentrated in vacuo. The crude material was purified by column chromatography (SiO$_2$, 2.5-5% MeOH in DCM), and freeze-dried from acetonitrile/water, to give the title compound (67 mg, 30%) as a white solid. $\delta_H$ (DMSO-d$_6$) 8.13 (s, 1H), 8.03-8.06 (m, 1H), 7.54 (d, 1H, J 8.3 Hz), 7.28-7.35 (m, 2H), 7.26 (t, 1H, J 73.9 Hz), 7.18 (dd, 1H, J 8.0, 0.6 Hz), 7.04-7.13 (m, 2H), 6.79 (dd, 1H, J 7.7, 1.3 Hz), 5.43 (s, 2H), 4.13 (s, 2H), 3.86 (t, 2H, J 5.2 Hz), 3.18-3.24 (m, 2H), 2.46 (s, 3H), 2.18 (s, 3H). LCMS (ES+) 479 (M+H)$^+$, RT 1.82 minutes.

Example 1053

1-[2-(Difluoromethoxy)benzyl]-2-(dimethylamino)-1H-benzimidazole-6-carbonitrile

Intermediate 40 (200 mg, 0.69 mmol) was dissolved in DCM (7 mL), then Hünig's base (0.13 mL, 0.76 mmol) and (dichloromethylene)dimethylammonium chloride (112 mg, 0.69 mmol) were added sequentially. The reaction mixture was then stirred under N$_2$ for 18 h. The reaction mixture was partitioned between DCM (10 mL) and 10% aqueous NaHCO$_3$ solution (10 mL). The organic layer was separated and dried with Na$_2$SO$_4$, then the solvent was removed under reduced pressure. The resulting oil was purified using silica-gel chromatography to afford the title compound (61 mg, 26%). LCMS (pH 10) 344 (M+H)$^+$, RT 2.34 minutes.

Example 1054

1-(2,5-Dichlorobenzyl)-2-[(4-oxocyclohexyl)methyl]-1H-benzimidazole-6-carbonitrile Intermediate 42 (1 g, 3.4 mmol) was combined with 2-(4-oxocyclohexyl)acetic acid (1.06 g, 6.8 mmol) in accordance with Method J to yield the title compound (142 mg, 10%). LCMS (pH 10) 412 (M+H)$^+$, RT 2.23 minutes.

Example 1055

1-{3-[(6-Bromo-1-{1-[2-(difluoromethoxy)phenyl]ethyl}-1H-benzimidazol-2-yl)-methoxy]phenyl}pyrrolidin-2-one (Isomer B)

2-[3-(2-Oxopyrrolidin-1-yl)phenoxy]acetic acid (0.36 g, 1.54 mmol) was reacted with Intermediate 131 in accordance with Method J to afford the title compound (0.19 g, 24%) as a pale solid. LCMS (pH 10) 557 (M+H)$^+$, RT 2.66 minutes.

Example 1056

1-{3-[(1-{1-[2-(Difluoromethoxy)phenyl]ethyl}-6-(6-oxopyridin-3-yl)benzimidazol-2-yl)methoxy]phenyl}pyrrolidin-2-one (Isomer B)

Example 1055 was coupled with 2-methoxypyridin-5-ylboronic acid (0.14 g, 0.91 mmol) in accordance with Method L. The resulting material was then demethylated in accordance with Method M to afford the title compound (37 mg, 16%). LCMS (pH 10) 572 (M+H)$^+$, RT 1.93 minutes.

Example 1057

1-{3-[(6-Bromo-1-{(1-[2-(difluoromethoxy)phenyl]ethyl}-1H-benzimidazol-2-yl)-methoxy]phenyl}pyrrolidin-2-one (Isomer A)

2-[3-(2-Oxopyrrolidin-1-yl)phenoxy]acetic acid (0.36 g, 1.54 mmol) was reacted with Intermediate 132 according to Method J to afford the title compound (0.45 g, 58%) as a pale solid. LCMS (pH 10) 557 (M+H)$^+$, RT 2.67 minutes.

Example 1058

6-Bromo-1-{(1R or 1S)-1-[2-(difluoromethoxy)phenyl]ethyl}-2-methylbenzimidazole (Isomer B)

Prepared from Intermediate 130 and 4-bromo-2-fluoronitrobenzene in accordance with Method K to afford the title compound (101 mg) as an off-white solid. $\delta_H$ (400 MHz, DMSO-d$_6$) 7.88 (1H, dd, J 7.7, 1.4 Hz), 7.50-7.45 (1H, m), 7.45-7.37 (2H, m), 7.28 (1H, d, J 1.8 Hz), 7.19 (1H, dd, J 8.5, 1.8 Hz), 7.15 (1H, br d, J 8.0 Hz), 7.12 (1H, t, J 73.8 Hz), 5.98 (1H, q, J 7.2 Hz), 2.58 (3H, s), 1.88 (3H, d, J 7.2 Hz). LCMS (pH 3): MH$^+$ m/z 212, RT 1.79 minutes (100%). LCMS (pH 10): MH$^+$ m/z 214, RT 2.33 minutes (100%).

Example 1059

4-[5-(5-Chloro-1-{[2-(difluoromethoxy)phenyl]methyl}-2-methylbenzimidazol-6-yl)-pyrimidin-2-yl]piperazin-2-one The title compound can be prepared from Intermediate 134 and piperazin-2-one in accordance with Method S. LCMS (pH=10): m/z 499.2 $^{35}$Cl (M+H)$^+$, 502.2 $^{37}$Cl (M+H)$^+$, RT 1.30 minutes.

Example 1060

2-[5-(1-{[2-(Difluoromethoxy)phenyl]methyl}-5-fluoro-2-methylbenzimidazol-6-yl)-pyrimidin-2-yl]propan-2-ol A mixture of Intermediate 50 (0.5 g, 1.543 mmol), 2-[5-(4,4,5,5-tetramethyl-1,3,2-dioxaborolan-2-yl)pyrimidin-2-yl]propan-2-ol (0.57 g, 2.16 mmol), Pd(dppf)Cl$_2$ (32 mg, 0.039 mmol) and 2M aqueous sodium carbonate solution (3 mL) in 1,4-dioxane (12 mL) was degassed and stirred at 110° C. The reaction mixture was partitioned between EtOAc/brine, and the organic layer was dried (MgSO$_4$). The solvent was evaporated and the crude material was purified by column chromatography (EtOAc:hexanes, 3:2 to 2:1). The resulting material was crystallised from diethyl ether/hexanes, filtered, washed with diethyl ether/hexanes and dried, to give the title compound (0.32 g, 50%) as a white solid. $\delta_H$ (400 MHz, DMSO-d$_6$) 8.97 (d, J 1.6 Hz, 2H), 7.81 (d, J 6.8 Hz, 1H), 7.59 (d, J 11.4 Hz, 1H), 7.39 (m, 1H), 7.33 (t, J 72, 76 Hz, 1H), 7.26 (m, 1H), 7.17 (m, 1H), 6.83 (m, 1H), 5.56 (s, 2H), 2.50 (s, 3H), 1.54 (s, 6H). LCMS (pH 10) MH+ 443, RT 2.09 minutes.

Example 1061

4-[5-(1-{[2-(Difluoromethoxy)phenyl]methyl}-5-fluoro-2-methylbenzimidazol-6-yl)-pyridin-2-yl]-1-methylpiperidin-4-ol TBAF in THF (1M, 0.82 mL) was added to a solution of Intermediate 138 (60%, 128 mg, 0.14 mmol) in THF (1 mL) and stirred at 20° C. for 2.5 h. The reaction mixture was concentrated under vacuum, diluted with EtOAc (5 mL) and washed with water (3×2 mL) and brine (2 mL), then dried over magnesium sulfate, filtered and concentrated under vacuum. The resulting crude product was purified by preparative HPLC (Method D) to afford the title compound (16 mg, 25%) as a pale brown solid. $\delta_H$ (500 MHz, CDCl$_3$) 8.62 (s, 1H), 7.88 (dt, J 8.2, 1.9 Hz, 1H), 7.52 (d, J 10.9 Hz, 1H), 7.43 (d, J 8.2 Hz, 1H), 7.35-7.30 (m, 1H), 7.17 (dd, J 15.2, 7.2 Hz, 2H), 7.10 (t, J 7.6 Hz, 1H), 6.81-6.48 (m, 2H), 5.40 (s, 2H), 5.23 (s, 1H), 2.82 (d, J 11.0 Hz, 2H), 2.61-2.51 (m, 5H), 2.39 (s, 3H), 2.14 (td, J 13.0, 4.4 Hz, 2H), 1.68 (d, J 11.6 Hz, 2H). LCMS Method D: MH$^+$ m/z 497.1, RT 1.41 minutes (100%).

Example 1062

4-[5-(1-{[2-(Difluoromethoxy)phenyl]methyl}-5-fluoro-2-methylbenzimidazol-6-yl)-pyrimidin-2-yl]-1-methylpiperidin-4-ol Intermediate 141 (232 mg, 0.59 mmol) and Intermediate 50 (150 mg, 0.39 mmol) were stirred in 1,4-dioxane (3 mL) and 2M aqueous sodium carbonate solution (0.61 mL) was added. The mixture was degassed with nitrogen for 5 minutes, then Pd(dppf)Cl$_2$ complex with DCM (0.02 g, 0.02 mmol) was added. The tube was sealed and the reaction mixture was heated at 85° C. for 1.5 h. The reaction mixture was cooled and TBAF in THF (1M, 2.34 mL) was added, and the reaction mixture was stirred for 19 h. The mixture was diluted with water (1 mL) and extracted into EtOAc (3×10 mL), then washed with brine (5 mL), dried over magnesium sulphate, filtered and concentrated under vacuum. The crude product was purified on a Biotage isolera 4 using SNAP HP 10 g column, eluting with 0-10% 7N methanolic ammonia in DCM. The resulting material was further purified by preparative HPLC (method D) to afford the title compound (28.7 mg, 14.8%) as a white solid. $\delta_H$ (250 MHz, CDCl$_3$) 8.85 (d, J 1.6 Hz, 2H), 7.56 (d, J 10.8 Hz, 1H), 7.41-7.29 (m, 1H), 7.23-7.06 (m, 3H), 6.65 (t, J 73.2 Hz, 1H), 6.65 (d, J 5.5 Hz, 1H), 5.41 (s, 2H), 4.51 (s, 1H), 2.83 (d, J 10.3 Hz, 2H), 2.61 (s, 3H), 2.60-2.42 (m, 4H), 2.39 (s, 3H), 1.67 (d, J 11.6 Hz, 2H). LCMS Method D: MH$^+$ m/z 498.1, RT 1.38 minutes (100%).

Example 1063

3-[5-(1-{[2-(Difluoromethoxy)phenyl]methyl}-5-fluoro-2-methylbenzimidazol-6-yl)-pyrimidin-2-yl]oxetan-3-ol Intermediate 142 (146 mg, 0.63 mmol) and Intermediate 143 (385 mg, 0.76 mmol) were dissolved in anhydrous 1,4-dioxane (8 mL) and 2M aqueous potassium carbonate solution (0.96 mL) was added. The mixture was degassed under nitrogen for 5 minutes. Pd(dppf)Cl$_2$ complex with DCM (23 mg, 0.032 mmol) was added. The mixture was heated at 105° C. in a sealed tube for 3 h. The reaction mixture was cooled, ethyl acetate (10 mL) was added and the mixture was filtered through a plug of Celite, washing with EtOAc (30 mL). The organic solution was washed with brine (15 mL), dried over sodium sulfate, and filtered, then the solvent was removed under vacuum. The resulting crude dark brown oil was purified using preparative HPLC (method C) to afford the title compound (39 mg, 14%) as an off white solid. $\delta_H$ (500 MHz, DMSO-d$_6$) 9.05 (d, J 1.5 Hz, 2H), 7.82 (d, J 6.8 Hz, 1H), 7.59 (d, J 11.3 Hz, 1H), 7.38 (td, J 8.3, 1.4 Hz, 1H), 7.33 (t, J 73.8 Hz, 1H), 7.25 (d, J 8.1 Hz, 1H), 7.18-7.13 (m, 1H), 6.81 (d, J 6.7 Hz, 1H), 6.39 (s, 1H), 5.56 (s, 2H), 5.02 (d, J 6.6 Hz, 2H), 4.71 (d, J 6.5 Hz, 2H), 3.32 (s, 3H). LCMS Method D: MH$^+$ m/z 457.1, RT 1.99 minutes (100%).

Example 1064

1-[5-(1-{[2-(Difluoromethoxy)phenyl]methyl}-5-fluoro-2-methylbenzimidazol-6-yl)-pyrimidin-2-yl]cyclobutanol Intermediate 142 (150 mg, 0.655 mmol) and Intermediate 144 (598 mg, 1.18 mmol) were dissolved in anhydrous 1,4-dioxane (8 mL) and 2M aqueous potassium carbonate solution (1.0 mL) was added. The mixture was degassed under nitrogen for 5 minutes. Pd(dppf)Cl$_2$ complex with DCM (24 mg, 0.033 mmol) was added. The mixture was heated at 105° C. in a sealed tube for 3 h. The reaction mixture was cooled, ethyl acetate (10 mL) was added and the mixture was filtered through a plug of Celite, washing with EtOAc (30 mL). The organic solution was washed with brine (15 mL), dried over sodium sulfate, and filtered, then the solvent removed under vacuum. The resulting crude dark brown oil was purified using a Biotage Isolera 4, eluting with 5% to 10% MeOH in DCM. The resulting material was purified using preparative HPLC (method D) to afford the title compound (27.8 mg, 9%) as a crystalline white solid. $\delta_H$ (500 MHz, CDCl$_3$) 8.89 (s, 2H), 7.59 (d, J 10.8 Hz, 1H), 7.41-7.32 (m, 1H), 7.22 (d, J 8.2 Hz, 1H), 7.19 (d, J 6.3 Hz, 1H), 7.14 (t, J 7.6 Hz, 1H), 6.70 (d, J 7.6 Hz, 1H), 6.67 (t, J 73.2 Hz, 1H), 5.44 (s, 2H), 5.03 (s, 1H), 2.76-2.66 (m, 2H), 2.65 (s, 3H), 2.55 (q, J 9.9 Hz, 2H), 2.21-2.11 (m, 1H), 2.07 (ddt, J 15.7, 10.4, 4.8 Hz, 1H). LCMS Method D: MH$^+$ m/z 456.1, RT 2.54 minutes (100%).

Example 1065

2-[5-(1-{[2-(Difluoromethoxy)phenyl]methyl}-5-fluoro-2-methylbenzimidazol-6-yl)-pyridin-2-yl] propan-2-ol To a stirring solution of Intermediate 148 (161 mg, 0.31 mmol) in acetonitrile (5 mL) was added TBAF in THF (1M, 1 mL) and the mixture was stirred at room temperature under nitrogen for 1 h. The reaction mixture was diluted with ethyl acetate (20 mL) and washed with water (20 mL). The organic layer was separated, dried over sodium sulfate and concentrated under vacuum. The resulting colourless oil (138 mg) was purified by preparative HPLC (method C) to afford the title compound (45 mg, 32%) as an off-white coloured solid. $\delta_H$ (500 MHz, CDCl$_3$) 8.61 (s, 1H), 7.88 (dt, J 8.2, 2.0 Hz, 1H), 7.54 (d, J 10.8 Hz, 1H), 7.43 (d, J 8.2 Hz, 1H), 7.37-7.31 (m, 1H), 7.21-7.15 (m, 2H), 7.11 (t, J 7.6 Hz, 1H), 6.68-6.65 (m, 1H), 6.65 (t, J 73.2 Hz, 1H), 5.41 (s, 2H), 2.62 (s, 3H), 1.58 (s, 6H). LCMS Method D: MH$^+$ m/z 442, RT 1.98 minutes (98%).

Example 1066 tert-Butyl 3-[5-(1-{[2-(difluoromethoxy)phenyl] methyl}-5-fluoro-2-methylbenzimidazol-6-yl)pyrimidin-2-yl]-3-hydroxyazetidine-1-carboxylate Intermediate 151 (570 mg, 1.27 mmol) and Intermediate 50 (94%, 420 mg, 1.03 mmol) were dissolved in 1,4-dioxane (20 mL) and 2M aqueous potassium carbonate solution (1.7 mL) was added. The mixture was degassed with nitrogen for 5 minutes. Pd(dppf)Cl$_2$ complex with DCM (45 mg, 0.055 mmol) was added. The mixture was stirred at 100° C. under nitrogen for 17 h. The reaction mixture was allowed to cool, filtered through sodium sulfate and concentrated under vacuum. The resulting dark oil (810 mg) was loaded onto a 25 g KP-silica cartridge and eluted on a Biotage Isolera 4, from a 0-100% ethyl acetate in heptanes gradient, to afford the title compound (269 mg, 44.4%) as a pale yellow solid. $\delta_H$ (500 MHz, CDCl$_3$) 8.91 (s, 2H), 7.59 (d, J 10.7 Hz, 1H), 7.36 (t, J 7.8 Hz, 1H), 7.23-7.16 (m, 2H), 7.13 (t, J 7.5 Hz, 1H), 6.71 (d, J 7.5 Hz, 1H), 6.65 (t, J 73.2 Hz, 1H), 5.43 (s, 2H), 5.25 (s, 1H), 4.41 (d, J 8.4 Hz, 2H), 4.25 (d, J 8.9 Hz, 2H), 2.65 (s, 3H), 1.48 (s, 9H). LCMS Method D: MH$^+$ m/z 556, RT 2.92 minutes (94%).

Example 1067

3-[5-(1-{[2-(Difluoromethoxy)phenyl]methyl}-5-fluoro-2-methylbenzimidazol-6-yl)-pyridin-2-yl] azetidin-3-ol formic acid salt A solution of Example 1066 (240 mg, 0.43 mmol) in 1,4-dioxane (2 mL) was treated with 4M hydrogen chloride in 1,4-dioxane (2 mL). The resulting sticky gum was placed in a sonic bath for 15 minutes, then stirred at room temperature for 1 h. The resulting fine suspension was concentrated under vacuum and the residue was triturated in 1:1 ethyl acetate in heptanes. The resulting solid was filtered off and dried in a vacuum oven. The resulting crude off-white solid was purified by preparative HPLC (method A) to afford the title compound (30 mg, 13%) as an off-white solid. $\delta_H$ (500 MHz, CD$_3$OD) 9.06 (d, J 1.5 Hz, 2H), 8.40 (s, 1H), 7.61 (d, J 6.5 Hz, 1H), 7.51 (d, J 11.0 Hz, 1H), 7.38 (td, J 8.3, 1.5 Hz, 1H), 7.24 (d, J 7.8 Hz, 1H), 7.17 (td, J 7.6, 0.9 Hz, 1H), 6.99-6.94 (m, 1H), 6.97 (t, J 73.6 Hz, 1H), 5.60 (s, 2H), 4.63 (d, J 11.8 Hz, 2H), 4.32 (d, J 11.7 Hz, 2H), 2.62 (s, 3H). LCMS Method D: MH$^+$ m/z 456, RT 1.26 minutes (95%).

Example 1068

4-[5-(1-{[2-(Difluoromethoxy)phenyl]methyl}-5-fluoro-2-methylbenzimidazol-6-yl)-pyrimidin-2-yl] tetrahydropyran-4-ol Intermediate 154 (57 mg, 0.15 mmol) and Intermediate 50 (52 mg, 0.14 mmol) were dissolved in a mixture of 2M aqueous potassium carbonate solution (0.23 mL) and 1,4-dioxane (1 mL). The solution was degassed for 10 minutes under a stream of nitrogen, then PdCl$_2$(dppf) complex with DCM (12 mg, 15 µmol) was added. The reaction mixture was heated under microwave irradiation at 110° C. for 1 h. The reaction mixture was cooled to ambient temperature and treated with TBAF in THF (1M, 0.9 mL) for 1 h. The reaction mixture was concentrated under vacuum and injected onto a Biotage isolera 4 (Snap HP-sil 10 g), eluting with 40-100% EtOAc in heptanes. The residue was purified by preparative HPLC (method A) to afford the title compound (18.6 mg, 24%) as a white solid. $\delta_H$ (500 MHz, CDCl$_3$) 8.87 (d, J 1.2 Hz, 2H), 7.58 (d, J 10.7 Hz, 1H), 7.38-7.31 (m, 1H), 7.19 (dd, J 10.6, 7.3 Hz, 2H), 7.12 (t, J 7.6 Hz, 1H), 6.68 (m, 2H), 5.42 (s, 2H), 4.02-3.92 (m, 4H), 2.63 (s, 3H), 2.44 (td, J 12.8, 6.1 Hz, 2H), 1.57 (d, J 11.9 Hz, 2H). LCMS Method D: MH$^+$ m/z 485, RT 2.22 minutes (95%).

Example 1069

2-[5-(1-{[2-(Difluoromethoxy)-5-fluorophenyl] methyl}-5-fluoro-2-methylbenzimidazol-6-yl)pyrimidin-2-yl]propan-2-ol Intermediate 156 (95%, 200 mg, 0.47 mmol), 2-[5-(4,4,5,5-tetramethyl-1,3,2-dioxaborolan-2-yl)pyrimidin-2-yl] propan-2-ol (137 mg, 0.52 mmol) and 2M aqueous sodium carbonate solution (0.71 mL) were dissolved in 1,4-dioxane (10 mL) and the mixture was degassed with nitrogen for 15 minutes. Pd(dppf)Cl$_2$ complex with DCM (19 mg, 0.02 mmol) was added. The mixture was further degassed with nitrogen for 5 minutes before being heated to 100° C. for 1 h. The reaction mixture was cooled to room temperature and diluted with ethyl acetate (10 mL), then filtered and evaporated under reduced pressure. The mixture was diluted with water and extracted with ethyl acetate. The organic phase was partitioned and dried over magnesium sulfate, then filtered, and the filtrate was evaporated under reduced pressure. The resulting crude material was purified by preparative HPLC (method C), and the resulting material was recrystallised from ethyl acetate/heptanes, to afford the title compound (107 mg, 49%) as a white solid. $\delta_H$ 500 MHz, DMSO-d$_6$) 8.98 (s, 2H), 7.89 (d, J 6.8 Hz, 1H), 7.58 (d, J 11.2 Hz, 1H), 7.34 (t, J 9.3 Hz, 1H), 7.20 (m, 1H), 7.10 (t, J 72.5 Hz, 1H), 6.86 (dd, J 5.9, 2.9 Hz, 1H), 5.61 (s, 2H), 5.13 (s, 1H), 2.55 (s, 3H), 1.54 (s, 6H). LCMS Method D: MH$^+$ m/z 461, RT 2.51 minutes (100%).)

Example 1070

2-[5-(1-{(1R or 1S)-1-[2-(Difluoromethoxy)phenyl]ethyl}-5-fluoro-2-methylbenzimidazol-6-yl)pyrimidin-2-yl]propan-2-ol (Isomer B)

A solution of 2-[5-(4,4,5,5-tetramethyl-1,3,2-dioxaborolan-2-yl)pyrimidin-2-yl]propan-2-ol (88 mg, 0.33 mmol) and Intermediate 158 (124 mg, 0.38 mmol) in 1,4-dioxane (6 mL) and 2M aqueous potassium carbonate solution (0.45 mL) was degassed with nitrogen for 10 minutes. Pd(dppf)Cl$_2$ complex with DCM (12 mg, 0.015 mmol) was added and the mixture was stirred at 100° C. under nitrogen for 1.5 h. The reaction mixture was allowed to cool to room temperature and filtered through sodium sulfate. The filtrate was concentrated under vacuum to give a dark oil which was loaded onto a 10 g HP-silica cartridge and eluted using Biotage Isolera 4 (from 0% to 85% ethyl acetate in heptanes). The resulting crude colourless solid (66 mg) was further purified by preparative HPLC (method D) to afford the title compound (43 mg, 32%) as a colourless solid. $\delta_H$ (500 MHz, CDCl$_3$) 8.73 (d, J 1.4 Hz, 2H), 7.73-7.67 (m, 1H), 7.54 (d, J 10.7 Hz, 1H), 7.47 (td, J 7.8, 1.2 Hz, 1H), 7.43-7.36 (m, 1H), 7.11 (d, J 8.1 Hz, 1H), 7.07 (d, J 6.5 Hz, 1H), 6.32 (dd, J 74.5, 72.3 Hz, 1H), 5.99 (q, J 7.2 Hz, 1H), 4.66 (s, 1H), 2.78 (s, 3H), 2.01 (d, J 7.2 Hz, 3H), 1.67 (s, 6H). LCMS Method D: MH$^+$ m/z 457, RT 2.26 minutes (94%).

Example 1071

2-[5-(1-{(1R or 1S)-1-[2-(Difluoromethoxy)phenyl]ethyl}-5-fluoro-2-methylbenzimidazol-6-yl)pyrimidin-2-yl]propan-2-ol (Isomer A)

A solution of 2-[5-(4,4,5,5-tetramethyl-1,3,2-dioxaborolan-2-yl)pyrimidin-2-yl]propan-2-ol (143 mg, 0.54 mmol) and Intermediate 160 (180 mg, 0.45 mmol) in 1,4-dioxane (8 mL) and 2M aqueous potassium carbonate solution (0.7 mL) was degassed with nitrogen for 10 minutes. Pd(dppf)Cl$_2$ complex with DCM (20 mg, 0.024 mmol) was added and the mixture was stirred at 100° C. under nitrogen for 1.5 h. The reaction mixture was allowed to cool to room temperature and filtered through sodium sulfate. The filtrate was concentrated under vacuum to give a dark oil (361 mg) which was loaded onto a 10 g HP-silica cartridge and eluted using Biotage Isolera 4 (from 0% to 85% ethyl acetate in heptanes). Product fractions were combined and concentrated under vacuum. The resulting crude colourless solid (110 mg) was further purified by preparative HPLC (method D) to afford the title compound (71 mg, 34.5%) as a colourless solid. $\delta_H$ (500 MHz, CDCl$_3$) 8.70 (d, J 1.4 Hz, 2H), 7.69-7.64 (m, 1H), 7.50 (d, J 10.8 Hz, 1H), 7.45 (td, J 7.9, 1.5 Hz, 1H), 7.39-7.32 (m, 1H), 7.09 (d, J 8.1 Hz, 1H), 7.03 (d, J 6.5 Hz, 1H), 6.29 (dd, J 74.6, 72.3 Hz, 1H), 5.96 (q, J 7.2 Hz, 1H), 4.65 (s, 1H), 2.74 (s, 3H), 1.98 (d, J 7.2 Hz, 3H), 1.64 (s, 6H). LCMS Method D: MH$^+$ m/z 457, RT 2.25 minutes (100%).

Example 1072

3-[5-(1-{[2-(Difluoromethoxy)-5-fluorophenyl]methyl}-5-fluoro-2-methylbenzimidazol-6-yl)pyrimidin-2-yl]oxetan-3-ol Intermediate 156 (200 mg, 0.5 mmol), Intermediate 161 (50%, 382 mg, 0.55 mmol) and 2M sodium carbonate solution (0.74 mL) were dissolved in 1,4-dioxane (10 mL) and the mixture was degassed with nitrogen for 15 minutes. Pd(dppf)Cl$_2$ complex with DCM (20 mg, 0.02 mmol) was added. The mixture was further degassed with nitrogen for 5 minutes before being heated at 100° C. for 2 h. The reaction mixture was cooled to room temperature and diluted with ethyl acetate (10 mL), then filtered and evaporated under reduced pressure. The crude material was dissolved in ethyl acetate (10 mL), then TBAF (1.24 mL) was added and the reaction mixture was stirred for 1 h at room temperature. The reaction mixture was washed with water (5 mL) and extracted with ethyl acetate (2×10 mL), then dried over magnesium sulfate, and filtered. The filtrate was evaporated under reduced pressure. The resulting crude material (100 mg) was purified by preparative HPLC (method C) to afford the title compound (46 mg, 19%) as a white solid. $\delta_H$ (500 MHz, DMSO-d$_6$) 9.04 (d, J 1.4 Hz, 2H), 7.89 (d, J 6.8 Hz, 1H), 7.57 (d, J 11.3 Hz, 1H), 7.31 (t, J 9.3 Hz, 1H), 7.20-7.13 (m, 1H), 7.08 (t, J 74 Hz, 1H), 6.84 (dd, J 6.0, 3.0 Hz, 1H), 6.38 (br s, 1H), 5.59 (s, 2H), 5.00 (d, J 6.6 Hz, 2H), 4.70 (d, J 6.6 Hz, 2H), 2.53 (s, 3H). LCMS Method A: MH$^+$ m/z 475, RT 3.21 minutes (99%).

Example 1073

5-(1-{[2-(Difluoromethoxy)phenyl]methyl}-2-methylbenzimidazol-6-yl)-1-(2,2,2-trifluoroethyl)pyridin-2-one Prepared by the method described above as Example 472: Alternative Preparation. The title compound (56 mg, 18%) was obtained as a white solid. $\delta_H$ (400 MHz, DMSO-d$_6$) 8.02 (d, 1H, J 2.3 Hz), 7.89 (dd, 1H, J 2.7, 9.6 Hz), 7.64-7.60 (m, 2H), 7.40-7.25 (m, 3H), 7.36 (t, 1H, J$_{H-F}$ 73.9 Hz), 7.17-7.12 (m, 1H), 6.69 (dd, 1H, J 1.4, 7.7 Hz), 6.58 (d, 1H, J 9.6 Hz), 5.52 (s, 2H), 4.90 (q, 2H, J$_{H-F}$ 9.2 Hz), 2.48 (s, 3H). LCMS (pH 10): MH$^+$ (464), RT 2.05 minutes, 98% purity by UV.

Example 1074

1-{[2-(Difluoromethoxy)phenyl]methyl}-2-methyl-6-{6-[4-(2,2-difluoroethyl)piperazin-1-yl]pyridin-3-yl}benzimidazole Example 490 and 2,2-difluoroethyl tosylate (125 mg, 0.53 mmol) were dissolved in acetonitrile (2 mL) and heated under microwave irradiation at 210° C. (18 bar pressure) for 30 minutes. The mixture was purified by column chromatography on silica gel (eluting with 0 to 5% methanol gradient in dichloromethane), then preparative HPLC, to give the title compound (63 mg, 22%) as a white solid after freeze drying. $\delta_H$ (400 MHz, DMSO-d$_6$) 8.42 (d, 1H, J 2.3 Hz), 7.82 (dd, 1H, J 2.5, 8.9 Hz), 7.64 (d, 1H, J 1.3 Hz), 7.59 (d, 1H, J 8.3 Hz), 7.43-7.36 (m, 2H), 7.35 (t, 1H, J$_{H-F}$ 73.8 Hz), 7.26 (d, 1H, J 8.3 Hz), 7.18-7.14 (m, 2H), 6.91 (d, 1H, J 8.9 Hz), 6.78 (dd, 1H, J 1.3, 8.3 Hz), 6.19 (tt, 1H, J 4.3, 55.7 Hz), 3.55-3.51 (m, 4H), 2.79 (dt, 2H, J 4.3, 15.7 Hz), 2.65-2.60 (m, 4H), 2.48 (s, 3H). LCMS (pH 10): MH+ (514.8), RT 2.42 minutes, 96% purity by UV.

Example 1075

1-[1-{[2-(Difluoromethoxy)phenyl]methyl}-6-(6-methoxypyridin-3-yl)benzimidazol-2-yl]-2,2,2-trifluoroethanol Intermediate 162 (1.00 g, 2.44 mmol) was dissolved in dry THF (30 mL) and trifluoromethyl trimethylsilane (416 mg, 2.93 mmol) was added, followed by caesium fluoride (445 mg, 2.93 mmol). The mixture was stirred at room temperature under nitrogen for 1 h. The mixture was quenched with saturated aqueous ammonium chloride solution (100 mL) and extracted with ethyl acetate (100 mL). The organic layer was dried (Na$_2$SO$_4$) and concentrated in vacuo. A quarter of the resulting material was dissolved in methanol (20 mL) and 2M aqueous sodium carbonate solution (20 mL) was added. After stirring for 1 h, the mixture was extracted into ethyl acetate and washed with water. The organic layer was dried (Na$_2$SO$_4$) and concentrated in vacuo. The residue was purified by chromatography on silica gel (eluting 0 to 6% methanol gradient in dichloromethane) to give the title compound (300 mg, 26%) as a pale purple solid. $\delta_H$ (400 MHz, DMSO-d$_6$) 8.43 (d, 1H, J 2.2 Hz), 7.97 (dd, 1H, J 8.6, 2.6 Hz), 7.82 (d, 1H, J 8.4 Hz), 7.60 (m, 2H), 7.34 (m, 4H), 7.10 (m, 1H), 6.89 (d, 1H, J 8.6 Hz), 6.62 (m, 1H), 5.73 (s, 2H), 5.64 (m, 1H), 3.87 (s, 3H). LCMS (pH 10): MH+ (480.6), RT 2.47 minutes, 98% purity by UV.

Example 1076

1-[1-{[2-(Difluoromethoxy)phenyl]methyl}-6-(6-methoxypyridin-3-yl)benzimidazol-2-yl]-2-methylpropan-1-ol Intermediate 162 (112 mg, 0.27 mmol) was dissolved in dry THF, cooled to −15° C. with an ice/CaCl$_2$ bath, and isopropylmagnesium chloride (2M in diethyl ether, 160 µL, 0.32 mmol) was added. The reaction mixture was warmed to room temperature and stirred for 3 h. The reaction mixture was quenched with water, extracted with ethyl acetate and concentrated in vacuo. Purification by preparative HPLC gave the title compound (14 mg, 11%) as a white solid. $\delta_H$ (400 MHz, DMSO-d$_6$) 8.43 (dd, 1H, J 2.5, 0.5 Hz), 7.97 (dd, 1H, J 8.6, 2.6 Hz), 7.73 (d, 1H, J 8.4 Hz), 7.63 (s, 1H), 7.49 (dd, 1H, J 8.4, 1.7 Hz), 7.32 (m, 4H), 7.10 (m, 1H), 6.88 (dd, 1H, J 8.6, 0.5 Hz), 6.55 (dd, 1H, J 7.8, 1.1 Hz), 5.71 (m, 3H), 4.38 (dd, 1H, J 8.6, 6.0 Hz), 3.87 (s, 3H), 2.16 (m, 1H), 1.01 (d, 3H, J 6.6 Hz), 0.70 (d, 3H, J 6.7 Hz). LCMS (pH 10): MH+ (454.7), RT 2.48 minutes, 95% purity by UV.

Example 1077

1-{[2-(Difluoromethoxy)phenyl]methyl}-6-[(6-methoxypyridin-2-yl)methyl]-2-methylbenzimidazole The title compound was prepared from Intermediate 165 and the appropriate boronic acid in accordance with Method L. QC LCMS m/z 410 [M+H]+, RT 1.56 minutes.

Example 1078

1-{[2-(Difluoromethoxy)phenyl]methyl}-2-methyl-6-[(2-methylpyridin-4-yl)methyl]-benzimidazole The title compound was prepared from Intermediate 165 and the appropriate boronic acid using a method analogous to Method L. QC LCMS m/z 394 [M+H]+, RT 1.41 minutes.

Example 1079

1-[2-(Difluoromethoxy)benzyl]-2-methyl-5-[(2-methylpyridin-4-yl)methyl]-1H-benzimidazole The title compound was prepared from Intermediate 166 and the appropriate boronic acid using a method analogous to Method L. QC LCMS m/z 394 [M+H]+, RT 1.55 minutes.

Example 1080

1-[2-(Difluoromethoxy)benzyl]-5-[(6-methoxypyridin-3-yl)methyl]-2-methyl-1H-benzimidazole The title compound was prepared from Intermediate 166 and the appropriate boronic acid using a method analogous to Method L. QC LCMS m/z 410 [M+H]+, RT 1.51 minutes.

Example 1081

1-[2-(Difluoromethoxy)benzyl]-2-methyl-5-{[6-(morpholin-4-yl)pyridin-3-yl]methyl}-1H-benzimidazole The title compound was prepared from Intermediate 166 and the appropriate boronic acid using a method analogous to Method L. QC LCMS m/z 465 [M+H]+, RT 1.53 minutes.

Example 1082

6-Bromo-1-(2,5-dichlorobenzyl)-5-fluoro-2-(methoxymethyl)-1H-benzimidazole

The title compound was prepared using a method analogous to Method K, starting from 1-bromo-2,5-difluoro-4-nitrobenzene and 2,5-dichlorobenzylamine, and effecting benzimidazole formation with methoxyacetic acid. LCMS (pH 10): m/z 419.5, RT 2.85 minutes.

Example 1083

5-{1-[2-(Difluoromethoxy)benzyl]-5-fluoro-2-(methoxymethyl)-1H-benzimidazol-6-yl}-pyridin-2(1H)-one The title compound was prepared from Intermediate 173 and 5-(4,4,5,5-tetramethyl-1,3,2-dioxaborolan-2-yl)-1H-pyridin-2-one in accordance with Method L. LCMS (pH 10): m/z 430.6, RT 1.70 minutes.

Example 1084

5-[1-(2,5-Dichlorobenzyl)-5-fluoro-2-(methoxymethyl)-1H-benzimidazol-6-yl]pyridin-2(1H)-one The title compound was prepared from Example 1082 and 5-(4,4,5,5-tetramethyl-1,3,2-dioxaborolan-2-yl)-1H-pyridin-2-one in accordance with Method L. LCMS (pH 10): m/z 432.6 [M+H]$^+$, RT 1.88 minutes.

Example 1085

Methyl 4-{1-[2-(difluoromethoxy)benzyl]-2-methyl-1H-benzimidazol-6-yl}piperidine-1-carboxylate The title compound was prepared using a method analogous to that used to prepare Example 533 from Intermediate 122 and methyl chloroformate. QC LCMS m/z 430 [M+H]$^+$, RT 1.46 minutes.

Example 1086

1-(2,5-Dichlorobenzyl)-2-methyl-6-(1H-1,2,3-triazol-1-ylmethyl)-1H-benzimidazole The title compound was prepared from Intermediate 165 and 1,2,3-triazole using a method analogous to Method B. QC LCMS m/z 372 [M+H]$^+$, RT 1.35 minutes.

Example 1087

N-{[1-(2,5-Dichlorobenzyl)-2-methyl-1H-benzimidazol-6-yl]methyl}-N,2-dimethyl-propanamide The title compound can be prepared from Intermediate 165 by treatment with methylamine followed by concentration in vacuo and subsequent acylation with 2-methylpropanoic acid using a method analogous to Method G. QC LCMS m/z 404 [M+H]$^+$, RT 1.47 minutes.

Example 1088

1-(2,5-Dichlorobenzyl)-2-methyl-5-[(2-methyl-1H-imidazol-1-yl)methyl]-1H-benzimidazole The title compound was prepared from Intermediate 166 and 2-methylimidazole using a method analogous to Method B. QC LCMS m/z 385 [M+H]$^+$, RT 1.41 minutes.

Example 1089

1-(2,5-Dichlorobenzyl)-2-methyl-5-(1H-1,2,3-triazol-1-ylmethyl)-1H-benzimidazole The title compound was prepared from Intermediate 166 and 1,2,3-triazole using a method analogous to Method B. QC LCMS m/z 372 [M+H]$^+$, RT 1.39 minutes.

Example 1090

N-{[1-(2,5-Dichlorobenzyl)-2-methyl-1H-benzimidazol-5-yl]methyl}-N-methyl-cyclopropanecarboxamide The title compound can be prepared from Intermediate 166 by treatment with methylamine followed by concentration in vacuo and subsequent acylation with cyclopropanecarboxylic acid using a method analogous to Method G. QC LCMS m/z 402 [M+H]$^+$, RT 1.48 minutes.

Example 1091

1-(2,5-Dichlorobenzyl)-2-methyl-1H-benzimidazol-6-yl methanesulfonate

The title compound was prepared from Intermediate 101 and methanesulphonyl chloride according to the preparation of Example 1014. QC LCMS m/z 385 [M+H]$^+$, RT 1.46 minutes.

Example 1092

1-(2,5-Dichlorobenzyl)-2-methyl-1H-benzimidazol-6-yl 4-methylbenzenesulfonate

The title compound was prepared from Intermediate 101 and toluenesulphonyl chloride according to the preparation of Example 1014. QC m/z 461 [M+H]$^+$, LCMS RT 1.66 minutes.

Example 1093

2-Methyl-1-(1-phenylethyl)-1H-benzimidazol-6-yl trifluoromethanesulfonate

The title compound was prepared from Intermediate 174 and trifluoromethane-sulphonyl chloride according to the preparation of Example 1014. QC LCMS m/z 385 [M+H]$^+$, RT 1.62 minutes.

Example 1094

1-(2,5-Dichlorobenzyl)-N,N,2-trimethyl-1H-benzimidazole-6-carboxamide

The title compound was prepared from Intermediate 100 and dimethylamine by a method analogous to that described for Example 1011. QC LCMS m/z 362 [M+H]$^+$, RT 1.35 minutes.

Example 1095

1-(2,5-Dichlorobenzyl)-2-methyl-5-(oxetan-3-yloxy)-1H-benzimidazole

The title compound was prepared from Intermediate 103 using a method analogous to that used to prepare Intermediate 102. QC LCMS m/z 363 [M+H]$^+$, RT 1.47 minutes.

Example 1096

2-{[1-(2,5-Dichlorobenzyl)-2-methyl-1H-benzimidazol-5-yl]oxy}-N,N-dimethyl-ethanamine The title compound was prepared from Intermediate 103 using a method analogous to that used to prepare Intermediate 102. QC LCMS m/z 378 [M+H]$^+$, RT 1.45 minutes.

Example 1097

1-(2,5-Dichlorobenzyl)-2-methyl-1H-benzimidazol-5-yl methanesulfonate

The title compound was prepared from Intermediate 103 and methanesulphonyl chloride according to the preparation of Example 1014. QC LCMS m/z 385 [M+H]$^+$, RT 1.48 minutes.

Example 1098

5-(Azetidin-3-yloxy)-1-(2,5-dichlorobenzyl)-2-methyl-1H-benzimidazole

The title compound was prepared from Intermediate 103 by a method analogous to that used to prepare Intermediate 102 and Example 1018. QC LCMS m/z 362 [M+H]$^+$, RT 1.37 minutes.

Example 1099

1-(3-{[1(2,5-Dichlorobenzyl)-2-methyl-1H-benzimidazol-5-yl]oxy}azetidin-1-yl)ethanone The title compound can be prepared from Example 1098 using the method of Example 1020. QC LCMS m/z 404 [M+H]$^+$, RT 1.41 minutes.

Example 1100

5-{1-[2-(Difluoromethoxy)benzyl]-2-methyl-1H-benzimidazol-6-yl}pyridin-2-amine

The title compound can be prepared from Intermediate 47 and the appropriate boronic acid using a method analogous to Method L. LCMS (pH 10): m/z 381 [M+H]$^+$, RT 1.79 minutes.

Example 1101

N-[5-(1-{[2-(Difluoromethoxy)phenyl]methyl}-2-methylbenzimidazol-6-yl)pyridin-2-yl]-Nrop-2-enoyl)prop-2-enamide The title compound can be prepared from Example 1100 by deprotonation of the aniline with 2 equivalents of sodium hydride and treatment with 2 equivalents of acryloyl chloride in tetrahydrofuran. LCMS (pH 10): m/z 489 [M+H]$^+$, RT 2.25 minutes.

Example 1102

{1-[(2,5-Dimethylphenyl)methyl]-6-[4-(piperazin-1-yl)phenyl]benzimidazol-2-yl}-(phenyl)methanol A mixture of Intermediate 175 (200 mg, 0.47 mmol), 4-[4-(tert-butoxycarbonyl)-piperazinyl]phenylboronic acid pinacol ester (364 mg, 0.95 mmol) and Pd(PPh$_3$)$_4$ (30 mg, 0.026 mmol) in 1,4-dioxane (10 mL) and 2M aqueous Na$_2$CO$_3$ solution (2 mL) was degassed and flushed with N$_2$ three times. The reaction mixture was heated with stirring at 90° C. until TLC or LCMS analysis indicated that the reaction was complete. The reaction mixture was allowed to cool to room temperature and evaporated in vacuo. The crude residue was suspended in EtOAc (30 mL) and washed with water. The aqueous phases were extracted with further EtOAc (4×30 mL) and the combined organic layers dried (MgSO$_4$), filtered and concentrated in vacuo. The crude product was purified by chromatography (SiO$_2$; 2-50% EtOAc in DCM). The resulting yellow solid (160 mg) was dissolved in DCM (5 mL) and a 4N solution of HCl in 1,4-dioxane (1 mL) was added. The mixture was stirred at r.t. for 2 h, then concentrated in vacuo. The residue was purified by preparative chromatography to afford the title compound (70 mg, 27%) as an off-white solid. $\delta_H$ (CD$_3$OD, 400 MHz) 7.75 (d, J 8.46 Hz, 1H), 7.52 (d, J 6.94 Hz, 1H), 7.39-7.50 (m, 4H), 7.15-7.25 (m, 4H), 7.03 (d, J 6.96 Hz, 3H), 6.86 (d, J 7.6 Hz, 1H), 6.18 (s, 1H), 5.93 (s, 1H), 5.50 (dd, J 17.0 Hz, 2H), 3.32-3.43 (m, 8H), 2.27 (s, 3H), 1.94 (s, 3H). LCMS (ES+) (M+H)$^+$ 502, RT 2.43 minutes.

Example 1103

{1-[(2,5-Dimethylphenyl)methyl]benzimidazol-2-yl}(3-fluoropyridin-4-yl)methanol

The title compound (162 mg, 19%) was synthesised from Intermediate 2 and 3-fluoropyridine-4-carbaldehyde in accordance with Method C. $\delta_H$ (400 MHz, DMSO-d$_6$) 8.46 (d, J 4.8 Hz, 1H), 8.43 (d, J 1.2 Hz, 1H), 7.76 (t, J 5.6 Hz, 1H), 7.62-7.68 (m, 1H), 7.34-7.40 (m, 1H), 7.20-7.29 (m, 2H), 7.10-7.12 (m, 1H), 6.95 (d, J 7.5 Hz, 1H), 6.20 (s, 1H), 6.09 (s, 1H), 5.64 (d, J 18.2 Hz, 2H), 2.36 (s, 3H), 2.02 (s, 3H). LCMS (pH 10): (ES+) (M+H)$^+$ 362, RT 1.98 minutes.

Example 1104

{1-[(2,5-Dimethylphenyl)methyl]-6-[4-(piperazin-1-yl)phenyl]benzimidazol-2-yl}-(pyridin-4-yl)methanol The title compound was synthesised from Intermediate 30 in accordance with the method described for Example 1102. QC LCMS: m/z 504 (M+H)$^+$, RT 1.99 minutes.

Example 1105

{1-[(2,5-Dimethylphenyl)methyl]-5-(trifluoromethyl)benzimidazol-2-yl}-(pyridin-4-yl)-methanol The title compound was synthesised from Intermediate 176 and pyridine-4-carbaldehyde in accordance with Method C. QC LCMS: m/z 412 (M+H)$^+$, RT 2.38 minutes.

The invention claimed is:

1. A compound represented by formula (IIB) or a pharmaceutically acceptable salt thereof:

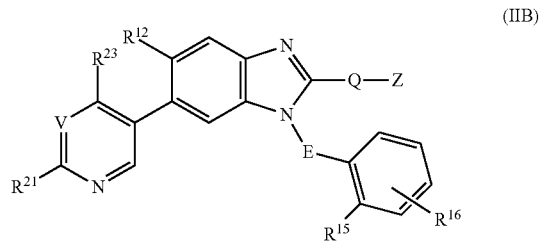

(IIB)

wherein

V represents C—R$^{22}$ or N;

R$^{21}$ represents hydrogen, halogen, cyano, C$_{1-6}$ alkyl, trifluoromethyl, C$_{2-6}$ alkenyl, C$_{2-6}$ alkynyl, hydroxy, hydroxy($C_{1-6}$)alkyl, $C_{1-6}$ alkoxy, difluoromethoxy, trifluoromethoxy, trifluoroethoxy, $C_{1-6}$ alkoxy($C_{1-6}$)alkyl, $C_{1-6}$ alkylthio, $C_{1-6}$ alkylsulphonyl, amino, $C_{1-6}$ alkylamino, di($C_{1-6}$)alkylamino, hydroxy($C_{1-6}$)alkylamino, ($C_{1-6}$)alkoxy($C_{1-6}$)alkylamino, [($C_{1-6}$)alkoxy](hydroxy)($C_{1-6}$)alkylamino, N—[($C_{1-6}$)alkyl]-N-[hydroxy($C_{1-6}$)alkyl]amino, [($C_{1-6}$)alkylthio](hydroxy)($C_{1-6}$)alkylamino, di($C_{1-6}$)alkylamino($C_{1-6}$)alkylamino, N-[di($C_{1-6}$)alkylamino($C_{1-6}$)alkyl]-N-[hydroxy($C_{1-6}$)alkyl]amino, hydroxy($C_{1-6}$)alkyl($C_{3-7}$)cycloalkylamino, (hydroxy)[($C_{3-7}$)cycloalkyl($C_{1-6}$)alkyl]amino, ($C_{3-7}$)heterocycloalkyl($C_{1-6}$)alkylamino, oxo($C_{3-7}$)heterocycloalkyl($C_{1-6}$)alkylamino, ($C_{1-6}$)alkylheteroarylamino, heteroaryl($C_{1-6}$)alkylamino, ($C_{1-6}$)alkylheteroaryl($C_{1-6}$)alkylamino, $C_{2-6}$ alkylcarbonylamino, N—[($C_{1-6}$)alkyl]-N—[($C_{2-6}$)alkylcarbonyl]amino, bis[($C_{3-6}$)alkenyl-carbonyl]amino, N-[carboxy($C_{1-6}$)alkyl]-N—[($C_{1-6}$)alkyl]amino, $C_{2-6}$ alkoxycarbonylamino, $C_{2-6}$ alkoxycarbonyl($C_{1-6}$)alkylamino, $C_{1-6}$ alkyl sulphonylamino, N—[($C_{1-6}$)alkyl]-N—[($C_{1-6}$)alkylsulphonyl]amino, formyl, $C_{2-6}$ alkylcarbonyl, carboxy, $C_{2-6}$ alkoxycarbonyl, aminocarbonyl, $C_{1-6}$ alkylaminocarbonyl, hydroxy($C_{1-6}$)alkylaminocarbonyl, di($C_{1-6}$)alkylaminocarbonyl, aminocarbonyl($C_{1-6}$)alkyl, aminosulphonyl, $C_{1-6}$ alkylaminosulphonyl or di($C_{1-6}$)alkylaminosulphonyl; or $R^{21}$ represents ($C_{3-7}$)cycloalkyl, ($C_{3-7}$)cycloalkyl($C_{1-6}$)alkyl, ($C_{4-7}$)cycloalkenyl, ($C_{4-9}$)bicycloalkyl, ($C_{3-7}$)heterocycloalkyl, ($C_{3-7}$)heterocycloalkyl($C_{1-6}$)alkyl, ($C_{3-7}$)heterocycloalkenyl, ($C_{4-9}$)heterobicycloalkyl or ($C_{4-9}$)spiroheterocycloalkyl, any of which groups may be optionally substituted by one or more substituents;

$R^{22}$ represents hydrogen, halogen or $C_{1-6}$ alkyl;

$R^{23}$ represents hydrogen or $C_{1-6}$ alkyl;

E represents —N($R^4$)—, —CH$_2$—, —CH(CH$_3$)— or —CH(CH$_2$CH$_3$)—;

Q represents a covalent bond; or Q represents —O—, —S—, —S(O)—, —S(O)$_2$—, —N($R^5$)—, —C(O)N($R^5$)—, —N($R^5$)C(O)—, —S(O)$_2$N($R^5$)— or —N($R^5$)S(O)$_2$—; or Q represents an optionally substituted straight or branched $C_{1-6}$ alkylene chain optionally comprising one, two or three heteroatom-containing linkages independently selected from —O—, —S—, —S(O)—, —S(O)$_2$—, —N($R^5$)—, —C(O)N($R^5$)—, —N($R^5$)C(O)—, —S(O)$_2$N($R^5$)— and —N($R^5$)S(O)$_2$—;

Z represents hydrogen, halogen or trifluoromethyl; or Z represents $C_{1-6}$ alkyl, $C_{3-7}$ cycloalkyl, aryl, $C_{3-7}$ heterocycloalkyl, $C_{3-7}$ heterocycloalkenyl or heteroaryl, any of which groups may be optionally substituted by one or more substituents; or Z represents —$Z^1$—$Z^2$ or —$Z^1$—C(O)—$Z^2$, either of which moieties may be optionally substituted by one or more substituents;

$Z^1$ represents a divalent radical derived from an aryl, $C_{3-7}$ heterocycloalkyl or heteroaryl group;

$Z^2$ represents aryl, $C_{3-7}$ heterocycloalkyl, $C_{3-7}$ heterocycloalkenyl, ($C_{4-9}$)heterobicycloalkyl, ($C_{4-9}$)spiroheterocycloalkyl or heteroaryl;

$R^4$ and $R^5$ independently represent hydrogen or $C_{1-6}$ alkyl;

$R^{12}$ represents hydrogen, halogen, trifluoromethyl or optionally substituted $C_{1-6}$ alkyl; and $R^{15}$ and $R^{16}$ independently represent hydrogen, halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, arylamino, $C_{2-6}$ alkylcarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl.

2. A compound as claimed in claim 1 wherein $R^{21}$ represents hydroxy($C_{1-6}$)alkyl.

3. A compound as claimed in claim 1 represented by formula (IIC), (IIE), (IIF), (IIG), (IIH), (IIJ), (IIK) or (IIL) or a pharmaceutically acceptable salt thereof:

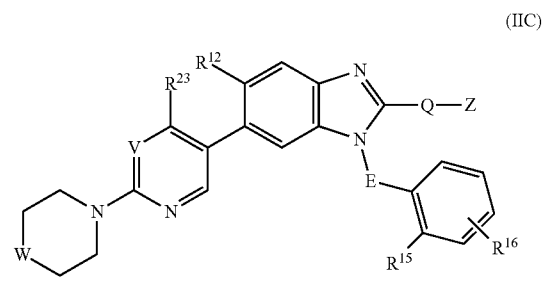

(IIC)

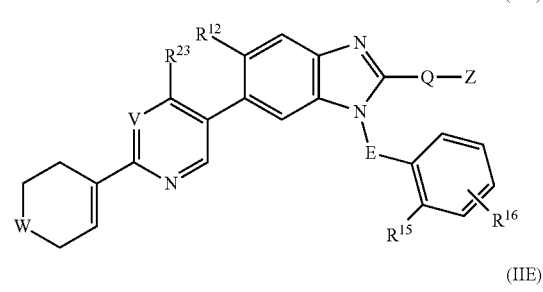

(IID)

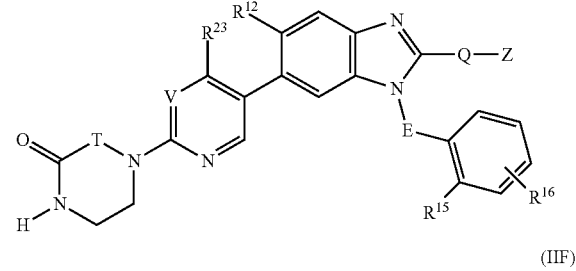

(IIE)

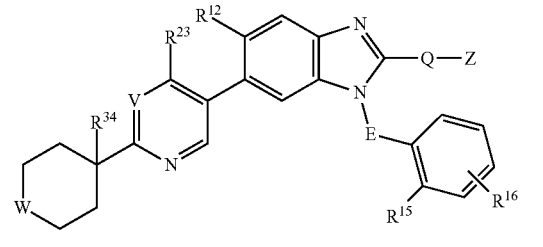

(IIF)

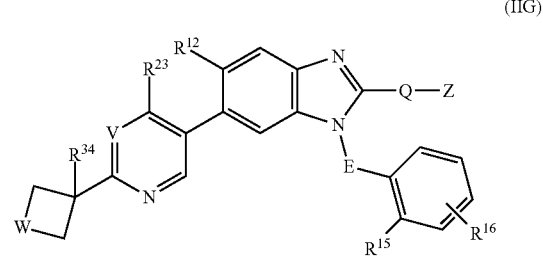

(IIG)

-continued

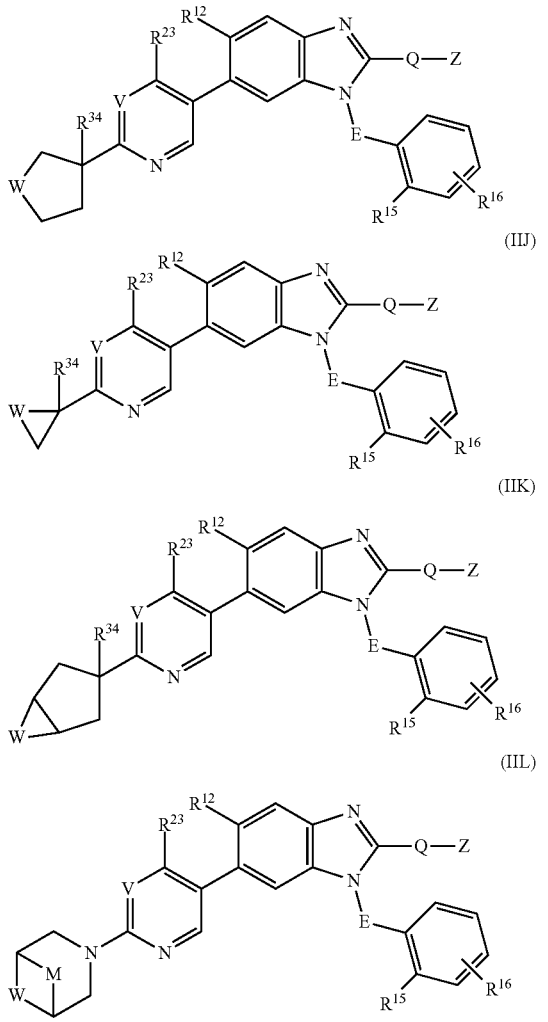

wherein
T represents —CH₂— or —CH₂CH₂—;
W represents O, S, S(O), S(O)₂, N(R³¹) or C(R³²)(R³³);
-M- represents —CH₂— or —CH₂CH₂—;
R³¹ represents hydrogen, hydroxy(C₁₋₆)alkyl, cyano(C₁₋₆)alkyl, C₁₋₆ alkyl, trifluoromethyl, difluoroethyl, trifluoroethyl, C₁₋₆ alkylsulphonyl, (C₁₋₆)alkylsulphonyl(C₁₋₆)alkyl, formyl, C₂₋₆ alkylcarbonyl, carboxy, carboxy(C₁₋₆)alkyl, C₂₋₆ alkoxycarbonyl, C₂₋₆ alkoxycarbonyl(C₁₋₆)alkyl, a carboxylic acid isostere or prodrug moiety Ω, —(C₁₋₆)alkyl-Ω, aminocarbonyl, C₁₋₆ alkylaminocarbonyl, di(C₁₋₆)alkylaminocarbonyl, aminosulphonyl or di(C₁₋₆)alkylaminosulphonyl;
R³² represents halogen, C₁₋₆ alkoxy, carboxy, carboxy(C₁₋₆)alkyl, C₂₋₆ alkoxycarbonyl, C₂₋₆ alkoxycarbonyl(C₁₋₆)alkyl, aminocarbonyl, a carboxylic acid isostere or prodrug moiety Ω, or —(C₁₋₆)alkyl-Ω;
R³³ represents hydrogen, halogen, C₁₋₆ alkyl or amino;
R³⁴ represents hydrogen, halogen, hydroxy, C₁₋₆ alkoxy, C₁₋₆ alkylthio, C₁₋₆ alkylsulphinyl, C₁₋₆ alkylsulphonyl, amino, C₁₋₆ alkylamino or di(C₁₋₆)alkylamino;
E represents —N(R⁴)—, —CH₂—, —CH(CH₃)— or —CH(CH₂CH₃)—;
Q represents a covalent bond; or Q represents —O—, —S—, —S(O)—, —S(O)₂—, —N(R⁵)—, —C(O)N(R⁵)—, —N(R⁵)C(O)—, —S(O)₂N(R⁵)— or —N(R⁵)S(O)₂—; or Q represents an optionally substituted straight or branched C₁₋₆ alkylene chain optionally comprising one, two or three heteroatom-containing linkages independently selected from —O—, —S—, —S(O)—, —S(O)₂—, —N(R⁵)—, —C(O)N(R⁵)—, —N(R⁵)C(O)—, —S(O)₂N(R⁵)— and —N(R⁵)S(O)₂—;
Z represents hydrogen, halogen or trifluoromethyl; or Z represents C₁₋₆ alkyl, C₃₋₇ cycloalkyl, aryl, C₃₋₇ heterocycloalkyl, C₃₋₇ heterocycloalkenyl or heteroaryl, any of which groups may be optionally substituted by one or more substituents; or Z represents —Z¹—Z² or —Z¹C(O)—Z², either of which moieties may be optionally substituted by one or more substituents;
Z¹ represents a divalent radical derived from an aryl, C₃₋₇ heterocycloalkyl or heteroaryl group;
Z² represents aryl, C₃₋₇ heterocycloalkyl, C₃₋₇ heterocycloalkenyl, (C₄₋₉)heterobicycloalkyl, (C₄₋₉)spiroheterocycloalkyl or heteroaryl;
R⁴ and R⁵ independently represent hydrogen or C₁₋₆ alkyl;
R¹² represents hydrogen, halogen, trifluoromethyl or optionally substituted C₁₋₆ alkyl; and
R¹⁵ and R¹⁶ independently represent hydrogen, halogen, cyano, nitro, C₁₋₆ alkyl, trifluoromethyl, hydroxy, C₁₋₆ alkoxy, difluoromethoxy, trifluoromethoxy, C₁₋₆ alkylthio, C₁₋₆ alkylsulfinyl, C₁₋₆ alkylsulfonyl, amino, C₁₋₆ alkylamino, di(C₁₋₆)alkylamino, aryl-amino, C₂₋₆ alkylcarbonylamino, C₁₋₆ alkylsulfonylamino, formyl, C₂₋₆ alkylcarbonyl, C₃₋₆ cycloalkylcarbonyl, C₃₋₆ heterocycloalkylcarbonyl, carboxy, C₂₋₆ alkoxycarbonyl, aminocarbonyl, C₁₋₆ alkylaminocarbonyl, di(C₁₋₆)alkylaminocarbonyl, aminosulfonyl, C₁₋₆ alkylaminosulfonyl, or di(C₁₋₆)alkylaminosulfonyl.

4. A compound as claimed in claim 3 wherein R³⁴ represents hydrogen or hydroxy.

5. A compound as claimed in claim 1 wherein E represents —CH₂— or —CH(CH₃)—.

6. A compound as claimed in claim 1 wherein R¹² represents hydrogen or fluoro.

7. A compound as claimed in claim 1 wherein R¹⁵ represents difluoromethoxy.

8. A pharmaceutical composition comprising a compound of formula (IIB),

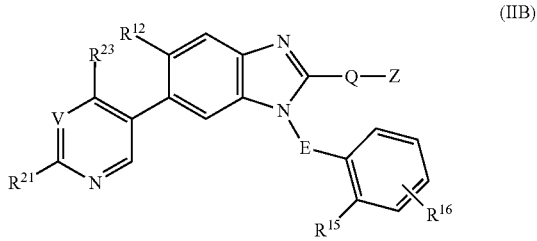

or a pharmaceutically acceptable salt thereof wherein
V represents C—R²² or N;
-E represents —N(R⁴)—, —CH₂—, —CH(CH₃)— or —CH(CH₂CH₃)—;
Q represents a covalent bond; or Q represents —O—, —S—, —S(O)—, —S(O)₂—, —N(R⁵)—, —C(O)N(R⁵)—, —N(R⁵)C(O)—, —S(O)₂N(R⁵)— or —N(R⁵)S(O)₂—; or Q represents an optionally substituted straight or branched C₁₋₆ alkylene chain optionally comprising one, two or three heteroatom-containing linkages independently selected from —O—, —S—, —S(O)—, —S(O)$_2$—, —N(R$^5$)—, —C(O)N(R$^5$)—, —N(R$^5$)C(O)—, —S(O)$_2$N(R$^5$)— and —N(R$^5$)S(O)$_2$—;

Z represents hydrogen, halogen or trifluoromethyl; or Z represents C$_{1-6}$ alkyl, C$_{3-7}$ cycloalkyl, aryl, C$_{3-7}$ heterocycloalkyl, C$_{3-7}$ heterocycloalkenyl or heteroaryl, any of which groups may be optionally substituted by one or more substituents; or Z represents —Z$^1$—Z$^2$ or —Z$^1$—C(O)—Z$^2$, either of which moieties may be optionally substituted by one or more substituents;

Z$^1$ represents a divalent radical derived from an aryl, C$_{3-7}$ heterocycloalkyl or heteroaryl group;

Z$^2$ represents aryl, C$_{3-7}$ heterocycloalkyl, C$_{3-7}$ heterocycloalkenyl, (C$_{4-9}$)heterobicycloalkyl, (C$_{4-9}$)spiroheterocycloalkyl or heteroaryl;

R$^4$ and R$^5$ independently represent hydrogen or C$_{1-6}$ alkyl;

R$^{12}$ represents hydrogen, halogen, trifluoromethyl or optionally substituted C$_{1-6}$ alkyl; and R$^{15}$ and R$^{16}$ independently represent hydrogen, halogen, cyano, nitro, C$_{1-6}$ alkyl, trifluoromethyl, hydroxy, C$_{1-6}$ alkoxy, difluoromethoxy, trifluoromethoxy, C$_{1-6}$ alkylthio, C$_{1-6}$ alkylsulfinyl, C$_{1-6}$ alkylsulfonyl, amino, C$_{1-6}$ alkylamino, di(C$_{1-6}$)alkylamino, arylamino, C$_{2-6}$ alkylcarbonylamino, C$_{1-6}$ alkylsulfonylamino, formyl, C$_{2-6}$ alkylcarbonyl, C$_{3-6}$ cycloalkylcarbonyl, C$_{3-6}$ heterocycloalkylcarbonyl, carboxy, C$_{2-6}$ alkoxycarbonyl, aminocarbonyl, C$_{1-6}$ alkylaminocarbonyl, di(C$_{1-6}$)alkylaminocarbonyl, aminosulfonyl, C$_{1-6}$ alkylaminosulfonyl or di(C$_{1-6}$)alkylaminosulfonyl;

R$^{21}$ represents hydrogen, halogen, cyano, C$_{1-6}$ alkyl, trifluoromethyl, C$_{2-6}$ alkenyl, C$_{2-6}$ alkynyl, hydroxy, hydroxy(C$_{1-6}$)alkyl, C$_{1-6}$ alkoxy, difluoromethoxy, trifluoro-methoxy, trifluoroethoxy, C$_{1-6}$ alkoxy(C$_{1-6}$)alkyl, C$_{1-6}$ alkylthio, C$_{1-6}$ alkylsulphonyl, amino, C$_{1-6}$ alkylamino, di(C$_{1-6}$)alkylamino, hydroxy(C$_{1-6}$)alkylamino, (C$_{1-6}$)alkoxy(C$_{1-6}$)alkylamino, [(C$_{1-6}$)alkoxy](hydroxy)(C$_{1-6}$)alkylamino, N—[(C$_{1-6}$)alkyl]-N-[hydroxy(C$_{1-6}$)alkyl]amino, [(C$_{1-6}$)alkylthio](hydroxy)(C$_{1-6}$)alkylamino, di(C$_{1-6}$)alkylamino(C$_{1-6}$)alkylamino, N-[di(C$_{1-6}$)alkylamino(C$_{1-6}$)alkyl]-N-[hydroxy(C$_{1-6}$)alkyl]amino, hydroxy(C$_{1-6}$)alkyl(C$_{3-7}$)cycloalkylamino, (hydroxy)[(C$_{3-7}$)cycloalkyl(C$_{1-6}$)alkyl]amino, (C$_{3-7}$)heterocycloalkyl(C$_{1-6}$)alkylamino, oxo(C$_{3-7}$)heterocycloalkyl(C$_{1-6}$)alkylamino, (C$_{1-6}$)alkylheteroarylamino, heteroaryl(C$_{1-6}$)alkylamino, (C$_{1-6}$)alkylheteroaryl, (C$_{1-6}$)alkylamino, C$_{2-6}$ alkylcarbonylamino, N—[(C$_{1-6}$)alkyl]-N—[(C$_{2-6}$)alkylcarbonyl]amino, bis[(C$_{3-6}$)alkenylcarbonyl]amino, N-[carboxy(C$_{1-6}$)alkyl]-N—[(C$_{1-6}$)alkyl]amino, C$_{2-6}$ alkoxycarbonylamino, C$_{2-6}$ alkoxycarbonyl(C$_{1-6}$)alkylamino, C$_{1-6}$ alkyl sulphonylamino, N—[(C$_{1-6}$)alkyl]-N—[(C$_{1-6}$)alkylsulphonyl]amino, formyl, C$_{2-6}$ alkylcarbonyl, carboxy, C$_{2-6}$ alkoxycarbonyl, aminocarbonyl, C$_{1-6}$ alkylaminocarbonyl, hydroxy(C$_{1-6}$)alkylaminocarbonyl, di(C$_{1-6}$)alkylaminocarbonyl, aminocarbonyl(C$_{1-6}$)alkyl, aminosulphonyl, C$_{1-6}$ alkylaminosulphonyl or di(C$_{1-6}$)alkylaminosulphonyl; or R$^{21}$ represents (C$_{3-7}$)cycloalkyl, (C$_{3-7}$)cycloalkyl(C$_{1-6}$)alkyl, (C$_{4-7}$)cycloalkenyl, (C$_{4-9}$)bicycloalkyl, (C$_{3-7}$)heterocycloalkyl, (C$_{3-7}$)heterocycloalkyl(C$_{1-6}$)alkyl, (C$_{3-7}$)heterocycloalkenyl, (C$_{4-9}$)heterobicycloalkyl or (C$_{4-9}$)spiroheterocycloalkyl, any of which groups may be optionally substituted by one or more substituents;

R$^{22}$ represents hydrogen, halogen or C$_{1-6}$ alkyl;

R$^{23}$ represents hydrogen or C$_{1-6}$ alkyl;

in association with a pharmaceutically acceptable carrier.

9. A pharmaceutical composition as claimed in claim 8 further comprising an additional pharmaceutically active ingredient.

10. The compound according to claim 2 wherein R$^{21}$ represents 2-hydroxyprop-2-yl.

\* \* \* \* \*